United States Patent
Guèdat et al.

(10) Patent No.: US 7,674,803 B2
(45) Date of Patent: Mar. 9, 2010

(54) THIAZOLYPIPERIDINE DERIVATIVES AS MTP INHIBITORS

(75) Inventors: Philippe Guèdat, Lyons (FR); Francois Collonges, Beynost (FR); Hervé Dumas, Vaulx Milieu (FR); Jean-Yves Ortholand, Saint Jean de Niost (FR); Jacques Decerprit, Neyron (FR); Jaxques Barbanton, Brignais (FR); Robert J. Foster, Cornwall (GB); Peter Kane, Cornwall (GB); Bernd Went, Weil (DE)

(73) Assignee: Merck Patent GmbH, Darmstadt (DE)

( * ) Notice: Subject to any disclaimer, the term of this patent is extended or adjusted under 35 U.S.C. 154(b) by 1026 days.

(21) Appl. No.: 10/561,989

(22) PCT Filed: Jun. 2, 2004

(86) PCT No.: PCT/EP2004/005931

§ 371 (c)(1),
(2), (4) Date: Dec. 23, 2005

(87) PCT Pub. No.: WO2005/003128

PCT Pub. Date: Jan. 13, 2005

(65) Prior Publication Data

US 2007/0054939 A1    Mar. 8, 2007

(30) Foreign Application Priority Data

Jun. 25, 2003    (FR) ................... 03 07670

(51) Int. Cl.
A61K 31/454    (2006.01)
A61K 31/4545    (2006.01)
C07D 417/14    (2006.01)

(52) U.S. Cl. ............... 514/326; 514/318; 546/194; 546/208; 546/209

(58) Field of Classification Search ............... 514/318, 514/326; 546/194, 208, 209
See application file for complete search history.

(56) References Cited

U.S. PATENT DOCUMENTS

2004/0034028 A1    2/2004  Guevel et al.
2006/0135501 A1*   6/2006  Knox et al. .......... 514/210.2

FOREIGN PATENT DOCUMENTS

FR    2 816 940 A      5/2002
WO    WO 03/047575 A   6/2003

OTHER PUBLICATIONS

RN 1022685-68-2 CAS (2008).*
Guedat et al. "Preparation of thiazolylpiperidines . . ." CA 142:93809 (2005).*
Haupt et al. Preparation of petides . . . CA 124:333070 (1996).*
Otte et al. "Preparation of theizolylpiperidines . . . " CA147:344079 (2007).*
Leban et al. "A novel class . . . " CA 147:479784 (2007).*
Sugasawa et al. "Preparation of azolecarboxamide . . . " CA 147:502346 (2007).*
EDupuis et al. "suzuki cross coupling . . . " Tetrahedron Lett. v.42, p. 6523-6526 (2001).*
Prodrug—online medical dictionary (2009) (one page from internet).*
Braga et al. "making crystals from crystals . . . " Chem. cumm. p. 3635-3645 (2005).*

* cited by examiner

*Primary Examiner*—Celia Chang
(74) *Attorney, Agent, or Firm*—Millen, White, Zelano & Branigan, P.C.

(57) ABSTRACT

The present invention relates to thiazolylpiperidine derivatives of the general formula (I):

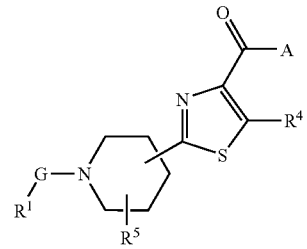

in which:
A represents a radical chosen from the radicals a1 and a2 below:

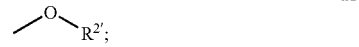

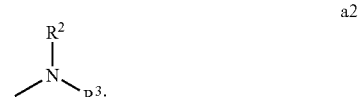

G represents a bond or a divalent radical chosen from the groups g1, g2 and g3 below:

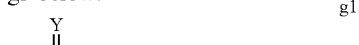

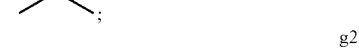

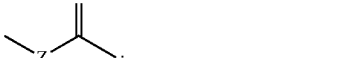

and $R^1$, $R^2$, $R^{2'}$, $R^3$, $R^4$, $R^5$, Y and Z are as defined in the description.

Application of the compounds of the formula (I) to the treatment of hypertriglyceridaemia, hypercholesterolaemia and dyslipidaemia.

20 Claims, No Drawings

THIAZOLYPIPERIDINE DERIVATIVES AS MTP INHIBITORS

The invention relates to compounds that are inhibitors of microsomal triglyceride transfer protein (MTP), to pharmaceutical compositions comprising same, and to the use thereof in medicine.

MTP (microsomal triglyceride transfer protein) is a transfer protein located in the reticulum of hepatocytes and enterocytes, which catalyses the assembly of biomolecules that transport triglycerides, the apo B lipoproteins.

The term apo B more particularly denotes apoprotein 48 of the intestine and apoprotein 100 of the liver.

Mutations in MTP or in the B apoproteins are reflected in man by very low levels or even an absence of apo B lipoproteins. The lipoproteins containing apo B (chylomicrons, very low density lipoproteins) and their metabolic residues (chylomicron remnants, low density lipoproteins) are recognized as being a major risk factor in the development of atherosclerosis, a major cause of death in industrialized countries. It is observed that, in individuals who are heterozygous for these mutations, levels reduced on average by a half are associated with a low cardiovascular risk (C. J. Glueck, P. S. Gartside, M. J. Mellies, P. M. Steiner, *Trans. Assoc. Am. Physicians,* 90, 184 (1977)). This suggests that modulation of the secretions of triglyceride-rich lipoprotein's by means of MTP antagonists and/or of secretion of apo B might be useful in the treatment of atherosclerosis and more broadly of pathologies characterized by an increase in apo B lipoproteins.

Molecules that inhibit MTP and/or the secretion of apo B might thus be useful for the treatment of hypertriglyceridaemia, hypercholesterolaemia and dyslipidaemia associated with diabetes, and also for the prevention of and treating obesity.

It has now been discovered that certain compounds of thiazolylpiperidine structure have inhibitory properties towards MTP and/or apoB secretion.

As a result of this activity, these compounds have an entirely advantageous possible application in the treatment of hypertriglyceridaemia, hypercholesterolaemia and dyslipidaemia associated with diabetes, and also with the prevention and treatment of obesity.

Thus, the present invention relates firstly to compounds of thiazolylpiperidine structure of the general formula (I):

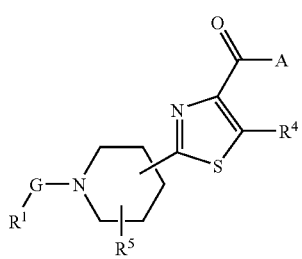

(I)

in which:

A represents a radical chosen from radicals a1 and a2 below:

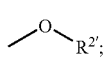

a1

-continued

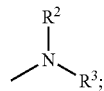

a2

G represents a divalent bond or radical chosen from groups g1, g2 and g3 below:

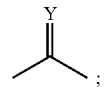

g1

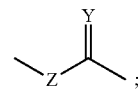

g2

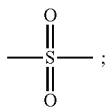

g3

$R^1$ is chosen from hydrogen and an alkyl, alkenyl, alkynyl, cycloalkyl, heterocycloalkyl, aryl, heteroaryl, alkylcarbonyl or alkoxycarbonyl radical;

$R^2$, $R^{2'}$ and $R^3$, which may be identical or different, are chosen, independently of each other, from a hydrogen atom, an alkyl, alkenyl, alkynyl, cycloalkyl, heterocycloalkyl, aryl or heteroaryl radical and a radical —NRR'; or $R^2$ and $R^3$ together form, with the nitrogen atom that bears them, a heterocycle;

$R^4$ and $R^5$, which may be identical or different, are chosen, independently of each other, from a hydrogen atom, an alkyl, alkenyl, alkynyl, cycloalkyl, heterocycloalkyl, aryl or heteroaryl radical and a radical —NRR';

R and R', which may be identical or different, represent, independently of each other, a hydrogen atom or a radical chosen from alkyl, alkenyl, alkynyl, cycloalkyl, heterocycloalkyl, aryl and heteroaryl; or together form, with the nitrogen atom that bears them, a heterocycle, or together form the double bond of an alken-1-yl radical;

Y represents an oxygen or sulfur atom; and

Z represents —NH— or an oxygen atom;

the possible geometrical and/or optical isomers, epimers and various tautomeric forms, and possible oxidized forms, especially amine oxides, thereof, the solvates and the hydrates of these compounds;

and also the possible pharmaceutically acceptable salts thereof with an acid or a base, or the pharmaceutically acceptable prodrugs of these compounds.

The definitions that follow specify the natures of the various groups and radicals defined above. Unless otherwise mentioned, these definitions apply for all the terms of the present invention thus explained.

The term "halogen atom" denotes a fluorine, chlorine, bromine or iodine atom.

The term "alkyl" denotes a linear or branched alkyl radical containing from 1 to 12 carbon atoms, optionally substituted by one or more chemical species, which may be identical or different, chosen from a halogen atom, an oxo, thioxo, hydroxyl, thiol, —NRR' (where R and R', which may be identical or different, are as defined above), cyano, nitro or carboxyl group, and an alkoxy, alkenyloxy, alkynyloxy, alkylthio, alkyldisulfanyl (alkyl-S—S—), alkylsulfinyl) (alkyl-S(═O)—), alkylsulfonyl (alkyl-S(═O)$_2$—), alkenylthio, alkynylthio, alkylcarbonyl, alkoxycarbonyl, alkylcarbonylamino, alkoxycarbonylamino, arylcarbonyl, arylcarbonylamino, (di)alkylaminocarbonyl, cycloalkyl, cycloalkoxy, cycloalkylthio, heterocycloalkyl, heterocycloalkoxy, heterocycloalkylthio, aryl, aryloxy, arylthio, heteroaryl, heteroarylcarbonyl, heteroaryloxy or heteroarylthio radical.

Examples of alkyl radicals, which may be optionally substituted as indicated above, are methyl, ethyl, propyl, isopropyl, butyl, isobutyl, tert-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl and 7,7-dimethyloctyl.

The term "alkenyl" denotes a linear or branched alkyl radical comprising at least one unsaturation in double bond form and containing from 2 to 12 carbon atoms, optionally substituted by one or more chemical species, which may be identical or different, chosen from a halogen atom, an oxo, thioxo, hydroxyl, thiol, —NRR' (in which R and R', which may be identical or different, are as defined above), cyano, nitro or carboxyl group, and an alkoxy, alkenyloxy, alkynyloxy, alkylthio, alkyldisulfanyl (alkyl-S—S—), alkylsulfinyl (alkyl-S(═O)—), alkylsulfonyl (alkyl-S(═O)$_2$—), alkenylthio, alkynylthio, alkylcarbonyl, alkoxycarbonyl, alkylcarbonylamino, alkoxycarbonylamino, arylcarbonyl, arylcarbonylamino, (di)-alkylaminocarbonyl, cycloalkyl, cycloalkoxy, cycloalkylthio, heterocycloalkyl, heterocycloalkoxy, heterocycloalkylthio, aryl, aryloxy, arylthio, heteroaryl, heteroarylcarbonyl, heteroaryloxy or heteroarylthio radical.

Examples of alkenyl radicals, which may be optionally substituted as indicated above, are ethylenyl, propenyl, propadienyl, butenyl, butadienyl, pentenyl, pentadienyl, hexenyl, hexadienyl, heptenyl, heptadienyl, octenyl, octadienyl, nonenyl, nonadienyl, decenyl and decadienyl, and also the branched isomers thereof, the absence of indication of the position of the double bond(s) being necessarily understood as meaning that no limitation is placed on the double bond(s). For example, the "pentenyl" radical includes, without preference, the pent-1-en-1-yl, pent-2-en-1-yl and pent-3-en-1-yl radicals, but also the pent-1-en-2-yl, pent-2-en-2-yl and pent-3-en-2-yl radicals, as well as the pent-1-en-3-yl, pent-2-en-3-yl and pent-3-en-3-yl radicals.

The term "alkynyl" denotes a linear or branched alkyl radical comprising at least one unsaturation in triple bond form and containing from 2 to 12 carbon atoms, optionally substituted by one or more chemical species, which may be identical or different, chosen from a halogen atom, an oxo, thioxo, hydroxyl, thiol, —NRR' (in which R and R', which may be identical or different, are as defined above), cyano, nitro or carboxyl group, and an alkoxy; alkenyloxy, alkynyloxy, alkylthio, alkyldisulfanyl (alkyl-S—S—), alkylsulfinyl (alkyl-S(═O)—), alkylsulfonyl (alkyl-S(═O)$_2$—), alkenylthio, alkynylthio, alkylcarbonyl, alkoxycarbonyl, alkylcarbonylamino, alkoxycarbonylamino, arylcarbonyl, arylcarbonylamino, (di)alkylaminocarbonyl, cycloalkyl, cycloalkoxy, cycloalkylthio, heterocycloalkyl, heterocycloalkoxy, heterocycloalkylthio, aryl, aryloxy, arylthio, heteroaryl, heteroarylcarbonyl, heteroaryloxy or heteroarylthio radical.

Examples of alkynyl radicals, which may be optionally substituted as indicated above, are ethynyl, propynyl, propadiynyl, butynyl, butadiynyl, pentynyl, pentadiynyl, hexynyl, hexadiynyl, heptynyl, heptadiynyl, octynyl, octadiynyl, nonynyl, nonadiynyl, decynyl and decadiynyl, and also the branched isomers thereof, the absence of indication of the position of the double bond(s) being necessarily understood as meaning that no limitation is placed on the double bond(s). For example, the "pentynyl" radical includes, without preference, the pent-1-yn-1-yl, pent-2-yn-1-yl and pent-3-yn-1-yl radicals, but also the pent-1-yn-2-yl, pent-2-yn-2-yl and pent-3-yn-2-yl radicals, as well as the pent-1-yn-3-yl, pent-2-yn-3-yl and pent-3-yn-3-yl radicals.

The term "cycloalkyl" denotes a monocyclic, bicyclic or tricyclic, bridged or unbridged cycloalkyl radical containing from 3 to 13 carbon atoms, optionally comprising one or more double bonds, also including spirane compounds, and optionally substituted by one or more chemical species, which may be identical or different, chosen from a halogen atom, an oxo, thioxo, hydroxyl, thiol, —NRR' (in which R and R', which may be identical or different, are as defined above), cyano, nitro or carboxyl group, and an alkyl, especially substituted by one or more halogen atoms, in particular perhaloalkyl, for instance trifluoromethyl, alkenyl, alkynyl, alkoxy, alkenyloxy, alkynyloxy, alkylthio, alkyldisulfanyl (alkyl-S—S—), alkylsulfinyl (alkyl-S(═O)—), alkylsulfonyl (alkyl-S(═O)$_2$—), alkenylthio, alkynylthio, alkylcarbonyl, alkoxycarbonyl, alkylcarbonylamino, alkoxycarbonylamino, arylcarbonyl, arylcarbonylamino, (di)alkylaminocarbonyl, cycloalkyl, cycloalkoxy, cycloalkylthio, heterocycloalkyl, heterocycloalkoxy, heterocycloalkyl-thio, aryl, aryloxy, arylthio, heteroaryl, heteroarylcarbonyl, heteroaryloxy or heteroarylthio radical.

Examples of cycloalkyl groups, which are optionally substituted as indicated above, are especially cyclopropyl, cyclobutyl, cyclopentyl, cyclohexyl, cycloheptyl, cyclooctyl and cyclodecyl, adamantyl, diamantyl, norbornyl and bornyl groups.

The term "heterocycloalkyl" denotes a monocyclic, bicyclic or tricyclic radical containing a total of from 3 to 13 atoms, among which 1, 2, 3 or 4 are chosen, independently of each other, from nitrogen, oxygen and sulfur, the other atoms being carbon atoms, the said heterocyclic radical also optionally comprising 1, 2, 3 or 4 double bonds, also including spirane compounds, and being optionally substituted by one or more chemical species, which may be identical or different, chosen from a halogen atom, an oxo, thioxo, hydroxyl, thiol, —NRR' (in which R and R', which may be identical or different, are as defined above), cyano, nitro or carboxyl group, and an alkyl, especially substituted by one or more halogen atoms, in particular perhaloalkyl, for instance trifluoromethyl, alkenyl, alkynyl, alkoxy, alkenyloxy, alkynyloxy, alkylthio, alkyldisulfanyl (alkyl-S—S—), alkylsulfinyl (alkyl-S(═O)—), alkylsulfonyl (alkyl-S(═O)$_2$—), alkenylthio, alkynylthio, alkylcarbonyl, alkoxycarbonyl, alkylcarbonylamino, alkoxycarbonylamino, arylcarbonyl, arylcarbonylamino, (di)alkylaminocarbonyl, cycloalkyl, cycloalkoxy, cycloalkylthio, heterocycloalkyl, heterocycloalkoxy, heterocycloalkylthio, aryl, aryloxy, arylthio, heteroaryl, heteroarylcarbonyl, heteroaryloxy or heteroarylthio radical.

In particular, saturated or partially unsaturated, monocyclic heterocycles of 5 to 8 atoms are saturated, or partially unsaturated, derivatives of the heteroaryls defined later. More particularly, among the heterocycloalkyl radicals that may be mentioned are morpholino, morpholinyl, piperidyl, thiazolidinyl, oxazolidinyl, tetrahydrothienyl, tetrahydrofuryl, tetrahydropyranyl, pyrrolidinyl, isoxazolidinyl, imidazolidinyl and pyrazolidinyl radicals.

The term "aryl" denotes a monocyclic, bicyclic or tricyclic aryl radical containing from 6 to 14 carbon atoms, optionally substituted by one or more chemical species, which may be identical or different, chosen from a halogen atom, an oxo, thioxo, hydroxyl, thiol, —NRR' (in which R and R', which may be identical or different, are as defined above), cyano, nitro or carboxyl group, and an alkyl, especially substituted by one or more halogen atoms, in particular perhaloalkyl, for instance trifluoromethyl, alkenyl, alkynyl, alkoxy, alkenyloxy, alkynyloxy, alkylthio, alkyldisulfanyl (alkyl-S—S—), alkylsulfinyl (alkyl-S(=O)—), alkylsulfonyl (alkyl-S(=O)$_2$—, alkenylthio, alkynylthio, a phosphoric acid derivative [(alkyl-O)$_2$—P—O-alkyl], alkylcarbonyl, alkoxycarbonyl, alkylcarbonylamino, alkoxycarbonylamino, arylcarbonyl, arylcarbonylamino, (di)alkylaminocarbonyl, cycloalkyl, cycloalkoxy, cycloalkylthio, heterocycloalkyl, heterocycloalkoxy, heterocycloalkylthio, aryl, aryloxy, arylthio, heteroaryl, heteroarylcarbonyl, heteroaryloxy or heteroarylthio radical.

Aryl radicals that may be mentioned, in a non-limiting manner, include phenyl, naphthyl, anthryl and phenanthryl radicals.

The term "heteroaryl" denotes a monocyclic, bicyclic or tricyclic aromatic radical containing a total of from 3 to 13 atoms, among which 1, 2, 3 or 4 are chosen, independently of each other, from nitrogen, oxygen and sulfur, optionally in oxidized form (in the case of nitrogen and sulfur), the other atoms being carbon atoms, the said heteroaryl radical being optionally substituted by one or more chemical species, which may be identical or different, chosen from a halogen atom, an oxo, thioxo, hydroxyl, thiol, —NRR' (in which R and R', which may be identical or different, are as defined above), cyano, nitro or carboxyl group, and an alkyl, especially substituted by one or more halogen atoms, in particular perhaloalkyl, for instance trifluoromethyl, alkenyl, alkynyl, alkoxy, alkenyloxy, alkynyloxy, alkylthio, alkyldisulfanyl (alkyl-S—S—), alkylsulfinyl (alkyl-S(=O)—), alkylsulfonyl (alkyl-S(=O)$_2$—), alkenylthio, alkynylthio, alkylcarbonyl, alkoxycarbonyl, alkylcarbonylamino, alkoxycarbonylamino, arylcarbonyl, arylcarbonylamino, (di)alkylaminocarbonyl, cycloalkyl, cycloalkoxy, cycloalkylthio, heterocycloalkyl, heterocycloalkoxy, heterocycloalkylthio, aryl, aryloxy, arylthio, heteroaryl, heteroaryloxy or heteroarylthio radical.

Preferably, at least one of the monocycles constituting the heterocycle contains from 1 to 4 endocyclic hetero atoms and more preferably from 1 to 4 endocyclic hetero atoms. According to the invention, the heterocyclic polycyclic nucleus consists of one or more monocycles each containing from 5 to 8 atoms included in the ring.

Examples of heteroaryl radicals, optionally substituted as has just been described, are radicals derived from heteroaromatic compounds, such as pyridine, furan, thiophene, pyrrole, imidazole, thiazole, isothiazole, isoxazole, furazane, pyridazine, pyrimidine, pyrazine, thiazines, oxazole, pyrazole, oxadiazole, triazole and thiadiazole. Among the preferred heteroaryls that may be mentioned are pyridyls, pyrimidinyls, triazolyls, thiadiazolyls, oxazolyls, thiazolyls and thienyls.

Examples of bicyclic heteroaryl radicals in which each monocycle contains from 5 to 8 endocyclic atoms are derived from aromatic compounds chosen from indolizine, indole, isoindole, benzofuran, benzothiophene, indazole, benzimidazole, benzothiazole, benzofurazane, benzothiofurazane, purine, quinoline, isoquinoline, cinnoline, phthalazine, quinazoline, quinoxaline, naphthyridines, pyrazolotriazines, pyrazolopyrimidine and pteridine.

Among the heteroaryls defined above, quinolyl, pyridyl, benzotriazolyl, triazolyl, acridyl, phenazinyl and carbazolyl radicals are preferred.

When the radicals $R^2$ and $R^3$ form, together with the nitrogen atom that bears them, a heterocycle, the said heterocycle is a monocycle, bicycle or tricycle containing a total of from 3 to 13 atoms including the nitrogen atom, among which 1, 2, 3 or 4 are chosen, independently of each other, from nitrogen, oxygen and sulfur, the other atoms being carbon atoms, the said heterocycle also optionally comprising 1, 2, 3 or 4 double bonds, also including spirane compounds, and being optionally substituted by one or more chemical species, which may be identical or different, chosen from a halogen atom, an oxo, thioxo, hydroxyl, thiol, —NRR' (in which R and R', which may be identical or different, are as defined above), cyano, nitro or carboxyl group, and an alkyl, alkenyl, alkynyl, alkoxy, alkenyloxy, alkynyloxy, alkylthio, alkyldisulfanyl (alkyl-S—S—), alkylsulfinyl (alkyl-S(=O)—), alkylsulfonyl (alkyl-S(=O)$_2$—), alkenylthio, alkynylthio, alkylcarbonyl, alkoxycarbonyl, alkylcarbonylamino, alkoxycarbonylamino, arylcarbonyl, arylcarbonylamino, (di)alkylaminocarbonyl, cycloalkyl, cycloalkoxy, cycloalkylthio, heterocycloalkyl, heterocycloalkoxy, heterocycloalkylthio, aryl, aryloxy, arylthio, heteroaryl, heteroaryloxy or heteroarylthio radical.

For the compounds of the formula (I) presented above, the term "geometrical isomer" means a cis/trans or E/Z isomerism. More particularly, the possible double bond(s) present in the various substituents of the compounds of the general formula (I) can be of E or Z configuration. These pure or impure geometrical isomers, alone or as a mixture, form an integral part of the compounds of the formula (I).

The term "optical isomer" includes all the isomeric forms, alone or as mixtures, resulting from the presence of one or more axes and/or centres of symmetry in the molecule, and resulting in the rotation of a beam of polarized light. The term "optical isomer" more particularly includes enantiomers and disasteroisomers, in pure form or as a mixture.

The acids capable of forming pharmaceutically acceptable salts with the compounds of the formula (I) above are organic or mineral acids. Non-limiting examples that may be mentioned include hydrochloric acid, hydrobromic acid, phosphoric acid, sulfuric acid, tartaric acid, citric acid, maleic acid, acetic acid, fumaric acid, alkanesulfonic acid, naphthalenesulfonic acid, para-toluenesulfonic acid, bis-trifluoroacetic acid and camphoric acid.

The bases capable of forming pharmaceutically acceptable salts with the compounds of the formula (I) above are mineral or organic bases. Among these bases, non-limiting examples that may be mentioned include sodium hydroxide, potassium hydroxide, ammonia, diethylamine, triethylamine, ethanolamine, diethanolamine, piperidine, piperazine, morpholine, basic amino acids, such as arginine and lysine, osamines, for example meglumine, and amino alcohols, such as 3-aminobutanol and 2-aminobutanol.

The invention especially covers the pharmaceutically acceptable salts, as indicated above, but also salts allowing a suitable separation or crystallization of the compounds of the formula (I), such as the salts obtained with chiral amines.

The compounds of the formula (I) above also comprise the prodrugs of these compounds.

The term "prodrugs" means compounds which, once administered to the patient, are chemically and/or biologically converted by the living body into compounds of the formula (I).

Among the compounds of the formula (I) according to the invention that are preferred are those for which the radical $R^5$ represents hydrogen, the possible geometrical and/or optical isomers, epimers and various tautomeric forms, and optional oxidized forms, especially amine oxides, thereof, and the solvates and hydrates of these compounds;

and also the possible pharmaceutically acceptable salts thereof with an acid or a base, or the pharmaceutically acceptable prodrugs of these compounds.

Preference is also given to the compounds of the formula (I) according to the invention for which the radical $R^4$ represents hydrogen, the possible geometrical and/or optical isomers, epimers and various tautomeric forms, and optional oxidized forms, especially amine oxides, thereof, and the solvates and hydrates of these compounds;

and also the possible pharmaceutically acceptable salts thereof with an acid or a base, or the pharmaceutically acceptable prodrugs of these compounds.

Another preferred group of compounds according to the present invention consists of compounds of the formula (I) in which the thiazolyl radical is branched in position 3 or in position 4 of the piperidine nucleus, preferably in position 4 of the piperidine nucleus.

Another preferred group of compounds according to the present invention consists of compounds of the general formula (I) in which G represents the radical g1, preferably in which Y represents an oxygen atom, the possible geometrical and/or optical isomers, epimers and various tautomeric forms, and optional oxidized forms, especially amine oxides, thereof, and the solvates and hydrates of these compounds;

and also the possible pharmaceutically acceptable salts thereof with an acid or a base, or the pharmaceutically acceptable prodrugs of these compounds.

Another preferred group of compounds according to the present invention consists of compounds of the general formula (I) in which the radical $R^4$ represents hydrogen, the radical $R^5$ represents hydrogen, the thiazolyl radical is branched in position 4 of the piperidine nucleus, and G represents the radical g1 in which Y represents an oxygen atom, the possible geometrical and/or optical isomers, epimers and various tautomeric forms, and optional oxidized forms, especially amine oxides, thereof, and the solvates and hydrates of these compounds;

and also the possible pharmaceutically acceptable salts thereof with an acid or a base, or the pharmaceutically acceptable prodrugs of these compounds.

Another preferred group of compounds of the invention consists of compounds of the general formula (I) in which $R^1$ represents an aryl radical, especially phenyl, substituted by one or more aryl and/or alkyl radicals. The compounds of the general formula (I) in which $R^1$ represents a biphenyl radical, optionally substituted by one or more alkyl radicals, preferably methyl, ethyl or propyl, and/or with a perhaloalkyl or perhaloalkoxy radical, are most particularly preferred. The compounds of the general formula (I) in which $R^1$ represents a substituted biphenyl radical, for example a trifluoromethylbiphenyl or methyltrifluoromethoxybiphenyl radical, are more particular preferred.

Among the compounds of the general formula (I), another preferred group of compounds consists of those for which A represents a2, the other substituents having the same definitions as those given above, the possible geometrical and/or optical isomers, epimers and various tautomeric forms, and optional oxidized forms, especially amine oxides, thereof, and the solvates and hydrates of these compounds;

and also the possible pharmaceutically acceptable salts thereof with an acid or a base, or the pharmaceutically acceptable prodrugs of these compounds.

Among the above compounds, the ones most particularly preferred are those for which a2 represents a radical of the formula a2' below:

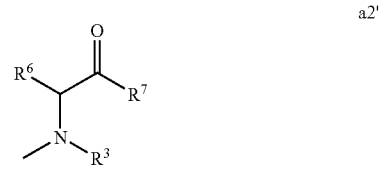

in which $R^6$ and $R^7$, which may be identical or different, and independently of each other, have the same definitions as the radicals $R^2$ and $R^3$ defined above, the other substituents having the same definitions as those given above, the possible geometrical and/or optical isomers, epimers and various tautomeric forms, and optional oxidized forms, especially amine oxides, thereof, and the solvates and hydrates of these compounds;

and also the possible pharmaceutically acceptable salts thereof with an acid or a base, or the pharmaceutically acceptable prodrugs of these compounds.

A preferred sub-group of compounds consists of compounds of the general formula (I) in which G represents the radical g1, with Y representing an oxygen atom, $R^1$ represents a biphenyl radical, optionally substituted by one or more alkyl radicals, preferably methyl, ethyl or propyl, and/or a trifluoromethyl or trifluoromethoxy radical, and A represents a2, the other substituents being as defined above, the possible geometrical and/or optical isomers, epimers and various tautomeric forms, and optional oxidized forms, especially amine oxides, thereof, and the solvates and hydrates of these compounds;

and also the possible pharmaceutically acceptable salts thereof with an acid or a base, or the pharmaceutically acceptable prodrugs of these compounds.

In this sub-group, the compounds that are more particularly preferred are those of the general formula (I) in which G represents the radical g1, with Y representing an oxygen atom, $R^1$ represents a biphenyl radical, optionally substituted by one or more alkyl radicals, preferably methyl, ethyl or propyl, and/or a trifluoromethyl or trifluoromethoxy radical, and A represents a2' as defined above, the other substituents being as defined above, the possible geometrical and/or optical isomers, epimers and various tautomeric forms, and optional oxidized forms, especially amine oxides, thereof, and the solvates and hydrates of these compounds;

and also the possible pharmaceutically acceptable salts thereof with an acid or a base, or the pharmaceutically acceptable prodrugs of these compounds.

Particularly preferred examples of compounds according to the present invention are chosen from:

N-ethyl-N-(1-methyl-2-oxo-2-phenylethyl)2-[1-(4'-trifluoromethylbiphenyl-2-carbonyl)piperid-4-yl]thiazole-4-carbamate;
N-ethyl-N-(1-methyl-2-oxo-2-pyrid-3-ylethyl)2-[1-(4'-trifluoromethylbiphenyl-2-carbonyl)piperid-4-yl]thiazole-4-carbamate;
N-ethyl-N-(1-methyl-2-oxo-2-phenylethyl)2-[1-(6-methyl-4'-trifluoromethoxybiphenyl-2-carbonyl)piperid-4-yl]thiazole-4-carboxamide;
N-ethyl-N-(1-methyl-2-oxo-2-pyrid-2-ylethyl)2-[1-(6-methyl-4'-trifluoromethoxybiphenyl-2-carbonyl)piperid-4-yl]thiazole-4-carbamate.
N-[cyano(4-fluorophenyl)methyl]-N-phenyl-2-[1-(4'-trifluoromethylbiphenyl-2-carbonyl)piperid-4-yl]thiazole-4-carboxamide;
N-(α-cyanobenzyl)-N-ethyl-2-[1-(4'-trifluoromethylbiphenyl-2-carbonyl)piperid-4-yl]thiazole-4-carboxamide;
2-{1-{4'-(trifluoromethyl)-1,1'-biphenyl-2-yl]carboxyl}piperid-4-yl}-1,3-thiazole-4-carboxylic acid
1-(4-{4-(3-hydroxypiperid-1-yl)methanoyl]thiazol-2-yl}piperid-1-yl)-1-(4'-trifluoromethylbiphenyl-2-yl)methanone
N-methyl-N-(1-methyl-2-oxo-2-phenethyl)-2-[1-(4'-trifluoromethylbiphenyl-2-carbonyl)piperid-4-yl]thiazole-4-carboxamide
N-methyl-N-(1-methyl)-2-oxo-2(S)-phenethyl)-2-[1-(4'-trifluoromethylbiphenyl-2-carbonyl)piperid-4-yl]thiazole-4-carboxamide
N-(7-oxo-7H-thieno[3,2-b]pyran-6-yl)-2-[1-(4'-trifluoromethylbiphenyl-2-carbonyl)piperid-4-yl]thiazole-4-carboxamide
N-(2-methyl-4-oxo-4H-chromen-3-yl)-2-[1-(6-methyl-4'-trifluoromethoxybiphenyl-2-carbonyl)piperid-4-yl]thiazole-4-carboxamide
N-(α-cyanobenzyl)-N-isopropyl-2-[1-(4'-trifluoromethylbiphenyl-2-carbonyl)piperid-4-yl]thiazole-4-carboxamide; and
N-[1-cyano-1-(pyrid-4-yl)methyl)-N-isopropyl-2-[1-(4'-trifluoromethylbiphenyl-2-carbonyl)piperid-4-yl]thiazole-4-carboxamide;

the optical isomers thereof, oxidized forms, solvates and hydrates of these compounds;

and also the possible pharmaceutically acceptable salts thereof with an acid, or the pharmaceutically acceptable prodrugs of these compounds.

The compounds of the present invention can be prepared from the compounds of the formula (II):

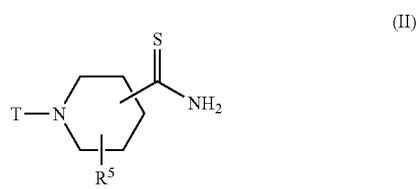

in which T represents a labile protecting group, for example tert-butoxy-carbonyl (BOC), and $R^5$ is as defined above, which is reacted with ethyl $R^4$-bromopyruvate, generally in equimolar proportions, in a polar solvent, for example dimethylformamide, in the presence of an excess of base, preferably an organic base, such as triethylamine, at a suitable temperature, for example at room temperature, for a time ranging from 1 to 40 hours and preferably between 4 and 18 hours, so as to form the thiazolyl ring and give the compound of the formula (III):

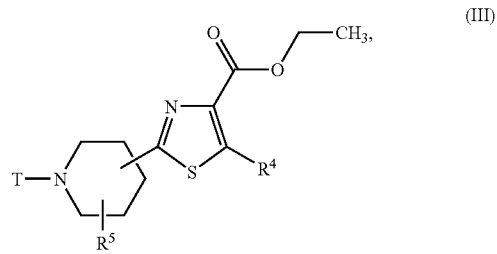

in which T, $R^4$ and $R^5$ are as defined above, which compound of the formula (III) is then saponified with a base, of alkali metal or alkaline-earth metal hydroxide type, for example sodium hydroxide, in polar medium, for instance tetrahydrofuran and/or water, especially a 2:1 tetrahydrofuran/water mixture, at room temperature, for a time ranging from 1 to 12 hours, so as to form the salt of the formula (IV):

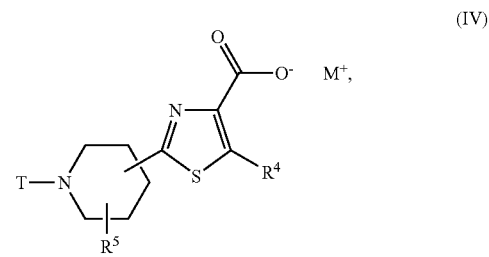

in which T, $R^4$ and $R^5$ are as defined above, and $M^+$ represents the alkali metal or alkaline-earth metal cation derived from the base that is useful for the saponification reaction, which compound of the formula (IV) is next hydrolysed and then/or esterified to a compound of the formula (V1):

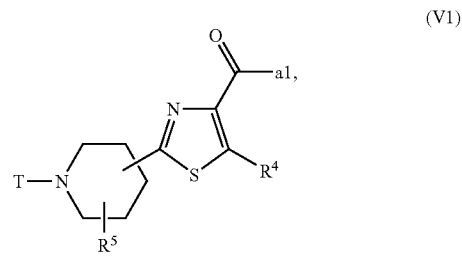

in which $R^4$, $R^5$, a1 and T are as defined above, or converted into the corresponding amide of the formula (V2):

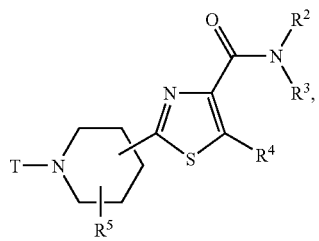

(V2)

in which R², R³, R⁴, R⁵ and T are as defined above, via the action of an amine of the formula HNR²R³, generally in equimolar proportions, in the presence of a base, preferably an organic base, such as diisopropylethylamine (DIPEA), and a catalyst, for example O-benzotriazol-1-yl-N,N,N',N'-tetraethyluronium hexafluorophosphate (HBTU), in a polar aprotic solvent, such as dimethylformamide, at room temperature, for a time that can range from 1 to 50 hours and generally from 4 to 20 hours, the compounds of the formulae (V1) and (V2) together forming the compound of the formula (V):

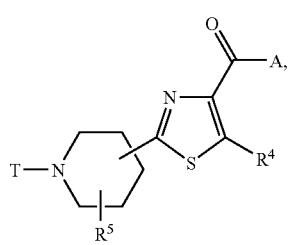

(V)

in which R⁴, R⁵, A and T are as defined above, which compound of the formula (V) is then used in a reaction for deprotection of the amine function of the piperidine ring, via the action of an organic or mineral acid, for example hydrochloric acid or trifluoroacetic acid, in dichloromethane (DCM) or dioxane medium, at room temperature, for a time ranging from a few minutes to a few hours, generally ranging from five minutes to 12 hours, to give the compound of the formula (VI):

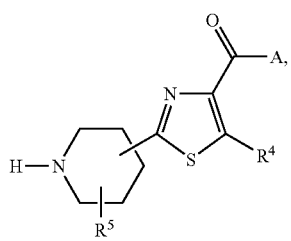

(VI)

which is a special case of the compounds of the formula (I), in which R¹ represents hydrogen, G represents a bond, A, R⁴ and R⁵ being as defined above, which is then subjected to the action of a compound chosen from:

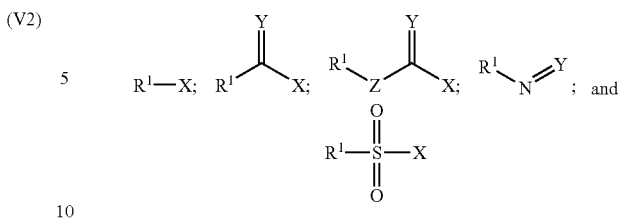

in which X represents a halogen atom, preferably chlorine, R¹, Y and Z being as defined above, in the presence of a base, preferably an organic base, such as diisopropylethylamine (DIPEA), and a catalyst, for example O-benzotriazol-1-yl-N,N,N',N'-tetraethyluronium hexafluorophosphate (HBTU), in a polar aprotic solvent, such as dimethylformamide, at room temperature, for a time that can range from 1 to 50 hours and generally from 4 to 20 hours, to give the compound of the formula (I) as defined above.

According to one variant, the compounds of the formula (I) can also be prepared by reacting a compound of the formula chosen from:

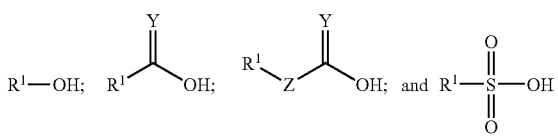

in which R1, Y and Z are as defined above,
with a compound of the formula (VII):

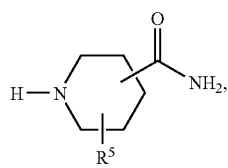

(VII)

in which R⁵ is as defined above, in the presence of an acyl chloride, such as oxalyl chloride, in basic medium, for example triethylamine, and in an apolar aprotic solvent, for example dichloromethane, at room temperature, for a time ranging from 1 to 50 hours and is generally from 4 to 20 hours, to give the compound of the formula (VIII):

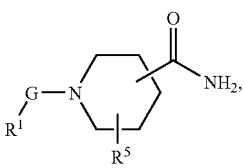

(VIII)

in which G, R¹ and R⁵ are as defined above, which is then converted into the corresponding thioamide of the formula (IX) via the action of Lawesson's reagent, in a polar solvent, for example dimethyl ether, at a temperature of about 50° C., for a time generally of about 2.5 hours:

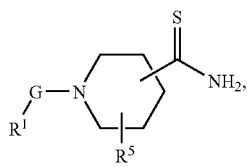

(IX)

in which G, R$^1$ and R$^5$ are as defined above, the thiazole ring then being formed in a manner similar to that presented above for the formation of the compound of the formula (III), via the action of ethyl R$^4$-bromopyruvate, to give the compound of the formula (X):

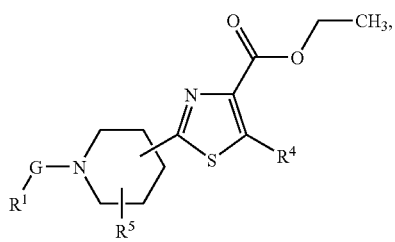

(X)

in which G, R$^1$, R$^4$ and R$^5$ are as defined above, which compound of the formula (X) is then saponified, in a manner similar to that for the formation of the compound of the formula (IV), to give the acid of the formula (I$_{OH}$):

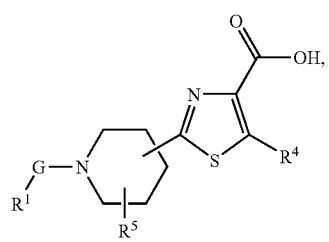

(I$_{OH}$)

which is a special case of the compound of the formula (I) in which A represents —O—R$^{2'}$, R$^{2'}$ representing a hydrogen atom, which compound of the formula (I$_{OH}$) is then optionally used in an esterification reaction, or subjected to the action of an amine of the formula HNR$^2$R$^3$, in order to give the compounds of the formula (I) in which A represents, respectively, a1, with R$^{2'}$ other than hydrogen, and a2.

In the processes described above, it should be understood that the operating conditions can vary substantially as a function of the different substituents G, R$^1$, R$^2$, R$^{2'}$, R$^3$, R$^4$, R$^5$, R$^6$ and R$^7$ present in the compounds of the formula (I) that it is desired to prepare. Such variations and adaptations are readily accessible to a person skilled in the art, for example from scientific reviews, the patent literature, Chemical Abstracts, and computer databases, including the Internet.

For the compounds of the general formula (I) for which A represents a2', the intermediate amine H-a2' below:

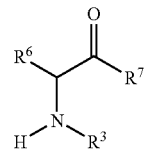

in which R$^3$, R$^6$ and R$^7$ are as defined above, which will be reacted with the compounds of the formulae (V2) and (I$_{OH}$) defined above, can advantageously be prepared according to one of the synthetic routes presented in the following scheme, and in which the various substituents are as defined in the present invention:

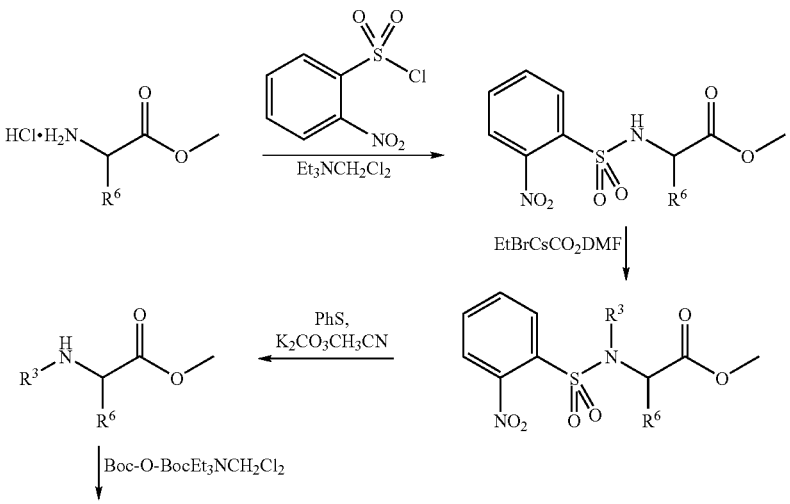

-continued

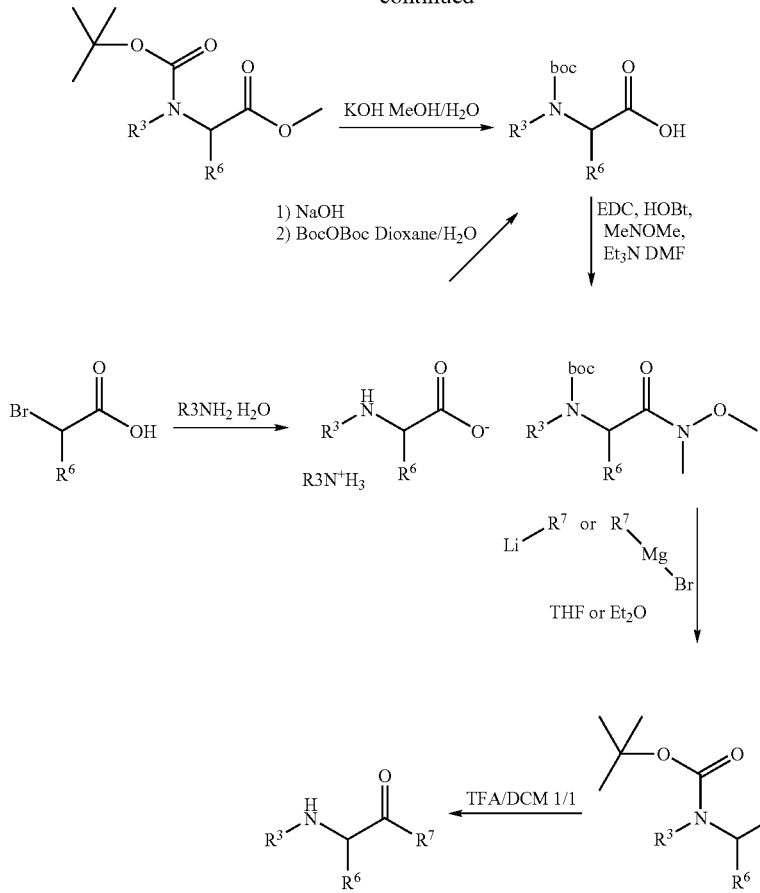

The present invention also relates to pharmaceutical compositions comprising an effective pharmaceutical amount of a compound of the formula (I), as defined above, in combination with one or more pharmaceutically acceptable vehicles.

These compositions can be administered orally in the form of immediate-release or controlled-release tablets, gel capsules or granules, intravenously in the form of an injectable solution, transdermally in the form of an adhesive transdermal device, or locally in the form of a solution, cream or gel.

A solid composition for oral administration is prepared by adding to the active principle a filler and, where appropriate, a binder, a disintegrating agent, a lubricant, a colorant or a flavour enhancer, and by forming the mixture into a tablet, a coated tablet, a granule, a powder or a capsule.

Examples of fillers include lactose, corn starch, sucrose, glucose, sorbitol, crystalline cellulose and silicon dioxide, and examples of binders include poly(vinyl alcohol), poly (vinyl ether), ethylcellulose, methylcellulose, acacia, gum tragacanth, gelatin, Shellac, hydroxypropylcellulose, hydroxypropylmethylcellulose, calcium citrate, dextrin and pectin.

Examples of lubricants include magnesium stearate, talc, polyethylene glycol, silica and hardened plant oils. The colorant can be any colorant permitted for use in medicaments.

Examples of flavour enhancers include cocoa powder, mint in herb form, aromatic powder, mint in oil form, borneol and cinnamon powder. It should be understood that the tablet or granule may be suitably coated with sugar, gelatin or the like.

An injectable form comprising the compound of the present invention as active principle is prepared, where appropriate, by mixing the said compound with a pH regulator, a buffer agent, a suspension agent, a solubilizer, a stabilizer, a tonicity agent and/or a preserving agent, and by converting the mixture into a form for intravenous, subcutaneous or intramuscular injection, according to a conventional process. Where appropriate, the injectable form obtained can be lyophilized via a conventional process.

Examples of suspension agents include methylcellulose, polysorbate 80, hydroxyethylcellulose, acacia, powdered gum tragacanth, sodium carboxymethylcellulose and polyethoxylated sorbitan monolaurate.

Examples of solubilizers include castor oil solidified with polyoxyethylene, polysorbate 80, nicotinamide, polyethoxylated sorbitan monolaurate and the ethyl ester of castor oil fatty acid.

In addition, the stabilizer includes sodium sulfite, sodium metasulfite and ether, while the preserving agent includes methyl para-hydroxybenzoate, ethyl para-hydroxybenzoate, sorbic acid, phenol, cresol and chlorocresol.

A subject of the present invention is also a use of a compound of the formula (I) of the invention for the preparation of a medicament for the treatment of hypertriglyceridaemia, hypercholesterolaemia and dyslipidaemia associated with diabetes, and also for the prevention of and treating obesity.

The examples that follow illustrate the present invention without limiting it in any way.

EXAMPLES OF THIAZOLYLPIPERIDINE COMPOUNDS ACCORDING TO THE INVENTION

Example 1

2-[1-(6-Methyl-4'-trifluoromethoxybiphenyl-2-carbonyl)piperid-4-yl]thiazol-4-carbonyl[N-ethyl-N-(1-methyl-2-oxo-2-phenylethyl)]amide Step a)

tert-Butyl 4-(4-ethoxycarbonylthiazol-2-yl)piperidine-1-carboxylate tert-Butyl 4-(aminocarbothioyl)tetrahydropyridine-1 (2H)-carboxylate (May-bridge) (85 mmol; 20.8 g) is dissolved in 250 ml of dimethylformamide and placed at 5° C. Ethyl bromopyruvate (1 eq.; 85 mmol; 16.6 g) dissolved in 50 ml of dimethylformamide is added dropwise. The reaction medium is stirred overnight and excess triethylamine is then added dropwise. The reaction medium is evaporated and the residual brown oil is taken up in ethyl acetate and washed with water (twice) and then with saturated sodium chloride solution (twice). The organic phase is dried over sodium sulfate and evaporated to dryness. The crude product is chromatographed on silica, eluting with dichloromethane to dichloromethane/3% methanol, to give 20.5 g of the expected product in the form of oily crystals. TLC: 1/1 ethyl acetate/hexane: Rf=0.55

Yield=71%.

Step b)

tert-Butyl 4-(4-carboxythiazol-2-yl)piperidine-1-carboxylate tert-Butyl 4-(4-ethoxycarbonylthiazol-2-yl)piperidine-1-carboxylate (60 mmol; 20.4 g) is dissolved in 225 ml of a mixture of tetrahydrofuran and water (2/1), and 1N sodium hydroxide (2 eq.; 120 mmol; 120 ml) is added dropwise. The reaction medium is stirred at room temperature overnight. The reaction medium is washed with ether and the aqueous phase is then acidified with saturated nitric acid solution. The precipitate is filtered off, washed with water and dried to give 15.5 g of cream-coloured crystals.

TLC: 1/1/1 $CH_2Cl_2$/EtOAc/MeOH: Rf=0.6.

Yield: 83%.

Step c)

tert-Butyl 4-{4-[ethyl(1-methyl-2-oxo-2-phenylethyl)carbamoyl]thiazol-2-yl}-piperidine-1-carboxylate tert-Butyl 4-(4-carboxythiazol-2-yl)piperidine-1-carboxylate (6.5 mmol; 2.03 g) is dissolved in 40 ml of anhydrous dimethylformamide and placed under an inert atmosphere, and 2-(ethylamino)propiophenone hydrochloride (1 eq.; 6.5 mmol; 1.39 g), HBTU (1 eq.; 6.5 mmol; 2.47 g) and N-ethyldiisopropylamine (3.5 eq.; 22.75 mmol; 3.97 ml) are then added. The reaction medium is stirred at room temperature overnight. The reaction medium is evaporated to dryness and then taken up in dichloromethane and washed with saturated potassium carbonate ($K_2CO_3$) solution, citric acid solution and water (twice). The organic phase is dried over sodium sulfate and then evaporated to dryness. The crude product is chromatographed on silica, using a 1/1 ethyl acetate/hexane mixture as eluent (Rf=0.55) to give 2.6 g of expected product in the form of an oil.

Yield: 85%.

Step d)

4-{4-[Ethyl(1-methyl-2-oxo-2-phenylethyl)carbamoyl]thiazol-2-yl}piperidinium chloride tert-Butyl 4-{4-[ethyl(1-methyl-2-oxo-2-phenylethyl)carbamoyl]thiazol-2-yl}-piperidine-1-carboxylate (5.5 mmol; 2.59 g) is dissolved in 13.75 ml of a 4M solution of hydrochloric acid in dioxane. The reaction medium is stirred at room temperature overnight and is then evaporated to dryness to give 2.24 g of a white solid.

Yield=quantitative.

Step e)

2-[1-(6-Methyl-4'-trifluoromethoxybiphenyl-2-carbonyl)piperid-4-yl]thiazol-4-carbonyl[N-ethyl-N-(1-methyl-2-oxo-2-phenylethyl)]amide The title compound was obtained according to a procedure similar to that used for the preparation of tert-butyl 4-{4-[ethyl(1-methyl-2-oxo-2-phenylethyl)carbamoyl]thiazol-2-yl}piperidine-1-carboxylate.

TLC: 1/1 $CH_2Cl_2$/EtOAc: Rf=0.47 LC-MS: (ES+) 650.4 (M+H) Yield: 88%.

Example 2

1-(4-{4-(1-morpholin-4-yl)methanoyl]thiazol-2-yl}piperid-1-yl)-1-(4'-trifluoromethylbiphenyl-2-yl) methanone Step a)

1-{[4'-(trifluoromethyl)-1,1'-biphenyl-2-yl]carbonyl}piperidine-4-carboxamide

4'-(Trifluoromethyl)-2-biphenylcarboxylic acid (20.5 g; 77 mmol) is dissolved in 340 ml of dimethylformamide and 200 ml of dichloromethane. The reaction medium is placed at 0° C. and oxalyl chloride (1.8 eq.; 138.6 mmol; 12 ml) is added. The reaction medium is stirred at room temperature for 3 hours and then evaporated to dryness. The crude product is taken up in 270 ml of dichloromethane, followed by addition of a solution of isonipecotamide (0.97 eq.; 74.7 mmol; 9.57 g) and triethylamine (2.7 eq.; 207.9 mmol; 29 ml) in 270 ml of dichloromethane, placed at 0° C. The mixture is allowed to warm to room temperature over 12 hours, saturated aqueous sodium hydrogen carbonate solution is then added (in a 1/1 proportion) and the resulting mixture is stirred for 30 minutes. The organic phase is washed with 1M sodium hydroxide solution and then with water, dried over sodium sulfate and evaporated to dryness. The crude product is dispersed in diisopropyl ether and then filtered off and dried to give 23.09 g of coupling product.

Yield: 79.6%.

Step b)

1-{[4'-(trifluoromethyl)-1,1'-biphenyl-2-yl]carbonyl}piperidine-4-carbothioamide 1-{[4'-(Trifluoromethyl)-1,1'-biphenyl-2-yl]carboxyl}piperidine-4-carboxamide (11.29 g; 30 mmol) is dissolved in a mixture of Lawesson's reagent (1 eq.; 30 mmol; 12.13 g), dimethyl ether (100 ml) and chloroform (40 ml). The reaction medium is heated at 50° C. for 2 hours 30 minutes and then evaporated to dryness and taken up in ethyl acetate. The organic phase is washed with saturated potassium carbonate solution and then with water, dried over sodium carbonate and evaporated to dryness. The yellow solid is dispersed in diisopropyl ether and then filtered off and dried to give 10.5 g of product.

Yield: 89%.

Step c)

Ethyl 2-{1-{[4'-(trifluoromethyl)-1,1'-biphenyl-2-yl]carbonyl}piperidine-4-yl}-1,3-thiazole-4-carboxylate 1-{[4'-(Trifluoromethyl)-1'-biphenyl-2-yl]carbonyl}piperidine-4-carbothioamide (10.5 g; 26.75 mmol) is dissolved in 100 ml of dimethylformamide and placed at 0° C. 90% [lacuna] bromopyruvate (1 eq.; 26.75 mmol; 3.73 ml) is added, the mixture is left at 0° C. for 30 minutes and is then allowed to warm to room temperature over 12 hours, followed by addition of 10 ml of triethylamine. The reaction medium is evaporated and the crude product is then extracted three times with ethyl acetate. The organic phase is washed with saturated aqueous sodium chloride solution (three times), with water (once) and again with sodium chloride, and is then dried over sodium sulfate and evaporated to dryness. The residue is chromatographed on silica (eluent: 97/3 dichloromethane/methanol) to give 10.33 g of the expected product.

Yield: 79%.

Step d)

2-{1-{4'-(Trifluoromethyl)-1,1'-biphenyl-2-yl]carboxyl}piperid-4-yl}-1,3-thiazole-4-carboxylic acid The title compound was obtained according to a procedure similar to that used for the preparation of tert-butyl 4-(4-carboxythiazol-2-yl)piperidine-1-carboxylate.

Yield: quantitative.

Step e)

1-(4-{4-(1-Morpholin-4-yl)methanoyl]thiazol-2-yl}piperid-1-yl)-1-(4'-trifluoromethyl-biphenyl-2-yl)methanone The title compound was obtained according to a procedure similar to that used for the preparation of tert-butyl 4-{4-[ethyl(1-methyl-2-oxo-2-phenylethyl)carbamoyl]thiazol-2-yl}piperidine-1-carboxylate.

Yield: 87%.

As an additional example, the procedure below shows a synthetic route that can be used for the preparation of an amine of the formula H-a2':

Preparation of
2-ethylamino-1-pyrid-2-ylpropan-1-one in the form of the acid salt with bis-trifluoroacetic acid Step a)

Methyl 2-(2-nitrobenzenesulfonylamino)propionate

DL-Alanine methyl ester hydrochloride (13.96 g; 0.1 mol) is dissolved in 800 ml of dichloromethane and placed at 0° C. Triethylamine (2.3 eq.; 230 mmol; 32 ml) is added dropwise, along with portionwise addition of 2-nitrobenzenesulfonyl chloride (1 eq.; 100 mmol; 22.16 g), and the reaction medium is allowed to return to room temperature overnight. The reaction medium is washed with water and then dried over sodium sulfate, filtered through silica and evaporated to dryness to give 25.3 g of solid corresponding to the title compound.

Yield: 88%.

Step b)

Methyl 2-[ethyl(2-nitrobenzenesulfonyl)amino]propionate

Methyl 2-(2-nitrobenzenesulfonylamino)propionate (17 g; 59 mmol) is dissolved in 600 ml of dimethylformamide, and caesium carbonate (1.5 eq.; 88 mmol; 28.6 g) is then added. The reaction medium is stirred for 30 minutes at room temperature, followed by dropwise addition of ethyl bromide (4 eq.; 236 mmol; 17.6 ml) and the resulting mixture is stirred overnight at room temperature. The reaction medium is evaporated to dryness, taken up in dichloromethane, filtered and evaporated to dryness. The crude product is chromatographed on silica (eluting with dichloromethane) to give 17.1 g of the expected product.

Yield: 92%.

Step c)

Methyl 2-ethylaminopropionate

Methyl 2-[ethyl(2-nitrobenzenesulfonyl)amino]propionate (8.07 g; 25.5 mmol) is dissolved in 250 ml of acetonitrile, and thiophenol (1.12 eq.; 28.7 mmol; 2.93 ml) and $K_2CO_3$ (3.25 eq.; 82.9 mmol; 11.45 g) are then added. The reaction medium is stirred overnight at room temperature. The crude product is evaporated to dryness and then taken up in ether. The organic phase is acidified with 1N hydrochloric acid and then washed with water. The aqueous phases are combined and then washed with ether and basified with potassium carbonate. The basic aqueous phase is extracted with ether three times. The three ether phases are washed with water and then with saturated aqueous sodium chloride solution, dried over sodium sulfate and evaporated to dryness to give 1.04 g of the expected product.

Yield: 31%.

Step d)

Methyl 2-(tert-butoxycarbonylethylamino)propionate

Methyl 2-ethylaminopropionate (0.96 g; 7.3 mmol) is dissolved in 10 ml of dichloromethane, and triethylamine (1 eq.; 7.3 mmol; 1 ml) and Boc-O-Boc (1.1 eq.; 8 mmol; 1.75 g) are added. The reaction medium is stirred for 12 hours at room temperature and then washed with water, dried over sodium sulfate and evaporated to dryness to give 1.28 g of the expected product.

Yield: 76%.

Step e)

2-(tert-Butoxycarbonylethylamino)propionic acid

Methyl 2-(tert-butoxycarbonylethylamino)propionate (1.27 g; 5.5 mmol) is dissolved in 5 ml of methanol, and potassium hydroxide (1.2 eq.; 6.6 mmol; 0.37 g) dissolved in 1.6 ml of water is then added. The reaction medium is left at room temperature for 12 hours and then evaporated to dryness, taken up in water and washed with ether. The aqueous phase is acidified by adding 1N hydrochloric acid and extracted three times with ether. The organic phases are combined, dried over sodium sulfate and evaporated to dryness to give 0.88 g of a white solid.

Yield: 74%.

Step e bis): Alternative Route:

DL-2-Bromopropionic acid (76.5 g; 0.5 mol) is dissolved in 250 ml of water and 70% ethylamine (4.7 eq.; 2.3 mol; 150 g) is added dropwise. The reaction medium is stirred at room temperature for 12 hours and then evaporated to dryness and taken up in 400 ml of water comprising 40 g of sodium hydroxide (1.0 mol). The reaction medium is again evaporated to dryness.

The crude product is dissolved in 500 ml of water and 250 ml of dioxane. The reaction medium is placed at 0° C. and di(tert-butyl) carbonate (1.1 eq.; 0.55 mol; 120 g) dissolved in 200 ml of dioxane is added dropwise. The pH is maintained at 10 by adding sodium hydroxide. The reaction medium is stirred at room temperature for 24 hours and then filtered. The filtrate is concentrated and then taken up in 700 ml of water and acidified to pH 2-3 with citric acid. The precipitate is filtered off and dried (108.6 g).

Yield: 62%.

Step f)

Dimethyl ethyl ethyl[1-(methoxymethylcarbamoyl)ethyl]carbamate 2-(tert-Butoxycarbonylethylamino)propionic acid (40 mmol; 873 mg) is dissolved in 5 ml of dimethylformamide, and N,O-dimethylhydroxylamine hydrochloride (1.25 eq.; 5.0 mmol; 490 mg), HOBT (1.25 eq.; 5.0 mmol; 676 mg), triethylamine (1.25 eq.; 5.0 mmol; 0.7 ml) and EDC (1.25 eq.; 5.0 mmol; 960 mg) are added. The reaction medium is stirred for 12 hours and then evaporated to dryness. The crude product is extracted with ether, washed successively, twice with aqueous 4% citric acid solution, twice with aqueous 4% sodium hydrogen sulfite solution, with water and then with saturated sodium chloride solution. The organic phase is dried over sodium sulfate, evaporated to dryness and chromatographed on silica (eluent: 1/2 ethyl acetate/hexane; Rf=0.45) to give 795 mg of a colourless product.

Yield: 76%.

Step g)

tert-Butyl ethyl(1-methyl-2-oxo-2-pyrid-2-ylethyl)carbamate

2-Bromopyridine (7.0 mmol; 667 μL) is dissolved in 40 ml of anhydrous tetrahydrofuran and placed at −100° C., followed by dropwise addition of a 1.6M solution of n-butyllithium in hexane (1 eq.; 7.0 mmol; 4.375 ml). The reaction medium is stirred for 30 minutes and dimethyl ethyl ethyl[1-(methoxymethylcarbamoyl)ethyl]carbamate (1 eq.; 7.0 mmol; 1.822 g) dissolved in 20 ml of anhydrous tetrahydrofuran is added dropwise. The reaction medium is stirred at −100° C. for 1 hour 30 minutes. The reaction medium is then removed from the ice bath, 200 ml of saturated aqueous sodium chloride solution are added and the mixture is then extracted with ether. The organic phase is dried over sodium sulfate, evaporated to dryness and chromatographed on silica (eluent: 1/2 ethyl acetate/heptane; Rf=0.23) to give 1.04 g of the expected product.

Yield: 53%.

Step h)

2-Ethylamino-1-pyrid-2-ylpropan-1-one-acid salt with bis-trifluoroacetic acid tert-Butyl ethyl(1-methyl-2-oxo-2-pyrid-2-ylethyl)carbamate (1.03 g; 3.7 mmol) is dissolved in 30 ml of a 1/1 dichloromethane/trifluoroacetic acid mixture. The reaction medium is stirred for one hour at room temperature and then evaporated to dryness to give 1.5 g of the expected salt.

Yield: quantitative.

The compounds of the general formula (I) presented in the table below were prepared according to procedures similar to those described above.

Other examples of compounds included in the scope of the present invention are presented in Table 1 below. All these compounds are obtained according to procedures similar to those presented above.

TABLE 1

| No. | FORMULA | NMR or mass |
|---|---|---|
| 1 | | (CDCl3): 1.27-1.22 (19H, m); 1.25-1.23 (1H, m); 1.27-1.24 (1H, m); 1.25-1.27 (13H, m). |
| 2 | | (CDCl3): 1.29-1.24 (16H, m); 1.29-1.24 (1H, m); 1.29-1.26 (9H, m). |

TABLE 1-continued
| No. | FORMULA | NMR or mass |
|---|---|---|
| 2d | 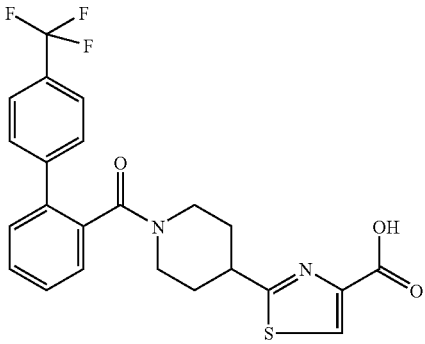 | (DMSO-d6): 1.23-1.29 (8H, m); 1.23-1.28 (1H, m); 1.21-1.20 (8H, m); 1.28-1.20 (1H, m); 11.29 (1H, s large). |
| 3 | 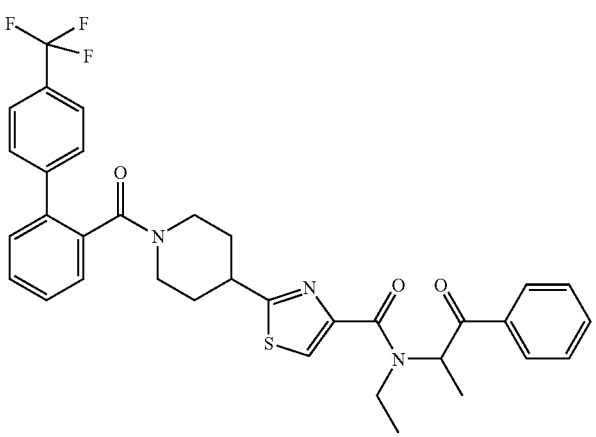 | (CDCl3): 1.29-,129 (3H, m); 1.29-1.25 (3H, m); 1.29-1.27 (7H, m); 1.21-1.22 (4H, m); 1.28-1.27 (1H, m); 1.20-1.25 (14H, m). |
| 4 | 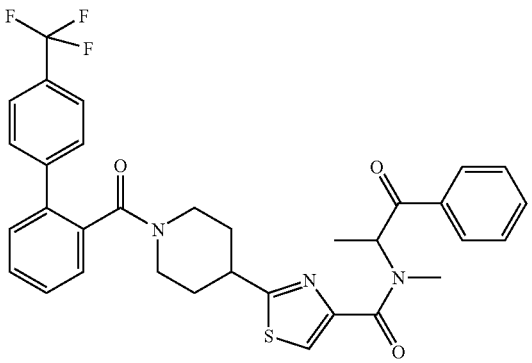 | (CDCl3): 1.20-1.25 (3H, d, J = 1.2 Hz); 1.27-1.28 (12H, m); 1.27-1.29 1.28-1.20 (14H, m). |
| 5 | 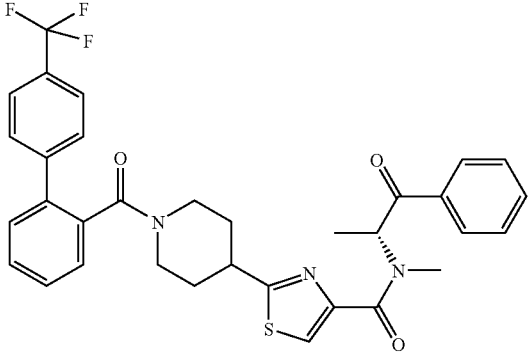 | (CDCl3) 1.23-1.24 (3H, d, J = 1.2 Hz); 1.26-1.20 (1H, m); 1.21-1.20 (1H, m); (1H, m); 1.29-1.20 (14H, m). |

TABLE 1-continued
| No. | FORMULA | NMR or mass |
|---|---|---|
| 6 | 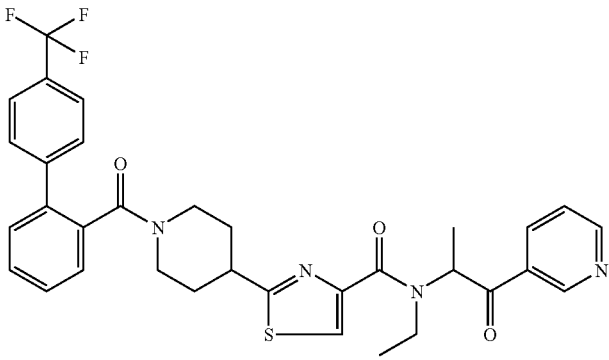 | (CDCl3): 1.23-1.24 (16H, m); 1.28-1.22 (1H, m); 1.21-1.24 (1H, m); 1.21-1.28 (13H, m). |
| 7 | 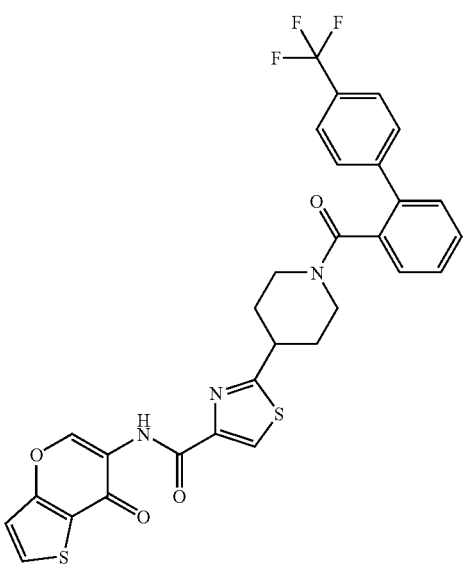<br>N-(7-oxo-7H-thieno[3,2-b]pyran-6-yl)-2-(1-{[4'-(trifluoromethyl)biphenyl-2-yl]-carbonyl}piperidin-4-yl)-1,3-thiazole-4-carboxamide | LC-MS: (ES+) 701.2 (M + H) |
| 8 | 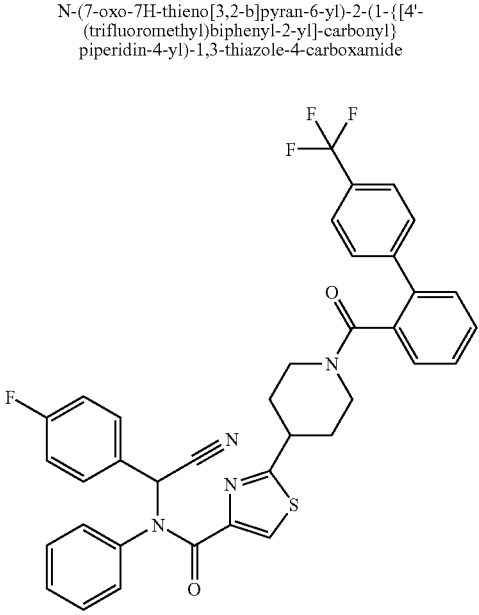 | LC-MS: (ES+) 661.2 (M + H) |

TABLE 1-continued
| No. | FORMULA | NMR or mass |
|---|---|---|
| 9 | 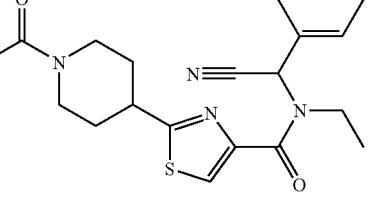 | |
| 10 |  | |
| 11 |  | |
| 12 |  | LC-MS: (ES+) 651.2 (M + H) |

TABLE 1-continued
| No. | FORMULA | NMR or mass |
|---|---|---|
| 13 | 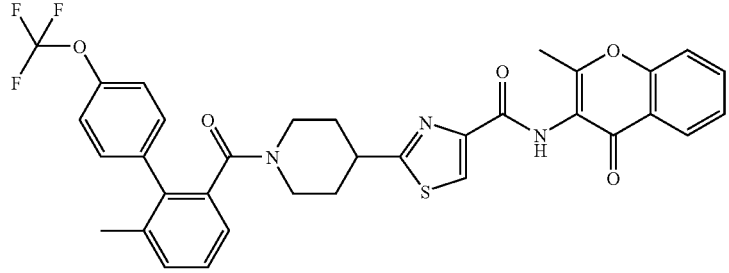 | (CDCl3): 1.25-1.21 (14H, m); 1.27-1.25 (1H, m); 1.29-1.24 (1H, m); 1.20-1.21 (9H, m); 1.23-1.25 (2H, m); 1.20-1.29 (1H, m). |
| 14 | 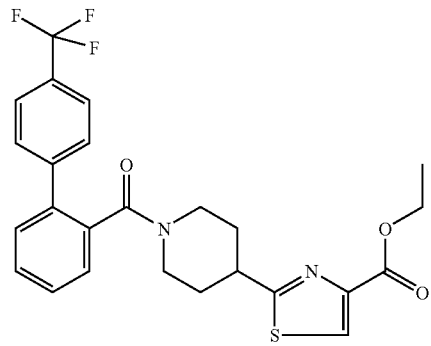 | (DMSO-d6): 1.27 (3H, t, J = 1.2 Hz); 1.21-1.22 (4H, m); 1.22-1.27 (4H, m); 1.26 (4H, q, J = 1.2 Hz); 1.26-1.26 (1H, m); 1.20-1.28 (8H, m); 1.29 (1H, s). |
| 15 | 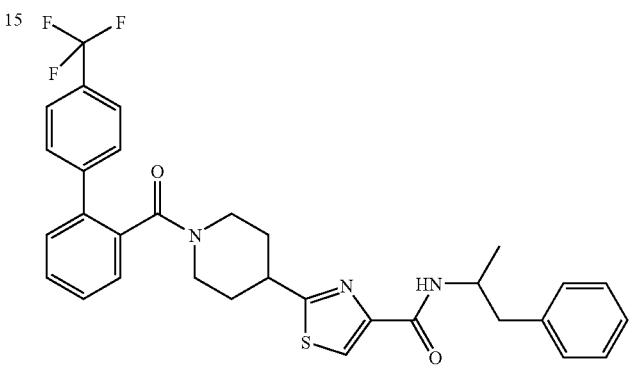 | (CDCl3): 1.28 (3H, d, J = 1.2 Hz); 1.26-1.24 (4H, m); 1.21-1.23 (5H, m); 1.25-1.28 (1H, m); 1.28-1.29 (1H, m); 1.23-1.27 (1H, m); 1.29-1.26 (14H, m); 1.22 (1H, s). |
| 16 | 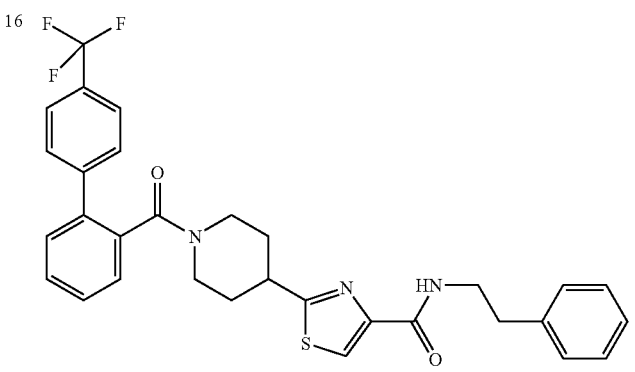 | (CDCl3): 1.27-1.24 (2H, m); 1.20-1.27 (6H, m); (4H, m); 1.20-1.23 1.27-1.26 (7H, m); 1.26-1.26 (7H, m); 1.27-1.28 (1H, m). |

TABLE 1-continued
| No. | FORMULA | NMR or mass |
|---|---|---|
| 17 | 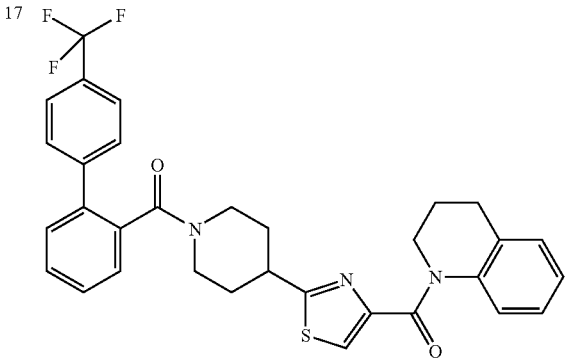 | (CDCl3): 1.26-1.26 (2H, m); 1.22-1.28 (4H, m); 1.22-1.28 (8H, m); 1.29-1.24 (1H, m); 1.20-1.23 (5H, m); 1.21-1.23 (8H, m). |
| 18 | 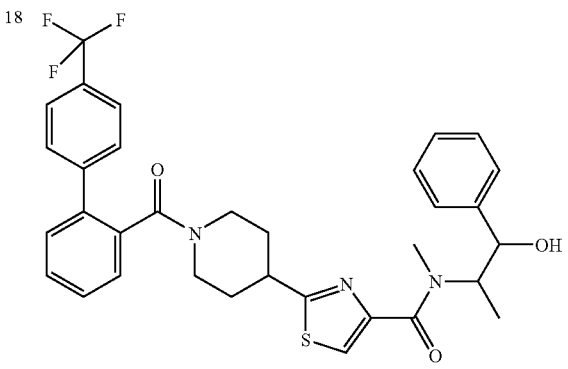 | (CDCl3): 1.21 (3H,s); 1.23(3H,s); 1.24-1.24 (7H, m); 1.25-1.26 (1H, m) 1.26-1.28 (3H, m); 1.23-1.21 (14H, m) |
| 19 | 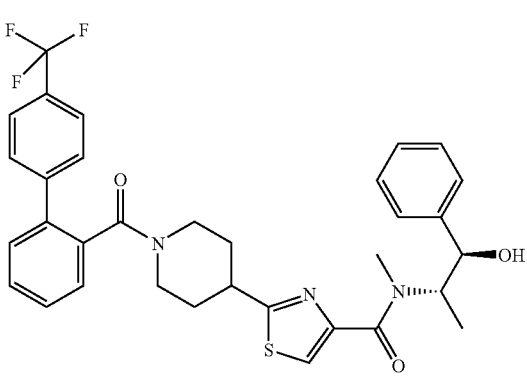 | (CDCl3); 1.25-1.20 (3H, m); 1.23-1.22 (1OH, m); 1.23-1.21 (1H, m); 1.26-1.23 (1H, m); 1.23-1.26 1.28-1.26 (14H, m). |
| 20 | 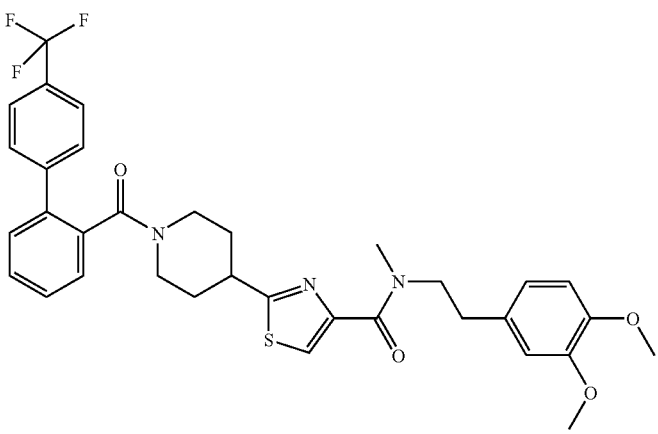 | (CDCl3): 1.20-1.28 (12H, m); 1.28-1.25 (1H, m); 1.20-1.27 (8H, m); 1.27-1.24 (1H, m); 1.29-1.26 (3H, m); 1.21-1.25 (9H, m). |

TABLE 1-continued

| No. | FORMULA | NMR or mass |
|---|---|---|
| 21 | (structure) | (CDCl3); 1.27-1.27 (4H, m); 1.21-1.21 (6H, m); 1.23-1.22 (3H, m); 1.21-1.27 (2H, m); 1.24-1.26 (5H, m); 1.29-1.28 (5H, m); 1.22-1.26 (8H, m); 1.29-1.22 1H, m). |
| 22 | (structure) | (CDCl3): 1.24-1.21 (4H, m); 1.20-1.24 (6H, m); 1.29-1.26 (3H, m); 1.29-1.24 (1H, m); 1.24-1.20 (1H, m); 1.24-1.28 1.20-1.26 (2H, m); 1.22-1.25 (9H, m); 1.21-1.20 (1H, m). |
| 23 | (structure) | (CDCl3): 1.27-1.28 (4H, m); 1.29-1.26 (2H, m); 1.26 (3H, s); 1.24-1.26(4H, m); 1.28-1.22 (2H, m); 1.21-1.28 (3H, m); 1.26-1.29 (14H, m). |
| 24 | (structure) | (CDCl3): 1.26-1.28 (7H, m); 1.22-1.25 (10H, m); 1.21-1.25 (3H, m); 1.21-1.24 (7H, m); 1.25-1.25 (7H, m). |

TABLE 1-continued
| No. | FORMULA | NMR or mass |
|---|---|---|
| 25 | 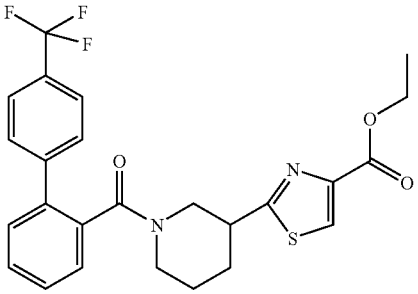 | (DMSO-d6): 1.28-1.27 (3H, m); 1.20-1.24 (8H, m); (3H, m); 1.27-1.26 (8H, m); 1.24-1.22 (1H, m). |
| 26 | 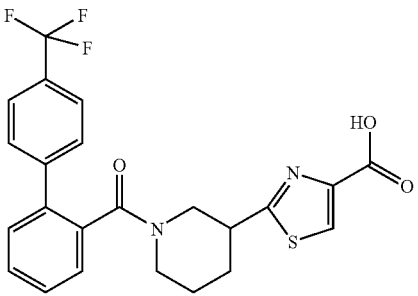 | (DMSO-d6): 1.24-1.22 (4H, m); 1.24-1.22 (4H, m); 1.29-1.20 (1H, m); 1.29-1.24 (8H, m); 1.23-1.22 (1H, m); 11.27 (1H, s large). |
| 27 | 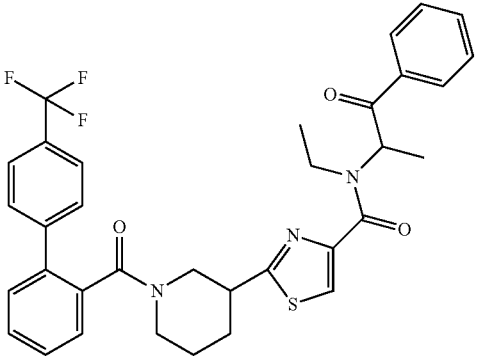 | (DMSO-d6): 1.24-1.25 (6H, m); 1.23-1.25 (10H, m); 1.20-1.24 (1H, m); 1.28-1.26 (1H, m); 1.23-1.27 (14H, m). |
| 28 | 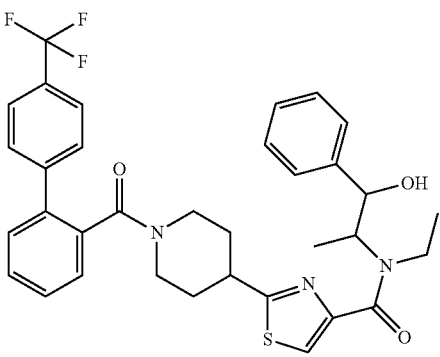 | (CDCl3): 1.29-1.23 (6H, m); 1.27-1.21 (10H, m); 1.23-1.28 (3H, m); 1.24-1.24 (1H, m large); 1.22-1.22 (14H, m). |

TABLE 1-continued
| No. | FORMULA | NMR or mass |
|---|---|---|
| 29 | 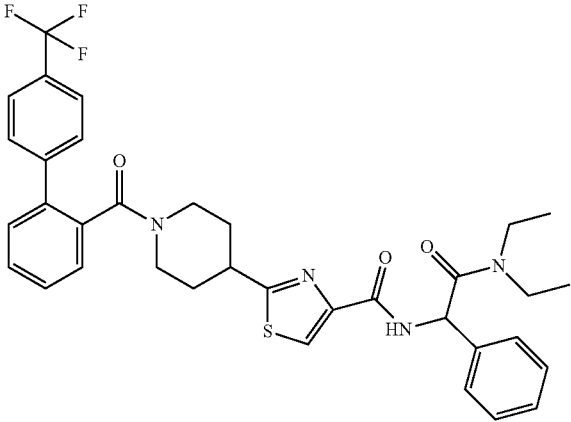 N-[2-(diethylamino)-2-oxo-1-phenylethyl]-2-(1-{[4'-(trifluoromethyl)-biphenyl-2-yl]carbonyl}piperidin-4-yl)-1,3-thiazole-4-carboxamide | (DMSO-d6): 1.22-1.26 (18H, m); 1.23-128 (1H, m); 1.20-1.22 (1H, m); (15H, m). |
| 30 | 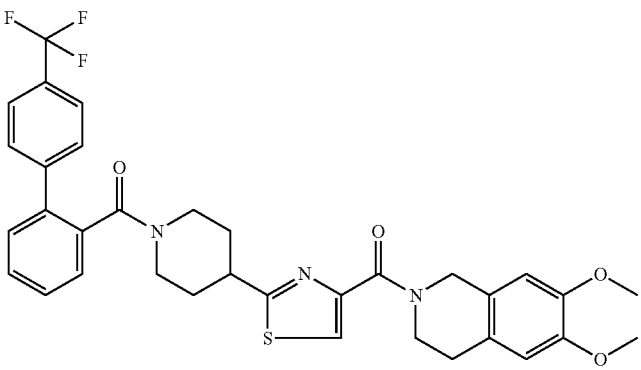 | (CDCl3): 1.20-1.21 (8H, m); 1.26-1.27 (1H, m); 1.28-1.27 (1H, m); 1.27-1.27 (8H, m); 1.20-1.25 (3H, m); 1.22 (1H, s); 1.24-1.29 (10H, m). |
| 31 | 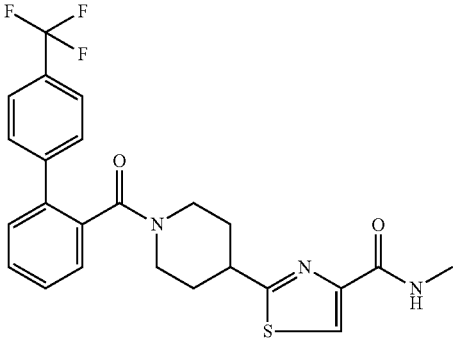 | (CDCl3): 1.22-1.25 (3H, m); 1.27-1.27 (7H, m); 1.24-1.20 (1H, m); 1.28-1.21 (1H, m); 1.25-1.22 (9H, m); 1.22-1.28 (1H, m). |
| 32 | 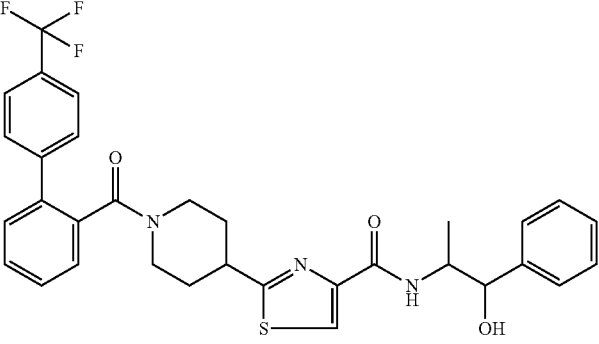 | (CDCl3): 1.21-1.26 (3H, m); 1.23-1.27 (6H, m); 1.26-1.24 (2H, m); 1.29-1.21 (1H, m); 1.22-1.24 (1H, m); 1.26-1.22 (1H, m); 1.24-1.20 (15H, m); 1.28-1.21 (1H, m). |

TABLE 1-continued
| No. | FORMULA | NMR or mass |
|---|---|---|
| 33 | 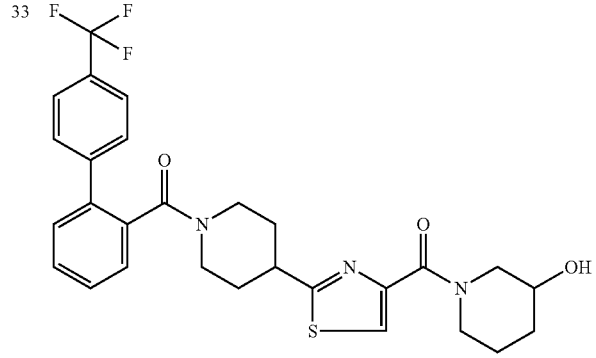 | (CDCl3): 1.23-1.25 (9H, m); 1.29-1.29 (4H, m); 1.29-1.24 (2H, m); (3H, m); 1.23-1.27 (10H, m). |
| 34 | 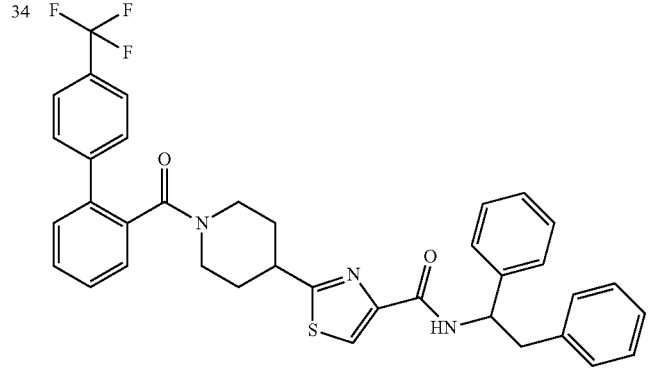 | (CDCl3): 1.24-1.28 (7H, m); 1.20-1.29 (3H, m); 1.26-1.22 (1H, m); 1.26-1.25 (1H, m); 1.29-1.26 (20H, m). |
| 35 | 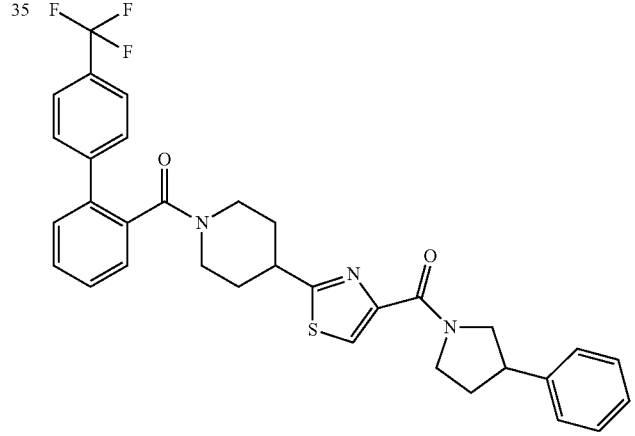 | (CDCl3): 1.29-1.24 (8H, m); 1.25-1.23 (7H, m); 1.26-1.25 (1H, m); 1.27-1.27 (13H, m); 1.28-1.22 (1H, m). |

TABLE 1-continued
| No. | FORMULA | NMR or mass |
|---|---|---|
| 36 | 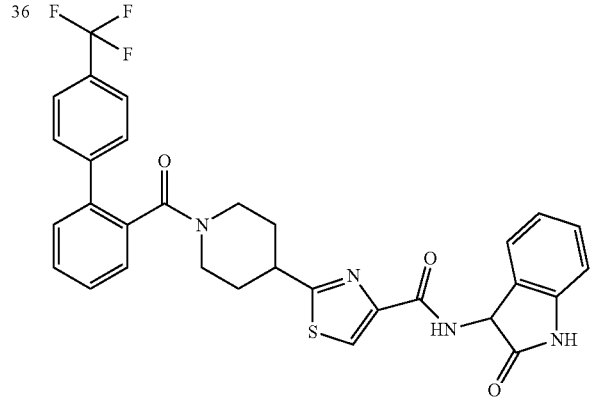<br>N-(2-oxo-2,3-dihydro-1H-indol-3-yl)-2-(1-{[4'-(trifluoromethyl)biphenyl-2-yl]carbonyl}piperidin-4-yl)-1,3-thiazole-4-carboxamide | (CDCl3): 1.22-1.29 (7H, m); 1.29-1.26 (2H, m); 1.26-1.21 (1H, m); 1.28-1.25 (15H, m). |
| 37 | 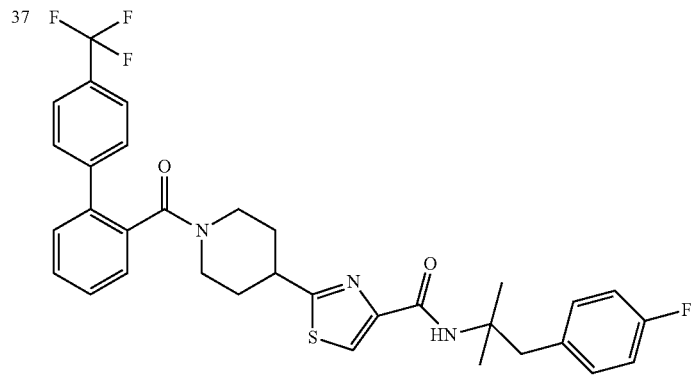<br>N-[2-(4-fluorophenyl)-1,1-dimethylethyl]-2-(1-{[4'-(trifluoromethyl)biphenyl-2-yl]carbonyl}piperidin-4-yl)-1,3-thiazole-4-carboxamide | (CDCl3): 1.21 (6H, s); 1.20-1.23 (7H, m); 1.26-1.20 (2H, m); 1.22-1.23 (1H, m); 1.22-1.20 (1H, m); 1.26-1.24 (13H, m); 1.23 (1H, s). |
| 38 | 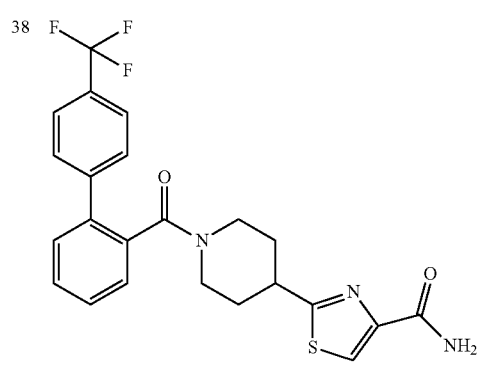 | (CDCl3): 1.21-1.23 (7H, m); 1.26-1.28 (1H, m); 1.20-1.28 (1H, m); 1.22 (1H, s large); 1.29 (1H, s large); 1.23-1.27 (8H, m); 1.26-1.22 (1H, m). |

TABLE 1-continued
| No. | FORMULA | NMR or mass |
|---|---|---|
| 39 | 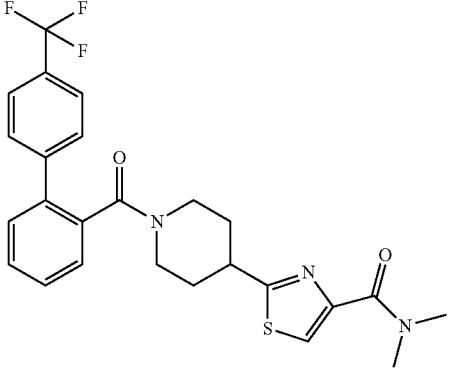 | (CDCl3): 1.24-1.24 (6H, m); 1.24-1.24 (7H, m); 1.24-1.23 (1H, m); 1.28-1.25 (1H, m); 1.21-1.25 (9H, m). |
| 40 | 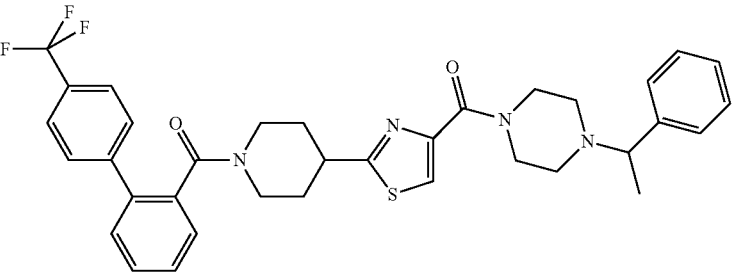<br>1-(1-phenylethyl)-4-{[2-(1-{[4'-(trifluoromethyl)biphenyl-2-yl]carbonyl}-piperidin-4-yl)-1,3-thiazol-4-yl]carbonyl}piperazine | (CDCl3): 1.27-1.24 (3H, m); 1.26-1.21 (11H, m); 1.28-1.23 (2H, m); 1.23-1.27 (4H, m); 1.20-1.24 (1H, m); 1.24-1.26 (14H, m). |
| 41 | 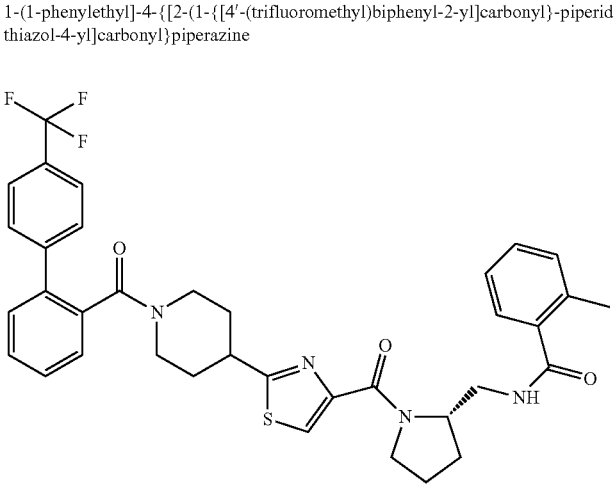 | (CDCl3): 1.23-1.22 (17H, m); 1.29-1.27 (2H, m); 1.22-1.29 1.22-1.21 (2H, m); 1.23-1.20 (12H, m). |
| 42 | 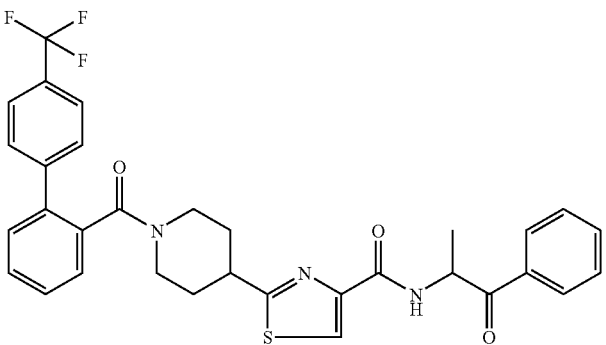 | (CDCl3): 1.25-1.26 (7H, m); 1.26-1.22 (5H, m); 1.25-1.26 (1H, m); 1.23-1.20 (13H, m); 1.28-1.22 (2H, m). |

TABLE 1-continued
| No. | FORMULA | NMR or mass |
|---|---|---|
| 43 | 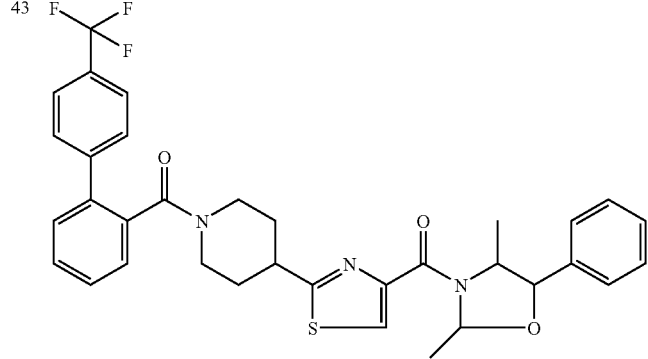 | (CDCl3): 1.28-1.27 (14H, m); 1.29-1.21 (4H, m); 1.22-1.24 (14H, m). |
| 44 | 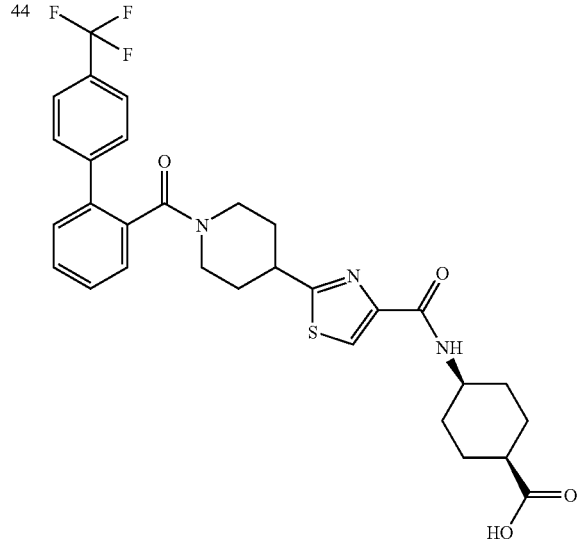 | |
| 45 | 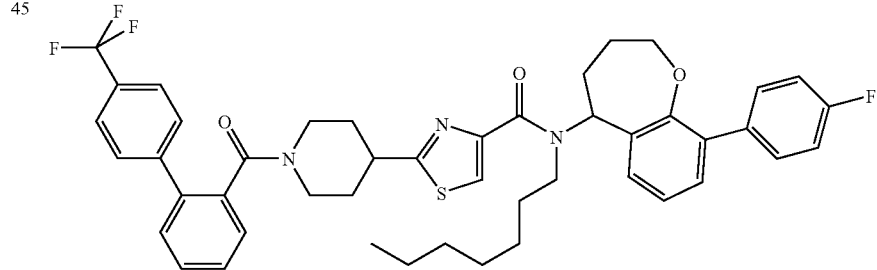 | |

TABLE 1-continued
| No. | FORMULA | NMR or mass |
|---|---|---|
| 46 | 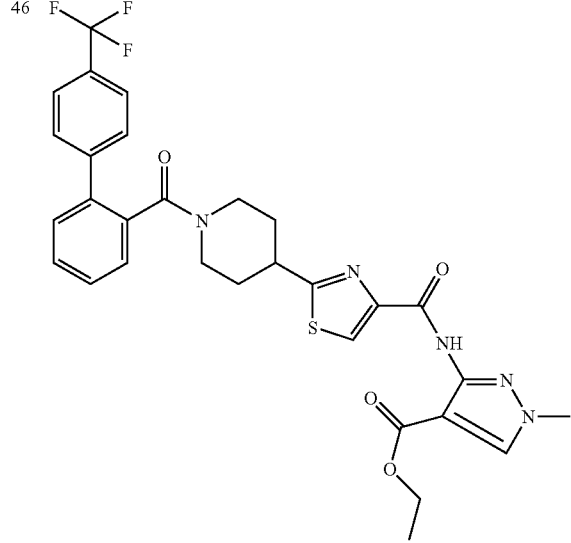 | |
| 47 | 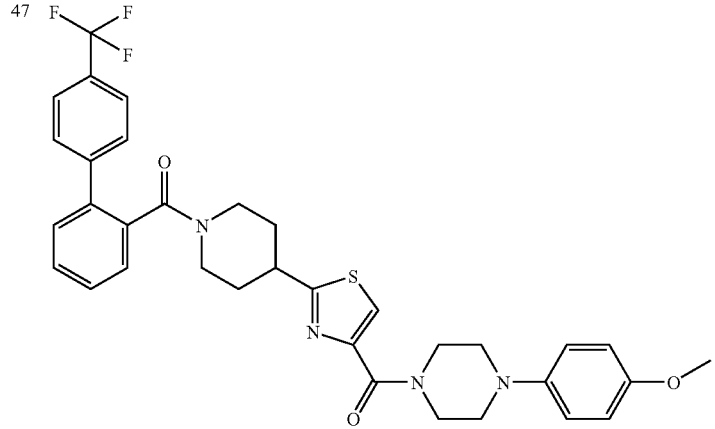 1-(4-methoxyphenyl)-4-{[2-(1-{[4'-(trifluoromethyl)biphenyl-2-yl]carbonyl}-piperidin-4-yl)-1,3-thiazol-4-yl]carbonyl}piperazine | |
| 48 | 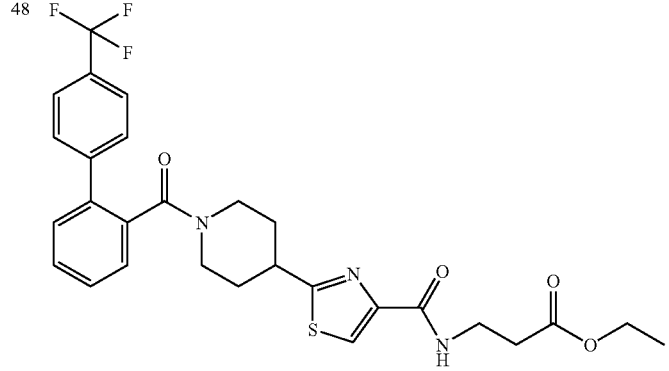 | |

TABLE 1-continued
| No. | FORMULA | NMR or mass |
|---|---|---|
49
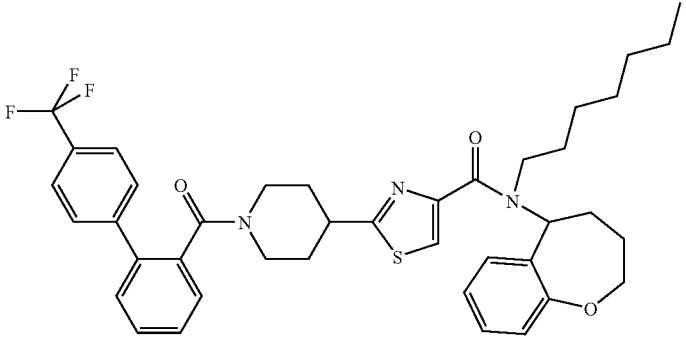
N-heptyl-N-(2,3,4,5-tetrahydro-1-benzoxepin-5-yl)-2-(1-{[4'-(trifluromethyl)-biphenyl-2-yl]-carbonyl}piperidin-4-yl)-1,3-thiazole-4-carboxamide
50
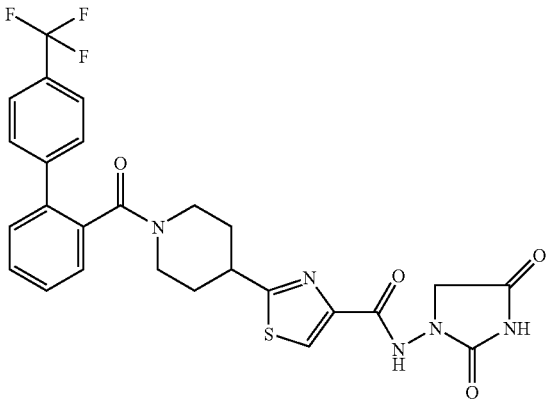
N-(2,4-dioxoimidazolidin-1-yl)-2-(1-{[4'-(trifluoromethyl)biphenyl-2-yl]-carbonyl}piperidin-4-yl)-1,3-thiazole-4-carboxamide
51
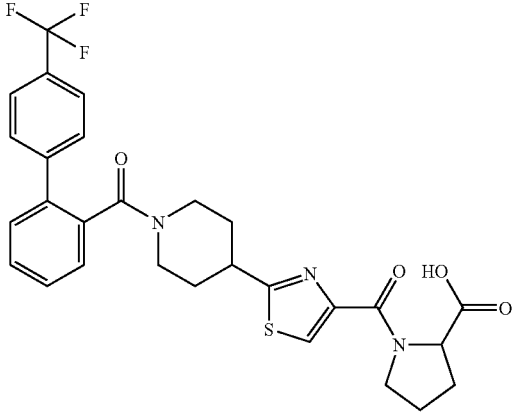
1-{[2-(1-{[4'-(trifluoromethyl)biphenyl-2-yl]carbonyl}piperidin-4-yl)-1,3-thiazol-4-yl]carbonyl}proline

| No. | FORMULA | NMR or mass |
|---|---|---|
| 52 | 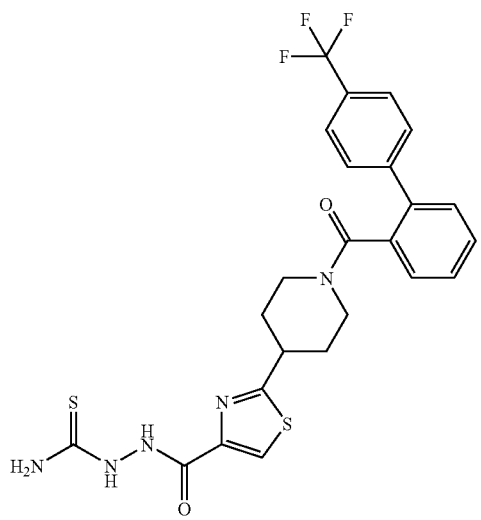 2-{[2-(1-{[4'-(trifluoromethyl)biphenyl-2-yl]carbonyl}piperidin-4-yl)-1,3-thiazol-4-yl]carbonyl}hydrazinecarbothioamide | |
| 53 | 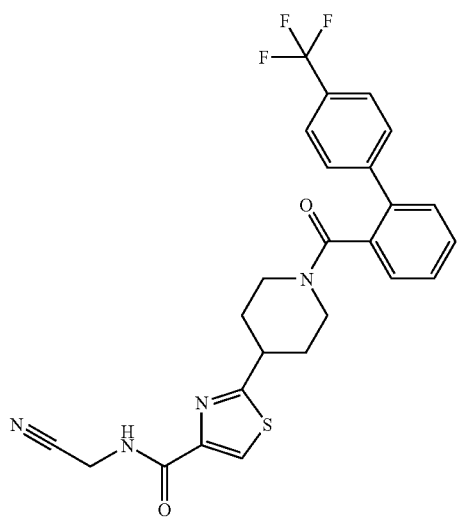 N-(cyanomethyl)-2-{[4'-(trifluoromethyl)biphenyl-2-yl]carbonyl}piperidin-4-yl)-1,3-thiazole-4-carboxamide | |

TABLE 1-continued
| No. | FORMULA | NMR or mass |
|---|---|---|
| 54 | 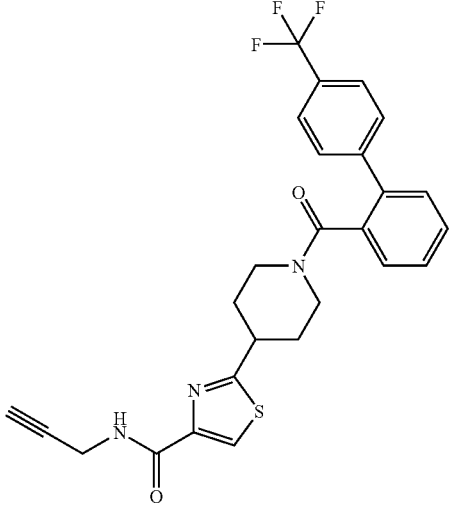 N-prop-2-yn-1-yl-2-(1-{[4'-(trifluoromethyl)biphenyl-2-yl]carbonyl}-piperidin-4-yl)-1,3-thiazole-4-carboxamide | |
| 55 | 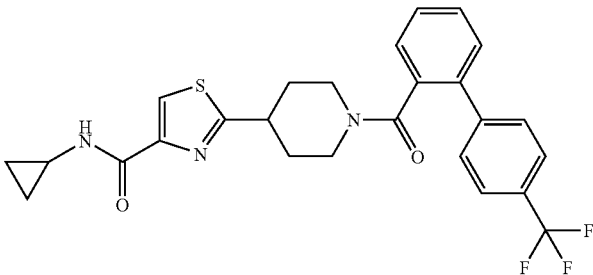 | |
| 56 | 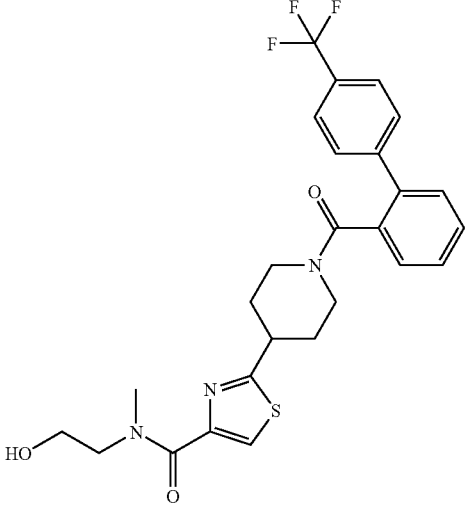 N-(2-hydroxyethyl)-N-methyl-2-(1-{[4'-(trifluoromethyl)biphenyl-2-yl]-carbonyl}piperidin-4-yl)-1,3-thiazole-4-carboxamide | |

| No. | FORMULA | NMR or mass |
|---|---|---|

57

N-pyrimidin-2-yl-2-(1-{[4'-(trifluoromethyl)blphenyl-2-yl]carbonyl}-piperidin-4-yl)-1,3-thiazole-4-carboxamide

58

4-{4-[(5-methyl-1H-pyrazol-1-yl)carbonyl]-1,3-thiazol-2-yl}-1-{[4'-(trifluromethyl)biphenyl-2-yl]carbonyl}piperidine TABLE 1-continued
| No. | FORMULA | NMR or mass |
|---|---|---|
| 59 | 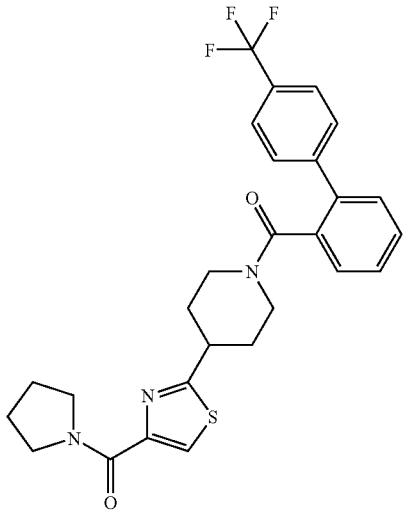 4-[4-(pyrrolidin-1-ylcarbonyl)-1,3-thiazol-2-yl]-1-{[4'-(trifluoromethyl)-biphenyl-2-yl]carbonyl}piperidine | |
| 60 | 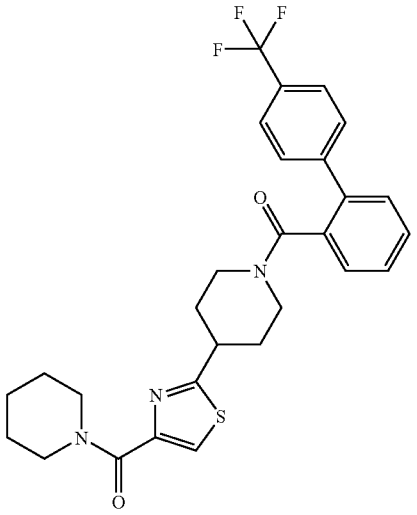 4-[4-(piperidin-1-ylcarbonyl)-1,3-thiazol-2-yl]-1-{[4'-(trifluromethyl)-biphenyl-2-yl]carbonyl)piperidine | |

TABLE 1-continued
| No. | FORMULA | NMR or mass |
|---|---|---|
| 61 | 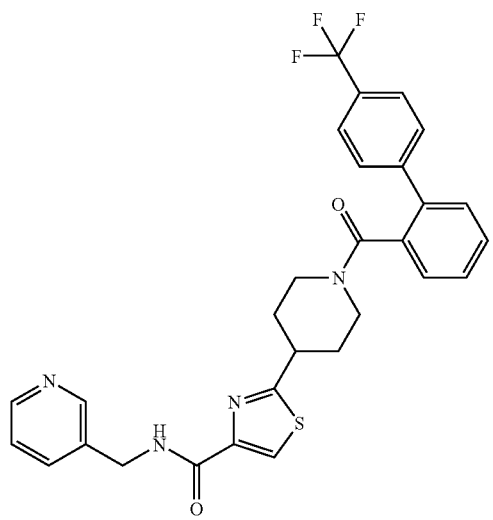 N-(pyridin-3-ylmethyl)-2-(1-{[4'-(trifluoromethyl)biphenyl-2-yl]carbonyl}-piperidin-4-yl)-1,3-thiazole-4-carboxamide | |
| 62 | 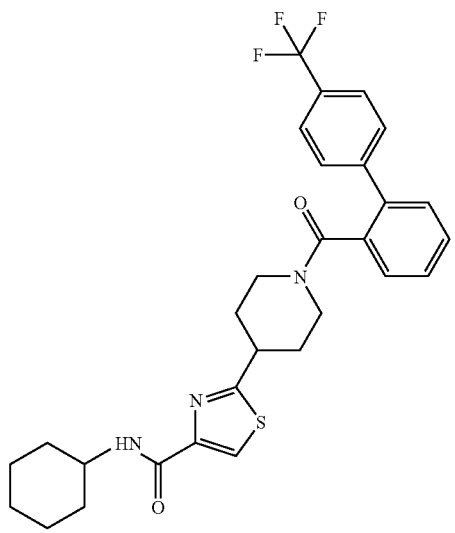 N-cyclohexyl-2-(1-{[4'-(trifluoromethyl)biphenyl-2-yl]carbonyl}piperidin-4-yl)-1,3-thiazole-4-carboxamide | |

TABLE 1-continued
| No. | FORMULA | NMR or mass |
|---|---|---|
| 63 | 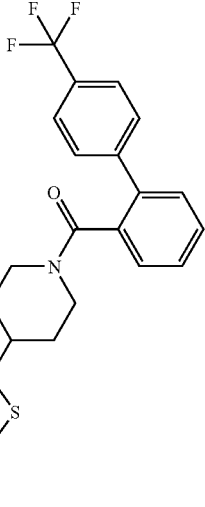 N-benzyl-2-(1-{[4'-(trifluoromethyl)biphenyl-2-yl]carbonyl}piperidin-4-yl)-1,3-thiazole-4-carboxamide | |
| 64 | 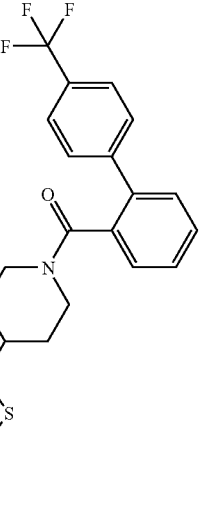 ethyl 4-{[2-(1-{[4'-(trifluoromethyl)biphenyl-2-yl]carbonyl}piperidin-4-yl)-1,3-thiazol-4-yl]carbonyl}piperazine-1-carboxylate | |
| 65 | 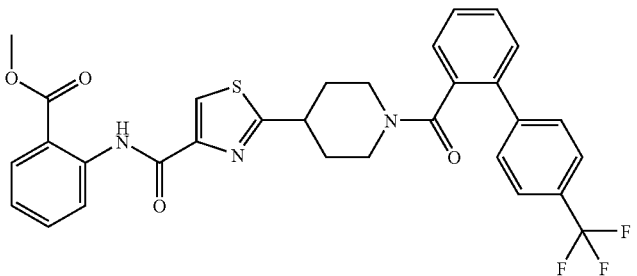 | |

TABLE 1-continued
| No. | FORMULA | NMR or mass |
|---|---|---|
| 66 | 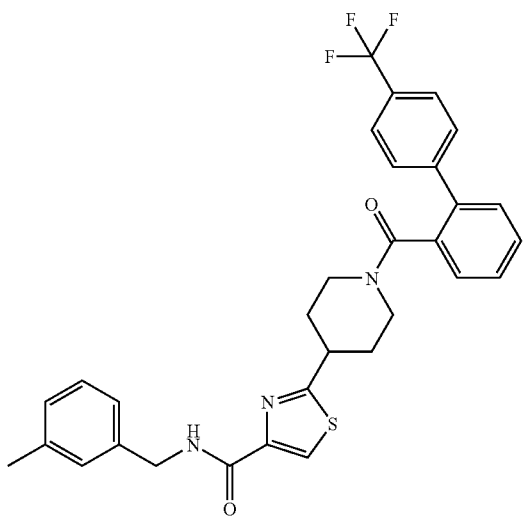 N-(3-methylbenzyl)-2-(1-{[4'-(trifluoromethyl)biphenyl-2-yl]carbonyl}-piperidin-4-yl)-1,3-thiazole-4-carboxamide | |
| 67 | 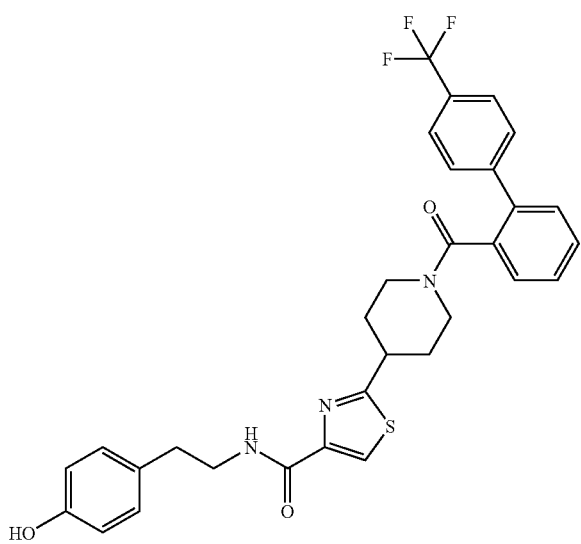 N-[2-(4-hydroxyphrnyl)ethyl]-2-(1-{[4'-(trifluoromethyl)biphenyl-2-yl]-carbonyl}piperidin-4-yl)-1,3-thiazole-4-carboxamide | |

| No. | FORMULA | NMR or mass |
|---|---|---|
| 68 | 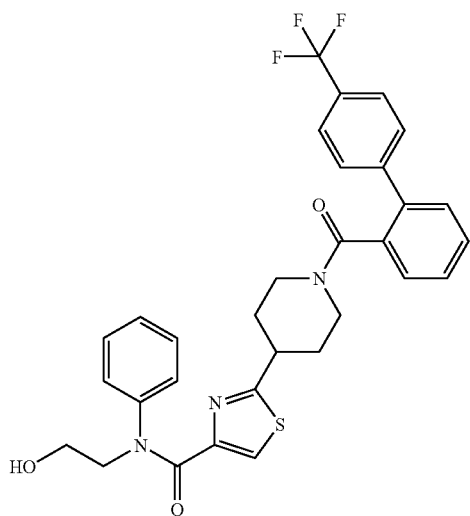 N-(2-hydroxyethyl)-N-phenyl-2-(1-{[4'-(trifluoromethyl)biphenyl-2-yl]-carbonyl}piperidin-4-yl)-1,3-thiazole-4-carboxamide | |
| 69 | 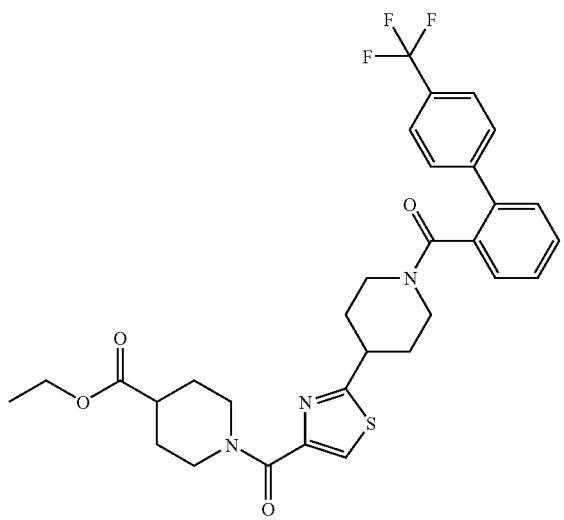 ethyl 1-{[2-(1-{[4'-(trifluoromethyl)biphenyl-2-yl]carbonyl}piperidin-4-yl)-1,3-thiazol-4-yl]carbonyl}piperidine-4-carboxylate | |

| No. | FORMULA | NMR or mass |
|---|---|---|
| 70 | 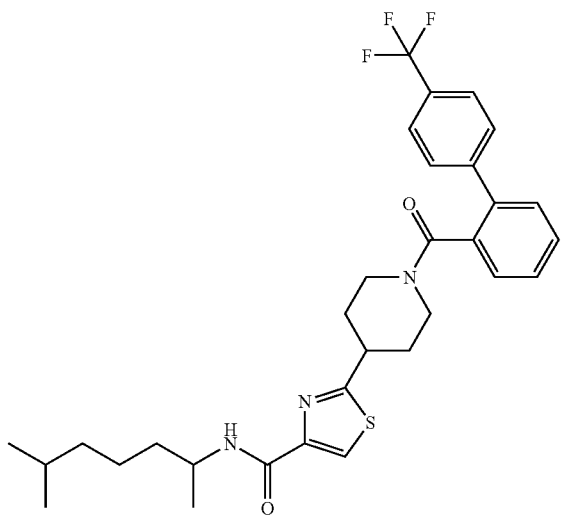 N-(1,5-dimethylhexyl)-2-(1-{[4'-(trifluoromethyl)biphenyl-2-yl]carbonyl}-piperidin-4-yl)-1,3-thiazole-4-carboxamide | |
| 71 | 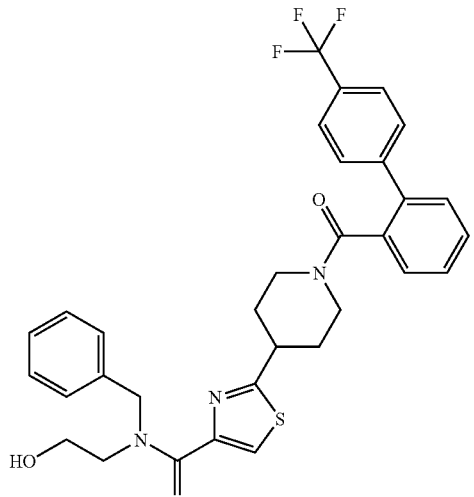 N-benzyl-N-(2-hydroxyethyl)-2-(1-{[4'-(trifluoromethyl)biphenyl-2-yl]-carbonyl}piperidin-4-yl)-1,3-thiazole-4-carboxamide | |

TABLE 1-continued
| No. | FORMULA | NMR or mass |
|---|---|---|
| 72 | 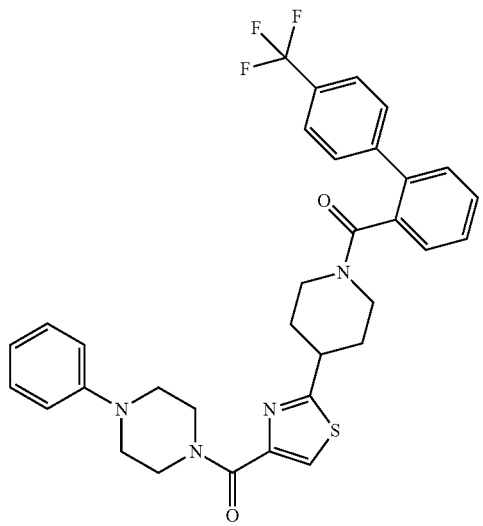 1-phenyl-4-{[2-(1-{[4'-(trifluoromethyl)biphenyl-2-yl]carbonyl}piperidin-4-yl)-1,3-thiazol-4-yl]carbonyl}piperazine | |
| 73 | 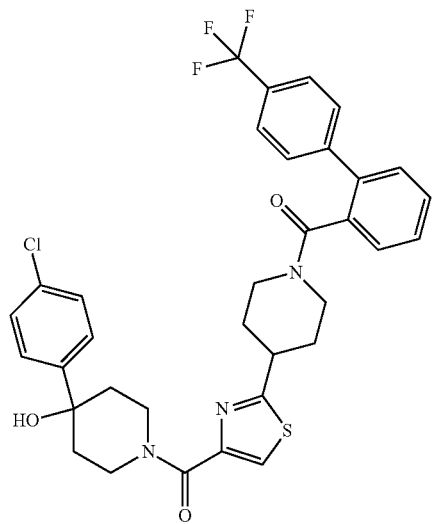 4-(4-chlorophenyl)-1-{[2-(1-{[4'-(trifluoromethyl)biphenyl-2-yl]carbonyl}-piperidin-4-yl)-1,3-thiazol-4-yl]carbonyl}piperidin-4-ol | |

| No. | FORMULA | NMR or mass |
|---|---|---|
| 74 | 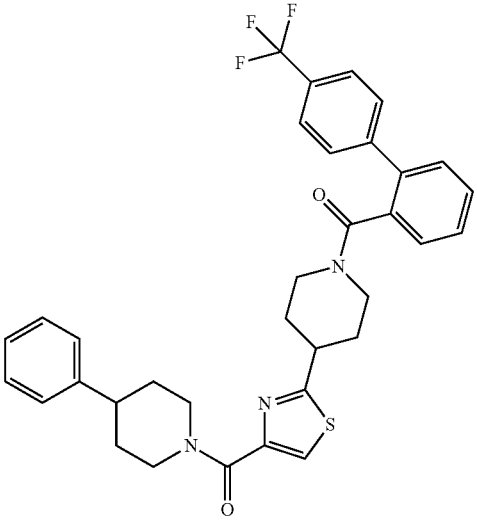<br>4-phenyl-1-{[2-(1-{[4'-(trifluoromethyl)biphenyl-2-yl]carbonyl}piperidin-4-yl)-1,3-thiazol-4-yl]carbonyl}piperidine | |
| 75 | 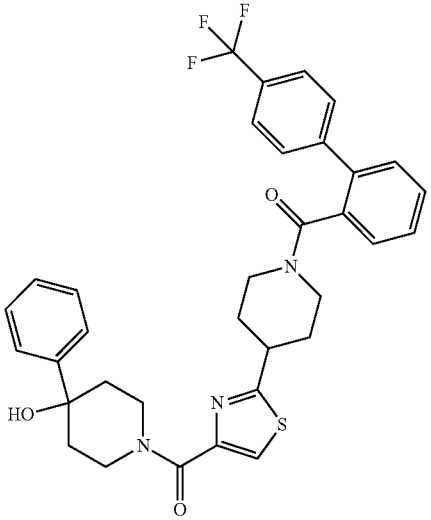<br>4-phenyl-1-{[2-(1-{[4'-(trifluoromethyl)biphenyl-2-yl]carbonyl}piperidin-4-yl)-1,3-thiazol-4-yl]carbonyl}piperidin-4-ol | |

| No. | FORMULA | NMR or mass |
|---|---|---|
| 76 | 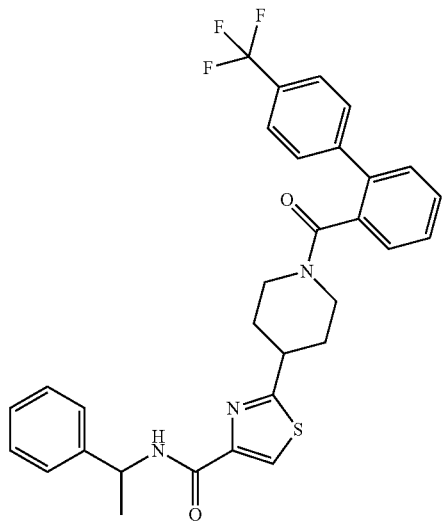<br>N-(1-phenylethyl)-2-(1-{[4'-(trifluoromethyl)biphenyl-2-yl]carbonyl}piperidin-4-yl)-1,3-thiazole-4-carboxamide | |
| 77 | 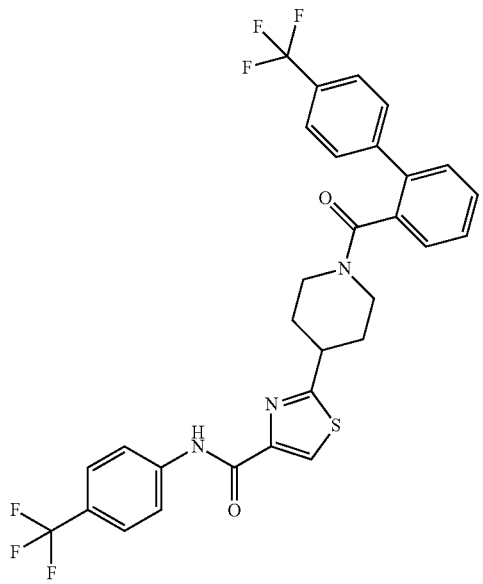<br>2-(1-{[4'-(trifluoromethyl)biphenyl-2-yl]carbonyl}piperidin-4-yl)-N-[4-(trifluoro-methyl)phenyl]-1,3-thiazole-4-carboxamide | |

| No. | FORMULA | NMR or mass |
|---|---|---|

78

1-{[2-(1-{[4'-(trifluoromethyl)biphenyl-2-yl]carbonyl}piperidin-4-yl)-1,3-thiazol-4-yl]carbonyl}azepane

79

1-(2-phenylpropyl)-4-{[2-(1-{[4'-(trifluoromethyl)biphenyl-2-yl]carbonyl}-piperidin-4-yl)-1,3-thiazol-4-yl]carbonyl}piperazine TABLE 1-continued
| No. | FORMULA | NMR or mass |
|---|---|---|
| 80 | 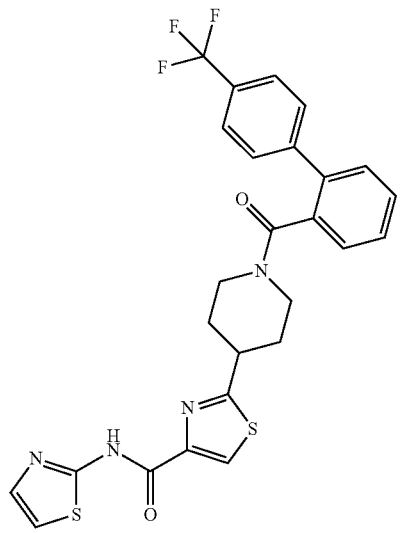<br>N-1,3-thiazol-2-yl-2-(1-{[4'-(trifluoromethyl)biphenyl-2-yl]carbonyl}piperidin-4-yl)-1,3-thiazole-4-carboxamide | |
| 81 | 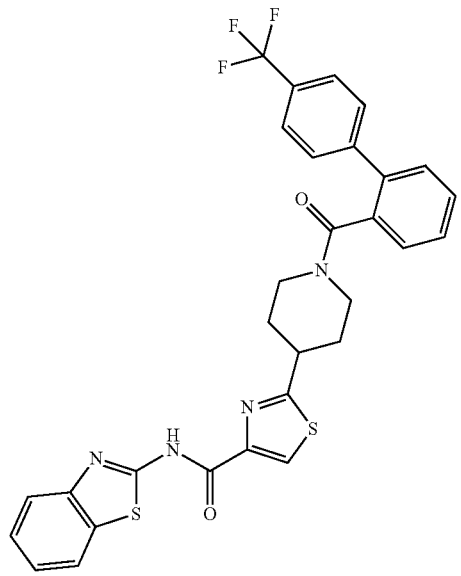<br>N-1,3-benzothiazol-2-yl-2-(1-{[4'-(trifluoromethyl)biphenyl-2-yl]carbonyl}-piperidin-4-yl)-1,3-thiazole-4-carboxamide | |

TABLE 1-continued
| No. | FORMULA | NMR or mass |
|---|---|---|
| 82 | 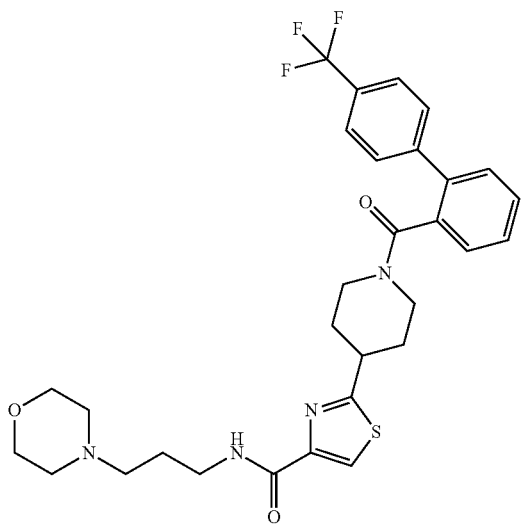 N-(3-morpholin-4-ylpropyl)-2-(1-{[4'-(trifluoromethyl)biphenyl-2-yl]carbonyl}-piperidin-4-yl)-1,3-thiazole-4-carboxamide | |
| 83 | 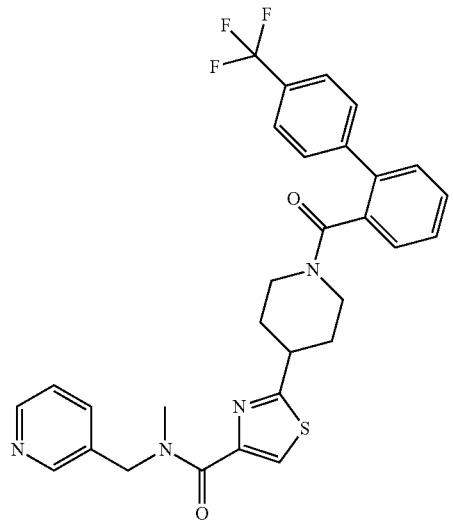 N-methyl-N-(pyridin-3-ylmethyl)-2-(1-{[4'-(trifluoromethyl)biphenyl-2-yl]-carbonyl}piperidin-4-yl)-1,3-thiazole-4-carboxamide | |

TABLE 1-continued
| No. | FORMULA | NMR or mass |
|---|---|---|
| 85 | 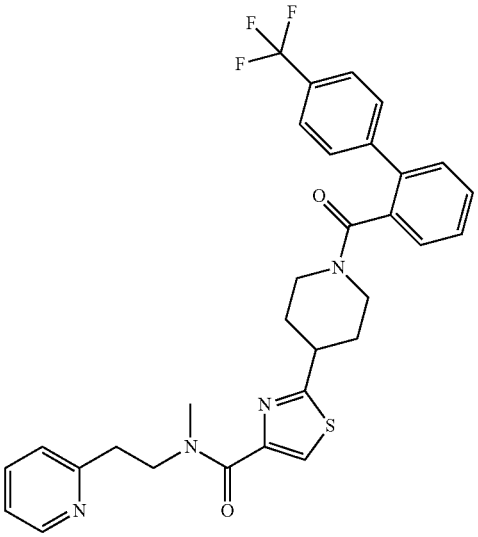 N-methyl-N-(2-pyridin-2-ylethyl)-2-(1-{[4'-(trifluoromethyl)biphenyl-2-yl]-carbonyl}piperidin-4-yl)-1,3-thiazole-4-carboxamide | |
| 86 | 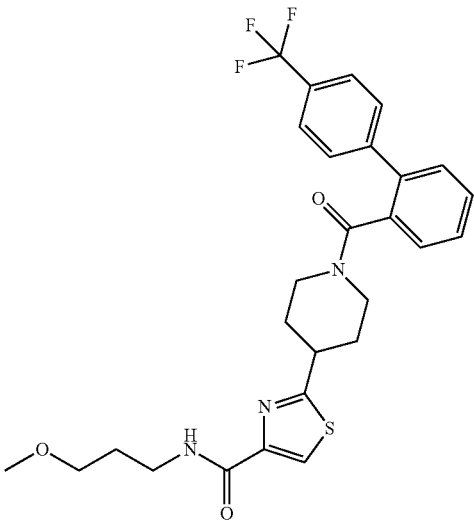 N-(3-methoxypropyl)-2-(1-{[4'-(trifluoromethyl)biphenyl-2-yl]carbonyl}-piperidin-4-yl)-1,3-thiazole-4-carboxamide | |

| No. | FORMULA | NMR or mass |
|---|---|---|
| 87 | 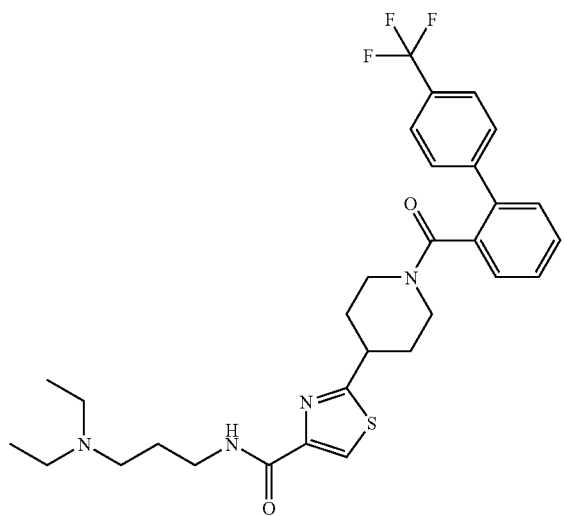<br>N-[3-(diethylamino)propyl]-2-(1-{[4'-(trifluoromethyl)biphenyl-2-yl]carbonyl}-piperidin-4-yl)-1,3-thiazole-4-carboxamide | |
| 88 | 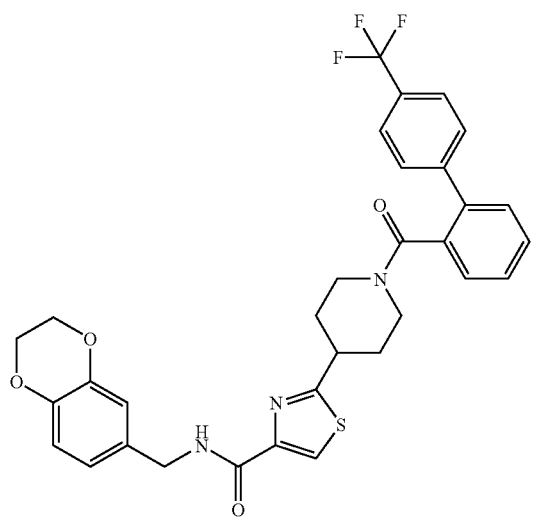<br>N-(2,3-dihydro-1,4-benzodioxin-6-ylmethyl)-2-(1-{[4'-(trifluoromethyl)-biphenyl-2-yl]carbonyl}piperidin-4-yl)-1,3-thiazole-4-carboxamide | |

TABLE 1-continued
| No. | FORMULA | NMR or mass |
|---|---|---|
| 89 | 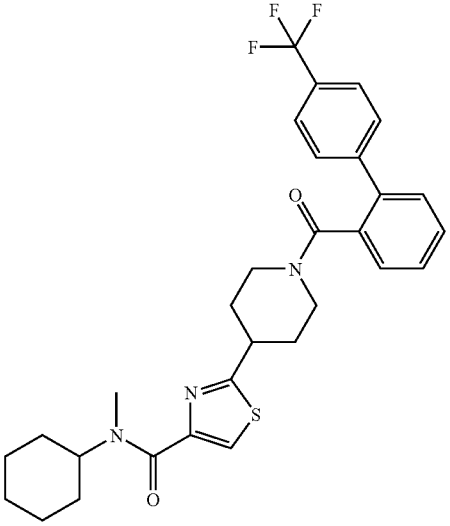 N-cyclohexyl-N-methyl-2-(1-{[4'-(trifluoromethyl)biphenyl-2-yl]carbonyl}-piperidin-4-yl)-1,3-thiazole-4-carboxamide | |
| 90 | 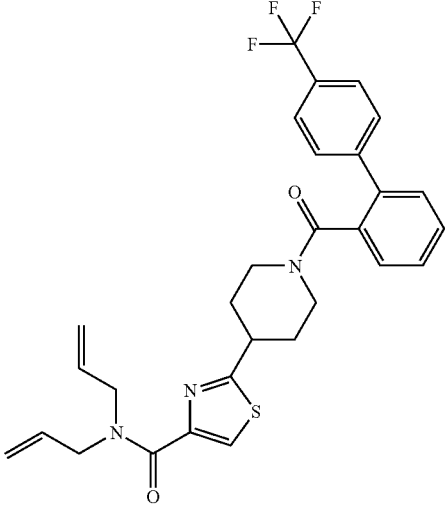 N,N-diallyl-2-(1-{[4'-(trifluoromethyl)biphenyl-2-yl]carbonyl}piperidin-4-yl)-1,3-thiazole-4-carboxamide | |

TABLE 1-continued
| No. | FORMULA | NMR or mass |
|---|---|---|
| 91 | 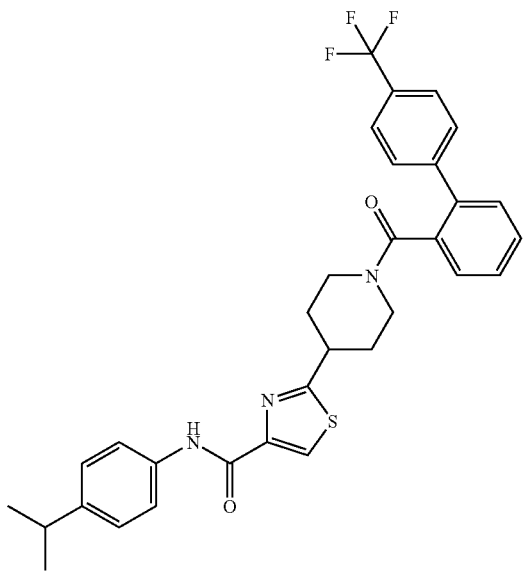<br>N-(4-isopropylphenyl)-2-(1-{[4'-(trifluoromethyl)biphenyl-2-yl]carbonyl}-piperidin-4-yl)-1,3-thiazole-4-carboxamide | |
| 92 | 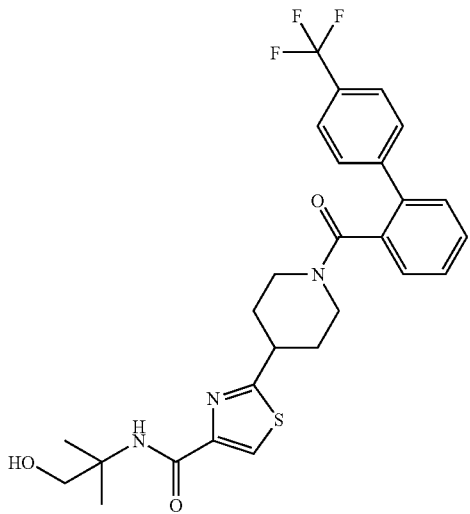<br>N-(2-hydroxy-1,1-dimethylethyl)-2-(1-{[4'-(trifluoromethyl)biphenyl-2-yl]-carbonyl}piperidin-4-yl)-1,3-thiazole-4-carboxamide | |

TABLE 1-continued
| No. | FORMULA | NMR or mass |
|---|---|---|
| 93 | 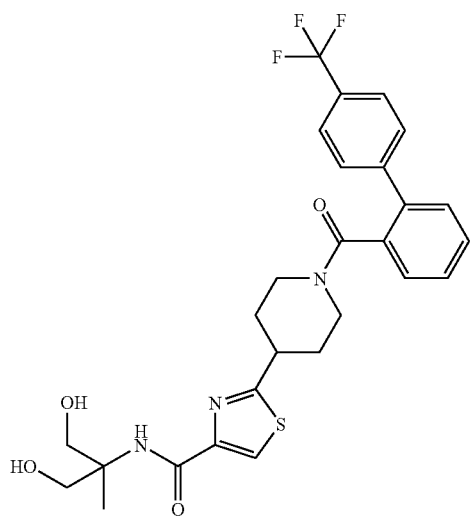 N-[2-hydroxy-1-(hydroxymethyl)-1-methylethyl]-2-(1-{[4'-(trifluoromethyl)-biphenyl-2-yl]carbonyl}piperidin-4-yl)-1,3thiazole-4-carboxamide | |
| 94 | 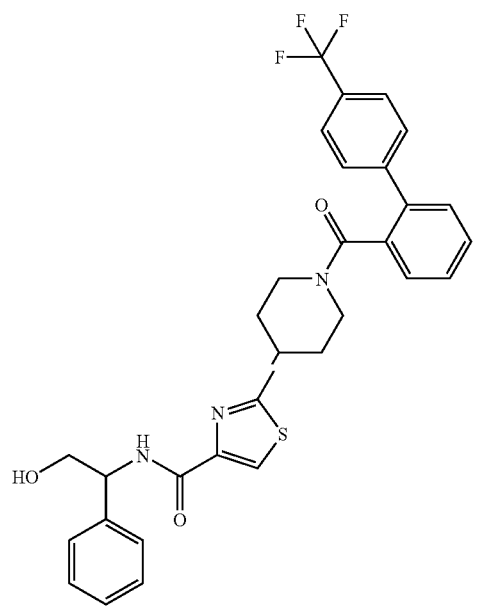 N-(2-hydroxy-1-phenylethyl)-2-(1-{[4'-(trifluoromethyl)biphenyl-2-yl]-carbonyl}piperidin-4-yl)-1,3-thiazole-4-carboxamide | |

TABLE 1-continued
| No. | FORMULA | NMR or mass |
|---|---|---|
| 95 | 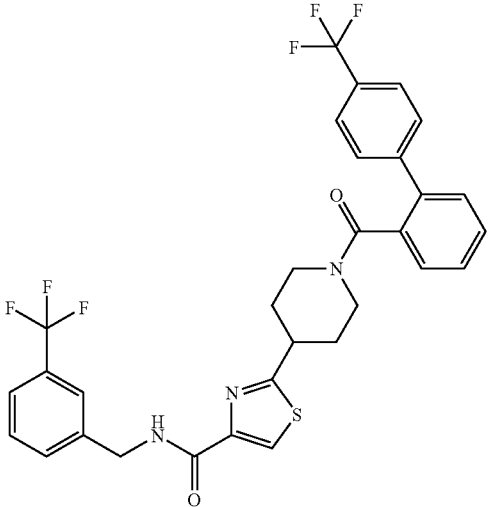<br>N-[3-(trifluoromethyl)benzyl]-2-(1-{[4'-(trifluoromethyl)biphenyl-2-yl]-carbonyl}piperidin-4-yl)-1,3-thiazole-4-carboxamide | |
| 96 | 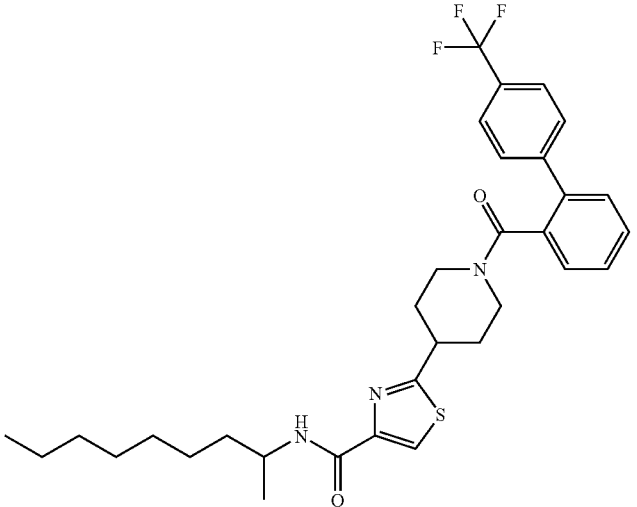<br>N-(1-methyloctyl)-2-(1-{[4'-(trifluoromethyl)biphenyl-2-yl]carbonyl}piperidin-4-yl)-1,3-thiazole-4-carboxamide | |

TABLE 1-continued
| No. | FORMULA | NMR or mass |
|---|---|---|
| 97 | 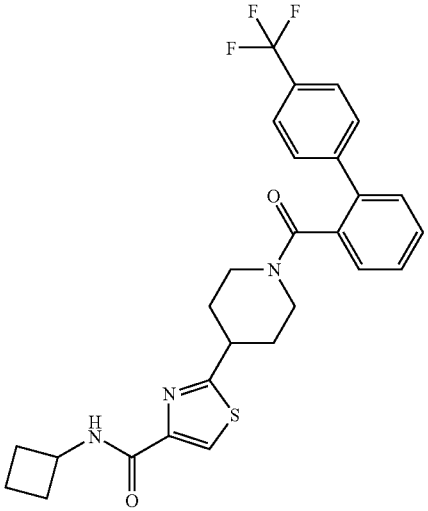 N-cyclobutyl-2-(1-{[4'-(trifluoromethyl)biphenyl-2-yl]carbonyl}piperidin-4-yl)-1,3-thiazole-4-carboxamide | |
| 98 | 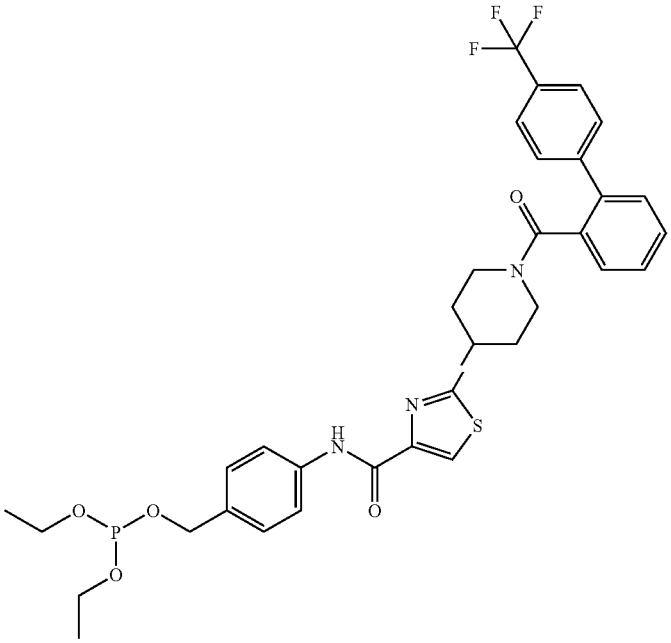 diethyl 4-({[2-(1-{[4'-(trifluoromethyl)biphenyl-2-yl]carbonyl}piperidin-4-yl)-1,3-thiazol-4-yl]carbonyl}amino)benzyl phosphite | |

TABLE 1-continued
| No. | FORMULA | NMR or mass |
|---|---|---|
| 99 | 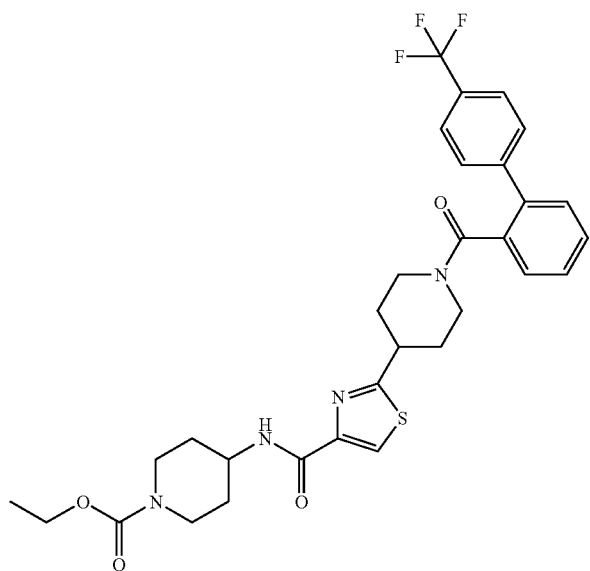
ethyl 4-({[2-(1-{[4'-(trifluoromethyl)biphenyl-2-yl]
carbonyl}piperidin-4-yl)-1,3-thiazol-4-yl]
carbonyl}amino)piperidine-1-carboxylate | |
| 100 | 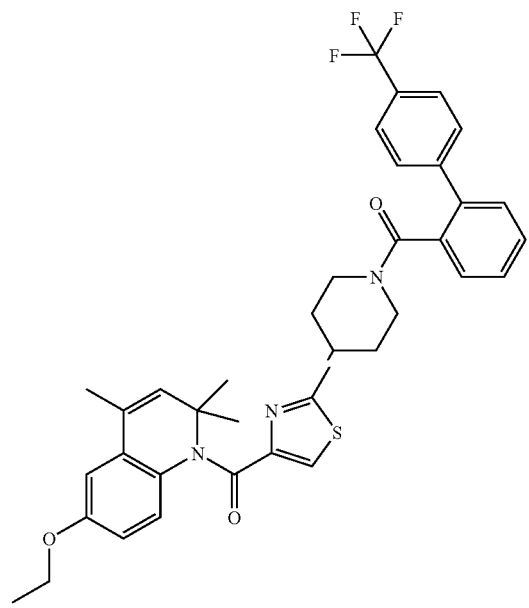
6-ethoxy-2,2,4-trimethyl-1-{[2-(1-{[4'-(trifluoromethyl)
biphenyl-2-yl]carbonyl}piperidin-4-yl)-1,3-
thiazol-4-yl]carbonyl}-1,2-dihydroquinoline | |

TABLE 1-continued
| No. | FORMULA | NMR or mass |
|---|---|---|
101 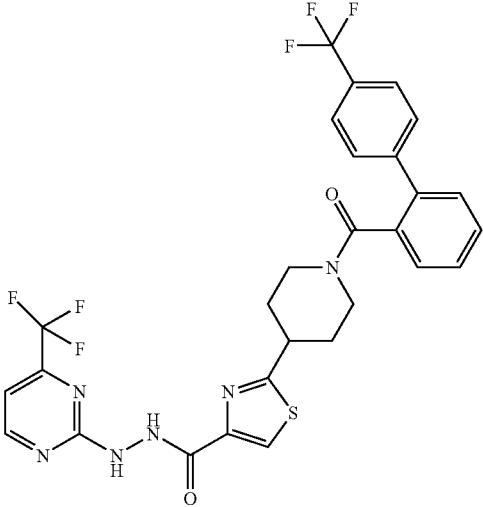
2-(1-{[4'-(trifluoromethyl)biphenyl-2-yl]carbonyl}piperidin-4-yl)-N'-[4-(trifluoromethyl)pyrimidin-2-yl]-1,3-thiazole-4-carbohydrazide
102 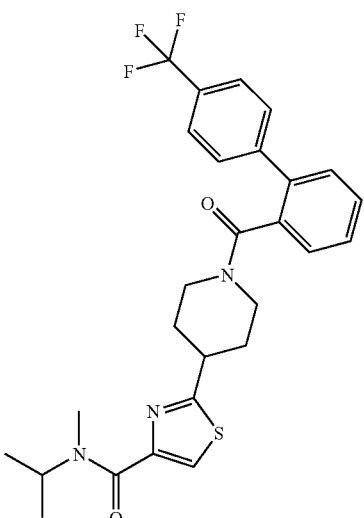
N-isopropyl-N-methyl-2-(1-{[4'-(trifluoromethyl)biphenyl-2-yl]carbonyl}-piperidin-4-yl)-1,3-thiazole-4-carboxamide TABLE 1-continued
| No. | FORMULA | NMR or mass |
|---|---|---|
| 103 | 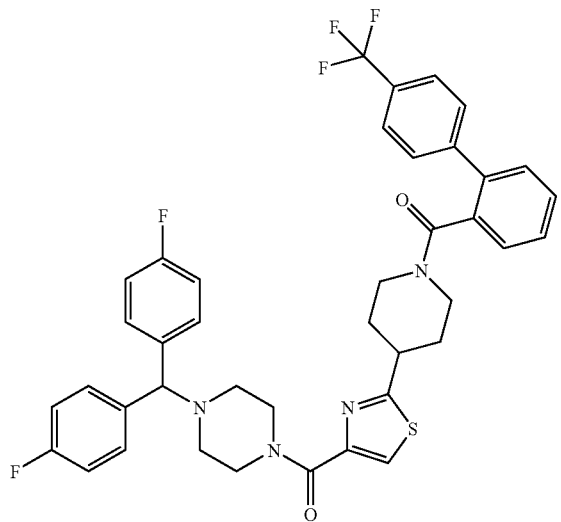 1-[bis(4-fluorophenyl)methyl]-4-{[2-(1-{[4'-(trifluoromethyl)biphenyl-2-yl]-carbonyl}piperidin-4-yl)-1,3-thiazol-4-yl]carbonyl}piperazine | |
| 104 | 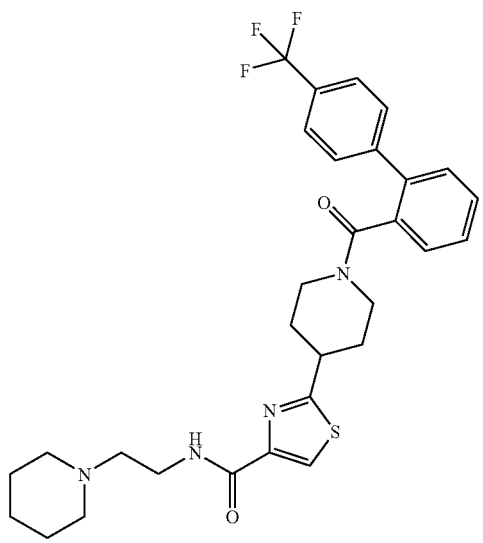 N-(2-piperidin-1-ylethyl)-2-(1-{[4'-(trifluoromethyl)biphenyl-2-yl]carbonyl}-piperidin-4-yl)-1,3-thiazole-4-carboxamide | |

TABLE 1-continued
| No. | FORMULA | NMR or mass |
|---|---|---|
| 105 | 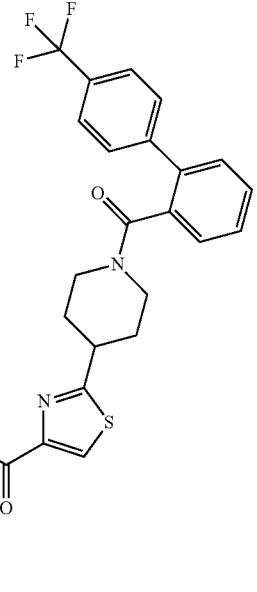 N-(1,2,3,4-tetrahydronaphthalen-1-yl)-2-(1-{[4'-(trifluoromethyl)biphenyl-2-yl]carbonyl}piperidin-4-yl)-1,3-thiazole-4-carboxamide | |
| 106 | 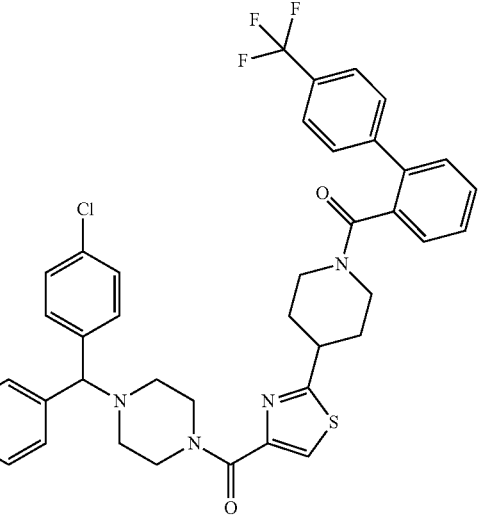 1-[bis(4-chlorophenyl)methyl]-4-{[2-(1-{[4'-(trifluoromethyl)biphenyl-2-yl]-carbonyl}piperidin-4-yl)-1,3-thiazol-4-yl]carbonyl}piperazine | |

TABLE 1-continued
| No. | FORMULA | NMR or mass |
|---|---|---|
107
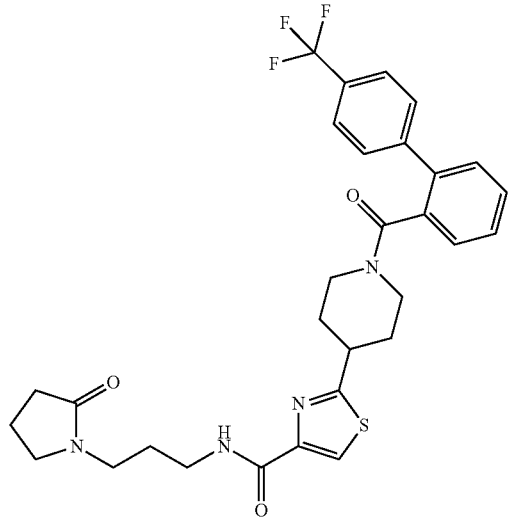
N-[3-(2-oxopyrrolidin-1-yl)propyl]-2-(1-{[4'-(trifluoromethyl)biphenyl-2-yl]-carbonyl}piperidin-4-yl)-1,3-thiazole-4-carboxamide
108
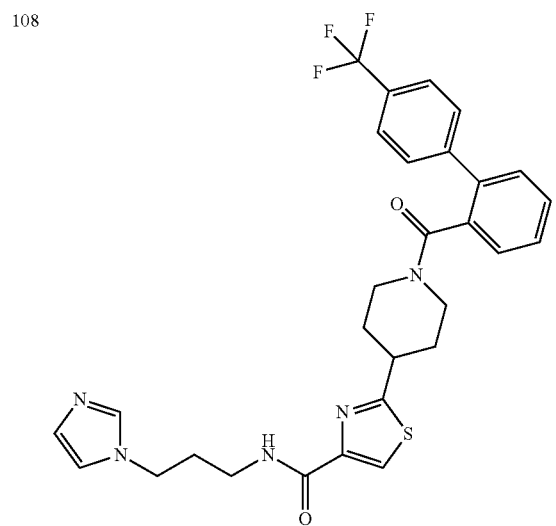
N-[3-(1H-imidazol-1-yl)propyl]-2-(1-{[4'-(trifluoromethyl)biphenyl-2-yl]-carbonyl}piperidin-4-yl)-1,3-thiazole-4-carboxamide TABLE 1-continued

| No. | FORMULA | NMR or mass |
|---|---|---|
| 109 | N-[3-(2-methylpiperidin-1-yl)propyl]-2-(1-{[4'-(trifluoromethyl)biphenyl-2-yl]-carbonyl}piperidin-4-yl)-1,3-thiazole-4-carboxamide | |
| 110 | N-[2-(1-methylpyrrolidin-2-yl)ethyl]-2-(1-{[4'-(trifluoromethyl)biphenyl-2-yl]-carbonyl}piperidin-4-yl)-1,3-thiazole-4-carboxamide | |

TABLE 1-continued
| No. | FORMULA | NMR or mass |
|---|---|---|
| 111 | 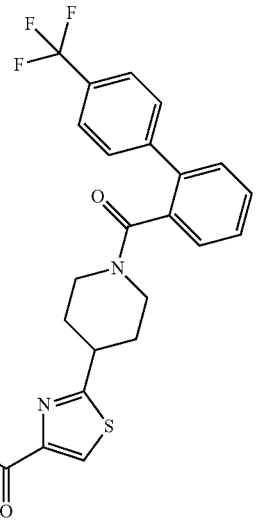 N-[2-(2-thienyl)ethyl]-2-(1-{[4'-(trifluoromethyl)biphenyl-2-yl]carbonyl}-piperidin-4-yl)-1,3-thiazole-4-carboxamide | |
| 112 | 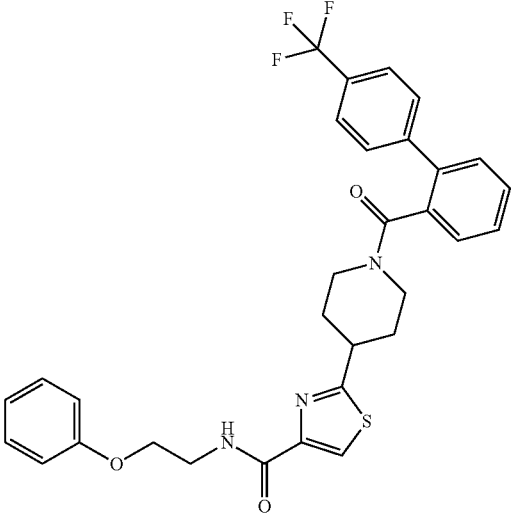 N-(2-phenoxyethyl)-2-(1-{[4'-(trifluoromethyl)biphenyl-2-yl]carbonyl}-piperidin-4-yl)-1,3-thiazole-4-carboxamide | |

TABLE 1-continued
| No. | FORMULA | NMR or mass |
|---|---|---|
| 113 | 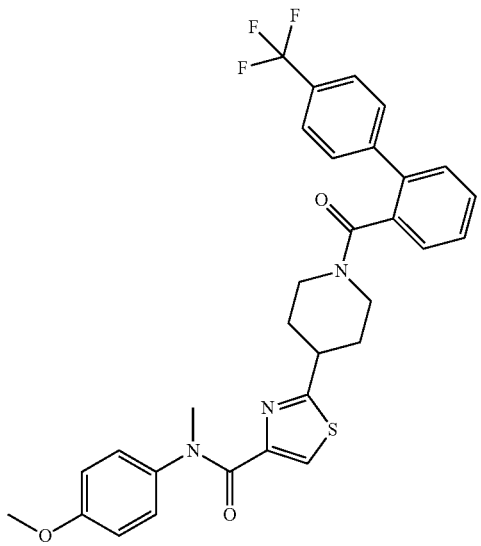<br>N-(4-methoxyphenyl)-N-methyl-2-(1-{[4'-(trifluoromethyl)biphenyl-2-yl]-carbonyl}-piperidin-4-yl)-1,3-thiazole-4-carboxamide | |
| 114 | 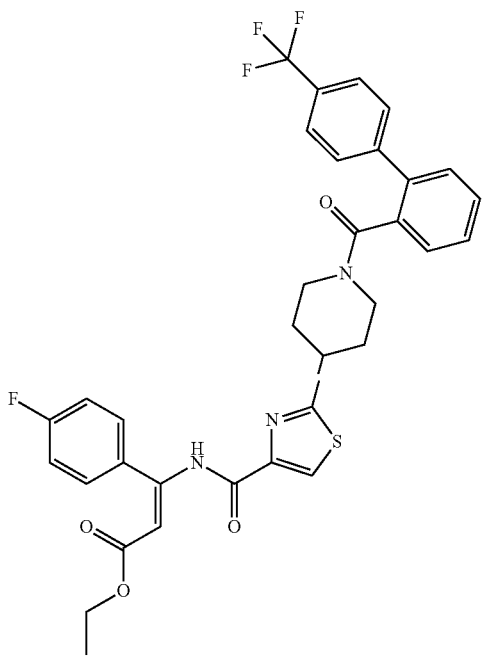<br>ethyl (2E)-3-(4-fluorophenyl)-3-({[2-(1-{[4'-(trifluoromethyl)biphenyl-2-yl]-carbonyl}piperidin-4-yl)-1,3-thiazol-4-yl]carbonyl}amino)acrylate | |

TABLE 1-continued
| No. | FORMULA | NMR or mass |
|---|---|---|
| 115 | 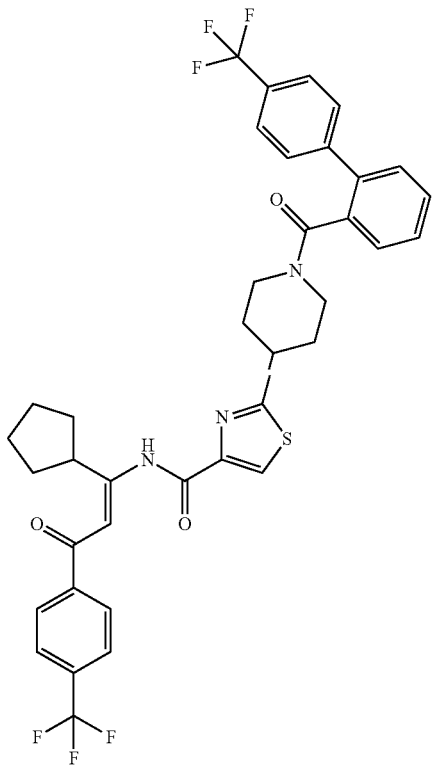 N-{(1E)-1-cyclopentyl-3-oxo-3-[4-(trifluoromethyl)phenyl]prop-1-en-1-yl}-2-(1-{[4'-(trifluoromethyl)biphenyl-2-yl]carbonyl}piperidin-4-yl)-1,3-thiazole-4-carbonamide | |
| 116 | 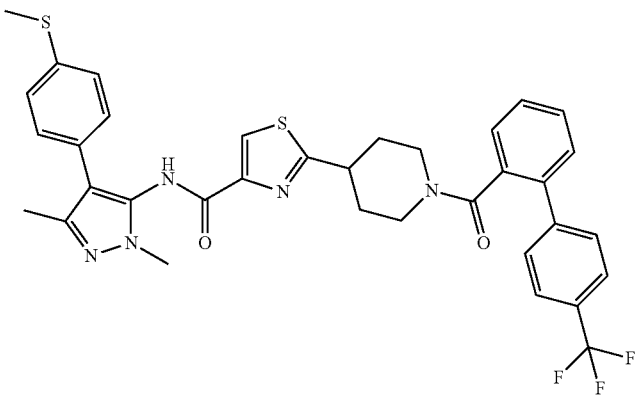 N-(1,3-dimethyl-4-[4-(methylthio)phenyl]-1H-pyrazol-5-yl)-2-(1-{[4'-(trifluoromethyl)biphenyl-2-yl]carbonyl}piperidin-4-yl)-1,3-thiazole-4-carboxamide | |

TABLE 1-continued
| No. | FORMULA | NMR or mass |
|---|---|---|
117
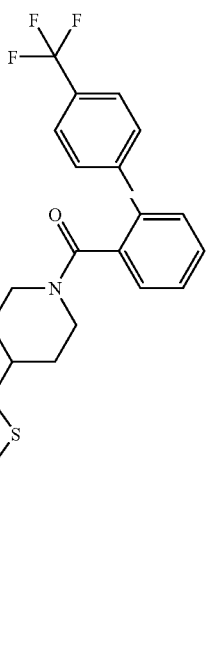
8,9-dimethoxy-1-{[2-(1-{[4'-(trifluoromethyl)biphenyl-2-yl]carbonyl}piperidin-4-yl)-1,3-thiazol-4-yl]carbonyl}-1,2,5,6-tetrahydro-3H-imidazo[2,1-b][1,3]-benzodiazepin-3-one
118
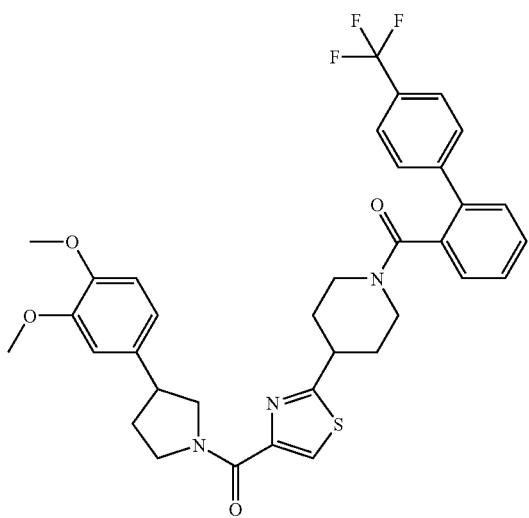
4-(4-{[3-(3,4-dimethoxyphenyl)pyrrolidin-1-yl]carbonyl}-1,3-thiazol-2-yl)-1-{[4'-(trifluoromethyl)biphenyl-2-yl]crbonyl}piperidine TABLE 1-continued
| No. | FORMULA | NMR or mass |
|---|---|---|
| 119 | 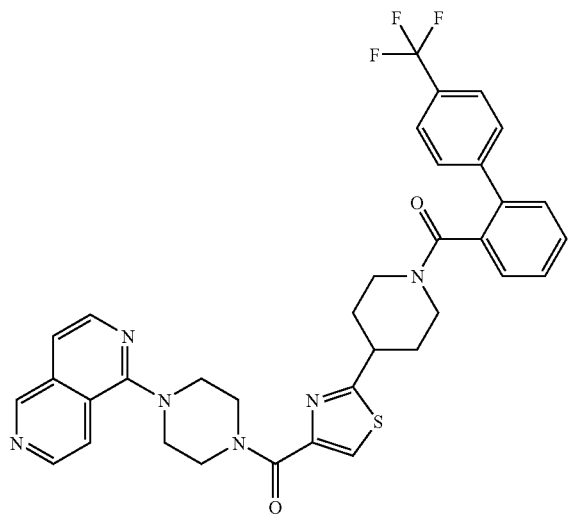 1-(4-{[2-(1-{[4'-(trifluoromethyl)biphenyl-2-yl]carbonyl}piperidin-4-yl)-1,3-thiazol-4-yl]carbonyl}piperazin-1-yl)-2,6-naphthyridine | |
| 120 | 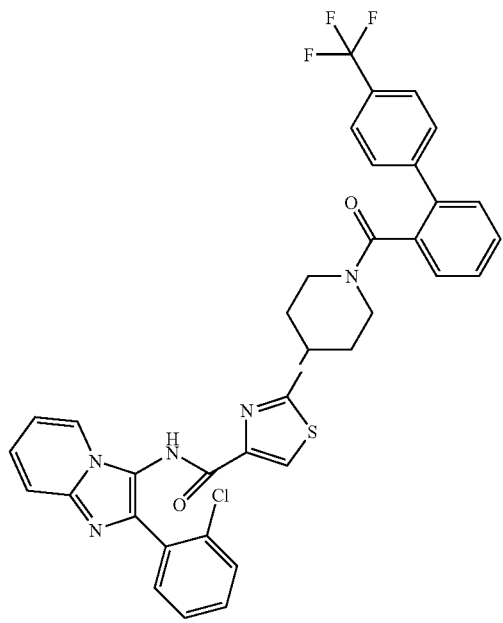 N-[2-(2-chlorophenyl)imidazol[1,2-a]pyridin-3-yl]-2-(1-{[4'-(trifluoromethyl)-biphenyl-2-yl]carbonyl}piperidin-4-yl)-1,3-thiazole-4-carboxamide | |

| No. | FORMULA | NMR or mass |
|---|---|---|
| 121 | 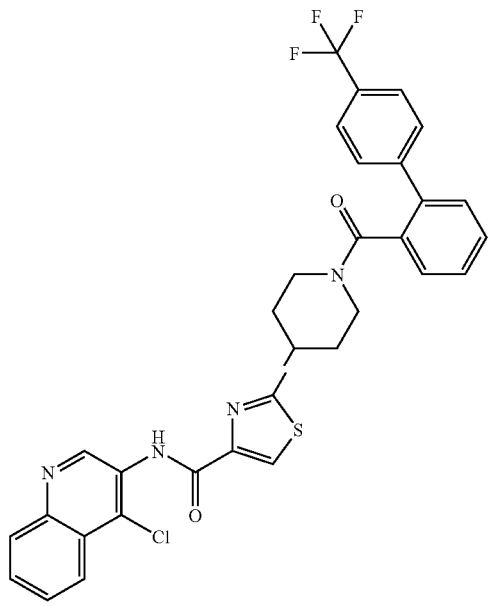<br>N-(4-chloroquinolin-3-yl)-2-(1-{[4'-(trifluoromethyl)biphenyl-2-yl]carbonyl}-piperidin-4-yl)-1,3-thiazole-4-carboxamide | |
| 122 | 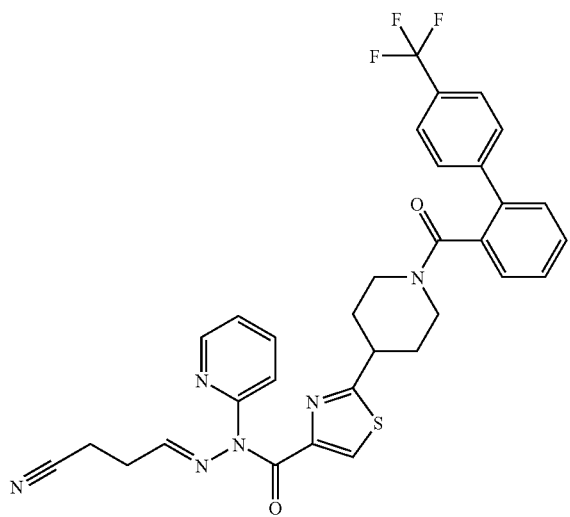<br>N'-[(1E)-3-cyanopropylidene]-N-pyridin-2-yl-2-(1-{[4'-(trifluoromethyl)-biphenyl-2-yl]carbonyl}piperidin-4-yl)-1,3-thiazole-4-carbohydrazide | |

| No. | FORMULA | NMR or mass |
|---|---|---|
| 123 | 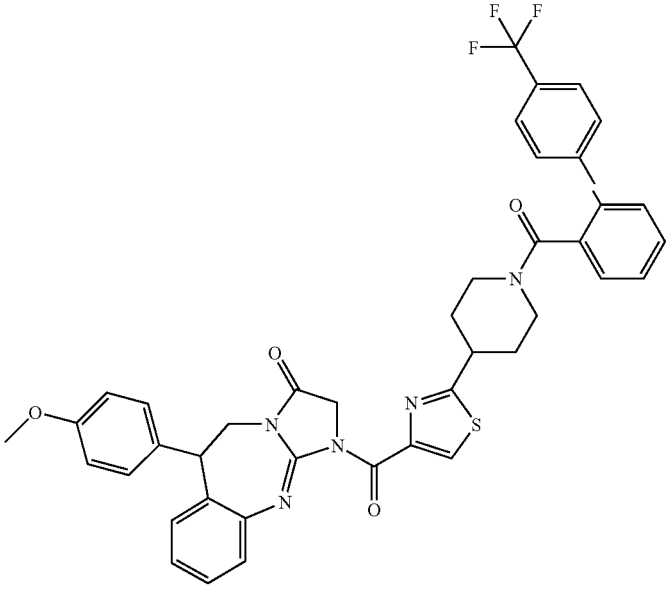<br>6-(4-methoxyphenyl)-1-{[2-(1-{[4'-(trifluoromethyl)biphenyl-2-yl]carbonyl}-piperidin-4-yl)-1,3-thiaol-4-yl]carbonyl}-1,2,5,6-tetrahydro-3H-imidazo[2,1-b][1,3]benzodiazepin-3-one | |
| 124 | 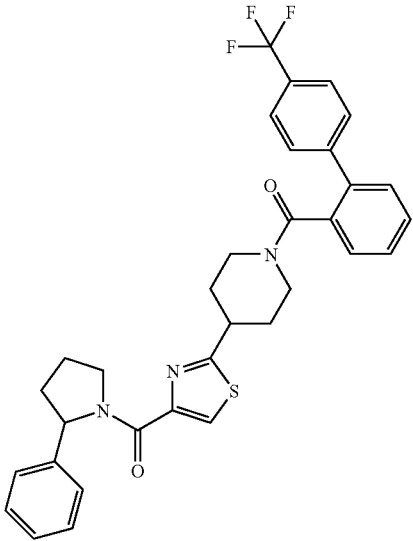<br>4-{4-[(2-phenylpyrrolidin-1-yl)carbonyl]-1,3-thiazol-2-yl}-1-{[4'-(trifluoromethyl)biphenyl-2-yl]carbonyl}piperidine | |

TABLE 1-continued
| No. | FORMULA | NMR or mass |
|---|---|---|
| 125 | 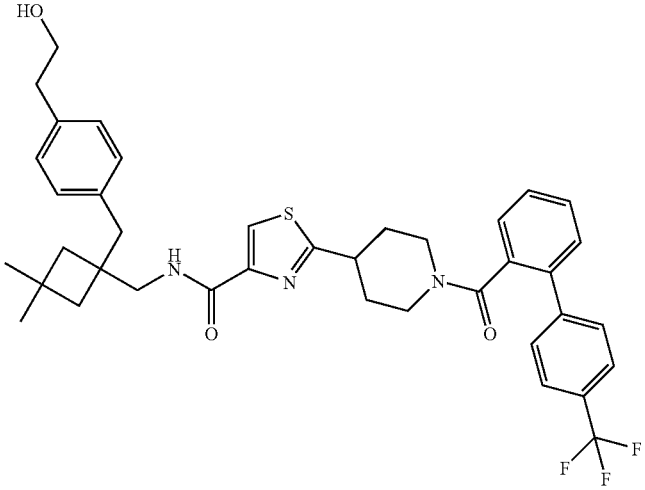 N-({1-[4-(2-hydroxyethyl)benzyl]-3,3-dimethylcyclobutyl}methyl)-2-(1-{[4'-(trifluoromethyl)biphenyl-2-yl]carbonyl}piperidin-4-yl)-1,3-thiazole-4-carboxamide | |
| 126 | 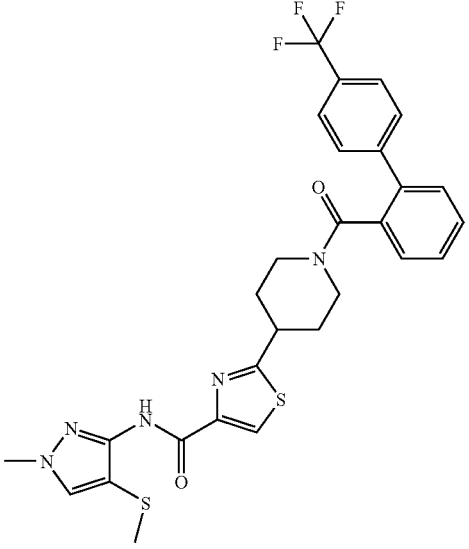 N-[1-methyl-4-(methylthio)-1H-pyrazol-3-yl]-2-(1-{[4'-(trifluoromethyl)-biphenyl-2-yl]carbonyl}piperidin-4-yl)-1,3-thiazole-4-carboxamide | |

TABLE 1-continued

| No. | FORMULA | NMR or mass |
|---|---|---|
| 127 | 4-(4-{[2-(methylthio)-4,5-diphenyl-1H-imidazol-1-yl]carbonyl}-1,3-thiazol-2-yl)-1-{[4'-(trifluoromethyl)biphenyl-2-yl]carbonyl}piperidine | |
| 128 | | |

| No. | FORMULA | NMR or mass |
|-----|---------|-------------|
| 129 | 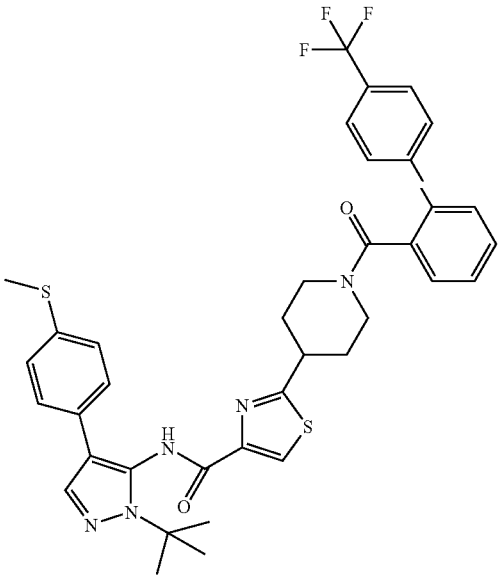<br>N-(1-tert-butyl-4-[4-(methylthio)phenyl]-1H-pyrazol-5-yl}-2-(1-{[4'-(trifluoromethyl)biphenyl-2-yl]carbonyl}piperidin-4-yl)1,3-thiazole-4-carboxamide | |
| 130 | 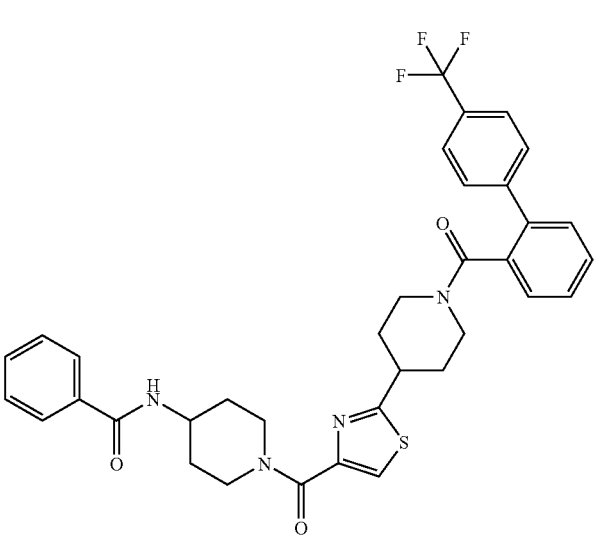<br>N-(1-{[2-(1-{[4'-(trifluoromethyl)biphenyl-2-yl]carbonyl}piperidin-4-yl)-1,3-thiazol-4-yl]carbonyl}piperidin-4-yl)benzamide | |
| 131 | 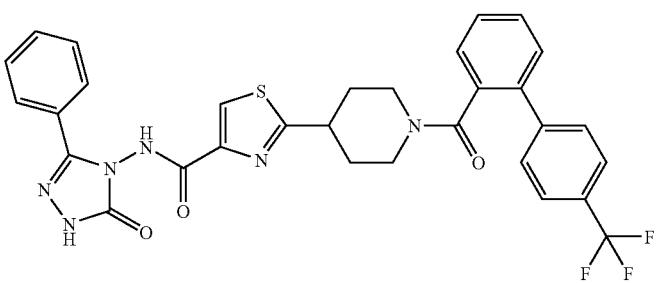 | |

TABLE 1-continued
| No. | FORMULA | NMR or mass |
|---|---|---|
| 132 | 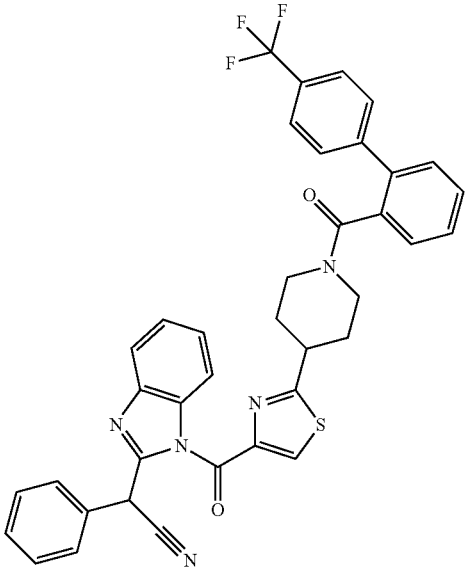 phenyl(1-{[2-(1-{[4'-(trifluoromethyl)biphenyl-2-yl]carbonyl}piperidin-4-yl)-1,3-thiazol-4-yl]carbonyl}-1H-benzimidazol-2-yl)acetonitrile | |
| 133 | 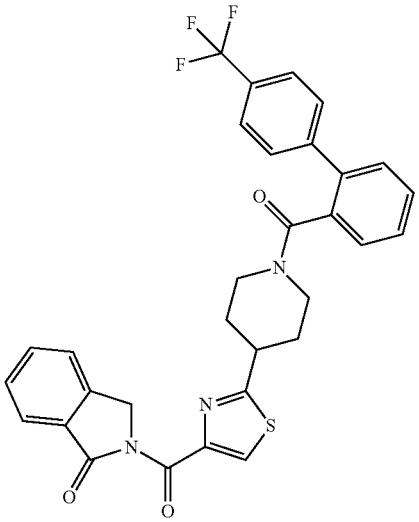 2-(1-{[2-(1-{[4'-(trifluoromethyl)biphenyl-2-yl]carbonyl}piperidin-4-yl)-1,3-thiazol-4-yl]carbonyl}piperidin-4-yl)isoindolin-1-one | |

TABLE 1-continued

| No. | FORMULA | NMR or mass |
|---|---|---|
| 134 | 3-(3-{[2-(1-{[4'-(trifluoromethyl)biphenyl-2-yl]carbonyl}piperidin-4-yl)-1,3-thiazol-4-yl]carbonyl}-1,3-thiazolidin-2-yl)pyridine | |
| 135 | 3-[(4-{[2-(1-{[4'-(trifluoromethyl)biphenyl-2-yl]carbonyl}piperidin-4-yl)-1,3-thiazol-4-yl]carbonyl}piperazin-1-yl)methyl]-2H-chromen-2-one | |

| No. | FORMULA | NMR or mass |
|---|---|---|
| 136 | 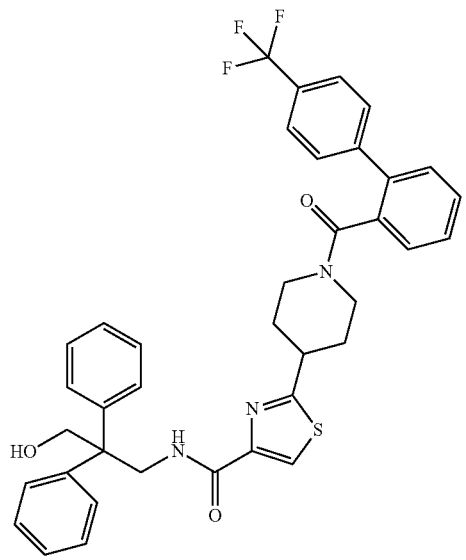<br>N-(3-hydroxy-2,2-diphenylpropyl)-2-(1-{[4'-(trifluoromethyl)biphenyl-2-yl]-carbonyl}piperidin-4-yl)-1,3-thiazole-4-carboxamide | |
| 137 | 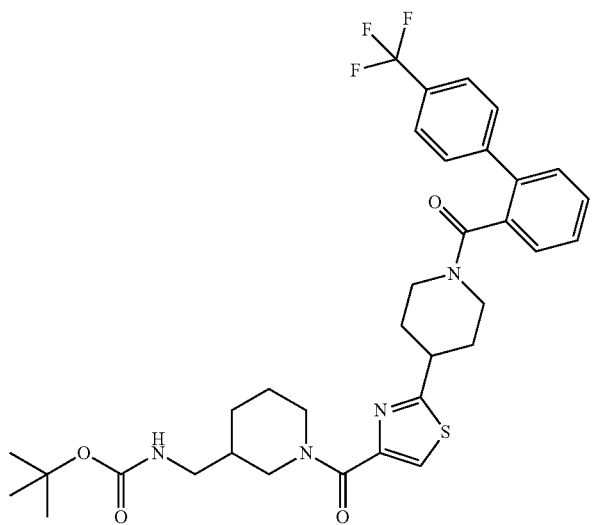<br>tert-butyl [(1-{[2-(1-{[4'-(trifluoromethyl)biphenyl-2-yl]carbonyl}piperidin-4-yl)-1,3-thiazol-4-yl]carbonyl}piperidin-3-yl)methyl]carbamate | |

TABLE 1-continued
| No. | FORMULA | NMR or mass |
|---|---|---|
138
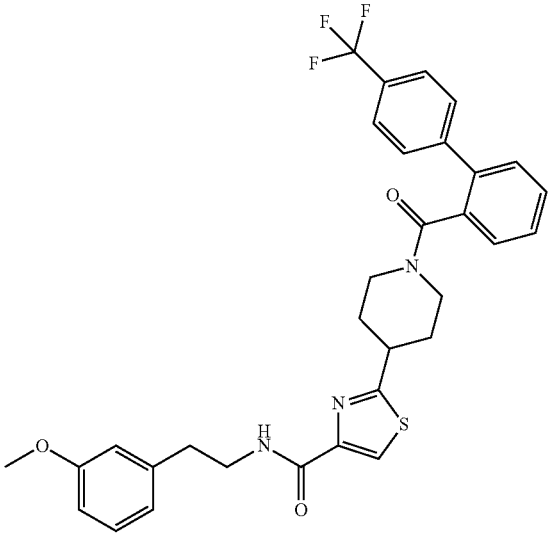
N-[2-(3-methoxyphenyl)ethyl]-2-(1-{[4'-(trifluoromethyl)biphenyl-2-yl]-carbonyl}piperidin-4-yl)-1,3-thiazole-4-carboxamide
139
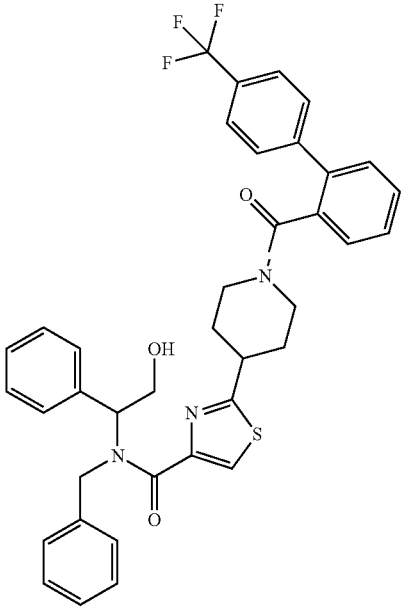
N-benzyl-N-(2-hydroxy-1-phenylethyl)-2-(1-{[4'-(trifluoromethyl)biphenyl-2-yl]carbonyl}piperidin-4-yl)-1,3-thiazole-4-carboxamide TABLE 1-continued
| No. | FORMULA | NMR or mass |
|---|---|---|
| 140 | 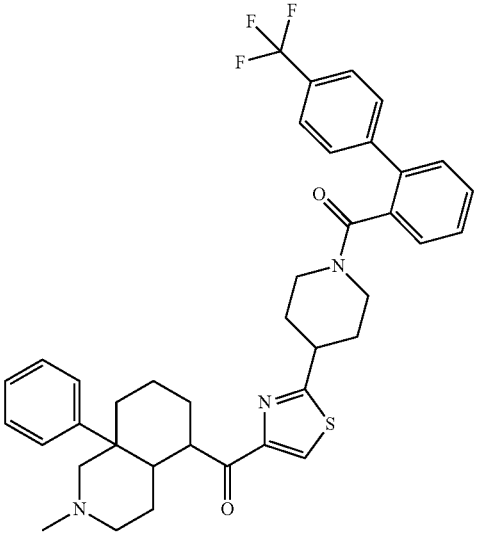 6-methyl-4a-phenyl-1-{[2-(1-{[4'-(trifluoromethyl)biphenyl-2-yl]carbonyl}-piperidin-4-yl)-1,3-thiazol-4-yl]carbonyl}decahydro-1,6-naphthyridine | |
| 141 | 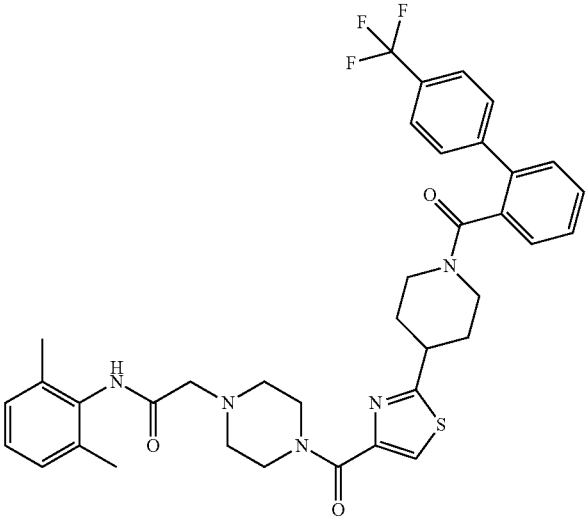 N-(2,6-dimethylphenyl)-2-(4-{[2-(1-{[4'-(trifluoromethyl)biphenyl-2-yl]-carbonyl}piperidin-4-yl)-1,3-thiazol-4-yl]carbonyl}piperazin-1-yl)acetamide | |

TABLE 1-continued
| No. | FORMULA | NMR or mass |
|---|---|---|
| 142 | 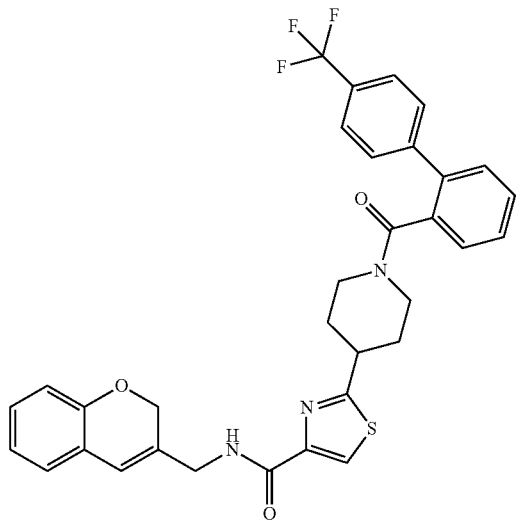 N-(2H-chromen-3-ylmethyl)-2-(1-{[4'-(trifluoromethyl)biphenyl-2-yl]carbonyl}-piperidin-4-yl)-1,3-thiazole-4-carboxamide | |
| 143 | 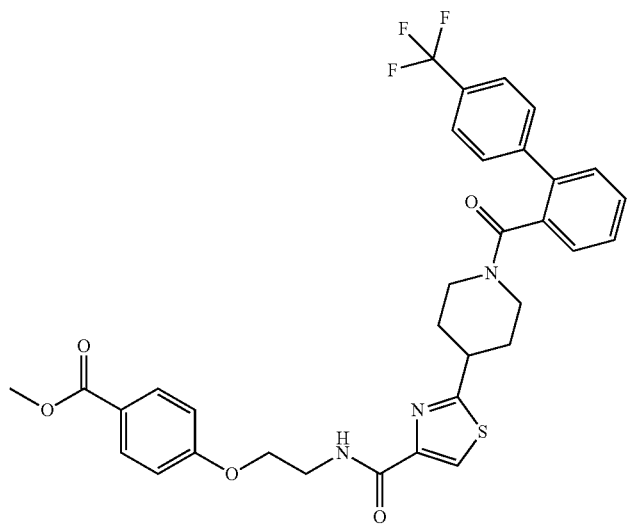 methyl 4-[2-({[2-(1-{[4'-(trifluoromethyl)biphenyl-2-yl]carbonyl}piperidin-4-yl)-1,3-thiazol-4-yl]carbonyl}amino)ethoxy]benzoate | |

TABLE 1-continued
| No. | FORMULA | NMR or mass |
|---|---|---|
| 144 | 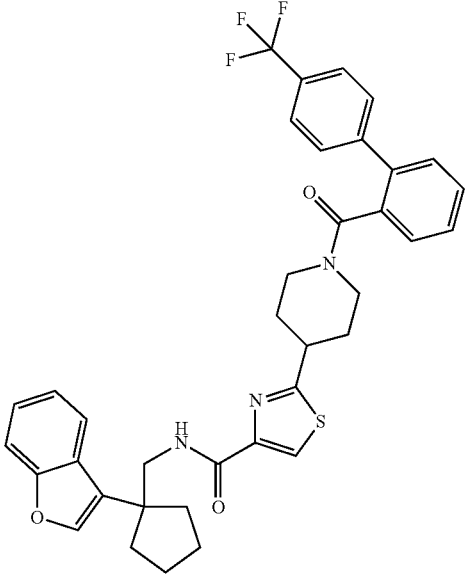 N-{[1-(1-benzofuran-3-yl)cyclopentyl]methyl}-2-(1-{[4'-(trifluoromethyl)-biphenyl-2-yl]carbonyl}piperidin-4-yl)-1,3-thiazole-4-carboxamide | |
| 145 | 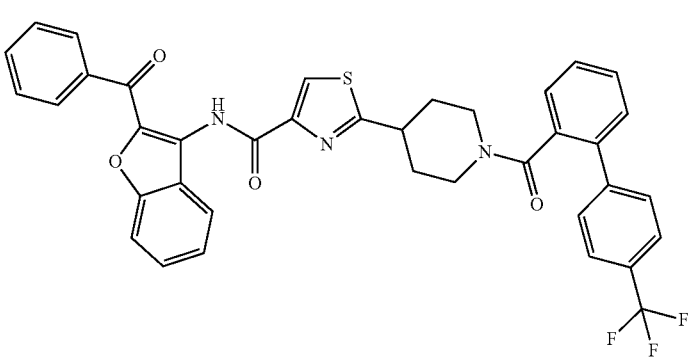 | |

TABLE 1-continued
| No. | FORMULA | NMR or mass |
|---|---|---|
146
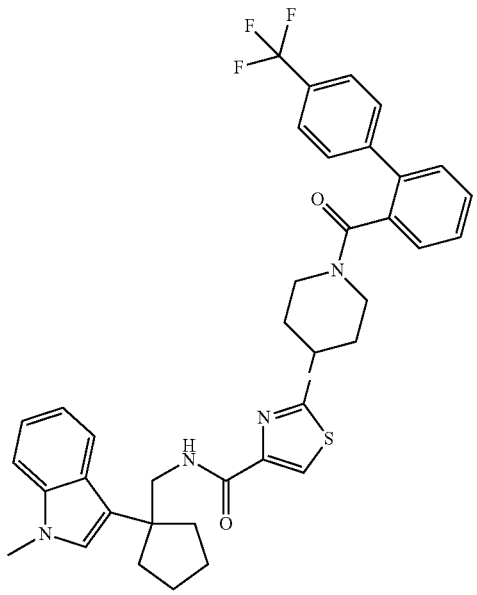
N-{[1-(1-methyl-1H-indol-3-yl)cyclopentyl]methyl}-2-(1-{[4'-(trifluoromethyl)-biphenyl-2-yl]carbonyl}piperidin-4-yl)-1,3-thiazole-4-carboxamide
147
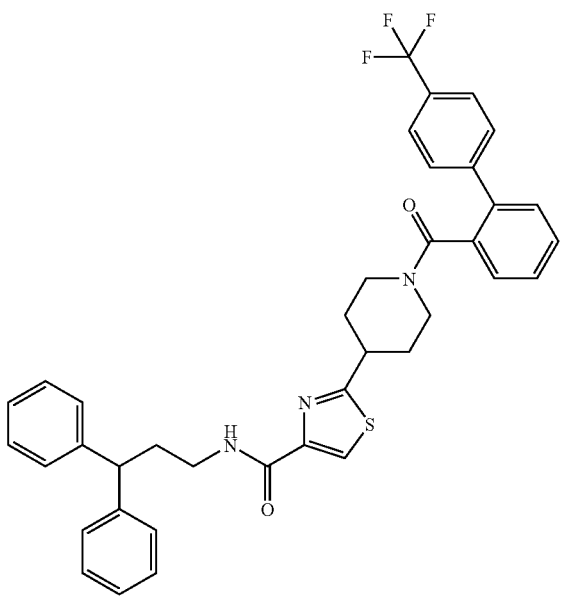
N-(3,3-diphenylpropyl)-2-(1-{[4'-(trifluoromethyl)biphenyl-2-yl]carbonyl}-piperidin-4-yl)-1,3-thiazole-4-carboxamide

TABLE 1-continued
| No. | FORMULA | NMR or mass |
|---|---|---|
| 148 | 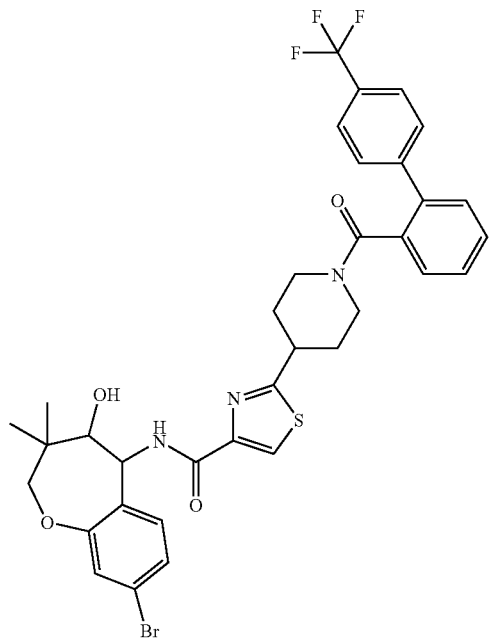 N-(8-bromo-4-hydroxy-3,3-dimethyl-2,3,4,5-tetrahydro-1-benzoexpin-5-yl)-2-(1-{[4'-(trifluromethyl)biphenyl-2-yl]carbonyl}piperidin-4-yl)-1,3-thiazole-4-carboxamide | |
| 149 | 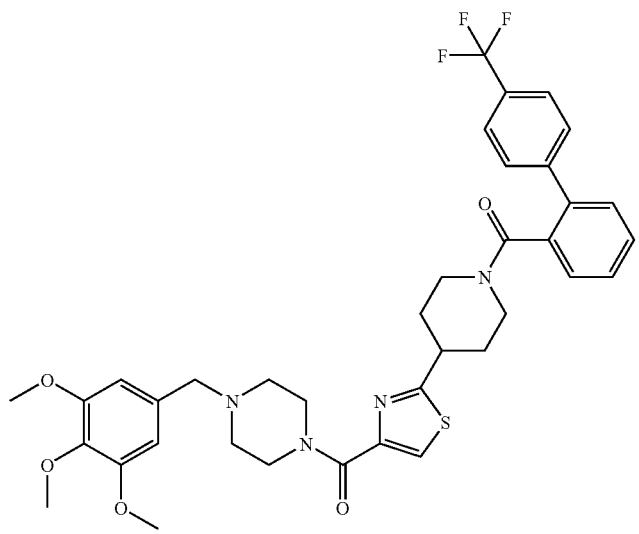 1-{[2-(1-{[4'-(trifluromethyl)biphenyl-2-yl]carbonyl}piperidin-4-yl)-1,3-thiazol-4-yl]carbonyl}-4-(3,4,5-trimethoxybenzyl)piperazine | |

TABLE 1-continued
| No. | FORMULA | NMR or mass |
|---|---|---|
| 150 | 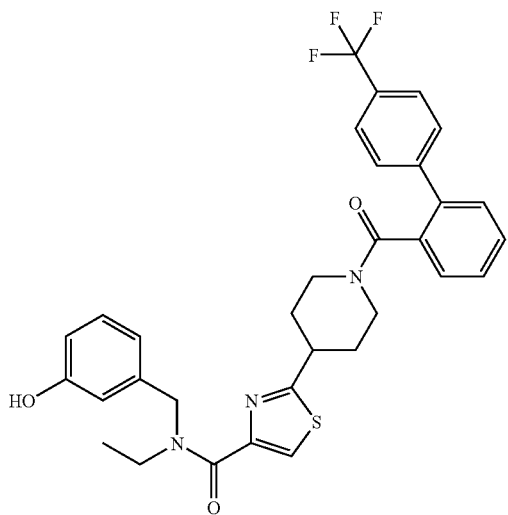 N-ethyl-n-(3-hydroxybenzyl)-2-(1-{[4'-(trifluoromethyl)biphenyl-2-yl]-carbonyl}piperidin-4-yl)-1,3-thiazole-4-carboxamide | |
| 151 | 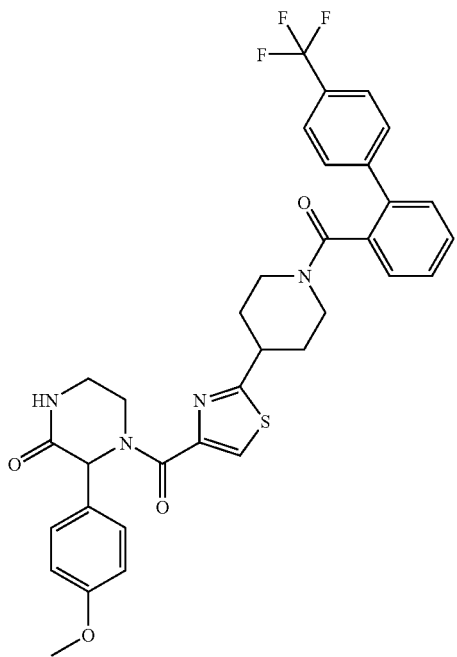 3-(4-methoxyphenyl)-4-{[2-(1-{[4'-trifluromethyl)biphenyl-2-yl}carbonyl}-piperidin-4-yl)-1,3-thiazol-4-yl]carbonyl}piperazin-2-one | |

TABLE 1-continued
| No. | FORMULA | NMR or mass |
|---|---|---|
| 152 | 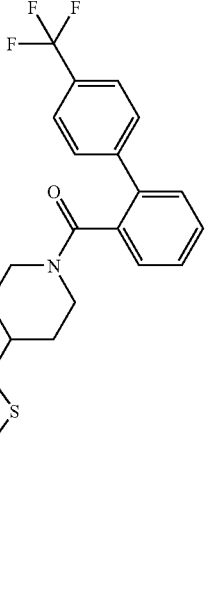 N-(6-cyano-3-hydroxy-2,2-dimethyl-3,4-dihydro-2H-chromern-4-yl)-2-(1-{[4'-(trifluoromethyl)biphenyl-2-yl]carbonyl}piperidin-4-yl)-1,3-thiazole-4-carboxamide | |
| 153 | 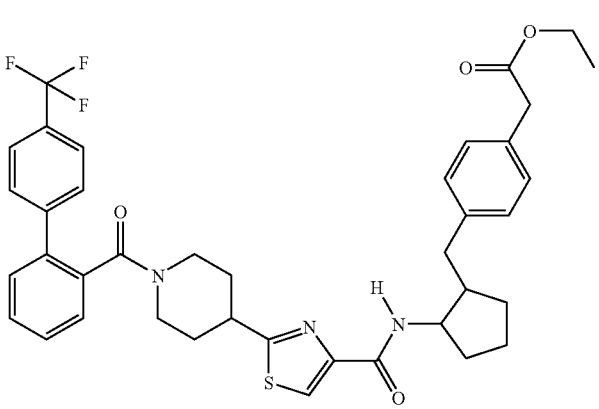 | |
| 154 | 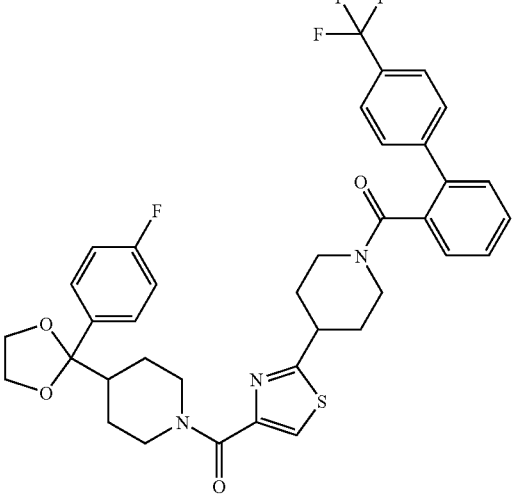 | |

TABLE 1-continued
| No. | FORMULA | NMR or mass |
|-----|---------|-------------|
155
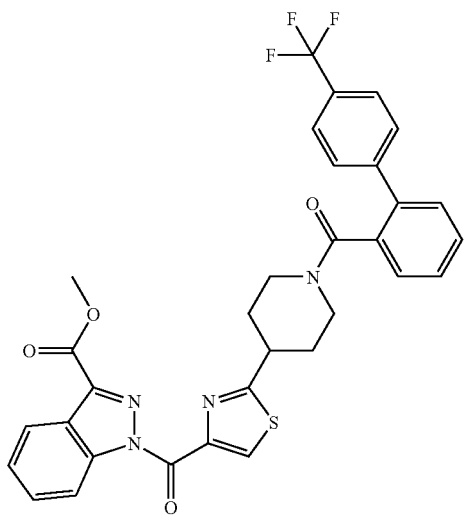
methyl 1-{[2-(1-{[4'-(trifluoromethyl)biphenyl-2-yl]carbonyl}piperidin-4-yl)-1,3-thiazol-4-yl]carbonyl}-1H-indazole-3-carboxylate
156
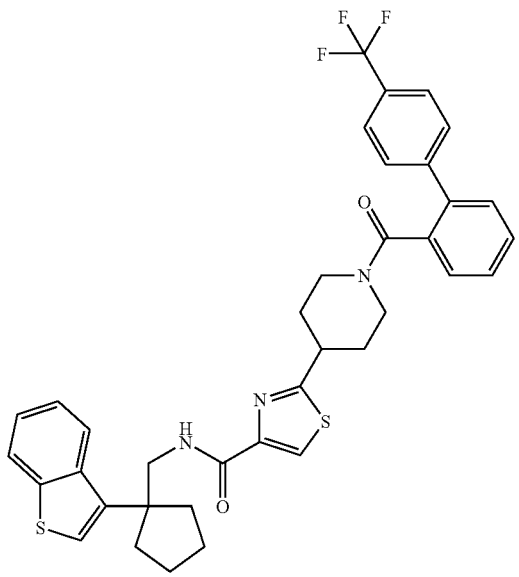
N-{[1-(1-benzothien-3-yl)cyclopentyl]methyl}-2-(1-{[4'-(trifluoromethyl)-biphenyl-2-yl]carbonyl}piperidin-4-yl)-1,3-thiazole-4-carboxamide TABLE 1-continued
| No. | FORMULA | NMR or mass |
|---|---|---|
| 157 | 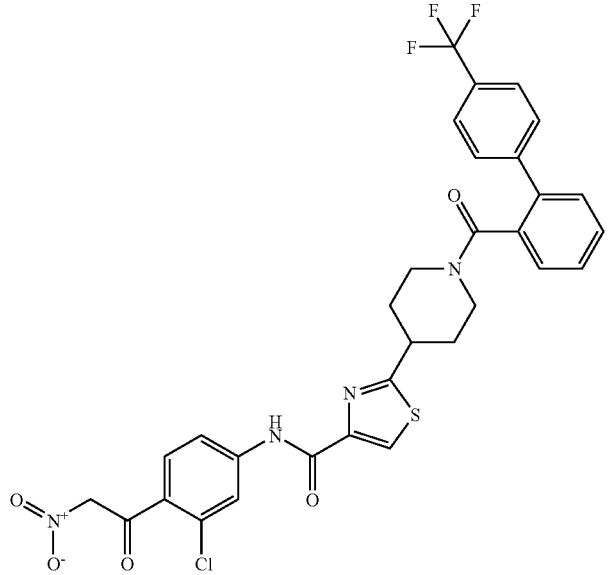 N-{3-chloro-4-(nitroacetyl)phenyl]-2-(1-{[4'-trifluoromethyl)biphenyl-2-yl]-carbonyl}piperidin-4-yl)-1,3-thiazole-4-carboxamide | |
| 158 | 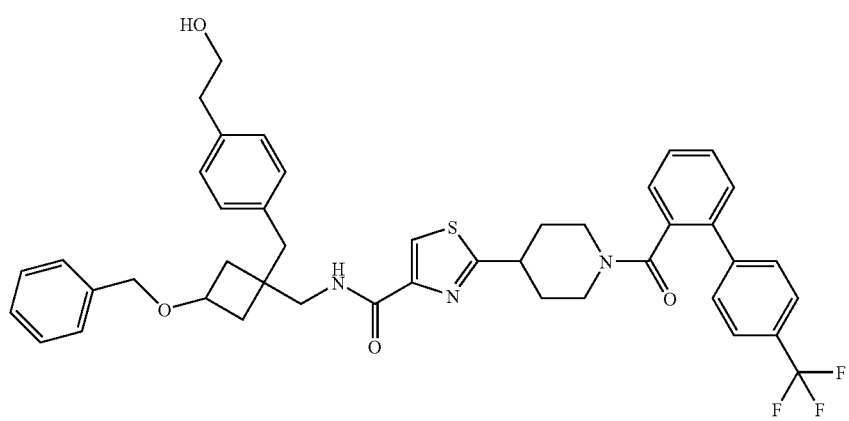 N-({3-(benzyloxy)-1-[4-(2-hydroxyethyl)benzyl]cyclobutyl}methyl)-2-(1-{[4'-(trifluromethyl)biphenyl-2-yl]-carbonyl}piperidin-4-yl)-1,3-thiazole-4-carboxamide | |

| No. | FORMULA | NMR or mass |
|---|---|---|
| 159 | 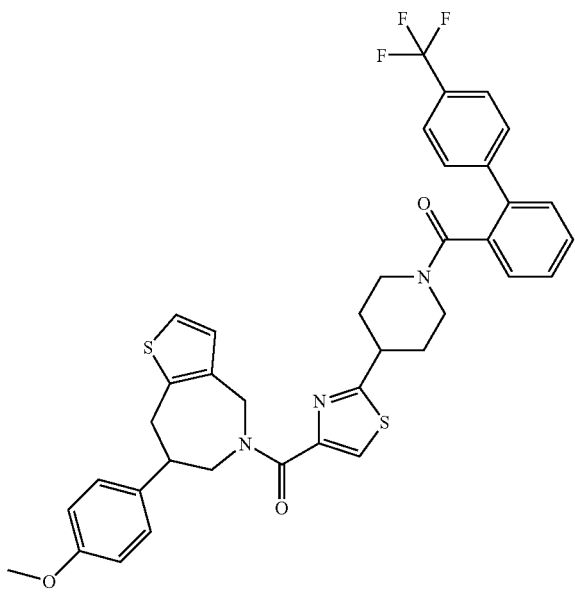<br>7-(4-methoxyphenyl)-5-{[2-(1-{[4'-(trifluoromethyl)biphenyl-2-yl]-carbonyl}-piperidin-4-yl)-1,3-thiazol-4-yl]carbonyl}-5,6,7,8-tetrahydro-4H-thieno[3,2-c]azepine | |
| 160 | 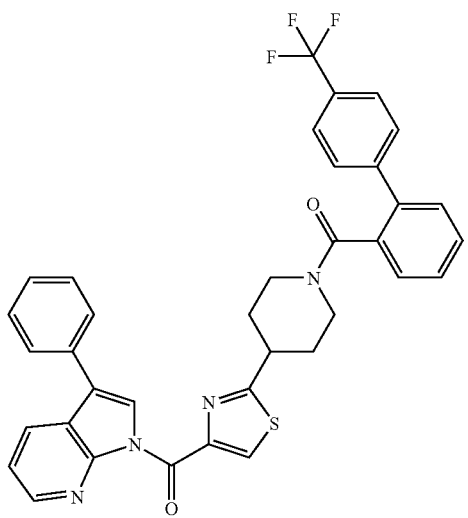<br>3-phenyl-1-{[2-(1-{[4'-(trifluoromethyl)biphenyl-2-yl]carbonyl}piperidin-4-yl)-1,3-thiazol-4-yl]carbonyl}-1H-pyrrolo[2,3-b]pyridine | |

TABLE 1-continued
| No. | FORMULA | NMR or mass |
|---|---|---|
| 161 | 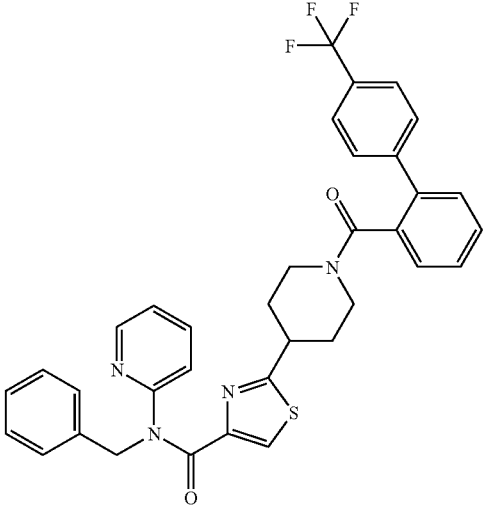 N-benzyl-n-pyridin-2-yl-2-(1-{[4'-(trifluromethyl)biphenyl-2-yl]carbonyl}-piperidin-4-yl)-1,3-thiazole-4-carboxamide | |
| 162 | 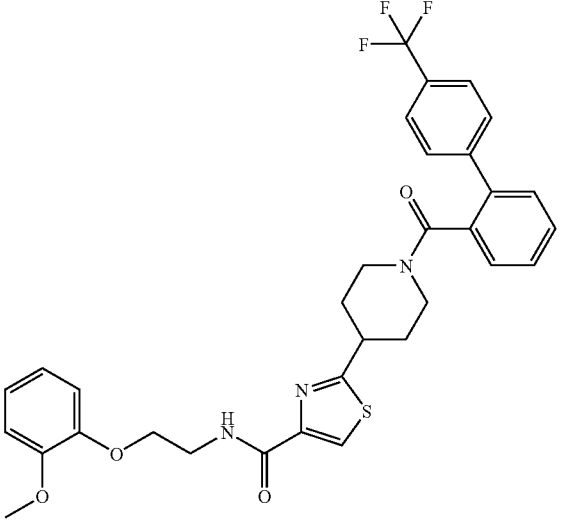 N-[2-(2-methoxyphenoxy)ethyl]-2-(1-{[4'-(trifluoromethyl)biphenyl-2-yl]-carbonyl}piperidin-4-yl)-1,3-thiazole-4-carboxamide | |
| 163 | 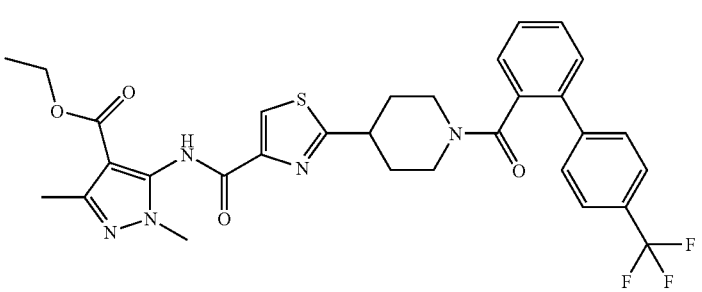 | |

TABLE 1-continued
| No. | FORMULA | NMR or mass |
|---|---|---|
| 164 | 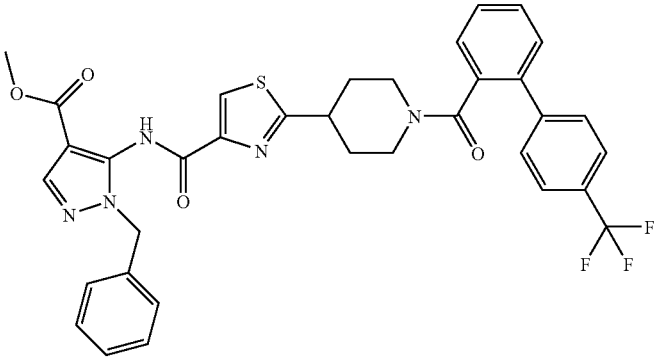 | |
| 165 | 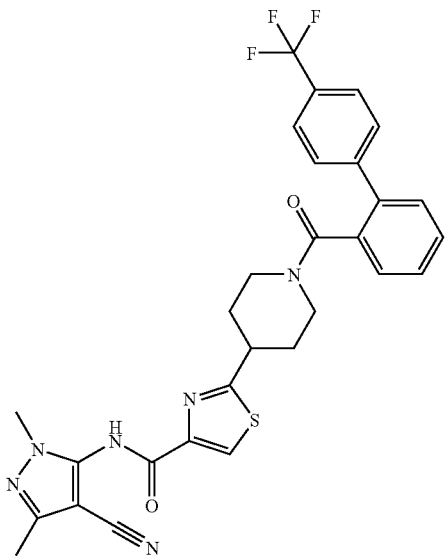 N-(4-cyano-1,3-dimethyl-1H-pyrazol-5-yl)-2-(1-{[4'-(trifluoromethyl)-biphenyl-2-yl]carbonyl}piperidin-4-yl)-1,3-thiazole-4-carboxamide | |
| 166 | 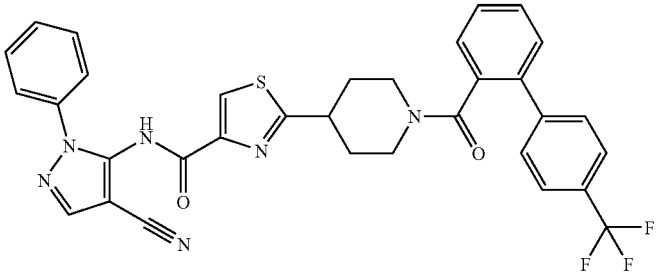 | |
| 167 | 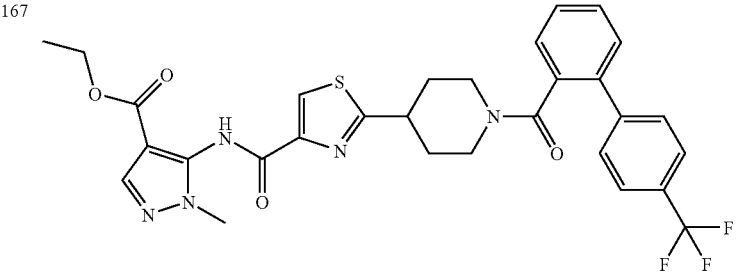 | |

TABLE 1-continued

| No. | FORMULA | NMR or mass |
|---|---|---|

168

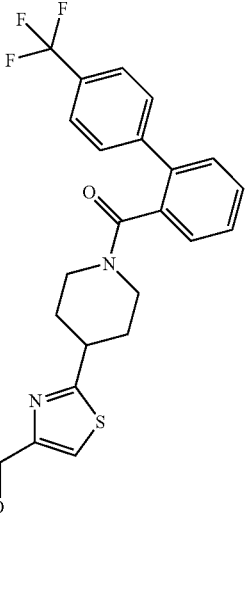

4-chlorophenyl 4-({[2-(1-{[4′-(trifluoromethyl)biphenyl-2-yl]carbonyl)piperidin-4-yl)-1,3-thiazol-4-yl]carbonyl}amino)benzoate

169

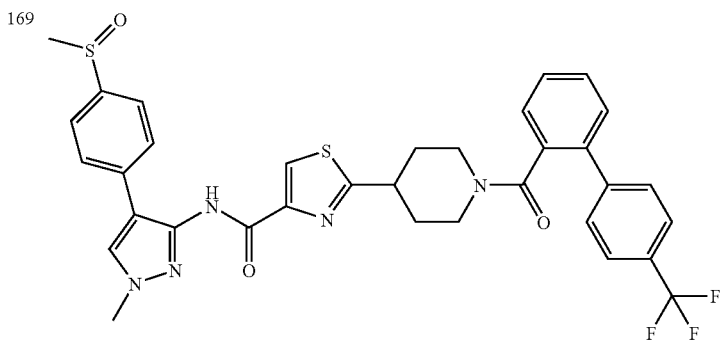

N-{1-methyl-4-[4-(methylsulfinyl)phenyl]-1H-pyrazol-3-yl}-2-(1-{[4′-(trifluoromethyl)-biphenyl-2-yl]carbonyl}piperidin-4-yl)-1,3-thiazole-4-carboxamide

170

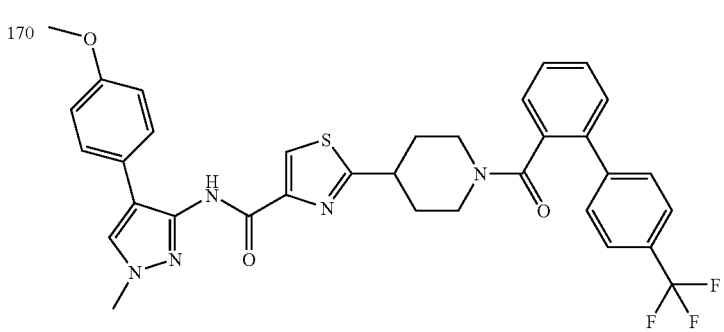

N-[4-(4-methoxyphenyl)-1-methyl-1H-pyrazol-3-yl]-2-(1-{[4′-(trifluoromethyl)-biphenyl-2-yl]carbonyl}piperidin-4-yl)-1,3-thiazole-4-carboxamide TABLE 1-continued
| No. | FORMULA | NMR or mass |
|---|---|---|
171 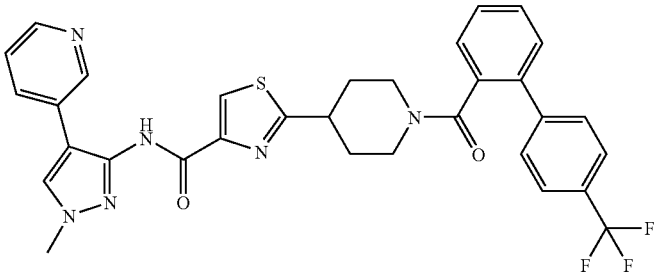
172 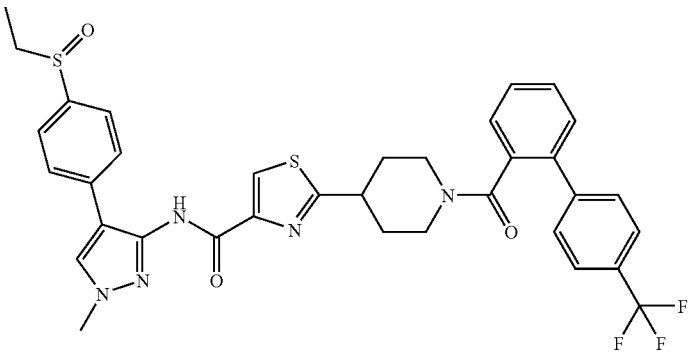
173 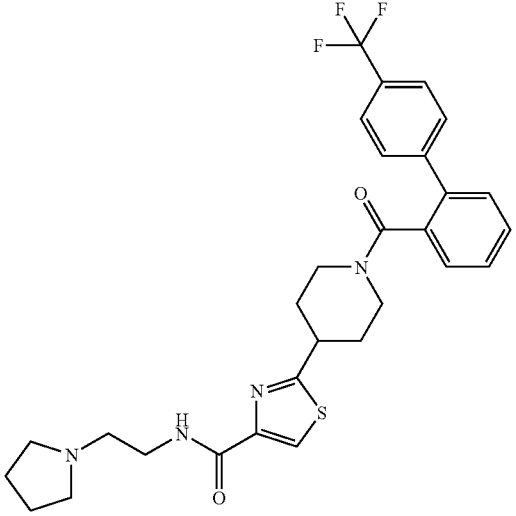
N-(2-pyrrolidin-1-ylethyl)-2-(1-{[4'-(trifluoromethyl)biphenyl-2-yl]-
carbonyl}-piperidin-4-yl)-1,3-thiazole-4-carboxamide

| No. | FORMULA | NMR or mass |
|---|---|---|
| 174 | 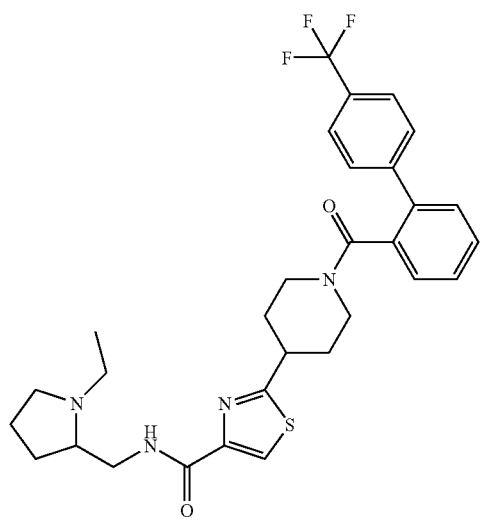<br>N-[(1-ethylpyrrolidin-2-yl)methyl]-2-(1-{[4'-(trifluoromethyl)biphenyl-2-yl]-carbonyl}piperidin-4-yl)-1,3-thiazole-4-carboxamide | |
| 175 | CHIRAL<br>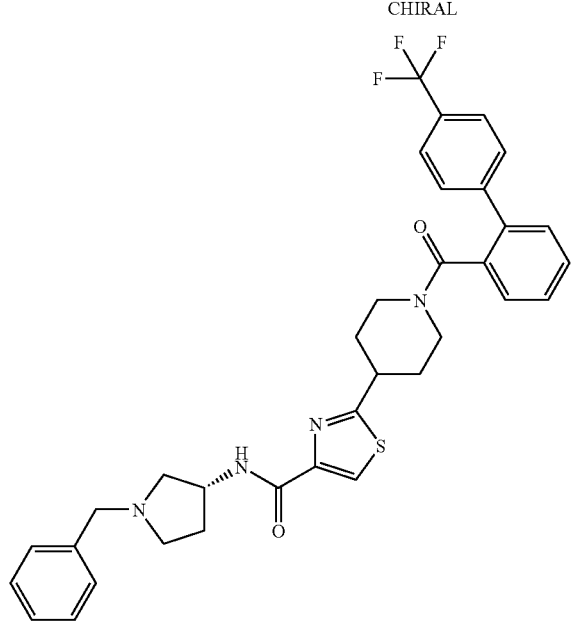<br>N-[(3R)-1-benzylpyrrolidin-3-yl]-2-{[4'-(trifluoromethyl)biphenyl-2-yl]-carbonyl}piperidin-4-yl-1,3-thiazole-4-carboxamide | |

| No. | FORMULA | NMR or mass |
|---|---|---|
| 176 | 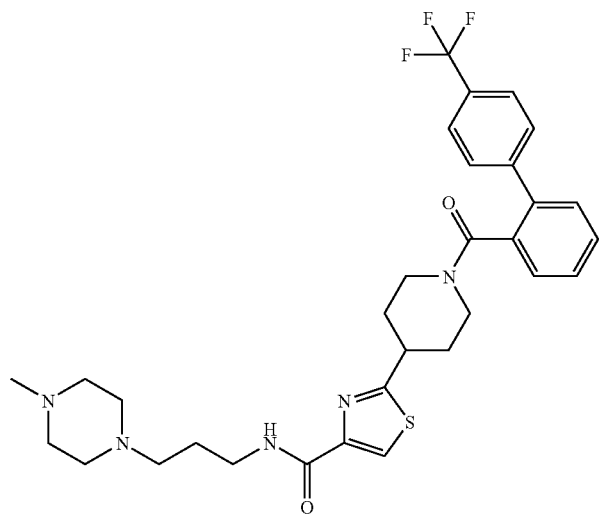<br>N-[3-(4-methylpiperazin-1-yl)propyl]-2-(1-{[4'-(trifluoromethyl)biphenyl-2-yl]-carbonyl}piperidin-4-yl)-1,3-thiazole-4-carboxamide | |
| 177 | 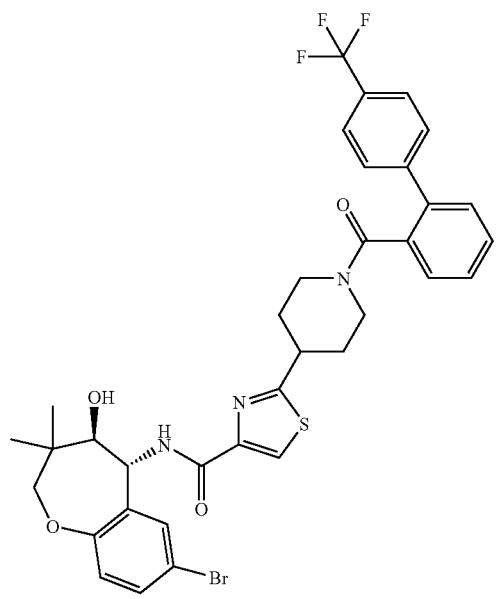<br>N-[(4R,5R)-7-bromo-4-hydroxy-3,3-dimethyl-2,3,4,5-tetrahydro-1-benz-oxepin-5-yl]-2-(1-{[4'-(trifluoromethyl)biphenyl-2-yl]carbonyl}piperidin-4-yl)-1,3-thiazole-4-carboxamide | |

TABLE 1-continued
| No. | FORMULA | NMR or mass |
|---|---|---|
| 178 | 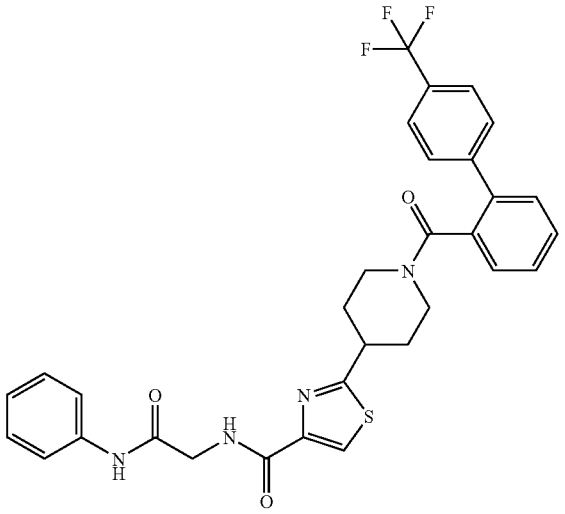 | |
| 179 |  | |
N'-[(1H-benzimidazol-2-ylthio)acetyl]-2-(1-{[4'-(trifluoromethyl)biphenyl-2-yl]-carbonyl}piperidin-4-yl)-1,3-thiazole-4-carbohydrazide
| 180 | 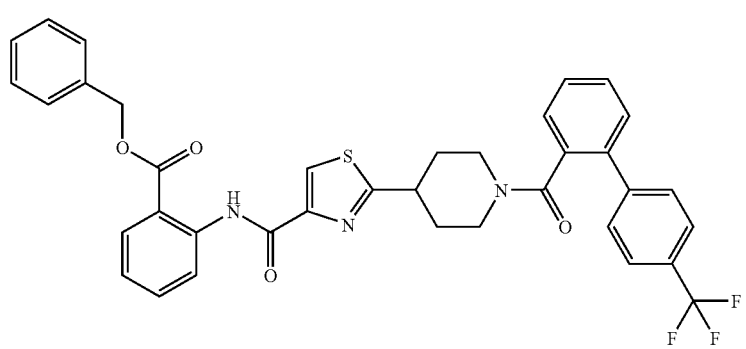 | |

| No. | FORMULA | NMR or mass |
|---|---|---|
| 181 | 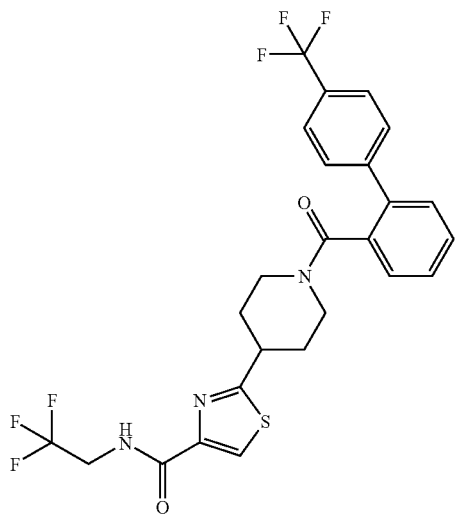 N-(2,2,2-trifluoroethyl)-2-(1-{[4'-(trifluoromethyl)biphenyl-2-yl]carbonyl}-piperidin-4-yl)-1,3-thiazole-4-carboxamide | |
| 182 | 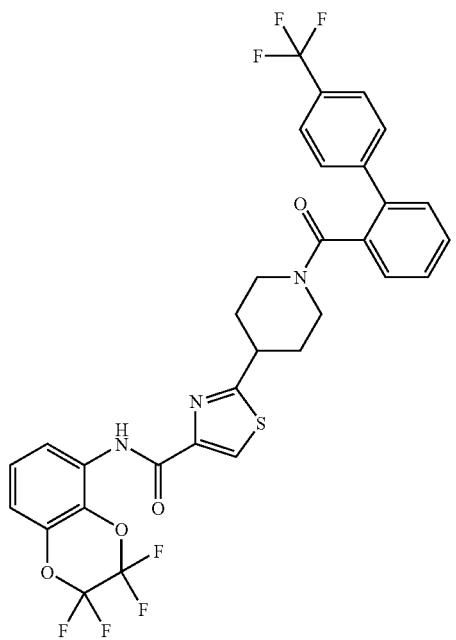 N-(2,2,3,3-tetrafluoro-2,3-dihydro-1,4-benzodioxin-5-yl)-2-(1-{[4'-(trifluoromethyl)biphenyl-2-yl]carbonyl}piperidin-4-yl)-1,3-thiazole-4-carboxamide | |

| No. | FORMULA | NMR or mass |
|---|---|---|
| 183 | 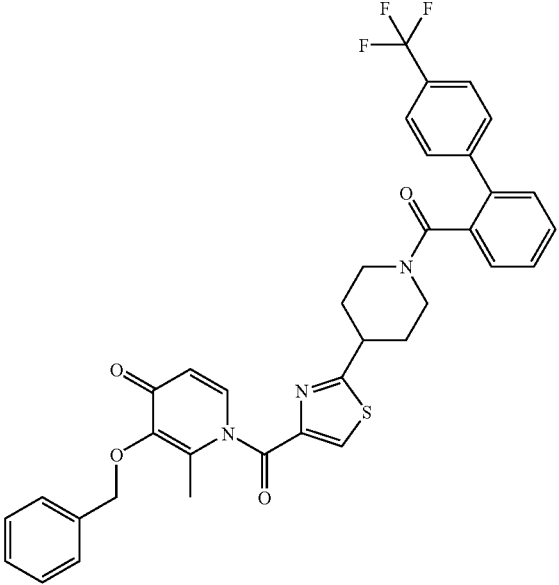<br>3-(benzyloxy)-2-methyl-1-{[2-(1-{[4'-(trifluoromethyl)biphenyl-2-yl]carbonyl}-piperidin-4-yl)-1,3-thiazol-4-yl]carbonyl}pyridin-4-(1H)-one | |
| 184 | 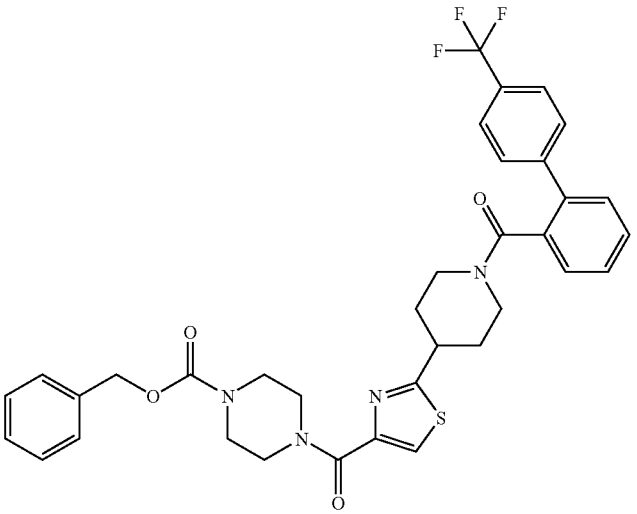<br>benzyl 4-{[2-(1-{[4'-(trifluoromethyl)biphenyl-2-yl]carbonyl}piperidin-4-yl)-1,3-thiazol-4-yl]carbonyl}piperazine-1-carboxylate | |

TABLE 1-continued
| No. | FORMULA | NMR or mass |
|---|---|---|
| 185 | 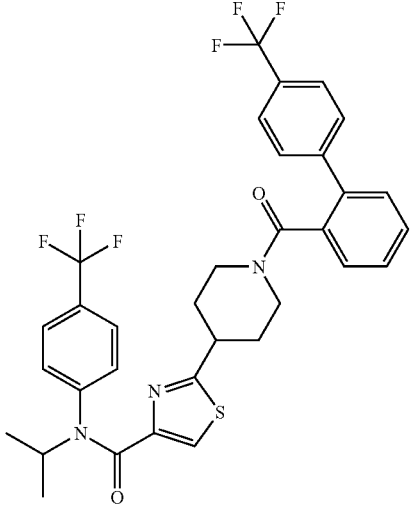 N-isopropyl-2-(1-{[4'-(trifluoromethyl)biphenyl-2-yl]carbonyl}piperidin-4-yl)-N-[4-(trifluoromethyl)phenyl]-1,3-thiazole-4-carboxamide | |
| 186 | 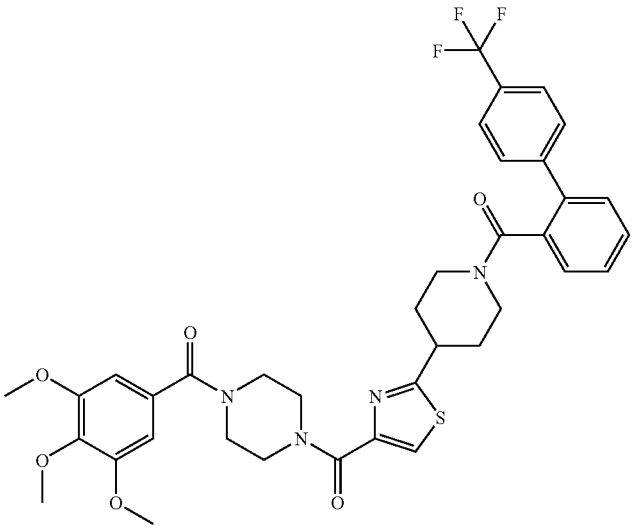 | |

TABLE 1-continued
| No. | FORMULA | NMR or mass |
|---|---|---|
| 187 | 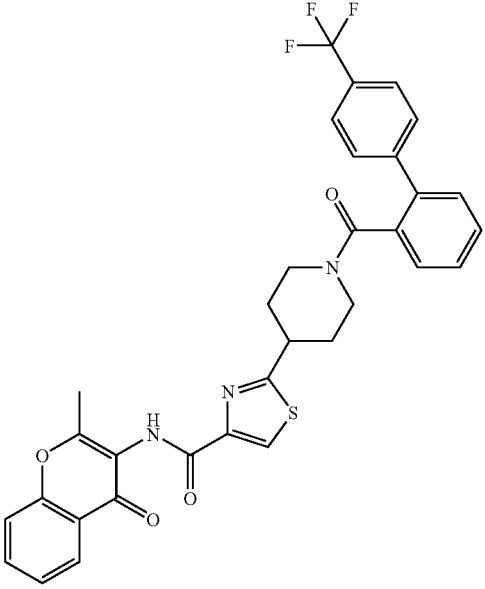 N-(2-methyl-4-oxo-4H-chromen-3-yl)-2-(1-{[4'-(trifluoromethyl)biphenyl-2-yl]-carbonyl}piperidin-4-yl)-1,3-thiazole-4-carboxamide | |
| 188 | 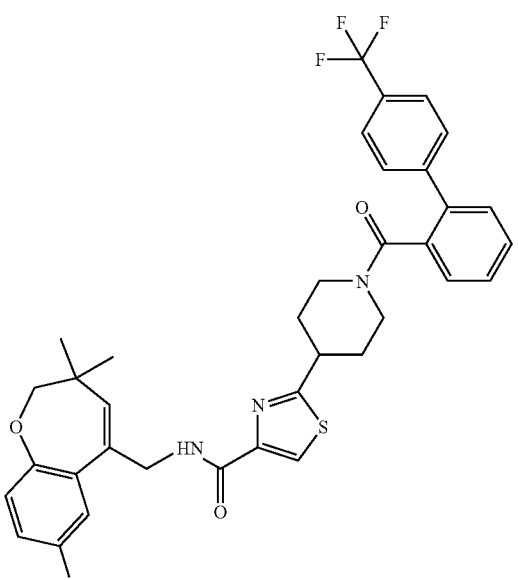 N-[(7-bromo-3,3-dimethyl-2,3-dihydro-1-benzoxepin-5-yl)methyl]-2-(1-{[4'-(trifluoromethyl)biphenyl-2-yl]carbonyl}piperidin-4-yl)-1,3-thiazole-4-carboxamide | |

| No. | FORMULA | NMR or mass |
|---|---|---|
| 189 | 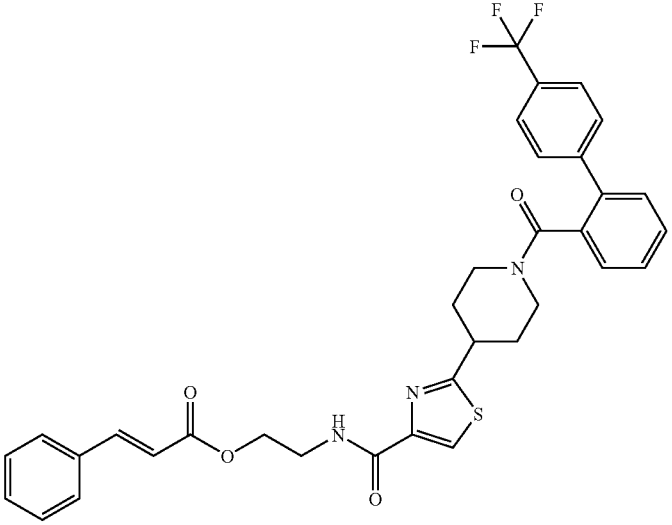 2-({[2-(1-{[4'-(trifluoromethyl)bipenyl-2-yl]carbonyl}piperidin-4-yl)-1,3-thiazol-4-yl]carbonyl}amino)ethyl(2E)-3-phenylacrylate | |
| 190 | 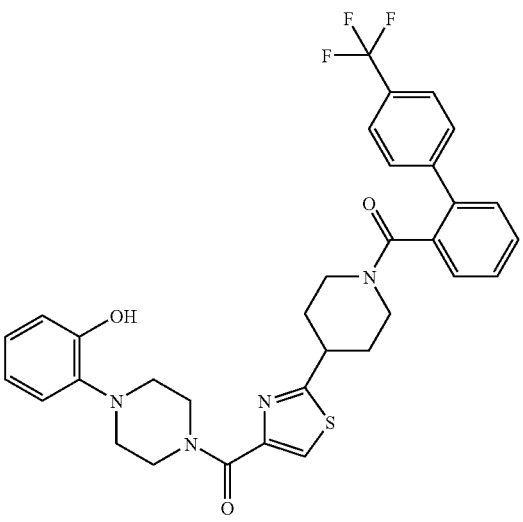 2-(4-{[2-(1-{[4'-(trifluoromethyl)biphenyl-2-yl]carbonyl}piperidin-4-yl)-1,3-thiazol-4-yl]carbonyl}piperazin-1-yl)phenol | |

TABLE 1-continued
| No. | FORMULA | NMR or mass |
|---|---|---|
| 191 | 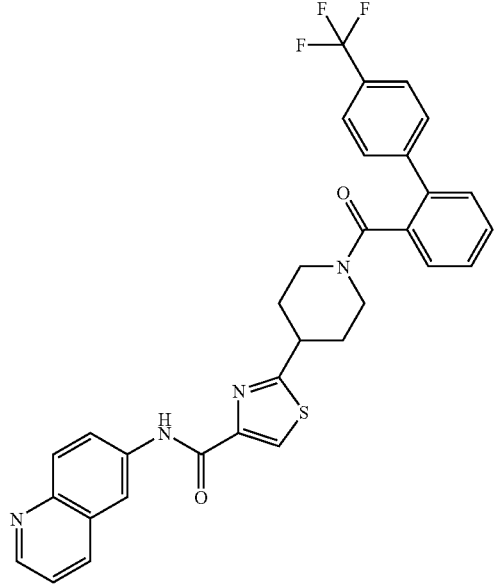 N-quinolin-6-yl-2-(1-{[4'-(trifluoromethyl)biphenyl-2-ly]carbonyl}piperidin-4-yl)-1,3-thiazole-4-carboxamide | |
| 192 | 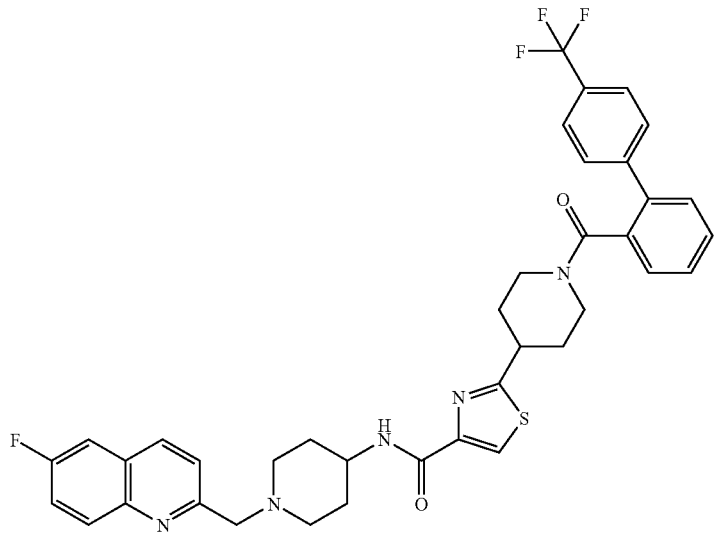 N-{1-[(6-fluroquinolin-2-yl)methyl]piperidin-4-yl}-2-(1-{[4'-(trifluromethyl)-biphenyl-2-yl]carbonyl}piperidin-4-yl)-1,3-thiazole-4-carboxamide | |

| No. | FORMULA | NMR or mass |
|---|---|---|
| 193 | 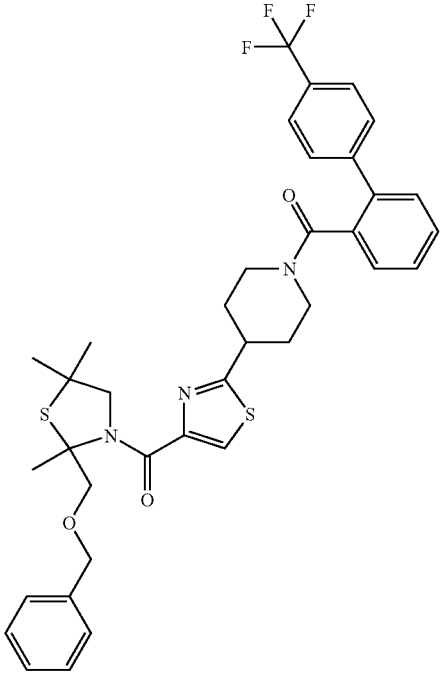<br>4-[4-({2-[(benzyloxy)methyl]-2,5,5-trimethyl-1,3-thiazolidin-3-yl}carbonyl)-1,3-thiazol-2-yl]-1-{[4'-(trifluoromethyl)biphenyl-2-yl]carbonyl}piperidine | |
| 194 | 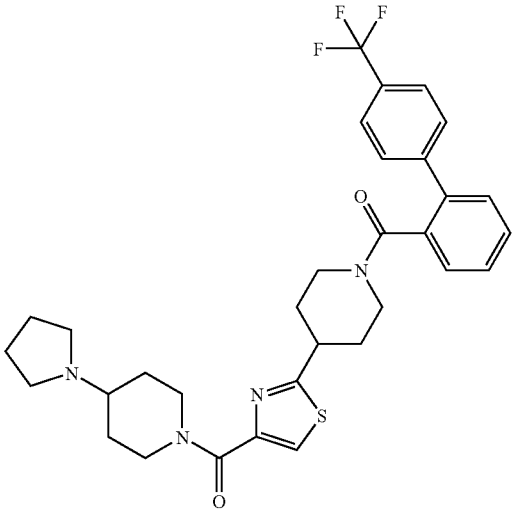<br>4-pyrrolidin-1-yl-1-{[2-(1-{[4'-(trifluoromethyl)biphenyl-2-yl]carbonyl}-piperidin-4-yl)-1,3-thiazol-4-yl]carbonyl}piperidine | |

TABLE 1-continued
| No. | FORMULA | NMR or mass |
|---|---|---|
| 195 | 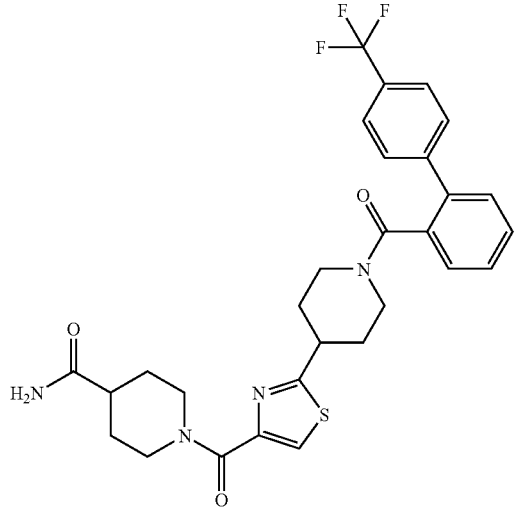 1-{[2-(1-{[4'-(trifluoromethyl)biphenyl-2-yl]carbonyl}piperidin-4-yl)-1,3-thiazol-4-yl]carbonyl}piperidine-4-carboxamide | |
| 196 | 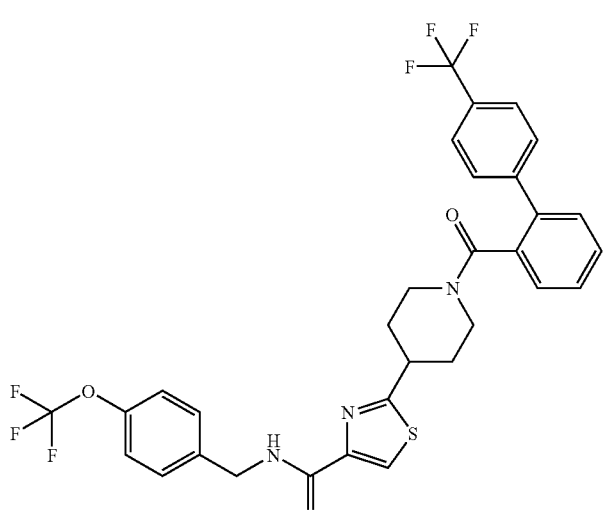 N-[4-(trifluoromethoxy)benzyl]-2-(1-{[4'-(trifluoromethyl)biphenyl-2-yl]-carbonyl}-piperidin-4-yl)-1,3-thiazole-4-carboxamide | |

TABLE 1-continued
| No. | FORMULA | NMR or mass |
|---|---|---|
| 197 | 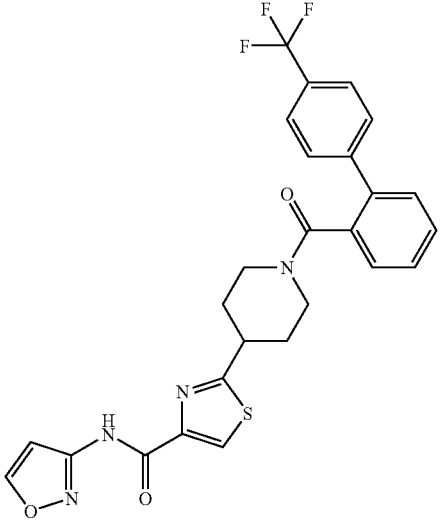<br>N-isoxazol-3-yl-2-(1-{[4'-(trifluoromethyl)biphenyl-2-yl]carbonyl}piperidin-4-yl)-1,3-thiazole-4-carboxamide | |
| 198 | 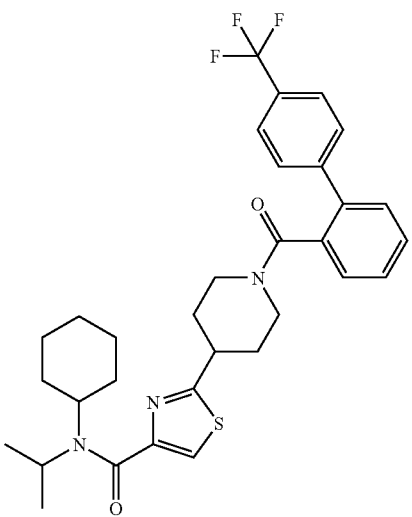<br>N-cyclohexyl-N-isopropyl-2-(1-{[4'-(trifluoromethyl)biphenyl-2-yl]carbonyl}-piperidin-4-yl)-1,3-thiazole-4-carboxamide | |

TABLE 1-continued
| No. | FORMULA | NMR or mass |
|---|---|---|
| 199 | 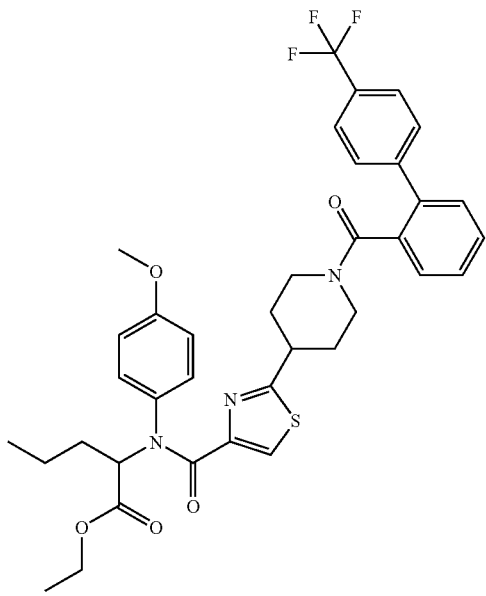 ethyl N-(4-methoxyphenyl)-N-{[2-(1-{[4'-(trifluoromethyl)biphenyl-2-yl]-carbonyl}piperidin-4-yl)-1,3-thiazol-4-yl]carbonyl}norvalinate | |
| 200 | 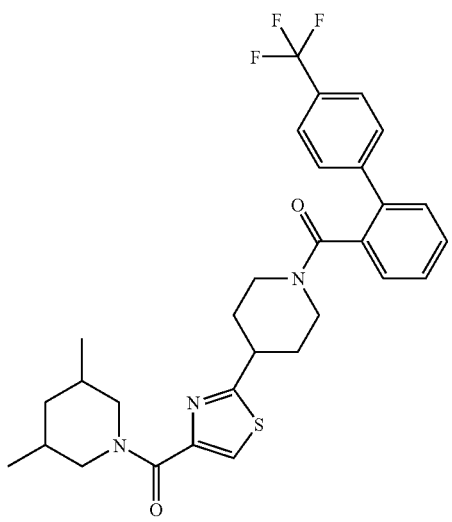 3,5-dimethyl-1-{[2-(1-{[4'-(trifluoromethyl)biphenyl-2-yl]carbonyl}piperidin-4-yl)-1,3-thiazol-4-yl]carbonyl}piperidine | |

TABLE 1-continued
| No. | FORMULA | NMR or mass |
|---|---|---|
| 201 | 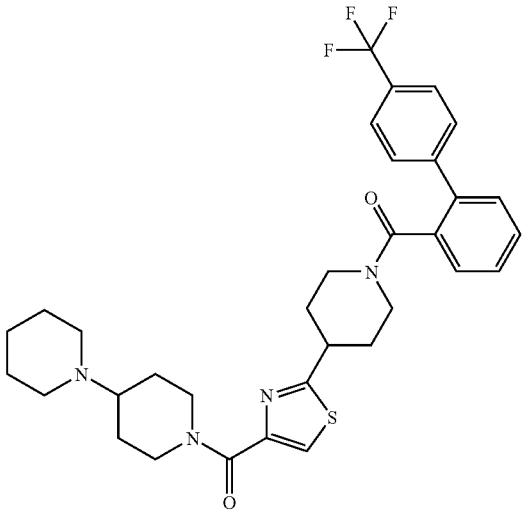 1'-{[2-(1-{[4'-(trifluoromethyl)biphenyl-2-yl]carbonyl}piperidin-4-yl)-1,3-thiazol-4-yl]carbonyl}-1,4'-bipiperidine | |
| 202 | 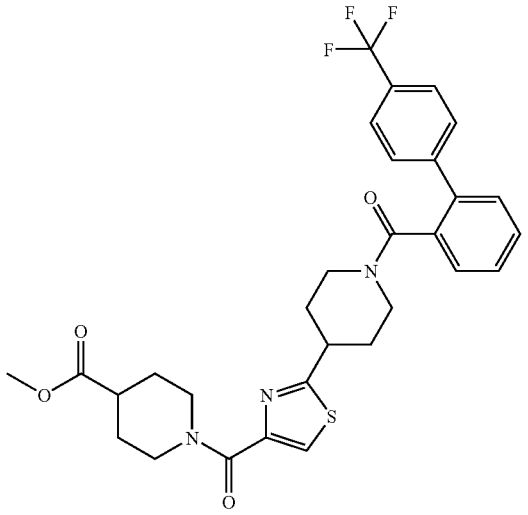 methyl 1-({2-(1-{[4'-(trifluoromethyl)biphenyl-2-yl]carbonyl}piperidin-4-yl)-1,3-thiazol-4-yl]carbonyl}piperidine-4-carboxylate | |

| No. | FORMULA | NMR or mass |
|---|---|---|
| 203 | 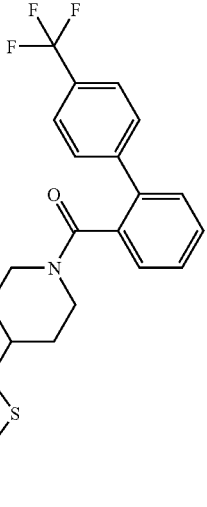 2-{[2-(1-{[4'-(trifluoromethyl)biphenyl-2-yl]carbonyl}piperidin-4-yl)-1,3-thiazol-4-yl]carbonyl}decahydroisoquinoline | |
| 204 | 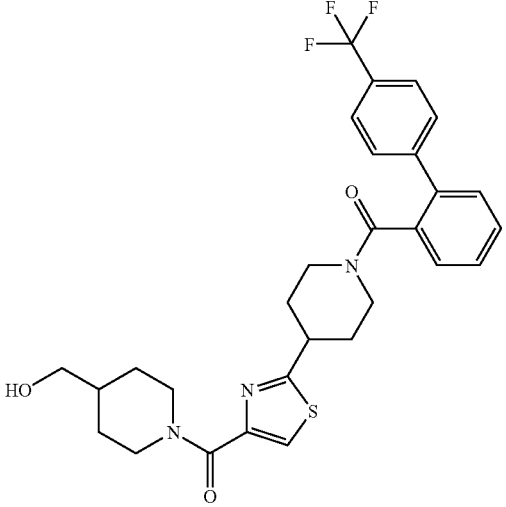 (1-{[2-(1-{[4'-(trifluoromethyl)biphenyl-2-yl]carbonyl}piperidin-4-yl)-1,3-thiazol-4-yl]carbonyl}piperidin-4-yl)methanol | |

| No. | FORMULA | NMR or mass |
|---|---|---|
| 205 | 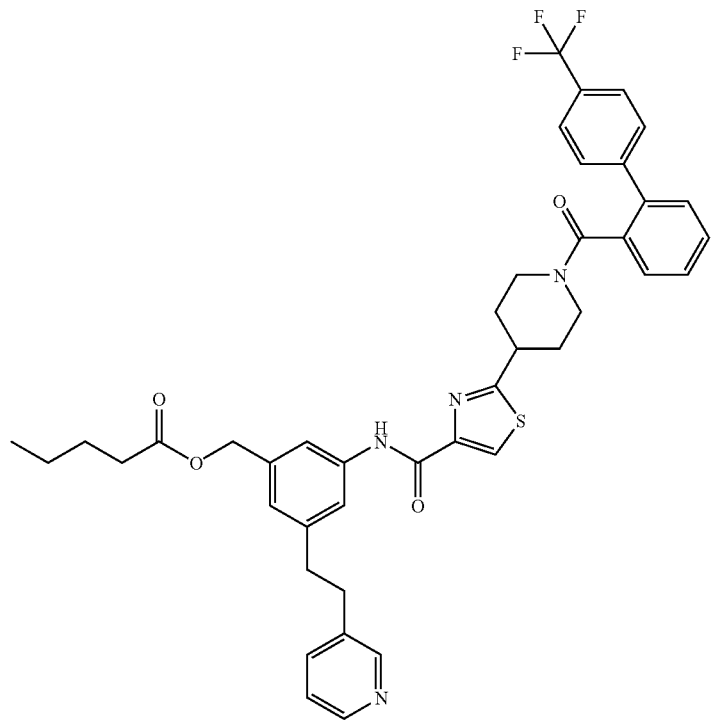 3-(2-pyridin-3-ylethyl)-5-({[2-(1-{[4'-(trifluoromethyl)biphenyl-2-yl]carbonyl}-piperidin-4-yl)-1,3-thiazol-4-yl]carbonyl}amino)benzyl pentanoate | |
| 206 | 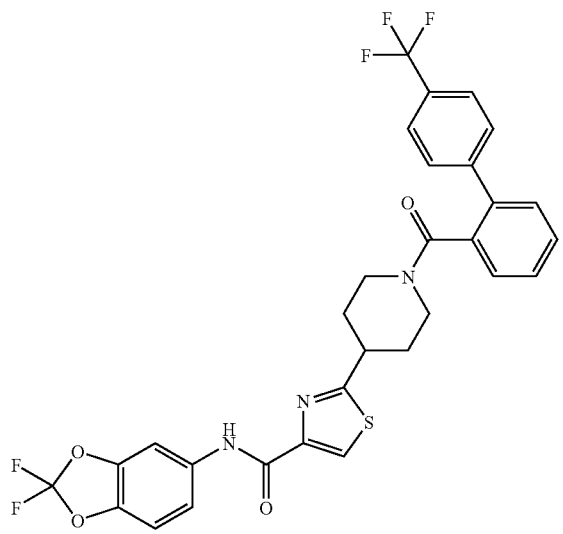 N-(2,2-difluoro-1,3-benzodioxol-5-yl)-2-(1-{[4'-(trifluoromethyl)biphenyl-2-yl]-carbonyl}piperidin-4-yl)-1,3-thiazole-4-carboxamide | |

| No. | FORMULA | NMR or mass |
|---|---|---|
| 207 | 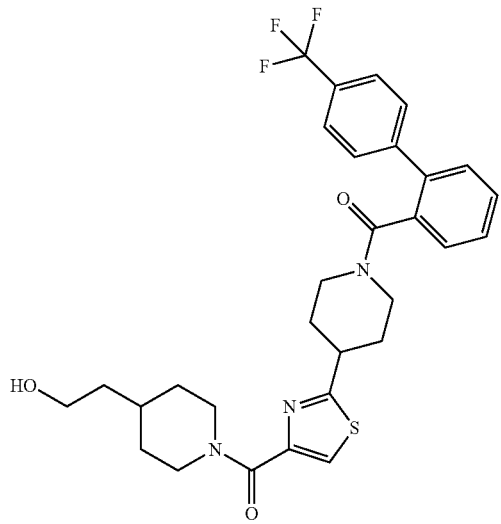<br>2-(1-{[2-(1-{[4'-(trifluoromethyl)biphenyl-2-yl]carbonyl}piperidin-4-yl)-1,3-thiazol-4-yl]carbonyl}piperidin-4-yl)ethanol | |
| 208 | 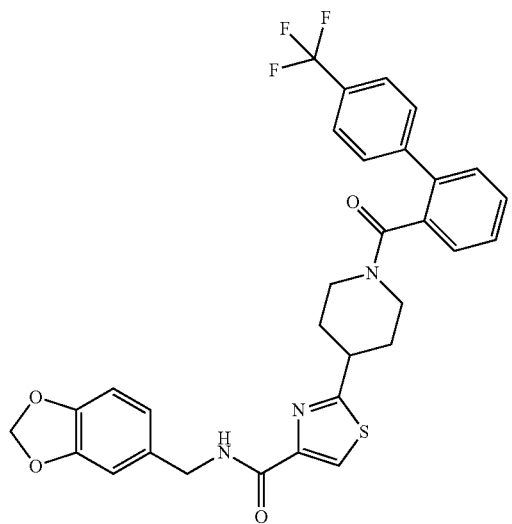<br>N-(1,3-benzodioxol-5-ylmethyl)-2-(1-{[4'-(trifluoromethyl)biphenyl-2-yl]-carbonyl}piperidin-4-yl)-1,3-thiazole-4-carboxamide | |

TABLE 1-continued
| No. | FORMULA | NMR or mass |
|-----|---------|-------------|
209
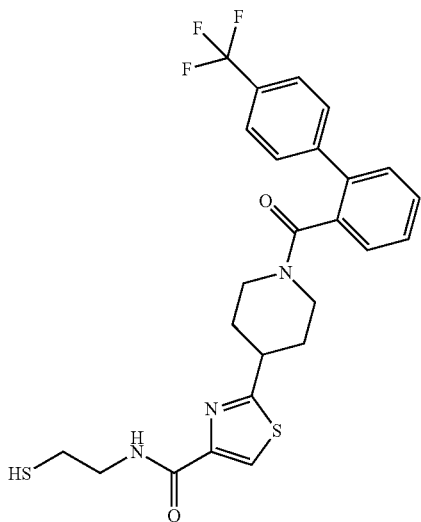
N-(2-mercaptoethyl)-2-(1-{[4'-(trifluoromethyl)biphenyl-2-yl]-carbonyl}-piperidin-4-yl)-1,3-thiazole-4-carboxamide
210
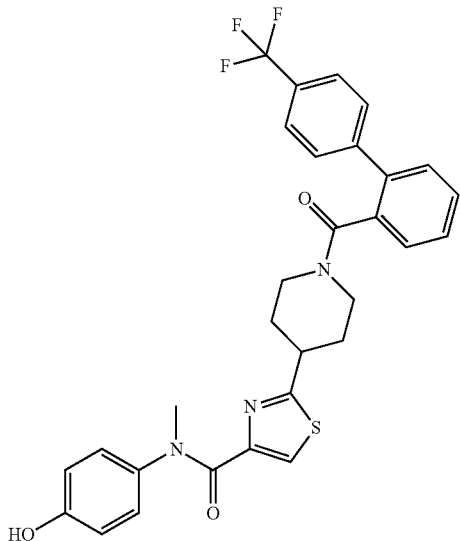
N-(4-hydroxyphenyl)-N-methyl-2-(1-{[4'-(trifluoromethyl)biphenyl-2-yl]-carbonyl}piperidin-4-yl)-1,3-thiazole-4-carboxamide TABLE 1-continued
| No. | FORMULA | NMR or mass |
|---|---|---|
| 211 | 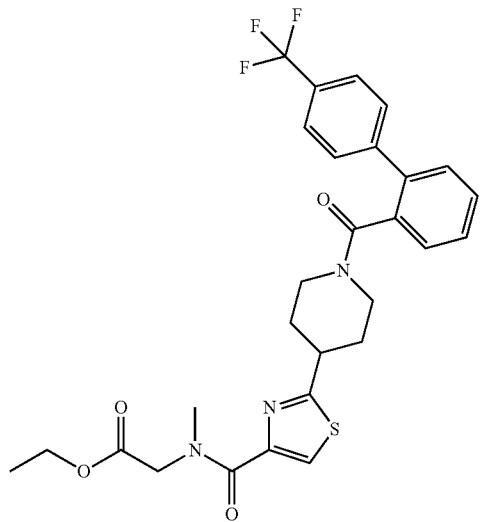 ethyl N-methyl-N-{[2-(1-{[4'-(trifluoromethyl)biphenyl-2-yl]carbonyl}piperidin-4-yl)-1,3-thiazol-4-yl]carbonyl}glycinate | |
| 212 | 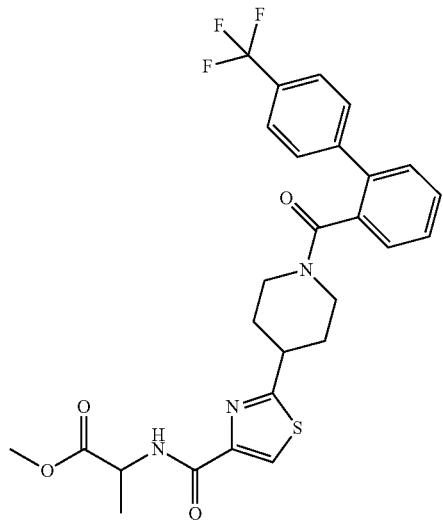 methyl N-{[2-(1-{[4'-(trifluoromethyl)biphenyl-2-yl]carbonyl}piperidin-4-yl)-1,3-thiazol-4-yl]carbonyl}alaninate | |

TABLE 1-continued
| No. | FORMULA | NMR or mass |
|---|---|---|
| 213 | 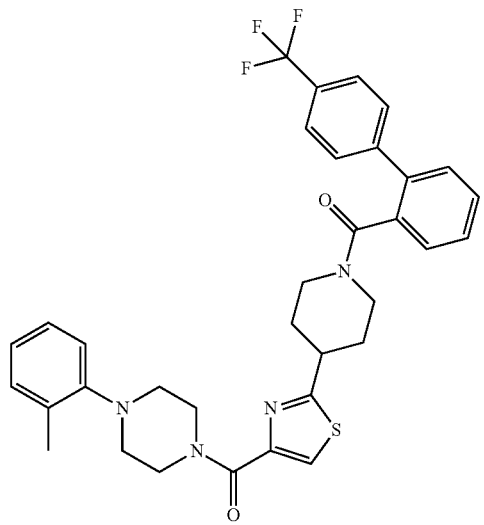 1-(2-methylphenyl)-4-{[2-(1-{[4'-(trifluoromethyl)biphenyl-2-yl]carbonyl}-piperidin-4-yl)-1,3-thiazol-4-yl]carbonyl}piperazine | |
| 214 | 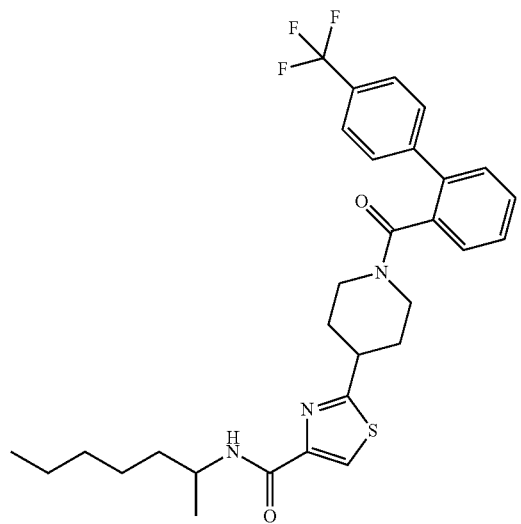 N-(1-methylhexyl)-2-(1-{[4'-(trifluoromethyl)biphenyl-2-yl]carbonyl}piperidin-4-yl)-1,3-thiazole-4-carboxamide | |

| No. | FORMULA | NMR or mass |
|---|---|---|
| 215 | 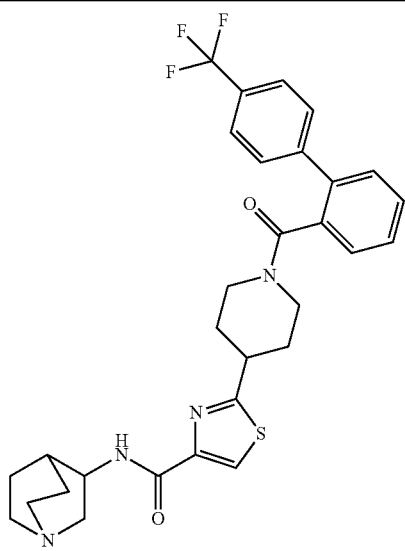 N-1-azabicyclo[2.2.2]oct-3-yl-2-(1-{[4'-(trifluoromethyl)biphenyl-2-yl]-carbonyl}piperidin-4-yl)-1,3-thiazole-4-carboxamide | |
| 216 | 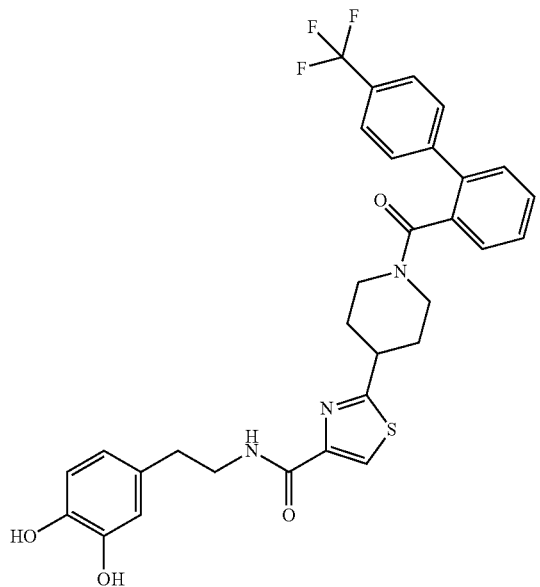 N-[2-(3,4-dihydroxyphenyl)ethyl]-2-(1-{[4'-(trifluoromethyl)biphenyl-2-yl]-carbonyl}piperidin-4-yl)-1,3-thiazole-4-carboxamide | |

TABLE 1-continued
| No. | FORMULA | NMR or mass |
|---|---|---|
| 217 | 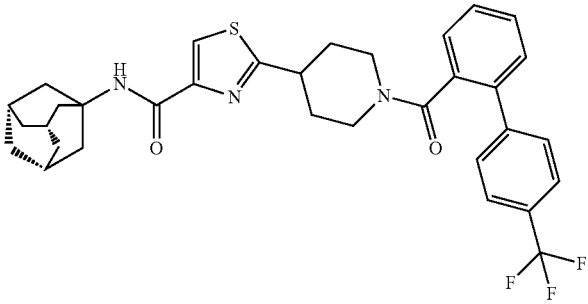 N-[(3s,5s,7s)-1-adamantyl]-2-(1-{[4'-(trifluoromethyl)biphenyl-2-yl]-carbonyl}piperidin-4-yl)-1,3-thiazole-4-carboxamide | |
| 218 | 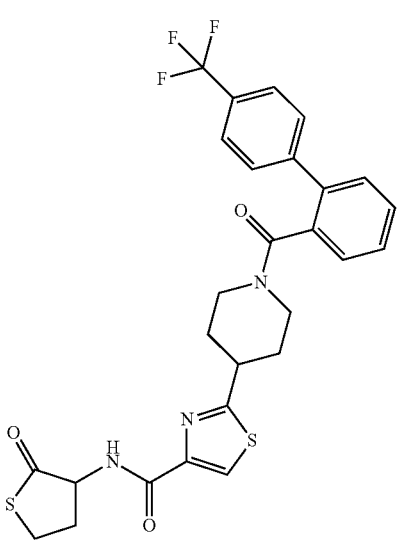 N-(2-oxotetrahydro-3-thienyl)-2-(1-{[4'-(trifluoromethyl)biphenyl-2-yl]-carbonyl}piperidin-4-yl)-1,3-thiazole-4-carboxamide | |
| 219 | 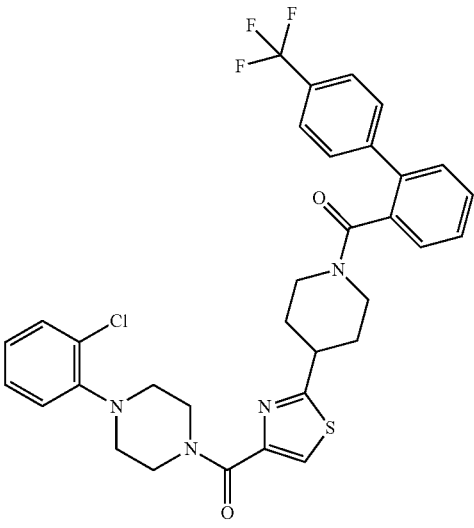 1-(2-chlorophenyl)-4-{[2-(1-{[4'-(trifluoromethyl)biphenyl-2-yl]carbonyl}-piperidin-4-yl)-1,3-thiazol-4-yl]carbonyl}piperazine | |

TABLE 1-continued
| No. | FORMULA | NMR or mass |
|---|---|---|
| 220 | 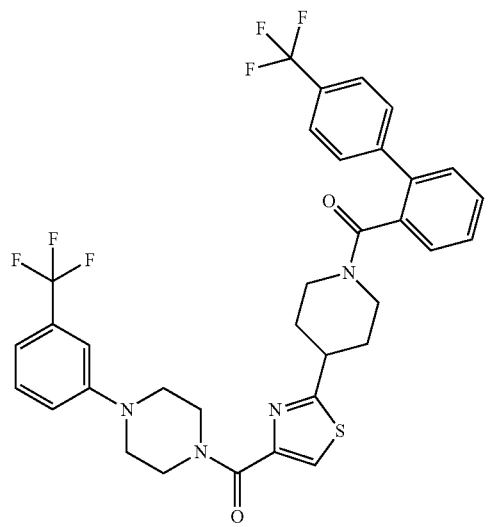<br>1-{[2-(1-{[4'-(trifluoromethyl)biphenyl-2-yl]carbonyl}piperidin-4-yl)-1,3-thiazol-4-yl]carbonyl}-4-[3-(trifluoromethyl)phenyl]piperazine | |
| 221 | 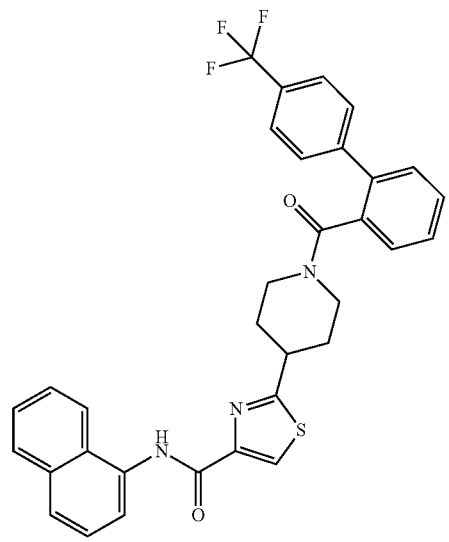<br>N-1-naphthyl-2-(1-{[4'-(trifluoromethyl)biphenyl-2-yl]carbonyl}piperidin-4-yl)-1,3-thiazole-4-carboxamide | |

TABLE 1-continued
| No. | FORMULA | NMR or mass |
|-----|---------|-------------|
| 222 | 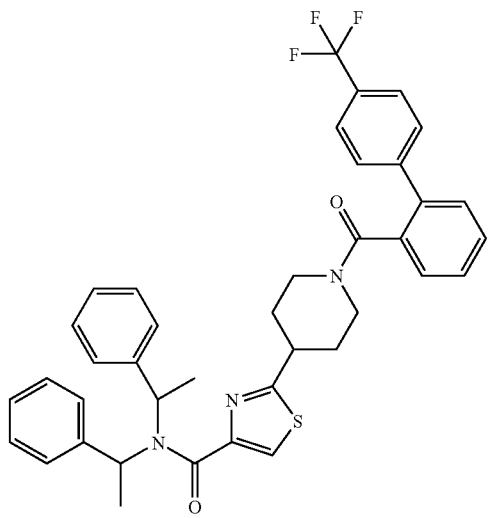 N,N-bis(1-phenylethyl)-2-(1-{[4'(trifluoromethyl) biphenyl-2-yl]carbonyl}-piperidin-4-yl)-1,3-thiazole-4-carboxamide | |
| 223 | 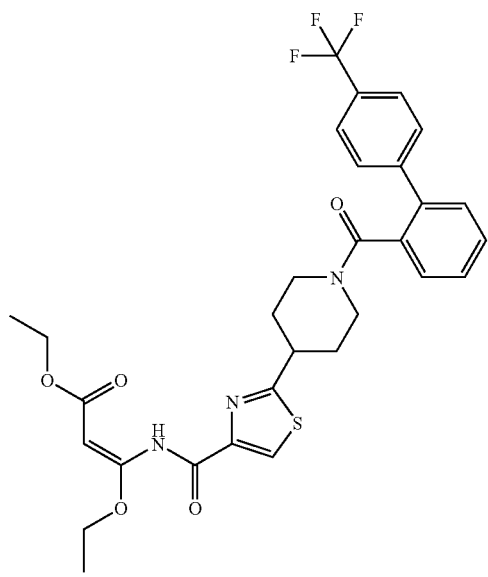 ethyl(2E)-3-ethoxy-3-({[2-(1-{[4'-(trifluoromethyl) biphenyl-2-yl]carbonyl}-piperidin-4-yl)-1,3-thiazol-4-yl] carbonyl}amino)acrylate | |

TABLE 1-continued
| No. | FORMULA | NMR or mass |
|---|---|---|
| 224 | 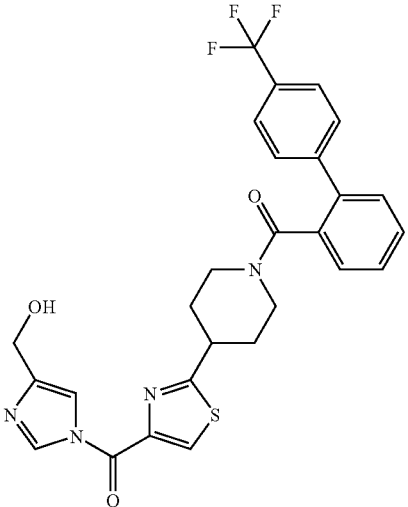 (1-{[2-(1-{[4'-(trifluoromethyl)biphenyl-2-yl]carbonyl} piperidin-4-yl)-1,3-thiazol-4-yl]carbonyl)-1H-imidazol-4-yl) methanol | |
| 225 | 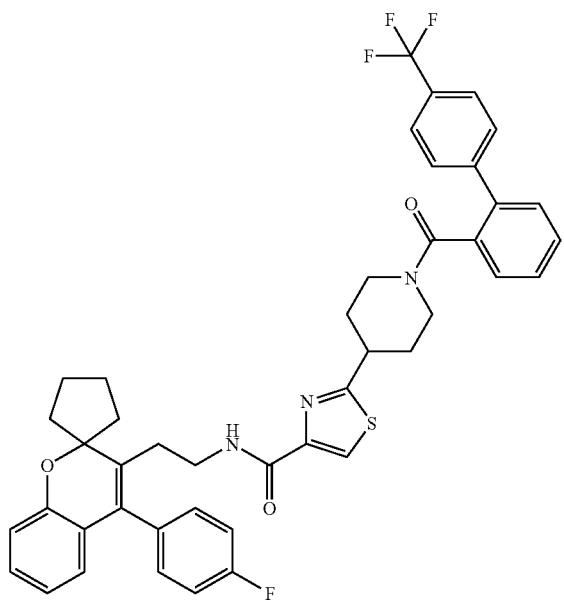 N-{2-[4-(4-fluorophenyl)spiro[chromene-2,1-cyclopentan]-3-yl] ethyl}-2-(1-{[4'-(trifluoromethyl)biphenyl-2-yl]carbonyl} piperidin-4-yl)-1,3-thiazole-4-carboxamide | |

TABLE 1-continued
| No. | FORMULA | NMR or mass |
|---|---|---|
| 226 | 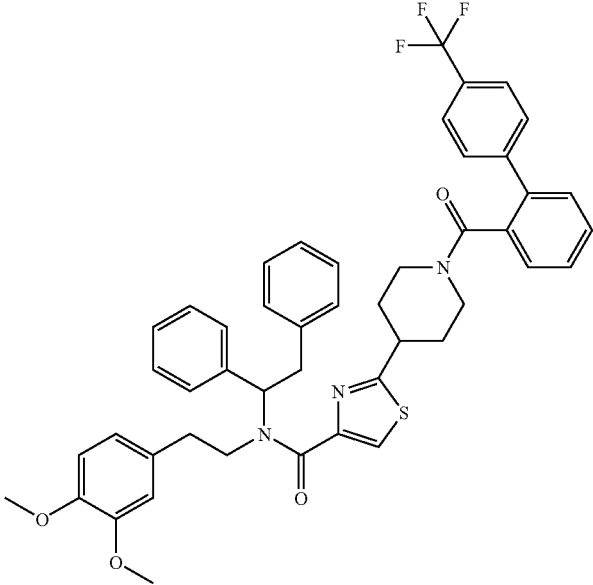 N-[2-(3,4-dimethoxyphenyl)ethyl]-N-(1,2-diphenylethyl)-2-(1-{[4'-(trifluoromethyl)biphenyl-2-yl]carbonyl}piperidin-4-yl)-1,3-thiazole-4-carboxamide | |
| 227 | 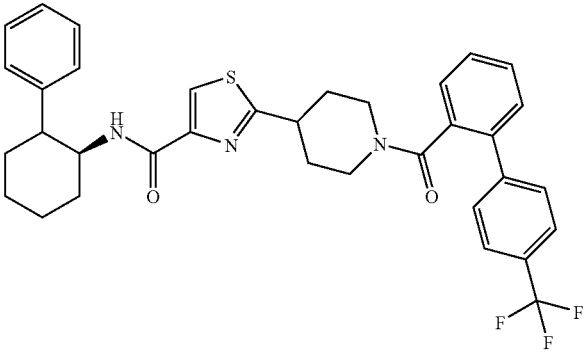 | |

TABLE 1-continued
| No. | FORMULA | NMR or mass |
|---|---|---|
| 228 | 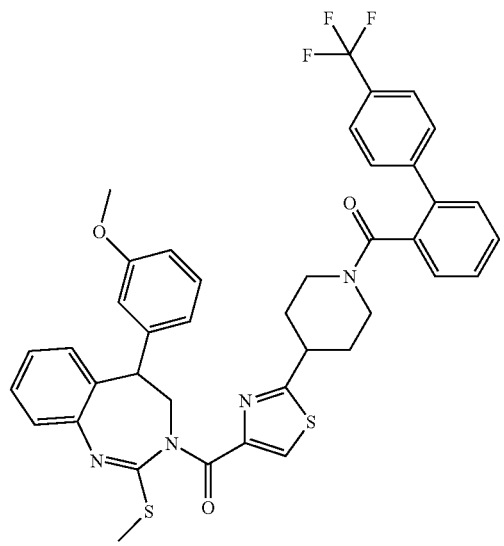 5-(3-methoxyphenyl)-2-(methylthio)-3-{[2-(1-{[4'(trifluoromethyl)biphenyl-2-yl]carbonyyl}piperidin-4-yl)-1,3-thiazol-4-yl]carbonyl}-4,5-dihydro-3H-1,3-benzodiazepine | |
| 229 | 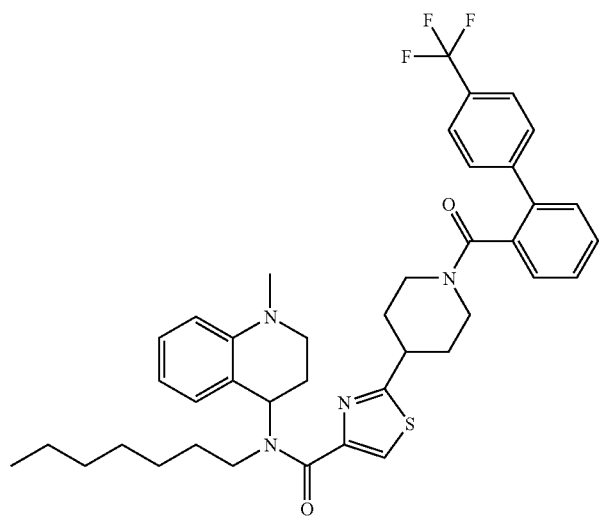 N-heptyl-N-(1-methyl-1,2,3,4-tetrahydroquinolin-4-yl)-2-(1-4{[4'-(trifluoromethyl)biphenyl-2-yl]carbonyl}piperidin-4-yl)-1,3-thiazole-4-carboxamide | |

TABLE 1-continued
| No. | FORMULA | NMR or mass |
|---|---|---|
| 230 | 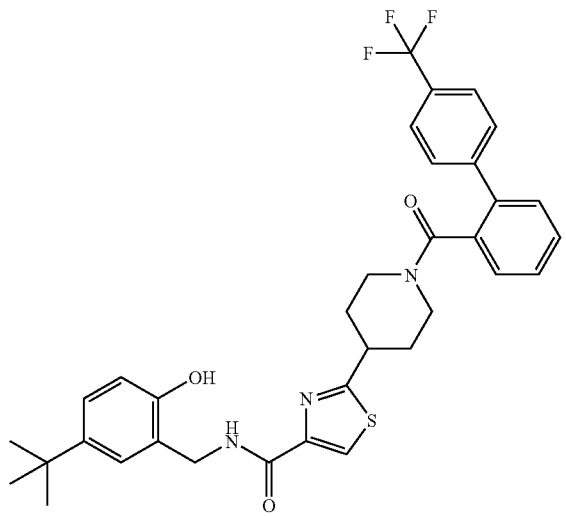 N-(5-tert-butyl-2-hydroxybenzyl)-2-(1-{[4'-(trifluoromethyl) biphenyl-2-yl]-carbonyl}piperidin-4-yl)-1,3-thiazole-4-carboxamide | |
| 231 | 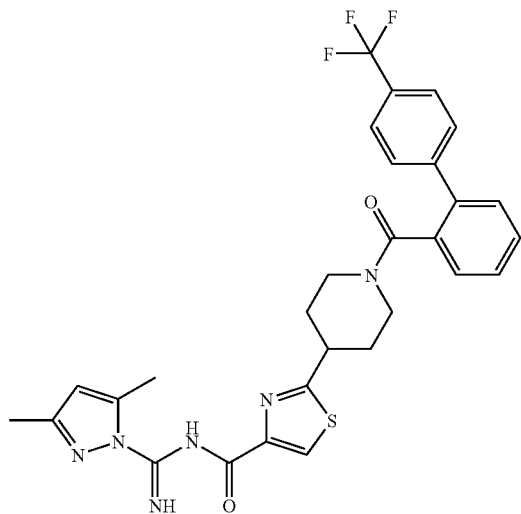 N-[(3,5-dimethyl-1H-pyrazol-1-yl)(mino) methyl]-2-(1-{[4'(trifluoromethyl)-biphenyl-2-yl] carbonyl}piperidin-4-yl)-1,3-thiazole-4-carboxamide | |

TABLE 1-continued
| No. | FORMULA | NMR or mass |
|---|---|---|
| 232 | 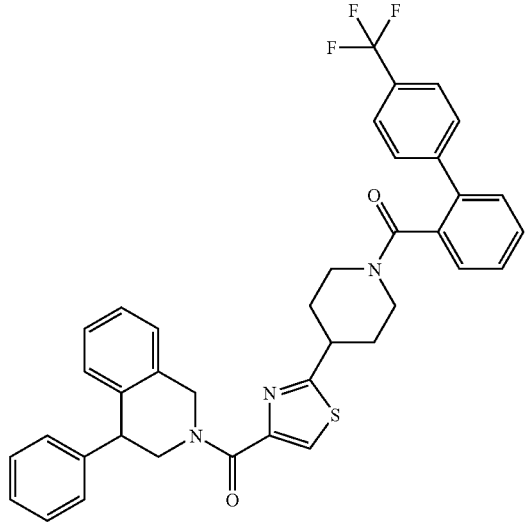 4-phenyl-2-{[2-(1-{[4'-(trifluoromethyl)biphenyl-2-yl]carbonyl}piperidin-4-yl)-1,3-thiazol-4-yl]carbonyl]-1,2,3,4-tetrahydroisoquinoline | |
| 233 | 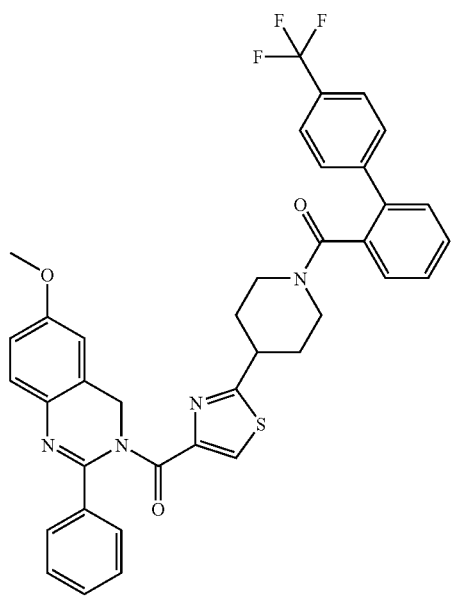 6-methoxy-2-phenyl-3-{[2-(1-{[4'-(trifluoromethyl)biphenyl-2-yl]carbonyl)-piperidin-4-yl)-1,3-thiazol-4-yl]carbonyl]-3,4-dihydroquinazoline | |

US 7,674,803 B2
TABLE 1-continued
| No. | FORMULA | NMR or mass |
|---|---|---|
| 234 | 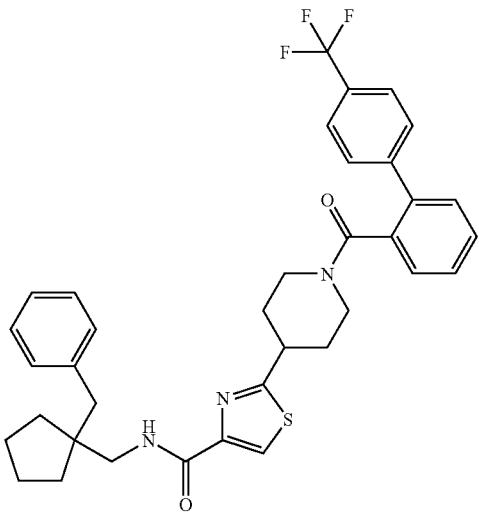 N-[(1-benzylcyclopentyl)methyl]-2-(1-{[4'-(trifluoromethyl)biphenyl-2-yl]-carbonyl}piperidin-4-yl)-1,3-thiazole-4-carboxamide | |
| 235 | 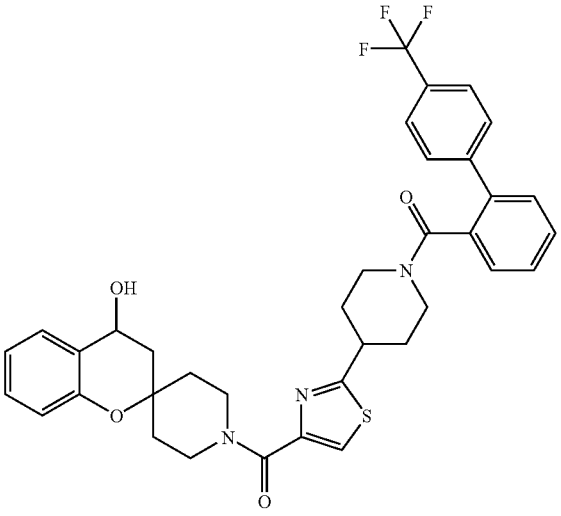 1'-{[2-(1-{[4'-(trifluoromethyl)biphenyl-2-yl]carbonyl}piperidin-4-yl)-1,3-thiazol-4-yl]carbonyl}-3,4-dihydrospiro[chromene-2,4'-piperidin]-4-ol | |

TABLE 1-continued
| No. | FORMULA | NMR or mass |
|---|---|---|
| 236 | 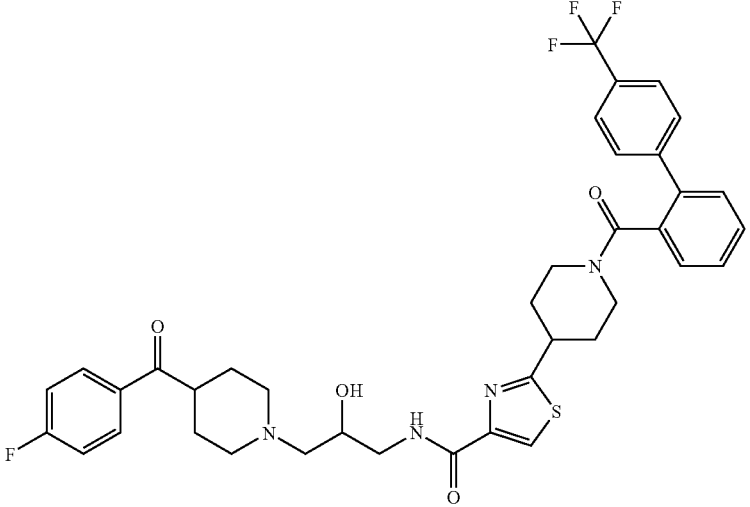 N-{3-[4-(4-fluorobenzoyl)piperidin-1-yl]-2-hydroxypropyl}-2-(1-{[4'-(trifluoromethyl)biphenyl-2-yl]carbonyl}piperidin-4-yl)-1,3-thiazole-4-carboxamide | |
| 237 | 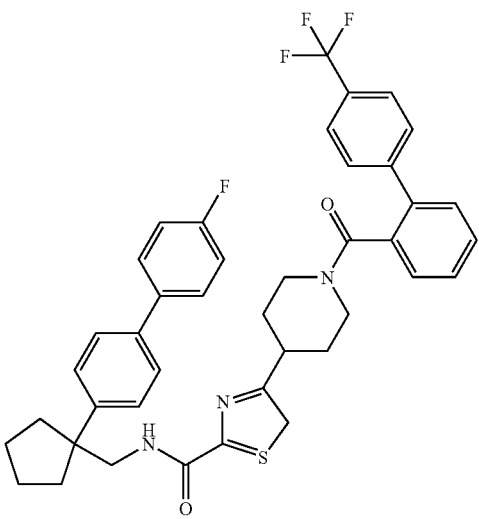 N-{[1-(4'-fluotobiphenyl-4-yl)cyclopentyl]methyl}-2-(1-{[4'-(trifluoromethyl)-biphenyl-2-yl]carbonyl}piperidin-4-yl)-1,3-thiazole-4-carboxamide | |

TABLE 1-continued
| No. | FORMULA | NMR or mass |
|---|---|---|
| 238 | 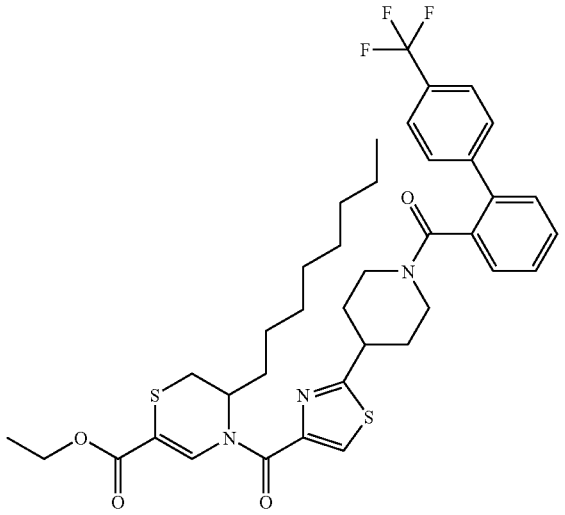 ethyl 3-octyl-4-{[2-(1-{[4'-(trifluoromethyl)biphenyl-2-yl]carbonyl}-piperidin-4-yl]carbonyl}-3,4-dihydro-2H-1,4-thiazine-6-carboxylate | |
| 239 | 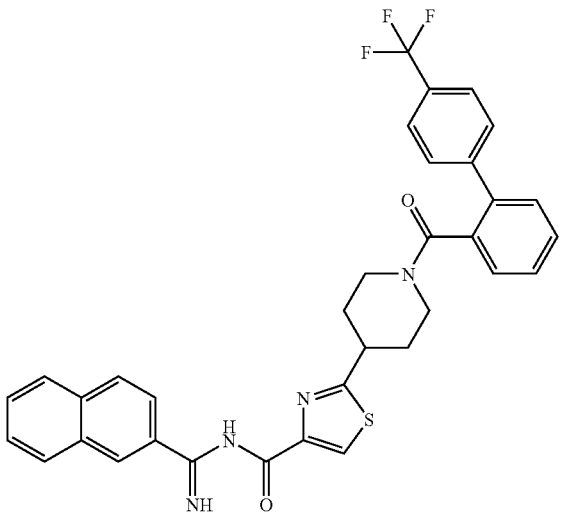 N-[imino(2-naphthyl)methyl]-2-(1-{[4'-(trifluoromethyl)biphenyl-2-yl]-carbonyl}piperidin-4-yl)-1,3-thiazole-4-carboxamide | |

TABLE 1-continued
| No. | FORMULA | NMR or mass |
|---|---|---|
| 240 | 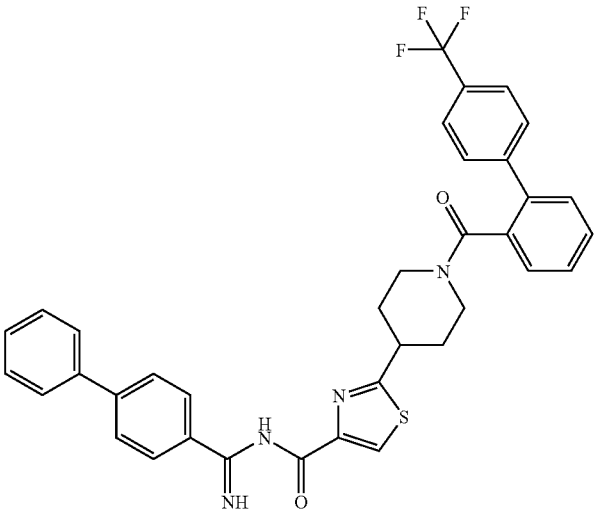 N-{biphenyl-4-yl(limino)methyl]-2-(1-{[4'-(trifluoromethyl)biphenyl-2-yl]carbonyl}-piperidin-4-yl)-1,3-thiazole-4-carboxamide | |
| 241 | 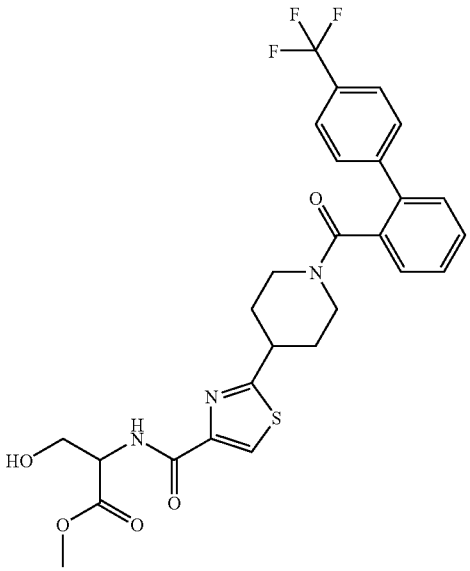 methyl N-{[2-(1-{[4'-(trifluoromethyl)biphenyl-2-yl]carbonyl}piperidin-4-yl)-1,3-thiazol-4-yl]carbonyl}serinate | |

| No. | FORMULA | NMR or mass |
|---|---|---|
| 242 | 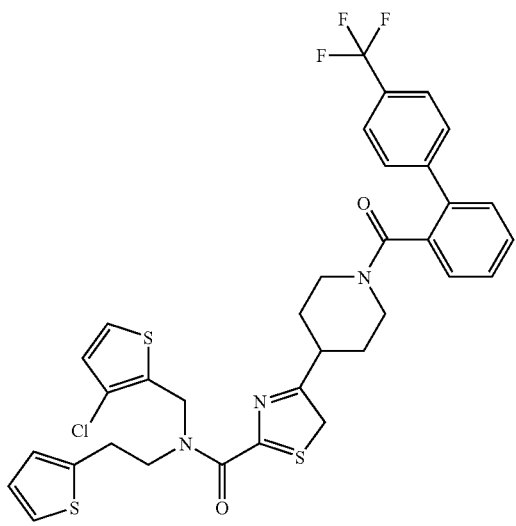 N-[(3-chloro-2-thienyl)methyl]-N-[2-(2-thienyl)ethyl-2-(1-{[4'-(trifluoromethyl)biphenyl-2-yl]carbonyl}piperidin-4-yl)-1,3-thiazole-4-carboxamide | |
| 243 | 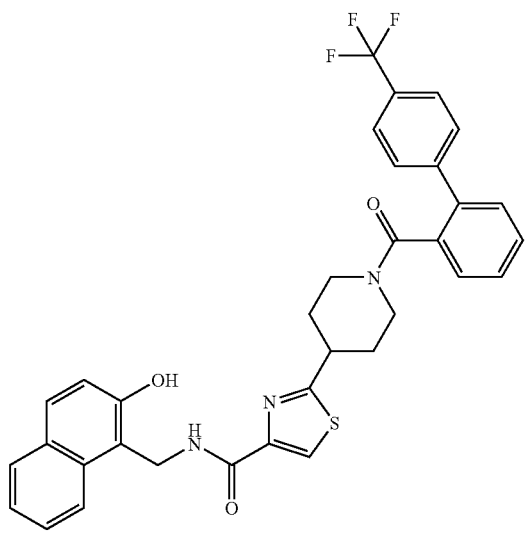 N-[(2-hydroxy-1-naphthyl)methyl]-2-(1-{[4'-(trifluromethyl)biphenyl-2-yl]carbonyl}piperidin-4-yl)-1,3-thiazole-4-carboxamide | |

TABLE 1-continued
| No. | FORMULA | NMR or mass |
|---|---|---|
244
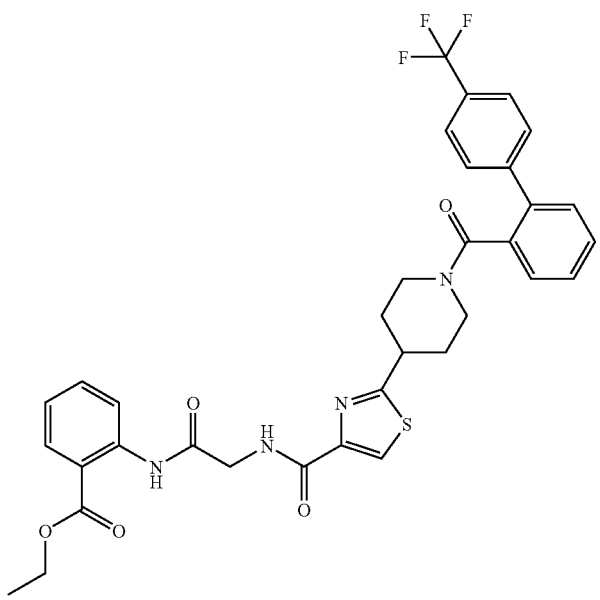
ethyl 2-[(N-{[2-(1-{[4'-(trifluoromethyl)biphenyl-2-yl]carbonyl}piperidin-4-yl)-1,3-thiazol-4-yl]carbonyl}glycyl)amino]benzoate
245
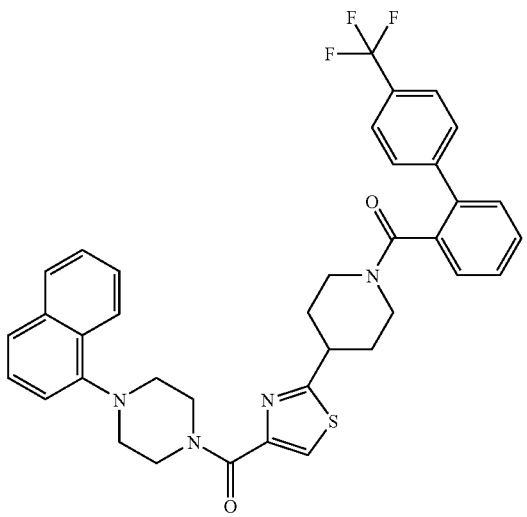
1-(1-naphthyl-4-{[2-(1-{[4'-(trifluoromethyl)biphenyl-2-yl]carbonyl}-piperidin-4-yl)-1,3-thiazol-4-yl]carbonyl}piperazine

| No. | FORMULA | NMR or mass |
|---|---|---|
| 246 | N-{[2-(1-{[4'-(trifluoromethyl)biphenyl-2-yl]carbonyl}piperidin-4-yl)-1,3-thiazol-4-yl]carbonyl}glycine | |
| 247 | | |
| 248 | 1-{[2-(-{[4'-(trifluoromethyl)biphenyl-2-yl]carbonyl}piperidin-4-yl)-1,3-thiazol-4-yl]carbonyl}piperidine-4-carboxylic acid | |

TABLE 1-continued
| No. | FORMULA | NMR or mass |
|-----|---------|-------------|
| 249 | 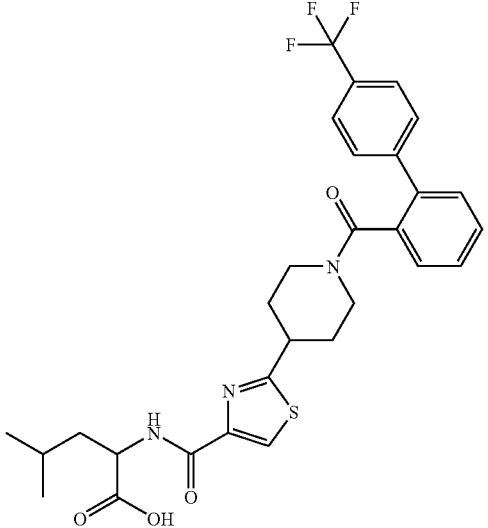 N-[[2-(1-{[4'-(trifluoromethyl)biphenyl-2-yl]carbonyl}piperidin-4-yl)-1,3-thiazol-4-yl]carbonyl}leucine | |
| 250 | 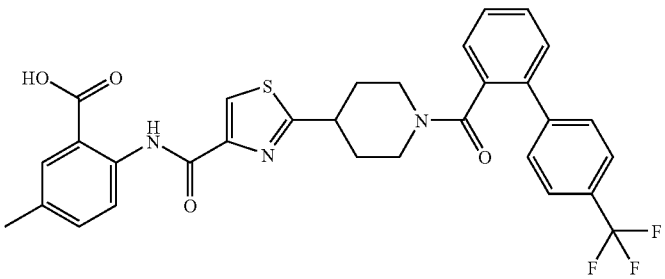 | |
| 251 | 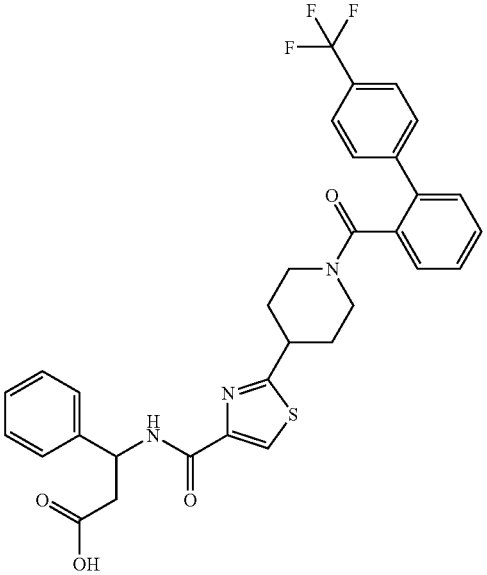 3-phenyl-3-({[2-(1-{[4'-(trifluoromethyl)biphenyl-2-yl]carbonyl}piperidin-4-yl)-1,3-thiazol-4-yl]carbonyl}amino)propanoic acid | |

TABLE 1-continued
| No. | FORMULA | NMR or mass |
|---|---|---|
| 252 | 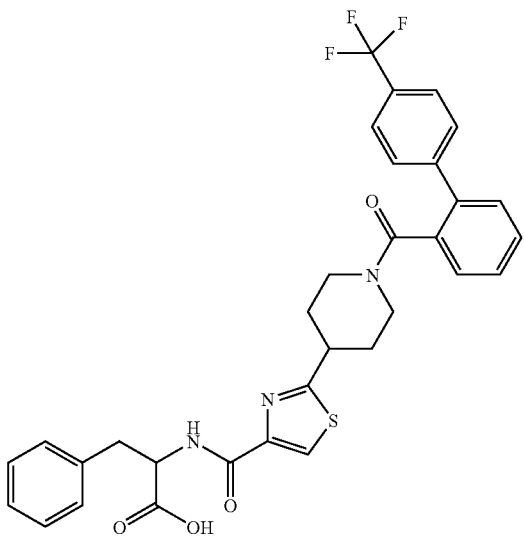 N-{[2-(1-{[4'-(trifluoromethyl)biphenyl-2-yl] carbonyl}piperidin-4-yl)-1,3-thiazol-4-yl] carbonyl}phenylalanine | |
| 253 | 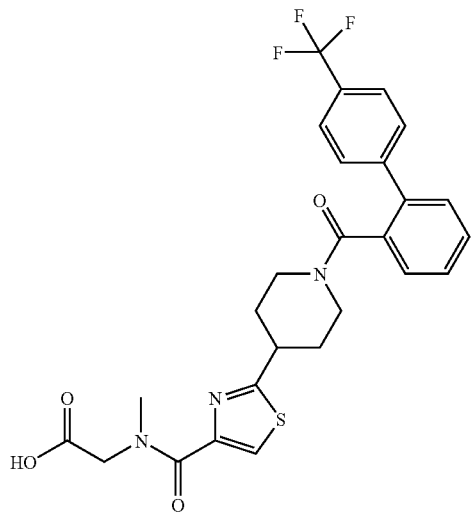 N-methyl-N-{[2-(1-{[4'-(trifluoromethyl)biphenyl-2-yl] carbonyl}piperidin-4-yl)-1,3-thiazol-4-yl] carbonyl}glycine | |

| No. | FORMULA | NMR or mass |
|---|---|---|
| 254 | 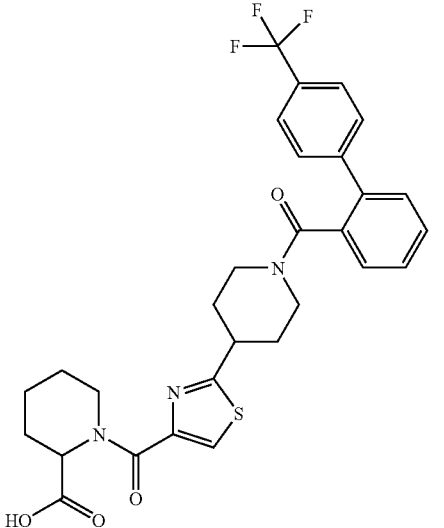<br>1-{[2-(1-{[4'-(trifluoromethyl)biphenyl-2-yl]carbonyl}piperidin-4-yl)-1,3-thiazol-4-yl]carbonyl}piperidin-2-carboxylic acid | |
| 255 | 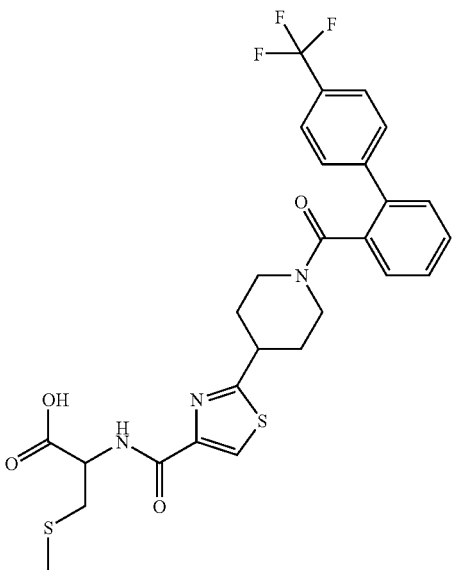<br>S-methyl-N-{[2-(1-{[4'-(trifluoromethyl)biphenyl-2-yl]carbonyl}piperidin-4-yl)-1,3-thiazol-4-yl]carbonyl}cysteine | |

TABLE 1-continued
| No. | FORMULA | NMR or mass |
|---|---|---|
| 256 | 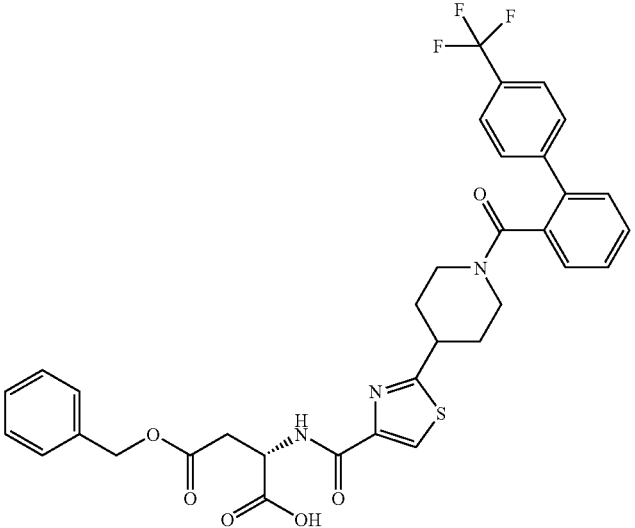 | |
| 257 | 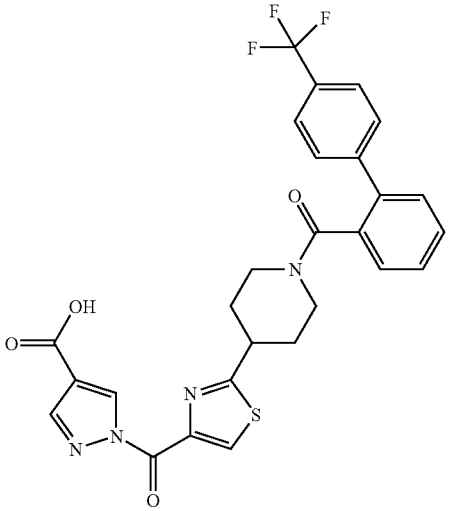 1-{[2-(1-{[4'-(trifluoromethyl)biphenyl-2-yl]carbonyl}piperidin-4-yl)-1,3-thiazol-4-yl]carbonyl}-1H-pyrazole-4-carboxylic acid | |

TABLE 1-continued
| No. | FORMULA | NMR or mass |
|---|---|---|
| 258 | 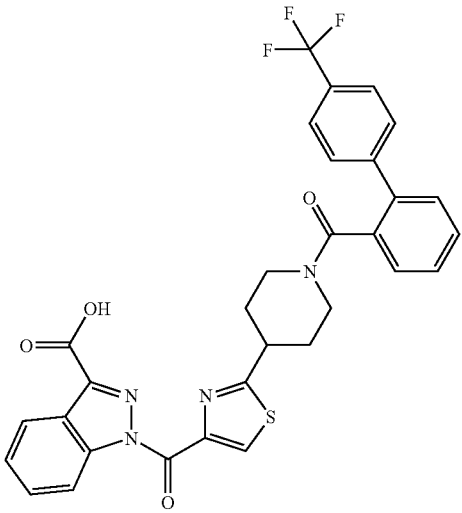 1-{[2-(1-{[4'-(trifluoromethyl)biphenyl-2-yl] carbonyl} piperidin-4-yl)-1,3-thiazol-4-yl]carbonyl}-1H-indazole-3-carboxylic acid | |
| 259 | 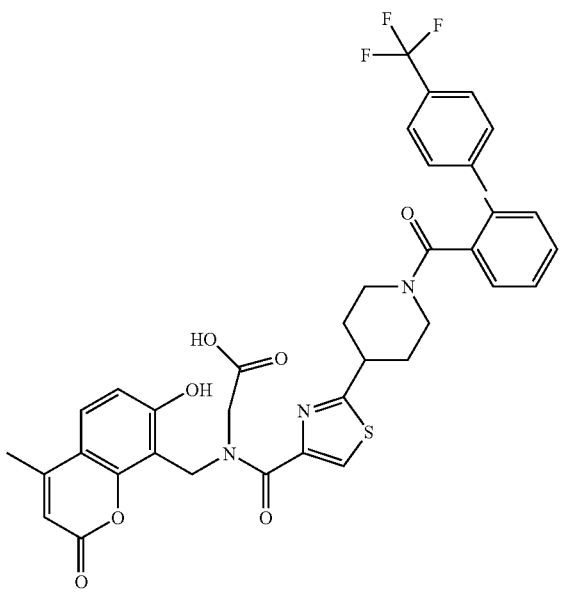 N-[(7-hydroxy-4-methyl-2-oxo-2H-chromen-8-yl) methyl]-N-{[2-(1-{[4'-(trifluoromethyl)biphenyl-2-yl] carbonyl}piperidin-4-yl)-1,3-thiazol-4-yl]-carbonyl}glycine | |
| 260 | 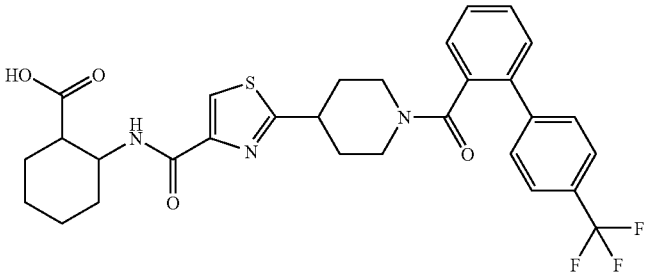 | |

TABLE 1-continued
| No. | FORMULA | NMR or mass |
|---|---|---|
261
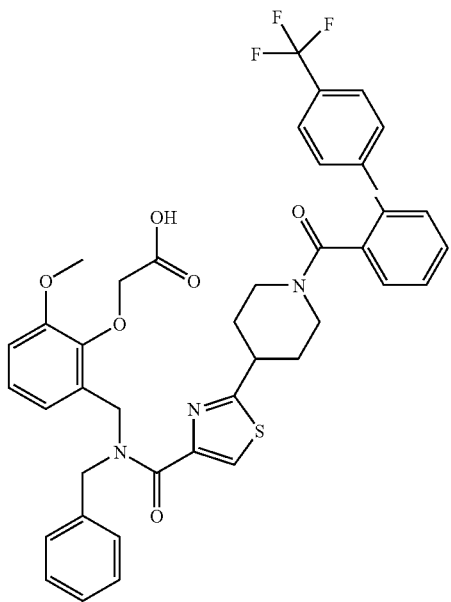
{2-[(benzyl{[2-(1-{[4'-(trifluoromethyl)biphenyl-2-yl]
carbonyl}piperidin-4-yl)-1,3-thiazol-4-yl]carbonyl}
amino)methyl]-6-methoxyphenoxy}acetic acid
262
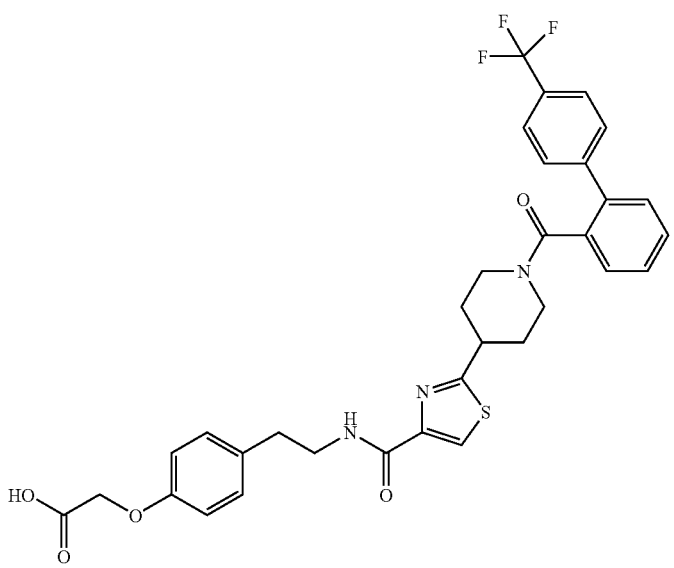
{4-[2-({[2-(1-{[4'-(trifluoromethyl)biphenyl-2-yl]carbonyl}
piperidin-4-yl)-1,3-thiazol-4-yl]carbonyl}amino)ethyl]
phenoxy}acetic acid

| No. | FORMULA | NMR or mass |
|---|---|---|
| 263 | 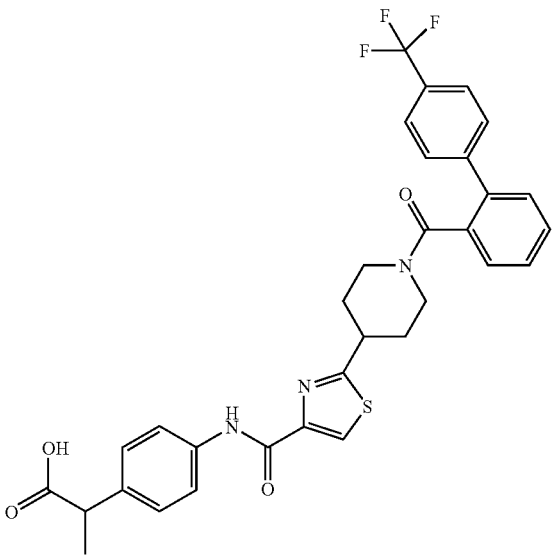<br>2-[4-({[2-(1-{[4'-(trifluoromethyl)biphenyl-2-yl]carbonyl}piperidin-4-yl)-1,3-thiazol-4-yl]carbonyl}amino)phenyl}propanoic acid | |
| 264 | 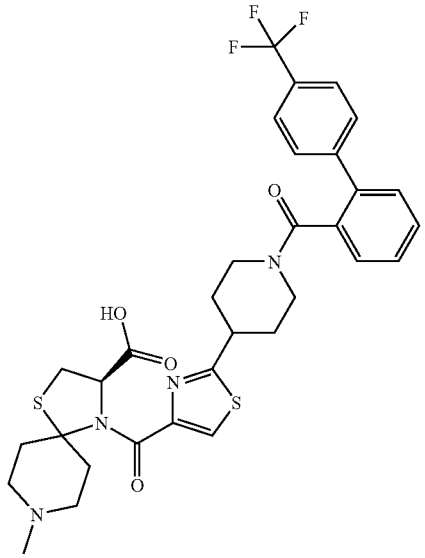<br>(3R)-8-methyl-4-{[2-(1-{[4'-(trifluoromethyl)biphenyl-2-yl]carbonyl}piperidin-4-yl)-1,3-thiazol-4-yl]carbonyl}-1-thia-4,8-diazaspiro[4.5]decane-3-carboxylic acid | |
| 265 | 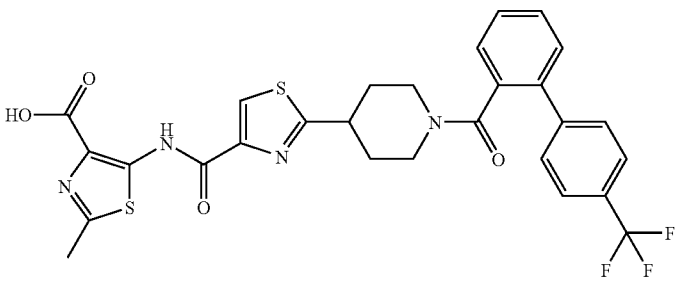 | |

TABLE 1-continued

| No. | FORMULA | NMR or mass |
|---|---|---|

266

2-(3,4-dichlorophenyl)-3-{[2-(1-{[4'-(trifluoromethyl)
biphenyl-2-yl]carbonyl}-piperidin-4-yl)-1,3-thiazol-4-yl]
carbonyl}-1,3-thiazolidine-4-carboxylic acid

267

2-[(N-methyl-N-{[2-(1-{[4'-(trifluoromethyl)biphenyl-2-yl]
carbonyl}piperidin-4-yl)-1,3-thiazol-4-yl]carbonyl}glycyl)
amino]benzoic acid

TABLE 1-continued
| No. | FORMULA | NMR or mass |
|---|---|---|
| 268 | 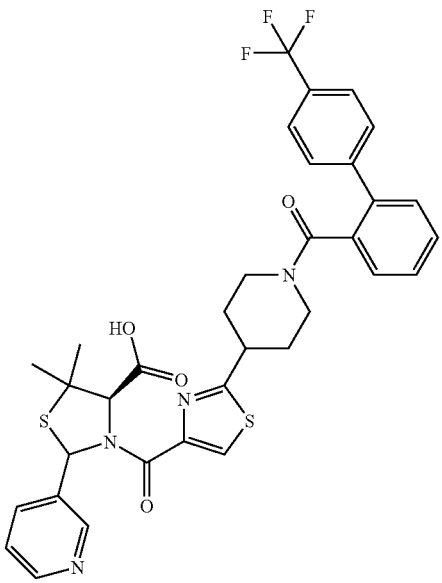<br>(4R)-5,5-dimethyl-2-pyridin-3-yl-3-{[2-(1-{[4'-(trifluoromethyl)biphenyl-2-yl]-carbonyl}piperidin-4-yl)-1,3-thiazol-4-yl]carbonyl}-1,3-thiazolidine-4-carboxylic acid | |
| 269 | 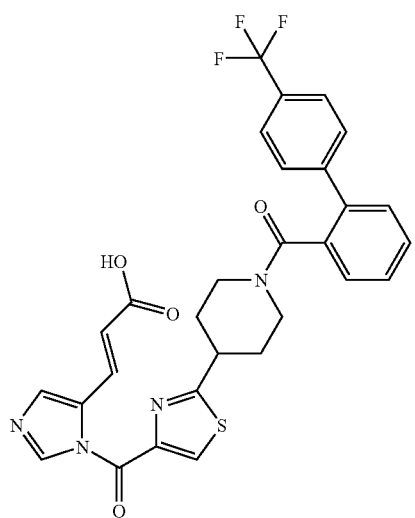<br>(2E)-3-(1-{[2-(1-{[4'-(trifluoromethyl)biphenyl-2-yl]carbonyl}piperidin-4-yl)-1,3-thiazol-4-yl]carbonyl}-1H-imidazol-5-yl)acrylic acid | |

| No. | FORMULA | NMR or mass |
|---|---|---|
| 270 | CHIRAL 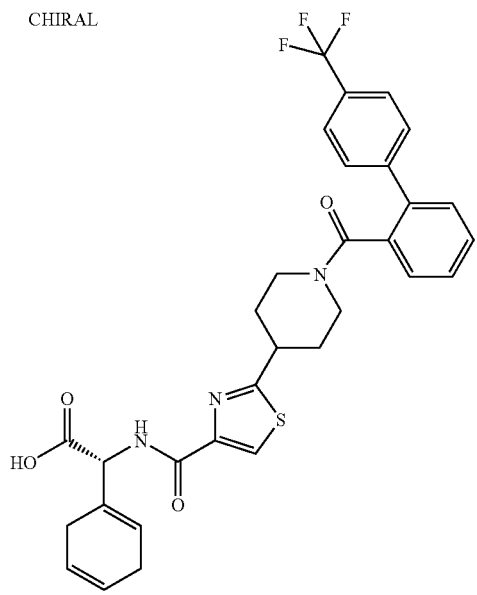 (2R)-cyclohexa-1,4-dien-1-yl({[2-(1-{[4'-(trifluoromethyl)biphenyl-2-yl]-carbonyl}piperidin-4-yl)-1,3-thiazol-4-yl]carbonyl}amino)acetic acid | |
| 271 | CHIRAL 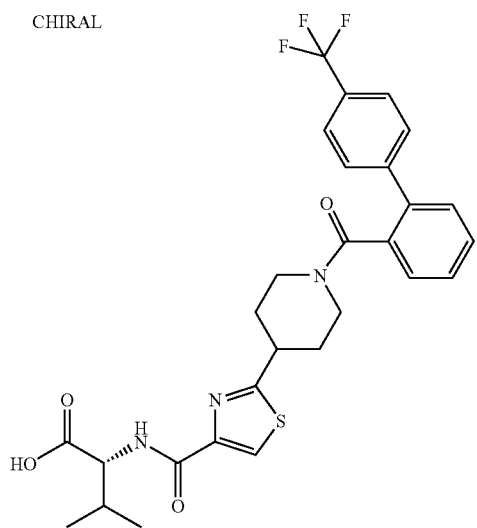 N-{[2-(1-{[4'-(trifluoromethyl)biphenyl-2-yl]carbonyl}piperidin-4-yl)-1,3-thiazol-4-yl]carbonyl}-D-valine | |

| No. | FORMULA | NMR or mass |
|---|---|---|
| 272 | 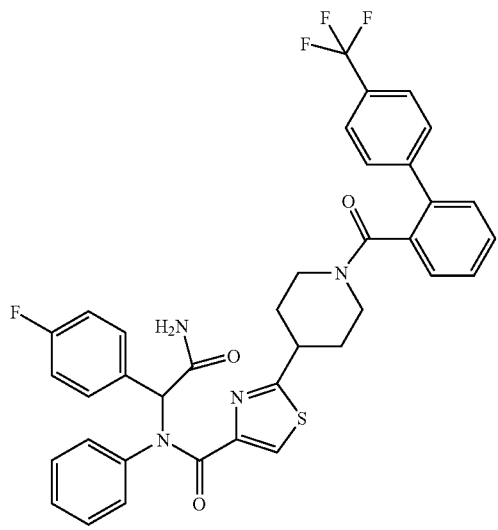<br>N-[2-amino-1-(4-fluorophenyl)-2-oxoethyl]-N-phenyl-2-(1-{[4'-(trifluoromethyl)biphenyl-2-yl]carbonyl}piperidin-4-yl)-1,3-thiazole-4-carboxamide | |
| 273 | 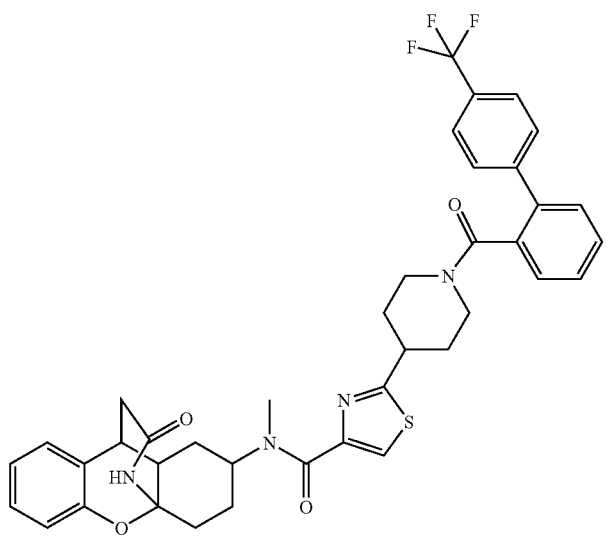<br>N-methyl-N-[12-oxo-1,2,3,4,9,9a-hexahydro-4a,9-(epiminoethano)xanthen-2-yl]-2-(1-{[4'-(trifluoromethyl)biphenyl-2-yl]carbonyl}piperidin-4-yl)-1,3-thiazole-4-carboxamide | |

TABLE 1-continued
| No. | FORMULA | NMR or mass |
|---|---|---|
| 274 | 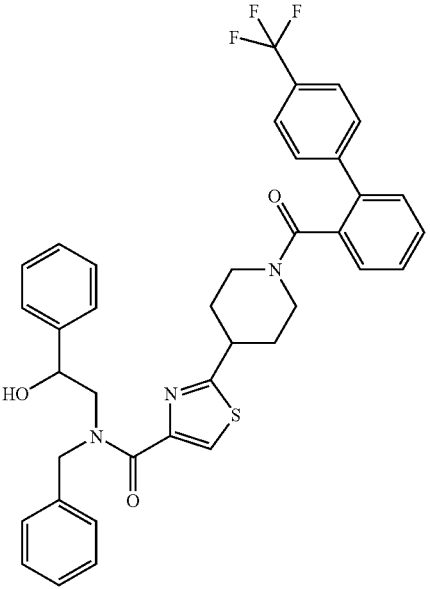  N-benzyl-N-(2-hydroxy-2-phenylethyl)-2-(1-{[4'-(trifluoromethyl)biphenyl-2-yl]carbonyl}piperidin-4-yl)-1,3-thiazole-4-carboxamide | |
| 275 | 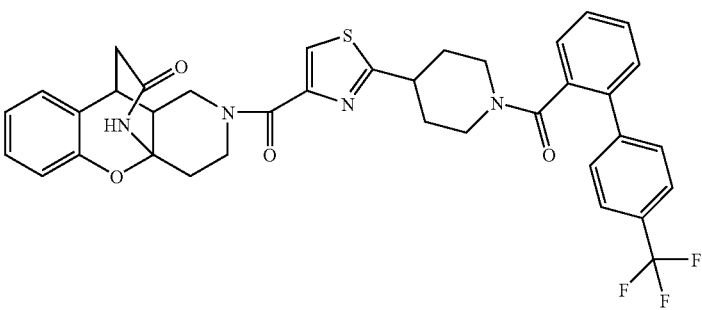 | |
| 276 | 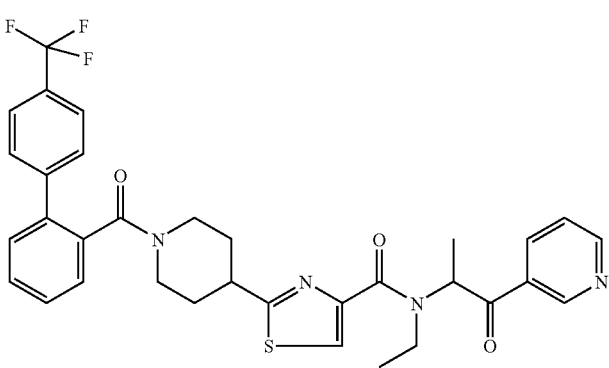 | |

US 7,674,803 B2
TABLE 1-continued
| No. | FORMULA | NMR or mass |
|---|---|---|
| 277 | 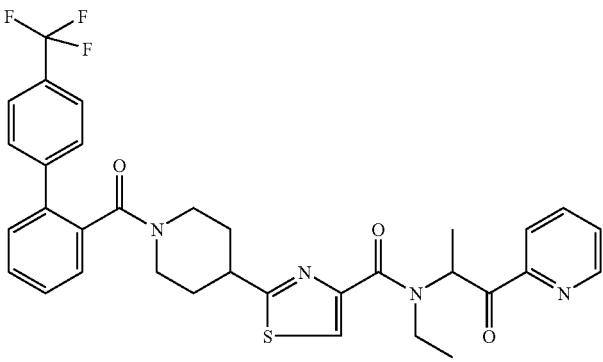 | |
| 278 | 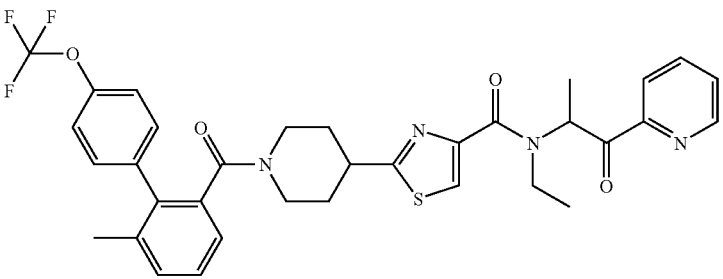 | |
| 279 | 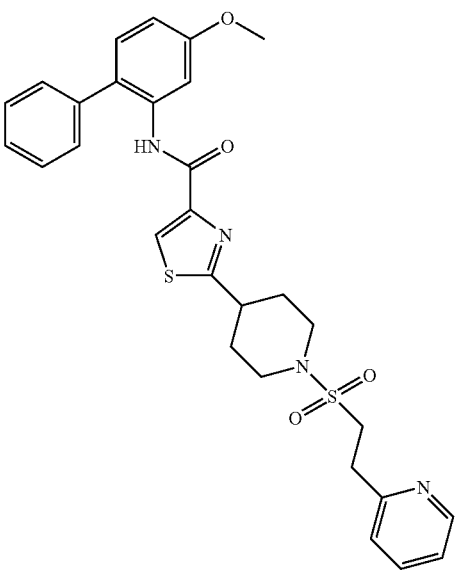<br>N-(4-methoxybiphenyl-2-yl)-2-{1-[(2-pyridin-2-ylethyl)sulfonyl]piperidin-4-yl}-1,3-thiazole-4-carboxamide | |

TABLE 1-continued
| No. | FORMULA | NMR or mass |
|---|---|---|
| 280 | 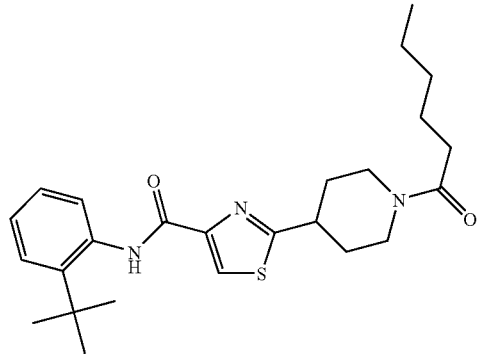 | |
| 281 | 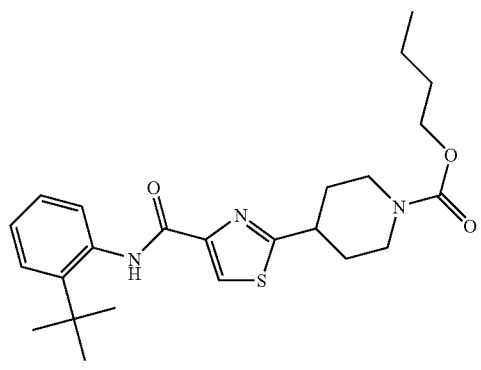 | |
| 282 | 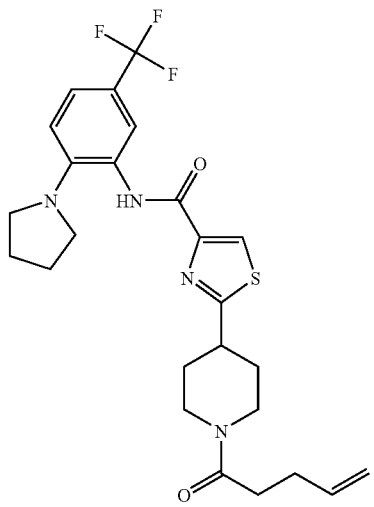<br>2-(1-pent-4-enoylpiperidin-4-yl)-N-[2-pyrrolidin-1-yl-5-(trifluoromethyl)-phenyl]-1,3-thiazole-4-carboxamide | |

TABLE 1-continued

| No. | FORMULA | NMR or mass |
|---|---|---|
| 283 | | |
| 284 | | |
| 285 | | |

| No. | FORMULA | NMR or mass |
|---|---|---|
| 286 | | |
| 287 | | |
| 288 | | |
| 289 | | |

TABLE 1-continued
| No. | FORMULA | NMR or mass |
|---|---|---|
| 290 | 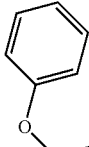 | |
| 291 |  | |
| 292 |  | |
| 293 |  | |

| No. | FORMULA | NMR or mass |
|---|---|---|
| 294 | 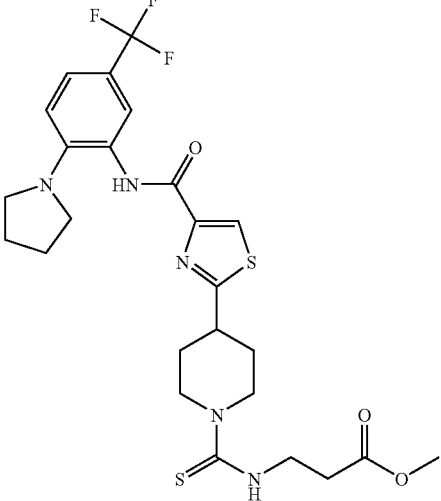 methyl N-({4-[4-({[2-pyrrolidin-1-yl-5-(trifluoromethyl)phenyl]amino}-carbonyl)-1,3-thiazol-2-yl]piperidin-1-yl}carbonothioyl)-beta-alaninate | |
| 295 | 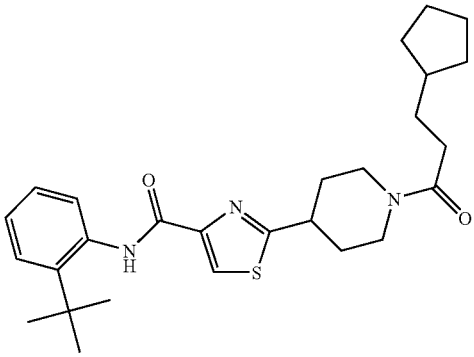 | |
| 296 | 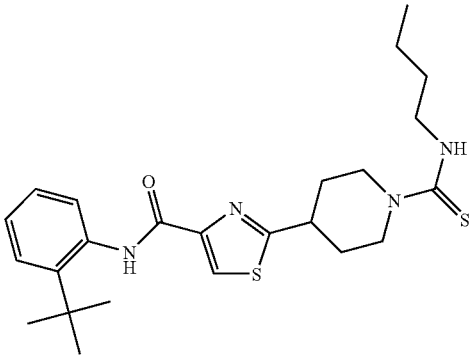 | |

TABLE 1-continued
| No. | FORMULA | NMR or mass |
|---|---|---|
| 297 | 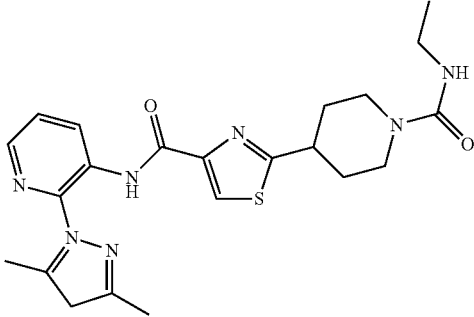 | |
| 298 | 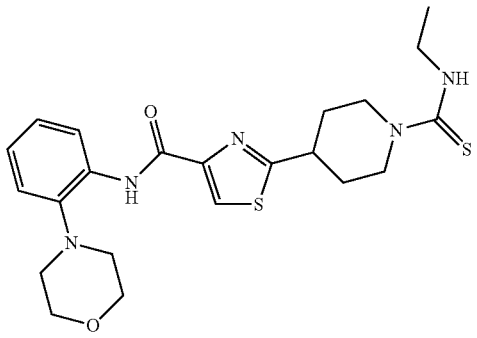 | |
| 299 | 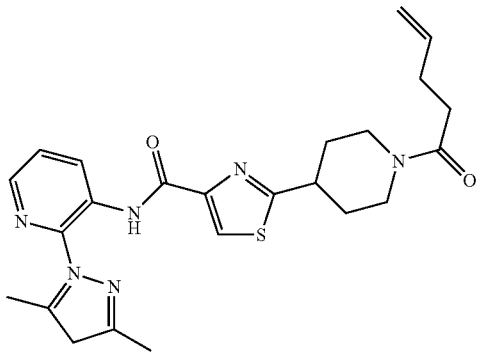 | |
| 300 | 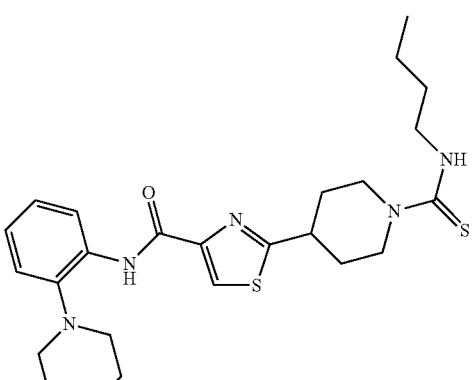 | |

TABLE 1-continued
| No. | FORMULA | NMR or mass |
|---|---|---|
| 301 | 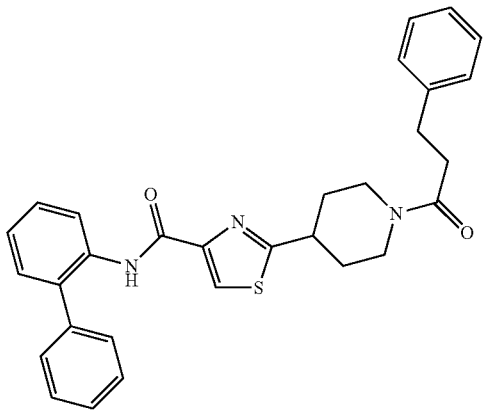 | |
| 302 | 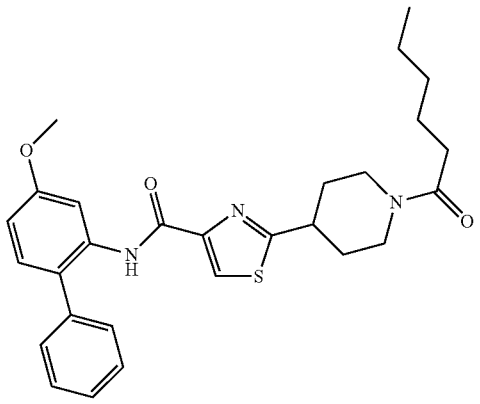 | |
| 303 | 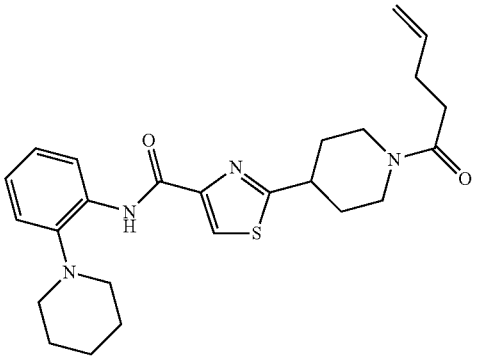 | |
| 304 | 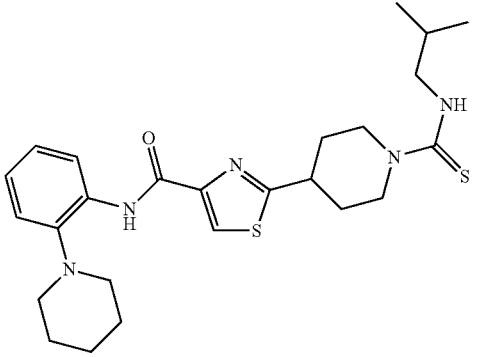 | |

TABLE 1-continued
| No. | FORMULA | NMR or mass |
|---|---|---|
305 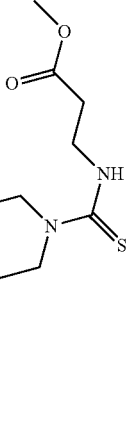
306 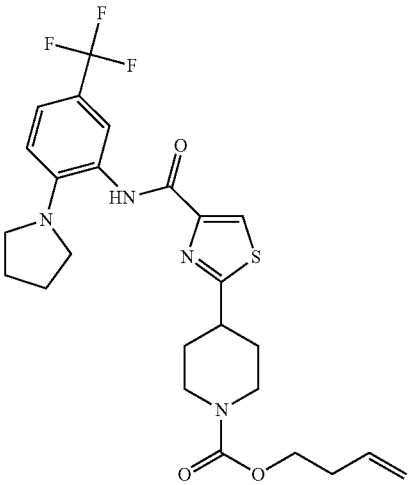
but-3-en-1-yl 4-[4-({[2-pyrrolidin-1-yl-5-(trifluoromethyl)-phenyl]amino}-carbonyl)-1,3-thiazol-2-yl]piperidine-1-carboxylate
307 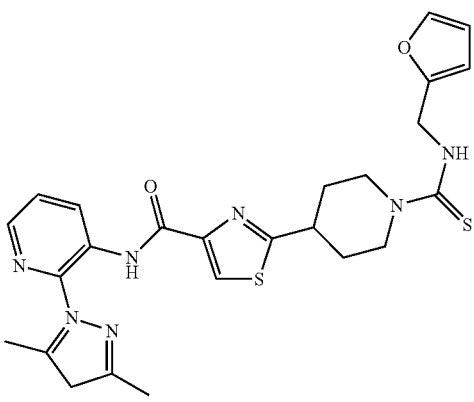
N-[2-(3,5-dimethyl-1H-pyrazol-1-yl)pyridin-3-yl]-2-(1-{[(2-furylmethyl)amino]-carbonothioyl}piperidin-4-yl)-1,3-thiazole-4-carboxamide TABLE 1-continued
| No. | FORMULA | NMR or mass |
|---|---|---|
| 308 | 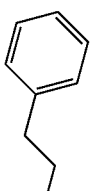 | |
| 309 | 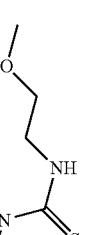 | |
| 310 |  | |
| 311 |  | |

TABLE 1-continued
| No. | FORMULA | NMR or mass |
|---|---|---|
312 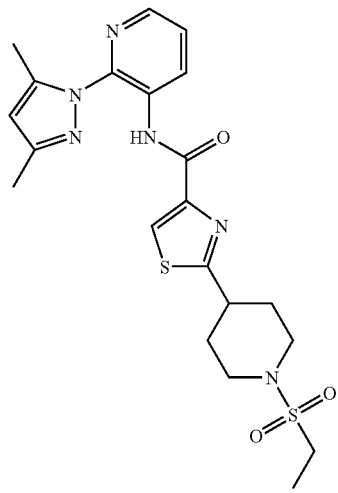
N-[2-(3,5-dimethyl-1H-pyrazol-1-yl)pyridin-3-yl]-2-[1-(ethylsulfonyl)piperidin-4-yl]-1,3-thiazole-4-carboxamide
313 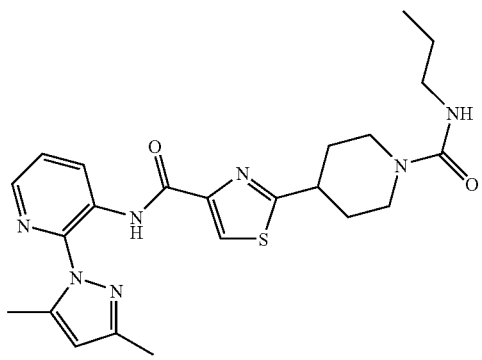
314 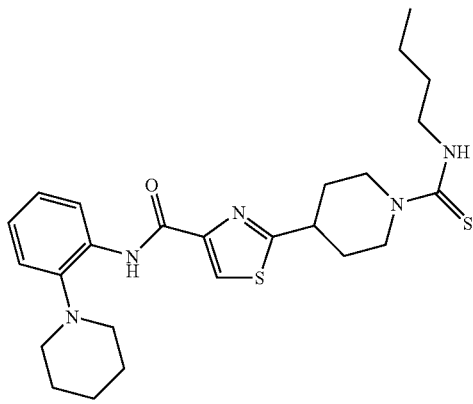

TABLE 1-continued

| No. | FORMULA | NMR or mass |
|---|---|---|
| 315 | N-(2-morpholin-4-ylphenyl)-2-[1-(propylsulfonyl)piperidin-4-yl]-1,3-thiazole-4-carboxamide | |
| 316 | | |
| 317 | ethyl N-({4-[4-({[2-pyrrolidin-1-yl-5-(trifluoromethyl)phenyl]amino}carbonyl)-1,3-thiazol-2-yl]piperidin-1-yl}carbonothioyl)glycinate | |

TABLE 1-continued
| No. | FORMULA | NMR or mass |
|---|---|---|
| 318 | 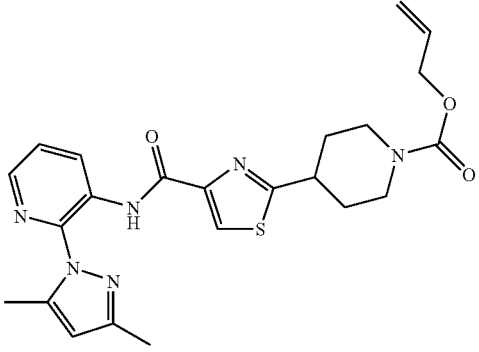 | |
| 319 | 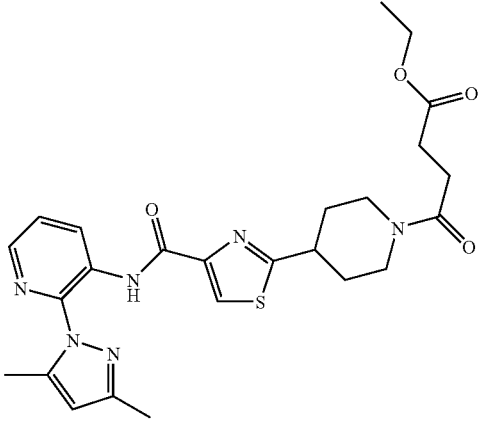 | |
| 320 | 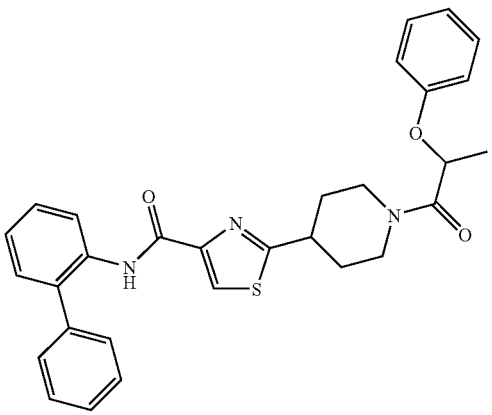 | |

TABLE 1-continued
| No. | FORMULA | NMR or mass |
|---|---|---|
| 321 | 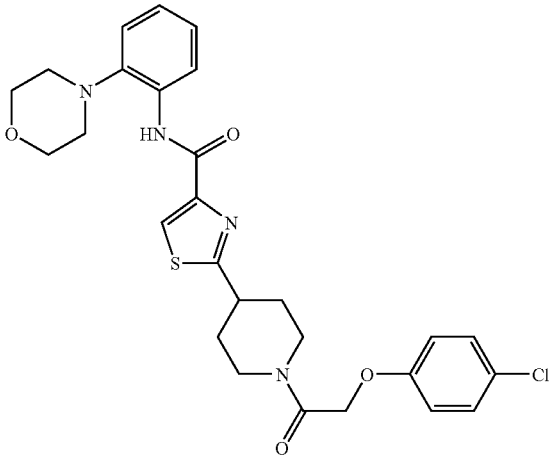 2-{1-[(4-chlorophenoxy)acetyl]piperidin-4-yl}-N-(2-morpholin-4-ylphenyl)-1,3-thiazole-4-carboxamide | |
| 322 | 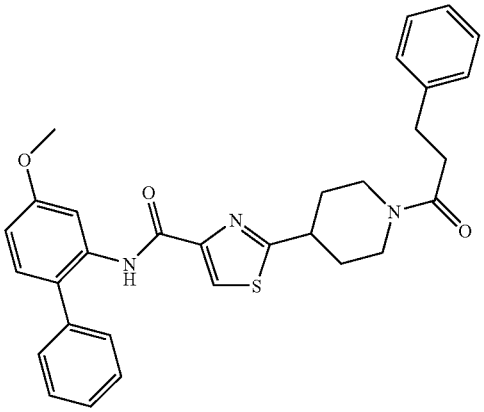 | |
| 323 | 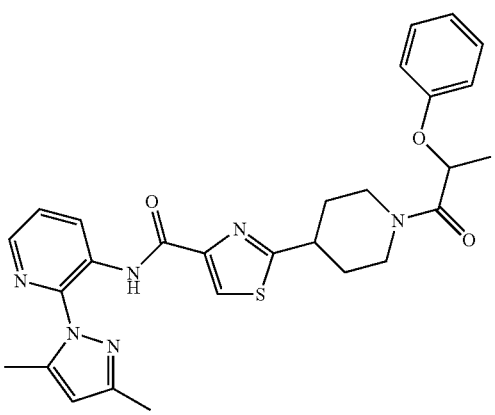 N-[2-(3,5-dimethyl-1H-pyrazol-1-yl)pyridin-3-yl]-2-[1-(2-phenoxy-propanoyl)-piperidin-4-yl]-1,3-thiazole-4-carboxamide | |

TABLE 1-continued
| No. | FORMULA | NMR or mass |
|---|---|---|
| 324 | 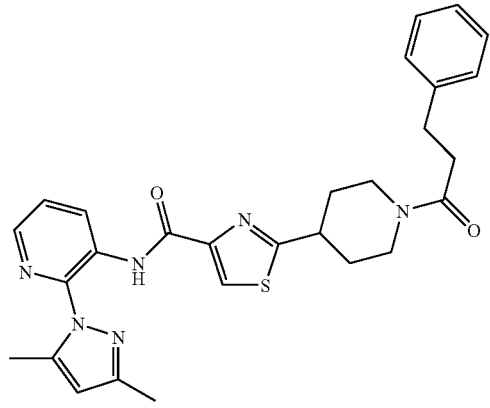 | |
| 325 | 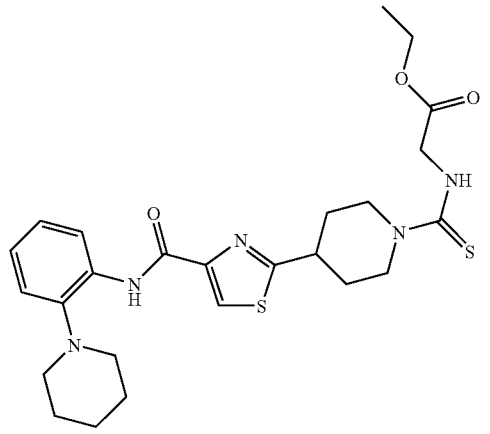 | |
| 326 | 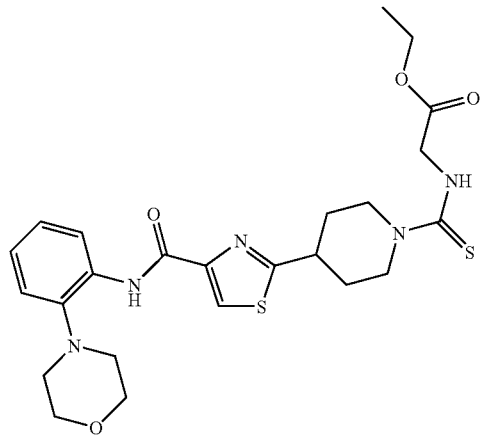 | |

TABLE 1-continued
| No. | FORMULA | NMR or mass |
|---|---|---|
| 327 | 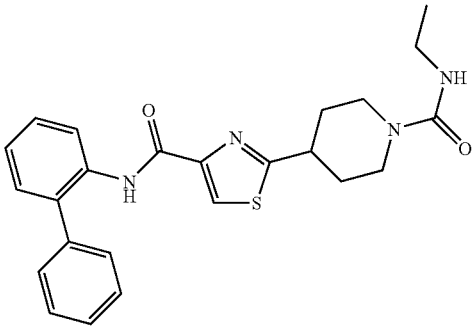 | |
| 328 | 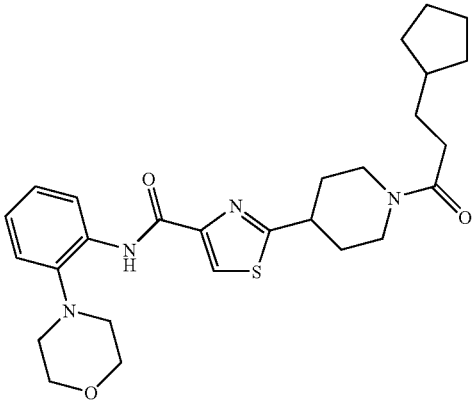 | |
| 329 | 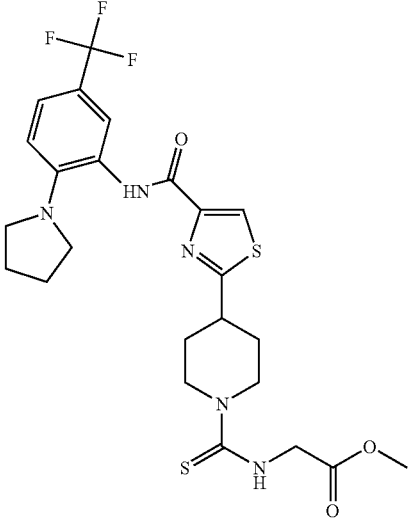<br>methyl N-({-4-[4[({[2-pyrrolidin-1-yl-5-(trifluoromethyl)phenyl]amino}-carbonyl)-1,3-thiazol-2-yl]piperidin-1-yl}carbonothioyl)glycinate | |

TABLE 1-continued

| No. | FORMULA | NMR or mass |
|---|---|---|

330

331

332

333

TABLE 1-continued
| No. | FORMULA | NMR or mass |
|---|---|---|
| 334 | 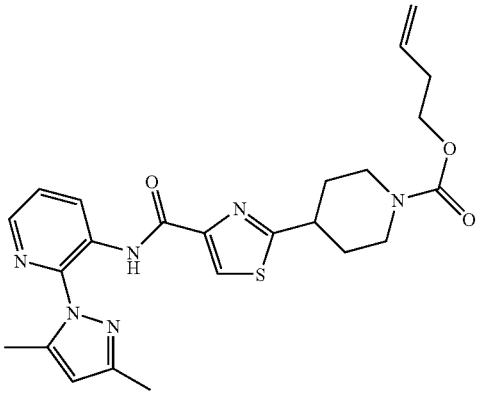 | |
| 335 | 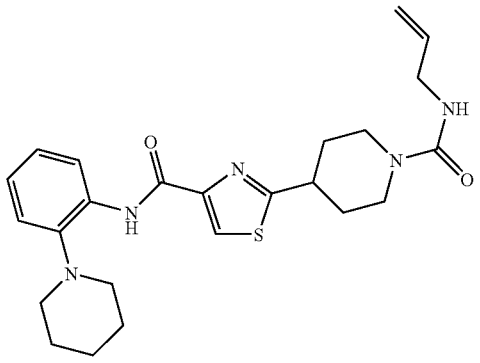 | |
| 336 | 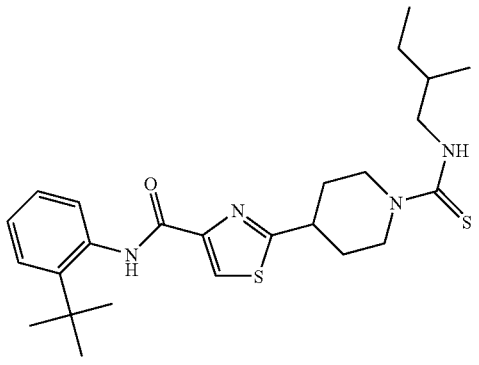 | |
| 337 | 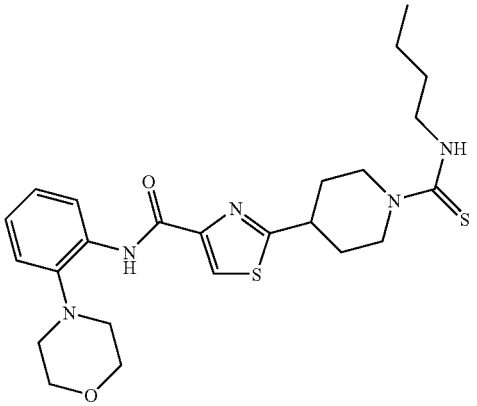 | |

TABLE 1-continued
| No. | FORMULA | NMR or mass |
|---|---|---|
| 338 | 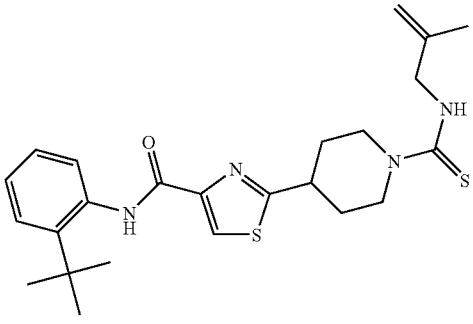 | |
| 339 | 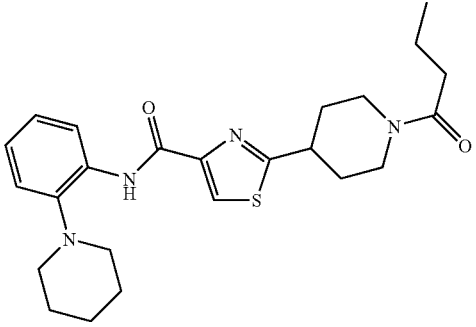 | |
| 340 | 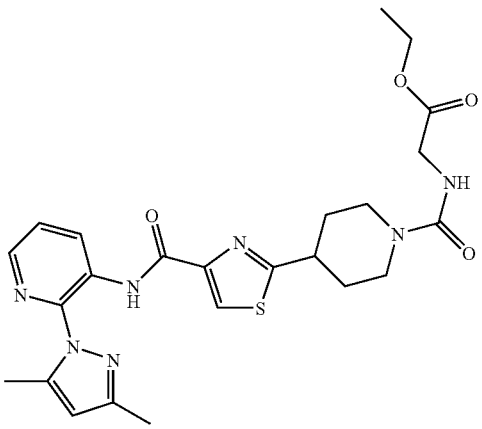 | |
| 341 | 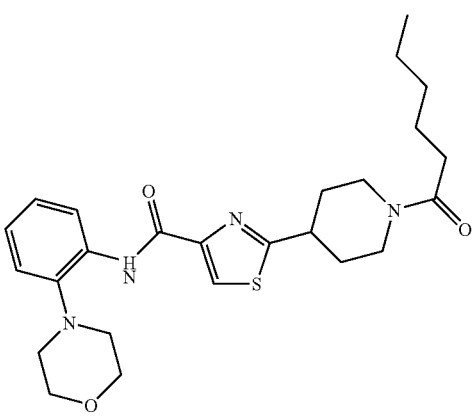 | |

TABLE 1-continued

| No. | FORMULA | NMR or mass |
|-----|---------|-------------|
| 342 | | |
| 343 | | |
| 344 | | |
| 345 | | |

TABLE 1-continued

| No. | FORMULA | NMR or mass |
|---|---|---|
| 346 | | |
| 347 | | |
| 348 | | |
| 349 | | |

TABLE 1-continued
| No. | FORMULA | NMR or mass |
|---|---|---|
| 350 | 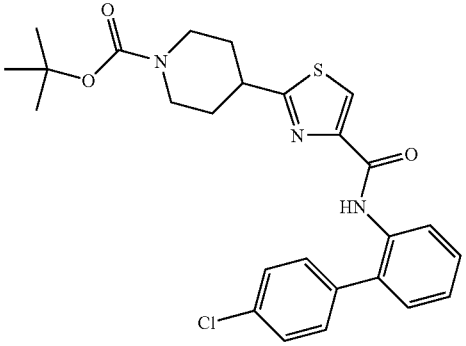 | |
| 351 | 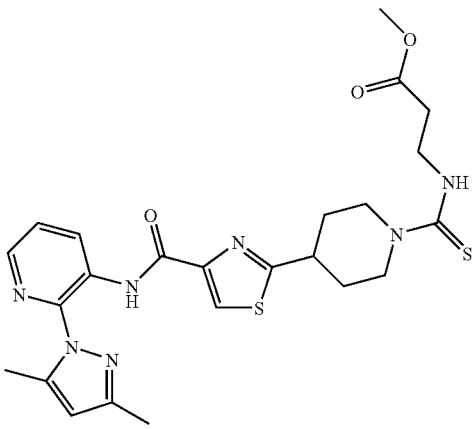<br>methyl N-({4-[4-({[2-(3,5-dimethyl-1H-pyrazol-1-yl)pyridin-3-yl]amino}-carbonyl)-1,3-thiazol-2-yl]piperidin-1-yl}carbonothioyl)-beta-alaninate | |
| 352 | 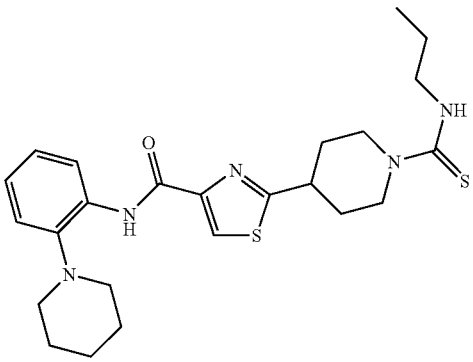 | |

US 7,674,803 B2
TABLE 1-continued
| No. | FORMULA | NMR or mass |
|---|---|---|
| 353 | 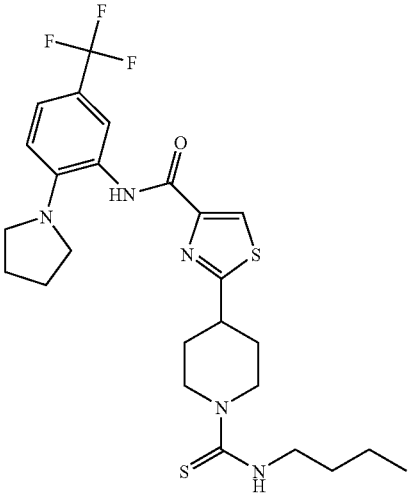 2-{1-[(butylamino)carbonothioyl]piperidin-4-yl}-N-[2-pyrrolidin-1-yl-5-(trifluoromethyl)phenyl]-1,3-thiazole-4-carboxamide | |
| 354 | 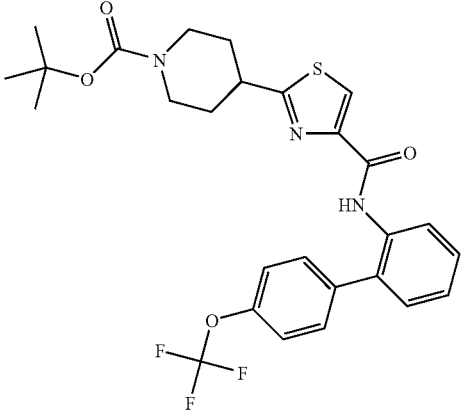 | |
| 355 | 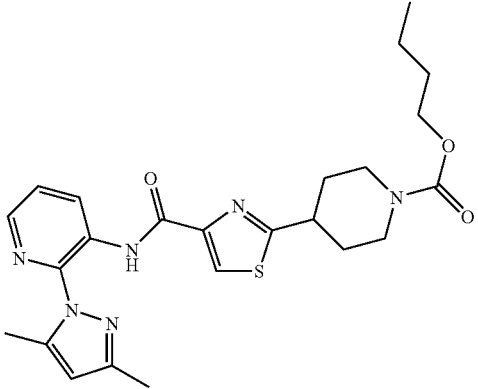 | |

TABLE 1-continued
| No. | FORMULA | NMR or mass |
|---|---|---|
| 356 | 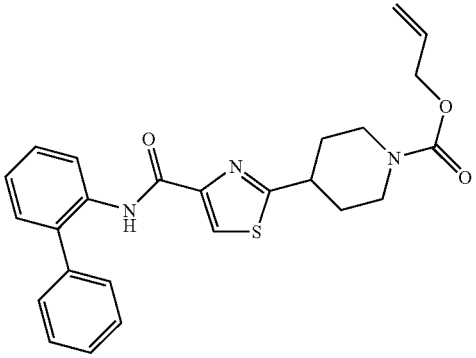 | |
| 357 | 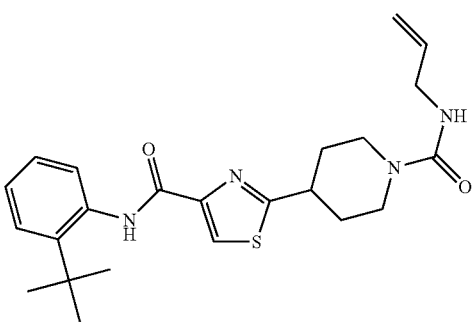 | |
| 358 | 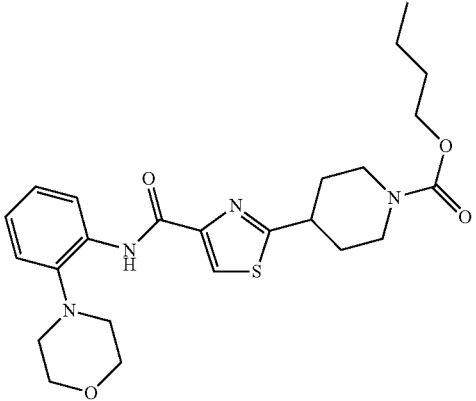 | |
| 359 | 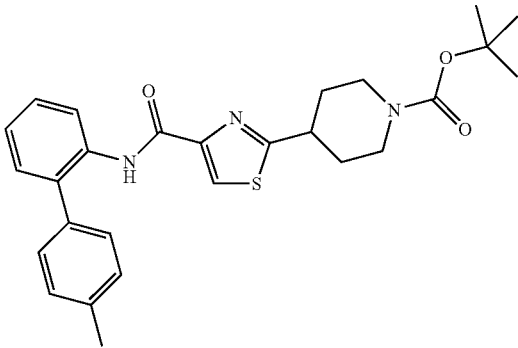 | |

TABLE 1-continued

| No. | FORMULA | NMR or mass |
|---|---|---|
| 360 | | |
| 361 | | |
| 362 | 2-{1-[(ethylamino)carbonothioyl]piperidin-4-yl}-N-[2-pyrrolidin-1-yl-5-(trifluoromethyl)phenyl]-1,3-thiazole-4-carboxamide | |

| No. | FORMULA | NMR or mass |
|---|---|---|
| 363 | 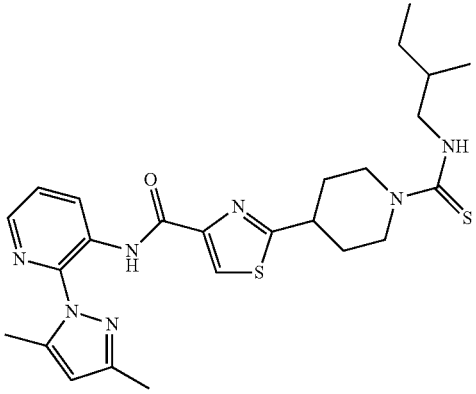 N-[2-(3,5-dimethyl-1H-pyrazol-1-yl)pyridin-3-yl]-2-(1-{[(2-methylbutyl)amino]-carbonothioul}piperidin-4-yl)-1,3-thiazole-4-carboxamide | |
| 364 | 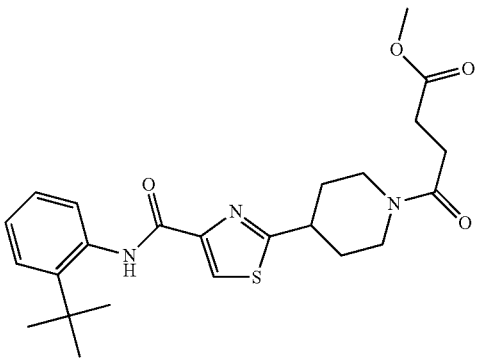 | |
| 365 | 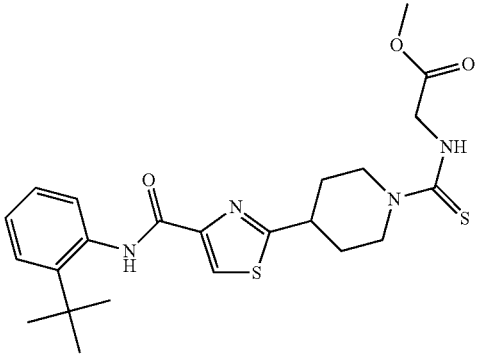 | |

TABLE 1-continued

| No. | FORMULA | NMR or mass |
|---|---|---|

366

2-{1-[(allylamino)carbonothioyl]piperidin-4-yl}-N-[2-pyrrolidin-1-yl-5-(trifluoro-methyl)phenyl]-1,3-thiazole-4-carboxamide

367

368

TABLE 1-continued
| No. | FORMULA | NMR or mass |
|---|---|---|
| 369 | 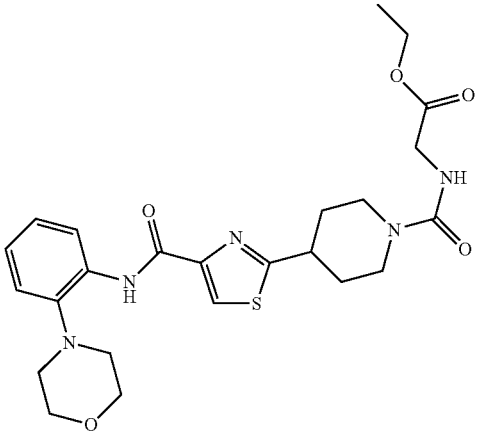 | |
| 370 | 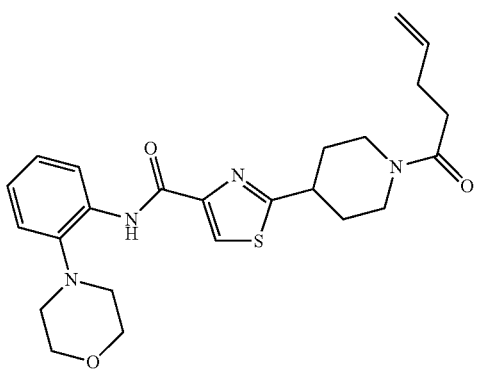 | |
| 371 | 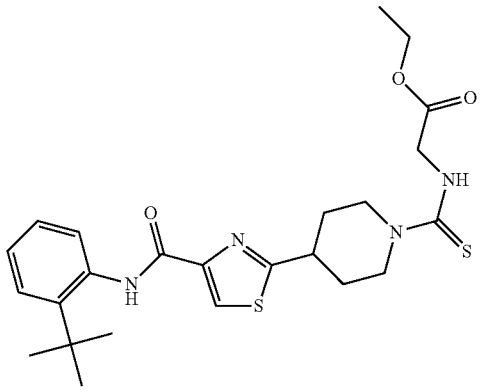 | |
| 372 | 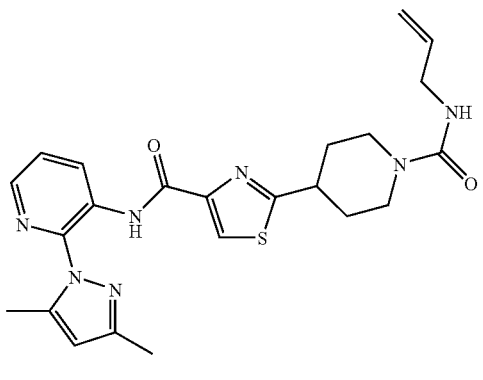 | |

TABLE 1-continued

| No. | FORMULA | NMR or mass |
|---|---|---|

373 ethyl N-({4-[4-({[2-pyrrolidin-1-yl-5-(trifluoromethyl)-phenyl]amino}-carbonyl}-1,3-thiazol-2-yl]piperidin-1-yl}carbonothioyl)alaninate

374

2-(1-{[(2-methylbutyl)amino]carbonothioyl}piperidin-4-yl)-N-[2-pyrrolidin-1-yl-5-(trifluoromethyl)phenyl]-1,3-thiazole-4-carboxamide TABLE 1-continued
| No. | FORMULA | NMR or mass |
|---|---|---|
| 375 | 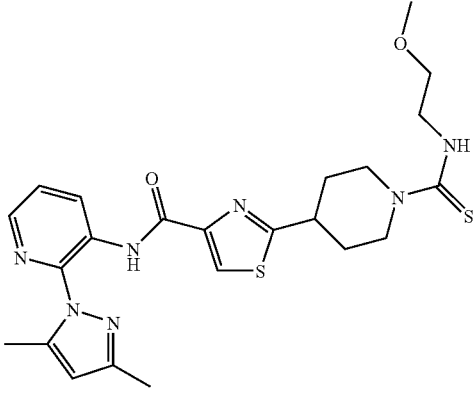 | |
| 376 | 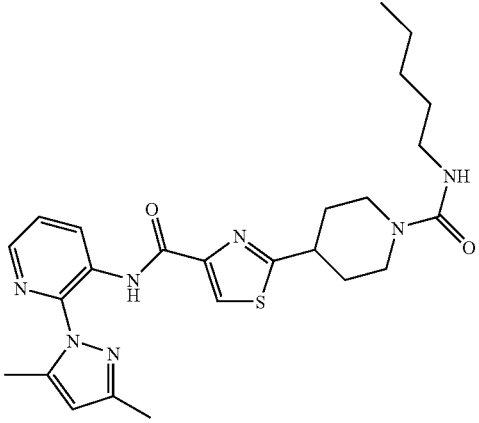 | |
| 377 | 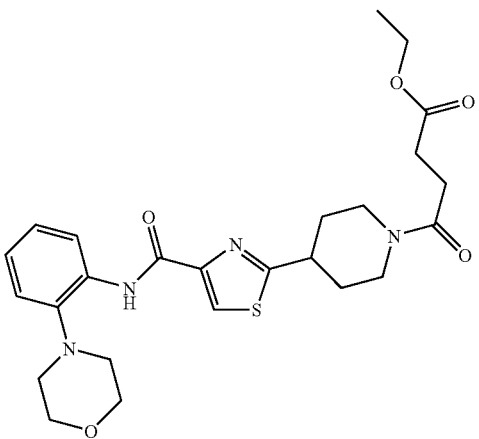 | |

TABLE 1-continued

| No. | FORMULA | NMR or mass |
|---|---|---|
| 378 | | |
| 379 | | |
| 380 | | |

TABLE 1-continued
| No. | FORMULA | NMR or mass |
|---|---|---|
| 381 | 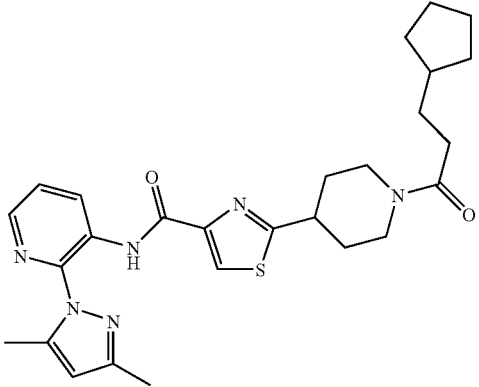 | |
| 382 | 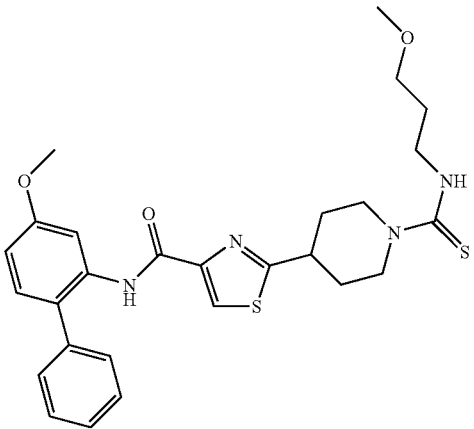 | |
| 383 | 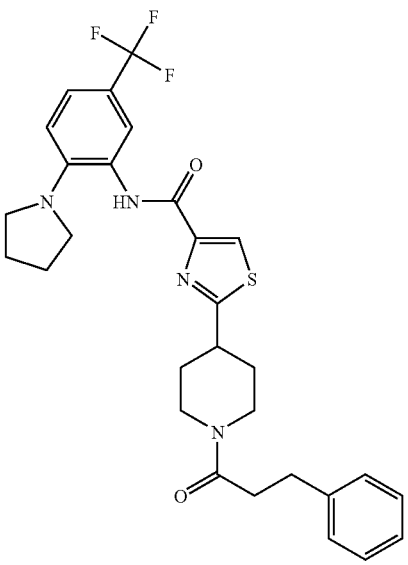 | |
2-[1-(3-phenylpropanoyl)piperidin-4-yl]-N-[2-pyrrolidin-1-yl-5-(trifluoro-methyl)phenyl]-1,3-thiazole-4-carboxamide TABLE 1-continued
| No. | FORMULA | NMR or mass |
|---|---|---|
| 384 | 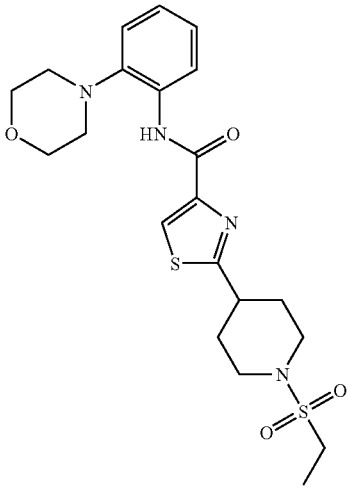 2-[1-(ethylsulfonyl)piperidin-4-yl]-N-(2-morpholin-4-ylphenyl)-1,3-thiazole-4-carboxamide | |
| 385 | 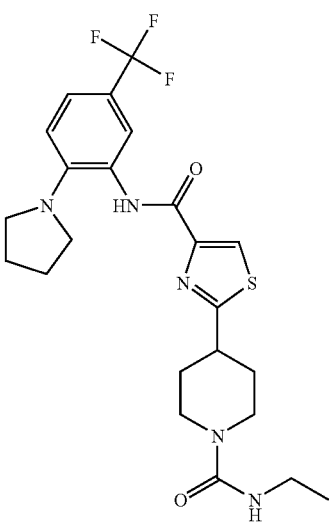 N-ethyl-4-[4-({[2-pyrrolidin-1-yl-5-(trifluoromethyl)phenyl]amino}-carbonyl)-1,3-thiazol-2-yl]piperidine-1-carboxamide | |
| 386 | 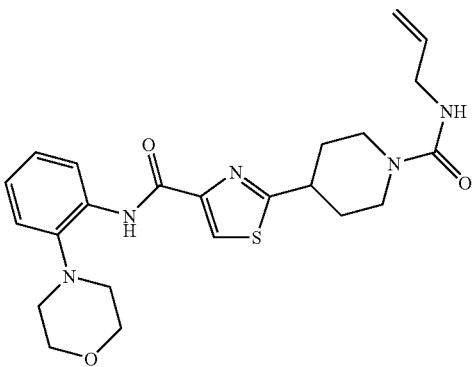 | |

TABLE 1-continued
| No. | FORMULA | NMR or mass |
|---|---|---|
| 387 | 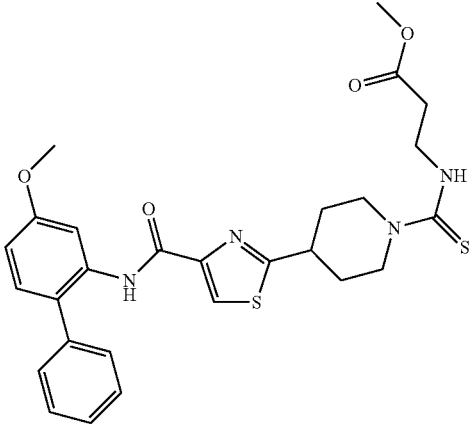 | |
| 388 | 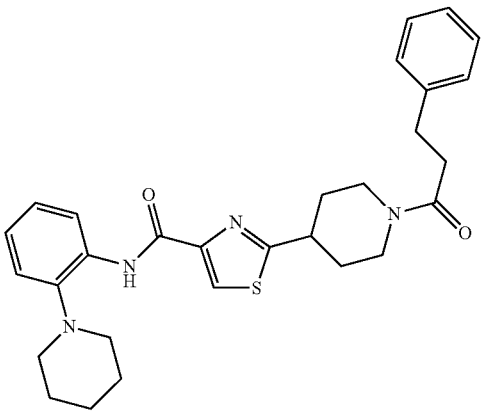 | |
| 389 | 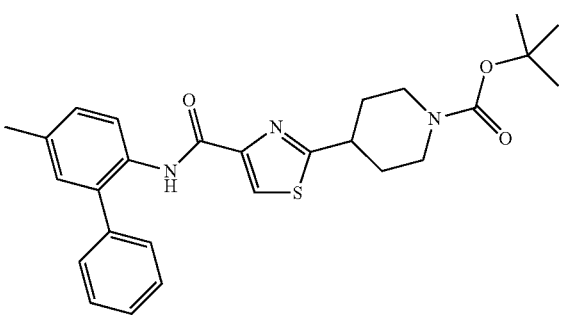 | |

TABLE 1-continued

| No. | FORMULA | NMR or mass |
|---|---|---|
| 390 | | | ethyl N-({4-[4-({[2-pyrrolidin-1-yl-5-(trifluoromethyl)phenyl]amino}carbonyl)-1,3-thiazol-2-yl]piperidin-1-yl}carbonyl)glycinate

| 391 | | |

| 392 | | |

TABLE 1-continued

| No. | FORMULA | NMR or mass |
|---|---|---|
| 393 | | |
| 394 | | |
| 395 | | |

395: N-butyl-4-[4-({[2-pyrrolidin-1-yl-5-(trifluoromethyl)phenyl]amino}carbonyl)-1,3-thiazol-2-yl]piperidine-1-carboxamide

TABLE 1-continued
| No. | FORMULA | NMR or mass |
|---|---|---|
| 396 | 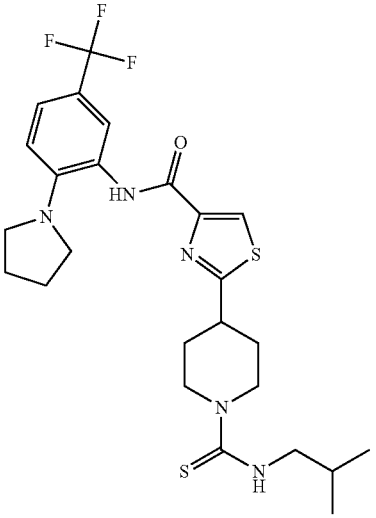 2-{1-[(isobutylamino)carbonothioyl]piperidin-4-yl}-N-[2-pyrrolidin-1-yl-5-(trifluoromethyl)phenyl]-1,3-thiazole-4-carboxamide | |
| 397 | 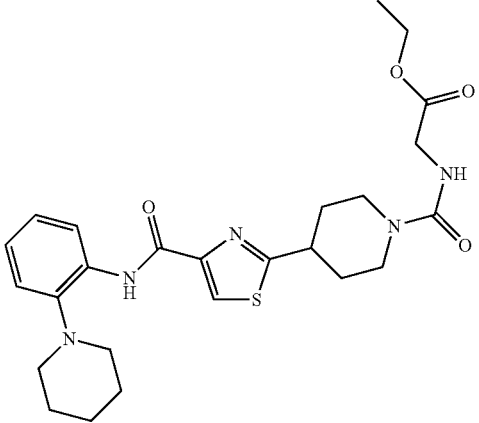 | |
| 398 | 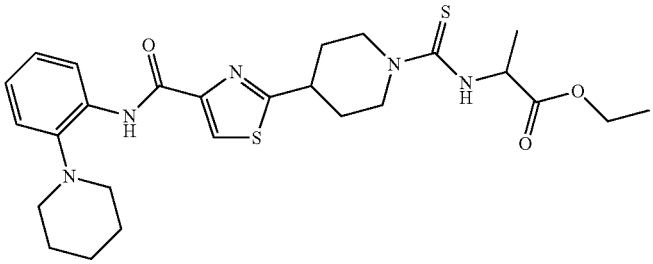 | |

TABLE 1-continued
| No. | FORMULA | NMR or mass |
|---|---|---|
| 399 | 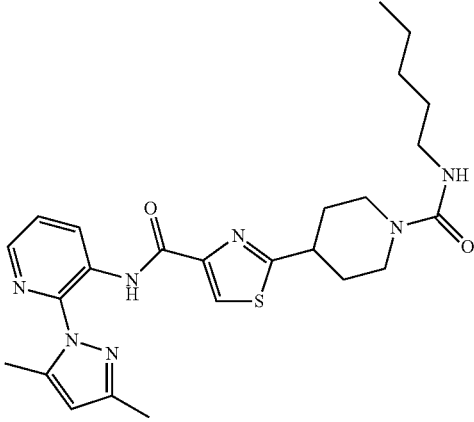 | |
| 400 | 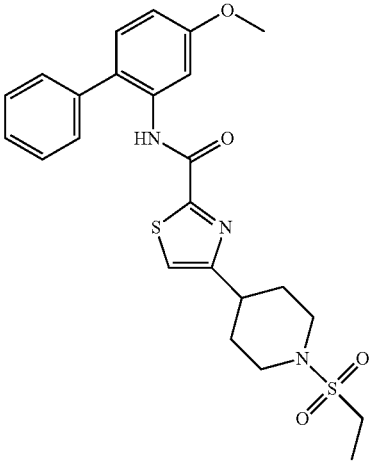 | |
| 401 | 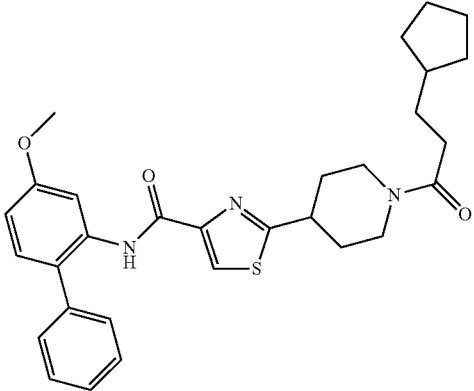 | |

TABLE 1-continued
| No. | FORMULA | NMR or mass |
|---|---|---|
| 402 | 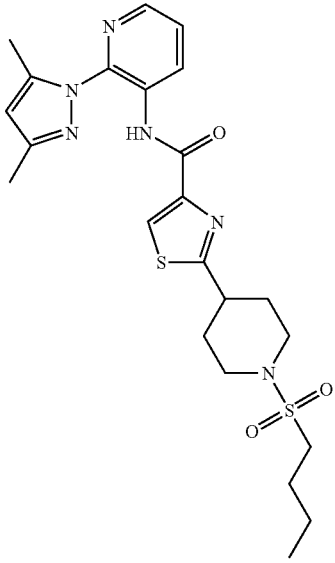 2-[1-(butylsulfonyl)piperidin-4-yl]-N-[2-(3,5-dimethyl-1H-pyrazol-1-yl)pryridin-3-yl]-1,3-thiazole-4-carboxamide | |
| 403 | 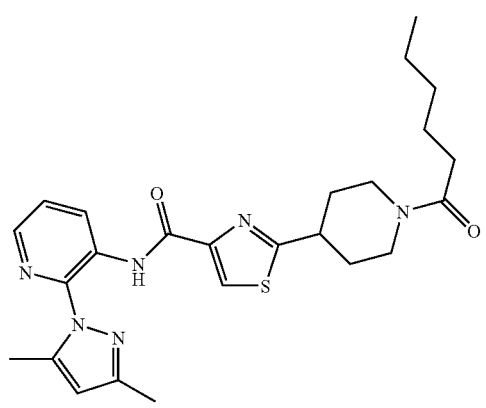 | |
| 404 | 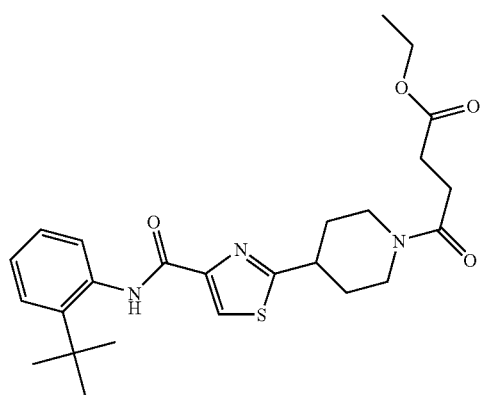 | |

TABLE 1-continued
| No. | FORMULA | NMR or mass |
|---|---|---|
| 405 | 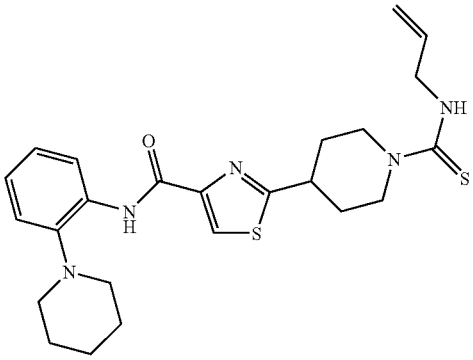 | |
| 406 | 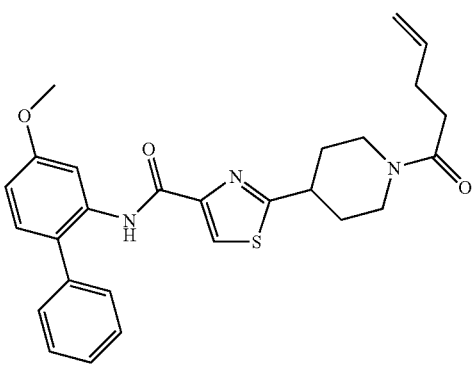 | |
| 407 | 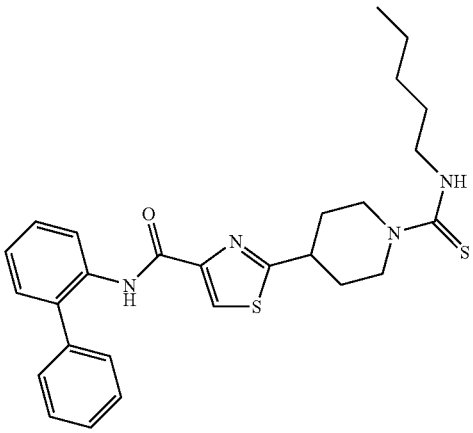 | |
| 408 | 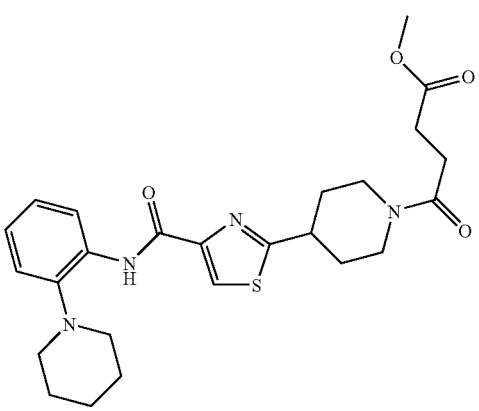 | |

TABLE 1-continued
| No. | FORMULA | NMR or mass |
|---|---|---|
| 409 | 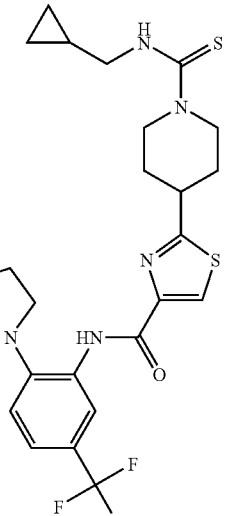 2-(1-{[(cyclopropylmethyl)amino]carbonothioyl}piperidin-4-yl)-N-[2-pyrrolidin-1-yl-5-(trifluoromethyl)phenyl]-1,3-thiazole-4-carboxamide | |
| 410 | 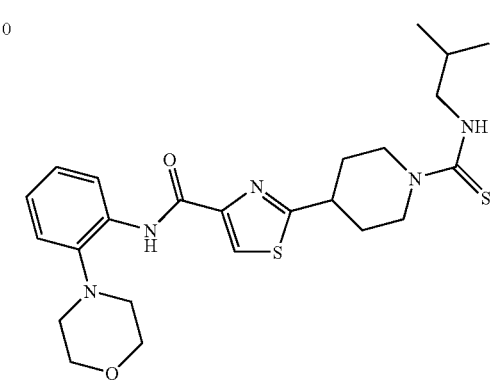 | |
| 411 | 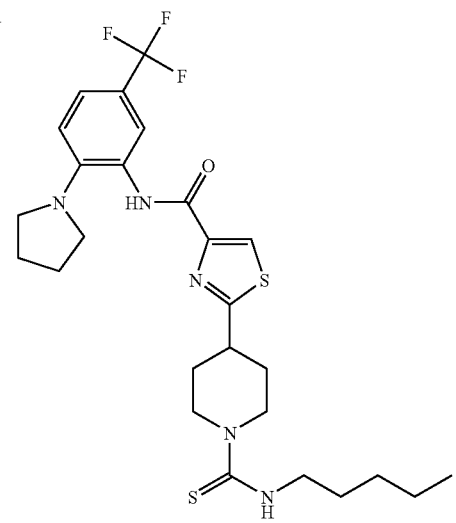 2-{1-[(pentylamino)carbonothioyl]piperidin-4-yl}-N-[2-pyrrolidin-1-yl-5-(trifluoromethyl)phenyl]-1,3-thiazole-4-carboxamide | |

TABLE 1-continued
| No. | FORMULA | NMR or mass |
|---|---|---|
| 412 | 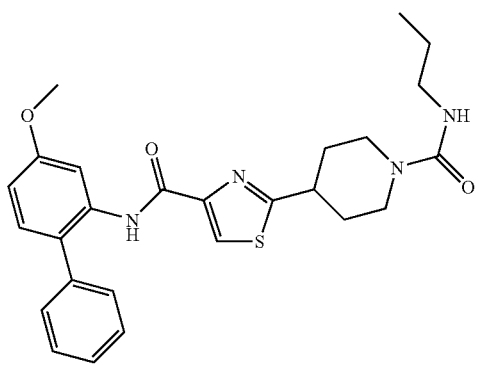 | |
| 413 | 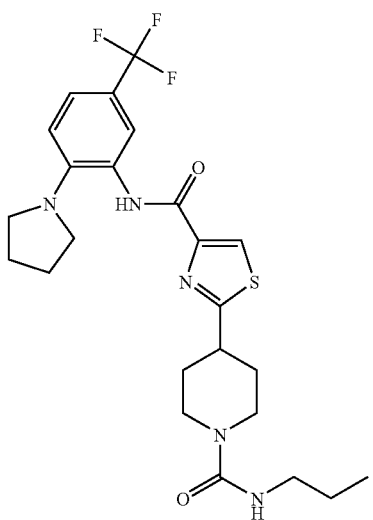<br>N-propyl-4-[4-({[2-pyrrolidin-1-yl-5-(trifluoromethyl)phenyl]amino}carbonyl)-1,3-thiazol-2-yl]piperidine-1-carboxamide | |
| 414 | 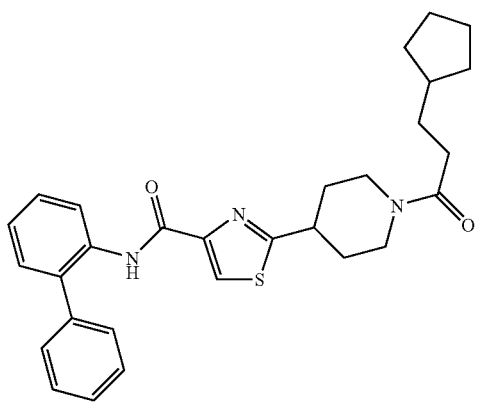 | |

TABLE 1-continued

| No. | FORMULA | NMR or mass |
|---|---|---|
| 415 | | |
| 416 | 2-(1-[{(2-furylmethyl)amino]carbonothioyl} piperidin-4-yl)-N-[2-pyrrolidin-1-yl-5-(trifluoromethyl)phenyl]-1,3-thiazole-4-carboxamide | |

TABLE 1-continued
| No. | FORMULA | NMR or mass |
|---|---|---|
| 417 | 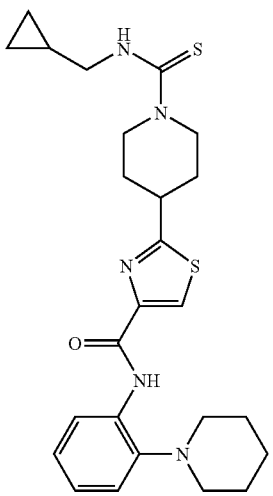 2-(1-{[(cyclopropylmethyl)amino]carbonothioyl}piperidin-4-yl)-N-(2-piperidin-1-ylphenyl)-1,3-thiazole-4-carboxamide | |
| 418 | 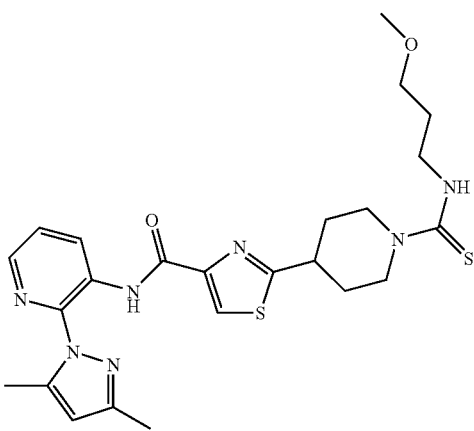 | |
| 419 | 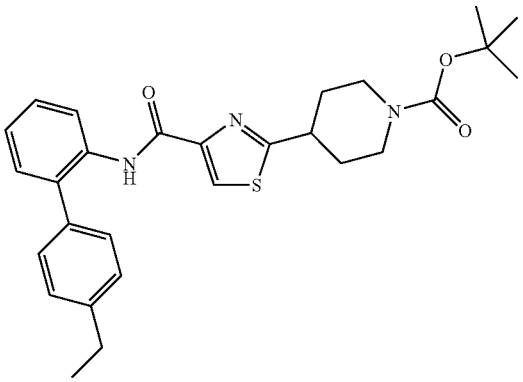 | |

TABLE 1-continued
| No. | FORMULA | NMR or mass |
|---|---|---|
| 420 | 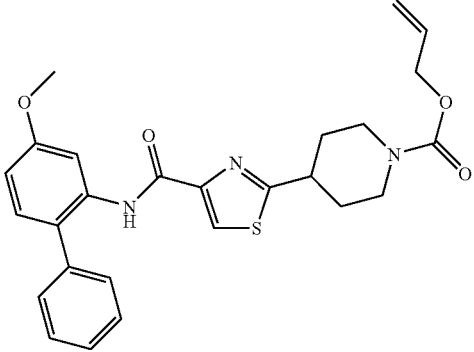 | |
| 421 | 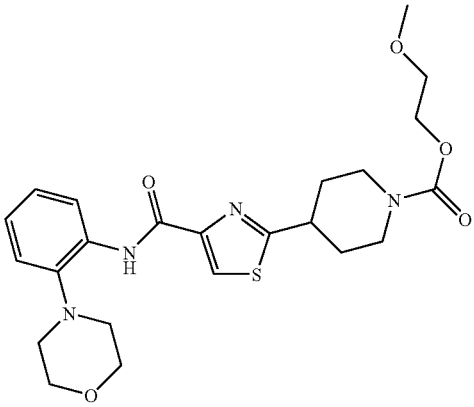 | |
| 422 | 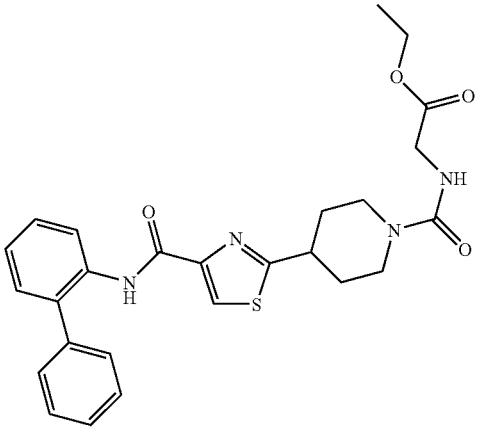 | |
| 423 | 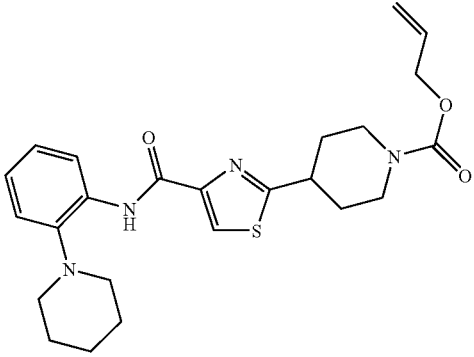 | |

TABLE 1-continued
| No. | FORMULA | NMR or mass |
|---|---|---|
| 424 | 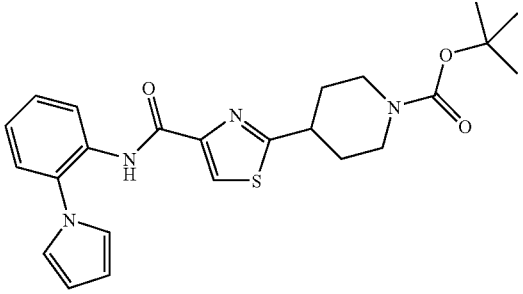 | |
| 425 | 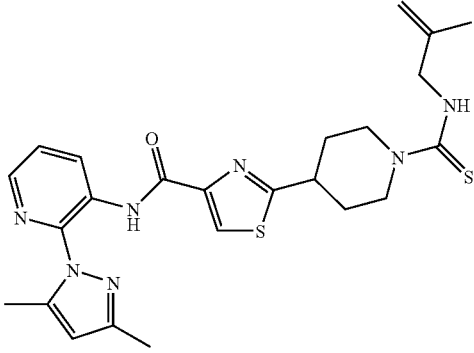 | |
| 426 | 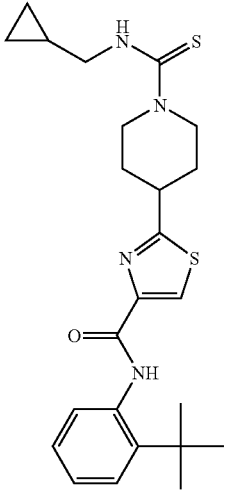 | |
N-(2-tert-butylphenyl)-2-(1-{[(cyclopropylmethyl)amino]carbonthioyl}-piperidin-4-yl)-1,3-thiazole-4-carboxamide TABLE 1-continued
| No. | FORMULA | NMR or mass |
|---|---|---|
| 427 | 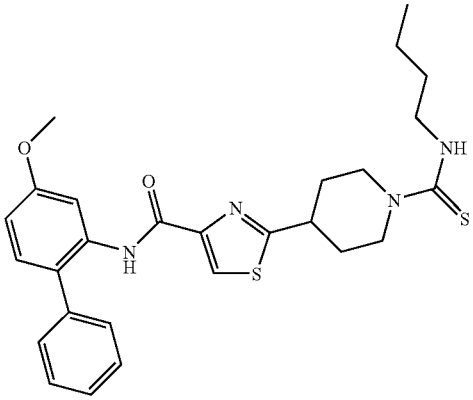 | |
| 428 | 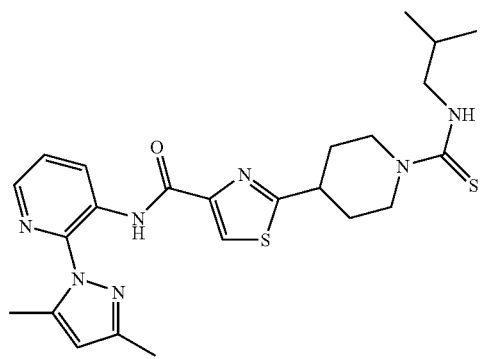 | |
| 429 | 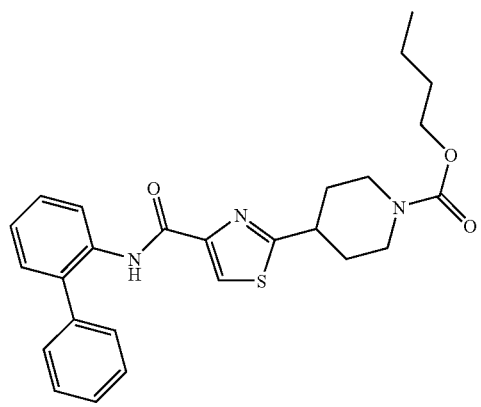 | |
| 430 | 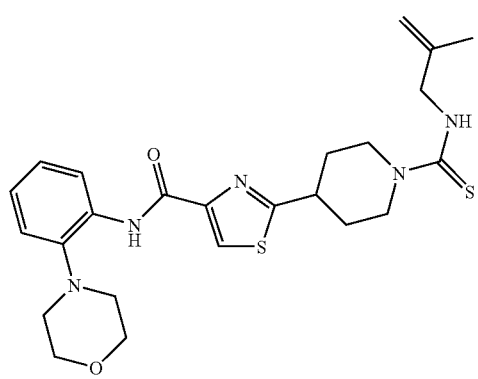 | |

TABLE 1-continued

| No. | FORMULA | NMR or mass |
|-----|---------|-------------|
| 431 | | |
| 432 | | |
| 433 | | |
| 434 | | |

TABLE 1-continued

| No. | FORMULA | NMR or mass |
|---|---|---|
| 435 | | |
| 436 | | |
| 437 | 2-(1-{[(cyclopropylmethyl)amino]carbonothioyl}piperidin-4-yl)-N-[2-(3,5-dimethyl-1H-pyrazol-1-yl)pyridin-3-yl]-1,3-thiazole-4-carboxamide | |

TABLE 1-continued
| No. | FORMULA | NMR or mass |
|---|---|---|
| 438 | 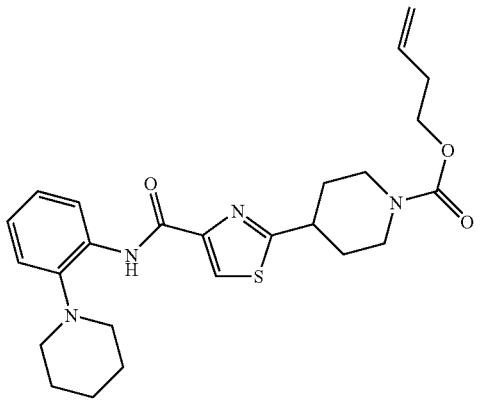 | |
| 439 | 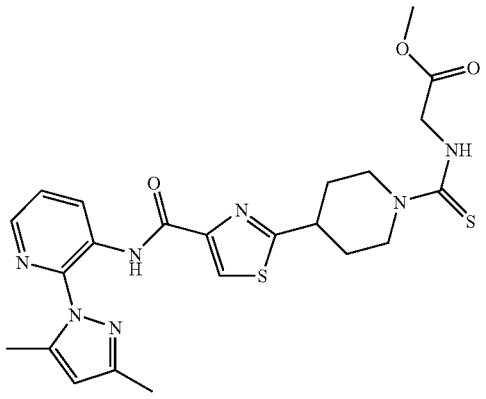 | |
| 440 | 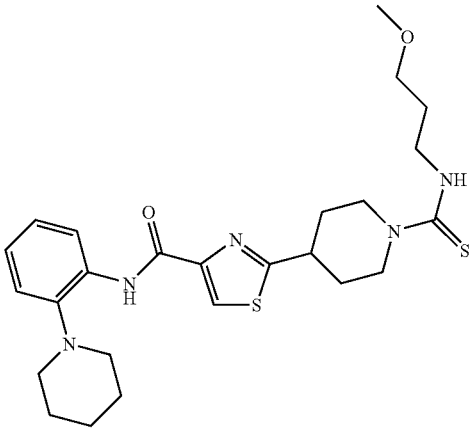 | |

TABLE 1-continued
| No. | FORMULA | NMR or mass |
|---|---|---|
| 441 | 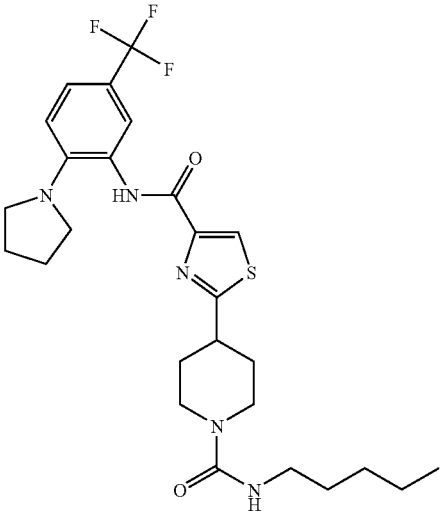<br>N-pentyl-4-[4-({[2-pyrrolidin-1-yl-5-(trifluoromethyl)phenyl]amino}carbonyl)-1,3-thiazol-2-yl]piperidine-1-carboxamide | |
| 442 | 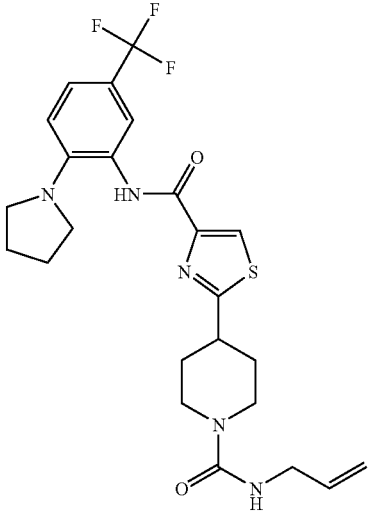<br>N-ally-4-[4-({[2-pyrrolidin-1-yl-5-(trifluoromethyl)phenyl]amino}carbonyl)-1,3-thiazol-2-yl]piperidine-1-carboxamide | |

TABLE 1-continued

| No. | FORMULA | NMR or mass |
|---|---|---|
| 443 | | |
| 444 | | |
| 445 | | |

TABLE 1-continued
| No. | FORMULA | NMR or mass |
|---|---|---|
| 446 | 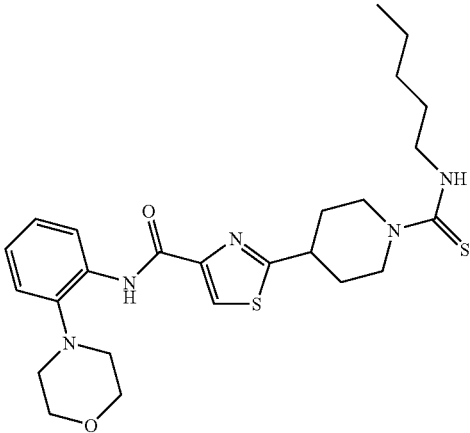 | |
| 447 | 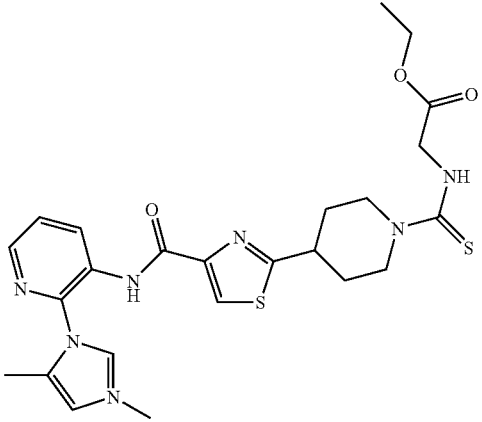 | |
| 448 | 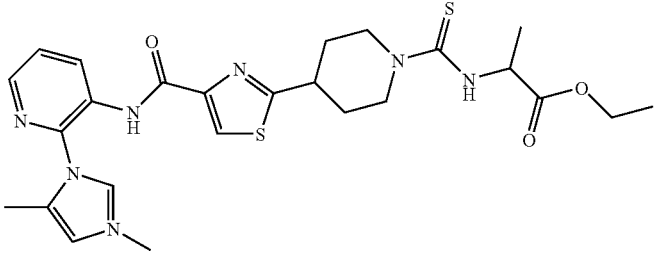 | |
| 449 | 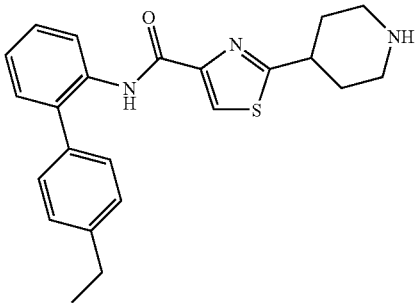 | |

TABLE 1-continued
| No. | FORMULA | NMR or mass |
|---|---|---|
450
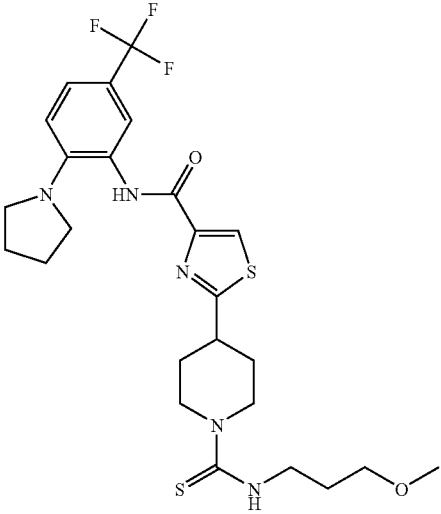
2-(1-{[(3-methoxypropyl)amino]carbonothioyl}
piperidin-4-yl)-N-[2-pyrrolidin-1-yl-5-
(trifluoromethyl)phenyl]-1,3-thiazole-4-carboxamide
451
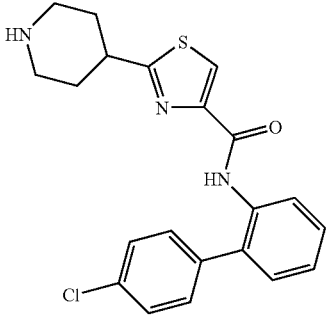
452
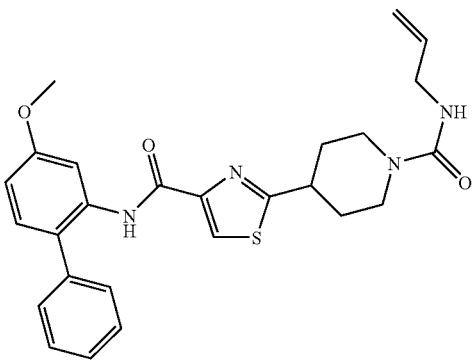

TABLE 1-continued

| No. | FORMULA | NMR or mass |
|-----|---------|-------------|
| 453 | | |
| 454 | | |
| 455 | 2-(1-{[(2-methoxyethyl)amino]carbonothioyl}piperidin-4-yl)-N-[2-pyrrolidin-1-yl-5-(trifluoromethyl)phenyl]-1,3-thiazole-4-carboxamide | |

| No. | FORMULA | NMR or mass |
|---|---|---|
| 456 | | |
| 457 | | |
| 458 | | |
| 459 | | |

TABLE 1-continued
| No. | FORMULA | NMR or mass |
|---|---|---|
| 460 | 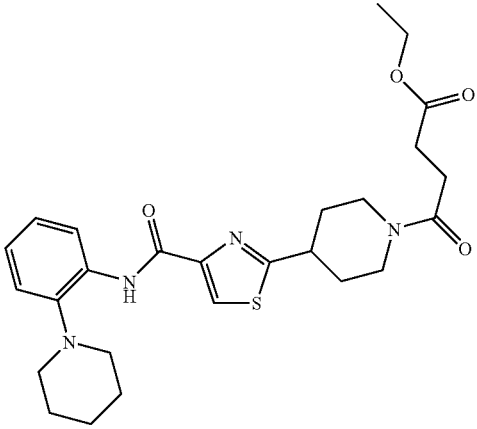 | |
| 461 | 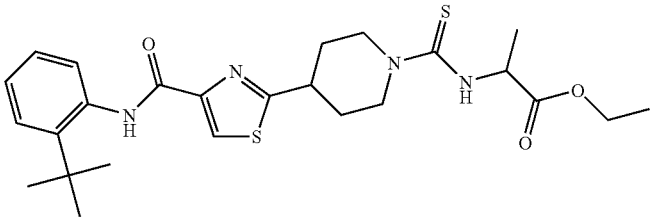 | |
| 462 | 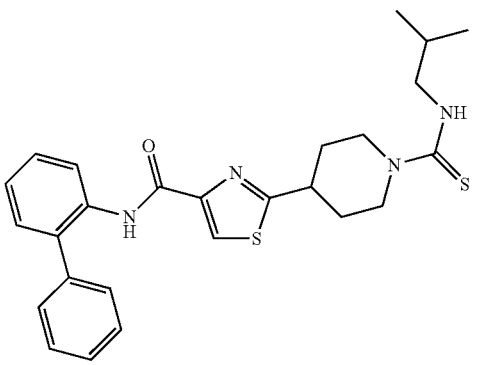 | |
| 463 | 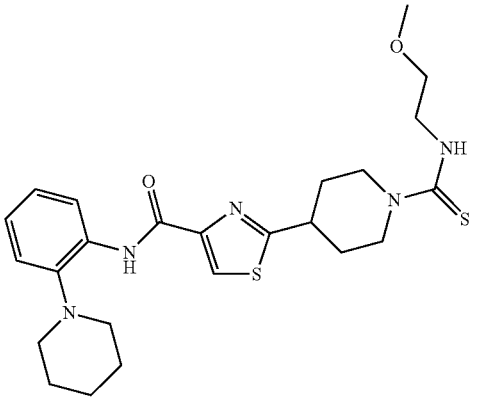 | |

TABLE 1-continued
| No. | FORMULA | NMR or mass |
|---|---|---|
| 464 | 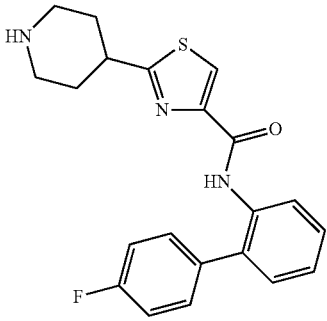 | |
| 465 | 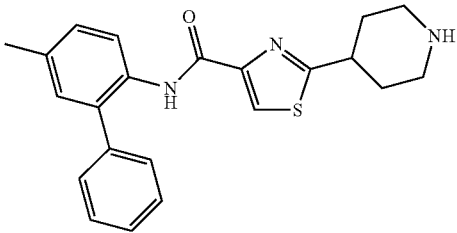 | |
| 466 | 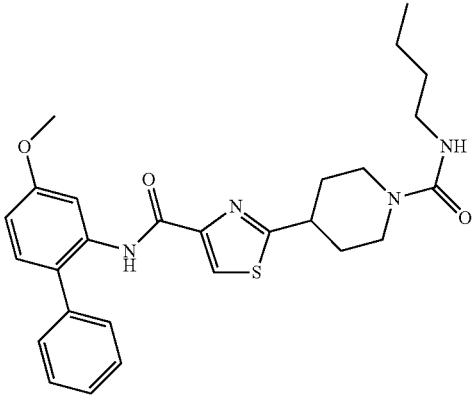 | |
| 467 | 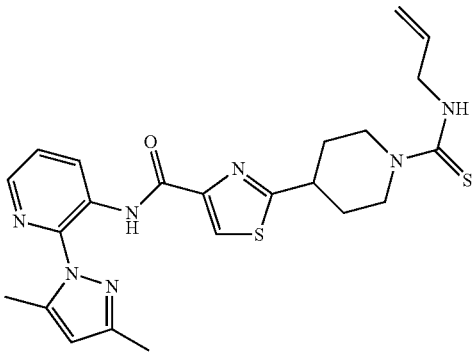 | |

| No. | FORMULA | NMR or mass |
|---|---|---|
| 468 | 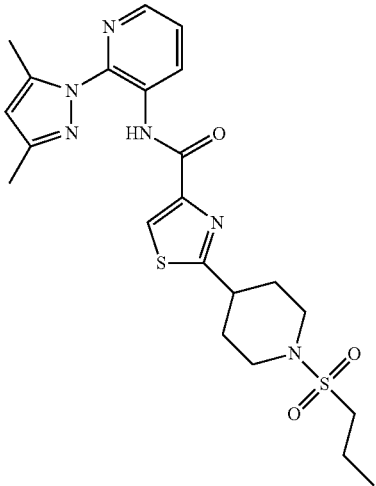 N-[2-(3,5-dimethyl-1H-pyrazol-1-yl)pyridin-3-yl]-2-[1-(propylsulfonyl)-piperidin-4-yl]-1,3-thiazole-4-carboxamide | |
| 469 | 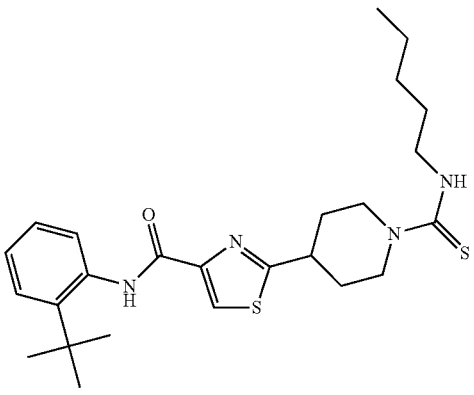 | |
| 470 | 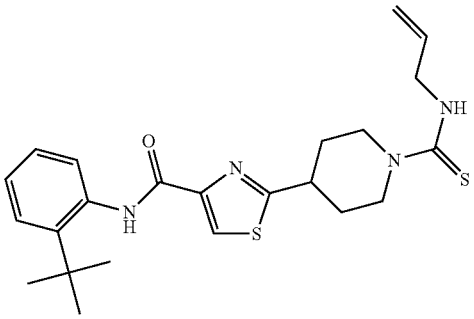 | |

TABLE 1-continued
| No. | FORMULA | NMR or mass |
|---|---|---|
| 471 | 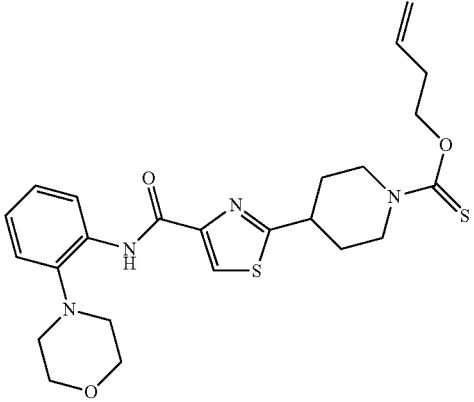 | |
| 472 | 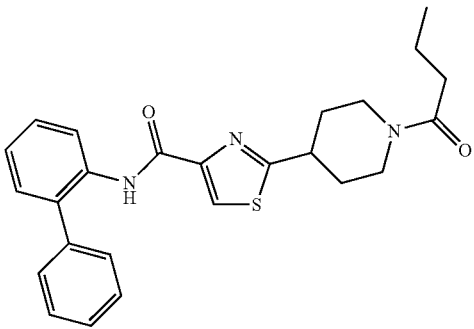 | |
| 473 | 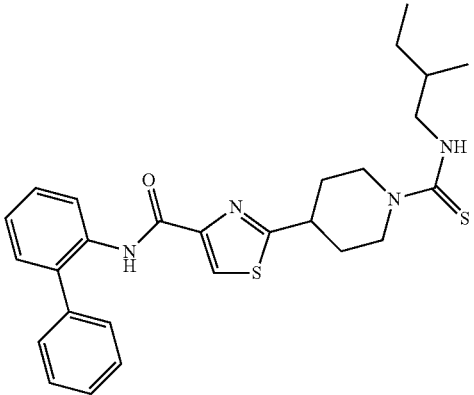 | |
| 474 | 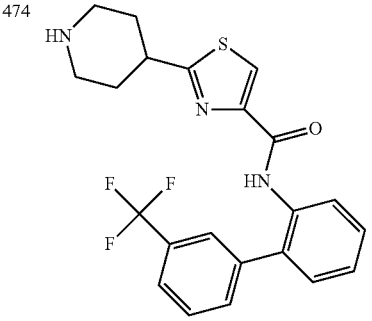 | |

TABLE 1-continued

| No. | FORMULA | NMR or mass |
|---|---|---|
| 475 | | |
| 476 | | |
| 477 | | |
| 478 | | |

TABLE 1-continued
| No. | FORMULA | NMR or mass |
|---|---|---|
| 479 | 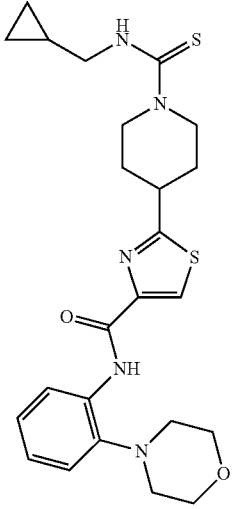 2-(1-{[(cyclopropylmethyl)amino]carbonothioyl}piperidin-4-yl)-N-(2-morpholin-4-ylphenyl)-1,3-thiazole-4-carboxamide | |
| 480 | 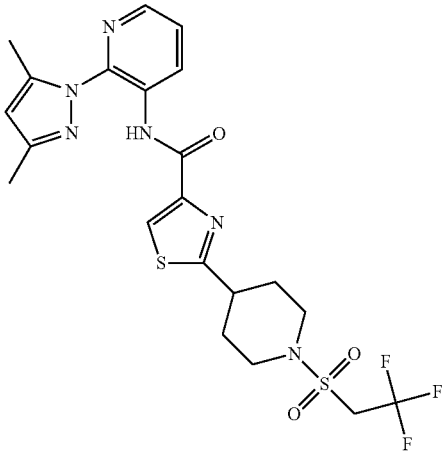 N-[2-(3,5-dimethyl-1H-pyrazol-1-yl)pyridin-3-yl]-2-{1-[(2,2,2-trifluoroethyl)-sulfonyl]piperidin-4-yl}-1,3-thiazole-4-carboxamide | |

| No. | FORMULA | NMR or mass |
|---|---|---|
| 481 | 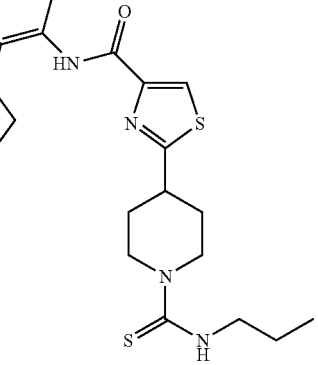 2-{1-[(propylamino)carbonothioyl]piperidin-4-yl}-N-[2-pyrrolidin-1-yl-5-(trifluoromethyl)phenyl]-1,3-thiazole-4-carboxamide | |
| 482 | 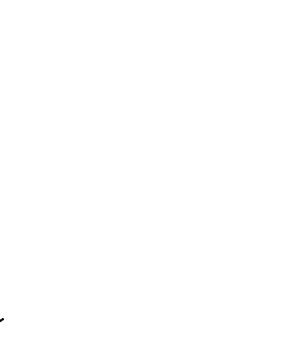 | |
| 483 | 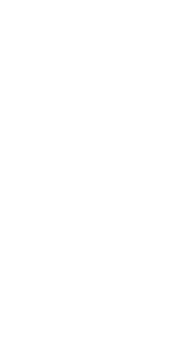 | |

TABLE 1-continued
| No. | FORMULA | NMR or mass |
|---|---|---|
| 484 | 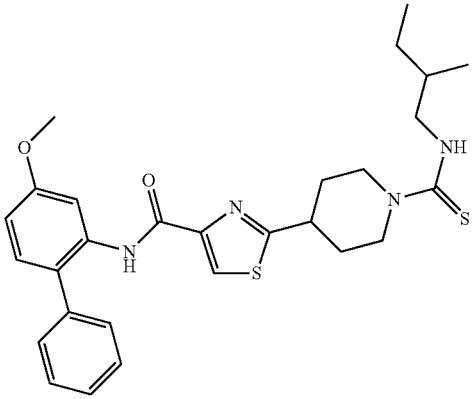 | |
| 485 | 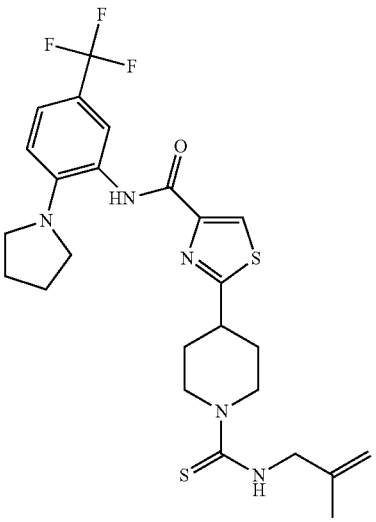 | |
2-(1-{[(2-methylprop-2-en-1yl)amino]carbonothioyl}piperidin-4-yl)-N-[2-pyrrolidin-1-yl-5-(trifluoromethyl)phenyl]-1,3-thiazole-4-carboxamide
| 486 | 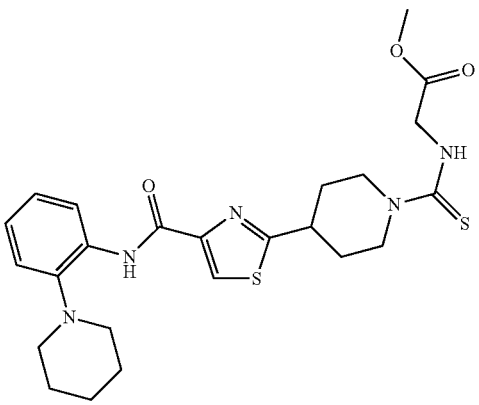 | |

TABLE 1-continued
| No. | FORMULA | NMR or mass |
|---|---|---|
| 487 | 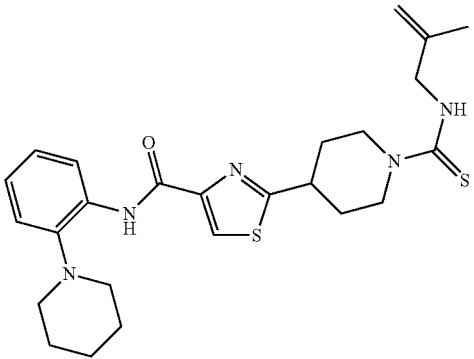 | |
| 488 | 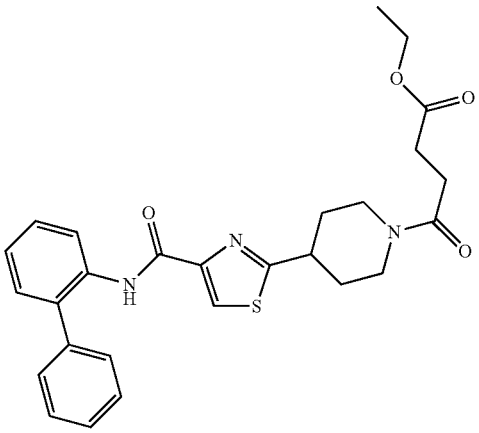 | |
| 489 | 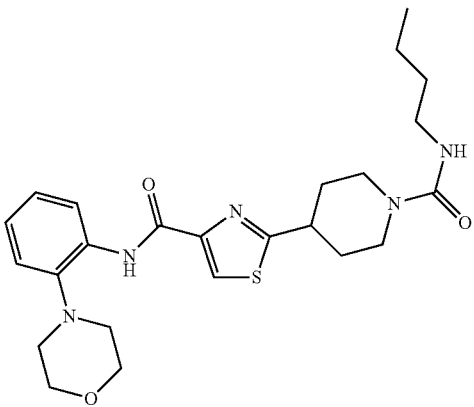 | |
| 490 | 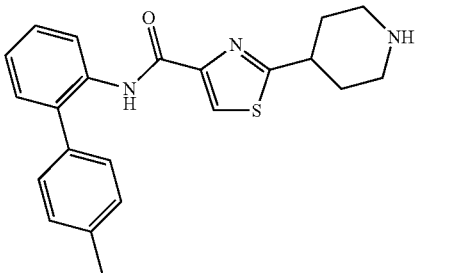 | |

TABLE 1-continued
| No. | FORMULA | NMR or mass |
|---|---|---|
| 491 | 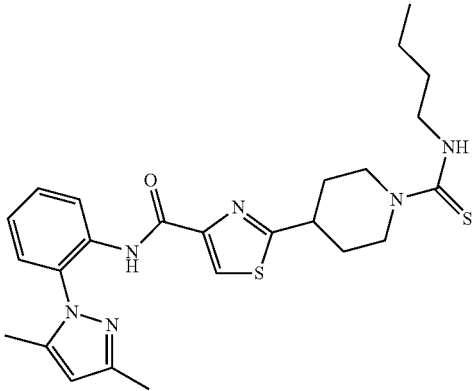 2-{1-[(butylamino)carbonothioyl]piperidin-4-yl}-N-[2-(3-5-dimethyl-1H-pyrazol-1-yl)pyridin-3-yl]-1,3-thiazole-4-carboxamide | |
| 492 | 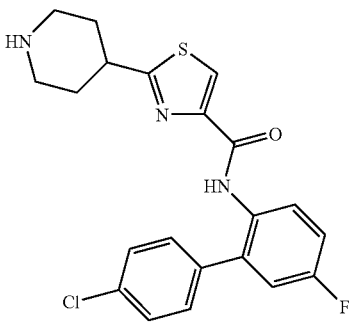 | |
| 493 | 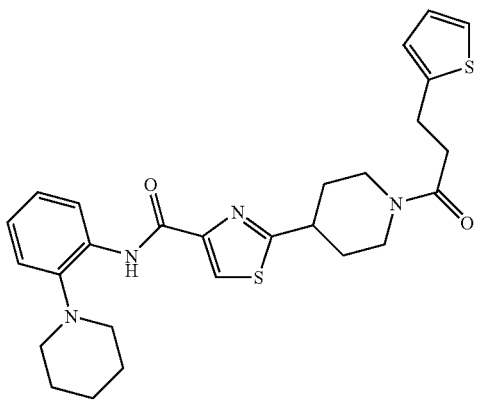 | |
| 494 | 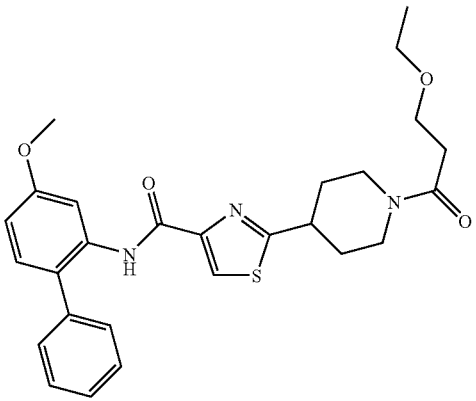 | |

TABLE 1-continued
| No. | FORMULA | NMR or mass |
|---|---|---|
| 495 | 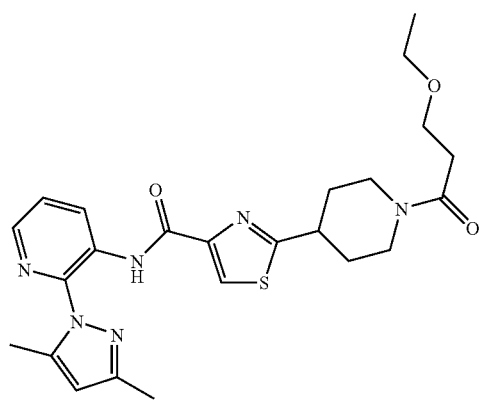 | |
| 496 | 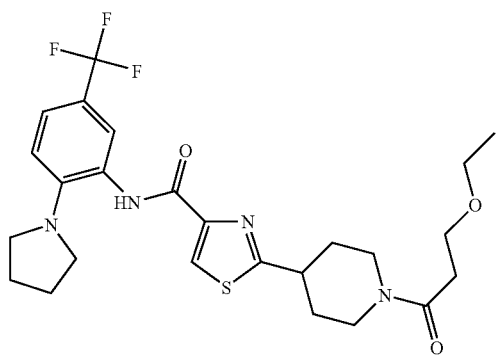 | |
| 497 | 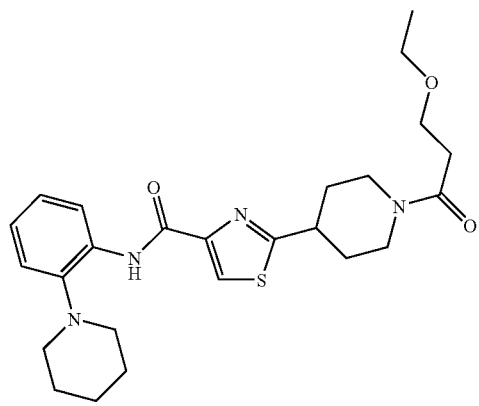 | |
| 498 | 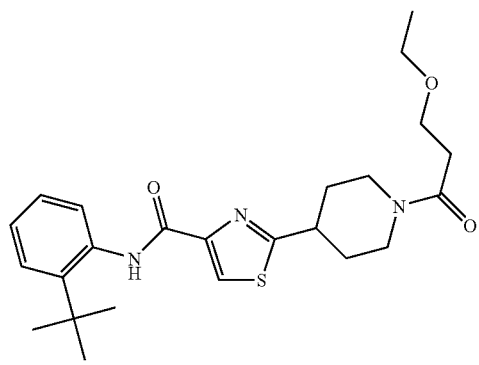 | |

TABLE 1-continued
| No. | FORMULA | NMR or mass |
|---|---|---|
| 499 | 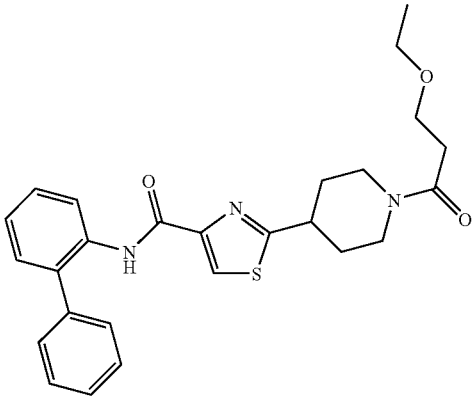 | |
| 500 | 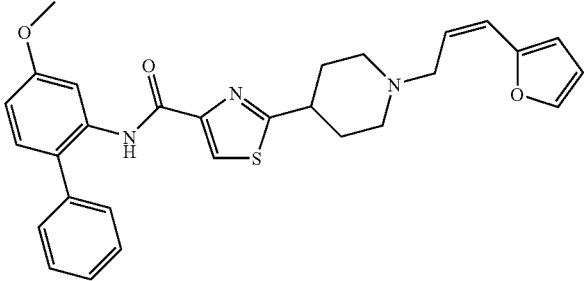 | |
| 501 | 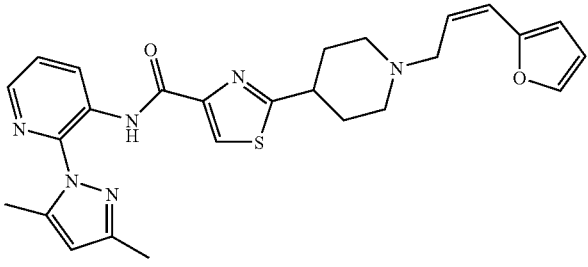 | |
| 502 | 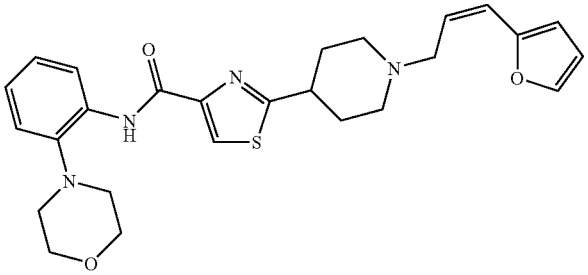 | |

TABLE 1-continued

| No. | FORMULA | NMR or mass |
|---|---|---|
| 503 | | |
| 504 | | |

N-[2-(3,5-dimethyl-1H-pyrazol-1-yl)pyridin-3-yl]-2-[1-(2-methyl-3-phenyl-propanoyl)piperidin-4-yl]-1,3-thiazole-4-carboxamide

| 505 | | |

TABLE 1-continued
| No. | FORMULA | NMR or mass |
|---|---|---|
| 506 | 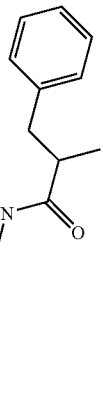 | |
| 507 |  | |
| 508 |  | |
| 509 | 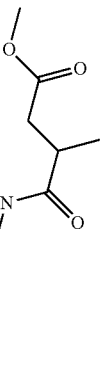 | |

TABLE 1-continued
| No. | FORMULA | NMR or mass |
|---|---|---|
| 510 | 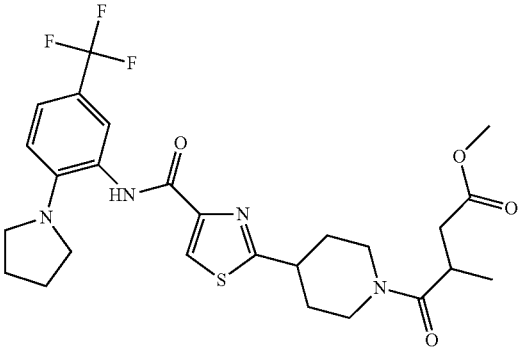 | |
| 511 | 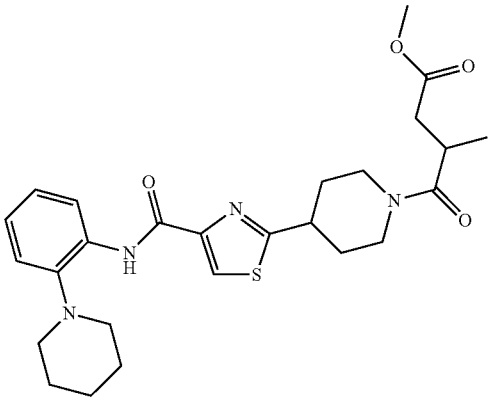 | |
| 512 | 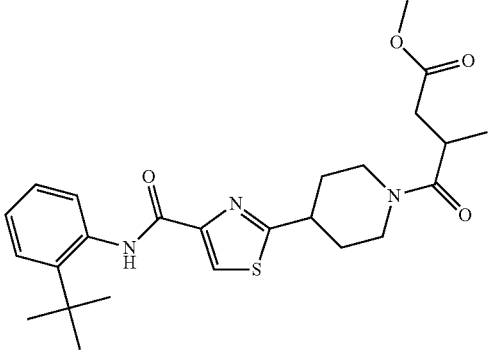 | |
| 513 | 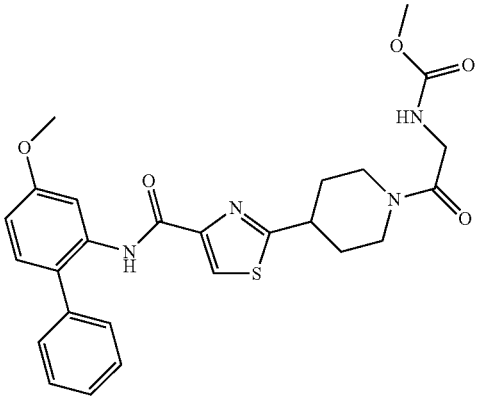 | |

TABLE 1-continued
| No. | FORMULA | NMR or mass |
|---|---|---|
| 514 | 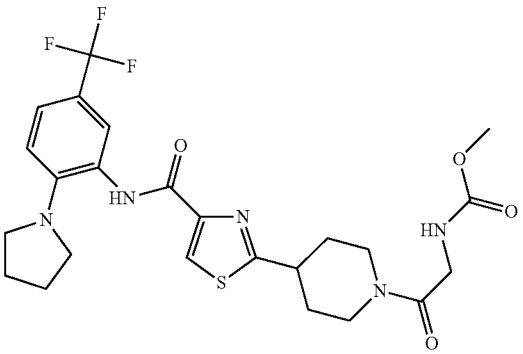 | |
| 515 | 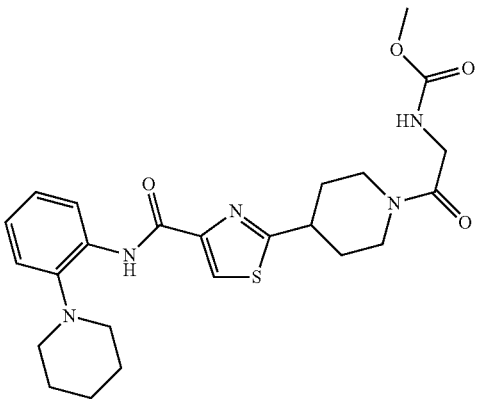 | |
| 516 | 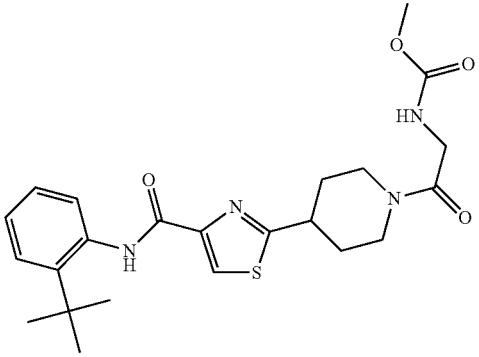 | |
| 517 | 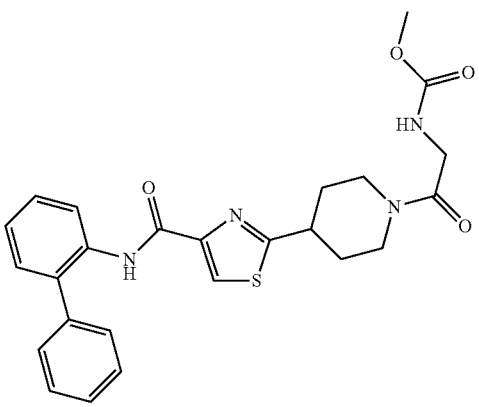 | |

TABLE 1-continued
| No. | FORMULA | NMR or mass |
|---|---|---|
| 518 | 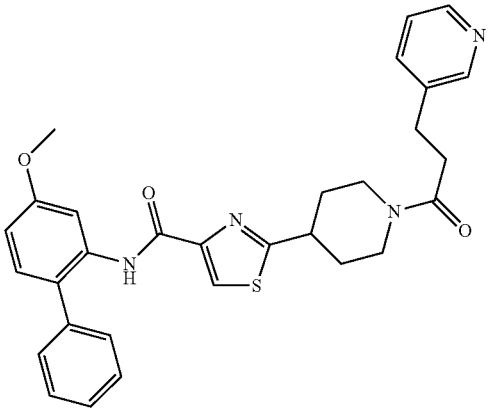 | |
| 519 | 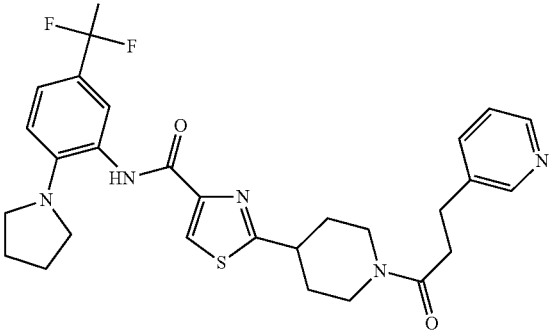 | |
| 520 | 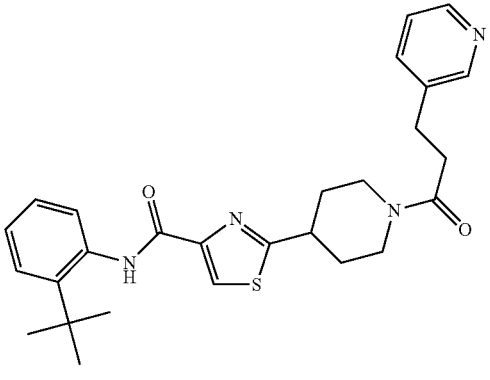 | |
| 521 | 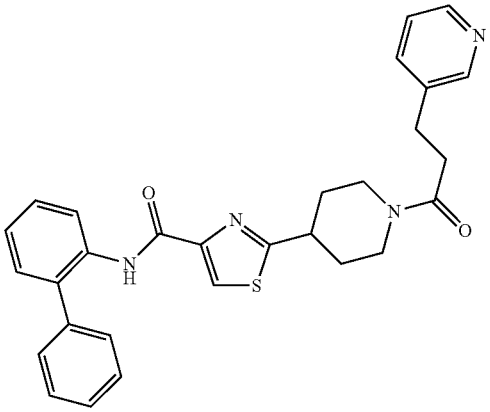 | |

TABLE 1-continued
| No. | FORMULA | NMR or mass |
|---|---|---|
| 522 | 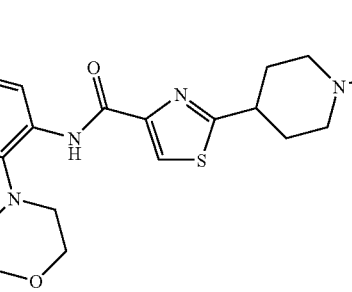 | |
| 523 | 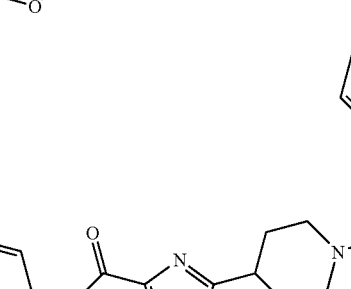 | |
| 524 | 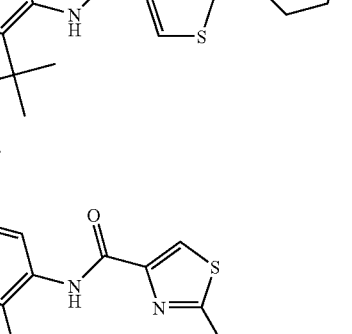 | |
| 525 | 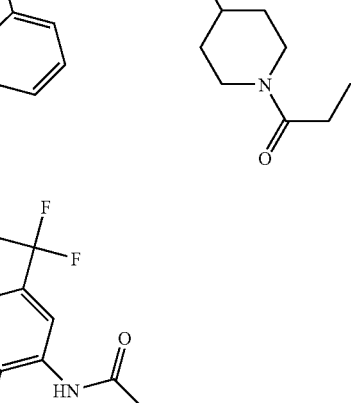 | |

TABLE 1-continued

| No. | FORMULA | NMR or mass |
|---|---|---|
| 526 | | |
| 527 | | |
| 528 | | |
| 529 | | |

TABLE 1-continued
| No. | FORMULA | NMR or mass |
|---|---|---|
| 530 | 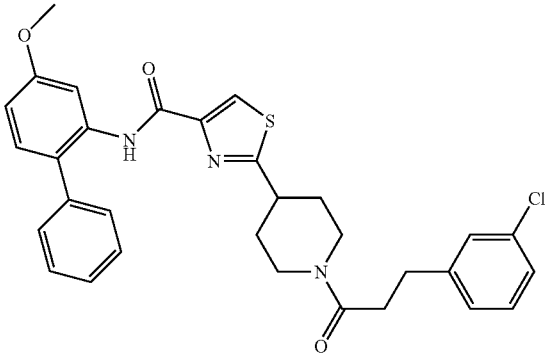 | |
| 531 | 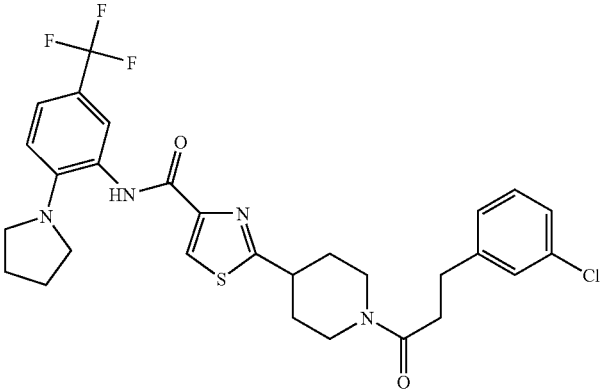 | |
| 532 | 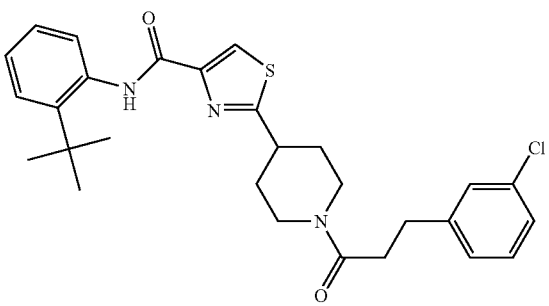 | |
| 533 | 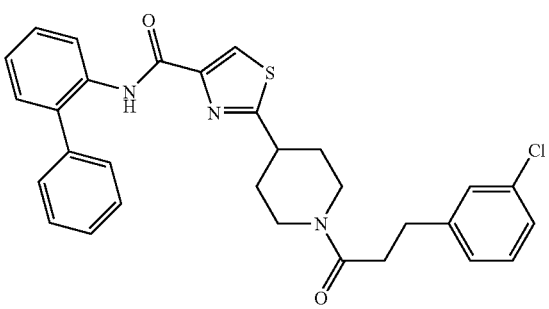 | |

TABLE 1-continued
| No. | FORMULA | NMR or mass |
|---|---|---|
| 534 | 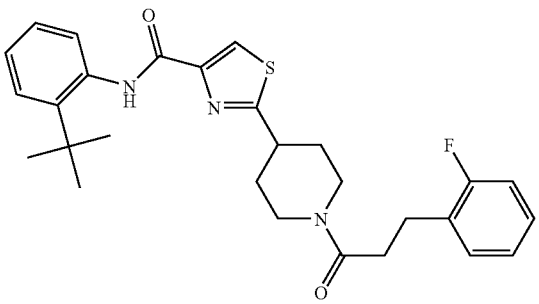 | |
| 535 | 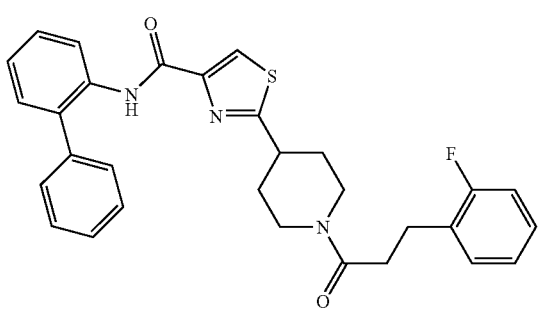 | |
| 536 | 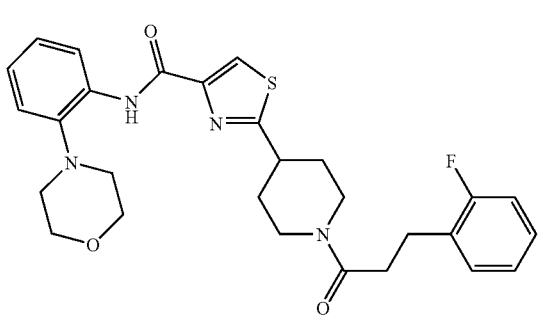 | |
| 537 | 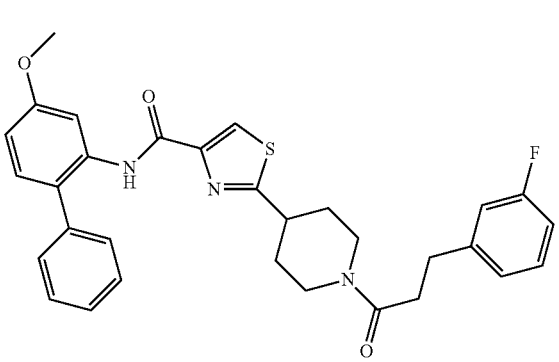 | |
| 538 | 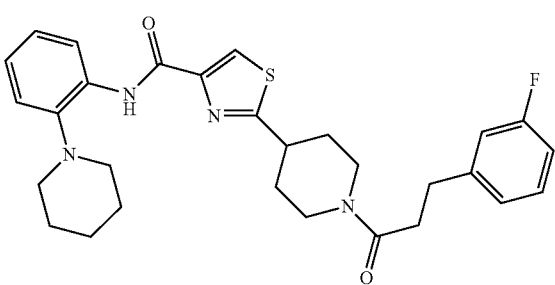 | |

TABLE 1-continued
| No. | FORMULA | NMR or mass |
|---|---|---|
| 539 | 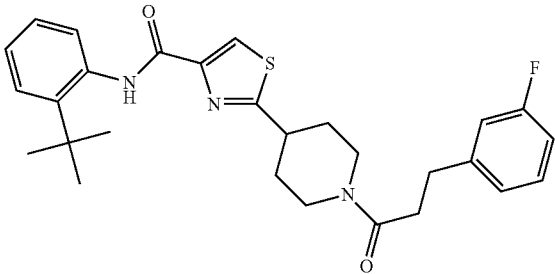 | |
| 540 | 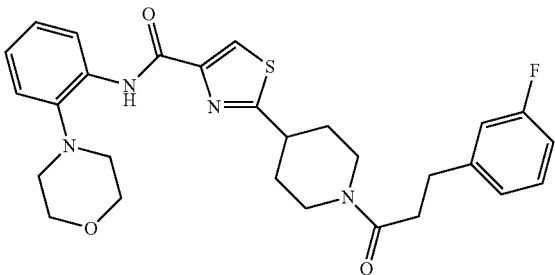 | |
| 541 | 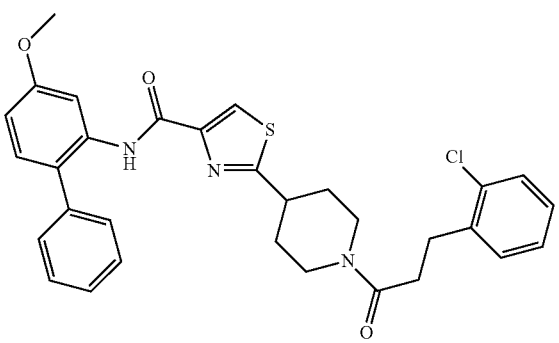 | |
| 542 | 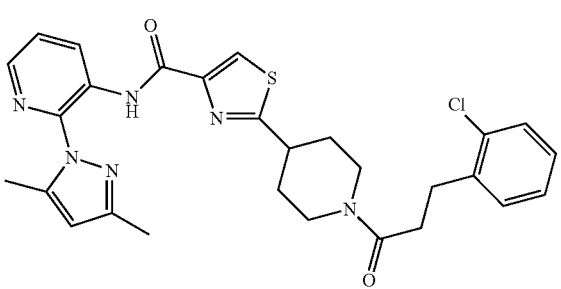 | |
| 543 | 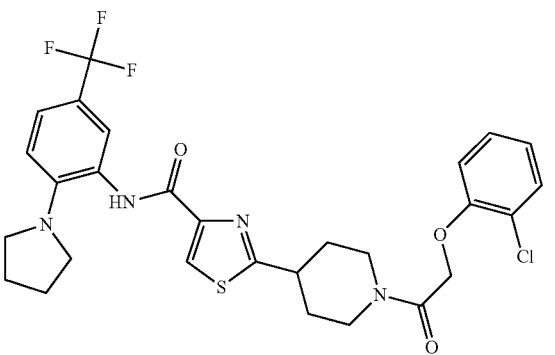 | |

TABLE 1-continued
| No. | FORMULA | NMR or mass |
|---|---|---|
| 544 | 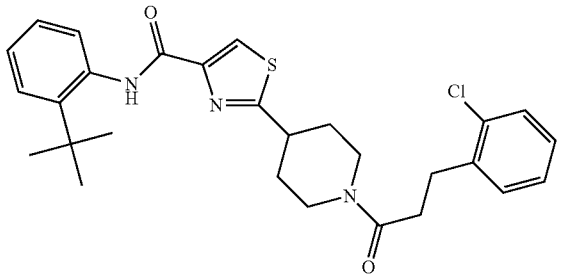 | |
| 545 | 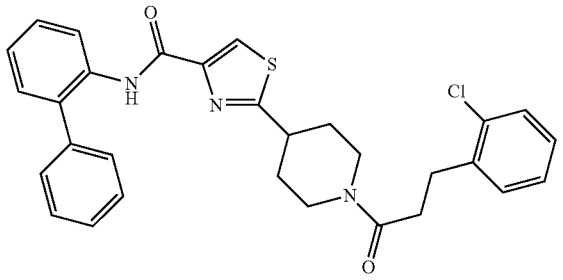 | |
| 546 | 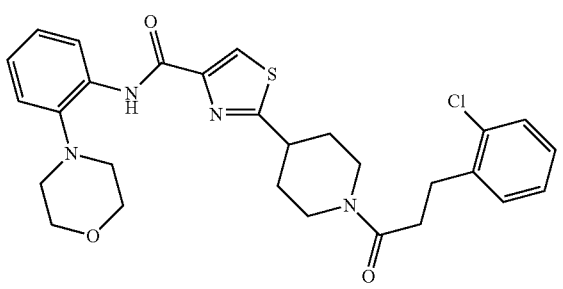 | |
| 547 | 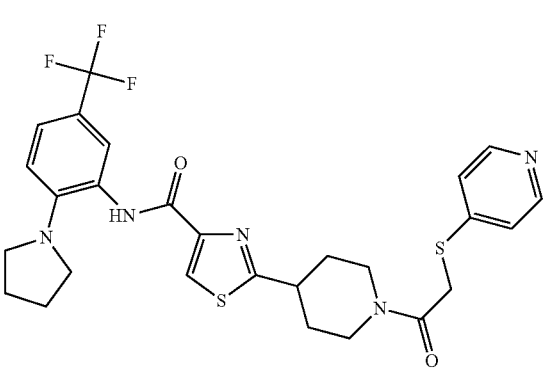 | |
| 548 | 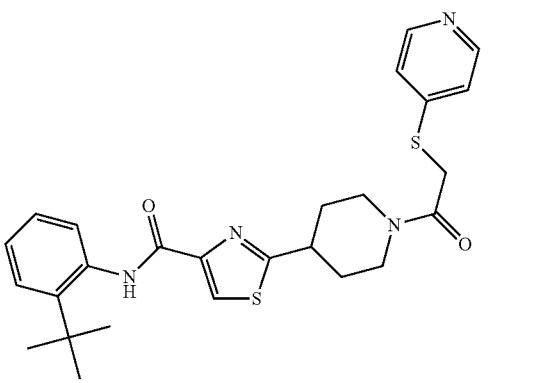 | |

TABLE 1-continued
| No. | FORMULA | NMR or mass |
|-----|---------|-------------|
549
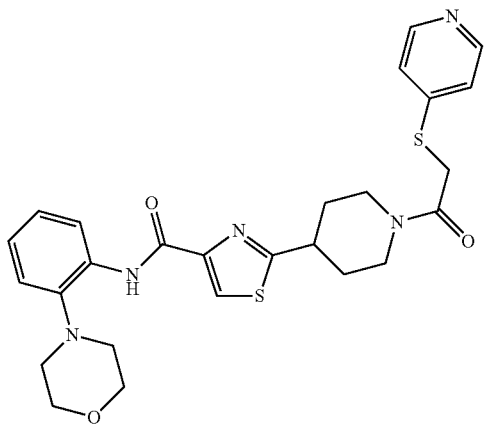
550
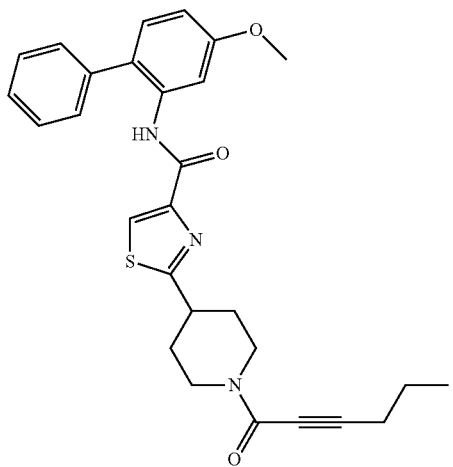
2-(1-hex-2-ynoylpiperidin-4-yl)-N-(4-methoxybiphenyl-2-yl)-1,3-thiazole-4-carboxamide
551
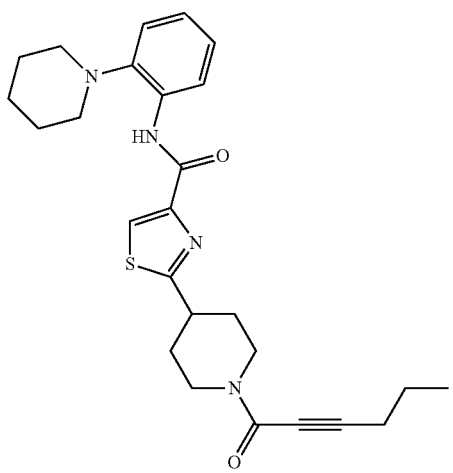
2-(1-hex-2-ynoylpiperidin-4-yl)-N-(2-piperidin-1-ylphenyl)-1,3-thiazole-4-carboxamide TABLE 1-continued
| No. | FORMULA | NMR or mass |
|---|---|---|
| 552 | 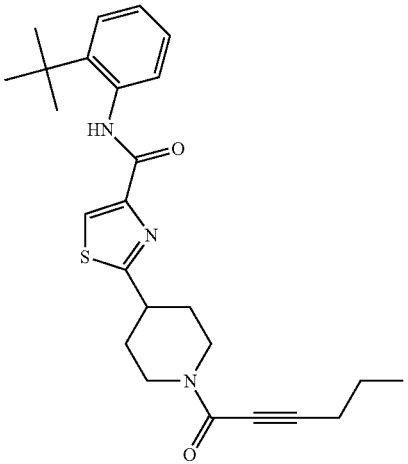 N-(2-tert-butylphenyl)-2-(1-hex-2-ynoylpiperidin-4-yl)-1,3-thiazole-4-carboxamide | |
| 553 | 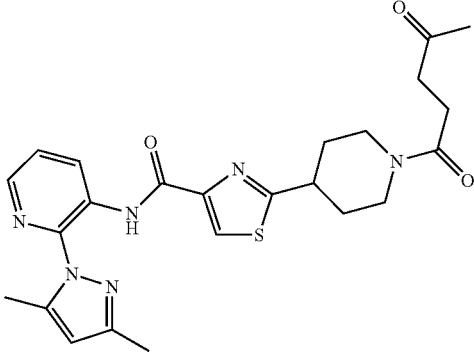 | |
| 554 | 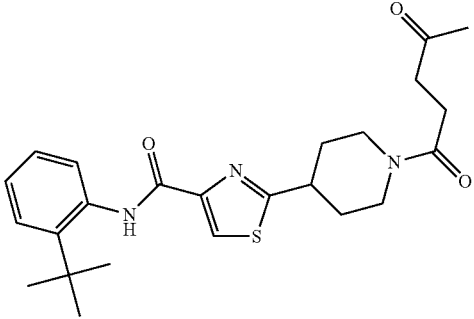 | |

421                                                                                                          422
TABLE 1-continued
| No. | FORMULA | NMR or mass |
|-----|---------|-------------|
555 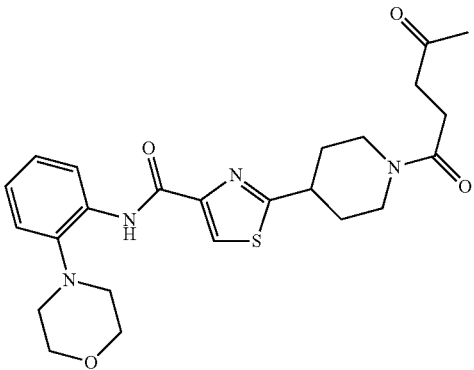
556 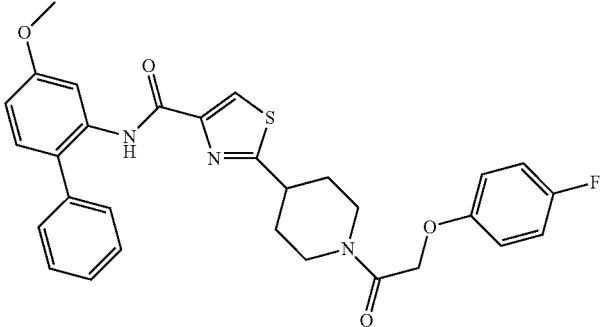
557 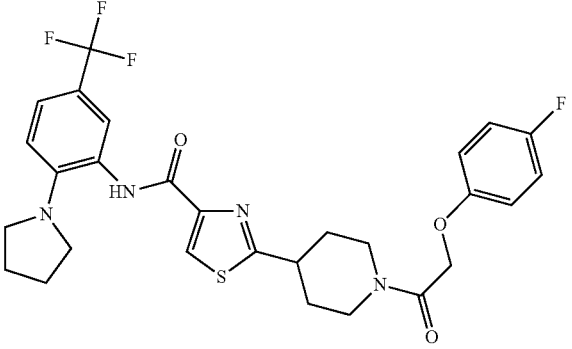
558 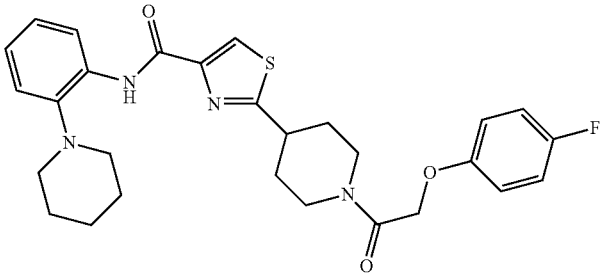

TABLE 1-continued

| No. | FORMULA | NMR or mass |
|---|---|---|
| 559 | | |
| 560 | | |
| 561 | | |
| 562 | | |
| 563 | | |

TABLE 1-continued
| No. | FORMULA | NMR or mass |
|---|---|---|
| 564 | 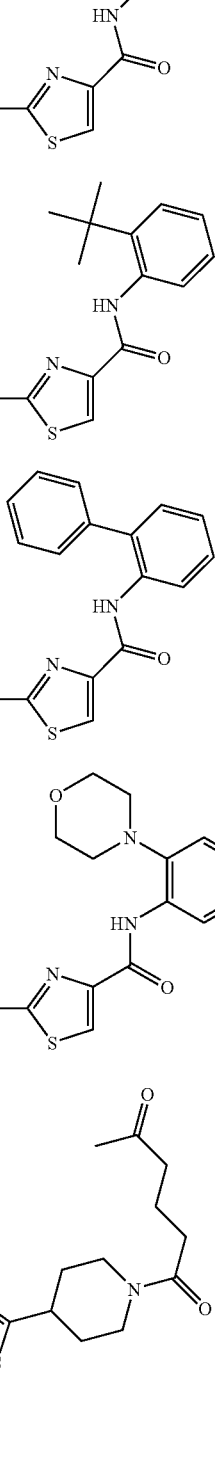 | |
| 565 | 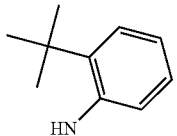 | |
| 566 | 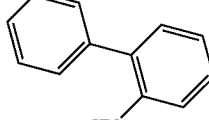 | |
| 567 | 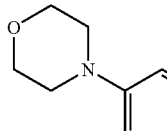 | |
| 568 |  | |

TABLE 1-continued
| No. | FORMULA | NMR or mass |
|---|---|---|
| 569 | 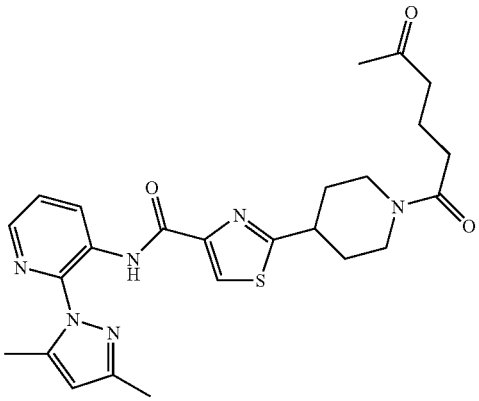 | |
| 570 | 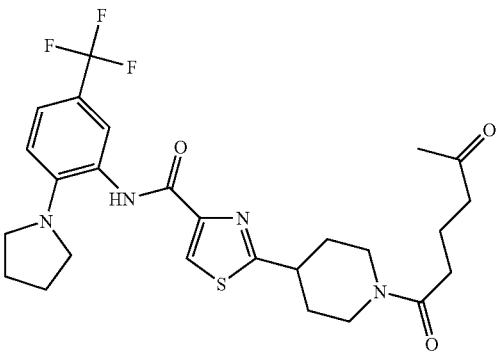 | |
| 571 | 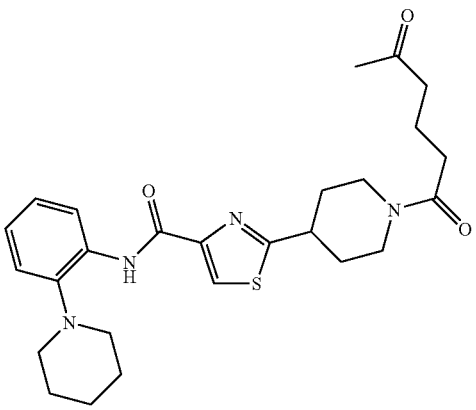 | |
| 572 | 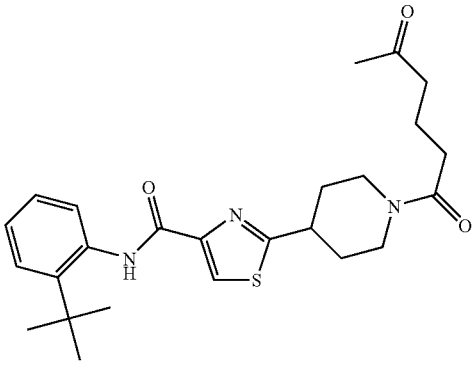 | |

TABLE 1-continued
| No. | FORMULA | NMR or mass |
|---|---|---|
| 573 | 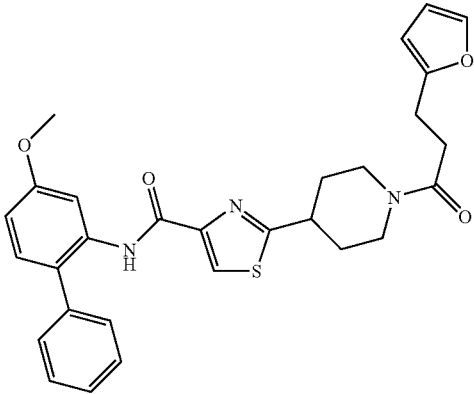 | |
| 574 | 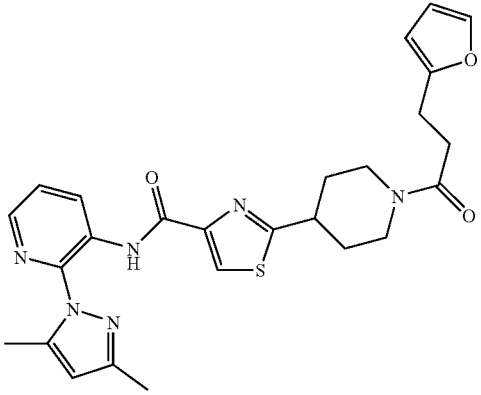 | |
| 575 | 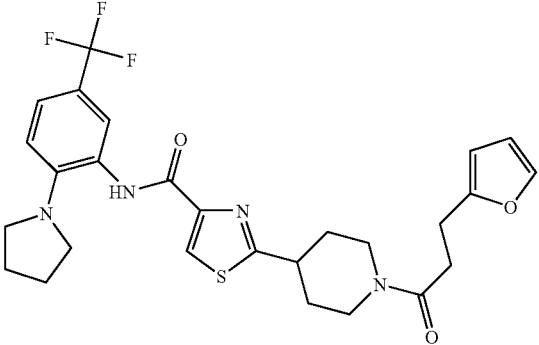 | |
| 576 | 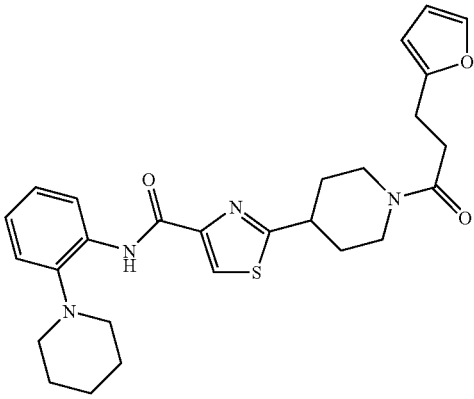 | |

TABLE 1-continued
| No. | FORMULA | NMR or mass |
|---|---|---|
| 577 | 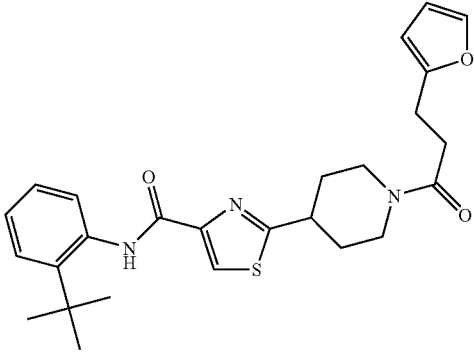 | |
| 578 | 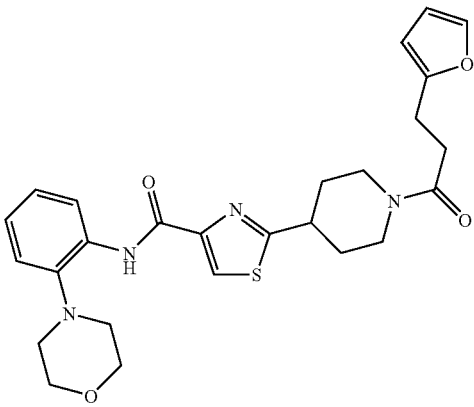 | |
| 579 | 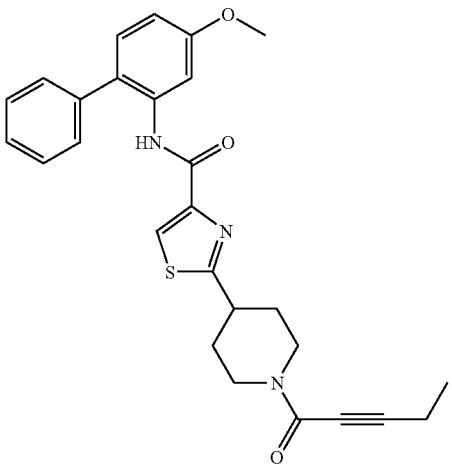 | |
N-(4-methoxybiphenyl-2-yl)-2-(1-pent-2-ynoylpiperidin-4-yl)-1,3-thiazole-4-carboxamide TABLE 1-continued
| No. | FORMULA | NMR or mass |
|---|---|---|
580
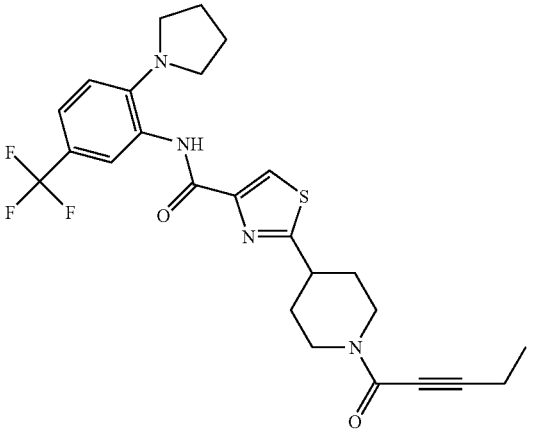
2-(1-pent-2-ynoylpiperidin-4-yl)-N-[2-pyrrolidin-1-yl-5-(trifluoromethyl)-phenyl]-1,3-thiazole-4-carboxamide
581
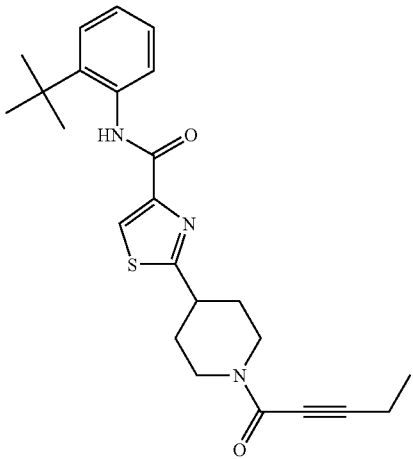
N-(2-tert-butylphenyl)-2-(pent-2-ynoylpiperidin-4-yl)-1,3-thiazole-4-carboxamide
582
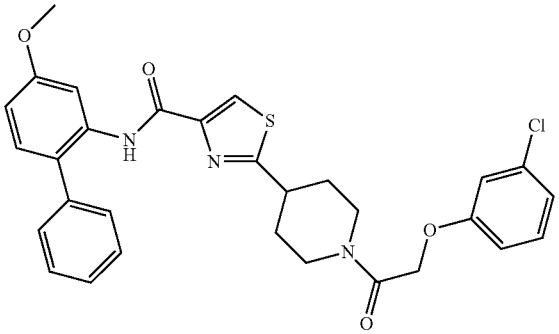

TABLE 1-continued
| No. | FORMULA | NMR or mass |
|---|---|---|
| 583 | 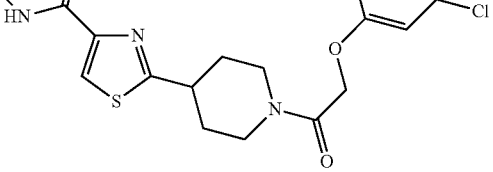 | |
| 584 | 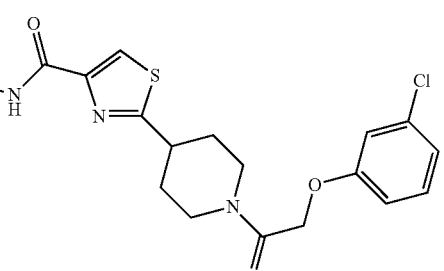 | |
| 585 | 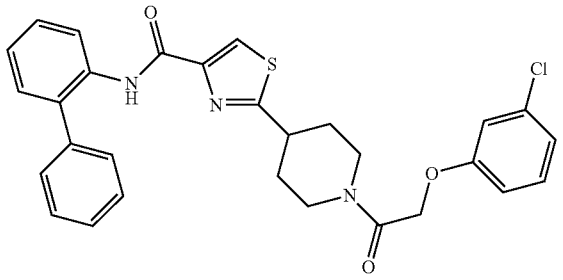 | |
| 586 | 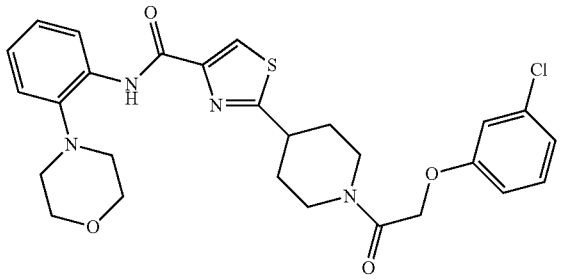 | |
| 587 | 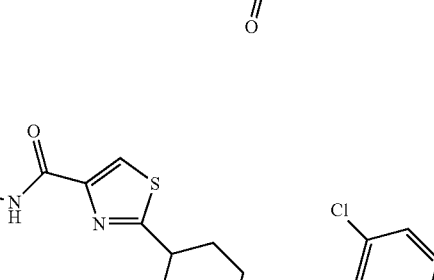 | |

TABLE 1-continued
| No. | FORMULA | NMR or mass |
|---|---|---|
| 588 | 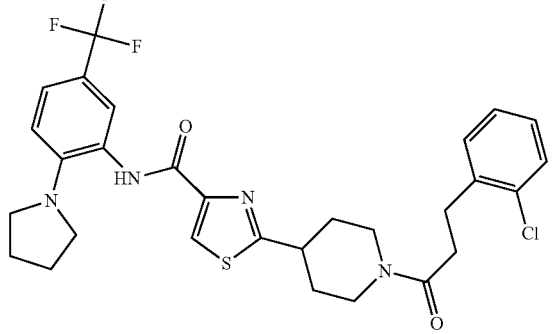 | |
| 589 | 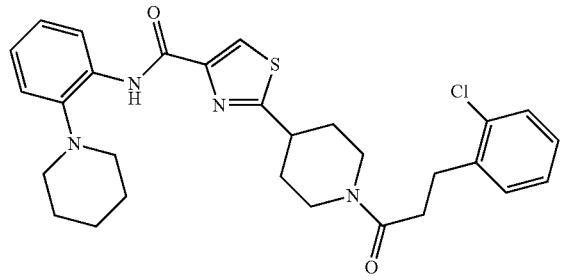 | |
| 590 | 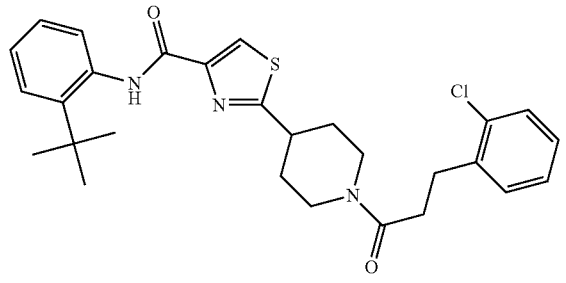 | |
| 591 | 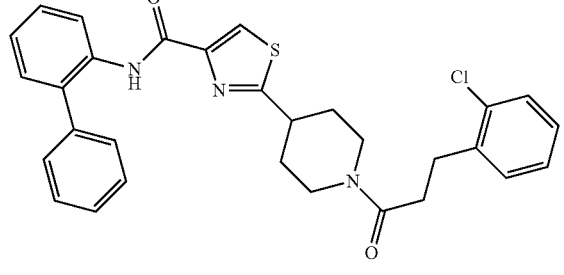 | |
| 592 | 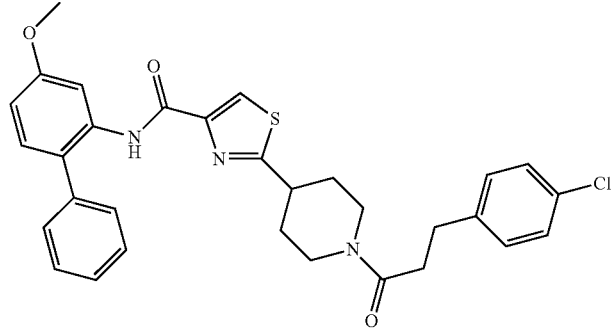 | |

TABLE 1-continued
| No. | FORMULA | NMR or mass |
|-----|---------|-------------|
| 593 | 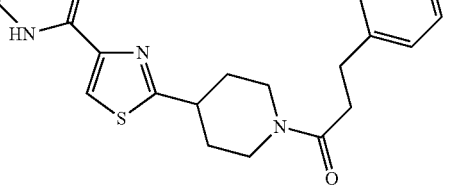 | |
| 594 | 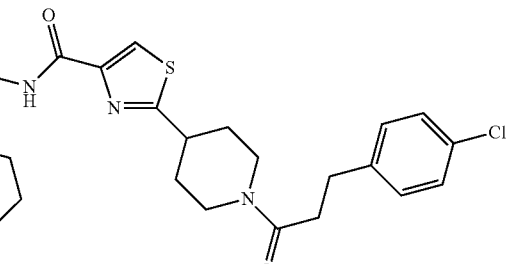 | |
| 595 | 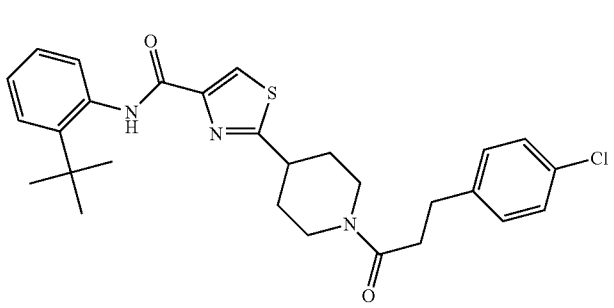 | |
| 596 | 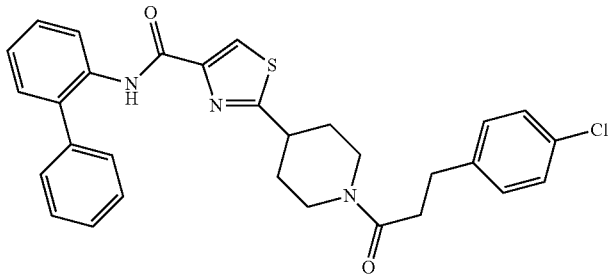 | |
| 597 | 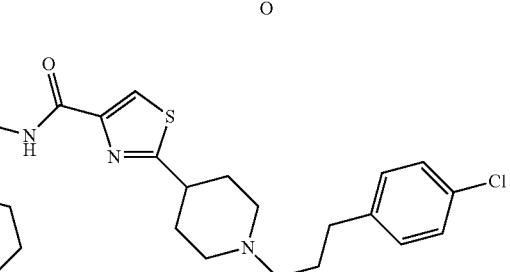 | |

| No. | FORMULA | NMR or mass |
|---|---|---|
| 598 | | |
| 599 | | |
| 600 | | |
| 601 | | |

TABLE 1-continued
| No. | FORMULA | NMR or mass |
|---|---|---|
| 602 | 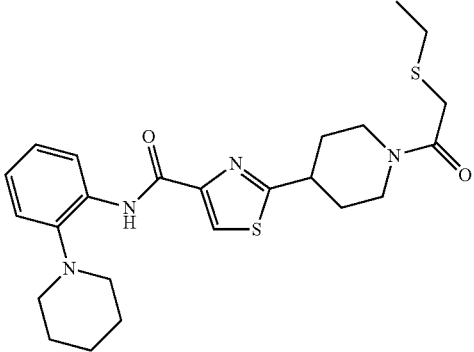 | |
| 603 | 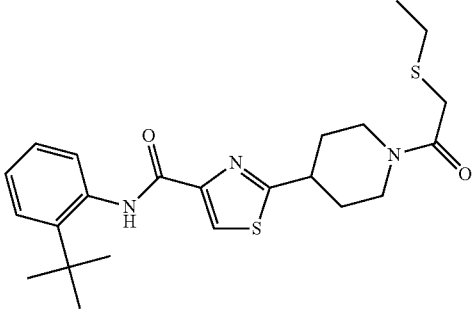 | |
| 604 | 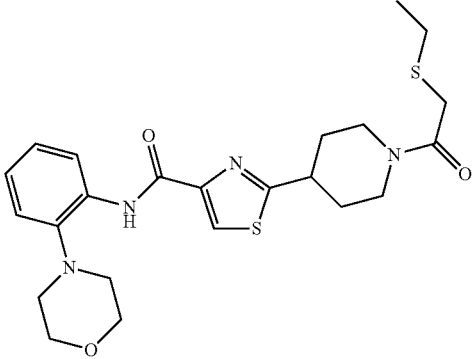 | |
| 605 | 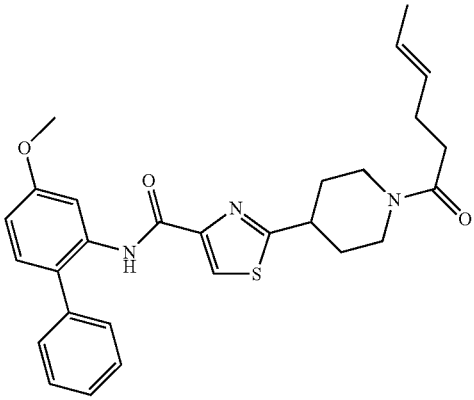 | |

TABLE 1-continued
| No. | FORMULA | NMR or mass |
|---|---|---|
| 606 | 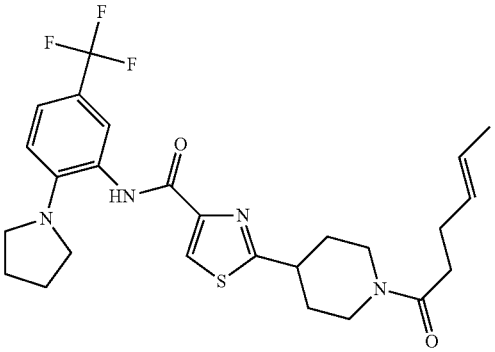 | |
| 607 | 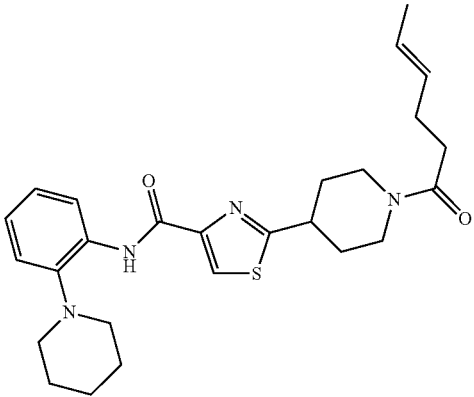 | |
| 608 | 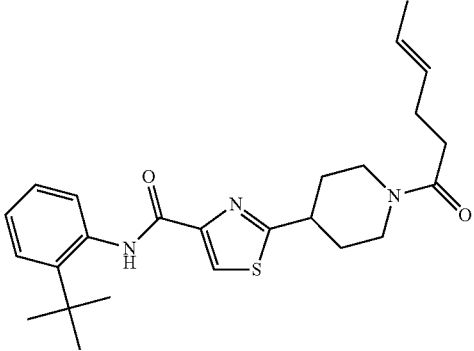 | |
| 609 | 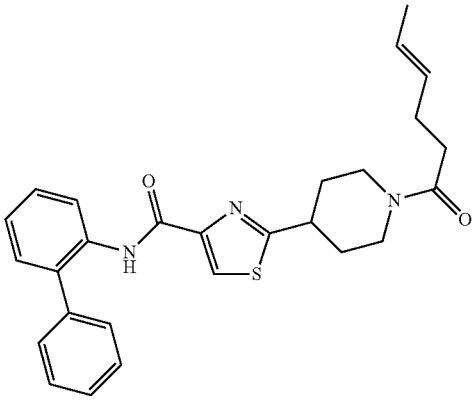 | |

TABLE 1-continued
| No. | FORMULA | NMR or mass |
|---|---|---|
| 610 | 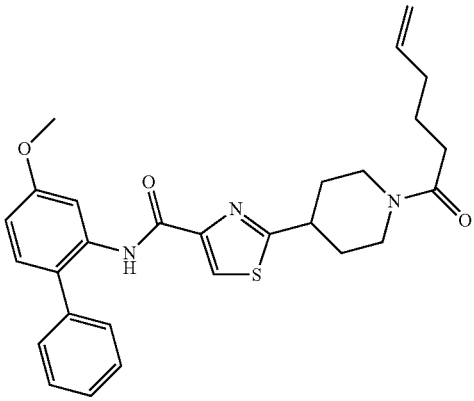 | |
| 611 | 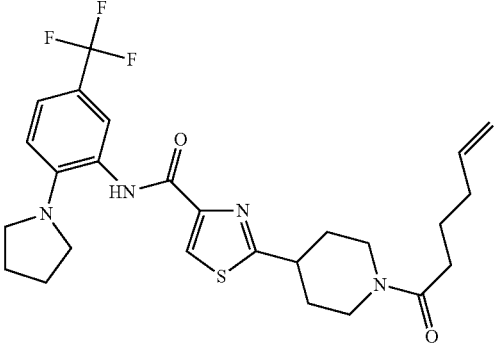 | |
| 612 | 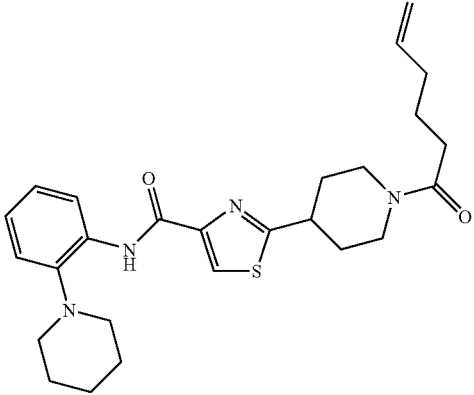 | |
| 613 | 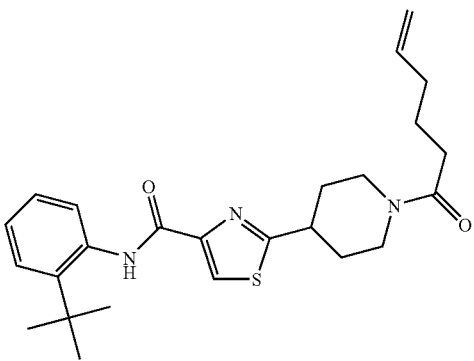 | |

TABLE 1-continued
| No. | FORMULA | NMR or mass |
|---|---|---|
| 614 | 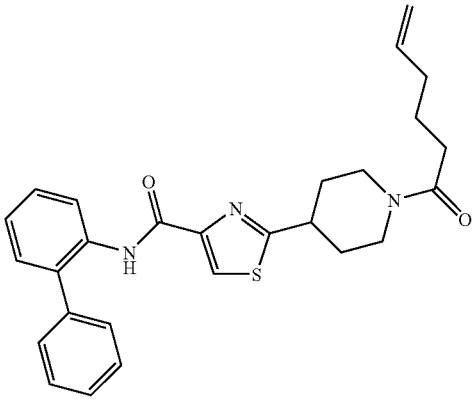 | |
| 615 | 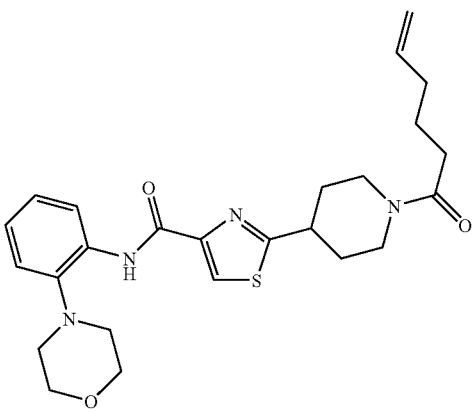 | |
| 616 | 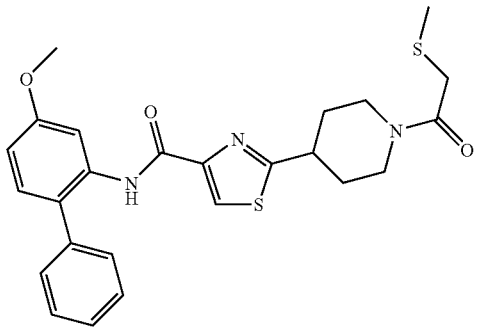 | |
| 617 | 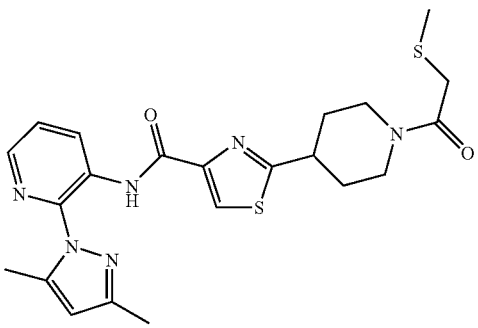 | |

TABLE 1-continued

| No. | FORMULA | NMR or mass |
|---|---|---|
| 618 | | |
| 619 | | |
| 620 | | |
| 621 | | |

TABLE 1-continued
| No. | FORMULA | NMR or mass |
|---|---|---|
| 622 | 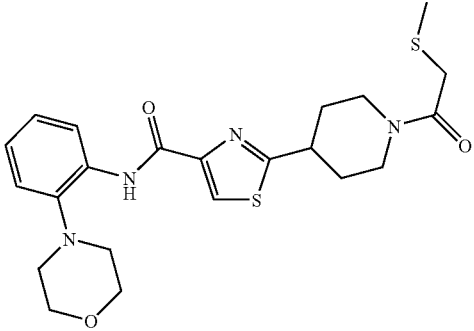 | |
| 623 | 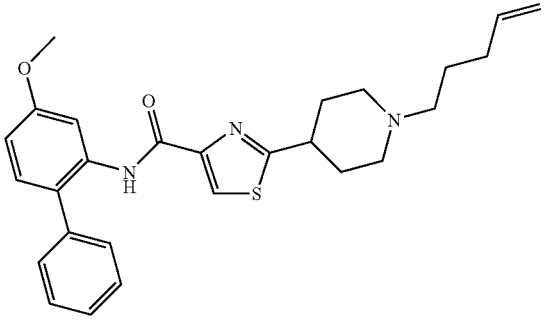 | |
| 624 | 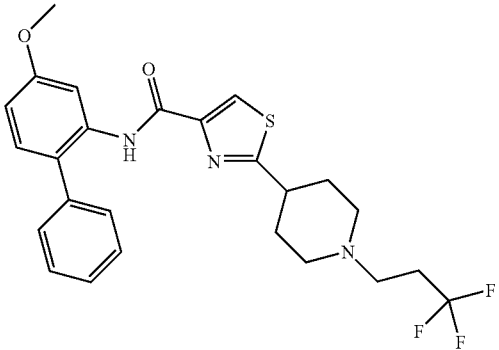 | |
| 625 | 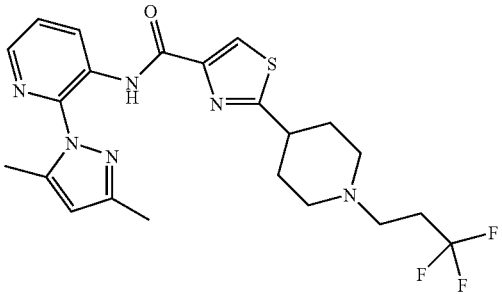 | |

TABLE 1-continued
| No. | FORMULA | NMR or mass |
|---|---|---|
| 626 | 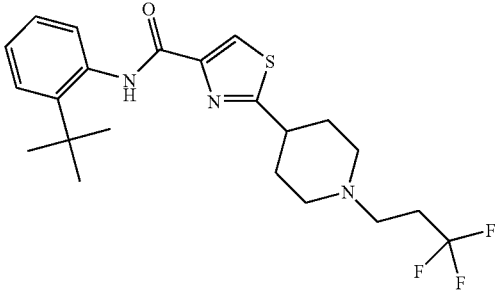 | |
| 627 | 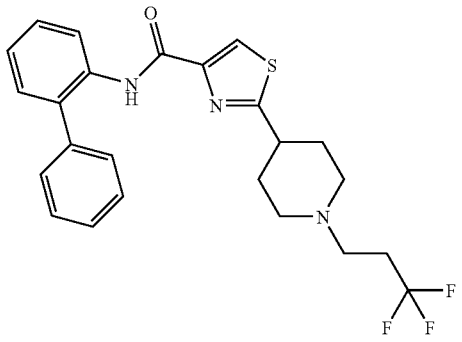 | |
| 628 | 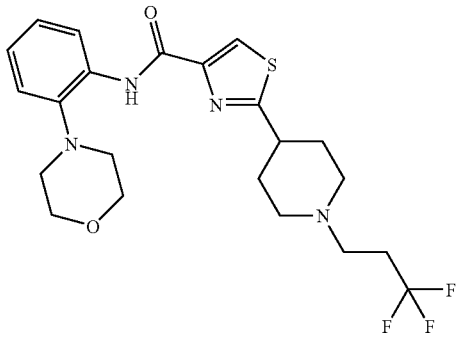 | |
| 629 | 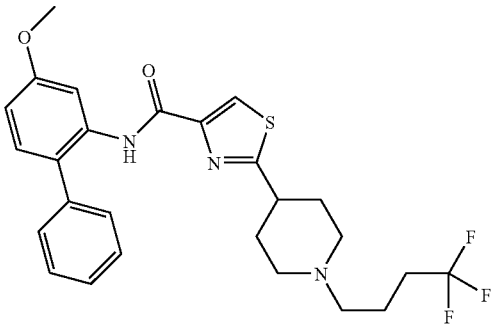 | |

TABLE 1-continued
| No. | FORMULA | NMR or mass |
|---|---|---|
| 630 | 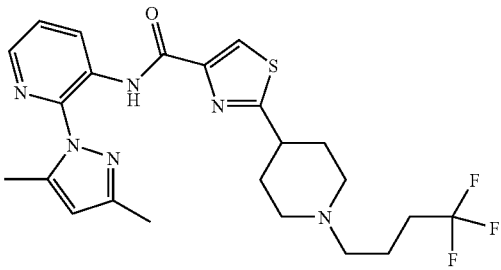 | |
| 631 | 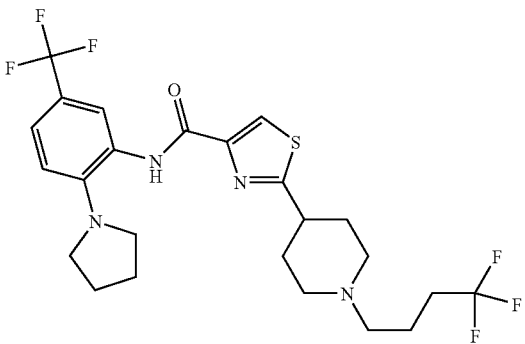 | |
| 632 | 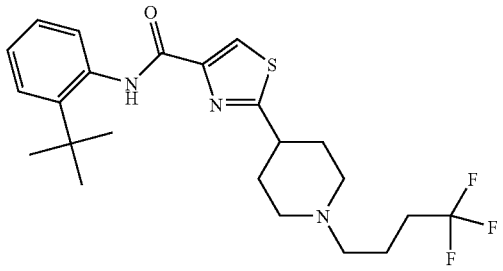 | |
| 633 | 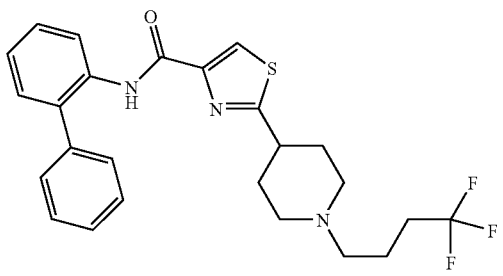 | |
| 634 | 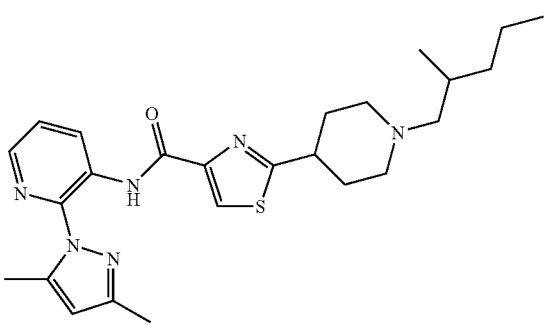 | |

TABLE 1-continued
| No. | FORMULA | NMR or mass |
|---|---|---|
| 635 | 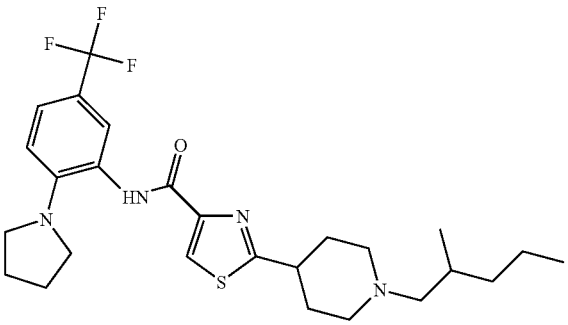 | |
| 636 | 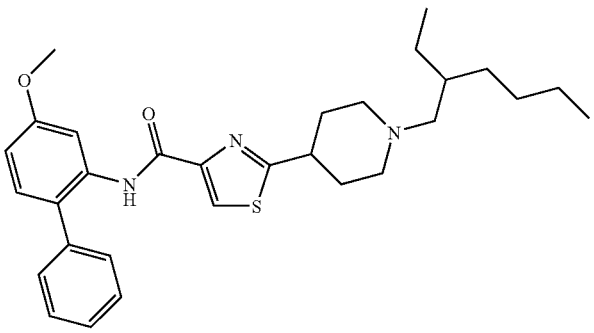 | |
| 637 | 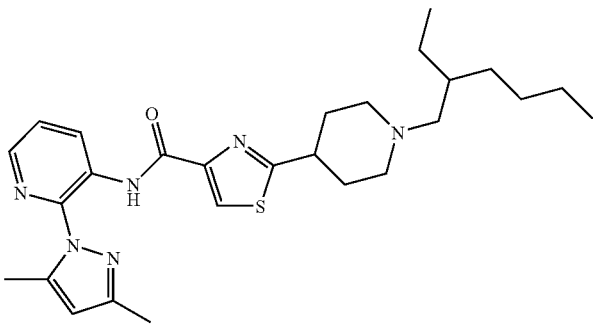 | |
| 638 | 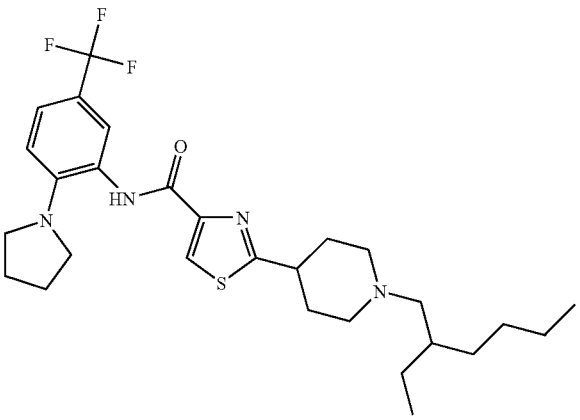 | |

TABLE 1-continued
| No. | FORMULA | NMR or mass |
|---|---|---|
| 639 | 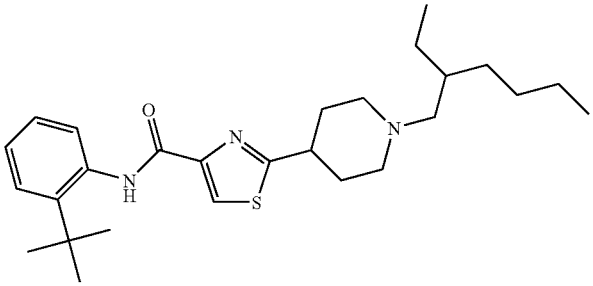 | |
| 640 | 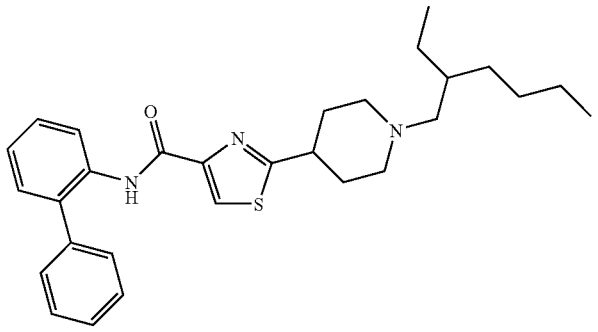 | |
| 641 | 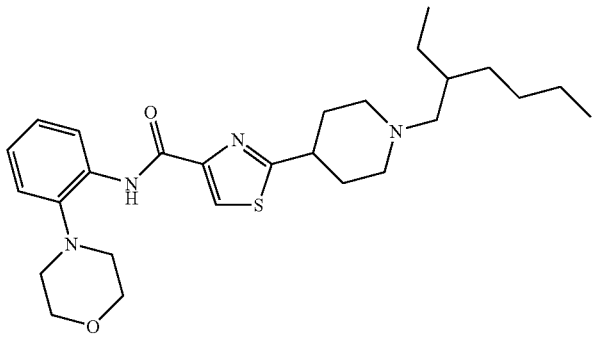 | |
| 642 | 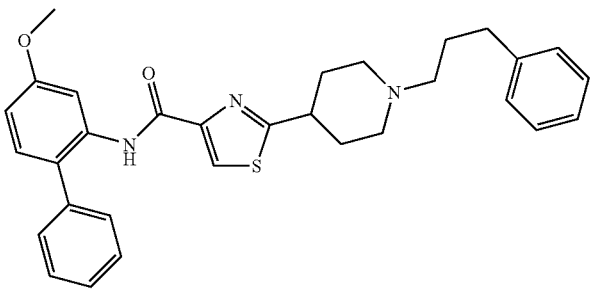 | |
| 643 | 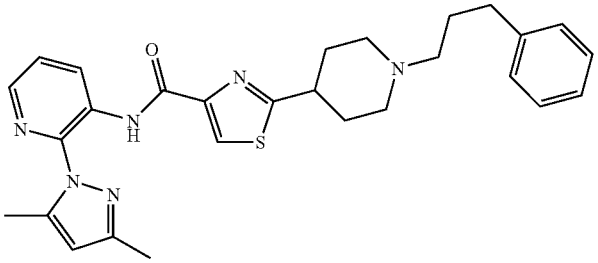 | |

TABLE 1-continued
| No. | FORMULA | NMR or mass |
|---|---|---|
| 644 | 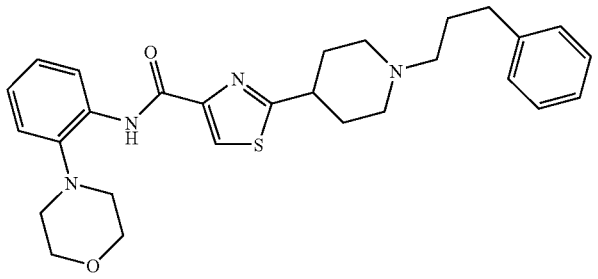 | |
| 645 | 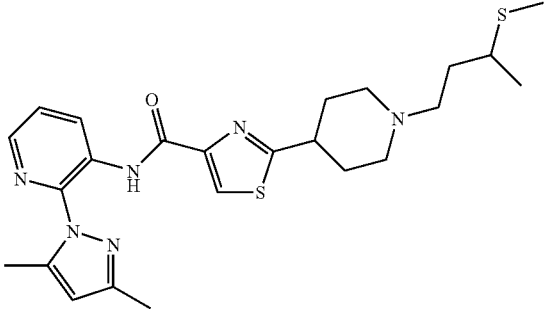 | |
| 646 | 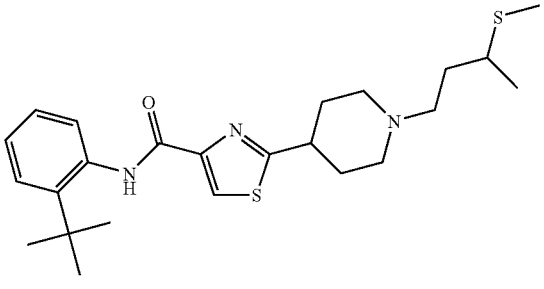 | |
| 647 | 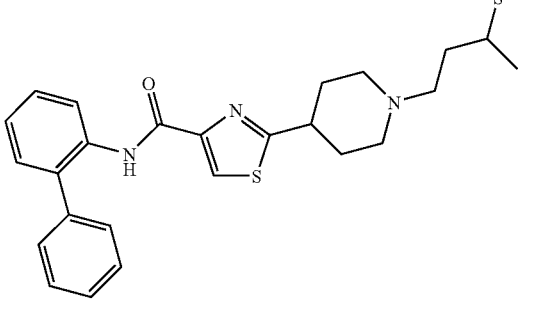 | |
| 648 | 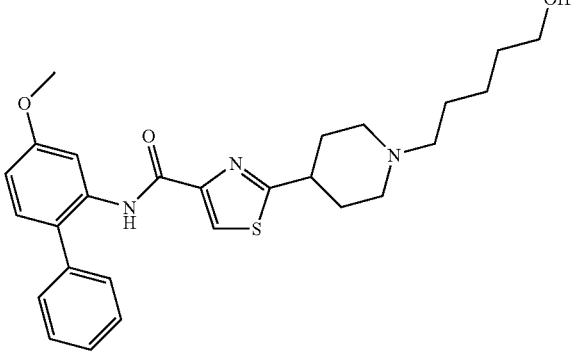 | |

TABLE 1-continued

| No. | FORMULA | NMR or mass |
|-----|---------|-------------|

649

650

651

652

TABLE 1-continued

| No. | FORMULA | NMR or mass |
|---|---|---|
| 653 | | |
| 654 | | |
| 655 | | |

TABLE 1-continued

| No. | FORMULA | NMR or mass |
|---|---|---|
| 656 | | |
| 657 | | |

2-(1-pent-4-enoylpiperidin-4-yl)-N-[4'-(trifluoromethoxy)
biphenyl-2-yl]-1,3-thiazole-4-carboxamide

| 658 | | |

N-(4'-fluorobiphenyl-2-yl)-2-(1-pent-4-enoylpiperidin-4-yl)
-1,3-thiazole-4-carboxamide TABLE 1-continued
| No. | FORMULA | NMR or mass |
|---|---|---|
| 659 | 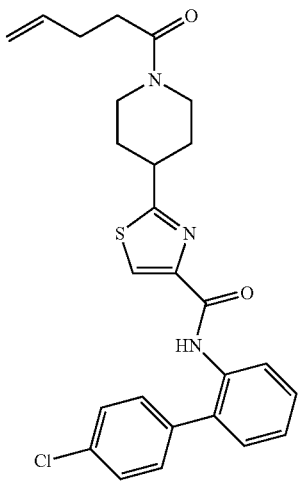 N-(4'-chlorobiphenyl-2-yl)-2-(1-pent-4-enoylpiperidin-4-yl)-1,3-thiazole-4-carboxamide | |
| 660 | 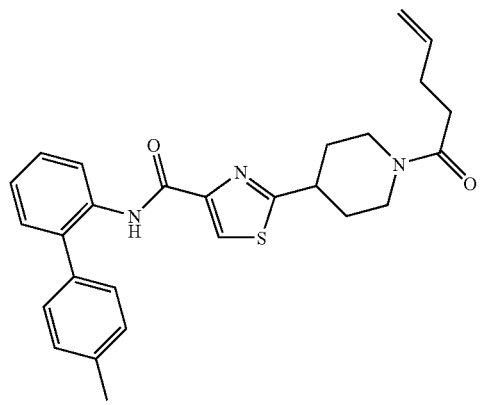 | |
| 661 | 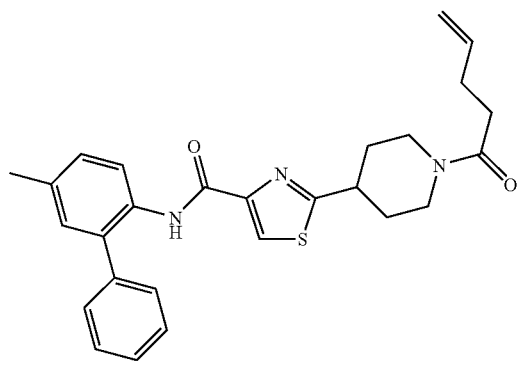 | |

TABLE 1-continued
| No. | FORMULA | NMR or mass |
|---|---|---|
| 662 | 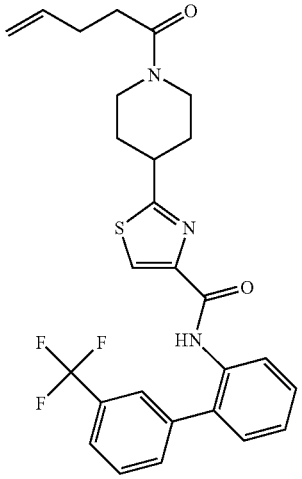 2-(1-pent-4-enoylpiperidin-4-yl)-N-[3'(trifluoromethyl)biphenyl-2-yl]-1,3-thiazole-4-carboxamide | |
| 663 | 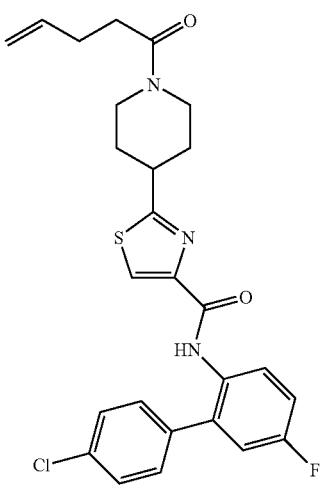 N-(4'-chloro-5-fluorobiphenyl-2-yl)-2-(1-pent-4-enoylpiperidin-4-yl)-1,3-thiazole-4-carboxamide | |
| 664 | 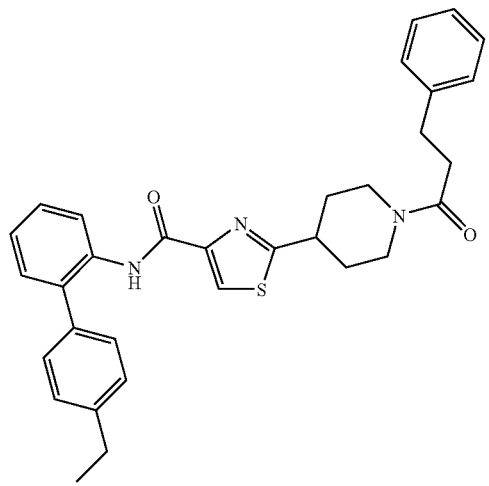 | |

TABLE 1-continued
| No. | FORMULA | NMR or mass |
|---|---|---|
| 665 | 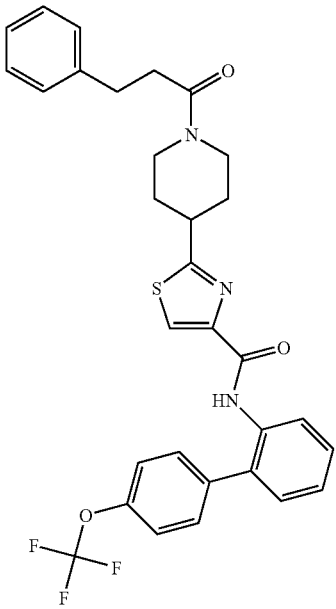 2-[1-(3-phenylpropanoyl)piperidin-4-yl]-N-[4'-(trifluoromethoxy)biphenyl-2-yl]-1,3-thiazole-4-carboxamide | |
| 666 | 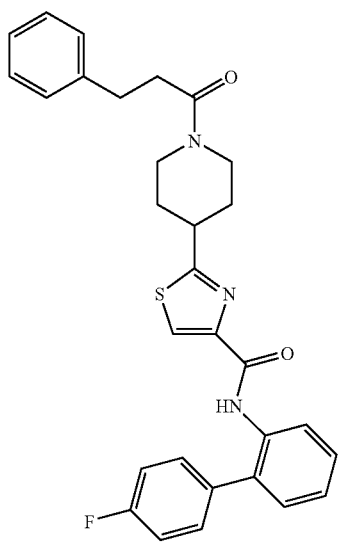 N-(4'-fluorobiphenyl-2-yl)-2-[1-(3-phenylpropanoyl)piperidin-4-yl]-1,3-thiazole-4-carboxamide | |

| No. | FORMULA | NMR or mass |
|---|---|---|
| 667 | 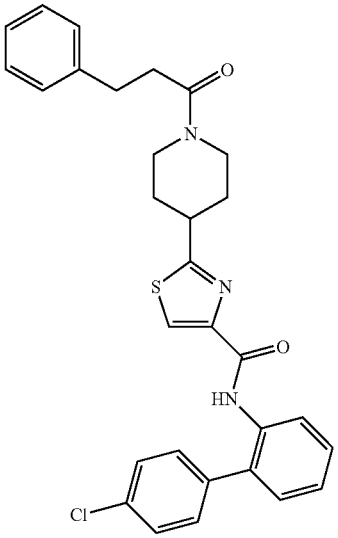 N-(4'-chlorobiphenyl-2-yl)-2-[1-(3-phenylpropanoyl)piperidin-4-yl]-1,3-thiazole-4-carboxamide | |
| 668 | 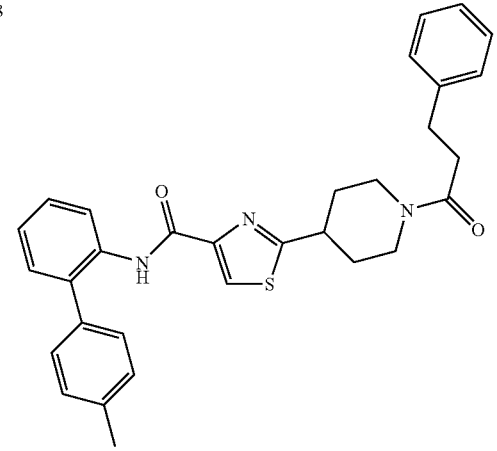 | |
| 669 | 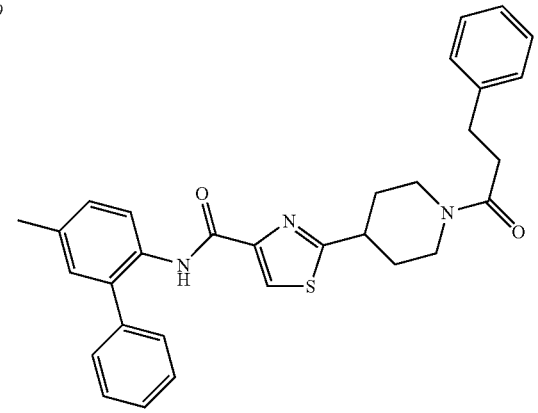 | |

TABLE 1-continued
| No. | FORMULA | NMR or mass |
|---|---|---|
| 670 | 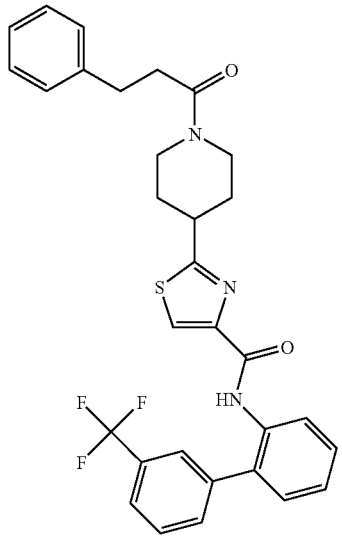 2-[1-(3-phenylpropanoyl)piperidin-4-yl]-N-[3'-(trifluoromethyl)biphenyl-2-yl]-1,3-thiazole-4-carboxamide | |
| 671 | 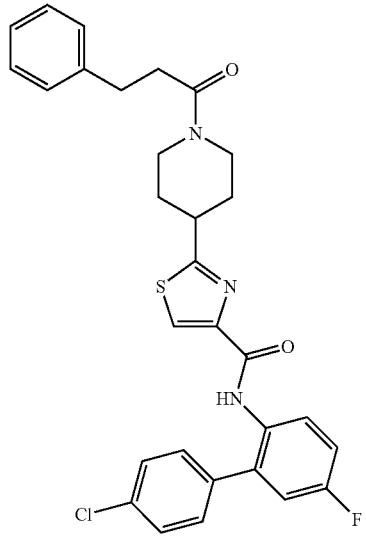 N-(4'-chloro-5-fluorobiphenyl-2-yl)-2-[1-(3-phenylpropanoyl)piperidin-4-yl]-1,3-thiazole-4-carboxamide | |

TABLE 1-continued
| No. | FORMULA | NMR or mass |
|---|---|---|
672
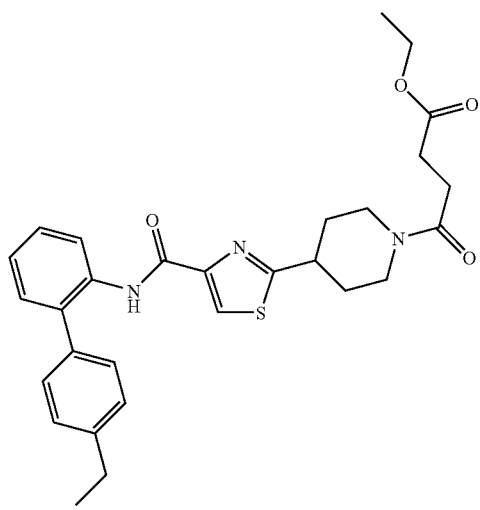
ethyl 4-[-(4-{[(4'-ethylbiphenyl-2-yl)amino]carbonyl}-1,3-thiazol-2-yl)-piperidin-1-yl]-4-oxobutanoate
673
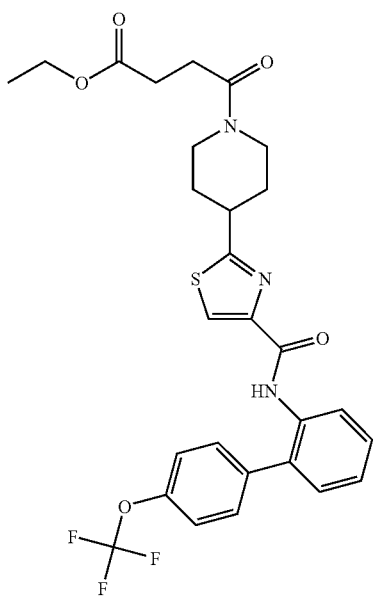
ethyl 4-oxo-4-{4-[4-({[4'-(trifluoromethoxy)biphenyl-2-yl]amino}-carbonyl)-1,3-thiazol-2-yl]piperidin-1-yl}butanoate

| No. | FORMULA | NMR or mass |
|---|---|---|
| 674 | 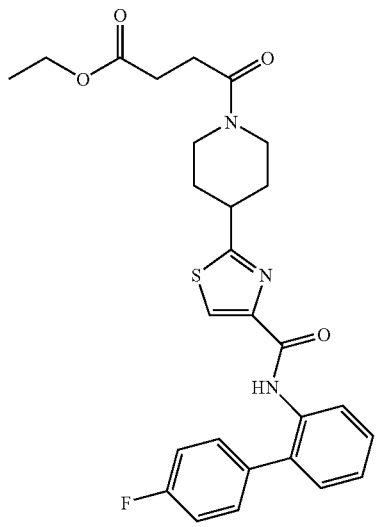
ethyl 4-[4-(4-{[(4'-flurobiphenyl-2-yl)amino]carbonyl}-1,3-thiazol-2-yl)-piperidin-1-yl]-4-oxobutanoate | |
| 675 | 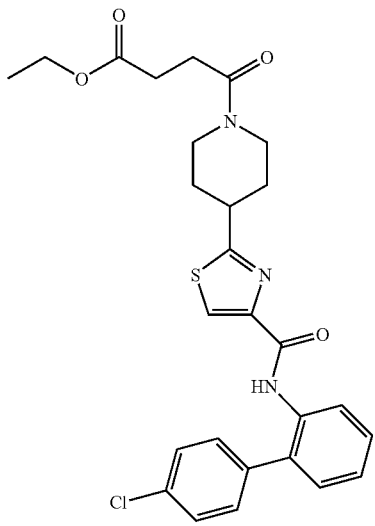
ethyl 4-[4(4-{[(4'-chlorobiphenyl-2-yl)amino]carbonyl}-1,3-thiazol-2-yl)-piperdin-1-yl]-4-oxobutanoate | |

TABLE 1-continued
| No. | FORMULA | NMR or mass |
|---|---|---|
| 676 | 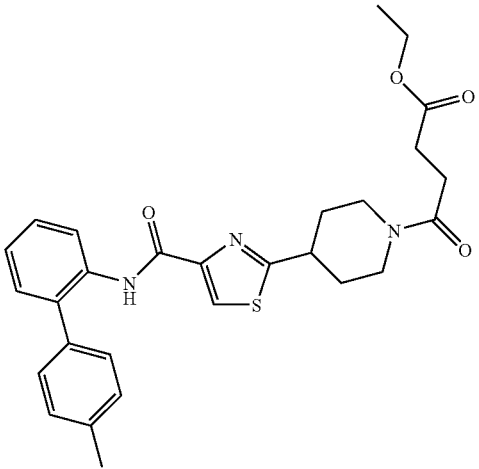 ethyl 4-[4-(4-{[(4'-methylbiphenyl-2-yl)amino]carbonyl}-1,3-thiazol-2-yl)-piperidin-1-yl]-4-oxobutanoate | |
| 677 | 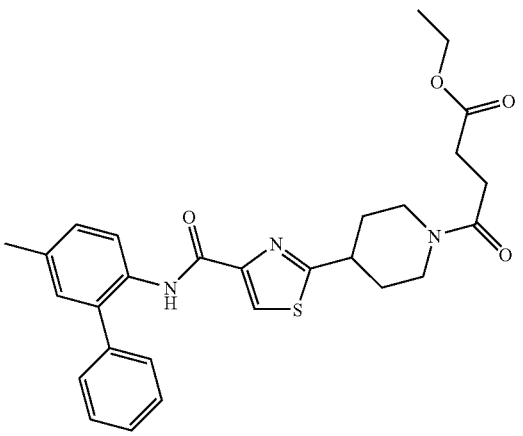 | |
| 678 | 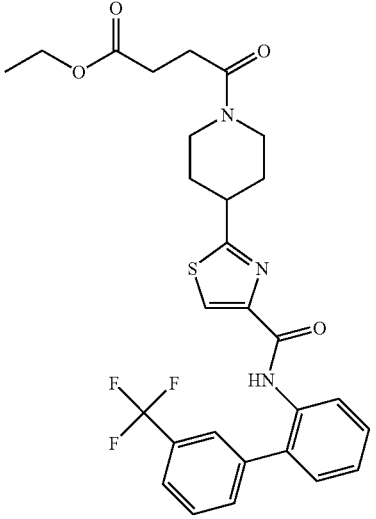 ethyl 4-oxo-4-{4-[4-({[3'-(trifluoromethyl)biphenyl-2-yl]amino}carbonyl)-1,3-thiazol-2-yl]piperidin-1-yl}butanoate | |

TABLE 1-continued
| No. | FORMULA | NMR or mass |
|---|---|---|
| 679 | 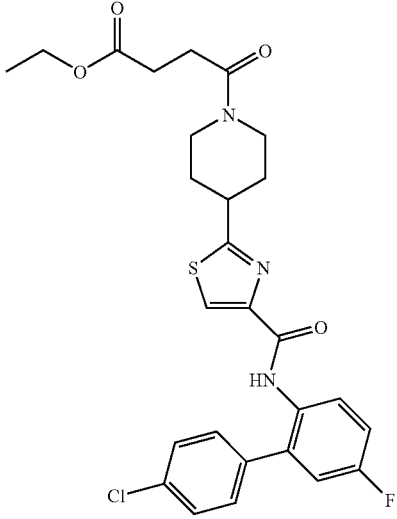 ethyl 4-[4-(4-{[(4'-chloro-5-fluorobiphenyl-2-yl)amino]carbonyl}-1,3-thiazol-2-yl)piperidin-1-yl]-4-oxobutanoate | |
| 680 | 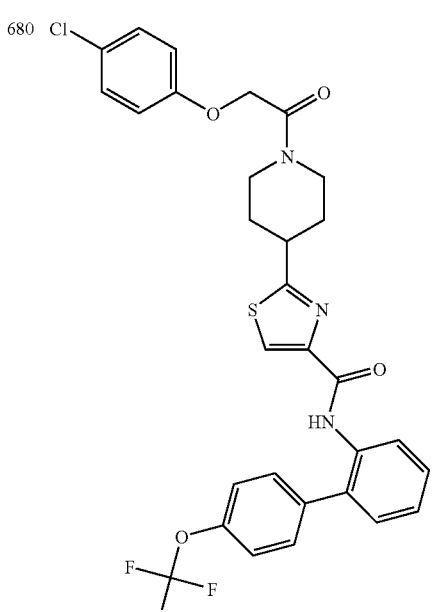 2-{1-[(4-chlorophenoxy)acetyl]piperidin-4-yl}-N-[4'-(trifluoromethoxy)-biphenyl-2-yl]-1,3-thiazole-4-carboxamide | |

TABLE 1-continued

| No. | FORMULA | NMR or mass |
|---|---|---|
| 681 | | |
| 682 | methyl 4-oxo-4-{4-[4-({[4'-(trifluoromethoxy)biphenyl-2-yl]amino}-carbonyl)-1,3-thiazol-2-yl]piperidin-1-yl}butanoate | |

| No. | FORMULA | NMR or mass |
|---|---|---|
| 683 | 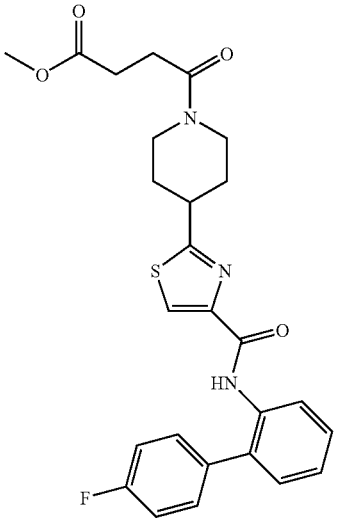 methyl 4-[4-(4-{[(4'-fluorobiphenyl-2-yl)amino]carbonyl}-1,3-thiazol-2-yl)-piperidin-1-yl]-4-oxobutanoate | |
| 684 | 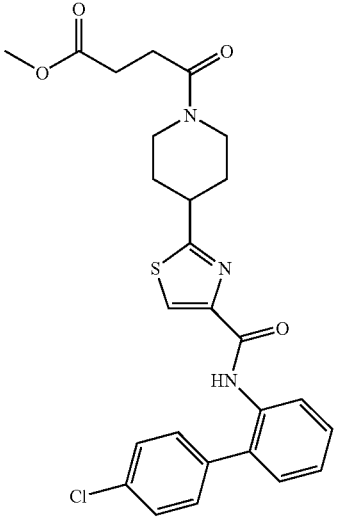 methyl 4-[4-(4-{[(4'-chlorobiphenyl-2-yl)amino]carbonyl}-1,3-thiazol-2-yl)-piperidin-1-yl]-4-oxobutanoate | |

TABLE 1-continued

| No. | FORMULA | NMR or mass |
|---|---|---|
| 685 | | |
| 686 | | |
| 687 | methyl 4-oxo-4-{4-[4-({[3'-(trifluoromethyl)biphenyl-2-yl]amino}carbonyl)-1,3-thiazol-2-yl]piperidin-1-yl}butanoate | |

TABLE 1-continued
| No. | FORMULA | NMR or mass |
|---|---|---|
| 688 | 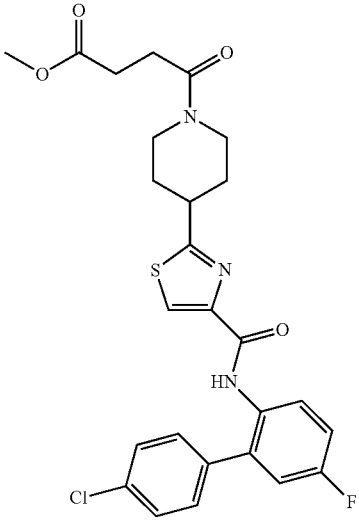 methyl 4-[4-(4-{[(4'-chloro-5-fluorobiphenyl-2-yl)amino]carbonyl}-1,3-thiazol-2-yl]piperidin-1-yl]-4-oxobutanoate | |
| 689 | 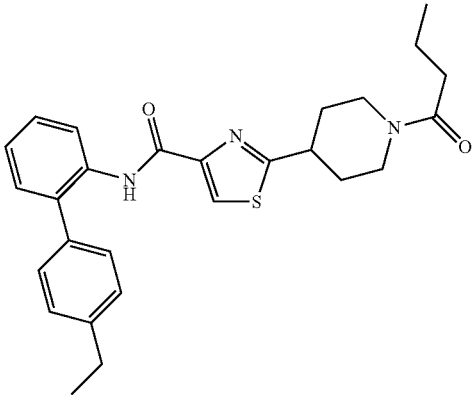 | |

TABLE 1-continued
| No. | FORMULA | NMR or mass |
|---|---|---|
| 690 | 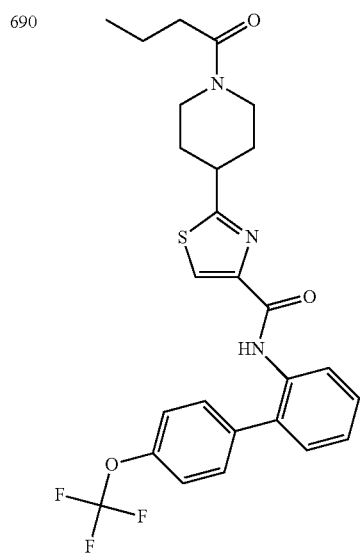 2-(1-butyrylpiperidin-4-yl)-N-[4'-(trifluoromethoxy)biphenyl-2-yl]-1,3-thiazole-4-carboxamide | |
| 691 | 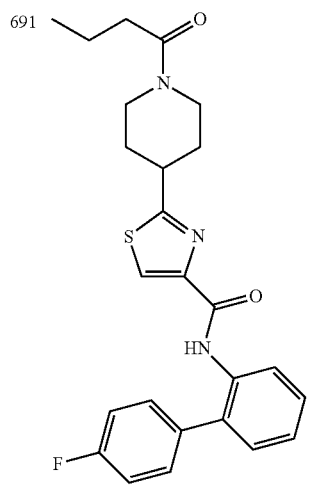 2-(1-butyrylpiperidin-4-yl)-N-(4'-fluorobiphenyl-2-yl)-1,3-thiazole-4-carboxamide | |

TABLE 1-continued
| No. | FORMULA | NMR or mass |
|-----|---------|-------------|
| 692 | 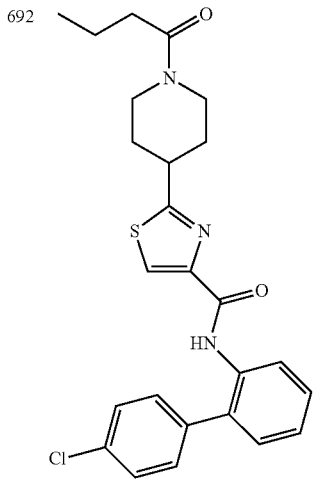 2-(1-butyrylpiperidin-4-yl)-N-(4'-chlorobiphenyl-2-yl)-1,3-thiazole-4-carboxamide | |
| 693 | 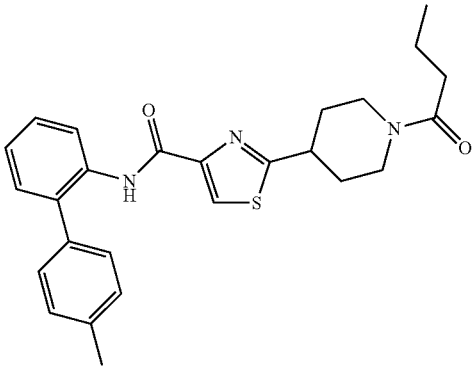 | |
| 694 | 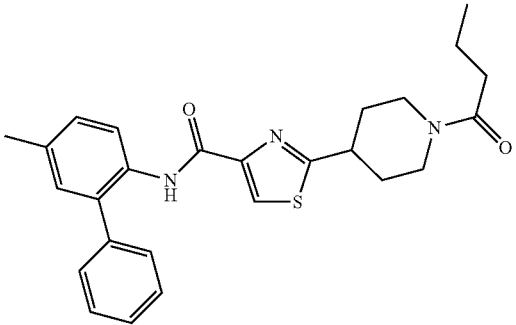 | |

TABLE 1-continued
| No. | FORMULA | NMR or mass |
|---|---|---|
| 695 | 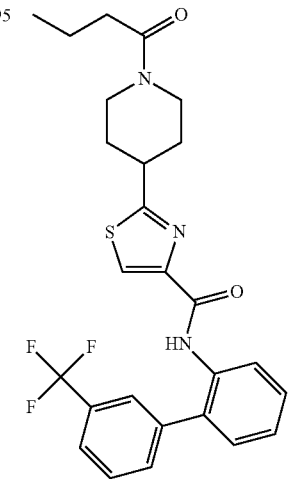 2-(1-butyrylpiperidin-4-yl)-N-[3'-(trifluoromethyl)biphenyl-2-yl]-1,3-thiazole-4-carboxamide | |
| 696 | 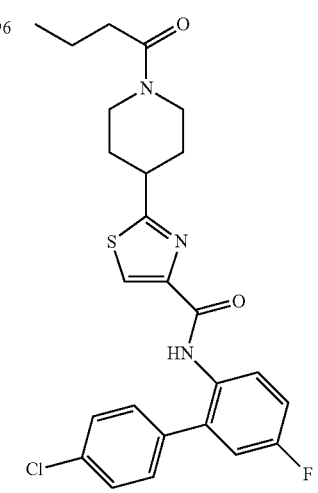 2-(1-butyrylpiperidin-4-yl)-N-(4'-chloro-5-fluorobiphenyl-2-yl)-1,3-thiazole-4-carboxamide | |
| 697 | 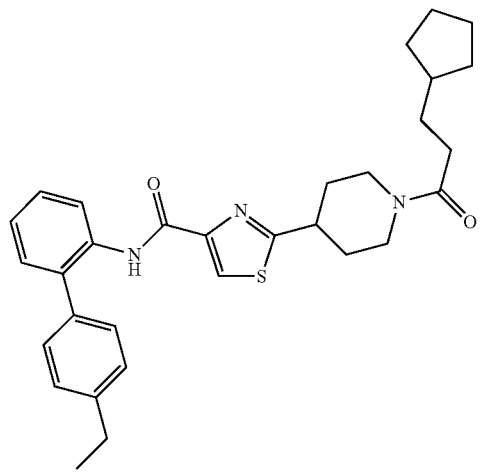 | |

TABLE 1-continued
| No. | FORMULA | NMR or mass |
|---|---|---|
| 698 | 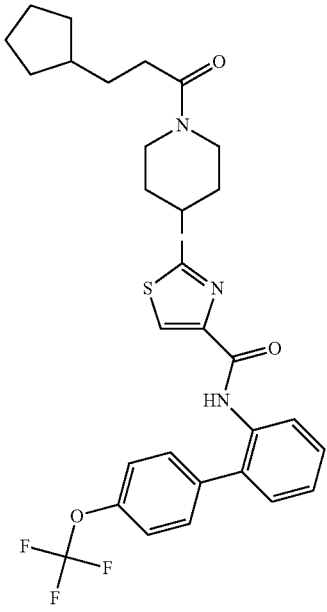 2-[1-(3-cyclopentylpropanoyl)piperidin-4-yl]-N-[4'-(trifluoromethoxy)biphenyl-2-yl]-1,3-thiazole-4-carboxamide | |
| 699 | 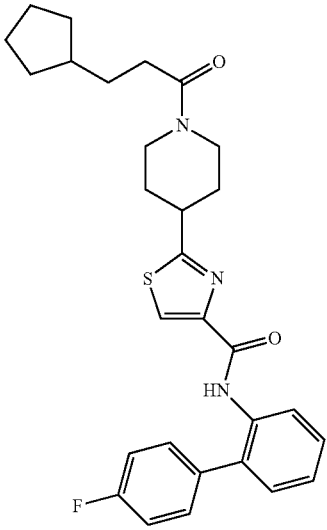 2-[1-(3-cyclopentylpropanoyl)piperidin-4-yl]-N-(4'-fluorobiphenyl-2-yl)-1,3-thiazole-4-carboxamide | |

| No. | FORMULA | NMR or mass |
|---|---|---|
| 700 | 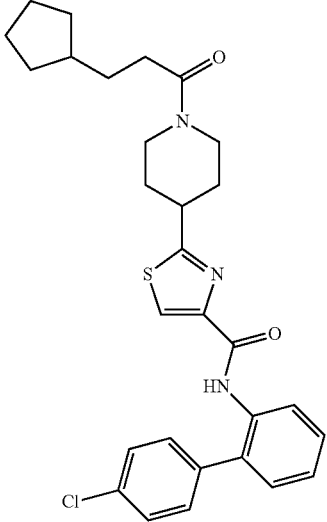 N-(4'-chlorobiphenyl-2-yl)-2-[1-(3-cyclopentylpropanoyl)piperidin-4-yl]-1,3-thiazole-4-carboxamide | |
| 701 | 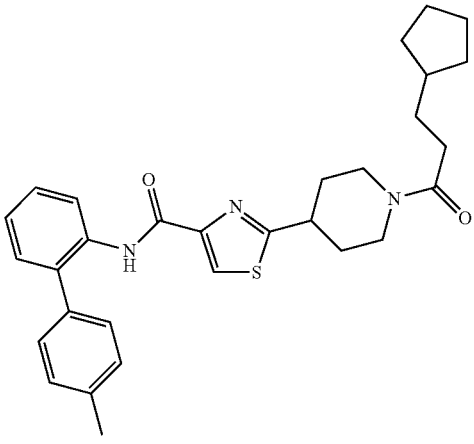 | |
| 702 | 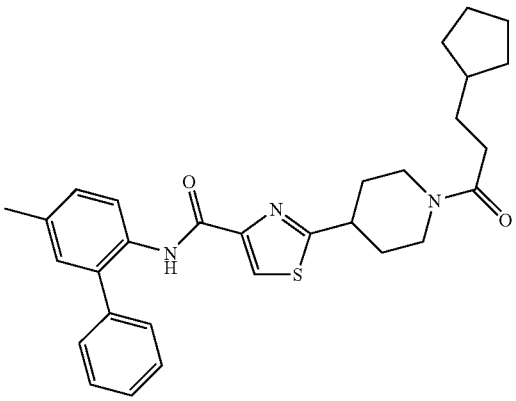 | |

TABLE 1-continued
| No. | FORMULA | NMR or mass |
|---|---|---|
| 703 | 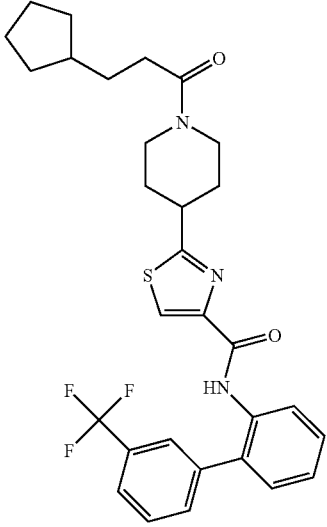 2-[1-(3-cyclopentylpropanoyl)piperidin-4-yl]-N-[3'-(trifluoromethyl)-biphenyl-2-yl]-1,3-thiazole-4-carboxamide | |
| 704 | 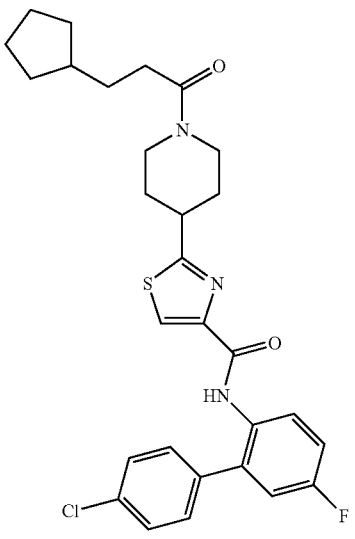 N-(4'-chloro-5-fluorobiphenyl-2-yl)-2-[1-(3-cyclopentylpropanoyl)-piperidin-4-yl]-1,3-thiazole-4-carboxamide | |

| No. | FORMULA | NMR or mass |
|---|---|---|
| 705 | 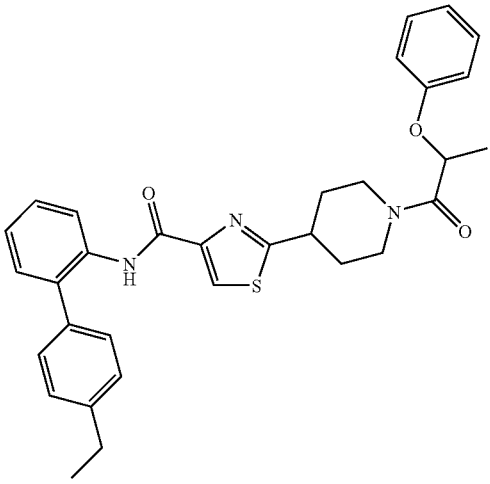 | |
| 706 | 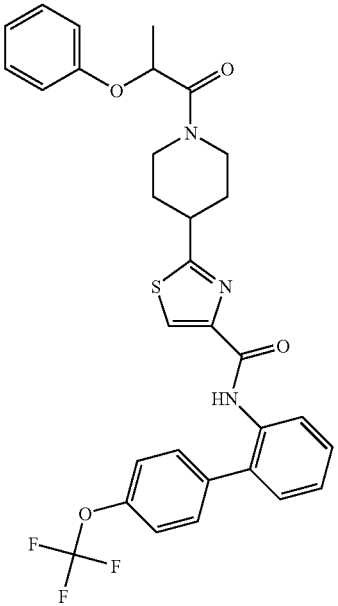 2-[1-(2-phenoxypropanoyl)piperidin-4-yl]-N-[4'-(trifluoromethoxy)biphenyl-2-yl]-1,3-thiazole-4-carboxamide | |

TABLE 1-continued
| No. | FORMULA | NMR or mass |
|---|---|---|
| 707 | 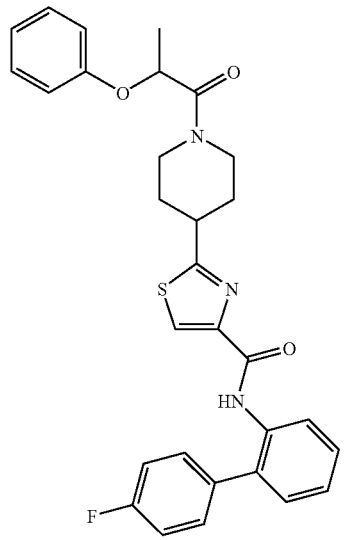 N-(4'-fluorobiphenyl-2-yl)-2-[1-(2-phenoxypropanoyl)piperidin-4-yl]-1,3-thiazole-4-carboxamide | |
| 708 | 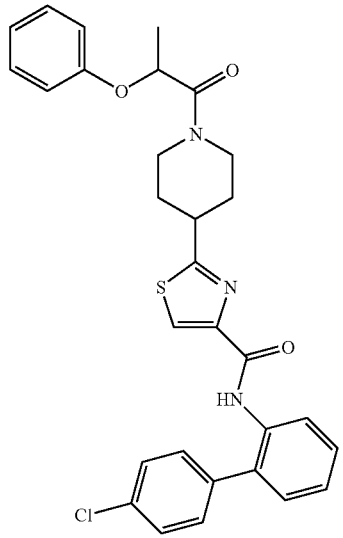 N-(4'-chlorobiphenyl-2-yl)-2-{1-(2-phenoxypropanoyl)piperidin-4-yl]-1,3-thiazole-4-carboxamide | |

TABLE 1-continued
| No. | FORMULA | NMR or mass |
|---|---|---|
| 709 | 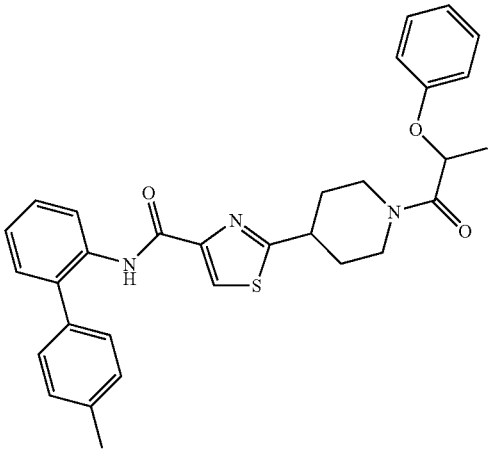 | |
| 710 | 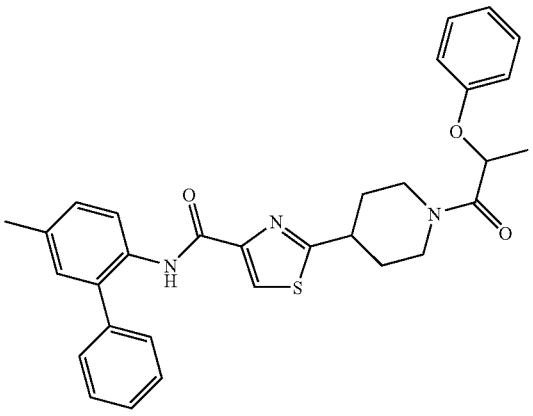 | |
| 711 | 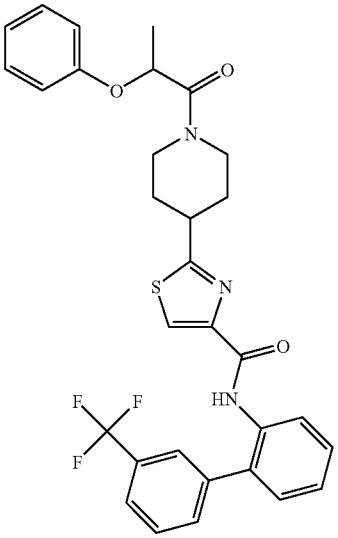 | |
2-[1-(2-phenoxypropanoyl)piperidin-4-yl]-N-[3'-(trifluoromethyl)biphenyl-2-yl]-1,3-thiazole-4-carboxamide TABLE 1-continued
| No. | FORMULA | NMR or mass |
|---|---|---|
| 712 | 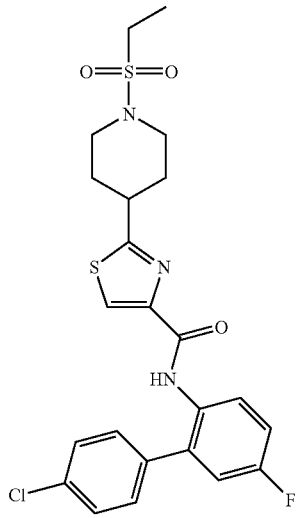 N-(4'-chloro-5-fluorobiphenyl-2-yl)-2-[1-(ethylsulfonyl)piperidin-4-yl]-1,3-thiazole-4-carboxamide | |
| 713 | 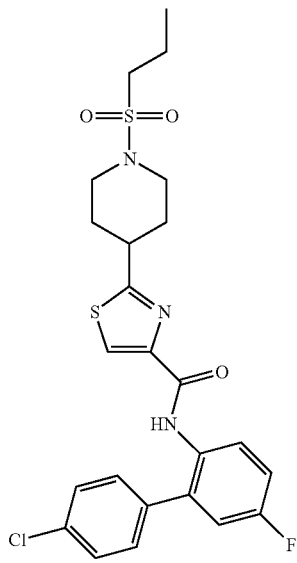 N-(4'-chloro-5-fluorobiphenyl-2-yl)-2-[1-(propylsulfonyl)piperidin-4-yl]-1,3-thiazole-4-carboxamide | |

TABLE 1-continued

| No. | FORMULA | NMR or mass |
|-----|---------|-------------|
| 714 | | |
| 715 | butyl 4-[4-({[4'-(trifluoromethoxy)biphenyl-2-yl]amino}carbonyl)-1,3-thiazol-2-yl]piperidine-1-carboxylate | |

TABLE 1-continued
| No. | FORMULA | NMR or mass |
|---|---|---|
| 716 | 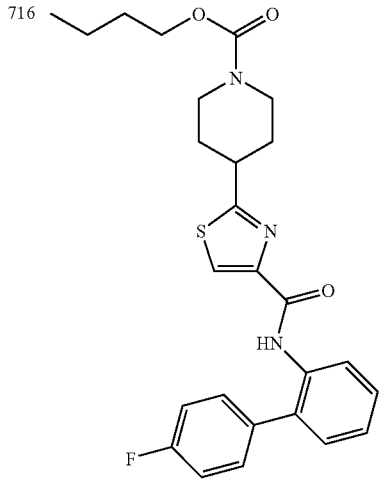 butyl 4-(4-{[(4'-fluorobiphenyl-2-yl)amino]carbonyl}-1,3-thiazol-2-yl)-piperidine-1-carboxylate | |
| 717 | 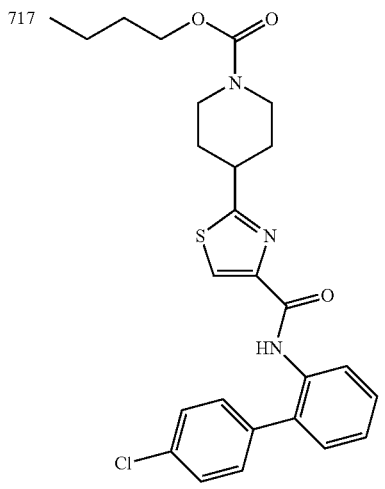 butyl 4-(4-{[(4'-chlorobiphenyl-2-yl)amino]carbonyl}-1,3-thiazol-2-yl)-piperidine-1-carboxylate | |
| 718 | 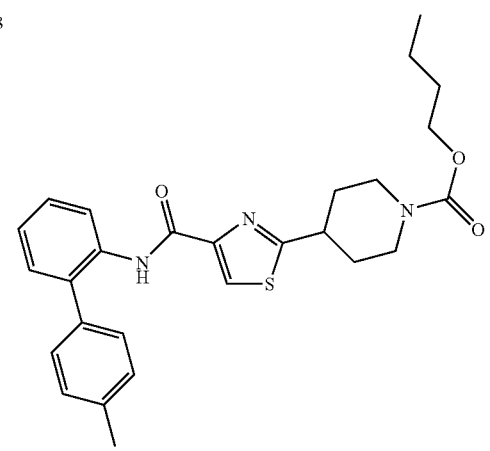 | |

TABLE 1-continued
| No. | FORMULA | NMR or mass |
|---|---|---|
| 719 | 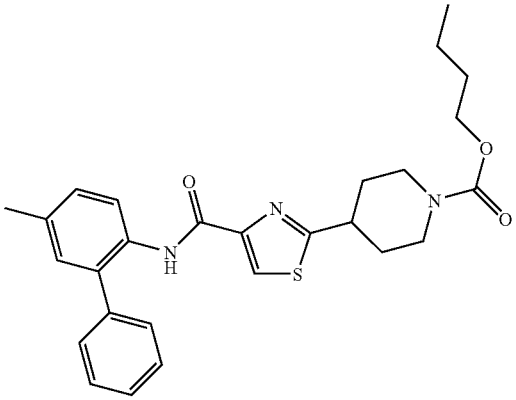 | |
| 720 | 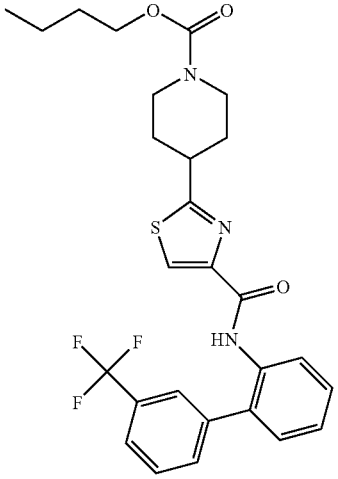  butyl 4-[4-({[3'-(trifluoromethyl)biphenyl-2-yl]amino}carbonyl)-1,3-thiazol-2-yl]piperidine-1-carboxylate | |
| 721 | 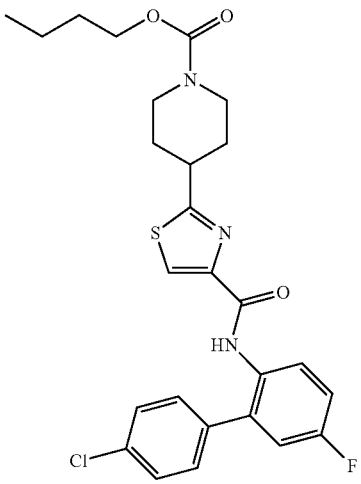  butyl 4-(4-{[(4'-chloro-5-fluorobiphenyl-2-yl)amino]carbonyl}-1,3-thiazol-2-yl)-piperidine-1-carboxylate | |

TABLE 1-continued
| No. | FORMULA | NMR or mass |
|---|---|---|
| 722 | 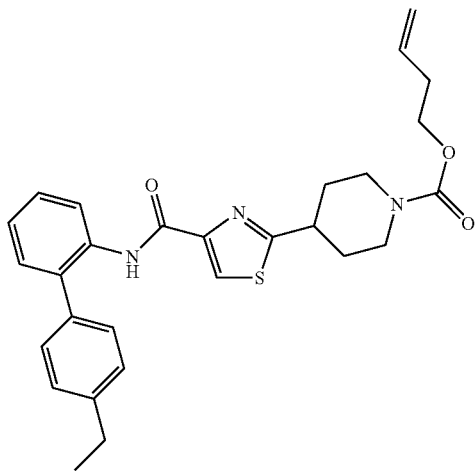 but-3-en-1-yl 4-(4-{[(4'-ethylbiphenyl-2-yl)amino]carbonyl}-1,3-thiazol-2-yl)-piperidine-1-carboxylate | |
| 723 | 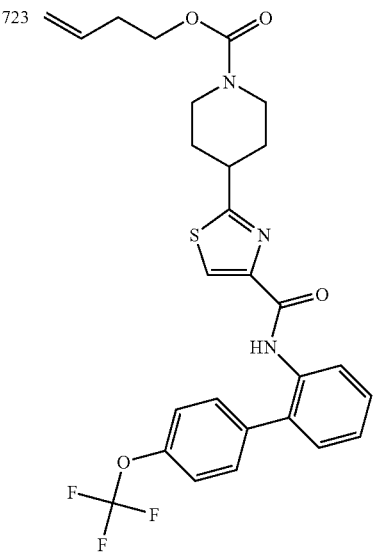 but-3-en-1-yl 4-[4-({[4'-(trifluoromethoxy)biphenyl-2-yl]amino}carbonyl)-1,3-thiazol-2-yl]piperidine-1-carboxylate | |

| No. | FORMULA | NMR or mass |
|---|---|---|
| 724 | 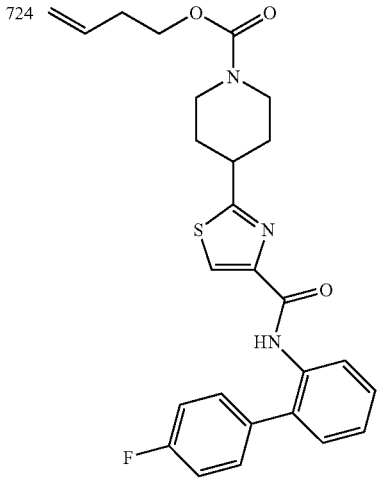 but-3-en-1-yl 4-(4-{[(4'-fluorobiphenyl-2-yl)amino]carbonyl}-1,3-thiazol-2-yl)-piperidine-1-carboxylate | |
| 725 | 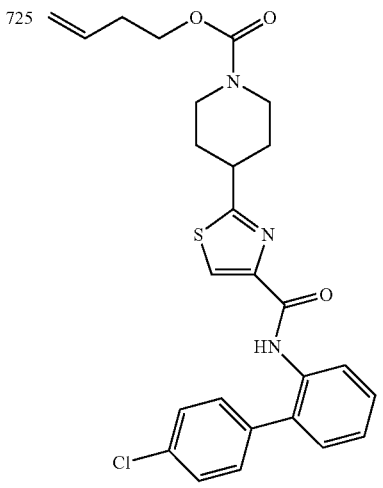 but-3-en-1-yl 4-(4-{[(4'-chlorobiphenyl-2-yl)amino]carbonyl}-1,3-thiazol-2-yl)-piperidine-1-carboxylate | |
| 726 | 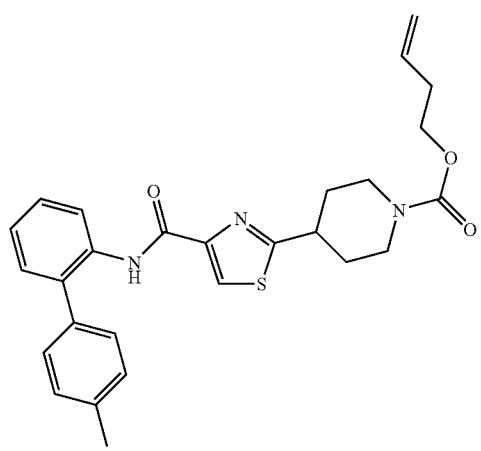 | |

TABLE 1-continued
| No. | FORMULA | NMR or mass |
|---|---|---|
727 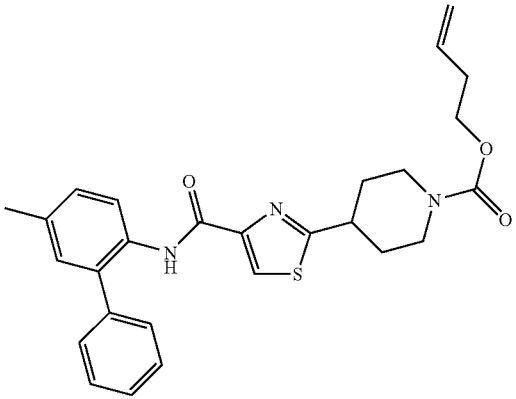
728 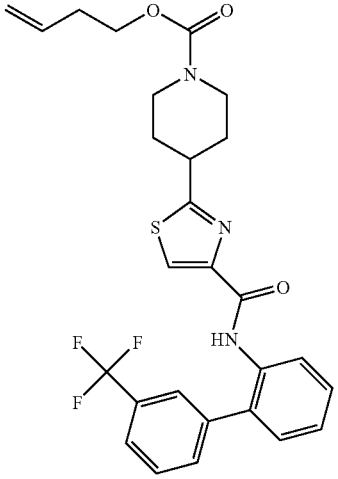
but-3-en-1-yl 4-[4-({[3'-(trifluoromethyl)biphenyl-2-yl]amino}carbonyl)-1,3-thiazol-2-yl]piperidine-1-carboxylate
729 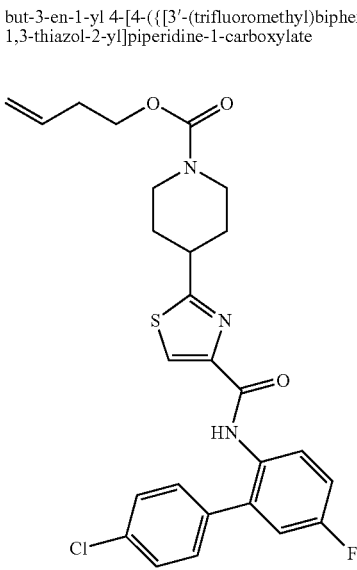
but-3-en-1-yl 4-(4-{[(4'-chloro-5-fluorobiphenyl-2-yl)amino]carbonyl}-1,3-thiazol-2-yl)piperidine-1-carboxylate TABLE 1-continued
| No. | FORMULA | NMR or mass |
|---|---|---|
| 730 | 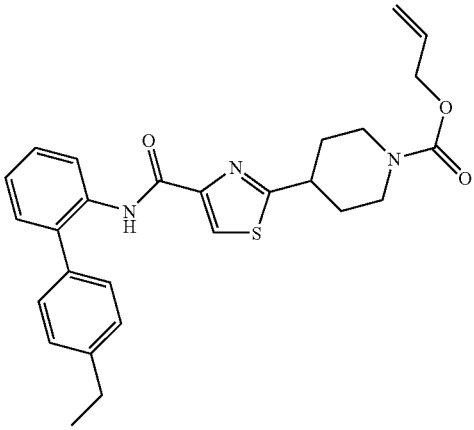 | |
| 731 | 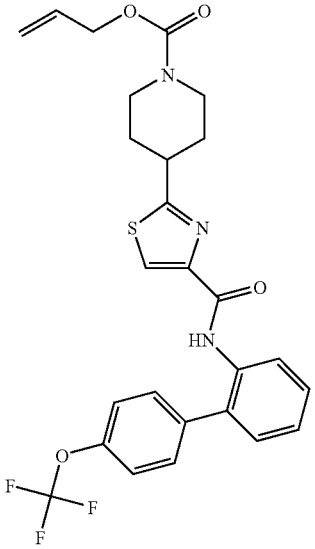   allyl 4-[4-({[4'-(trifluoromethoxy)biphenyl-2-yl]amino}carbonyl)-1,3-thiazol-2-yl]piperidine-1-carboxylate | |
| 732 | 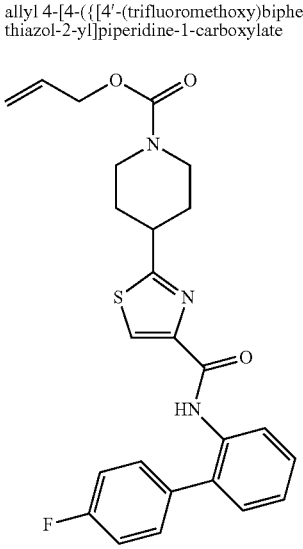   allyl 4-(4-{[(4'-fluorobiphenyl-2-yl)amino]carbonyl}-1,3-thiazol-2-yl)piperidine-1-carboxylate | |

| No. | FORMULA | NMR or mass |
|---|---|---|
| 733 | 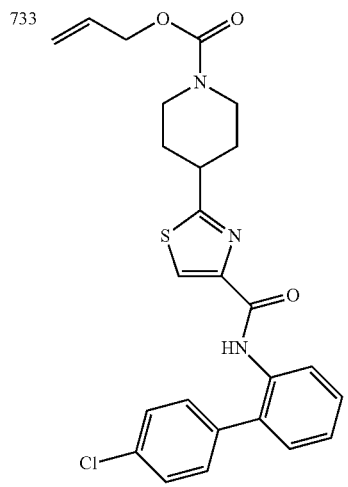 allyl 4-(4-{[(4'-chlorobiphenyl-2-yl)amino]carbonyl}-1,3-thiazol-2-yl)-piperidine-1-carboxylate | |
| 734 | 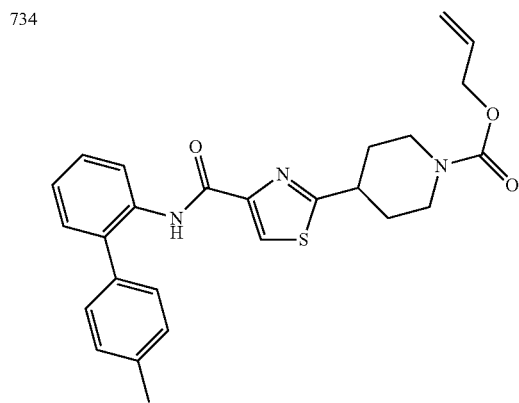 | |
| 735 | 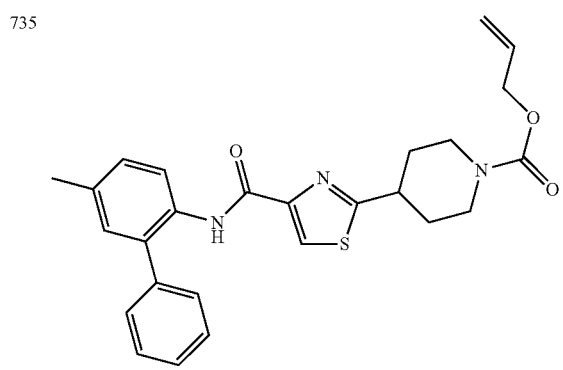 | |

TABLE 1-continued
| No. | FORMULA | NMR or mass |
|---|---|---|
| 736 | 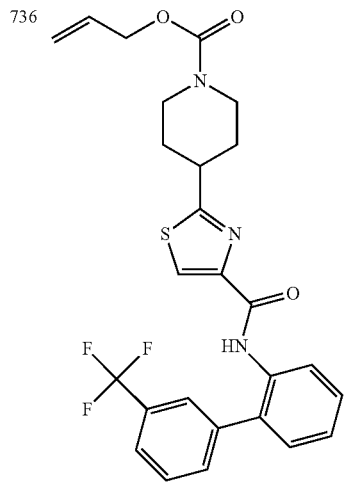 allyl 4-[4-({[3'-(trifluoromethyl)biphenyl-2-yl]amino}carbonyl)-1,3-thiazol-2-yl)piperidine-1-carboxylate | |
| 737 | 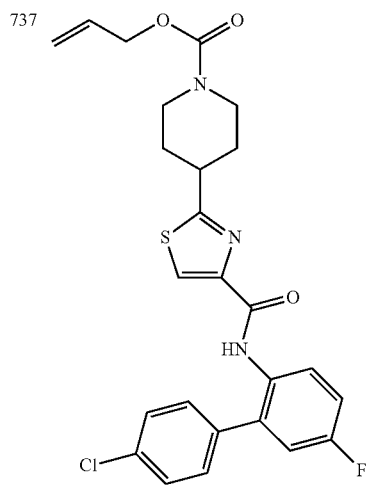 allyl 4-(4-{[(4'-chloro-5-fluorobiphenyl-2-yl)amino]carbonyl}-1,3-thiazol-2-yl)-piperidine-1-carboxylate | |

TABLE 1-continued
| No. | FORMULA | NMR or mass |
|---|---|---|
| 738 | 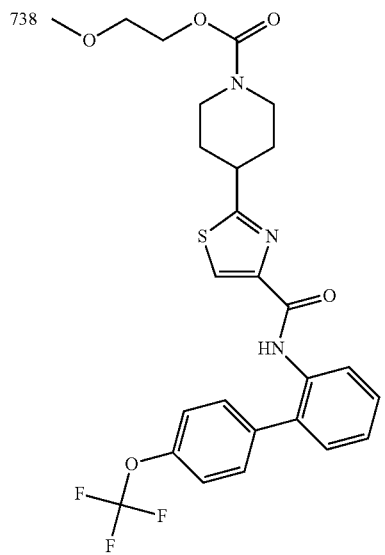 2-methoxyethyl 4-[4-({[4'-(trifluoromethoxy)biphenyl-2-yl]amino}carbonyl)-1,3-thiazol-2-yl]piperidine-1-carboxylate | |
| 739 | 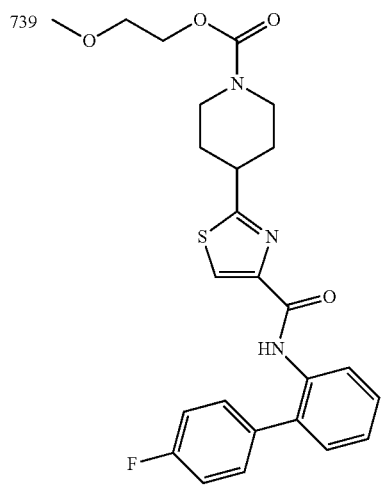 2-methoxyethyl 4-(4-{[(4'-fluorobiphenyl-2-yl)amino]carbonyl}-1,3-thiazol-2-yl)piperidine-1-carboxylate | |

TABLE 1-continued
| No. | FORMULA | NMR or mass |
|---|---|---|
| 740 | 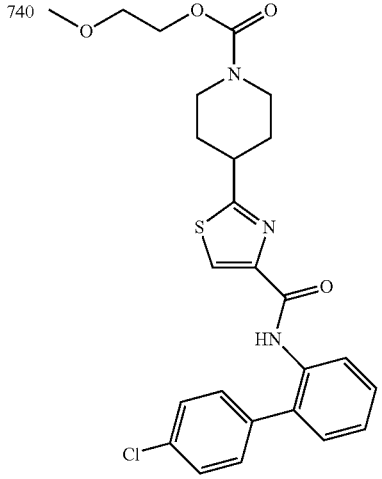 | |
2-methoxyethyl 4-(4-{[(4'-chlorobiphenyl-2-yl)amino]carbonyl}-1,3-thiazol-2-yl)piperidine-1-carboxylate
| 741 | 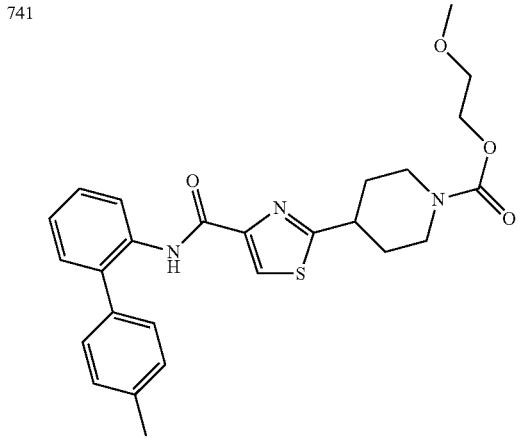 | |
| 742 | 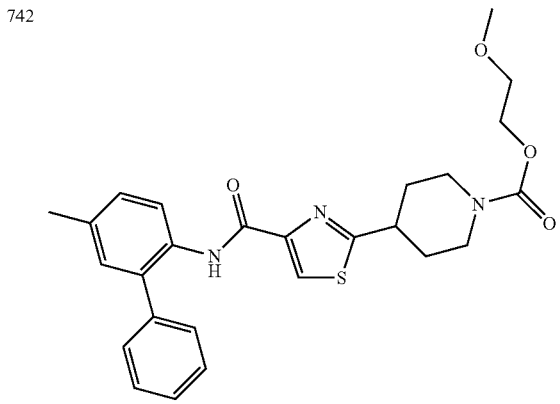 | |

| No. | FORMULA | NMR or mass |
|---|---|---|
| 743 | 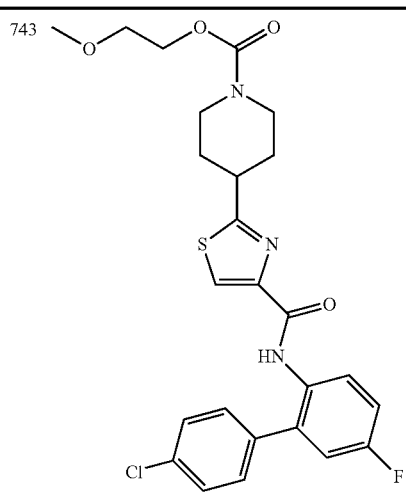<br>2-methoxyethyl 4-(4-{[(4'-chloro-5-fluorobiphenyl-2-yl)amino]carbonyl}-1,3-thiazol-2-yl)piperidine-1-carboxylate | |
| 744 | 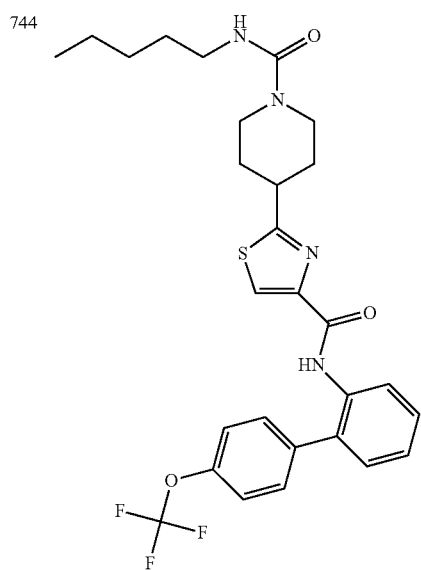<br>N-pentyl-4-[4-({[4'-(trifluoromethoxy)biphenyl-2-yl]amino}carbonyl)-1,3-thiazol-2-yl]piperidine-1-carboxamide | |

TABLE 1-continued

| No. | FORMULA | NMR or mass |
|---|---|---|
| 745 | 4-(4-{[(4'-fluorobiphenyl-2-yl)amino]carbonyl}-1,3-thiazol-2-yl)-N-pentyl-piperidine-1-carboxamide | |
| 746 | 4-(4-{[(4'-chlorobiphenyl-2-yl)amino]carbonyl}-1,3-thiazol-2-yl)-N-pentyl-piperidine-1-carboxamide | |
| 747 | | |

TABLE 1-continued
| No. | FORMULA | NMR or mass |
|---|---|---|
| 748 | 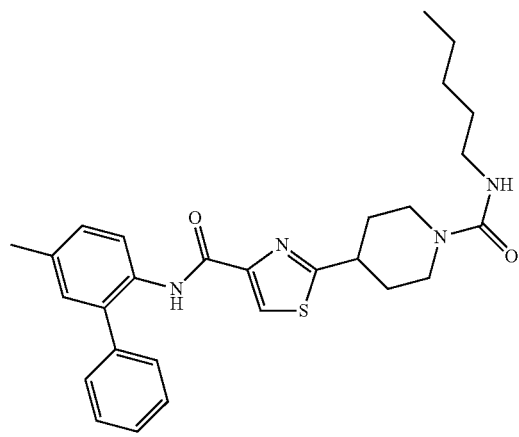 | |
| 749 | 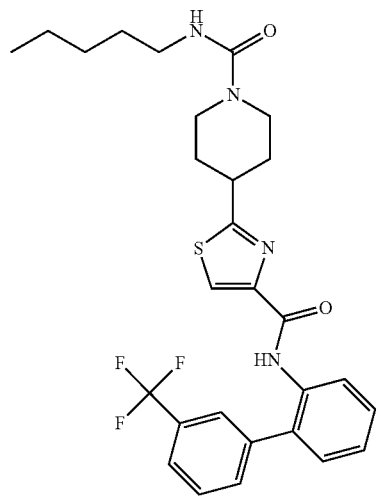 N-pentyl-4-[4-({[3'-(trifluoromethyl)biphenyl-2-yl]amino}carbonyl)-1,3-thiazol-2-yl]piperidine-1-carboxamide | |
| 750 | 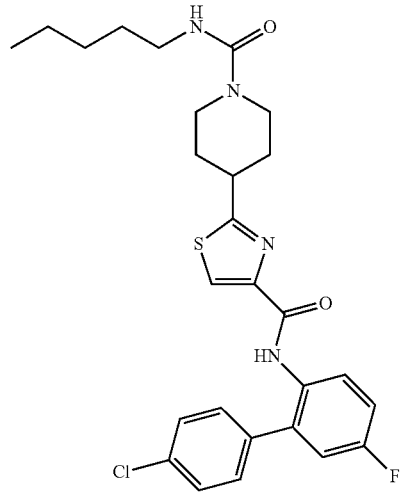 4-(4-{[(4'-chloro-5-fluorobiphenyl-2-yl)amino]carbonyl}-1,3-thiazol-2-yl)-N-pentylpiperidine-1-carboxamide | |

TABLE 1-continued
| No. | FORMULA | NMR or mass |
|---|---|---|
| 751 | 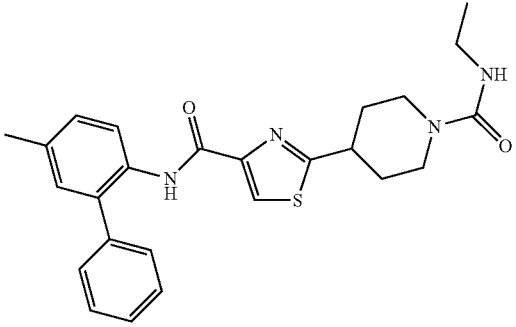 | |
| 752 | 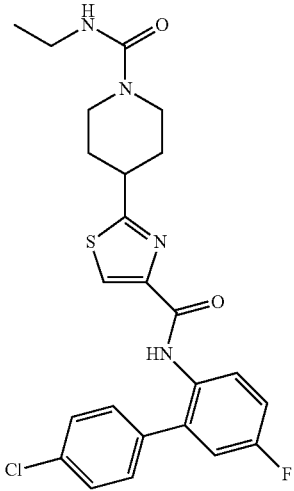<br>4-(4-{[(4'-chloro-5-fluorobiphenyl-2-yl)amino]carbonyl}-1,3-thiazol-2-yl)-N-ethylpiperidine-1-carboxamide | |
| 753 | 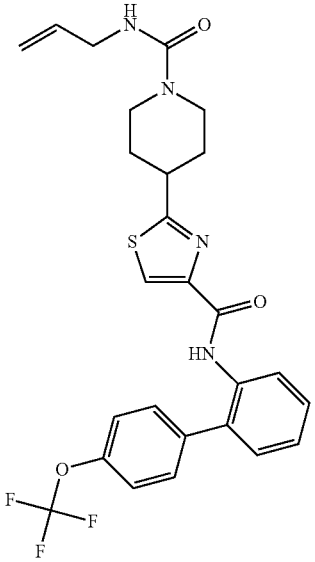<br>N-allyl-4-[4-({[4'-(trifluoromethoxy)biphenyl-2-yl]amino}carbonyl)-1,3-thiazol-2-yl]piperidine-1-carboxamide | |

| No. | FORMULA | NMR or mass |
|-----|---------|-------------|
754
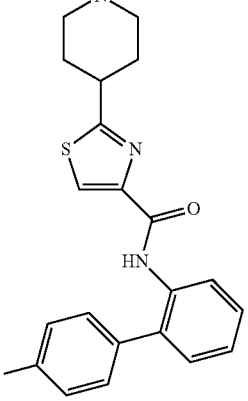
N-allyl-4-(4-{[(4'-fluorobiphenyl-2-yl)amino]carbonyl}-1,3-thiazol-2-yl)-piperidine-1-carboxamide
755
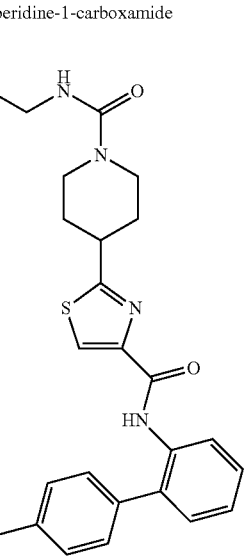
N-allyl-4-(4-{[(4'-chlorobiphenyl-2-yl)amino]carbonyl}-1,3-thiazol-2-yl)-piperidine-1-carboxamide
756
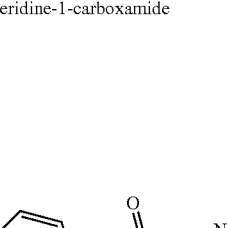

TABLE 1-continued
| No. | FORMULA | NMR or mass |
|-----|---------|-------------|
757
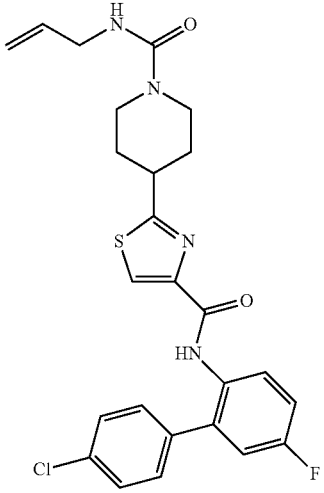
N-allyl-4-(4-{[(4'-chloro-5-fluorobiphenyl-2-yl)amino]carbonyl}-1,3-thiazol-2-yl)piperidine-1-carboxamide
758
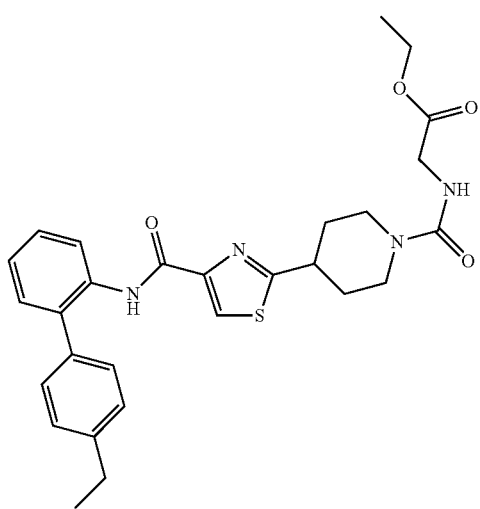
ethyl N-{[4-(4-{[(4'-ethylbiphenyl-2-yl)amino]carbonyl}-1,3-thiazol-2-yl)-piperidin-1-yl]carbonyl}glycinate TABLE 1-continued
| No. | FORMULA | NMR or mass |
|---|---|---|
| 759 | 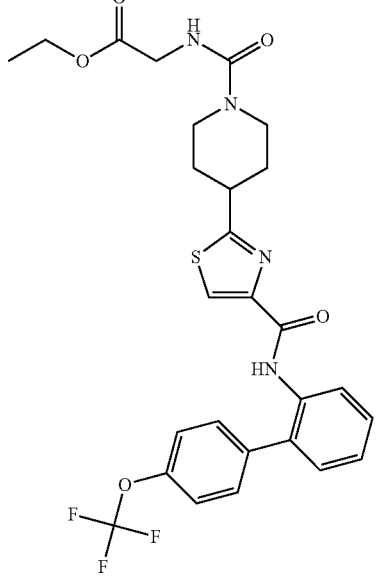 ethyl N-({4-[4-({[4'-(trifluoromethoxy)biphenyl-2-yl]amino}carbonyl)-1,3-thiazol-2-yl]piperidin-1-yl}carbonyl)glycinate | |
| 760 | 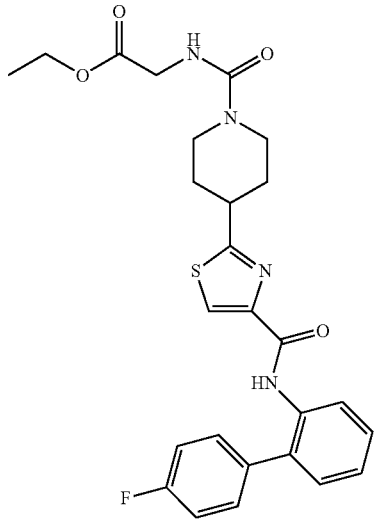 ethyl N-{[4-[4-{[(4'-fluorobiphenyl-2-yl)amino]carbonyl}-1,3-thiazol-2-yl)-piperidin-1-yl]carbonyl}glycinate | |

TABLE 1-continued

| No. | FORMULA | NMR or mass |
|-----|---------|-------------|
| 761 | | |
| 762 | | |
| 763 | | |

TABLE 1-continued
| No. | FORMULA | NMR or mass |
|---|---|---|
| 764 | 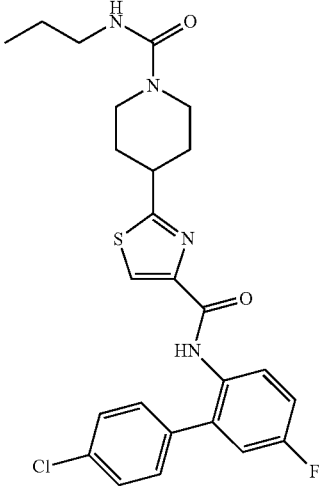 4-(4-{[(4'-chloro-5-fluorobiphenyl-2-yl)amino]carbonyl}-1,3-thiazol-2-yl)-N-propylpiperidine-1-carboxamide | |
| 765 | 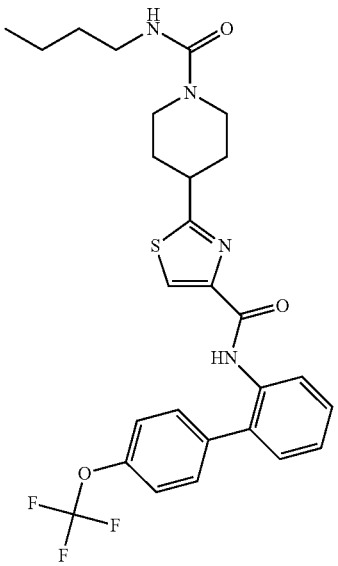 N-butyl-4-[4-({[4'-(trifluoromethoxy)biphenyl-2-yl]amino}carbonyl)-1,3-thiazol-2-yl]piperidine-1-carboxamide | |

TABLE 1-continued
| No. | FORMULA | NMR or mass |
|---|---|---|
| 766 | 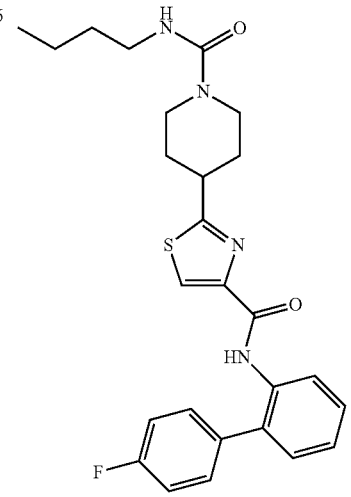 N-butyl-4-(4-{[(4'-fluorobiphenyl-2-yl)amino]carbonyl}-1,3-thiazol-2-yl)-piperidine-1-carboxamide | |
| 767 | 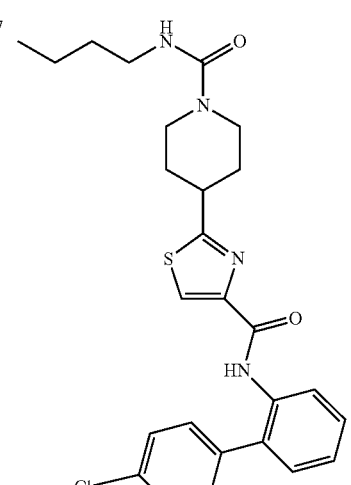 N-butyl-4-(4-{[(4'-chlorobiphenyl-2-yl)amino]carbonyl}-1,3-thiazol-2-yl)-piperidine-1-carboxamide | |
| 768 | 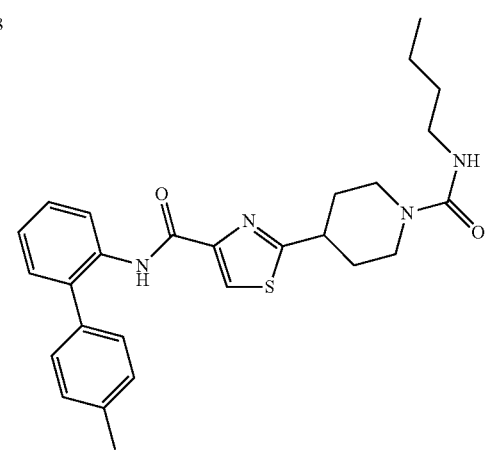 | |

TABLE 1-continued
| No. | FORMULA | NMR or mass |
|---|---|---|
769
770
N-butyl-4-[4-({[3'-(trifluoromethyl)biphenyl-2-yl]amino}carbonyl)-1,3-thiazol-2-yl]piperidine-1-carboxamide
771 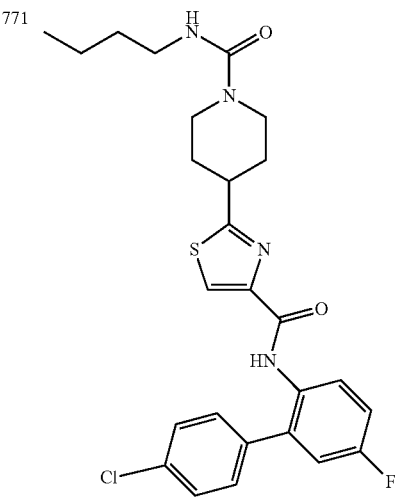
N-butyl-4-(4-{[(4'-chloro-5-fluorobiphenyl-2-yl)amino]carbonyl}-1,3-thiazol-2-yl)piperidine-1-carboxamide

| No. | FORMULA | NMR or mass |
|---|---|---|
| 772 | 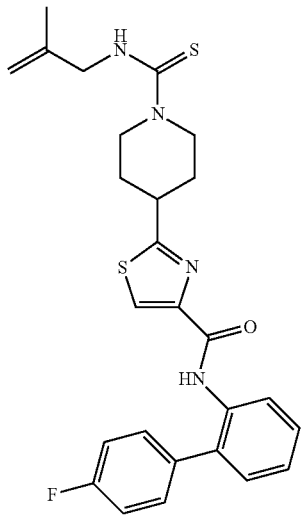 N-(4'-fluorobiphenyl-2-yl)-2-(1-{[(2-methylprop-2-en-1-yl)amino]carbonothioyl}piperidin-4-yl)-1,3-thiazole-4-carboxamide | |
| 773 | 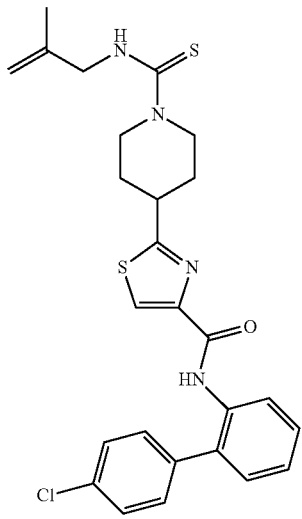 N-(4'-chlorobiphenyl-2-yl)-2-(1-{[(2-methylprop-2-en-1-yl)amino]carbonothioyl}piperidin-4-yl)-1,3-thiazole-4-carboxamide | |

| No. | FORMULA | NMR or mass |
|---|---|---|
| 774 | 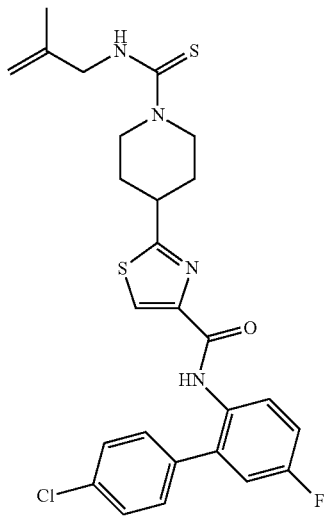 N-(4'-chloro-5-fluorobiphenyl-2-yl)-2-(1-{[(2-methylprop-2-en-1-yl)amino]-carbonothioyl}piperidin-4-yl)-1,3-thiazole-4-carboxamide | |
| 775 | 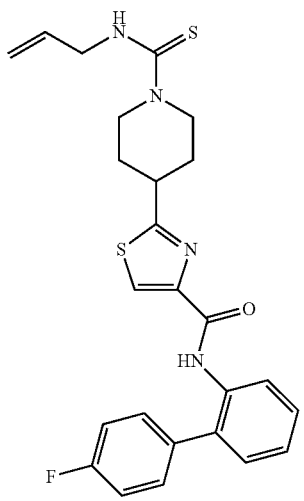 2-{1-[(allylamino)carbonothioyl]piperidin-4-yl}-N-(4'-fluorobiphenyl-2-yl)-1,3-thiazole-4-carboxamide | |

TABLE 1-continued

| No. | FORMULA | NMR or mass |
|---|---|---|
| 776 | 2-{1-[(allylamino)carbonothioyl]piperidin-4-yl}-N-(4'-chlorobiphenyl-2-yl)-1,3-thiazole-4-carboxamide | |
| 777 | 2-{1-[(allylamino)carbonothioyl]piperidin-4-yl}-N-(4'-chloro-5-fluorobiphenyl-2-yl)-1,3-thiazole-4-carboxamide | |

| No. | FORMULA | NMR or mass |
|---|---|---|
| 778 | 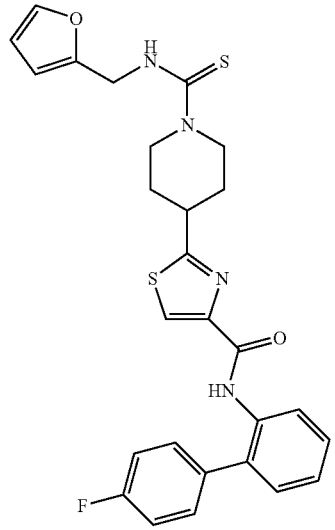 N-(4'-fluorobiphenyl-2-yl)-2-(1-{[(2-furylmethyl)amino]-carbonothioyl}-piperidin-4-yl)-1,3-thiazole-4-carboxamide | |
| 779 | 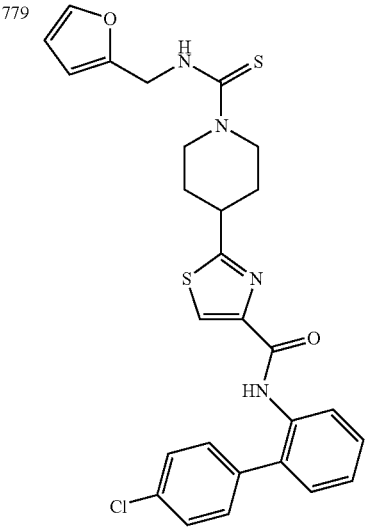 N-(4'-chlorobiphenyl-2-yl)-2-(1-{[(2-furylmethyl)amino]carbonothioyl}-piperidin-4-yl)-1,3-thiazole-4-carboxamide | |

| No. | FORMULA | NMR or mass |
|---|---|---|
| 780 | 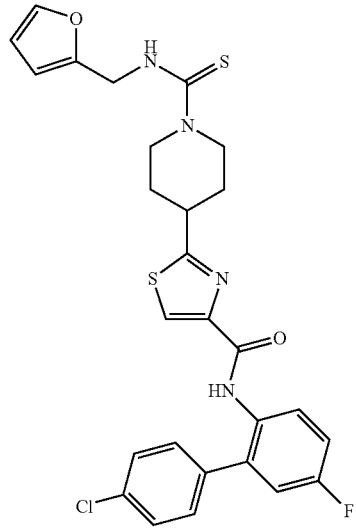<br>N-(4'-chloro-5-fluorobiphenyl-2-yl)-2-(1-{[(2-furylmethyl)amino]carbonothioyl}piperidin-4-yl)-1,3-thiazole-4-carboxamide | |
| 781 | 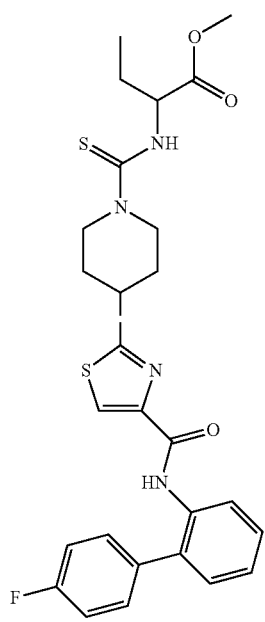<br>methyl 2-({[4-(4-{[(4'-fluorobiphenyl-2-yl)amino]carbonyl}-1,3-thiazol-2-yl)-piperidin-1-yl]carbonothioyl}amino)butanoate | |

TABLE 1-continued
| No. | FORMULA | NMR or mass |
|-----|---------|-------------|
| 782 | 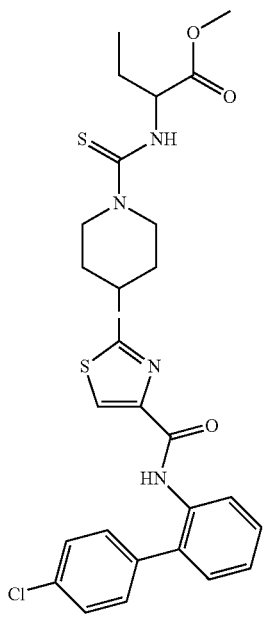 methyl 2-({[4-(4-{[(4'-chlorobiphenyl-2-yl)amino]carbonyl}-1,3-thiazol-2-yl)-piperidin-1-yl]carbonothioyl}amino)butanoate | |
| 783 | 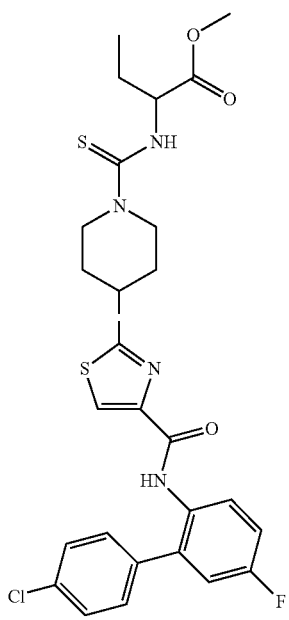 methyl 2-({[4-(4-{[(4'-chloro-5-fluorobiphenyl-2-yl)amino]carbonyl}-1,3-thiazol-2-yl)piperidin-1-yl]carbonothioyl}amino)butanoate | |

| No. | FORMULA | NMR or mass |
|---|---|---|
| 784 | 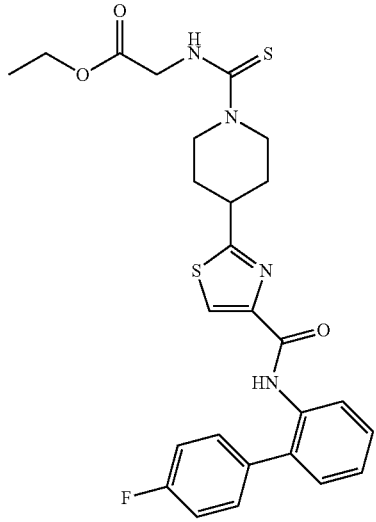 ethyl N-{[4-(4-{[(4'-fluorobiphenyl-2-yl)amino]carbonyl}-1,3-thiazol-2-yl)-piperidin-1-yl]carbonothioyl}glycinate | |
| 785 | 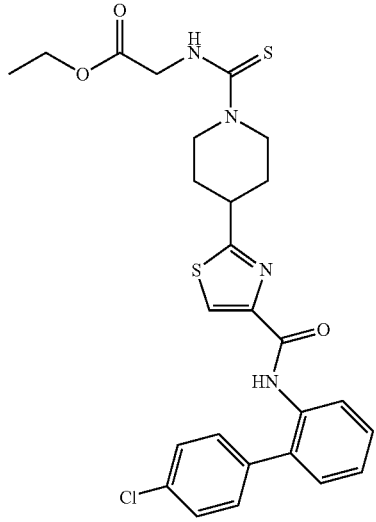 ethyl N-{[4-(4-{[(4'-chlorobiphenyl-2-yl)amino]carbonyl}-1,3-thiazol-2-yl)-piperidin-1-yl]carbonothioyl}glycinate | |

| No. | FORMULA | NMR or mass |
|---|---|---|
| 786 | 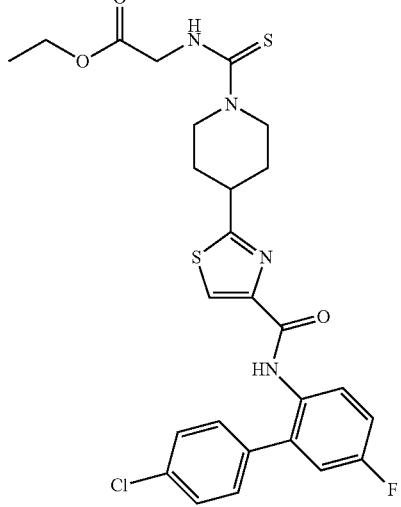 ethyl N-{[4-(4-{[(4'-chloro-5-fluorobiphenyl-2-yl)amino]carbonyl}-1,3-thiazol-2-yl)piperidin-1-yl]carbonothioyl}glycinate | |
| 787 | 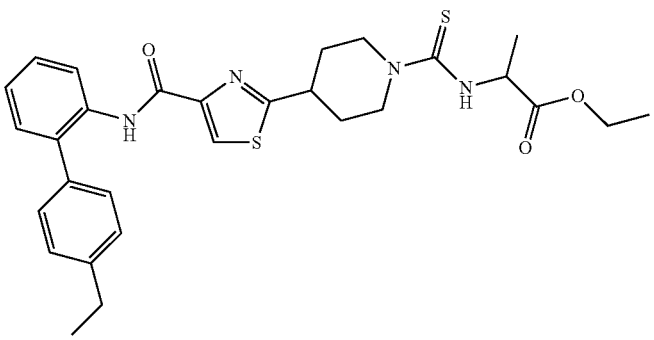 | |

| No. | FORMULA | NMR or mass |
|---|---|---|
788
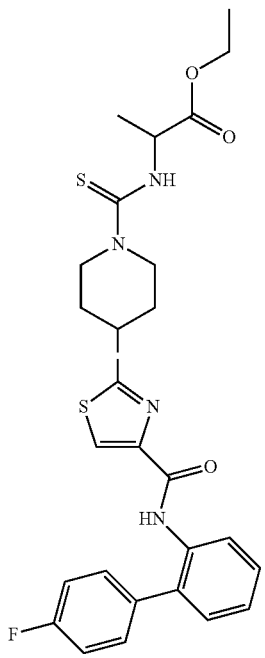
ethyl N-{[4-(4-{[(4'-fluorobiphenyl-2-yl)amino]carbonyl}-1,3-thiazol-2-yl)-piperidin-1-yl]carbonothioyl}alaninate
789
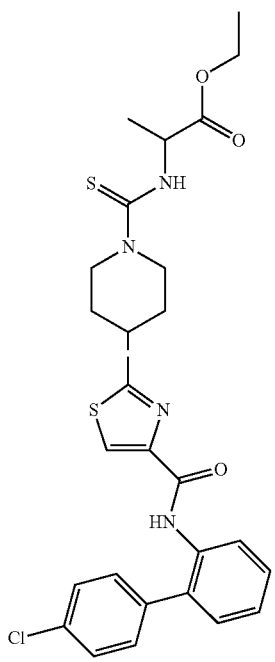
ethyl N-{[4-(4-{[(4'-chlorobiphenyl-2-yl)amino]carbonyl}-1,3-thiazol-2-yl)-piperidin-1-yl]carbonothioyl}alaninate TABLE 1-continued
| No. | FORMULA | NMR or mass |
|---|---|---|
| 790 | 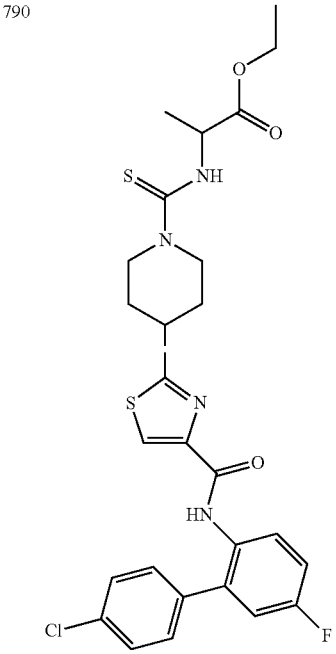 ethyl N-{[4-(4-{[(4'-chloro-5-fluorobiphenyl-2-yl)amino]carbonyl}-1,3-thiazol-2-yl)piperidin-1-yl]carbonothioyl}alaninate | |
| 791 | 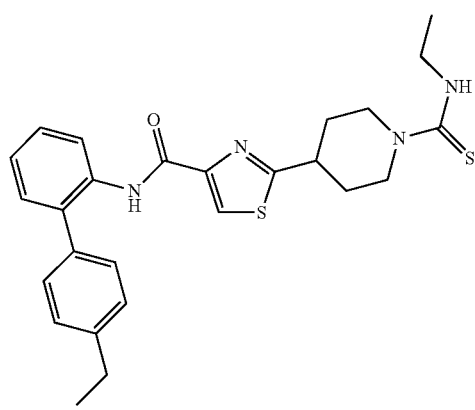 | |

TABLE 1-continued
| No. | FORMULA | NMR or mass |
|---|---|---|
| 792 | 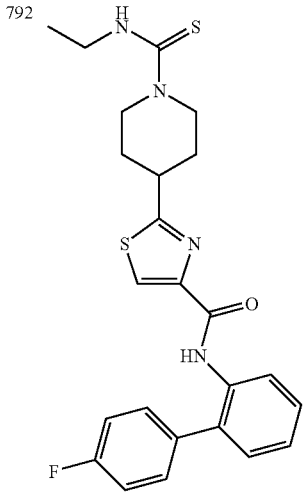 2-{1-[(ethylamino)carbonothioyl]piperidin-4-yl}-N-(4'-fluorobiphenyl-2-yl)-1,3-thiazole-4-carboxamide | |
| 793 | 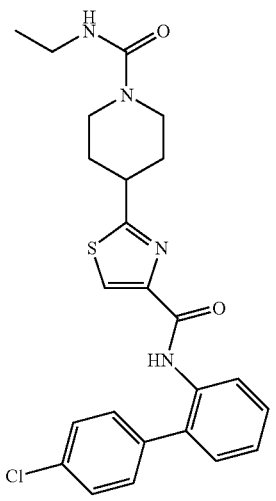 N-(4'-chlorobiphenyl-2-yl)-2-{1-[(ethylamino)carbonothioyl]piperidin-4-yl}-1,3-thiazole-4-carboxamide | |

TABLE 1-continued

| No. | FORMULA | NMR or mass |
|---|---|---|

794

N-(4-chloro-5-fluorobiphenyl-2-yl)-2-{1-[(ethylamino)carbonothioyl]-piperidin-4-yl}-1,3-thiazole-4-carboxamide

795

796

N-(4-fluorobiphenyl-2-yl-2-{1-{(propylamino)carbonthioyl]piperidin-4-yl}-1,3-thiazole-4-carboxamide

TABLE 1-continued
| No. | FORMULA | NMR or mass |
|---|---|---|
| 797 | 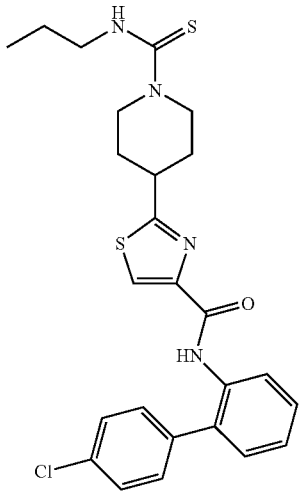 N-(4'-chlorobiphenyl-2-yl)-2-{1-[(propylamino)carbonthioyl]piperidin-4-yl}-1,3-thiazole-4-carboxamide | |
| 798 | 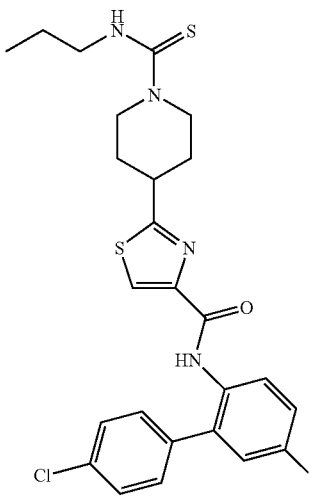 N-(4-chloro-5-fluorobiphenyl-2-yl)-2-{1-[(propylamino)carbonthioyl]-piperidin-4-yl}-1,3-thiazole-4-carboxamide | |

| No. | FORMULA | NMR or mass |
|---|---|---|
| 799 | 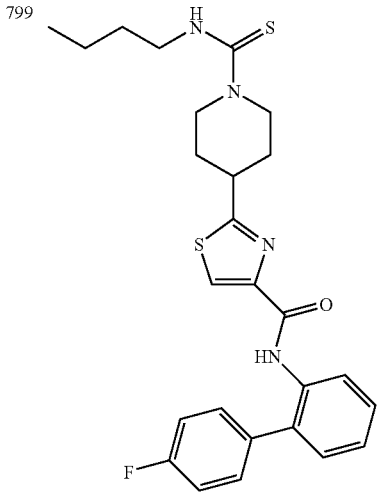<br>2-{1-[(butylamino)carbonthioyl]piperidin-4-yl}-N-(4'-fluorobiphenyl-2-yl)-1,3-thiazole-4-carboxamide | |
| 800 | 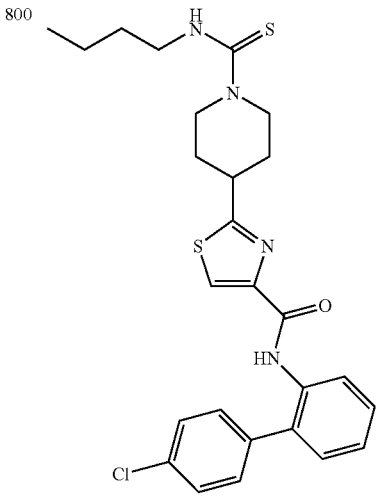<br>2-{1-[(butylamino)carbonothioyl]piperidin-4-yl]-N-(4'-chlorobiphenyl-2-yl)-1,3-thiazole-4-carboxamide | |

TABLE 1-continued

| No. | FORMULA | NMR or mass |
|-----|---------|-------------|

801

2-{1-[(butylamino)carbonthioyl]piperidin-4-yl}-N-(4'-chloro-5-fluorobiphenyl-2-yl)-1,3-thiazole-4-carboxamide

802

| No. | FORMULA | NMR or mass |
|---|---|---|
| 803 | 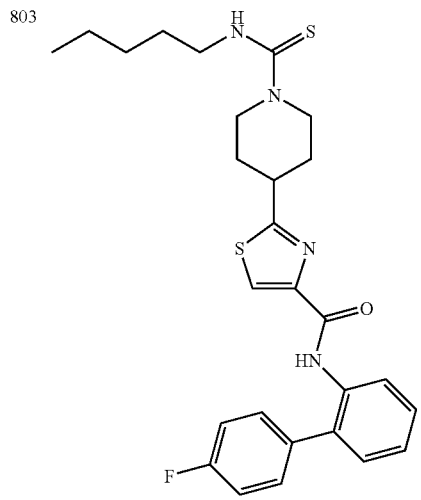<br>N-(4'-fluorobiphenyl-2-yl)-2-{1-[(pentylamino)carbonothioyl]piperidin-4-yl}-1,3-thiazole-4-carboxamide | |
| 804 | 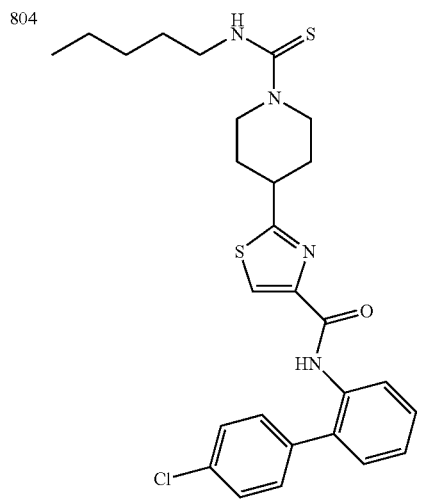<br>N-(4'-chlorobiphenyl-2-yl)-2-{1-[(pentylamino)carbonthioyl]piperidin-4-yl}-1,3-thiazole-4-carboxamide | |

TABLE 1-continued
| No. | FORMULA | NMR or mass |
|---|---|---|
| 805 | 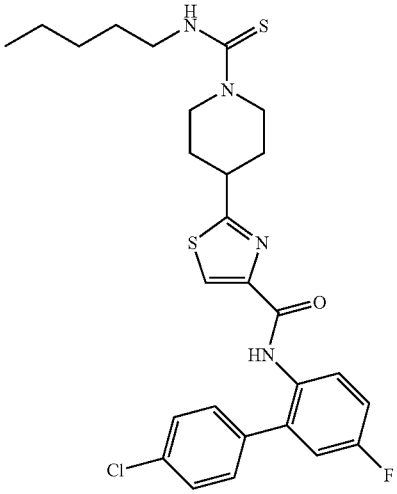 N-(4'-chloro-5-fluorobiphenyl-2-yl)-2-{1-[(pentylamino)carbonthioyl]-piperidin-4-yl}-1,3-thiazole-4-carboxamide | |
| 806 | 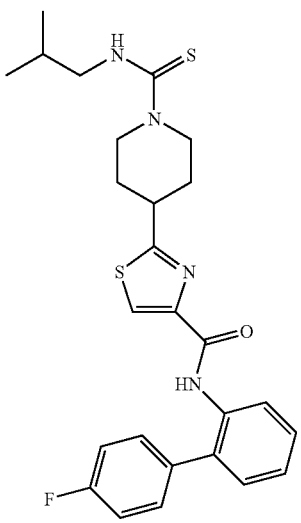 N-(4'-fluorobiphenyl-2-yl)-2-{1-{(isobutylamino)carbonothioyl]piperidin-4-yl}-1,3-thiazole-4-carboxamide | |

TABLE 1-continued
| No. | FORMULA | NMR or mass |
|-----|---------|-------------|
807
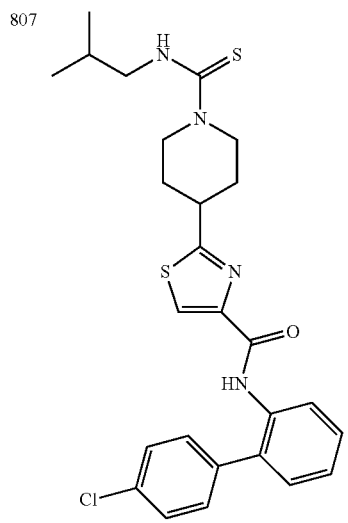
N-(4'-chlorobiphenyl-2-yl)-2-{1-[(isobutylamino)carbonothioyl]piperidin-4-yl}-1,3-thiazole-4-carboxamide
808
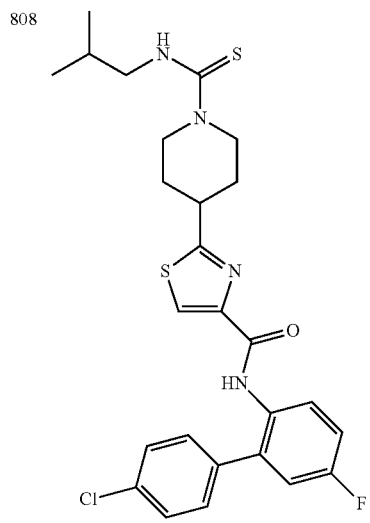
N-(4'-chloro-5-fluorobiphenyl-2-yl)-2-{1-[(isobutylamino)carbonothioyl]-piperidin-4-yl}-1,3-thiazole-4-carboxamide

| No. | FORMULA | NMR or mass |
|---|---|---|
| 809 | 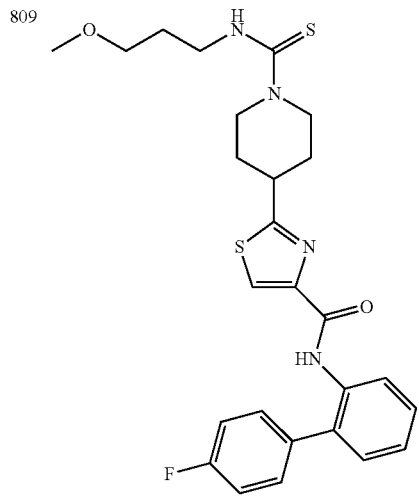<br>N-(4'-fluorobiphenyl-2-yl)-2-(1-{[(3-ethoxypropyl)amino]carbonothioyl}-piperidin-4-yl)-1,3-thiazole-4-carboxamide | |
| 810 | 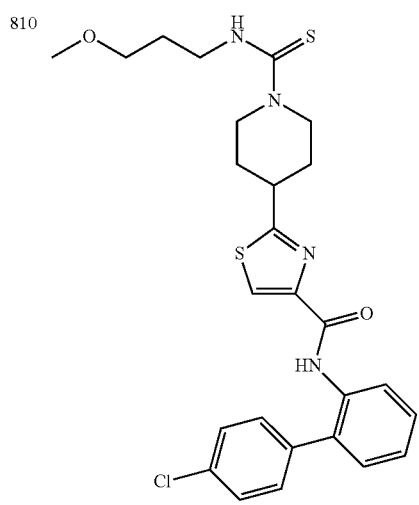<br>N-(4'-chlorobiphenyl-2-yl)-2-(1-{[(3-methoxypropyl)amino]-carbonothioyl}-piperidin-4-yl)-1,3-thiazole-4-carboxamide | |

TABLE 1-continued
| No. | FORMULA | NMR or mass |
|---|---|---|
| 811 | 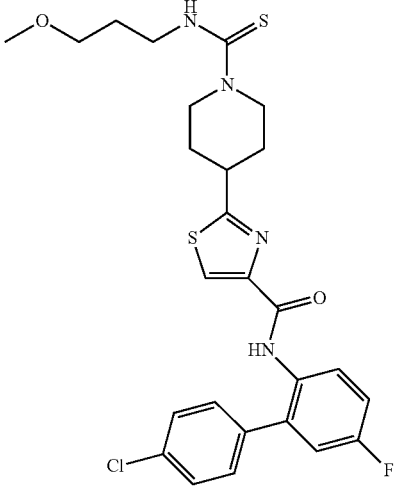 N-(4'-chloro-5-fluorobiphenyl-2-yl)-2-(1-{[(3-methoxypropyl)-amino]carbono-thioyl}piperidin-4-yl)-1,3-thiazole-4-carboxamide | |
| 812 | 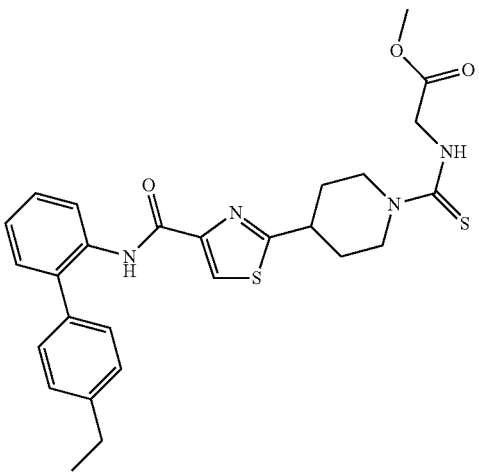 | |

TABLE 1-continued
| No. | FORMULA | NMR or mass |
|---|---|---|
| 813 | 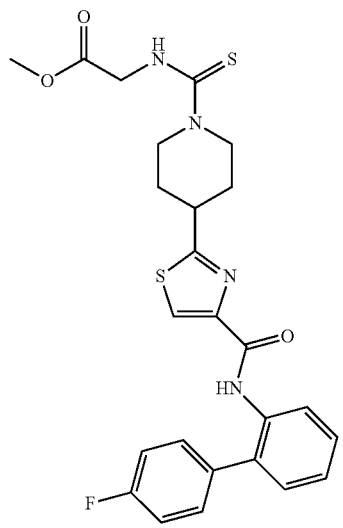methyl N-{[4-(4-{[(4'-fluorobiphenyl-2-yl)amino]carbonyl}-1,3-thiazol-2-yl)-piperidin-1-yl]carbonothioyl}glycinate | |
| 814 | 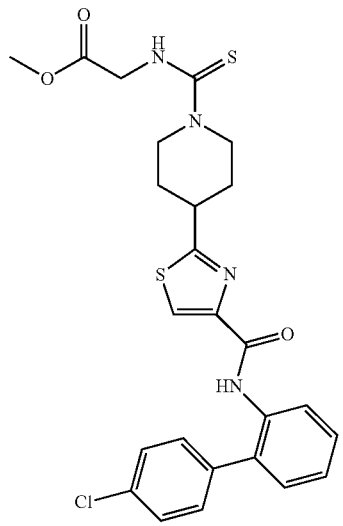methyl N-{[4-(4-{[(4'-chlorobiphenyl-2-yl)amino]carbonyl}-1,3-thiazol-2-yl)-piperidin-1-yl]carbonothioyl}glycinate | |

TABLE 1-continued
| No. | FORMULA | NMR or mass |
|---|---|---|
| 815 | 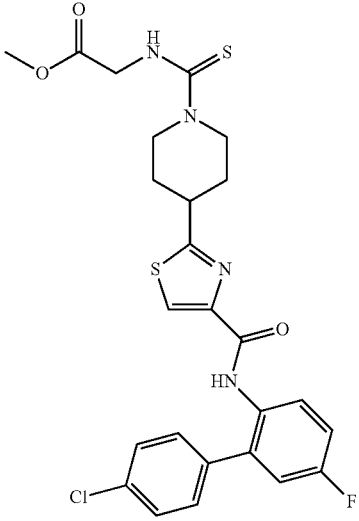 methyl N-{[4-(4-{[(4'-chloro-5-fluorobiphenyl-2-yl)amino]carbonyl}-1,3-thiazol-2-yl)piperidin-1-yl]carbonothioyl}glycinate | |
| 816 | 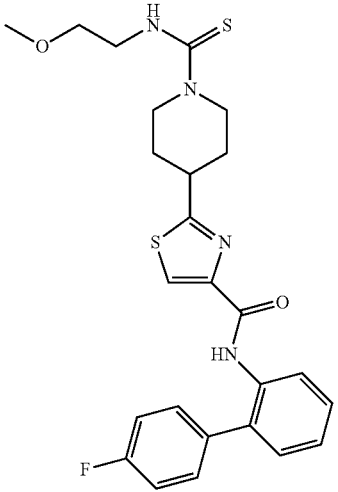 N-(4'-fluorobiphenyl-2-yl)-2-(1-{[(2-methoxyethyl)amino]-carbonothioyl}-piperidin-4-yl)-1,3-thiazole-4-carboxamide | |

| No. | FORMULA | NMR or mass |
|---|---|---|
| 817 | 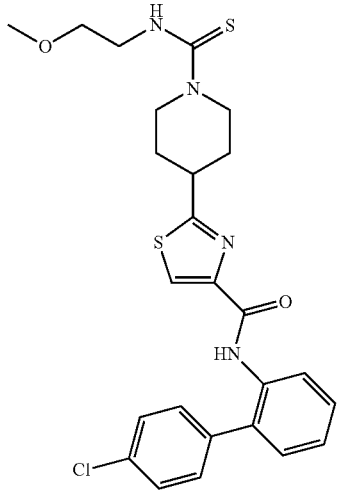<br>N-(4'-chlorobiphenyl-2-yl)-2-(1-{[(2-methoxyethyl)amino]-carbonothioyl}-piperidin-4-yl)-1,3-thiazole-4-carboxamide | |
| 818 | 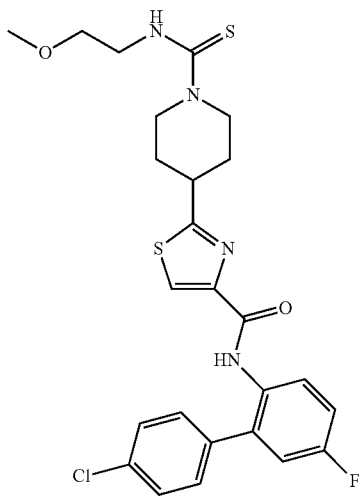<br>N-(4'-chloro-5-fluorobiphenyl-2-yl)-2-(1-{[(2-methoxyethyl)amino]-carbono-thioyl}piperidin-4-yl)-1,3-thiazole-4-carboxamide | |

TABLE 1-continued
| No. | FORMULA | NMR or mass |
|---|---|---|
| 819 | 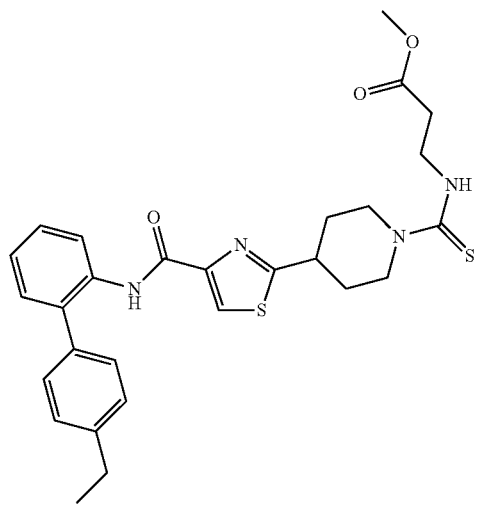 methyl N-{[4-(4-{[(4'-ethylbiphenyl-2-yl)amino]carbonyl}-1,3-thiazol-2-yl)-piperidin-1-yl]carbonothioyl}-beta-alaninate | |
| 820 | 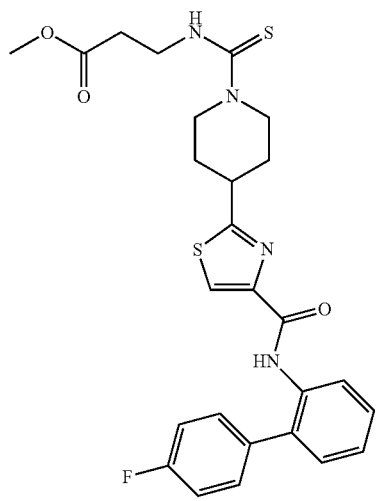 methyl N-{[4-(4-{[(4'-fluorobiphenyl-2-yl)amino]carbonyl}-1,3-thiazol-2-yl)-piperidin-1-yl]carbonothioyl}-beta-alaninate | |

TABLE 1-continued
| No. | FORMULA | NMR or mass |
|---|---|---|
| 821 | 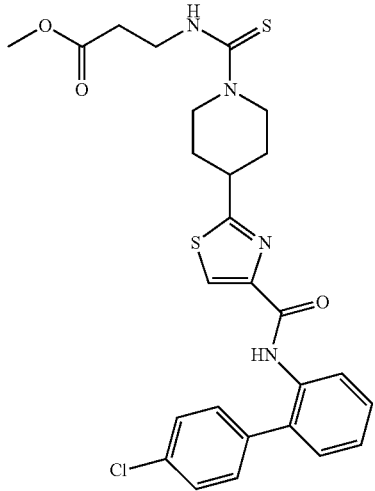methyl N-{[4-(4-{[(4'-chlorobiphenyl-2-yl)amino]carbonyl}-1,3-thiazol-2-yl)-piperidin-1-yl]carbonothioyl}-beta-alaninate | |
| 822 | 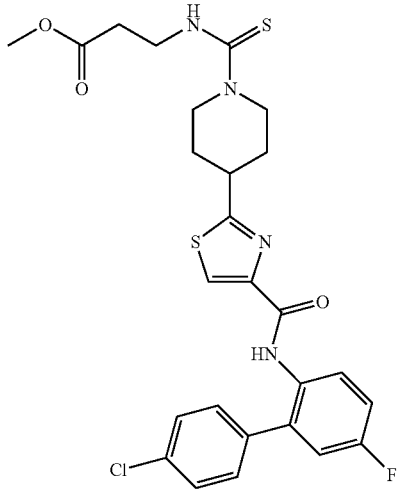methyl N-{[4-(4-{[(4'-chloro-5-fluorobiphenyl-2yl)amino]carbonyl}-1,3-thiazol-2-yl)piperidin-1-yl]carbonothioyl}-beta-alaninate | |

TABLE 1-continued
| No. | FORMULA | NMR or mass |
|---|---|---|
| 823 | 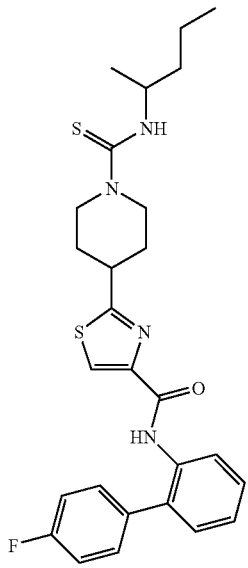 N-(4'-fluorobiphenyl-2-yl)-2-(1-{[(1-methylbutyl)amino]-carbonothioyl}-piperidin-4-yl)-1,3-thiazole-4-carboxamide | |
| 824 | 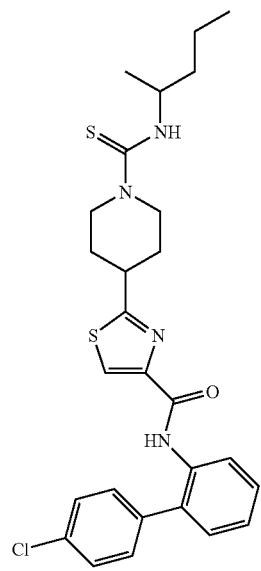 N-(4'-chlorobiphenyl-2-yl)-2-(1-{[(1-methylbutyl)amino]-carbonothioyl}-piperidin-4-yl)-1,3-thiazole-4-carboxamide | |

TABLE 1-continued
| No. | FORMULA | NMR or mass |
|---|---|---|
825 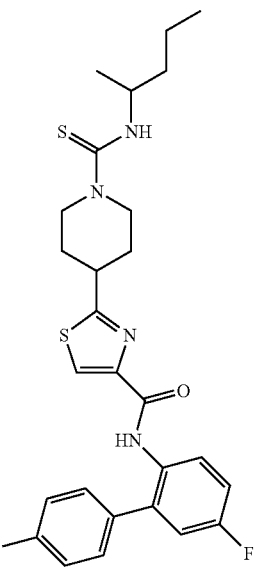
N-(4'-chloro-5-fluorobiphenyl-2-yl)-2-{[(1-methylbutyl)
amino]-carbonothioyl}piperidin-4-yl)-1,3-
thiazole-4-carboxamide
826 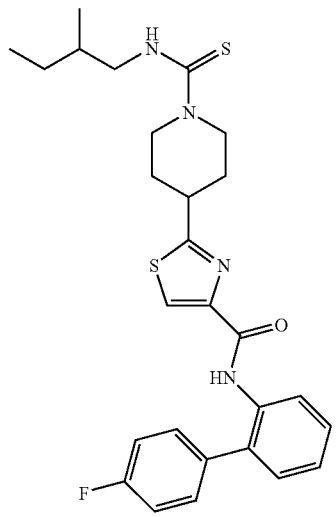
N-(4'-fluorobiphenyl-2-yl)-2-(1-{[(2-methylbutyl)
amino]carbonothioyl}-piperidin-4-yl)-1,3-
thiazole-4-carboxamide

| No. | FORMULA | NMR or mass |
|---|---|---|
827
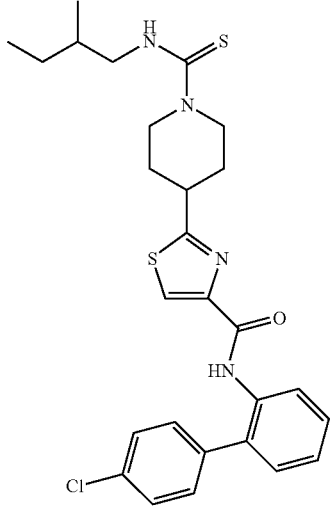
N-(4'-chlorobiphenyl-2-yl)-2-(1-{[(2-methylbutyl)
amino]-carbonothioyl}-piperidin-4-yl)1,3-
thiazole-4-carboxamide
828
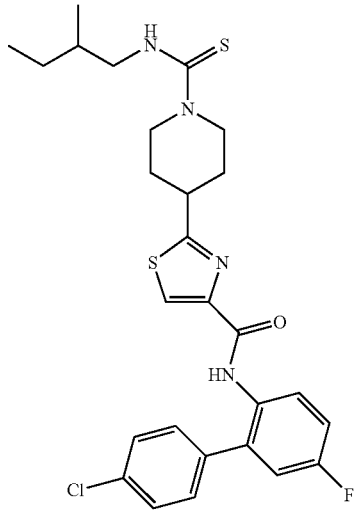
N-(4'-chloro-5-fluorobiphenhl-2-yl)-2-(1-{[(2-methylbutyl)
amino]-carbonothioyl}piperidin-4-yl)1,3-
thiazole-4-carboxamide
829
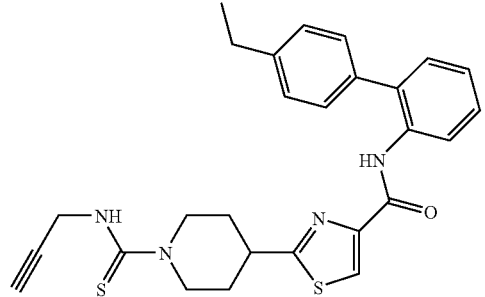

TABLE 1-continued
| No. | FORMULA | NMR or mass |
|---|---|---|
| 830 | 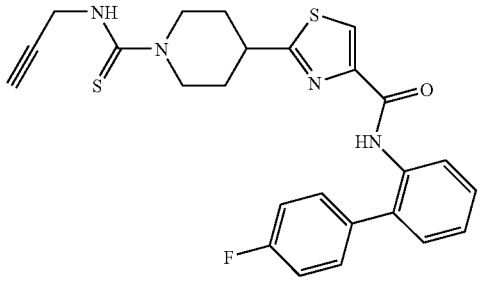 | |
| 831 | 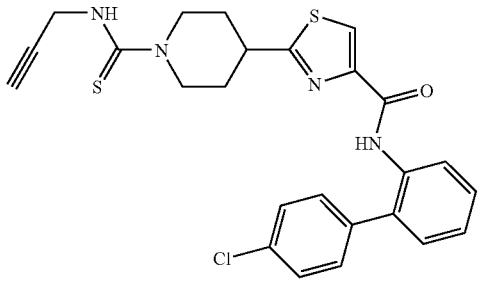 | |
| 832 | 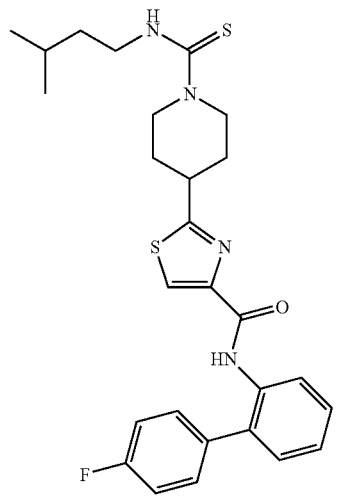 <br> N-(4'-fluorobiphenyl-2-yl)-2-(1-{[(3-methylbutyl)amino]-carbonothioyl}-piperidin-4-yl)1,3-thiazole-4-carboxamide | |

TABLE 1-continued
| No. | FORMULA | NMR or mass |
|---|---|---|
| 833 | 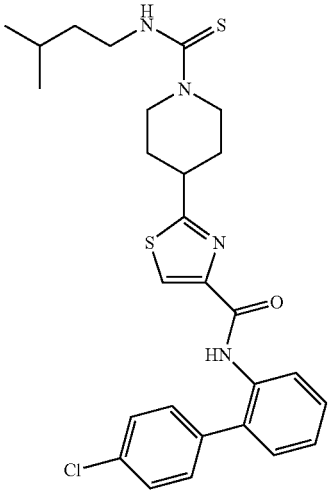 N-(4'-chlorobiphenyl-2-yl)-2-(1-{[(3-methylbutyl)amino]-carbonothioyl}-piperidin-4-yl)1,3-thiazole-4-carboxamide | |
| 834 | 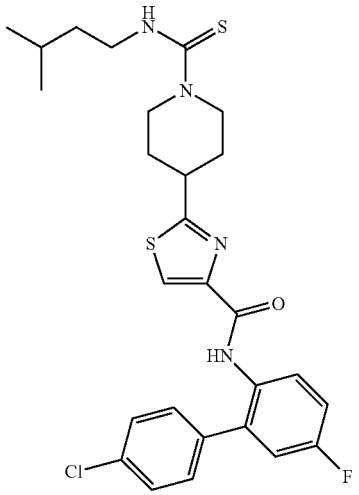 N-(4'-chloro-5-fluorobiphenyl-2-yl)-2-(1-{[(3-methylbutyl)amino]-carbonothioyl}piperidin-4-yl)1-3,-thiazole-4-carboxamide | |

| No. | FORMULA | NMR or mass |
|---|---|---|
| 835 | 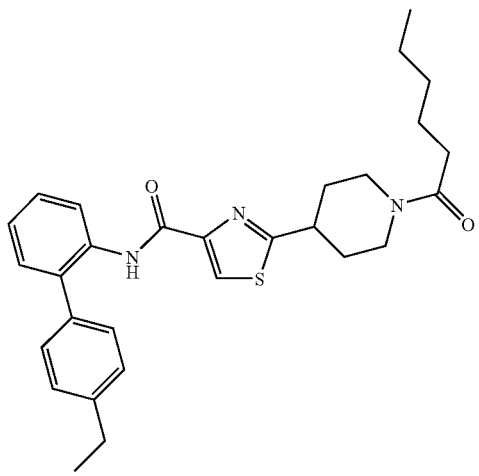<br>N-(4'-ethylbiphenyl-2-yl)-2-(1-hexanoylpiperidin-4-yl)-1,3-thiazole-4-carboxamide | |
| 836 | 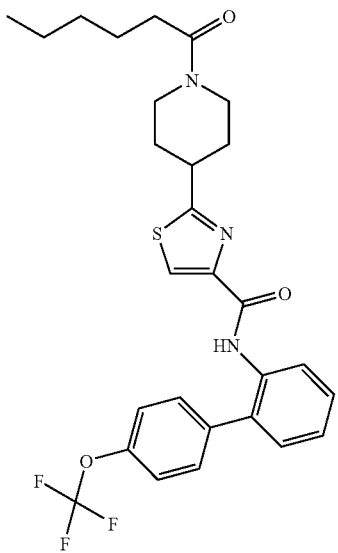<br>2-(1-hexanoylpiperidin-4-yl)-N-[4'-(trifluoromethoxy)biphenyl-2-yl]-1,3-thiazole-4-carboxamide | |

TABLE 1-continued
| No. | FORMULA | NMR or mass |
|---|---|---|
| 837 | 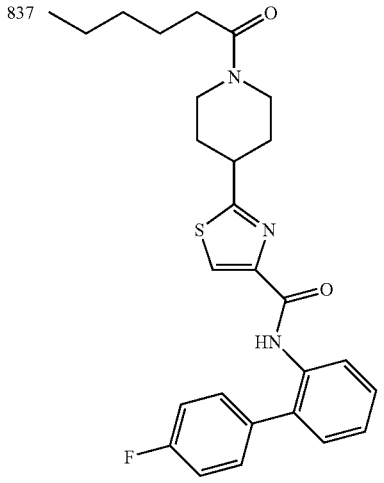 N-(4'-fluorobiphenyl-2-yl)-2-(1-hexanoylpiperidin-4-yl)-1,3-thiazole-4-carboxamide | |
| 838 | 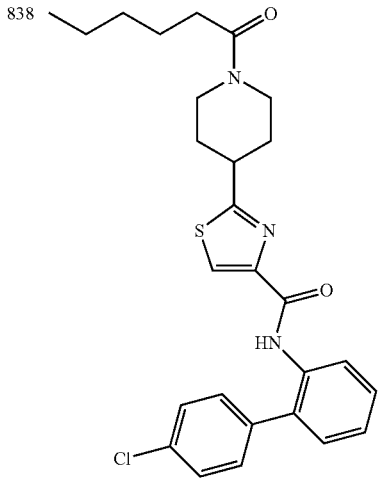 N-(4'-chlorobiphenyl-2-yl)-2-(1-hexanoylpiperidin-4-yl)-1,3-thiazole-4-carboxamide | |
| 839 | 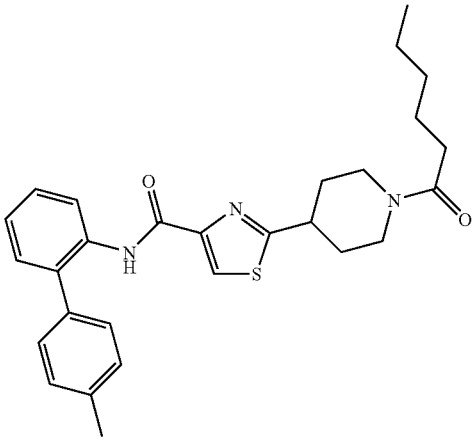 | |

TABLE 1-continued
| No. | FORMULA | NMR or mass |
|---|---|---|
| 840 | 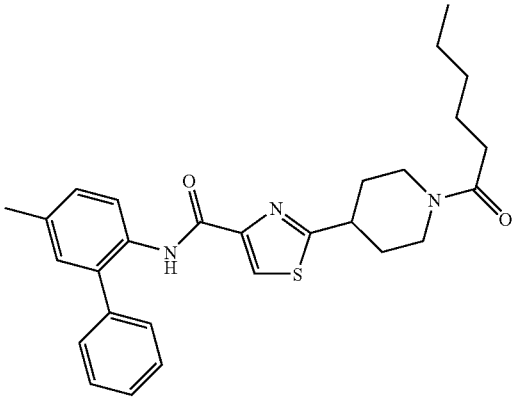 | |
| 841 | 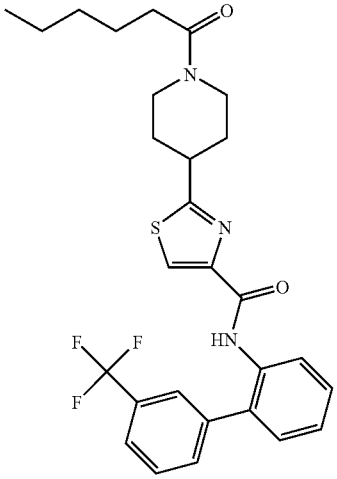 2-(1-hexanoylpiperidin-4-yl)-N-[3'-(trifluoromethyl)biphenyl-2-yl]-1,3-thiazole-4-carboxamide | |
| 842 | 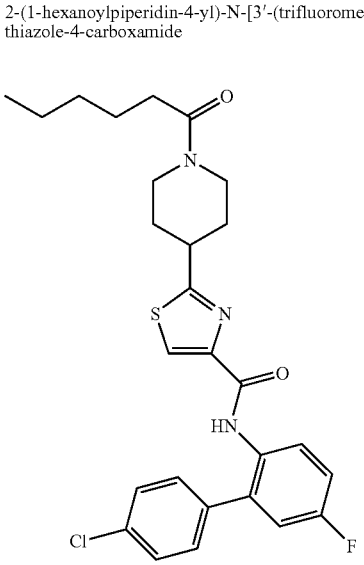 N-(4'-chloro-5-fluorobiphenyl-2-yl)-2-(1-hexanoylpiperidin-4-yl)-1,3-thiazole-4-carboxamide | |

TABLE 1-continued
| No. | FORMULA | NMR or mass |
|---|---|---|
| 843 | 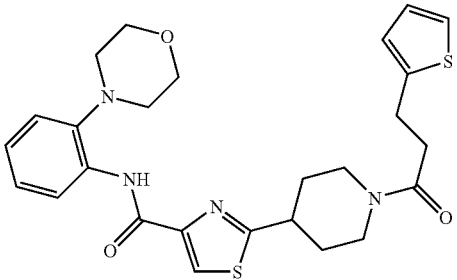 | |
| 844 | 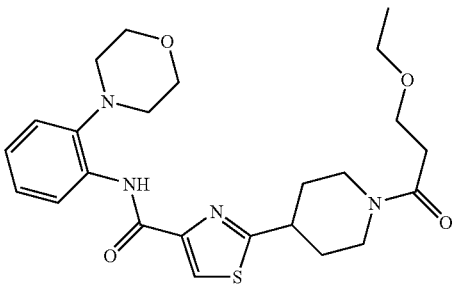 | |
| 845 | 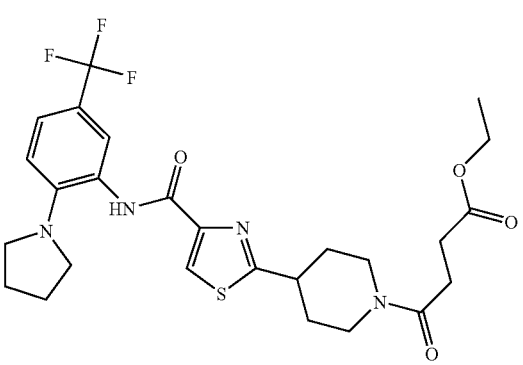 | |
| 846 | 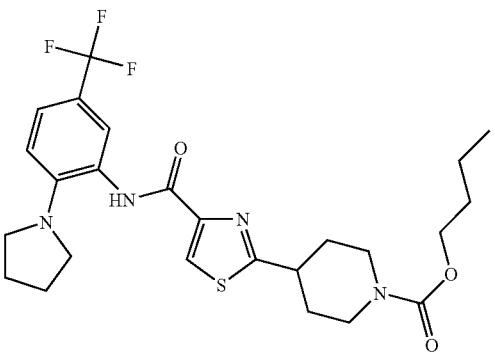 | |
| 847 | 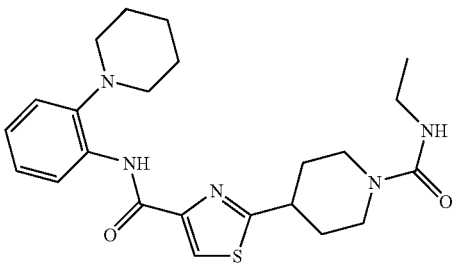 | |

TABLE 1-continued
| No. | FORMULA | NMR or mass |
|---|---|---|
| 848 | 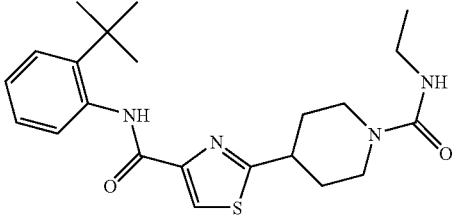 | |
| 849 | 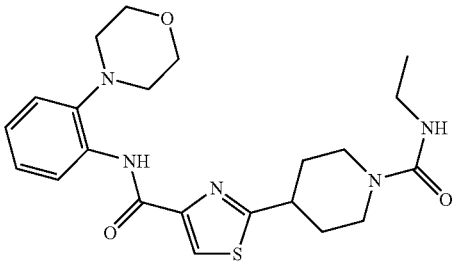 | |
| 850 | 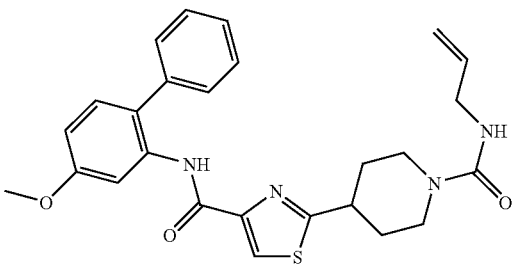 | |
| 851 | 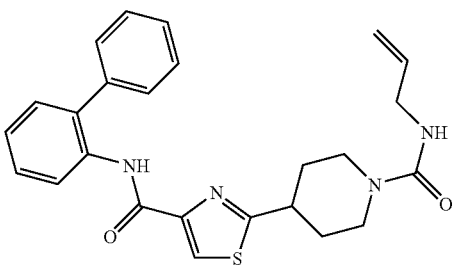 | |
| 852 | 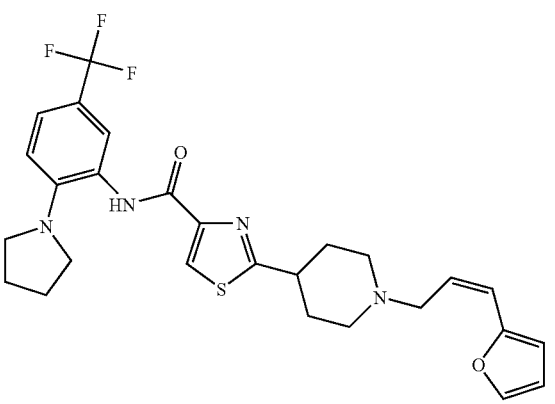 | |

TABLE 1-continued
| No. | FORMULA | NMR or mass |
|---|---|---|
| 853 | 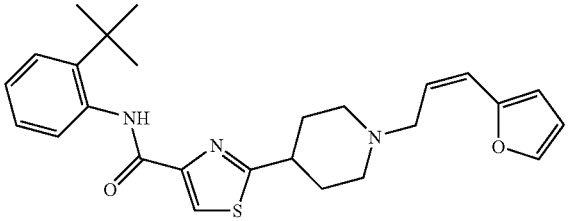 | |
| 854 | 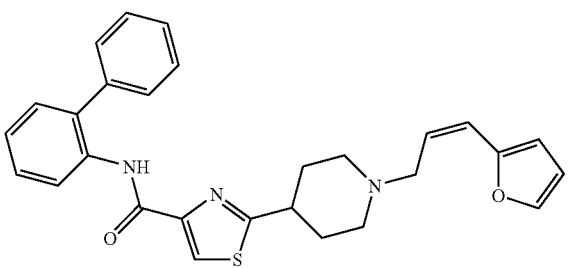 | |
| 855 | 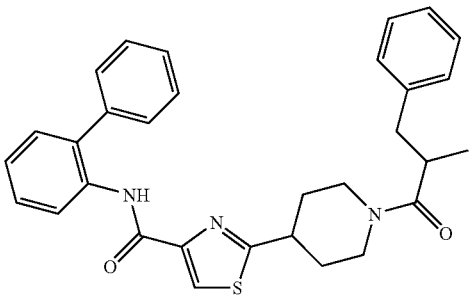 | |
| 856 | 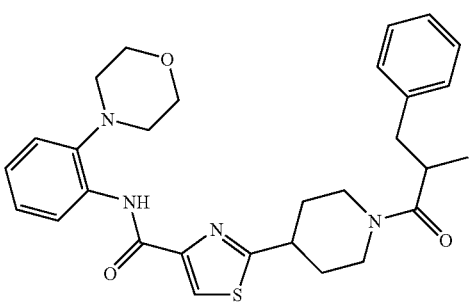 | |
| 857 | 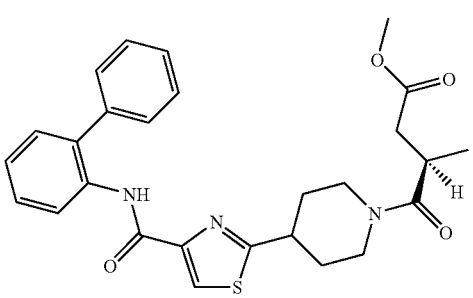 | |

TABLE 1-continued

| No. | FORMULA | NMR or mass |
|---|---|---|
| 858 | | |
| 859 | | |
| 860 | | |
| 861 | | |
| 862 | | |

TABLE 1-continued
| No. | FORMULA | NMR or mass |
|---|---|---|
| 863 | 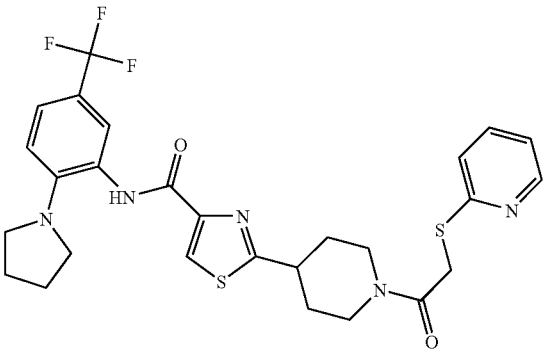 | |
| 864 | 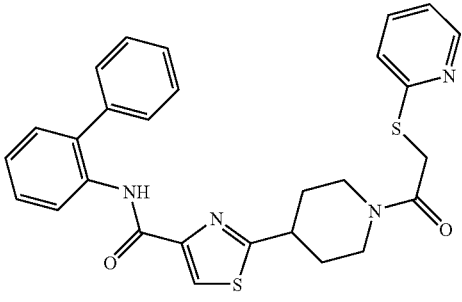 | |
| 865 | 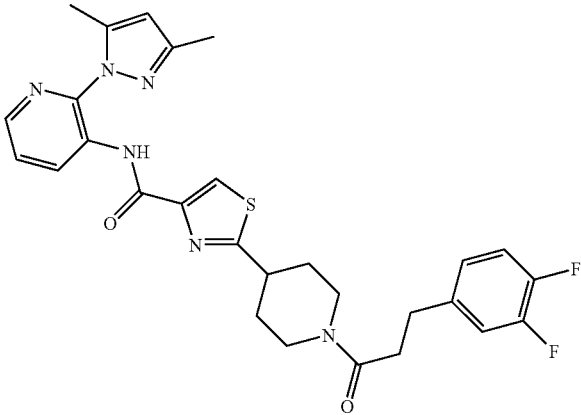 | |
2-{1-[3-(3,4-difluorophenyl)propanoyl]piperidin-4-yl}-N-[2-(3,5-dimethyl-1H-pyrazol-1-yl)pyridin-3-yl]-1,3-thiazole-4-carboxamide TABLE 1-continued
| No. | FORMULA | NMR or mass |
|---|---|---|
| 866 | 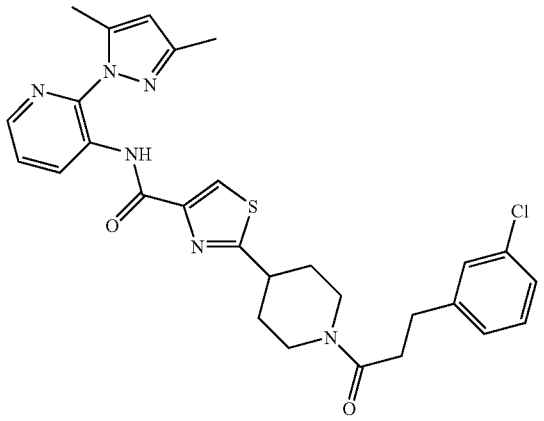 2-{1-[3-(3-chlorophenyl)propanoyl]piperidin-4-yl}-N-[2-(3,5-dimethyl-1H-pyrazol-1-yl)pyridin-3-yl]-1,3-thiazole-4-carboxamide | |
| 867 | 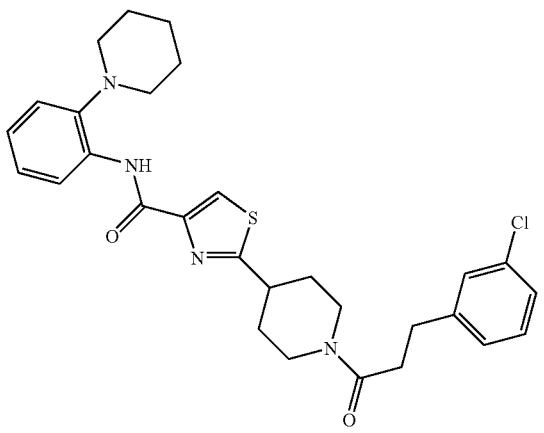 2-{1-[3-(3-chlorophenyl)propanoyl]piperidin-4-yl}-N-(2-piperidin-1-ylphenyl)-1,3-thiazole-4-carboxamide | |
| 868 | 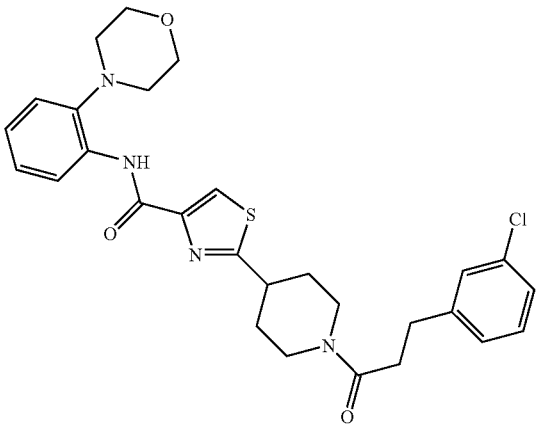 2-{1-[3-(3-chlorophenyl)propanoyl]piperidin-4-yl}-N-(2-morpholin-4-ylphenyl)-1,3-thiazole-4-carboxamide | |

| No. | FORMULA | NMR or mass |
|---|---|---|
| 869 | 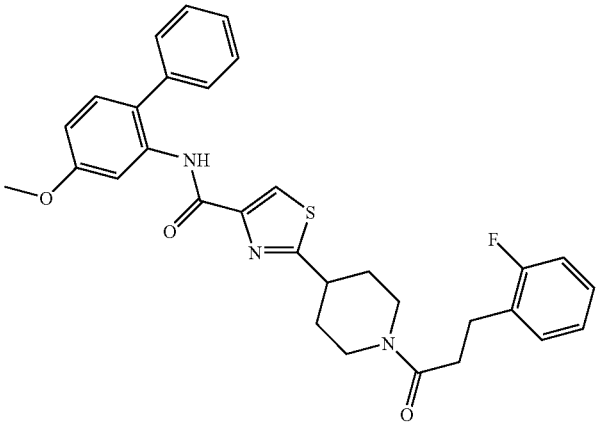<br>2-{1-[3-(2-fluorophenyl)propanoyl]piperidin-4-yl}-N-(4-methoxybiphenyl-2-yl)-1,3-thiazole-4-carboxamide | |
| 870 | 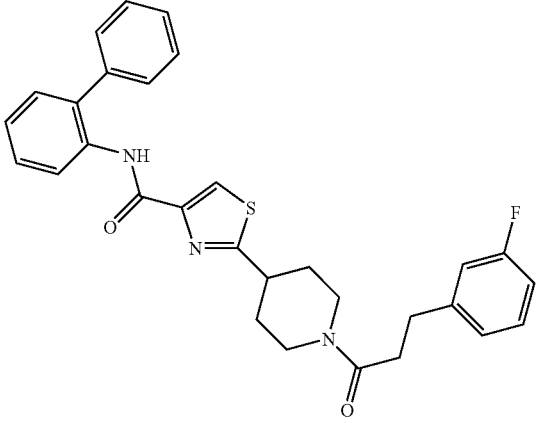<br>N-biphenyl-2-yl-2-{1-[3-(3-fluorophenyl)propanoyl]piperidin-4-yl}-1,3-thiazole-4-carboxamide | |
| 871 | 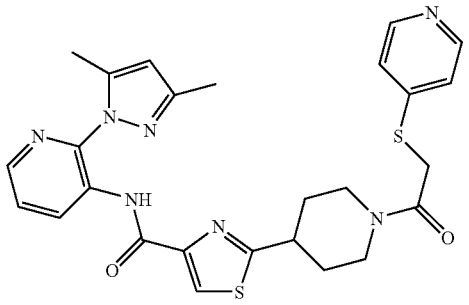 | |
| 872 | 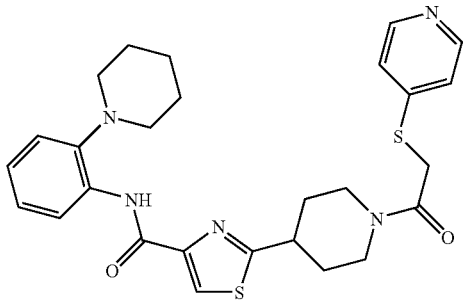 | |

TABLE 1-continued
| No. | FORMULA | NMR or mass |
|---|---|---|
873
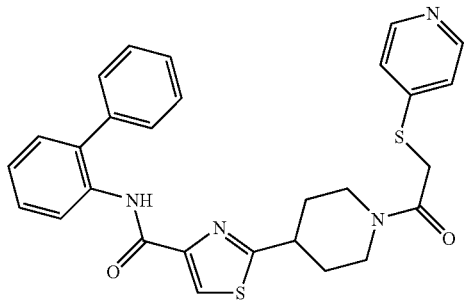
874
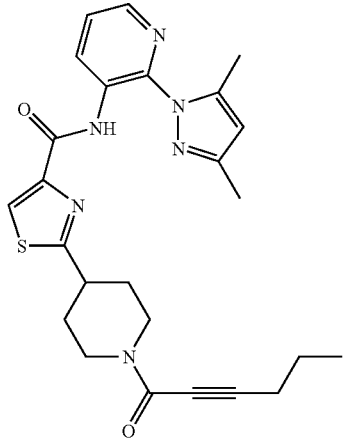
N-[2-(3,5-dimethyl-1H-pyrazol-1-yl)pyridin-3-yl]-2-(1-hex-2-ynoylpiperidin-4-yl)-1,3-thiazole-4-carboxamide
875
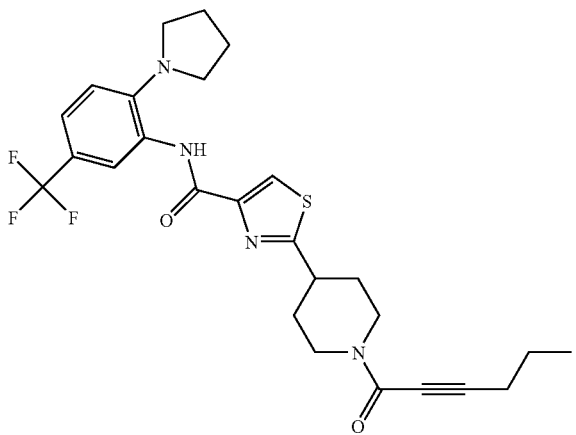
2-(1-hex-2-ynoylpiperidin-4-yl)-N-[2-pyrrolidin-1-yl-5-(trifluoromethyl)phenyl]-1,3-thiazole-4-carboxamide TABLE 1-continued
| No. | FORMULA | NMR or mass |
|---|---|---|
| 876 | 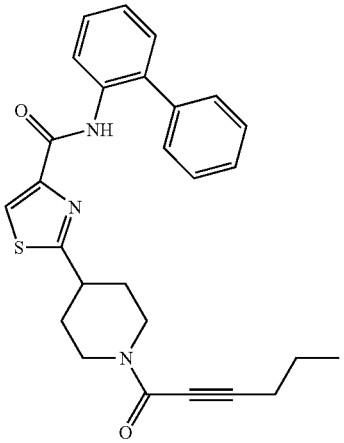 N-biphenyl-2-yl-2-(1-hex-2-ynoylpiperidin-4-yl)-1,3-thiazole-4-carboxamide | |
| 877 | 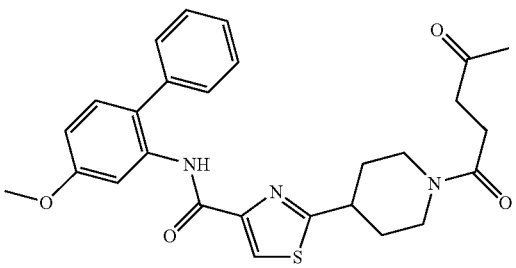 | |
| 878 | 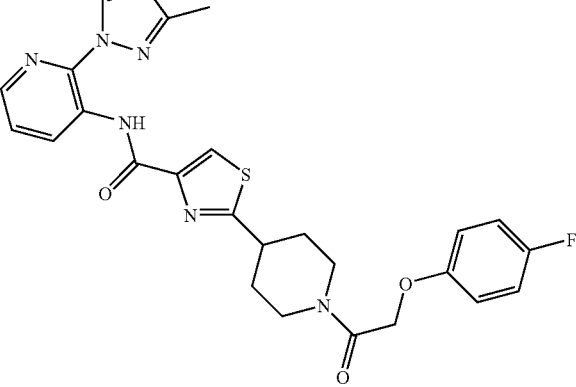 N-[2-(3,5-dimethyl-1H-pyrazol-1-yl)pyridin-3-yl]-2-{1-[(4-fluorophenoxy)-acetyl]piperidin-4-yl}-1,3-thiazole-4-carboxamide | |
| 879 | 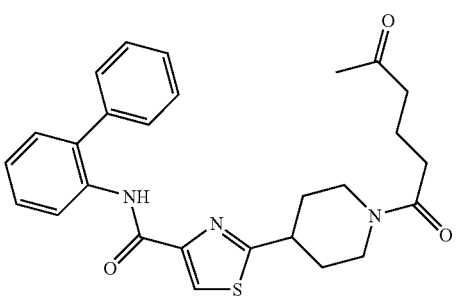 | |

TABLE 1-continued
| No. | FORMULA | NMR or mass |
|---|---|---|
| 880 | 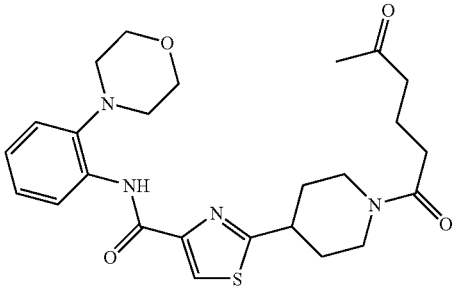 | |
| 881 | 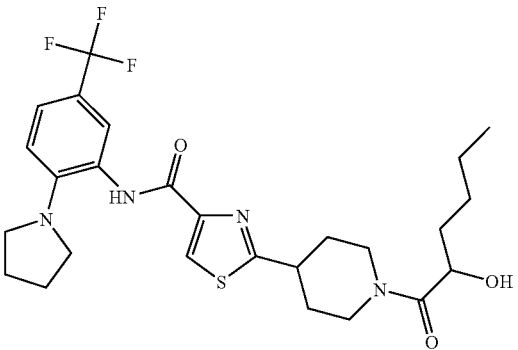 | |
| 882 | 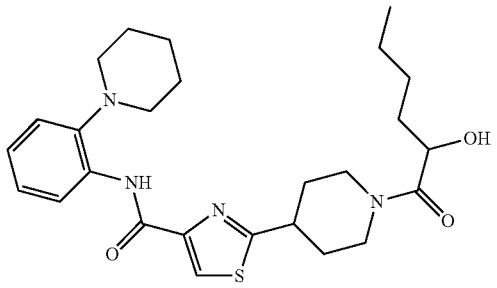 | |
| 883 | 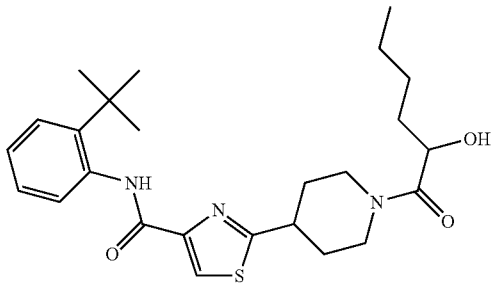 | |
| 884 | 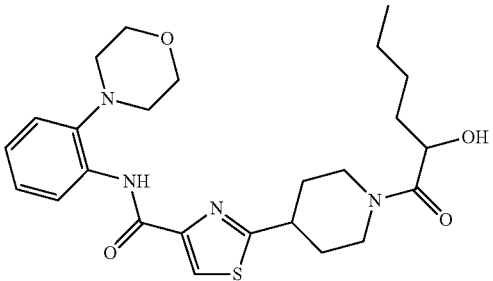 | |

TABLE 1-continued
| No. | FORMULA | NMR or mass |
|---|---|---|
| 885 | 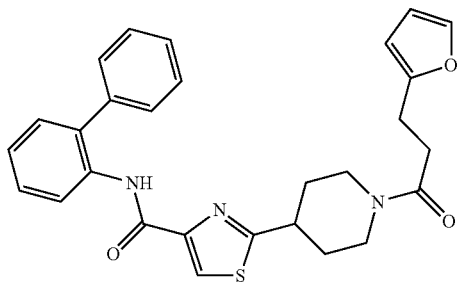 | |
| 886 | 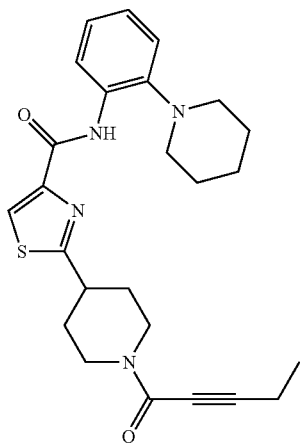<br>2-(1-pent-2-ynoylpiperidin-4-yl)-N-(2-piperidin-1-ylphenyl)-1,3-thiazole-4-carboxamide | |
| 887 | 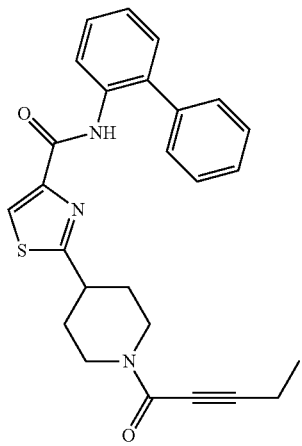<br>N-biphenyl-2-yl-2-(1-pent-2-ynoylpiperidin-4-yl)-1,3-thiazole-4-carboxamide | |

TABLE 1-continued
| No. | FORMULA | NMR or mass |
|---|---|---|
888
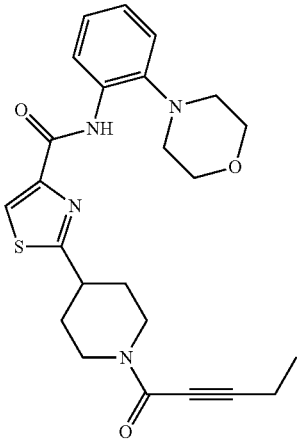
N-(2-morpholin-4-ylphenyl)-2-(1-pent-2-ynoylpiperidin-4-yl)-1,3-thiazole-4-carboxamide
889
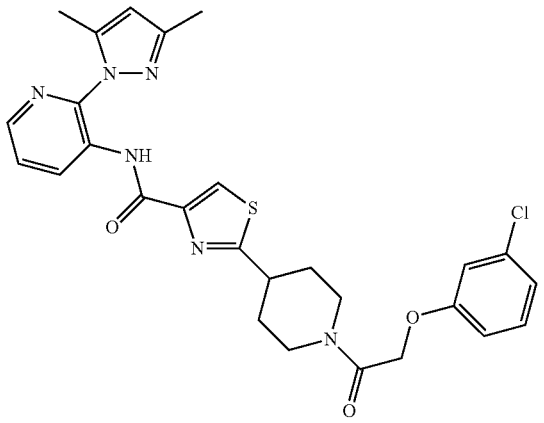
2-{1-[(3-chlorophenoxy)acetyl]piperidin-4-yl}-N-[2-(3,5-dimethyl-1H-pyrazol-1-yl)pyridin-3-yl]-1,3-thiazole-4-carboxamide
890
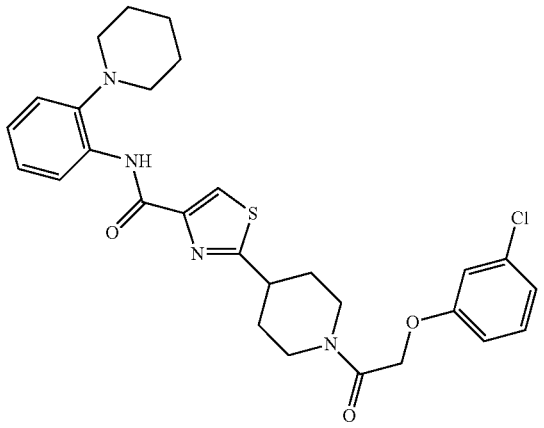
2-{1-[(3-chlorophenoxy)acetyl]piperidin-4-yl}-N-(2-piperidin-1-ylphenyl)-1,3-thiazole-4-carboxamide TABLE 1-continued

| No. | FORMULA | NMR or mass |
|---|---|---|
| 891 | | |

2-{1-[3-(2-chlorophenyl)propanoyl]piperidin-4-yl}-N-[2-(3,5-dimethyl-1H-pyrazol-1-yl)pyridin-3-yl]-1,3-thiazole-4-carboxamide

| 892 | | |

2-{1-[3-(2-chlorophenyl)propanoyl]piperidin-4-yl}-N-[2-morpholin-4-yl-phenyl]-1,3-thiazole-4-carboxamide

| 893 | | |

| 894 | | |

TABLE 1-continued
| No. | FORMULA | NMR or mass |
|---|---|---|
| 895 | 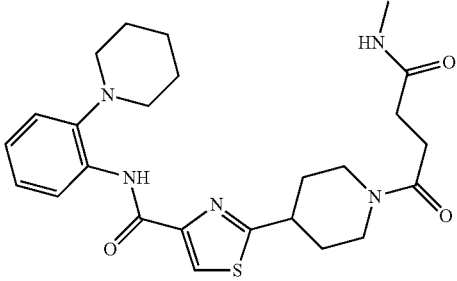 | |
| 896 | 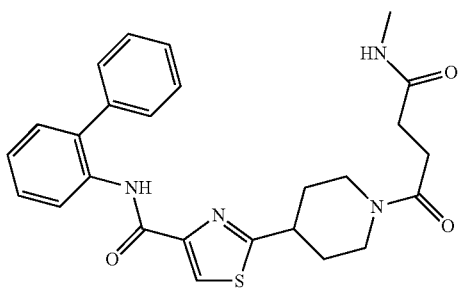 | |
| 897 | 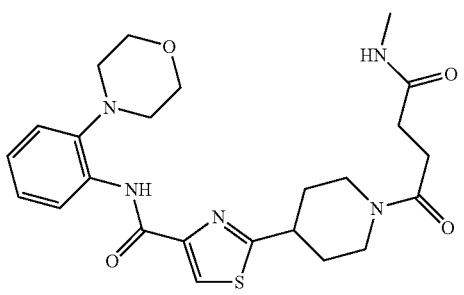 | |
| 898 | 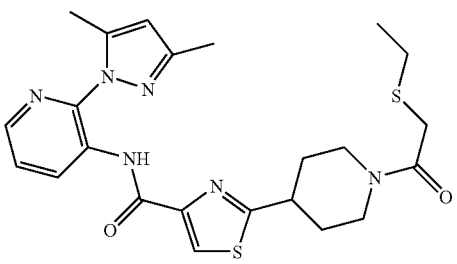 | |
| 899 | 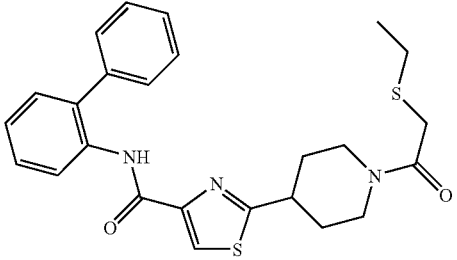 | |

TABLE 1-continued
| No. | FORMULA | NMR or mass |
|---|---|---|
| 900 | 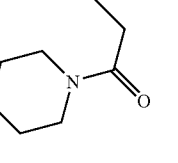 | |
| 901 |  | |
| 902 |  | |
| 903 | 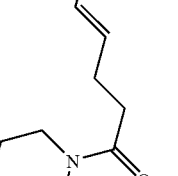 | |
| 904 | 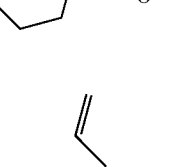 | |

TABLE 1-continued
| No. | FORMULA | NMR or mass |
|---|---|---|
| 905 | 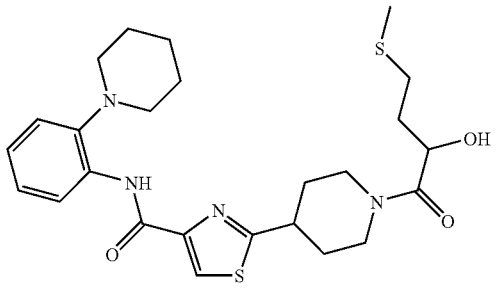 | |
| 906 | 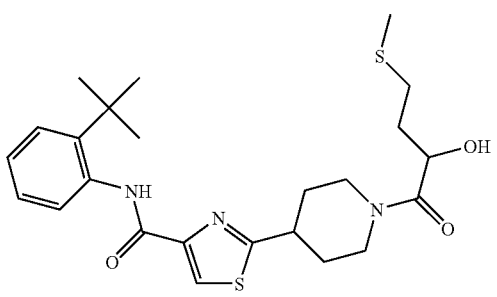 | |
| 907 | 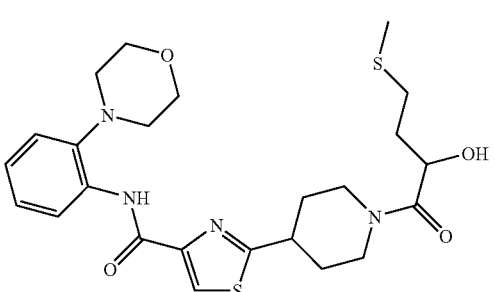 | |
| 908 | 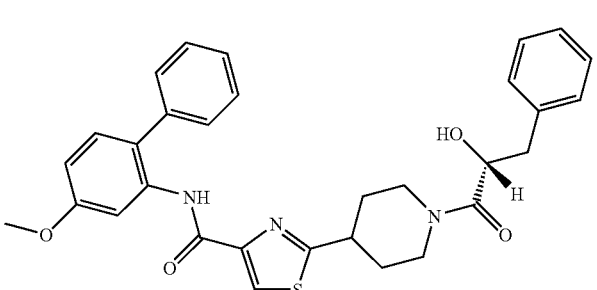 | |
| 909 | 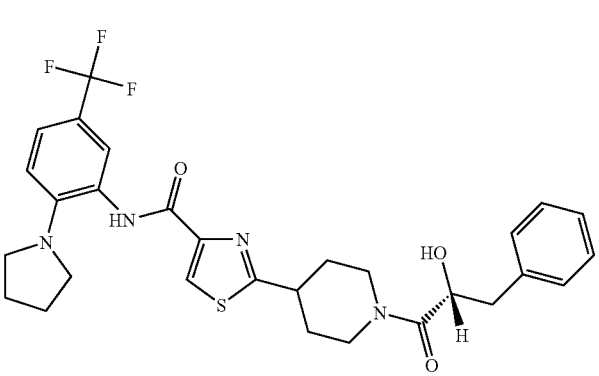 | |

TABLE 1-continued
| No. | FORMULA | NMR or mass |
|---|---|---|
| 910 | 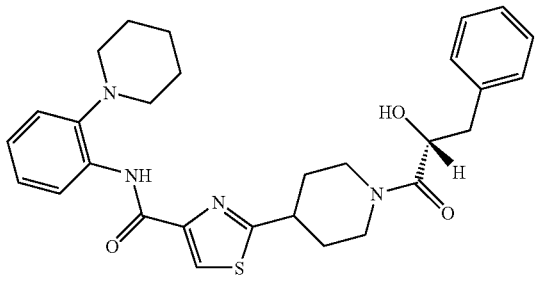 | |
| 911 | 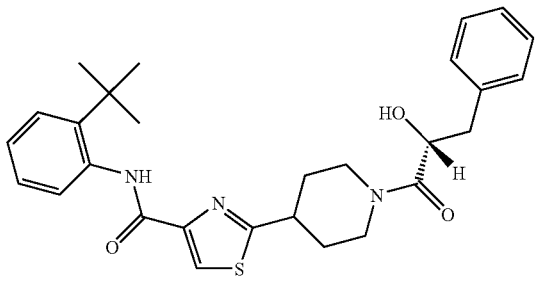 | |
| 912 | 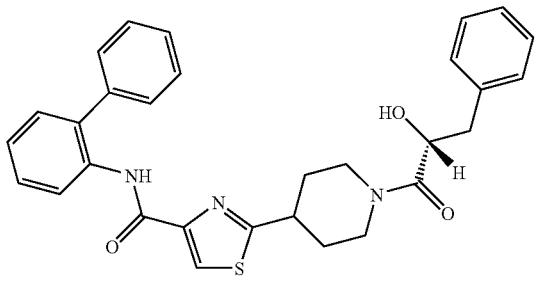 | |
| 913 | 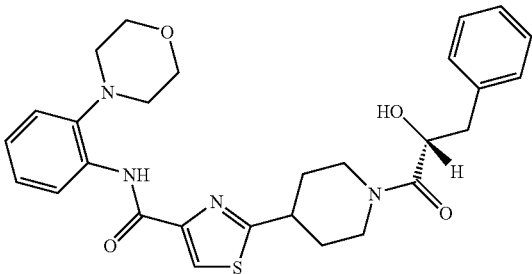 | |
| 914 | 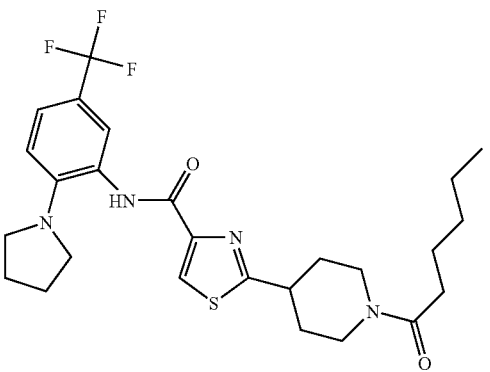 | |

TABLE 1-continued
| No. | FORMULA | NMR or mass |
|-----|---------|-------------|
| 915 | 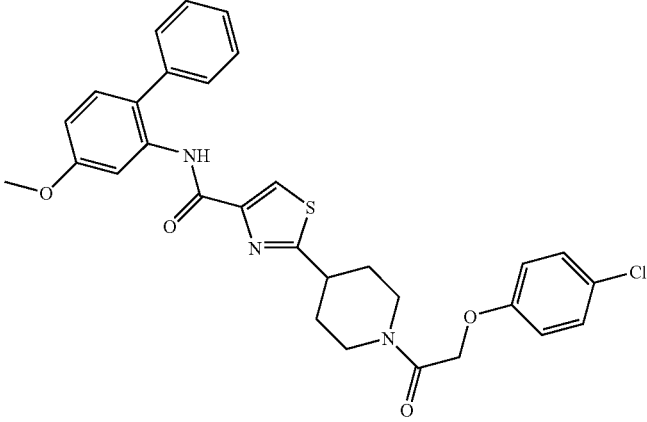 | |
| 916 | 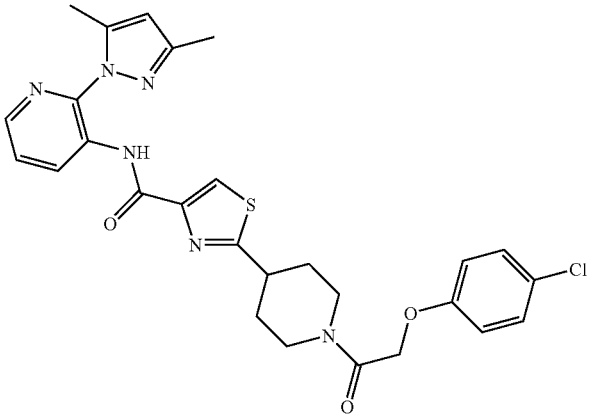 | |
| 917 | 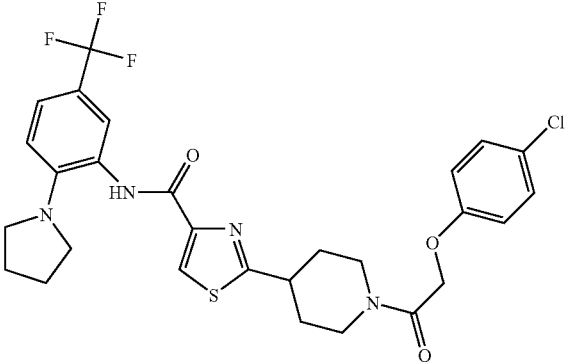 | |

TABLE 1-continued
| No. | FORMULA | NMR or mass |
|---|---|---|
918 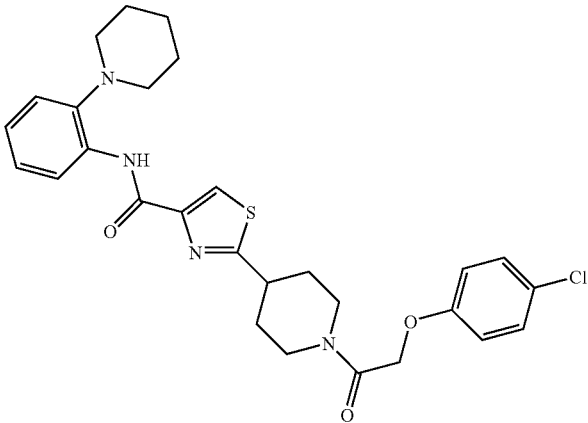
919 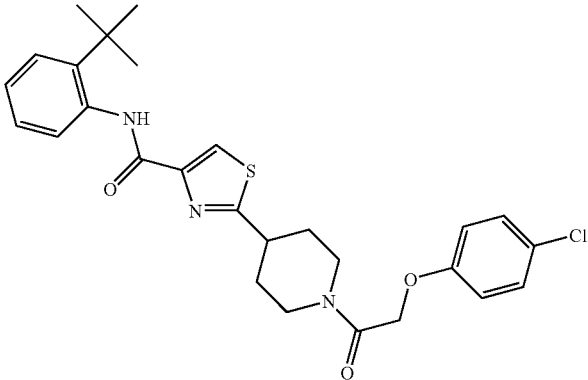
920 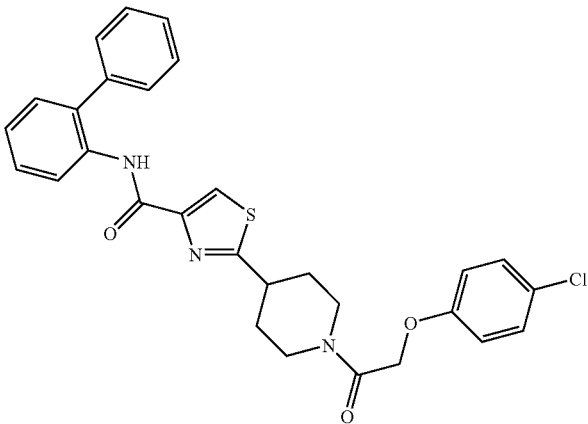

TABLE 1-continued

| No. | FORMULA | NMR or mass |
|-----|---------|-------------|
| 921 | | |
| 922 | | |
| 923 | | |
| 924 | | |

TABLE 1-continued
| No. | FORMULA | NMR or mass |
|---|---|---|
| 925 | 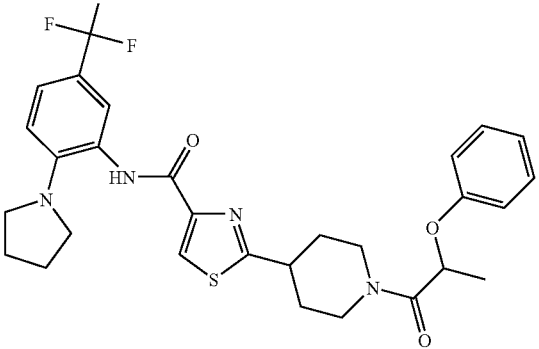 | |
| 926 | 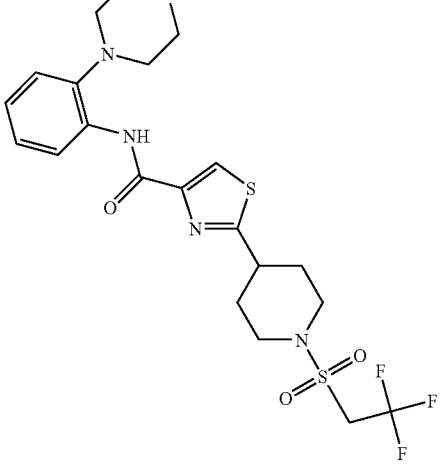  N-(2-morpholin-4-ylphenyl)-2-{1-[(2,2,2-trifluoroethyl)sulfonyl]piperidin-4-yl}-1,3-thiazole-4-carboxamide | |
| 927 | 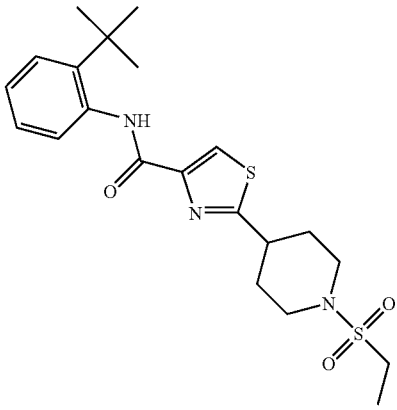  N-(2-tert-butylphenyl)-2-[1-(ethylsulfonyl)piperidin-4-yl]-1,3-thiazole-4-carboxamide | |

TABLE 1-continued
| No. | FORMULA | NMR or mass |
|---|---|---|
| 928 | 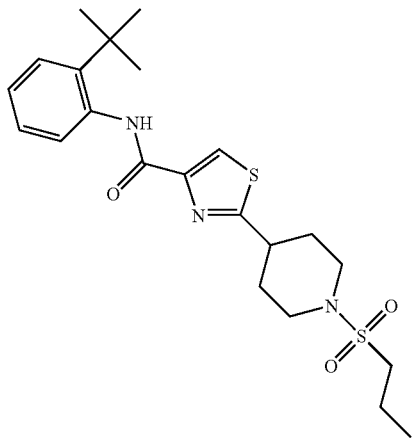 N-(2-tert-butylphenyl)-2-[1-(propylsulfonyl)piperidin-4-yl]-1,3-thiazole-4-carboxamide | |
| 929 | 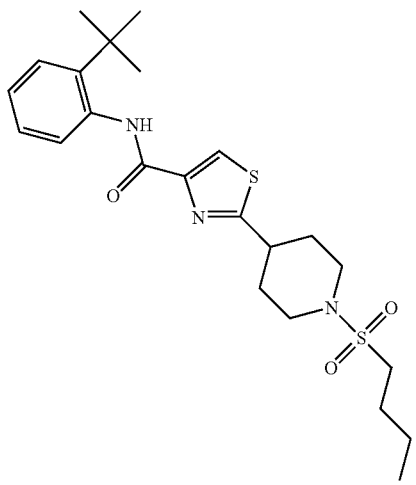 N-(2-tert-butylphenyl)-2-[1-(butylsulfonyl)piperidin-4-yl]-1,3-thiazole-4-carboxamide | |

TABLE 1-continued
| No. | FORMULA | NMR or mass |
|---|---|---|
| 930 | 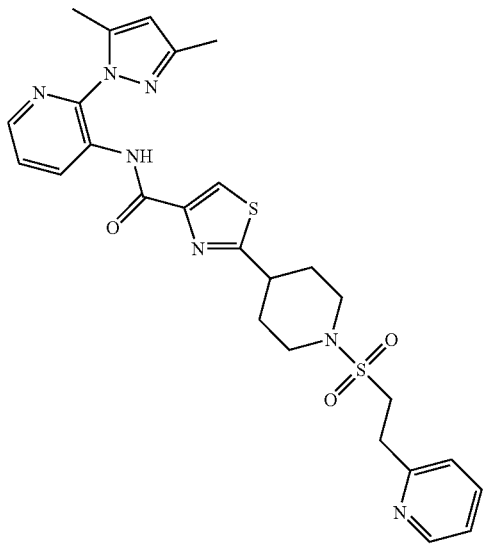 N-[2-(3,5-dimethyl-1H-pyrazol-1-yl)pyridin-3-yl]-2-{1-[(2-pyridin-2-ylethyl)-sulfonyl]piperidin-4-yl}-1,3-thiazole-4-carboxamide | |
| 931 | 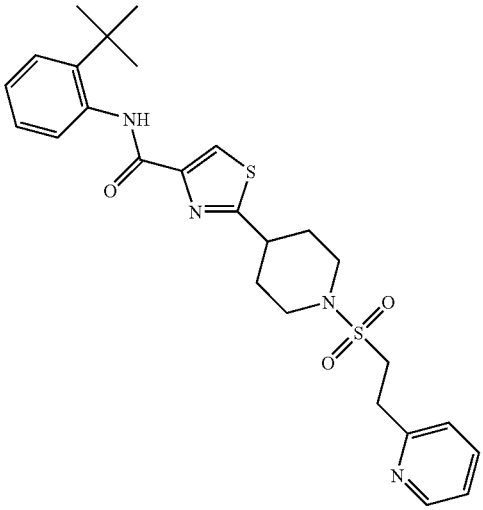 N-(2-tert-butylphenyl)-2-{1-[(2-pyridin-2-ylethyl)sulfonyl]piperidin-4-yl}-1,3-thiazole-4-carboxamide | |

TABLE 1-continued

| No. | FORMULA | NMR or mass |
|---|---|---|
| 932 | N-(2-morpholin-4-ylphenyl)-2-(1-{[(2-pyridin-2-ylethyl)sulfonyl]piperidin-4-yl}-1,3-thiazole-4-carboxamide | |
| 933 | | |
| 934 | | |
| 935 | | |

TABLE 1-continued
| No. | FORMULA | NMR or mass |
|---|---|---|
| 936 | 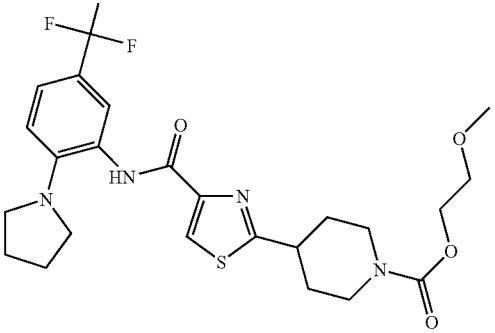 | |
| 937 | 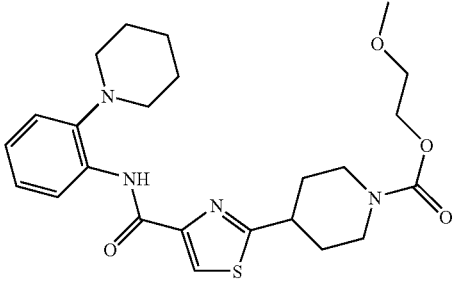 | |
| 938 | 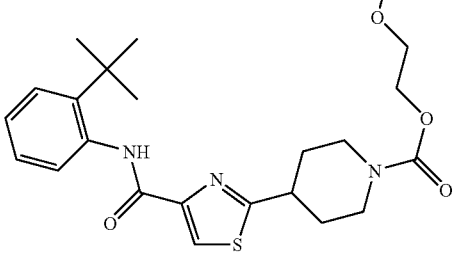 | |
| 939 | 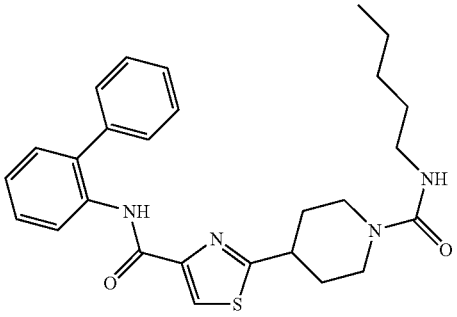 | |
| 940 | 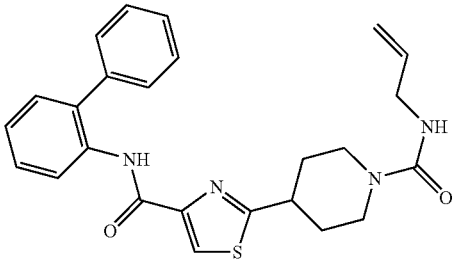 | |

TABLE 1-continued
| No. | FORMULA | NMR or mass |
|---|---|---|
| 941 | 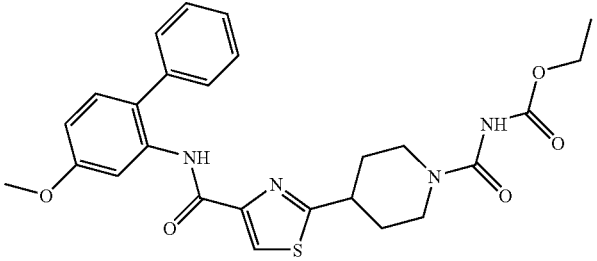 | |
| 942 | 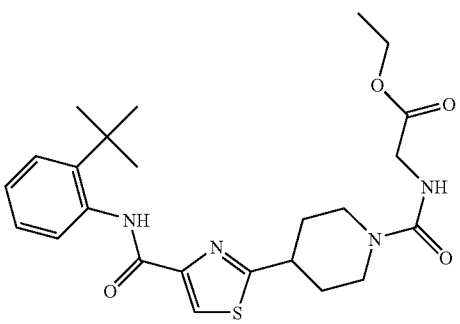 | |
| 943 | 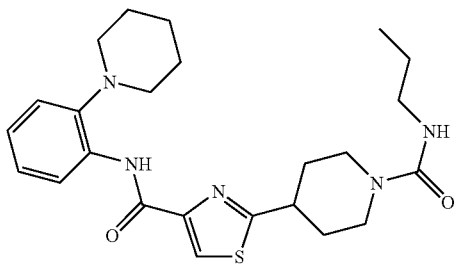 | |
| 944 | 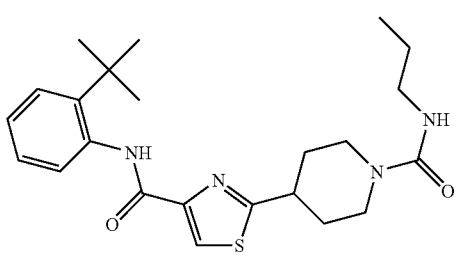 | |
| 945 | 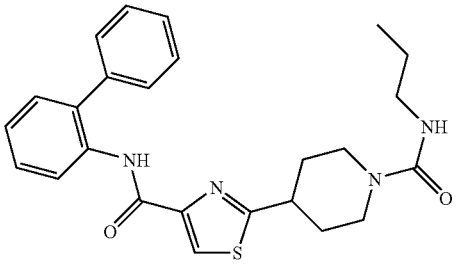 | |

TABLE 1-continued
| No. | FORMULA | NMR or mass |
|---|---|---|
| 946 | 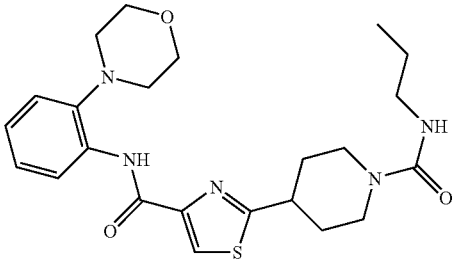 | |
| 947 | 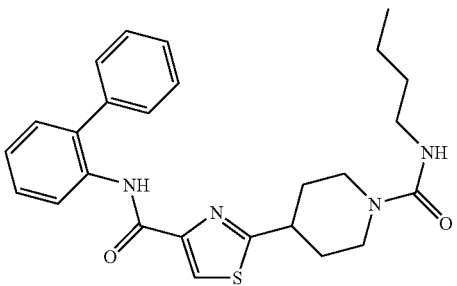 | |
| 948 | 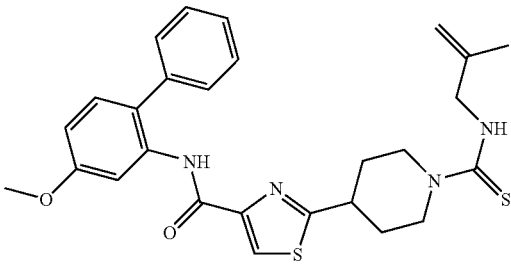 | |
| 949 | 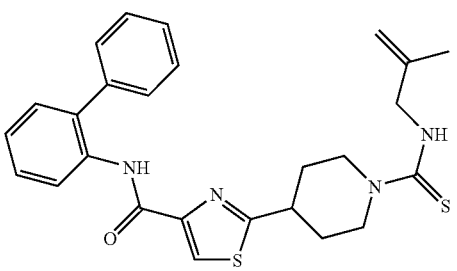 | |
| 950 | 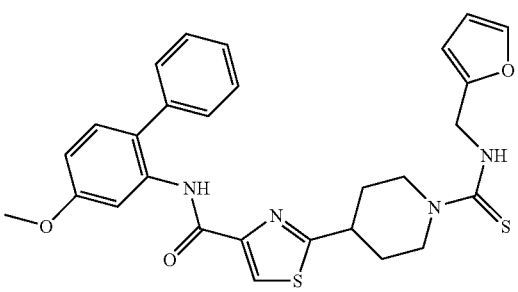 | |

TABLE 1-continued
| No. | FORMULA | NMR or mass |
|---|---|---|
| 951 | 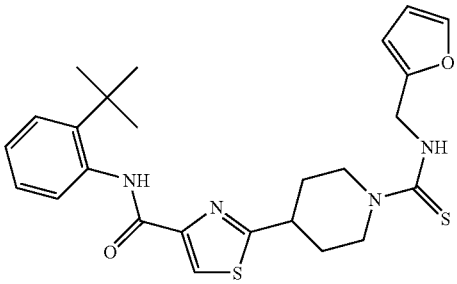 | |
| 952 | 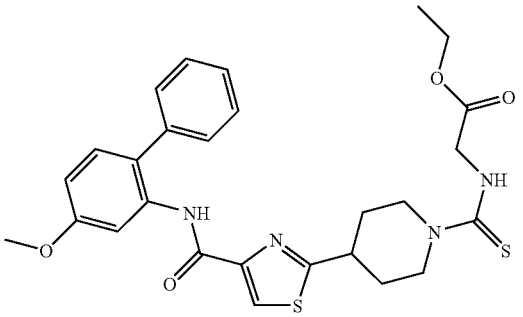 | |
| 953 | 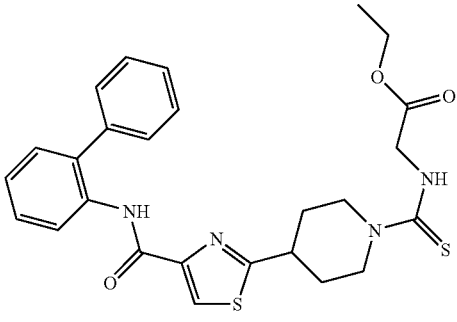 | |
| 954 | 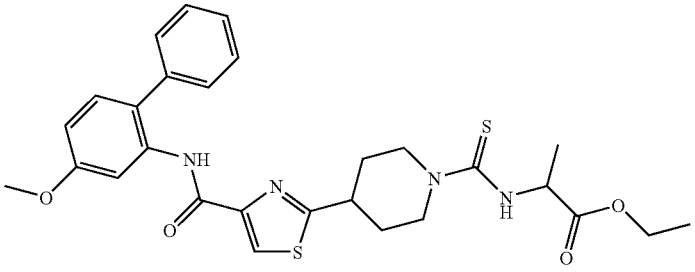 | |
| 955 | 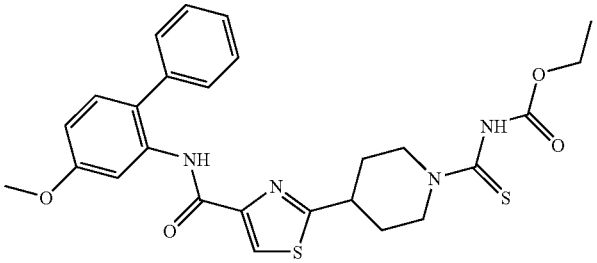 | |

TABLE 1-continued
| No. | FORMULA | NMR or mass |
|---|---|---|
| 956 | 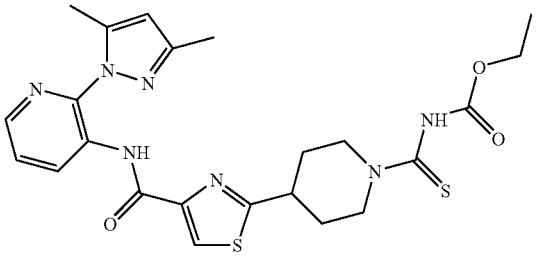 | |
| 957 | 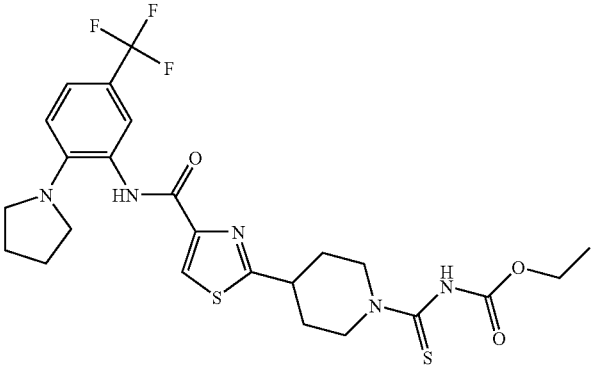 | |
| 958 | 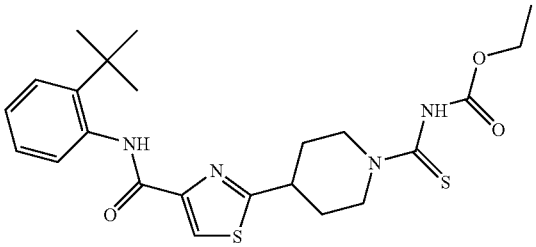 | |
| 959 | 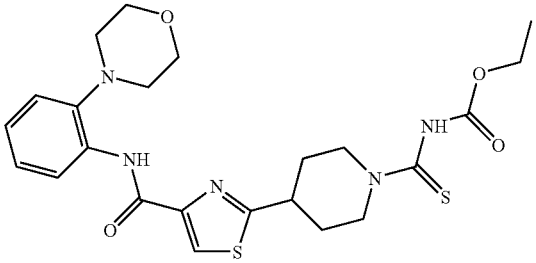 | |
| 960 | 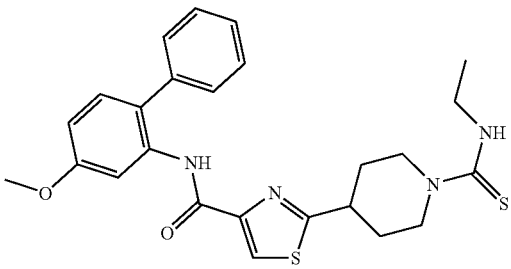 | |

TABLE 1-continued
| No. | FORMULA | NMR or mass |
|---|---|---|
| 961 | 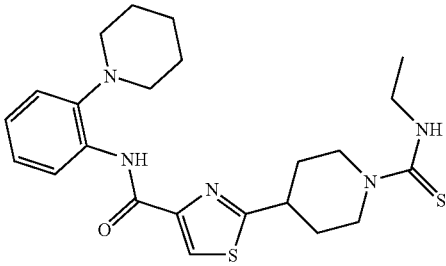 | |
| 962 | 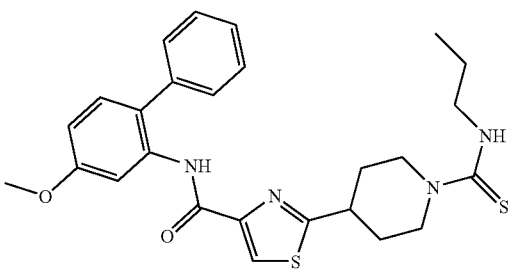 | |
| 963 | 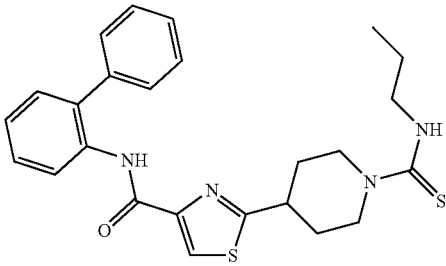 | |
| 964 | 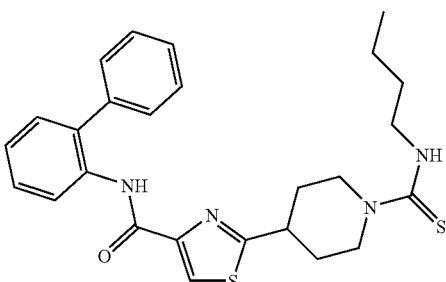 | |
| 965 | 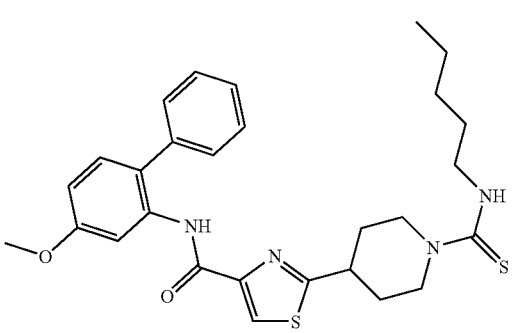 | |

TABLE 1-continued
| No. | FORMULA | NMR or mass |
|---|---|---|
| 966 | 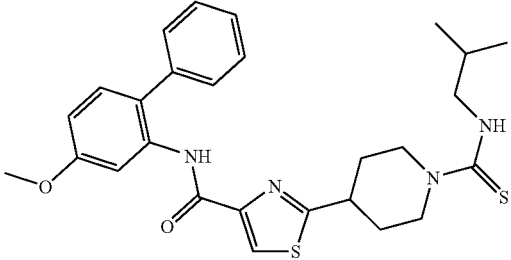 | |
| 967 | 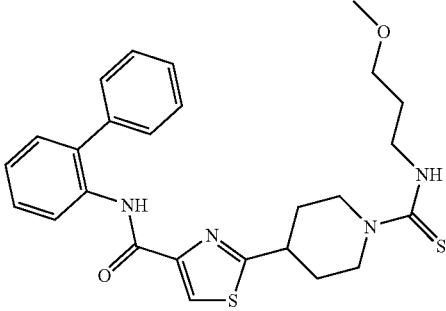 | |
| 968 | 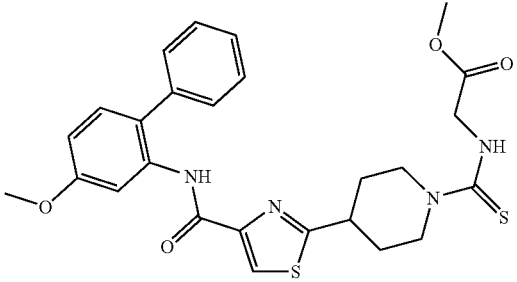 | |
| 969 | 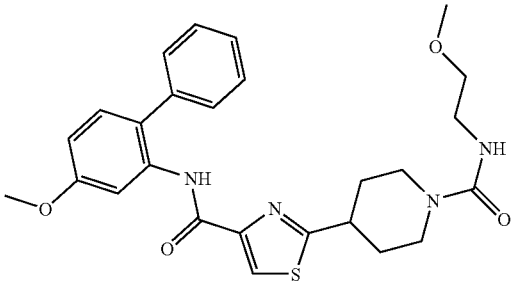 | |

TABLE 1-continued
| No. | FORMULA | NMR or mass |
|---|---|---|
970
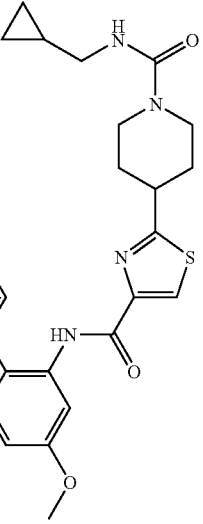
2-(1-{[(cyclopropylmethyl)amino]carbonothioyl}piperidin-4-yl)-N-(4-methoxybiphenyl-2-yl)-1,3-thiazole-4-carboxamide
971
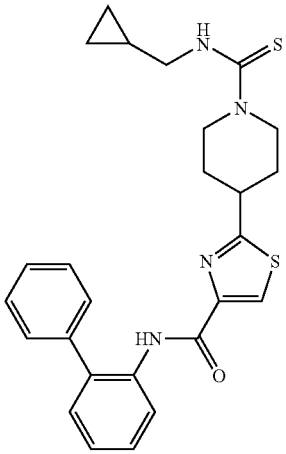
N-biphenyl-2-yl-2-(1-{[(cyclopropylmethyl)amino]carbonothioyl}piperidin-4-yl)-1,3-thiazole-4-carboxamide
972
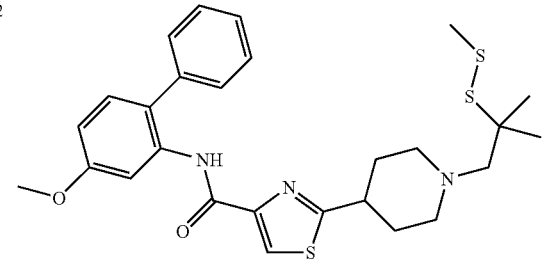

TABLE 1-continued
| No. | FORMULA | NMR or mass |
|---|---|---|
| 973 | 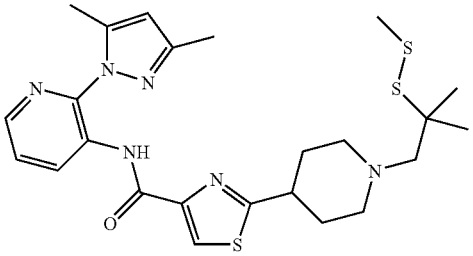 | |
| 974 | 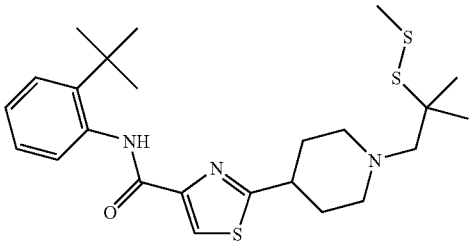 | |
| 977 | 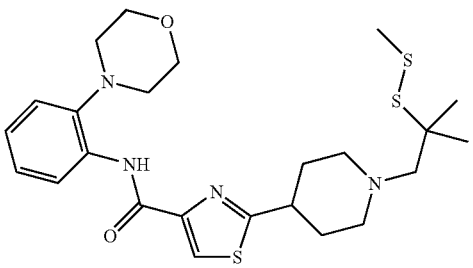 | |
| 978 | 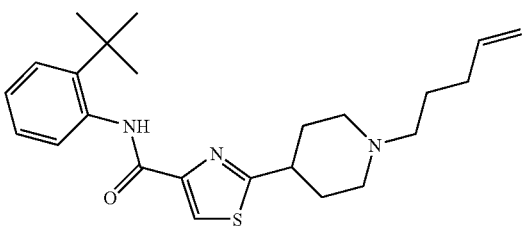 | |
| 979 | 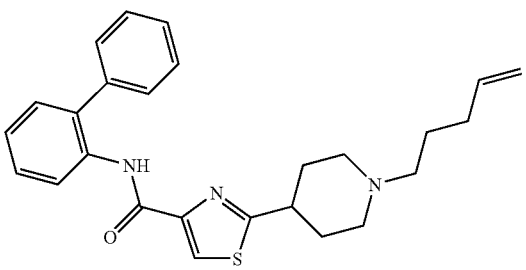 | |
| 980 | 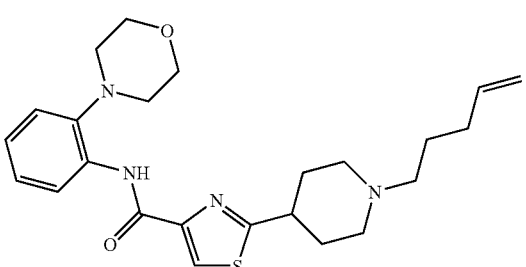 | |

TABLE 1-continued
| No. | FORMULA | NMR or mass |
|---|---|---|
981
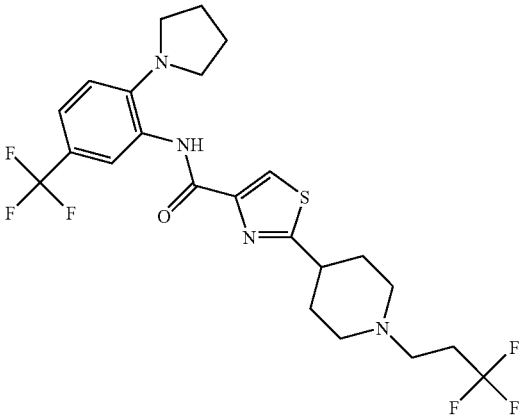
N-[2-pyrrolidin-1-yl-5-(trifluoromethyl)phebyl]-2-[1-(3,3,3-trifluoropropyl)-piperidin-4-yl]-1,3-thiazole-4-carboxamide
982
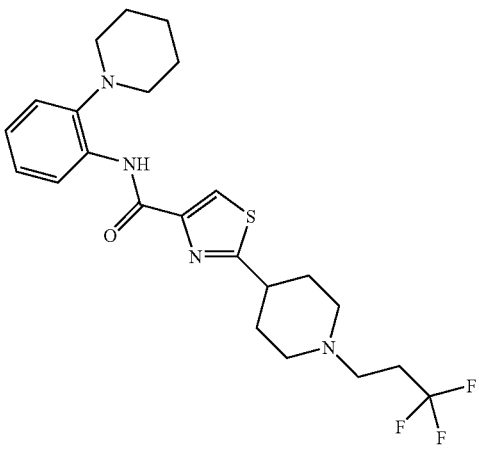
N-(2-piperidin-1-ylphenyl)-2-[1-(3,3,3-trifluoropropyl)piperidin-4-yl]-1,3-thiazole-4-carboxamide
983
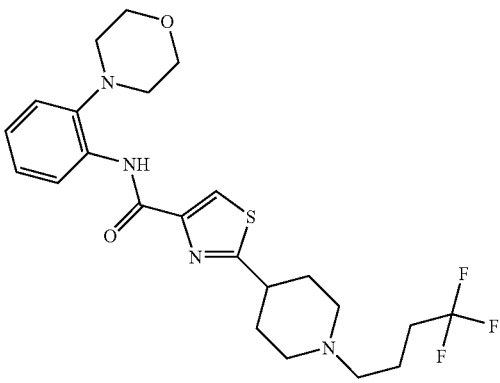
N-(2-morpholin-4-ylphenyl)-2-[1-(4,4,4-trifluorobutyl)piperidin-4-yl]-1,3-thiazole-4-carboxamide

TABLE 1-continued
| No. | FORMULA | NMR or mass |
|---|---|---|
| 984 | 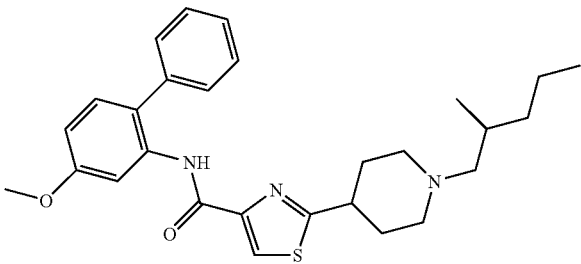 | |
| 985 | 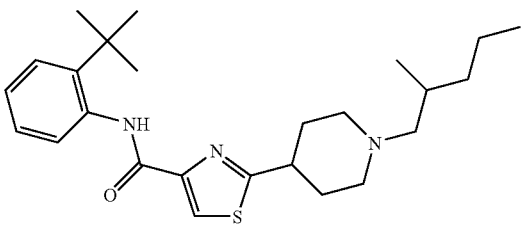 | |
| 986 | 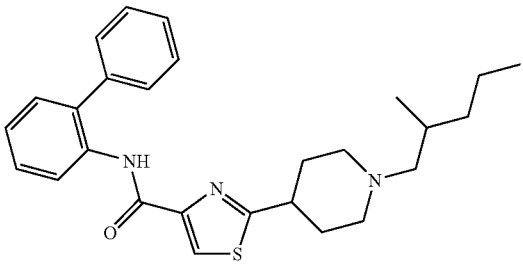 | |
| 987 | 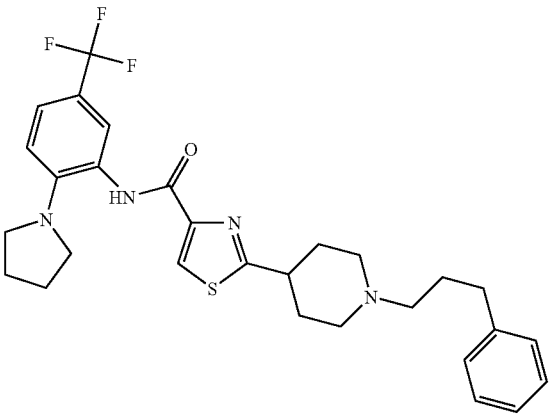 | |
2-[1-(3-phenylpropyl)plperidin-4-yl]-N-[2-pyrrolidin-1-yl-5-(trifluoromethyl)-phenyl]-1,3-thiazole-4-carboxamide
| 988 | 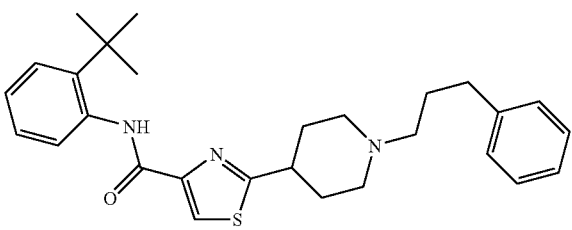 | |

TABLE 1-continued
| No. | FORMULA | NMR or mass |
|---|---|---|
| 989 | 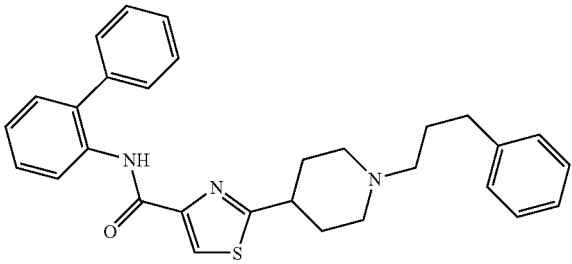 | |
| 990 | 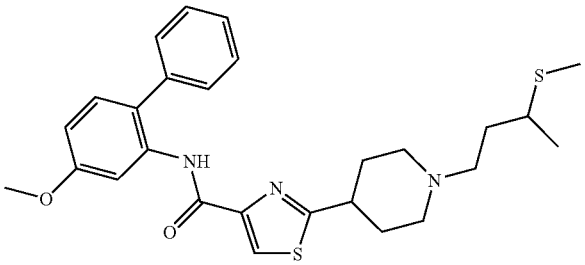 | |
| 991 | 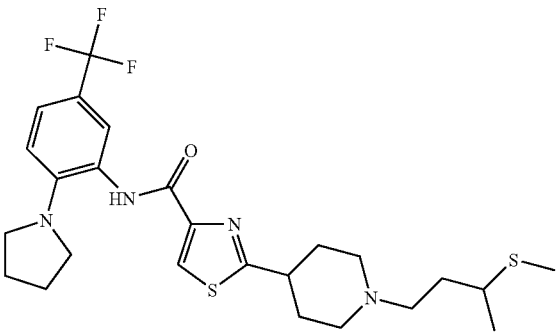 | |
| 992 | 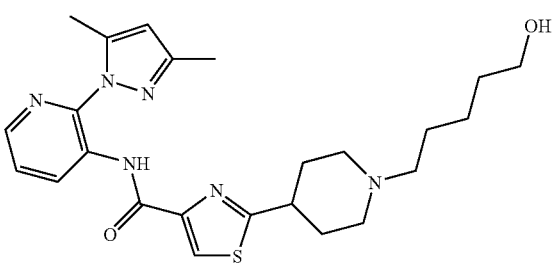 | |
| 993 | 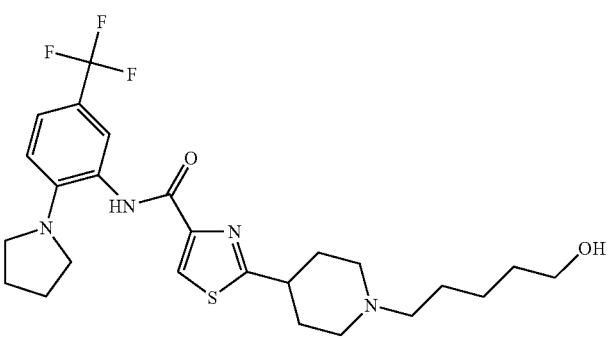 | |

TABLE 1-continued

| No. | FORMULA | NMR or mass |
|-----|---------|-------------|

994

995

996

997

998

| No. | FORMULA | NMR or mass |
|---|---|---|
| 999 | 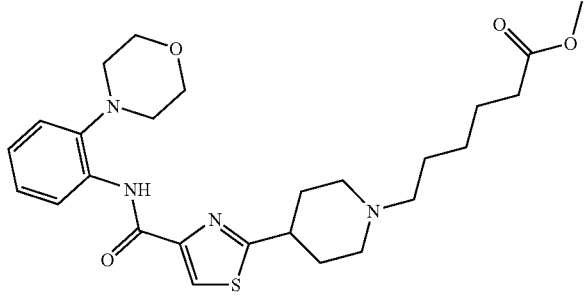 | |
| 1000 | 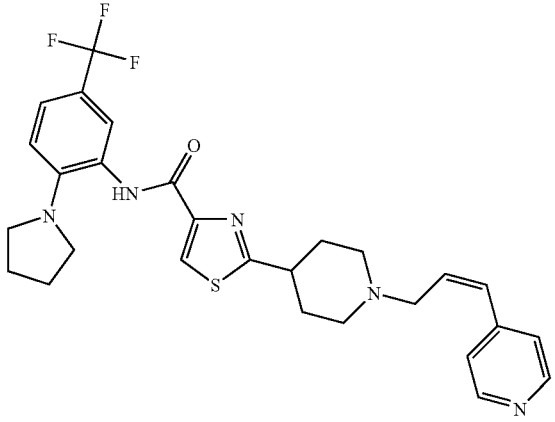<br>2-{1[(2Z)-3-pyridin-4-ylprop-2-en-1-yl]piperidin-4-yl}-N-[2-pyrrolidin-1-yl-5-(trifluoromethyl)phenyl]-1,3-thiazole-4-carboxamide | |
| 1001 | 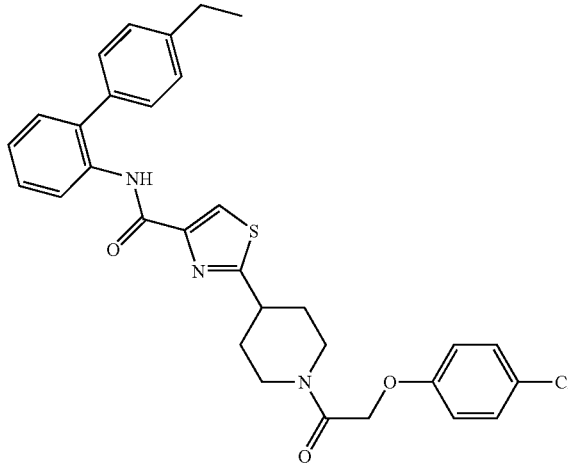<br>2-{1-[(4-chlorophenoxy)acetyl]piperidin-4-yl}-N-(4'-ethylbiphenyl-2-yl)-1,3-thiazole-4-carboxamide | |

TABLE 1-continued
| No. | FORMULA | NMR or mass |
|-----|---------|-------------|
| 1002 | 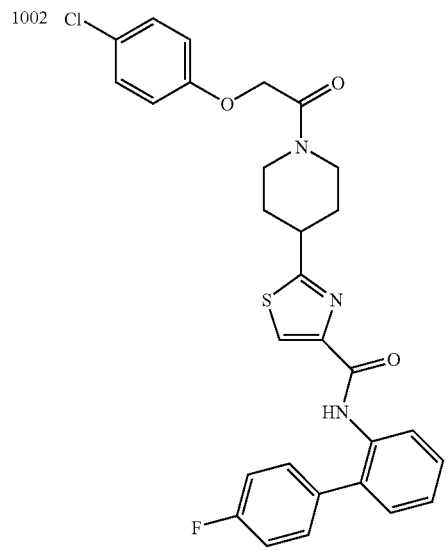<br>2-{1-[(4-chlorophenoxy)acetyl]piperidin-4-yl)-N-(4'-fluorobiphenyl-2-yl)-1,3-thiazole-4-carboxamide | |
| 1003 | 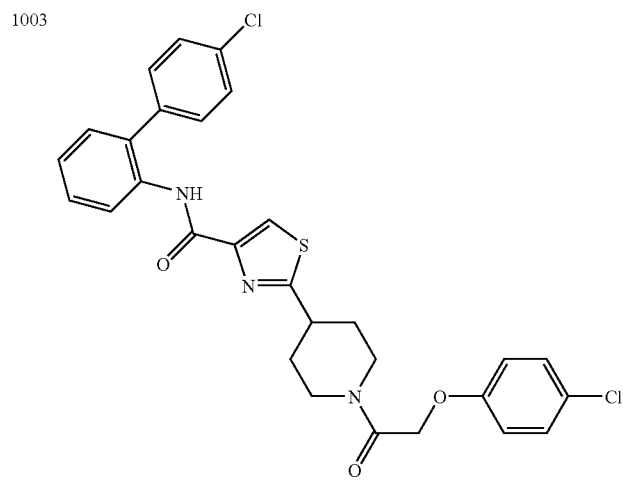<br>N-(4'-chlorobiphenyl-2-yl)-2-{1-[(4-chlorophenoxy)acetyl]piperidin-4-yl}-1,3-thiazole-4-carboxamide | |

TABLE 1-continued
| No. | FORMULA | NMR or mass |
|---|---|---|
1004
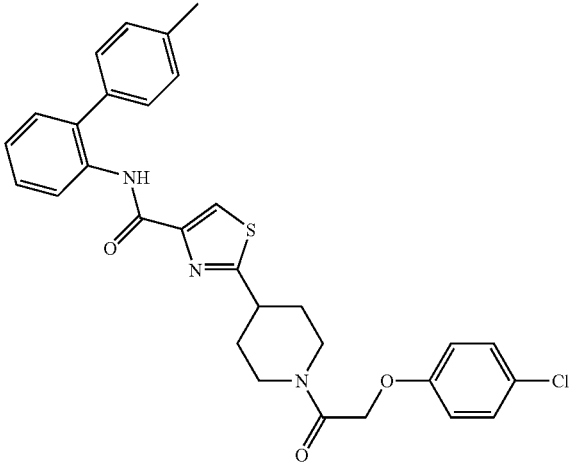
2-{1-[(4-chlorophenoxy)acetyl]piperidin-4-yl}-N-
(4'-methylbiphenyl-2-yl)-1,3-thiazole-4-carboxamide
1005
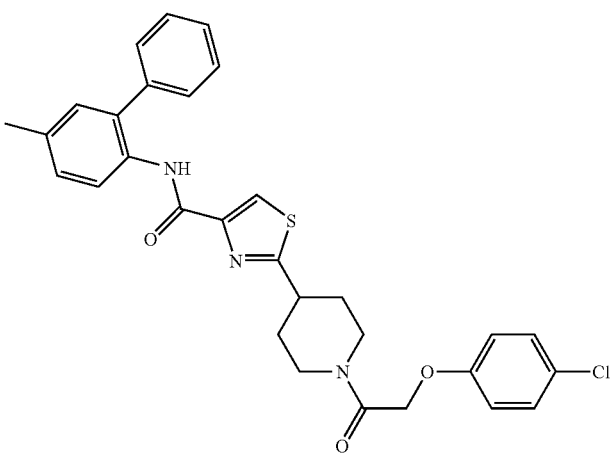
2-{1-[(4-chlorophenoxy)acetyl]piperidin-4-yl}-N-
(5-methylbiphenyl-2-yl)-1,3-thiazole-4-carboxamide TABLE 1-continued
| No. | FORMULA | NMR or mass |
|---|---|---|
1006 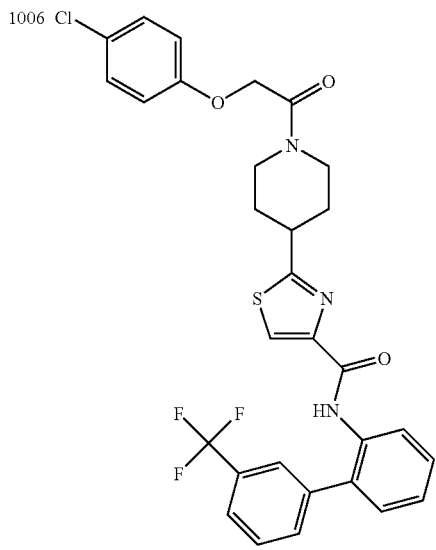
2-{1-{(4-chlorophenoxy)acetyl]piperidin-4-yl}-N-
[3'-(trifluoromethyl)biphenyl-2-yl]-1,3-
thiazole-4-carboxamide
1007 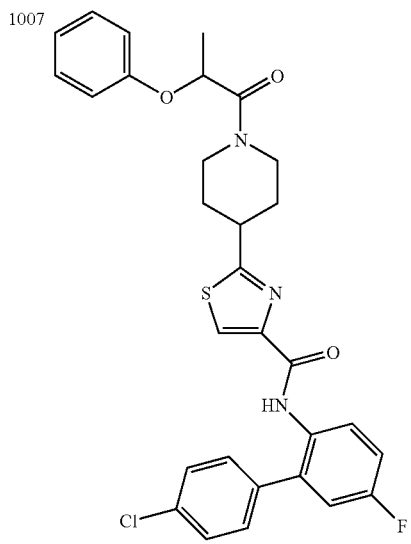
N-(4'-chloro-5-fluorobiphenyl-2-yl)-2-[1-(2-
phenoxypropanoyl)piperidin-4-yl]-
1,3-thiazole-4-carboxamide TABLE 1-continued
| No. | FORMULA | NMR or mass |
|---|---|---|
| 1008 | 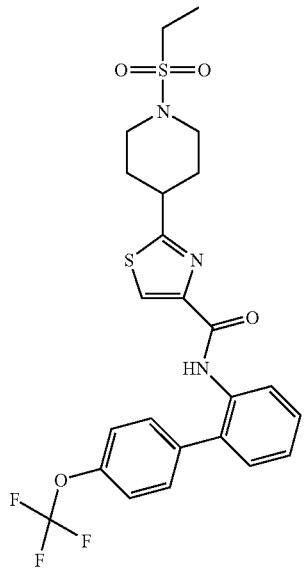 2-[1-(ethylsulfonyl)piperidin-4-yl]-N-[4'-(trifluoromethoxy)biphenyl-2-yl]-1,3-thiazole-4-carboxamide | |
| 1009 | 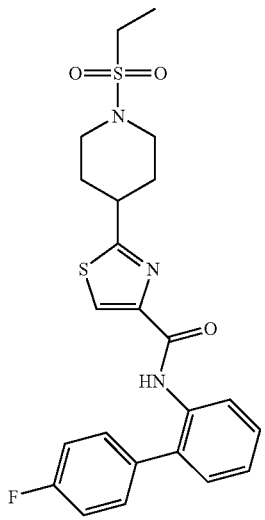 2-[1-(ethylsulfonyl)piperidin-4-yl]-N-(4'-fluorobiphenyl-2-yl)-1,3-thiazole-4-carboxamide | |

TABLE 1-continued
| No. | FORMULA | NMR or mass |
|---|---|---|
| 1010 | 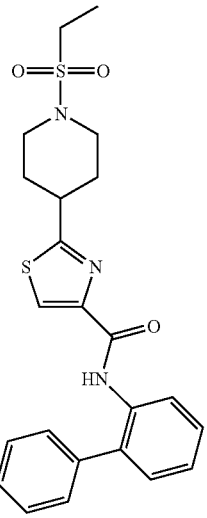<br>N-(4'-chlorobiphenyl-2-yl)-2-[1-ethylsulfonyl)piperidin-4-yl]-1,3-thiazole-4-carboxamide | |
| 1011 | 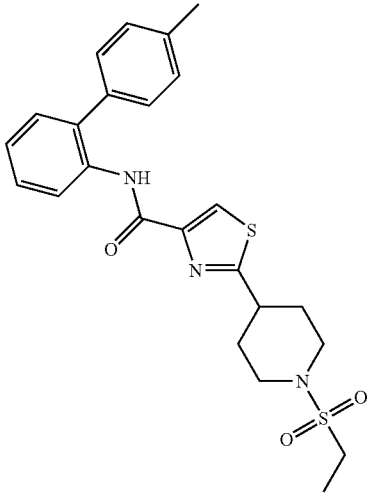<br>2-[1-(ethylsulfonyl)piperidin-4-yl]-N-(4'-methylbiphenyl-2-yl)-1,3-thiazole-4-carboxamide | |

TABLE 1-continued
| No. | FORMULA | NMR or mass |
|---|---|---|
| 1012 | 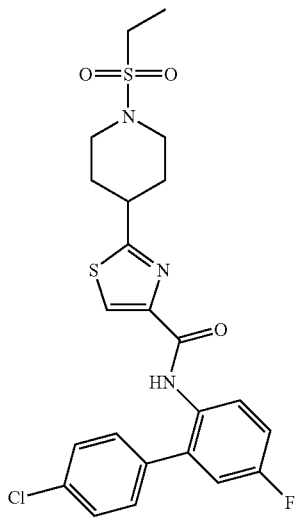 | |
| 1013 | 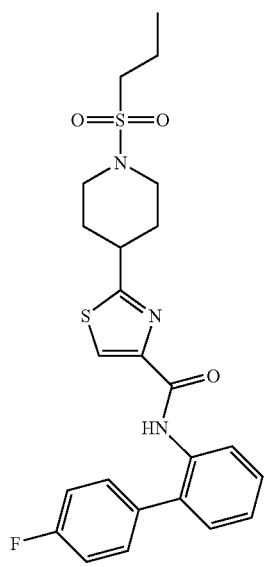<br>N-(4'-fluorobiphenyl-2-yl)-2[1-(propylsulfonyl)<br>piperidin-4-yl]-1,3-thiazole-4-carboxamide | |

TABLE 1-continued
| No. | FORMULA | NMR or mass |
|---|---|---|
| 1014 | 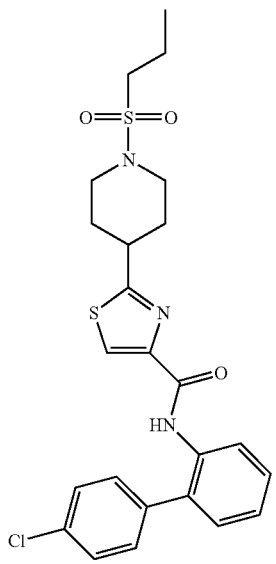 N-(4'-chlorobiphenyl-2-yl)-2[1-(propylsulfonyl)piperidin-4-yl]-1,3-thiazole-4-carboxamide | |
| 1015 | 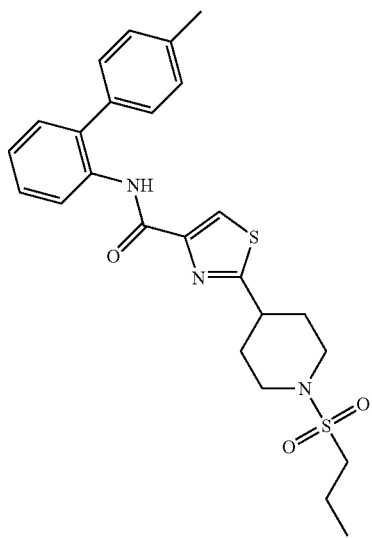 N-(4'-methylbiphenyl-2-yl)-2-[1-(propylsulfonyl)piperidin-4-yl]-1,3-thiazole-4-carboxamide | |

TABLE 1-continued
| No. | FORMULA | NMR or mass |
|---|---|---|
| 1016 | 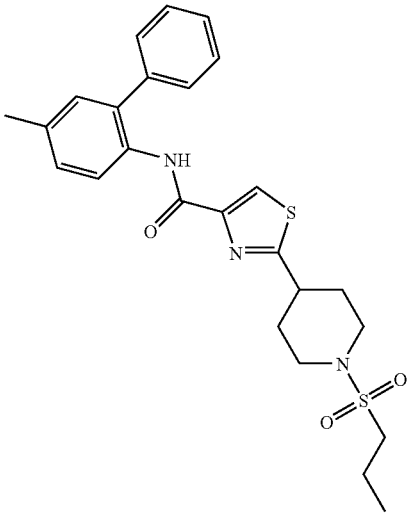 N-(5-methylbiphenyl-2-yl)-2-[1-(propylsulfonyl)piperidin-4-yl]-1,3-thiazole-4-carboxamide | |
| 1017 | 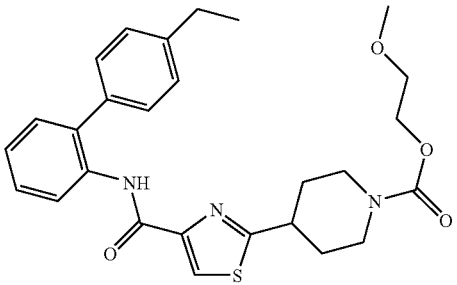 | |
| 1018 | 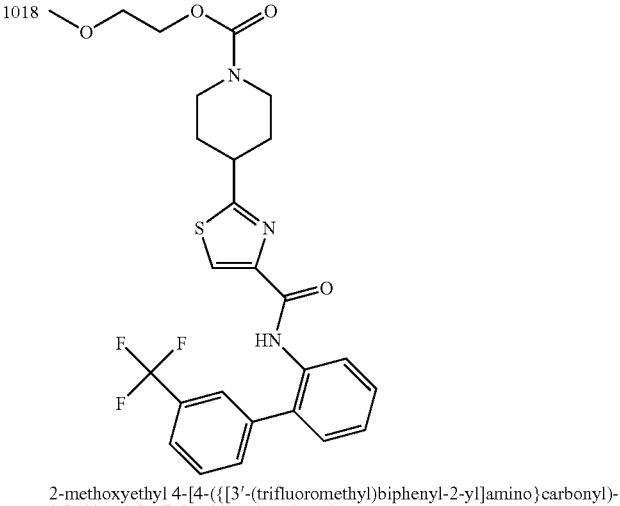 2-methoxyethyl 4-[4-({[3'-(trifluoromethyl)biphenyl-2-yl]amino}carbonyl)-1,3-thiazol-2-yl]piperidine-1-carboxylate | |

TABLE 1-continued
| No. | FORMULA | NMR or mass |
|---|---|---|
1019
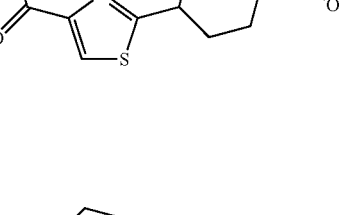
1020
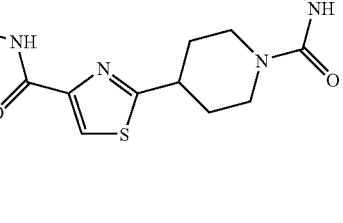
1021
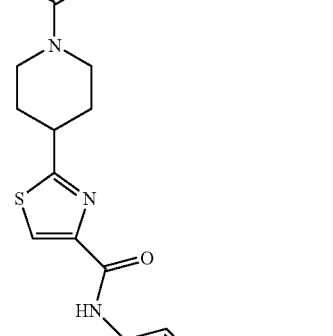
N-ethyl-4-[4-({[4'-(trifluoromethoxy)biphenyl-2-yl]amino}carbonyl)-1,3-thiazol-2-yl]piperidine-1-carboxamide

TABLE 1-continued
| No. | FORMULA | NMR or mass |
|---|---|---|
| 1022 | 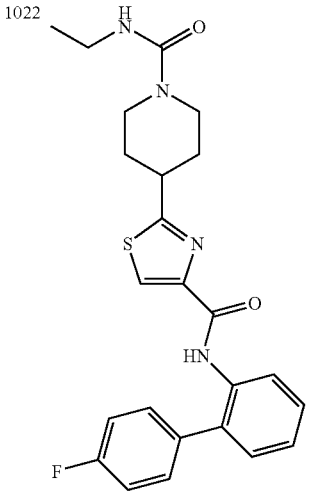 N-ethyl-4-(4-{[(4'-fluorobiphenyl-2-yl)amino]carbonyl}-1,3-thiazol-2-yl)-piperidine-1-carboxamide | |
| 1023 | 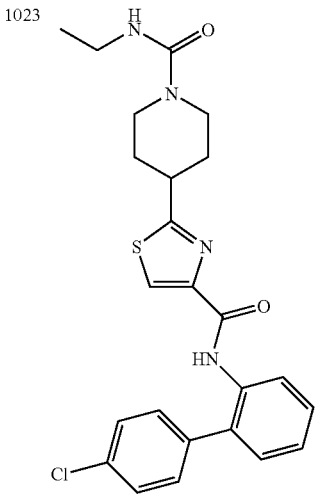 4-(4-{[(4'-chlorobiphenyl-2-yl)amino]carbonyl}-1,3-thiazol-2-yl)-N-ethyl-piperidine-1-carboxamide | |
| 1024 | 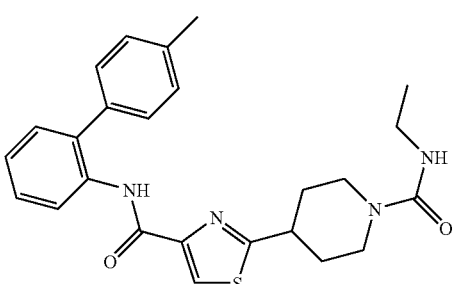 | |

TABLE 1-continued
| No. | FORMULA | NMR or mass |
|---|---|---|
1025
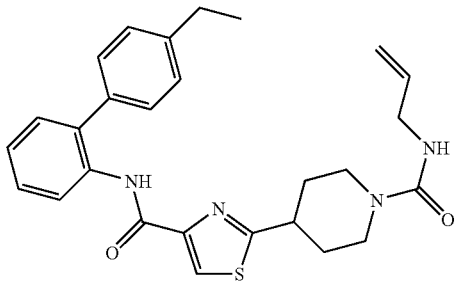
1026
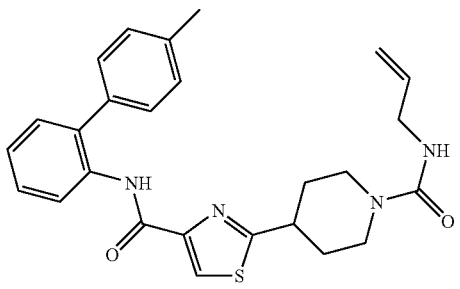
1027
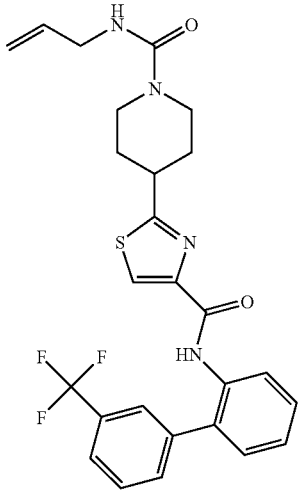
N-allyl-4-[4-({[3'-(trifluoromethyl)biphenyl-2-yl]amino}carbonyl)-1,3-thiazol-2-yl]piperidine-1-carboxamide TABLE 1-continued
| No. | FORMULA | NMR or mass |
|---|---|---|
| 1028 | 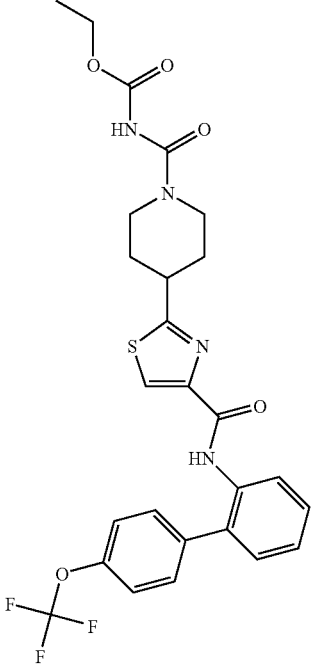 ethyl ({4-[4-({[4'-(trifluoromethoxy)biphenyl-2-yl]amino}carbonyl)-1,3-thiazol-2-yl]piperidin-1-yl}carbonyl)carbamate | |
| 1029 | 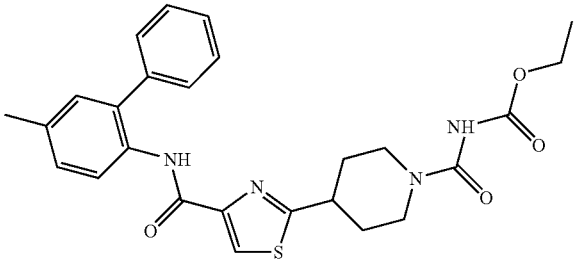 | |

TABLE 1-continued
| No. | FORMULA | NMR or mass |
|---|---|---|
1030 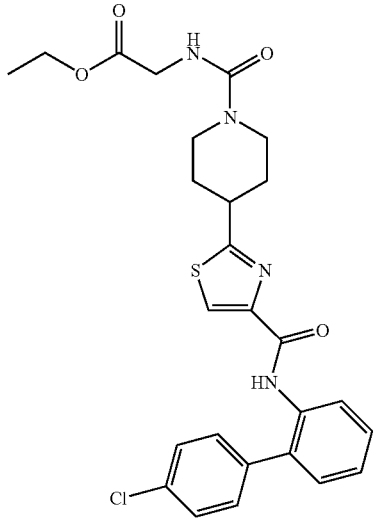
ethyl N-{[4-(4-{[(4'-chlorobiphenyl-2-yl)amino)carbonyl}-1,3-thiazol-2-yl)-piperidin-1-yl]carbonyl}glycinate
1031 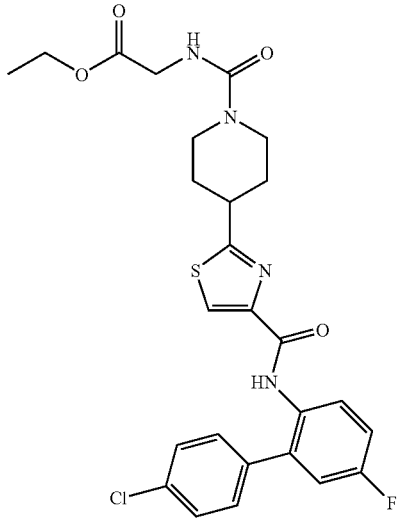
ethyl N-{[4-(4-{[(4'-chloro-5-fluorobiphenyl-2-yl)amino]carbonyl}-1,3-thiazol-2-yl)piperidin-1-yl]carbonyl}glycinate TABLE 1-continued
| No. | FORMULA | NMR or mass |
|---|---|---|
| 1032 | 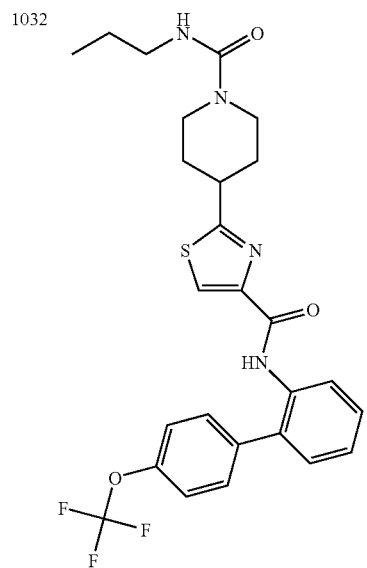 N-propyl-4-[4-({[4'-(trifluoromethoxy)biphenyl-2-yl]amino}carbonyl)-1,3-thiazol-2-yl]piperidine-1-carboxamide | |
| 1033 | 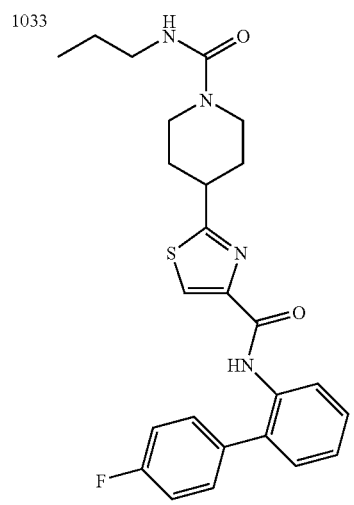 4-(4-{[(4'-fluorobiphenyl-2-yl)amino]carbonyl}-1,3-thiazol-2-yl)-N-propyl-piperidine-1-carboxamide | |

TABLE 1-continued
| No. | FORMULA | NMR or mass |
|-----|---------|-------------|
| 1034 | 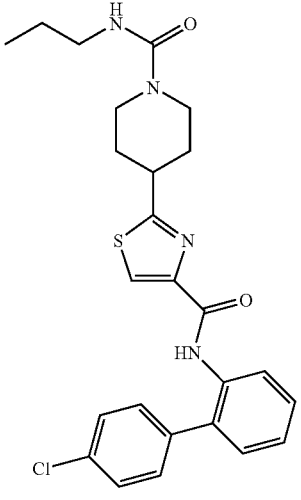 4-(4-{[(4'-chlorobiphenyl-2-yl)amino]carbonyl}-1,3-thiazol-2-yl)-N-propyl-piperidine-1-carboxamide | |
| 1035 | 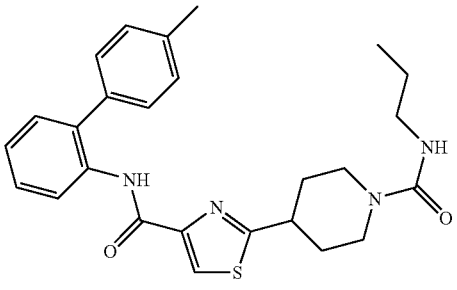 | |
| 1036 | 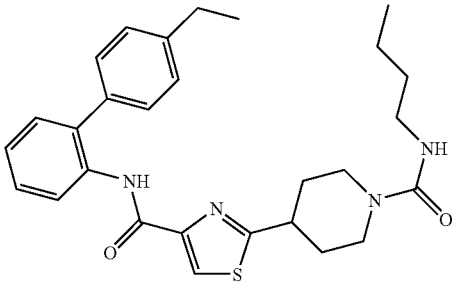 | |
| 1037 | 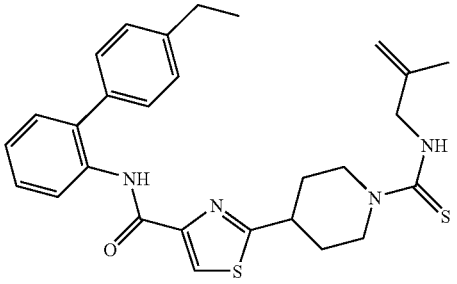 | |

TABLE 1-continued
| No. | FORMULA | NMR or mass |
|---|---|---|
| 1038 | 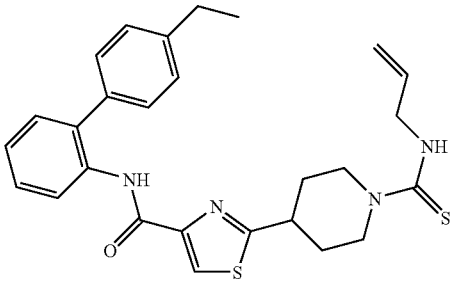 | |
| 1039 | 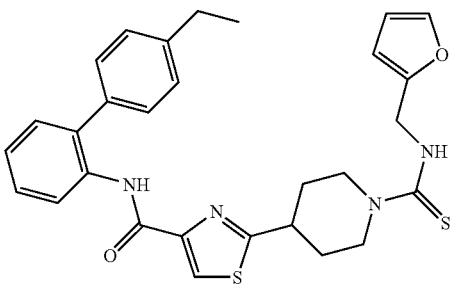 | |
| 1040 | 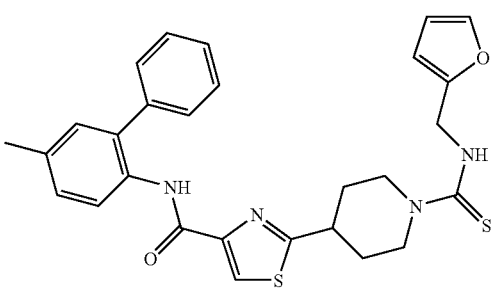 | |
| 1041 | 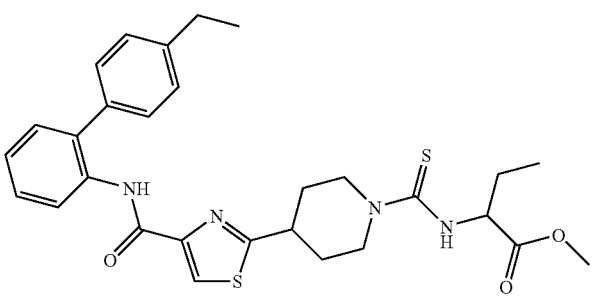 | |
| 1042 | 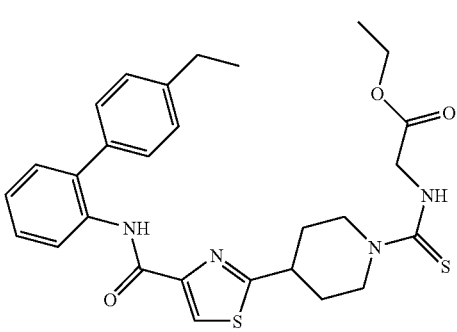 | |

TABLE 1-continued

| No. | FORMULA | NMR or mass |
|---|---|---|

1043

1044

2-{1-[(ethylamino)carbonothioyl]piperidin-4-yl}-N-
[4'-(trifluoromethoxy)-biphenyl-2-yl]-1,3-
thiazole-4-carboxamide

1045

1046

TABLE 1-continued
| No. | FORMULA | NMR or mass |
|---|---|---|
| 1047 | 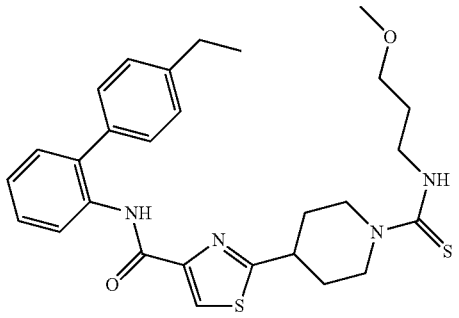 | |
| 1048 | 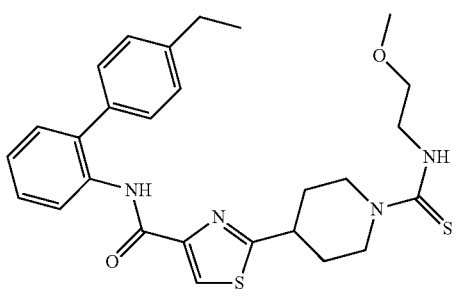 | |
| 1049 | 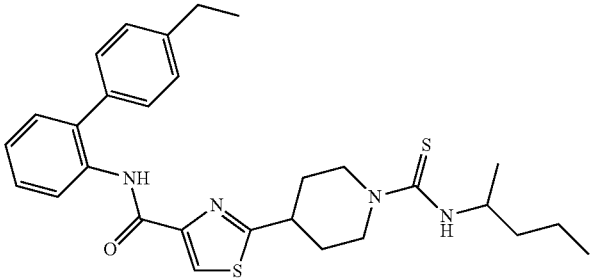 | |
| 1050 | 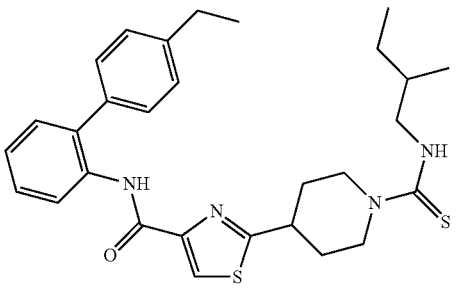 | |
| 1051 | 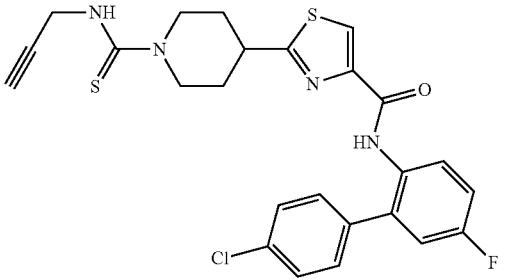 | |

TABLE 1-continued
| No. | FORMULA | NMR or mass |
|---|---|---|
| 1052 | 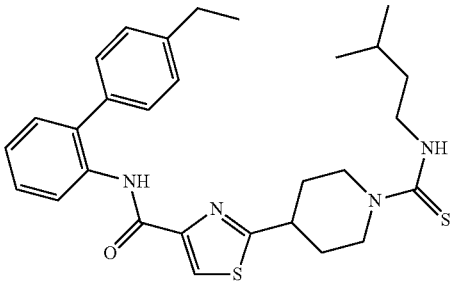 | |
| 1053 | 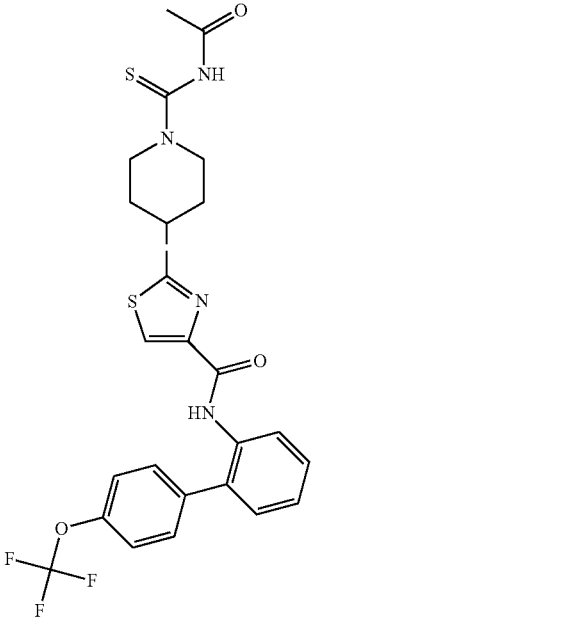<br>2-{1-[(acetylamino)carbonothioyl]piperidin-4-yl}-N-[4'-(trifluoromethoxy)-biphenyl-2-yl]-1,3-thiazole-4-carboxamide | |
| 1054 | 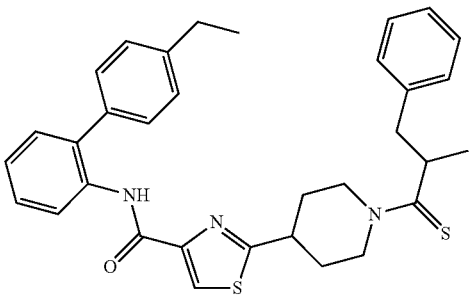 | |

TABLE 1-continued
| No. | FORMULA | NMR or mass |
|---|---|---|
1055 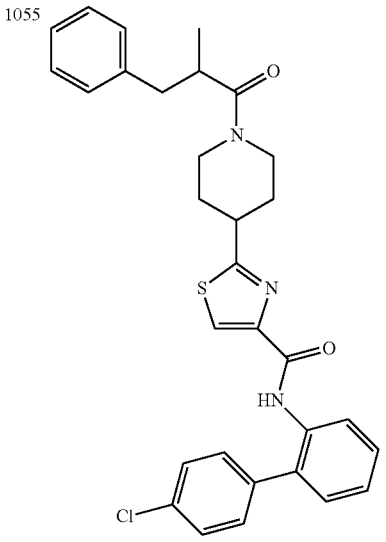
N-(4'-chlorobiphenyl-2-yl]-2-[1-(2-methyl-3-phenylpropanoyl)piperidin-4-yl]-1,3-thiazole-4-carboxamide
1056 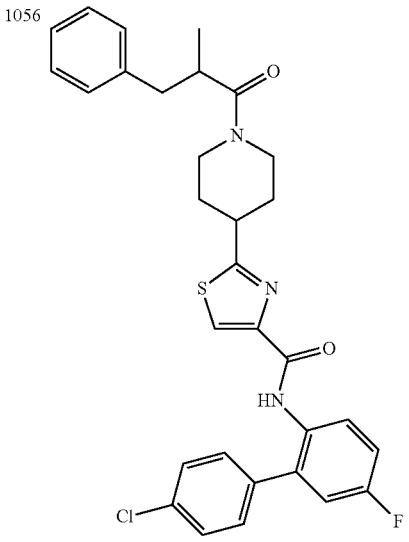
N-(4'-chloro-5-fluorobiphenyl-2-yl)-2-[1-(2-methyl-3-phenylpropanoyl)-piperidin-4-yl]-1,3-thiazole-4-carboxamide
1057 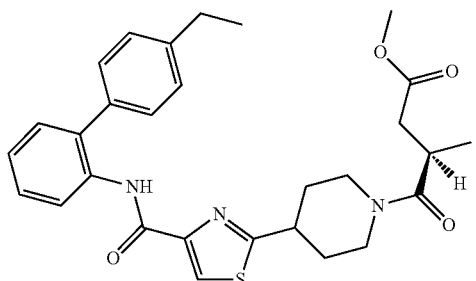

| No. | FORMULA | NMR or mass |
|---|---|---|
| 1058 | 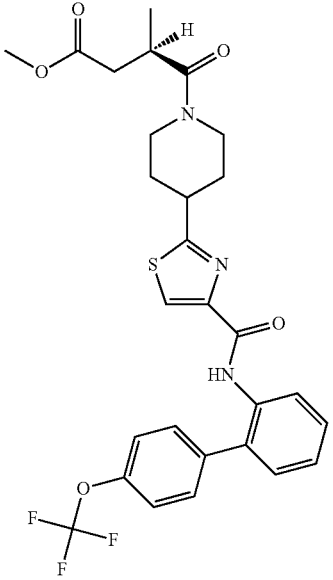 methyl (3R)-3-methyl-4-oxo-4-{4-({[4'-(trifluoromethoxy)biphenyl-2-yl]-amino}carbonyl)-1,3-thiazol-2-yl]piperidin-1-yl}butanoate | |
| 1059 | 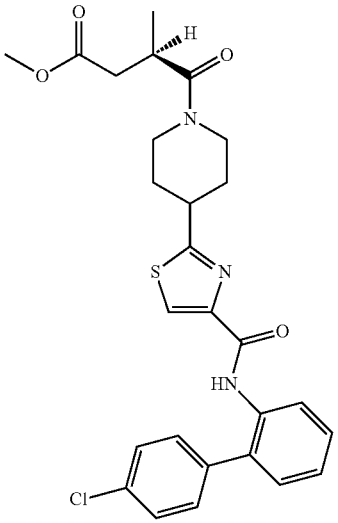 methyl (3R)-4-[4-{[(4'-chlorobiphenyl-2-yl)amino]carbonyl}-1,3-thiazol-2-yl)piperidin-1-yl]-3-methyl-4-oxobutanoate | |
| 1060 | 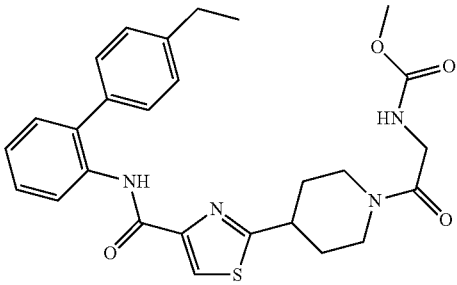 | |

TABLE 1-continued

| No. | FORMULA | NMR or mass |
|---|---|---|
| 1061 | | |
| 1062 | | |
| 1063 | | |

TABLE 1-continued
| No. | FORMULA | NMR or mass |
|---|---|---|
| 1064 | 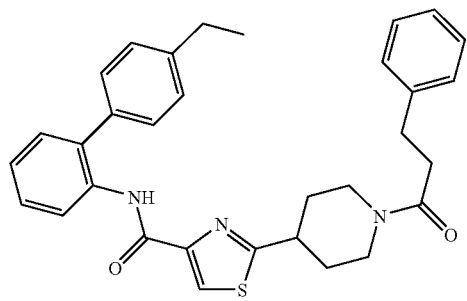 | |
| 1065 | 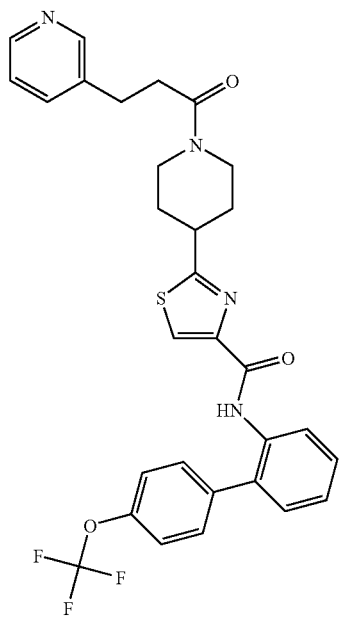 | |
2-[1-(3-pyridin-3-ylpropanoyl)piperidin-4-yl]-N-[4'-(trifluoromethoxybiphenyl-2-yl]-1,3-thiazole-4-carboxamide
| 1066 | 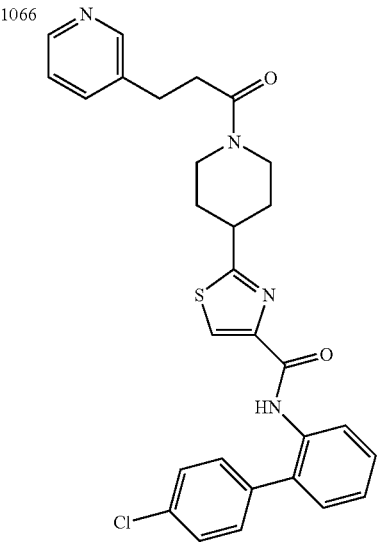 | |
N-(4'-chlorobiphenyl-2-yl)-2-[1-(3-pyridin-3-ylpropanoyl)piperidin-4-yl]-1,3-thiazole-4-carboxamide

| No. | FORMULA | NMR or mass |
|---|---|---|
| 1067 | 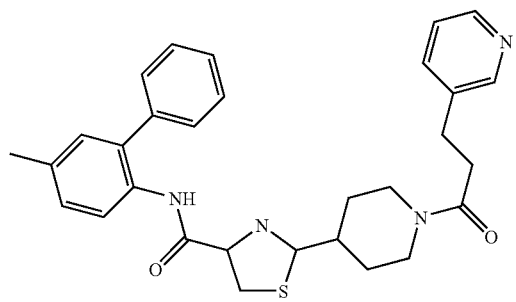 | |
| 1068 | 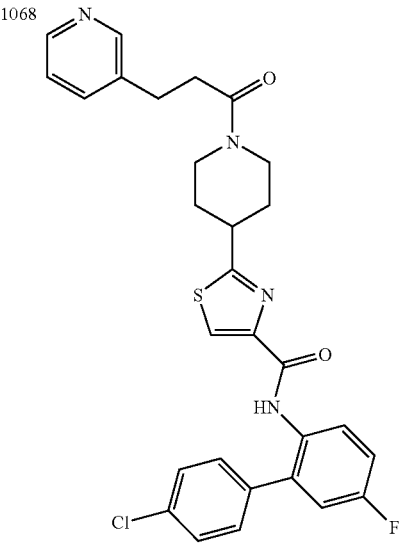 N-(4'-chloro-5-fluorobiphenyl-2-yl)-2-[-1(3-pyridin-3-ylpropanoyl)-piperidin-4-yl}-1,3-thiazole-4-carboxamide | |
| 1069 | 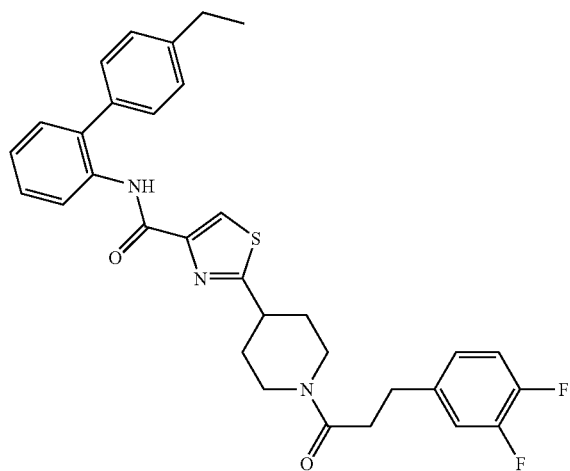 | |

| No. | FORMULA | NMR or mass |
|---|---|---|
| 1070 | 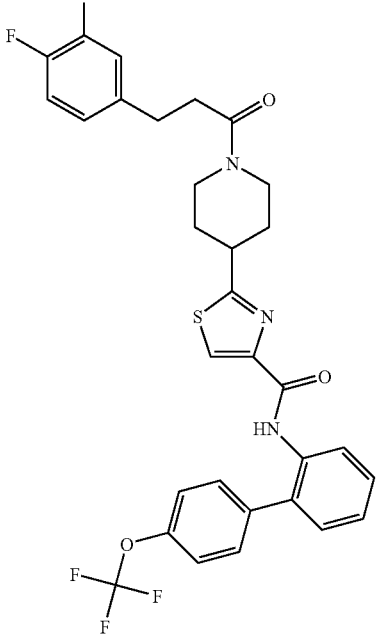 2-{1-[3-(3,4-difluorophenyl)propanoyl]piperidin-4-yl}-N-[4'-(trifluoromethoxy)-biphenyl-2-yl]-1,3-thiazole-4-carboxamide | |
| 1071 | 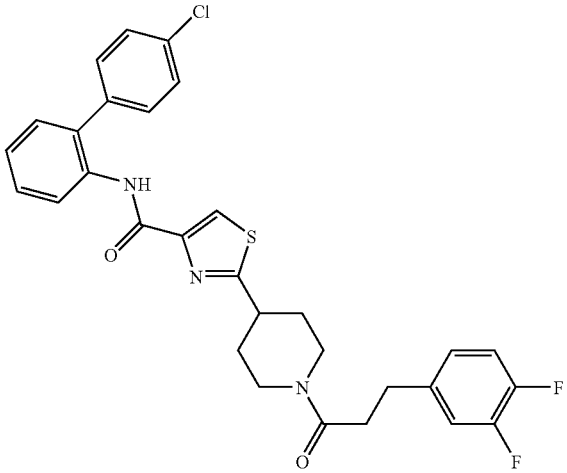 N-(4'-chlorobiphenyl-2-yl)-2-{1-[3-(3,4-difluorophenyl)propanoyl]-piperidin-4-yl}-1,3-thiazole-4-carboxamide | |

TABLE 1-continued
| No. | FORMULA | NMR or mass |
|---|---|---|
1072
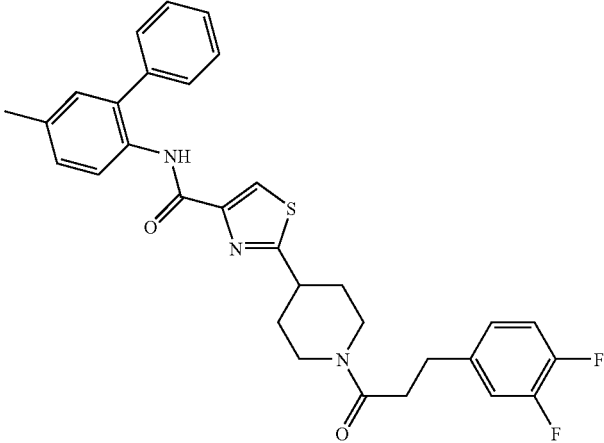
2-{1-[3-(3,4-difluorophenyl)propanoyl]piperidin-4-yl}-N-(5-methylbiphenyl-2-yl)-1,3-thiazole-4-carboxamide
1073
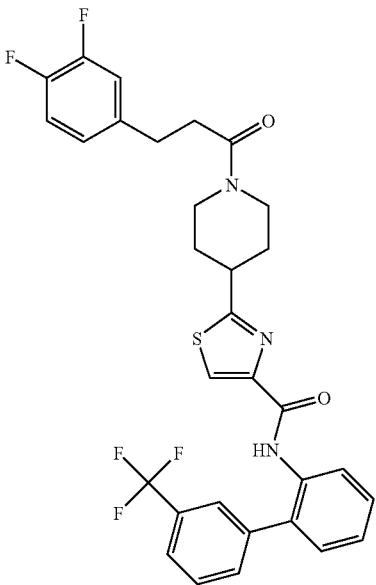
2-{1-[3-(3,4-difluorophenyl)propanoyl]piperidin-4-yl}-N-[3′-(trifluoromethyl)-biphenyl-2-yl]-1,3-thiazole-4-carboxamide

TABLE 1-continued
| No. | FORMULA | NMR or mass |
|-----|---------|-------------|
| 1074 | 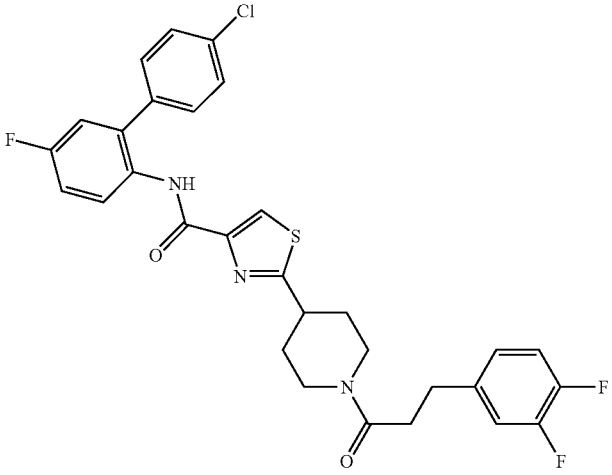 N-(4-chloro-5-fluorobiphenyl-2-yl)-2-{1-[3-(3,4-difluorophenyl)propanoyl]-piperidin-4-yl}-1,3-thiazole-4-carboxamide | |
| 1075 | 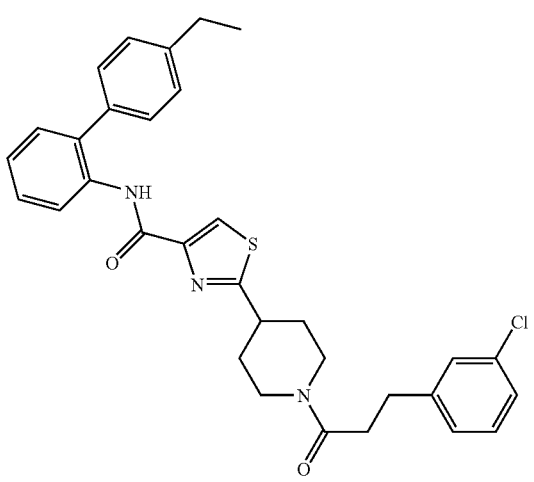 2-{1-[3-(3-chlorophenyl)propanoyl]piperidin-4-yl}-N-(4'-ethylbiphenyl-2-yl)-1,3-thiazole-4-carboxamide | |
| 1076 | 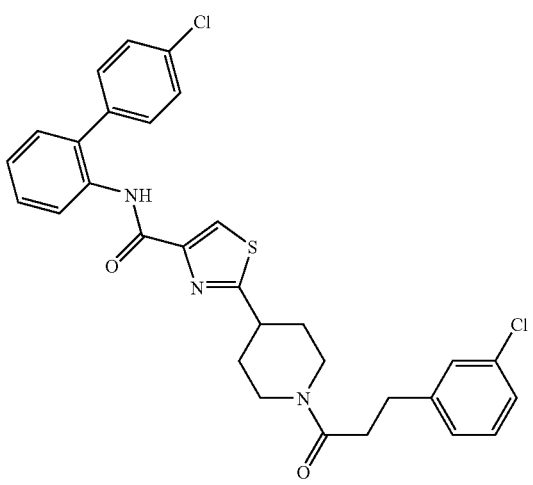 N-(4'-chlorobiphenyl-2-yl)-2-{1-[3-(3-chlorophenyl)propanoyl]piperidin-4-yl}-1,3-thiazole-4-carboxamide | |

| No. | FORMULA | NMR or mass |
|---|---|---|
1077
1078
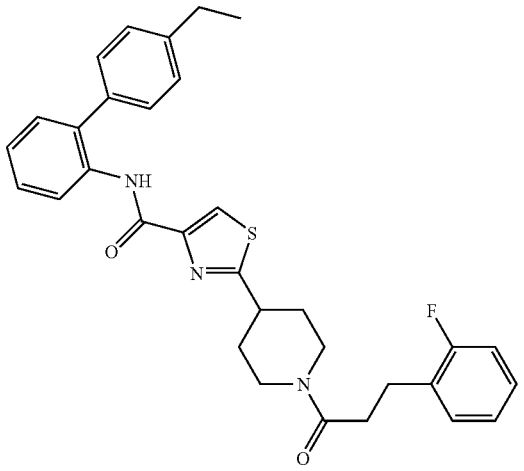
N-(4'-ethylbiphenyl-2-yl)-2-{1-[3-(2-fluorophenyl)propanoyl]piperidin-4-yl}-1,3-thiazole-4-carboxamide
1079
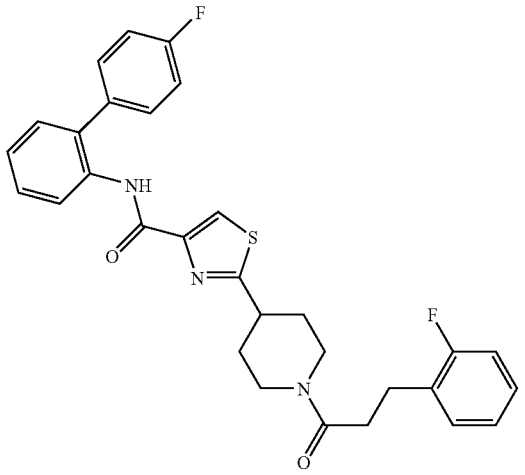
1080
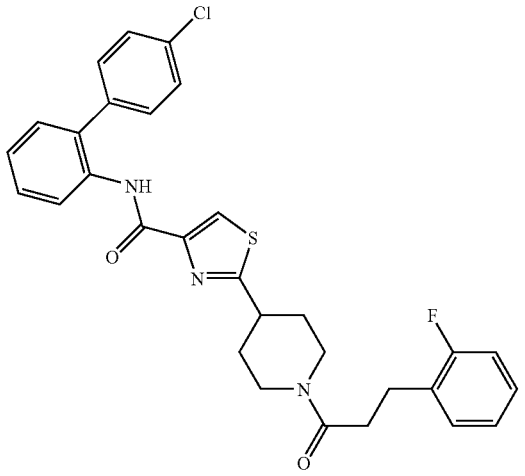

TABLE 1-continued

| No. | FORMULA | NMR or mass |
|---|---|---|
| 1081 | | |
| 1082 | | |
| 1083 | | |
| 1084 | | |
| 1085 | 2-{1-[(2-chlorophenoxy)acetyl]piperidin-4-yl}-N-(4'-ethylbiphenyl-2-yl)-1,3-thiazole-4-carboxamide | |

TABLE 1-continued
| No. | FORMULA | NMR or mass |
|---|---|---|
| 1086 | 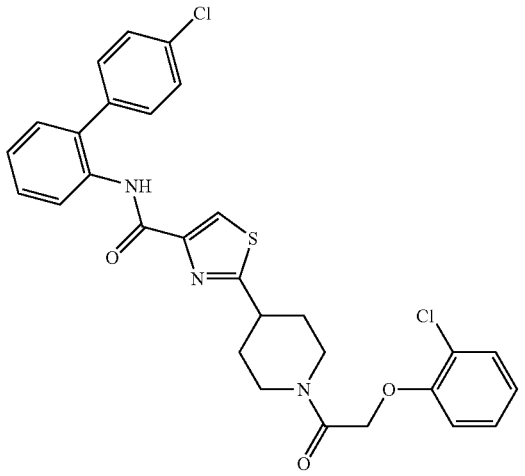 N-(4'-chlorobiphenyl-2-yl)-2-{1-[(2-chlorophenoxy)acetyl]piperidin-4-yl}-1,3-thiazole-4-carboxamide | |
| 1087 | 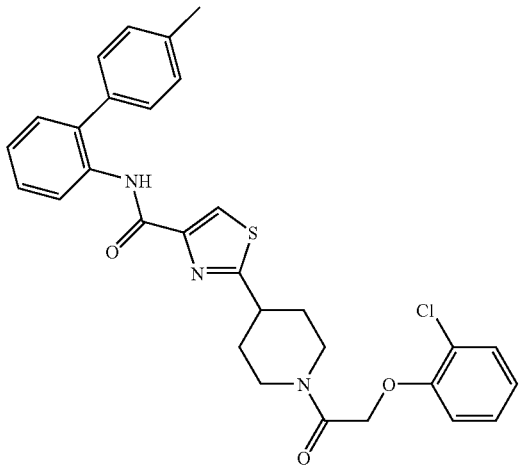 2-{1[(2-chlorophenoxy)acetyl]piperidin-4-yl}-N-(4'-methylbiphenyl-2-yl)-1,3-thiazole-4-carboxamide | |
| 1088 | | |
| 1089 | 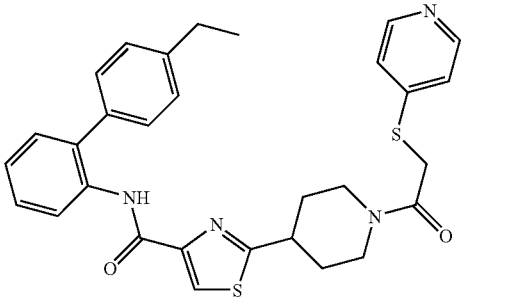 | |

TABLE 1-continued
| No. | FORMULA | NMR or mass |
|---|---|---|
1090 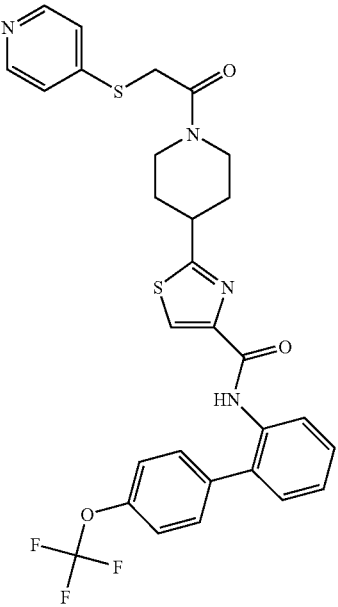
2-{1-[(pyridin-4-ylthio)acetyl]piperidin-4-yl}-N-[4-(trifluoromethoxy)-biphenyl-2-yl]-1,3-thiazole-4-carboxamide
1091 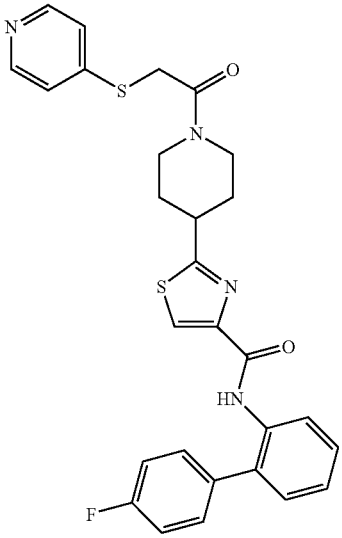
N-(4'-fluorobiphenyl-2-yl)-2-{1-[(pyridin-4-ylthio)acetyl]piperidin-4-yl}-1,3-thiazole-4-carboxamide TABLE 1-continued
| No. | FORMULA | NMR or mass |
|-----|---------|-------------|
1092
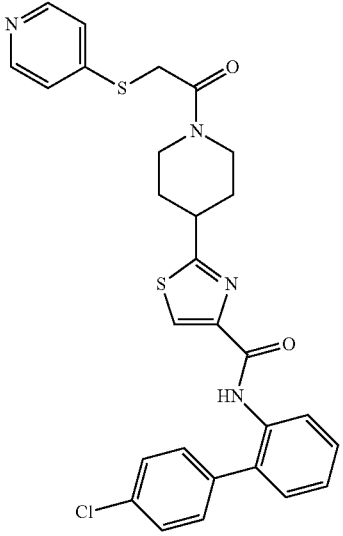
N-(4'-chlorobiphenyl-2-yl)-2-{1-[(pyridin-4-ylthio)acetyl]piperidin-4-yl}-1,3-thiazole-4-carboxamide
1093
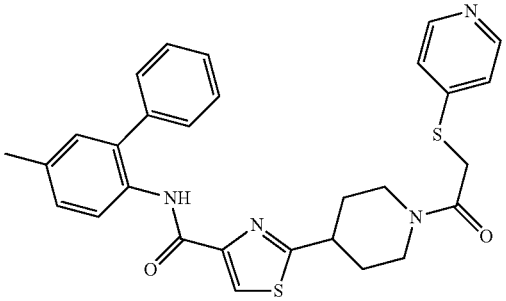
1094
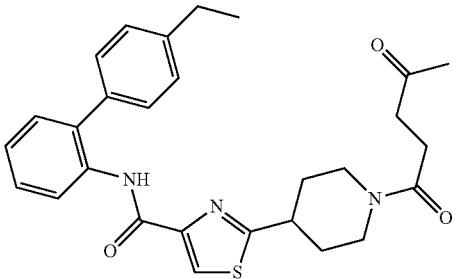

TABLE 1-continued
| No. | FORMULA | NMR or mass |
|---|---|---|
| 1095 | 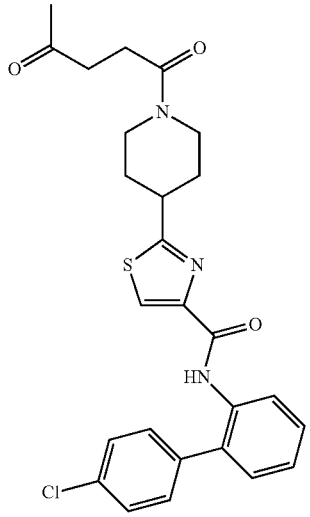 N-(4'-chlorobiphenyl-2-yl)-2-[1-(4-oxopentanoyl)piperidin-4-yl]-1,3-thiazole-4-carboxamide | |
| 1096 | 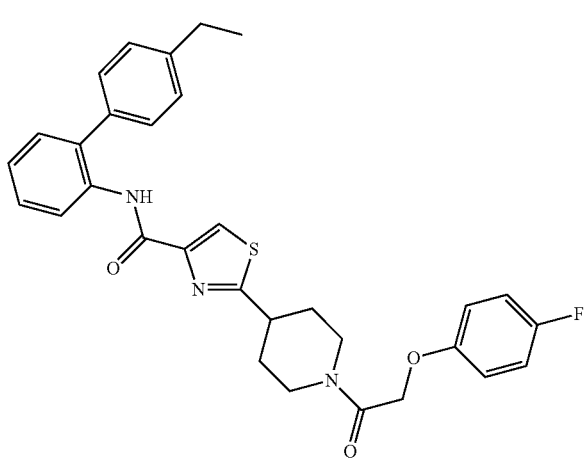 N-(4'-ethylbiphenyl-2-yl)-2-{1-[(4-fluorophenoxy)acetyl]piperidin-4-yl}-1,3-thiazole-4-carboxamide | |
| 1097 | 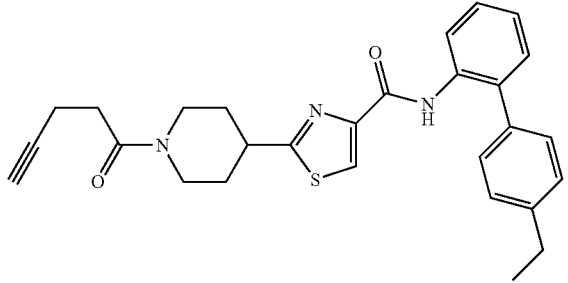 | |

TABLE 1-continued

| No. | FORMULA | NMR or mass |
|---|---|---|
| 1098 | | |
| 1099 | | |
| 1100 | | |
| 1101 | | |

TABLE 1-continued
| No. | FORMULA | NMR or mass |
|---|---|---|
| 1102 | 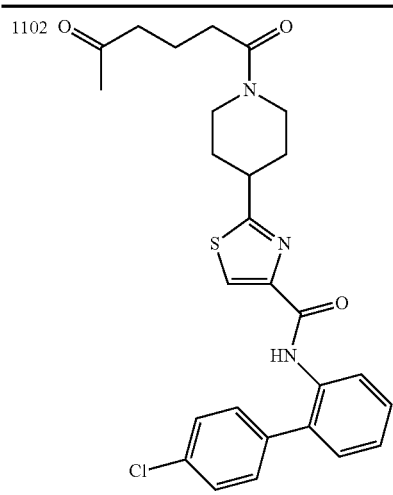 N-(4'-chlorobiphenyl-2-yl)-2-[1-(5-oxohexanoyl)piperidin-4-yl]-1,3-thiazole-4-carboxamide | |
| 1103 | 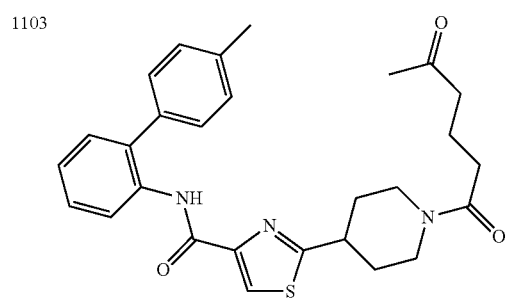 | |
| 1104 | 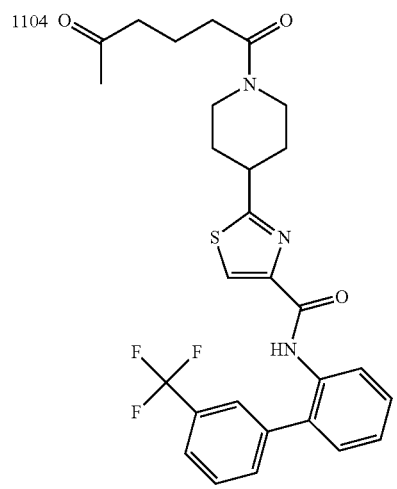 2-[1-(5-oxohexanoyl)piperidin-4-yl]-N-[3'-(trifluoromethyl)biphenyl-2-yl]-1,3-thiazole-4-carboxamide | |

TABLE 1-continued
| No. | FORMULA | NMR or mass |
|---|---|---|
| 1105 | 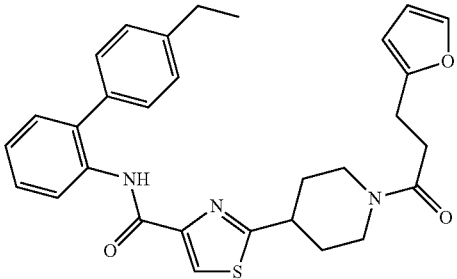 | |
| 1106 | 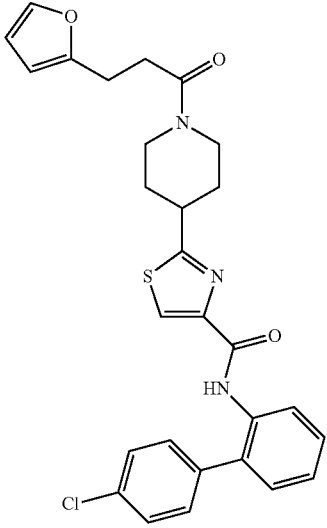 | |
| 1107 | 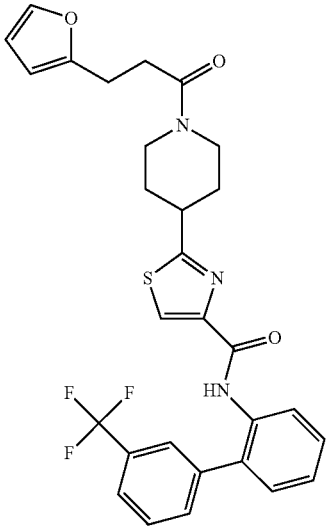 | |
2-{1-[3-(2-furyl)propanoyl]piperidin-4-yl}-N-[3′-(trifluoromethyl)biphenyl-2-yl]-1,3-thiazole-4-carboxamide TABLE 1-continued
| No. | FORMULA | NMR or mass |
|---|---|---|
| 1108 | 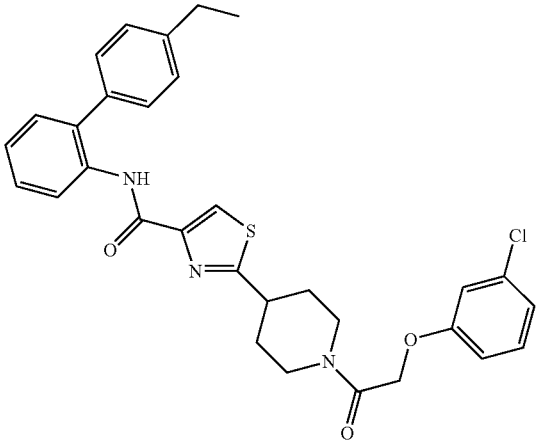 2-{1-[(3-chlorophenoxy)acetyl]piperidin-4-yl}-N-(4'-ethylbiphenyl-2-yl)-1,3-thiazole-4-carboxamide | |
| 1109 | 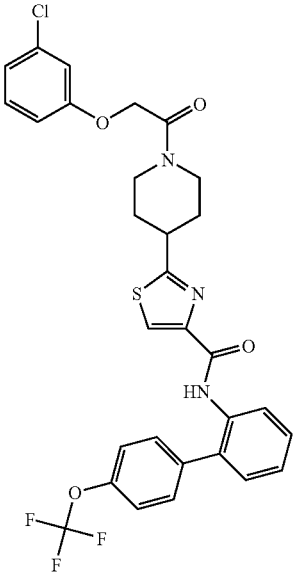 2-{1-[(3-chlorophenoxy)acetyl]piperidin-4-yl}-N-[4'-(trifluoromethoxy)-biphenyl-2-yl]-1,3-thiazole-4-carboxamide | |

TABLE 1-continued
| No. | FORMULA | NMR or mass |
|---|---|---|
| 1110 | 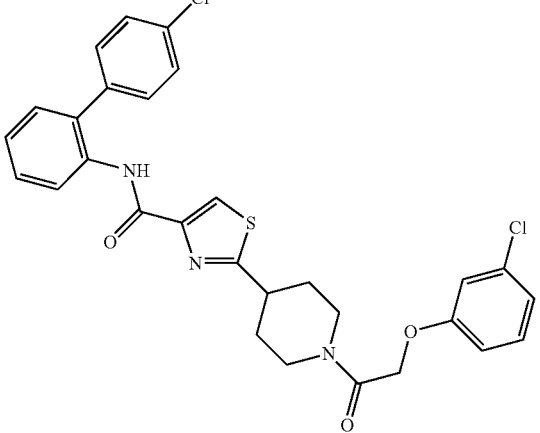 N-(4'-chlorobiphenyl-2-yl)-2-{1-[(3-chlorophenoxy)acetyl]piperidin-4-yl}-1,3-thiazole-4-carboxamide | |
| 1111 | 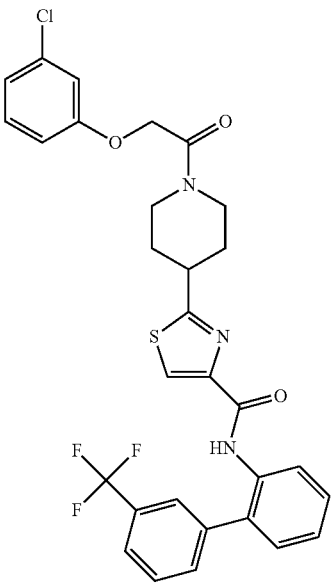 2-{1-[(3-chlorophenoxy)acetyl]piperidin-4-yl}-N-[3'-(trifluoromethyl)biphenyl-2-yl]-1,3-thiazole-4-carboxamide | |
| 1112 | 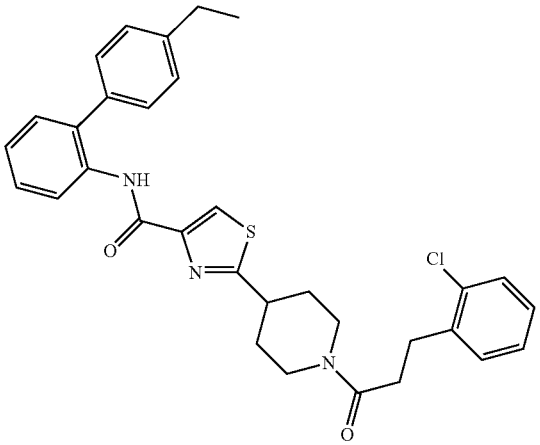 | |

TABLE 1-continued
| No. | FORMULA | NMR or mass |
|---|---|---|
1113
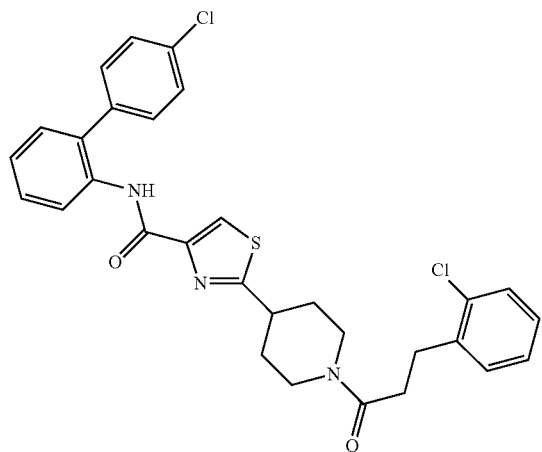
N-(4'-chlorobiphenyl-2-yl)-2-{1-[3-(2-chlorophenyl)propanoyl]piperidin-4-yl}-1,3-thiazole-4-carboxamide
1114
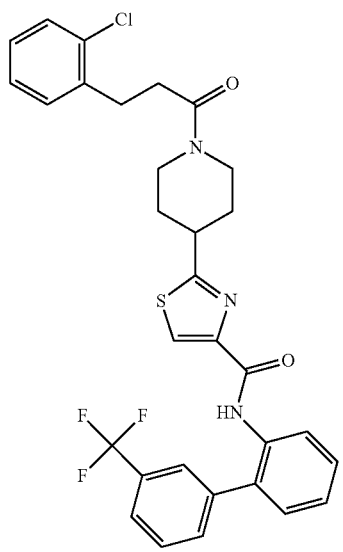
2-{1-[3-(2-chlorophenyl)propanoyl]piperidin-4-yl}-N-[3'-(trifluoromethyl)-biphenyl-2-yl]-1,3-thiazole-4-carboxamide TABLE 1-continued
| No. | FORMULA | NMR or mass |
|---|---|---|
1115
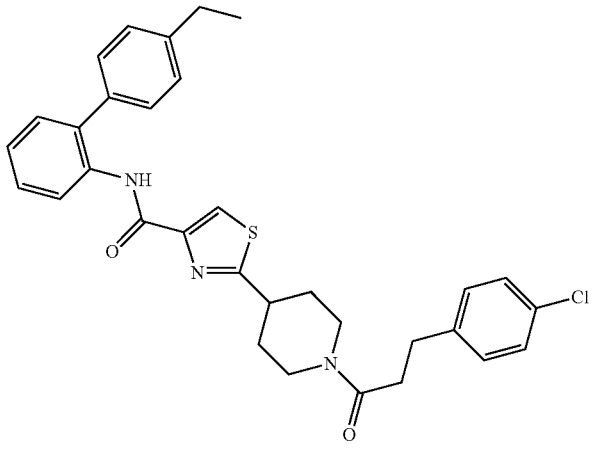
2-{1-[3-(4-chlorophenyl)propanoyl]piperidin-4-yl}-N-(4'-ethylbiphenyl-2-yl)-1,3-thiazole-4-carboxamide
1116
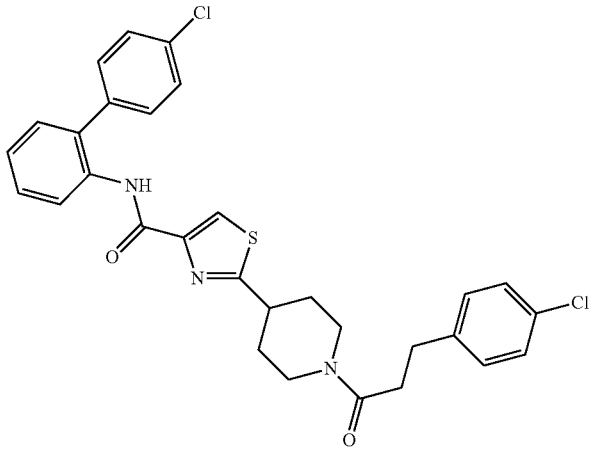
N-(4'-chlorobiphenyl-2-yl)-2-{1-[3-(4-chlorophenyl)propanoyl]piperidin-4-yl}-1,3-thiazole-4-carboxamide
1117
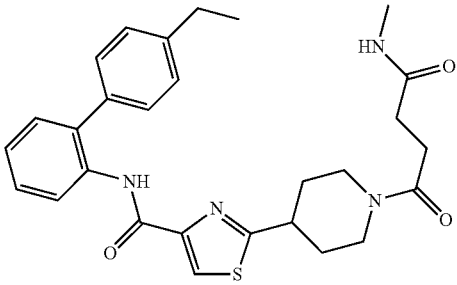

TABLE 1-continued
| No. | FORMULA | NMR or mass |
|---|---|---|
| 1118 | 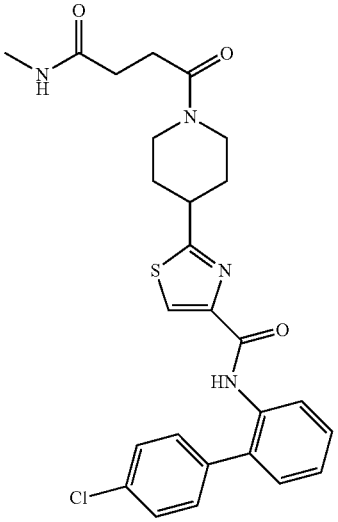 | |
| 1119 | 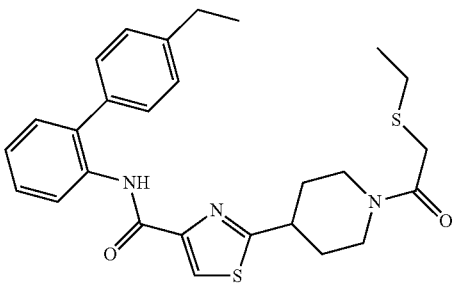 | |
| 1120 | 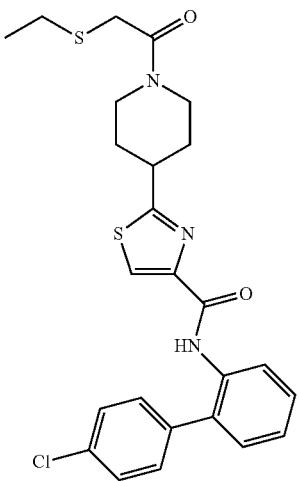 | |
N-(4'-chlorobiphenyl-2-yl)-2-{1-[(ethylthio)acetyl]piperidin-4-yl}-1,3-thiazole-4-carboxamide TABLE 1-continued
| No. | FORMULA | NMR or mass |
|---|---|---|
| 1121 | 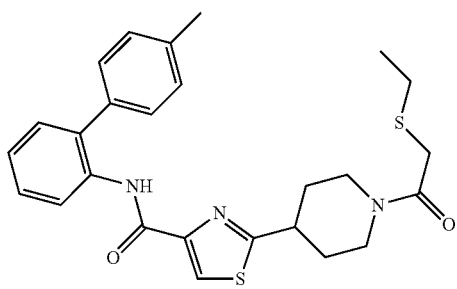 | |
| 1122 | 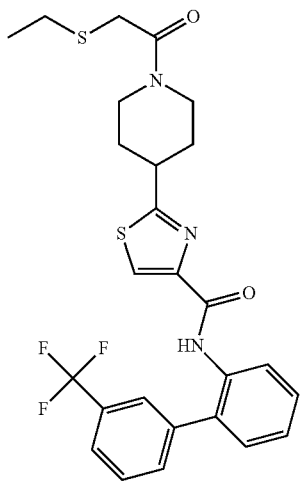 2-{1-[(ethylthio)acetyl]piperidin-4-yl}-N-[3'-(trifluoromethyl)biphenyl-2-yl]-1,3-thiazole-4-carboxamide | |
| 1123 | 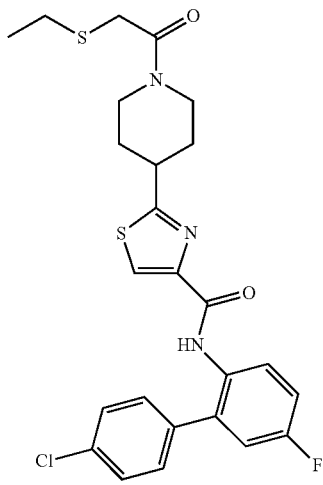 N-(4'-chloro-5-fluorobiphenyl-2-yl)-2-{1-[(ethylthio)acetyl]piperidin-4-yl}-1,3-thiazole-4-carboxamide | |

TABLE 1-continued
| No. | FORMULA | NMR or mass |
|---|---|---|
| 1124 | 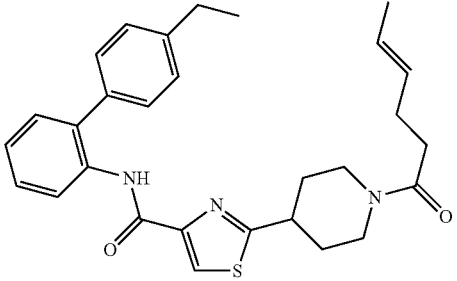 | |
| 1125 | 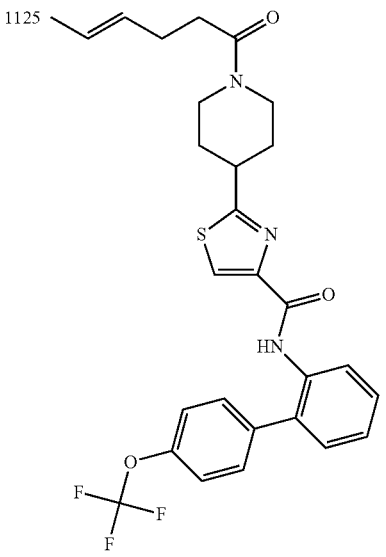 | |
2-{1-[(4E)-hex-4-enoyl]piperidin-4-yl}-N-[4'-(trifluoromethoxy)biphenyl-2-yl]-1,3-thiazole-4-carboxamide
| 1126 |  | |
N-(4'-chlorobiphenyl-2-yl)-2-{1-[(4E)-hex-4-enoyl]piperidin-4-yl}-1,3-thiazole-4-carboxamide TABLE 1-continued
| No. | FORMULA | NMR or mass |
|---|---|---|
1127 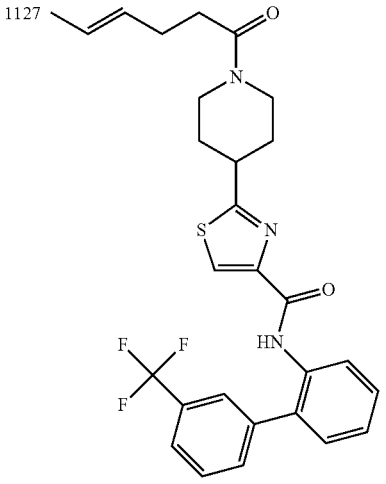
2-{1-[(4E)-hex-4-enoyl]piperidin-4-yl}-N-[3'-(trifluoromethyl)biphenyl-2-yl]-1,3-thiazole-4-carboxamide
1128 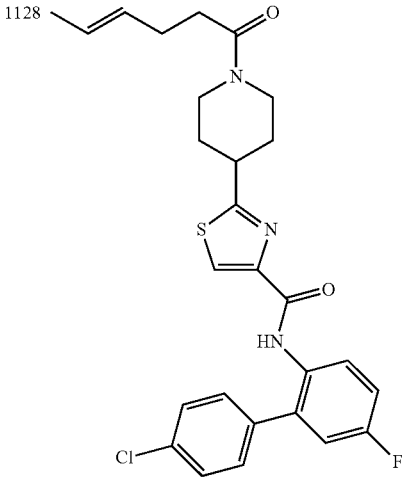
N-(4'-chloro-5-fluorobiphenyl-2-yl)-2-{1-[(4E)-hex-4-enoyl]piperidin-4-yl}-1,3-thiazole-4-carboxamide
1129 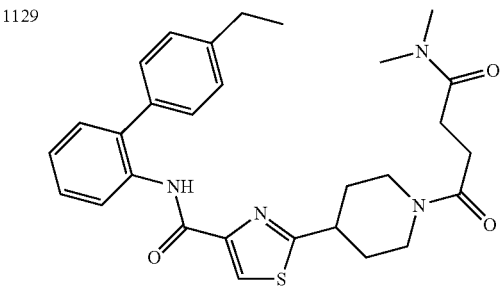

| No. | FORMULA | NMR or mass |
|---|---|---|
1130 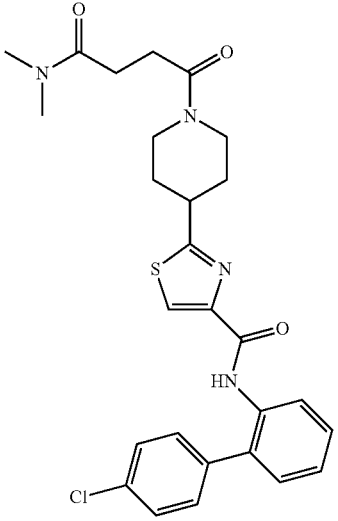
N-(4'-chlorobiphenyl-2-yl)-2-{1-[4-(dimethylamino)-4-
oxobutanoyl]piperidin-4-yl}-1,3-thiazole-4-carboxamide
1131 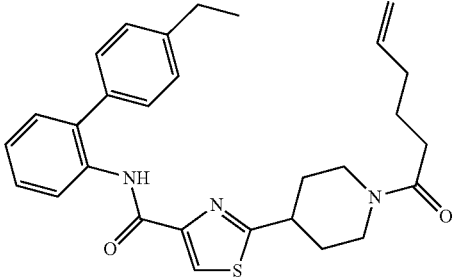
1132 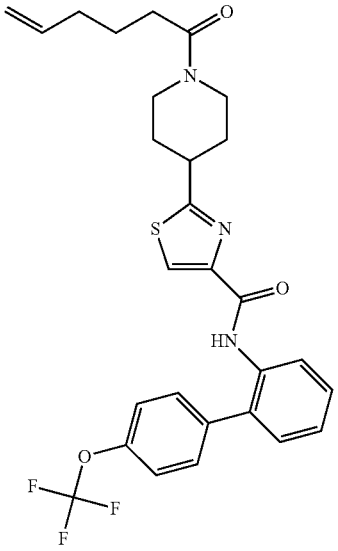
2-(1-hex-5-enoylpiperidin-4-yl)-N-[4'-(trifluoromethoxy)biphenyl-2-yl]-
1,3-thiazole-4-carboxamide TABLE 1-continued
| No. | FORMULA | NMR or mass |
|---|---|---|
| 1133 | 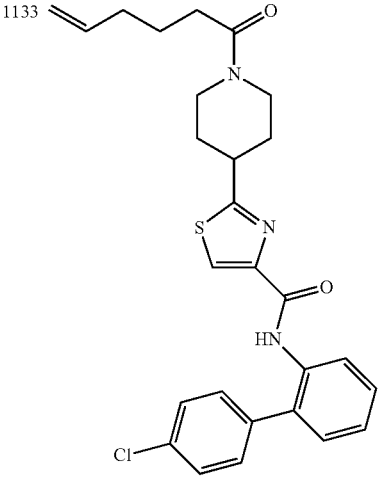 N-(4'-chlorobiphenyl-2-yl)-2-(1-hex-5-enoylpiperidin-4-yl)-1,3-thiazole-4-carboxamide | |
| 1134 | 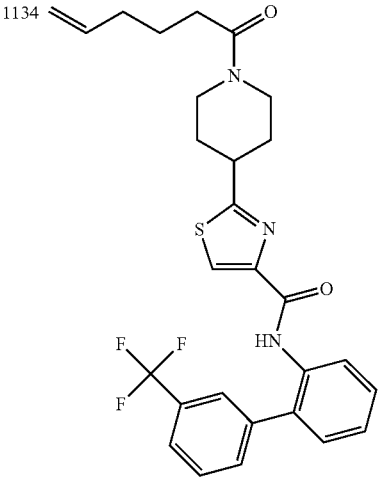 2-(1-hex-5-enoylpiperidin-4-yl)-N-[3'-(trifluoromethyl)biphenyl-2-yl]-1,3-thiazole-4-carboxamide | |

TABLE 1-continued
| No. | FORMULA | NMR or mass |
|---|---|---|
| 1135 | 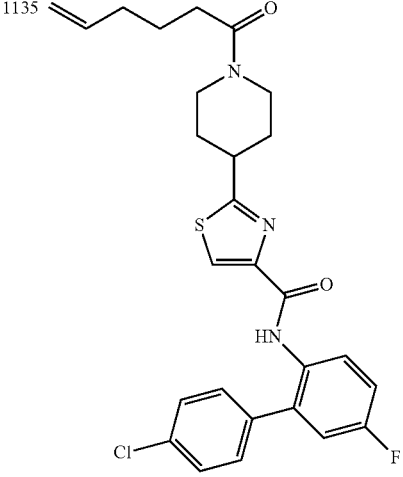 N-(4'-chloro-5-fluorobiphenyl-2-yl)-2-(1-hex-5-enoylpiperidin-4-yl)-1,3-thiazole-4-carboxamide | |
| 1136 | 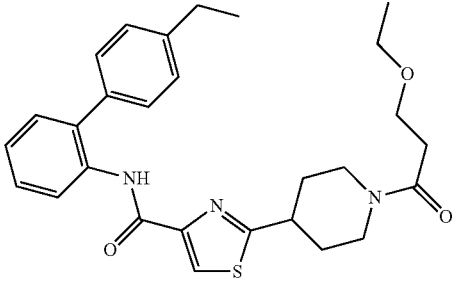 | |
| 1137 | 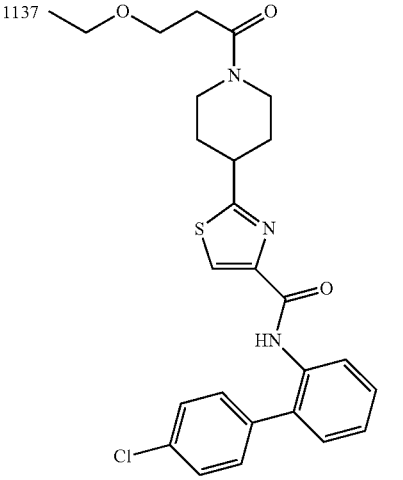 N-(4'-chlorobiphenyl-2-yl)-2-[1-(3-ethoxypropanoyl)piperidin-4-yl]-1,3-thiazole-4-carboxamide | |

TABLE 1-continued
| No. | FORMULA | NMR or mass |
|---|---|---|
| 1138 | 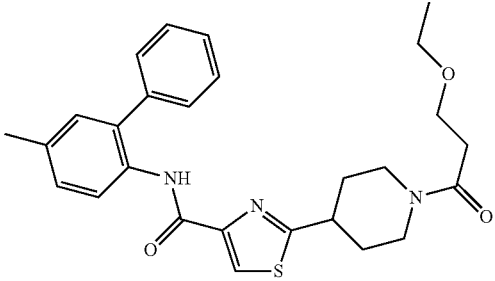 | |
| 1139 | 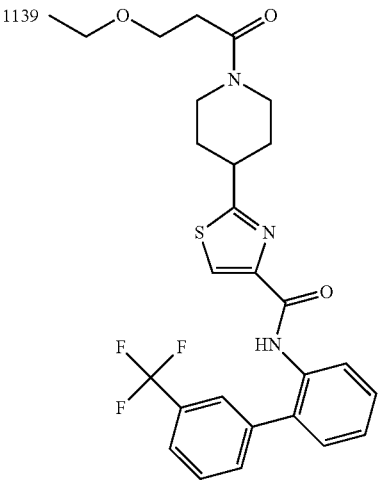 | |
| 1140 | 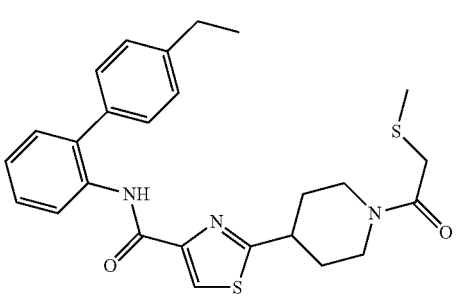 | |

TABLE 1-continued
| No. | FORMULA | NMR or mass |
|---|---|---|
| 1141 | 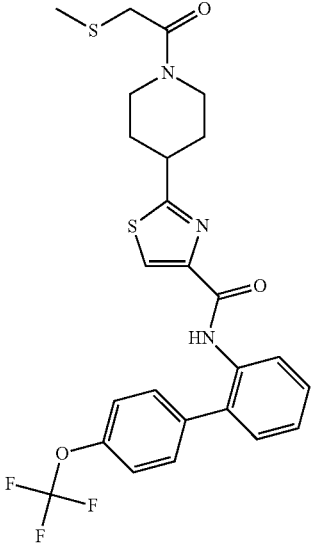 2-{1-[(methylthio)acetyl]piperidin-4-yl}-N-[4'-(trifluoromethoxy)biphenyl-2-yl]-1,3-thiazole-4-carboxamide | |
| 1142 | 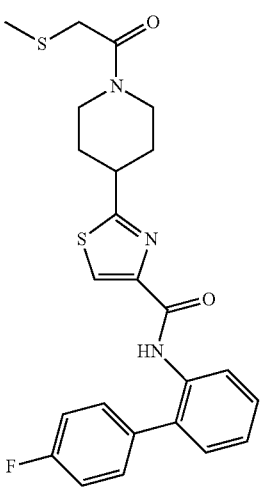 | |

| No. | FORMULA | NMR or mass |
|-----|---------|-------------|
| 1143 | 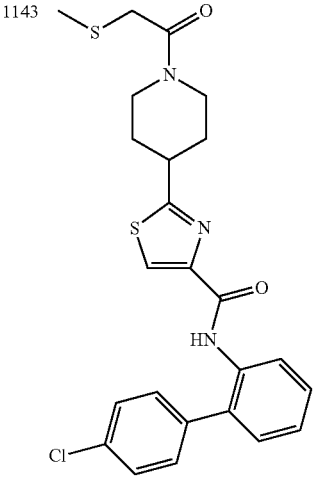 N-(4'-chlorobiphenyl-2-yl)-2-(1-[(methylthio)acetyl]piperidin-4-yl}-1,3-thiazole-4-carboxamide | |
| 1144 | 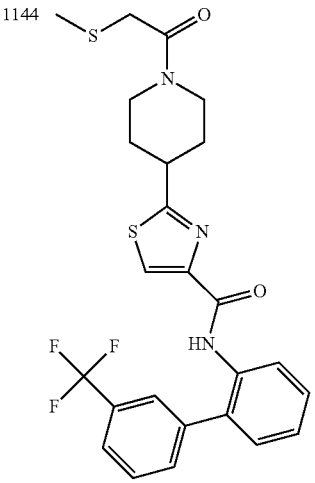 2-{1-[(methylthio)acetyl]piperidin-4-yl}-N-[3'-(trifluoromethyl)biphenyl-2-yl]-1,3-thiazole-4-carboxamide | |

| No. | FORMULA | NMR or mass |
|---|---|---|
| 1145 | 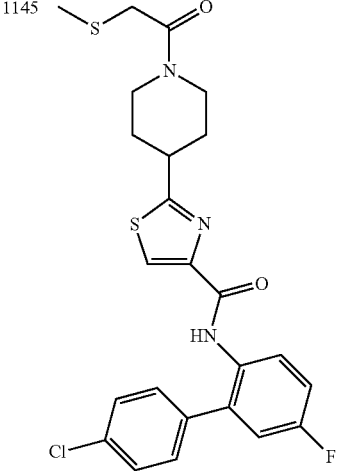 N-(4'-chloro-5-fluorobiphenyl-2-yl)-2-{1-[(methylthio)acetyl]piperidin-4-yl}-1,3-thiazole-4-carboxamide | |
| 1146 | 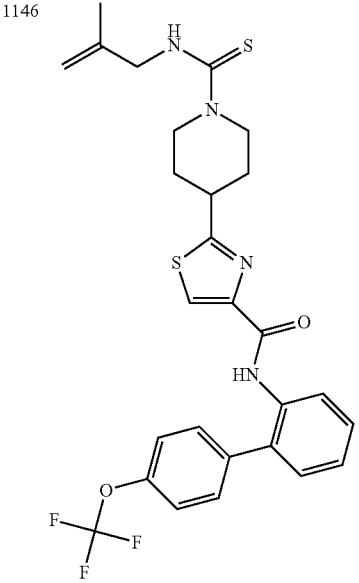 2-(1-{[(2-methylprop-2-en-1-yl)amino]carbonothioyl}piperidin-4-yl)-N-[4'-(trifluoromethoxy)biphenyl-2-yl]-1,3-thiazole-4-carboxamide | |
| 1147 | 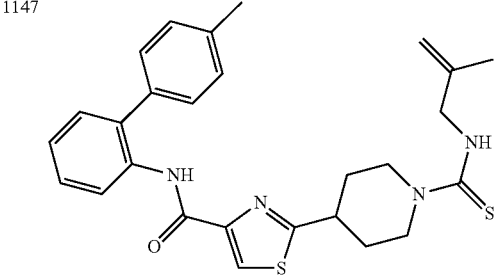 | |

TABLE 1-continued
| No. | FORMULA | NMR or mass |
|---|---|---|
| 1148 | 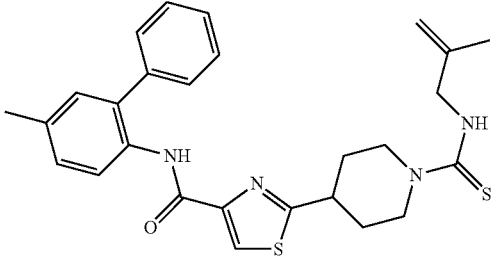 | |
| 1149 | 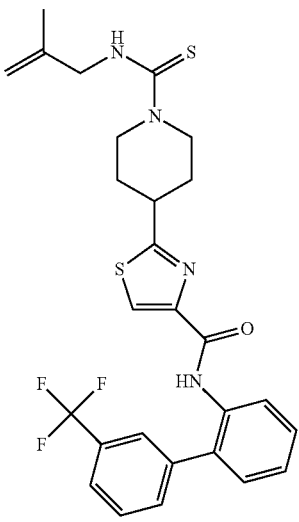 2-(1-{[(2-methylprop-2-en-1-yl)amino]carbonothioyl}piperidin-4-yl)-N-[3'-(trifluoromethyl)biphenyl-2-yl]-1,3-thiazole-4-carboxamide | |
| 1150 | 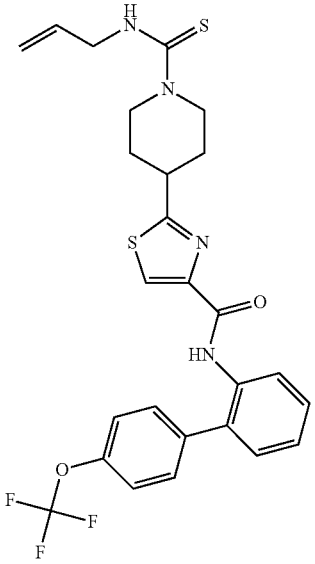 2-{1-[(allylamino)carbonothioyl]piperidin-4-yl}-N-[4'-(trifluoromethoxy)-biphenyl-2-yl]-1,3-thiazole-4-carboxamide | |

TABLE 1-continued

| No. | FORMULA | NMR or mass |
|---|---|---|
| 1151 | | |
| 1152 | | |
| 1153 | 2-{1-[(allylamino)carbonothioyl]piperidin-4-yl}-N-[3'-(trifluoromethyl)biphenyl-2-yl]-1,3-thiazole-4-carboxamide | |

TABLE 1-continued

| No. | FORMULA | NMR or mass |
|---|---|---|
| 1154 | 2-(1-{[(2-furylmethyl)amino]carbonothioyl}piperidin-4-yl)-N-[4'-(trifluoro-methoxy)biphenyl-2-yl]-1,3-thiazole-4-carboxamide | |
| 1155 | | |
| 1156 | 2-(1-{[(2-furylmethyl)amino]carbonothioyl}piperidin-4-yl)-N-[3'-(trifluoro-methyl)biphenyl-2-yl]-1,3-thiazole-4-carboxamide | |

TABLE 1-continued
| No. | FORMULA | NMR or mass |
|---|---|---|
1157
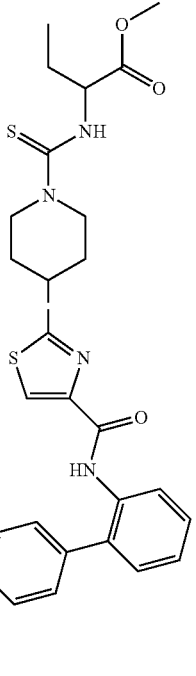
methyl 2-[({4-[4-({[4'-(trifluoromethoxy)biphenyl-2-yl]amino}carbonyl)-1,3-thiazol-2-yl]piperidin-1-yl}carbonothioyl)amino]butanoate
1158
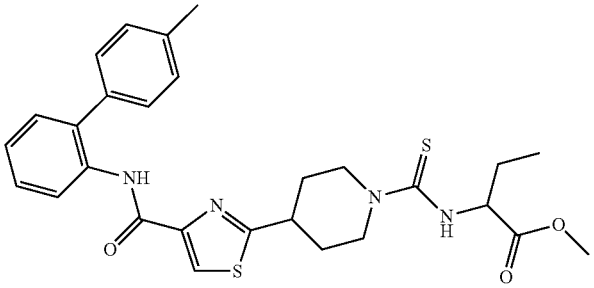
1159
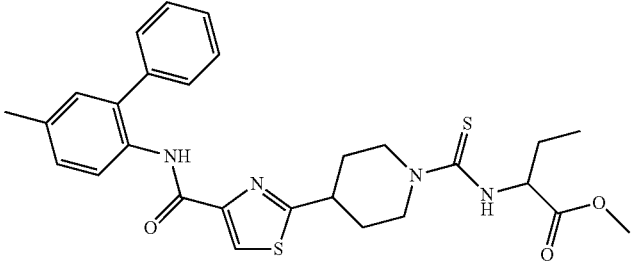

TABLE 1-continued
| No. | FORMULA | NMR or mass |
|---|---|---|
| 1160 | 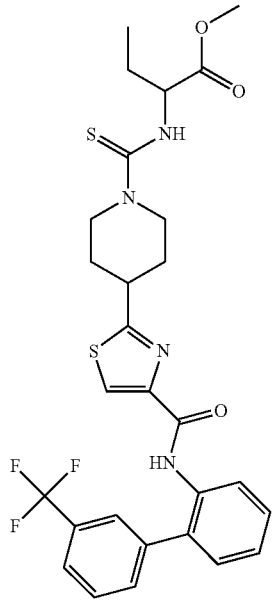 methyl 2-[({4-[4-({[3'-(trifluoromethyl)biphenyl-2-yl]amino}carbonyl)-1,3-thiazol-2-yl]piperidin-1-yl}carbonothioyl)amino]butanoate | |
| 1161 | 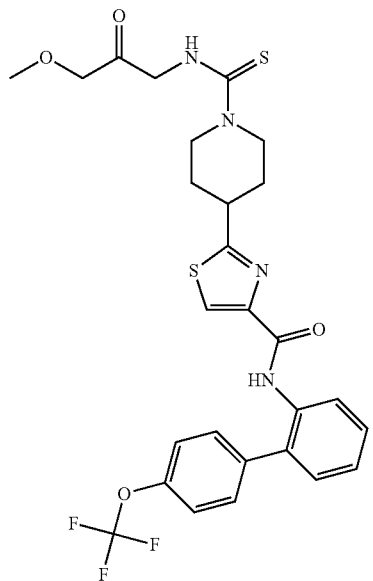 ethyl N-({4-[4-({[4'-(trifluoromethoxy)biphenyl-2-yl]amino}carbonyl)-1,3-thiazol-2-yl]piperidin-1-yl}carbonothioyl)glycinate | |

TABLE 1-continued

| No. | FORMULA | NMR or mass |
|---|---|---|
| 1162 | | |
| 1163 | | |
| 1164 | | | ethyl N-({4-[4-({[3'-(trifluoromethyl)biphenyl-2-yl]amino}carbonyl)-1,3-thiazol-2-yl]piperidin-1-yl}carbonothioyl)glycinate

TABLE 1-continued
| No. | FORMULA | NMR or mass |
|---|---|---|
| 1165 | 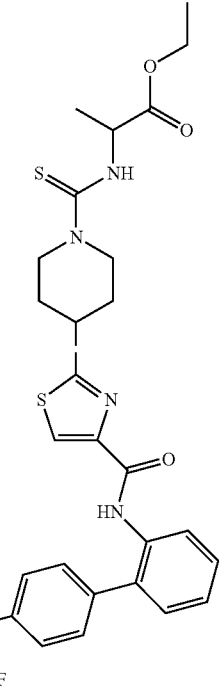 ethyl N-({4-[4-({[4'-(trifluoromethoxy)biphenyl-2-yl]amino}carbonyl)-1,3-thiazol-2-yl]piperidin-1-yl}carbonothioyl)alaninate | |
| 1166 | 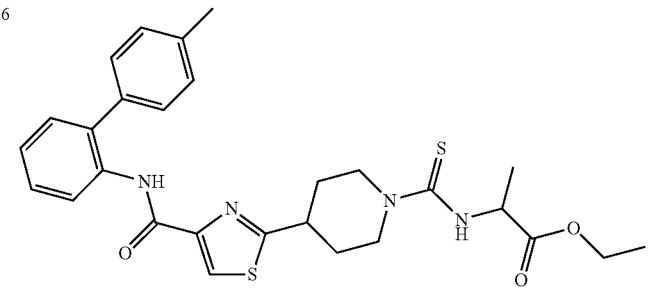 | |
| 1167 | 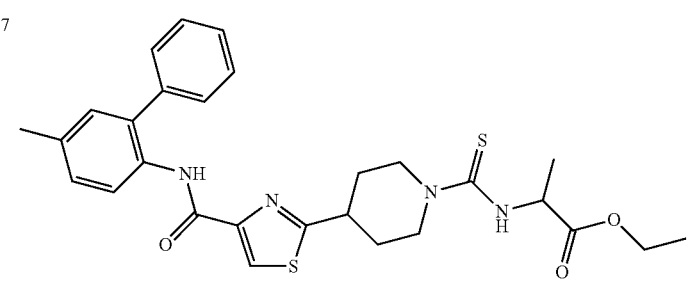 | |

TABLE 1-continued
| No. | FORMULA | NMR or mass |
|---|---|---|
1168
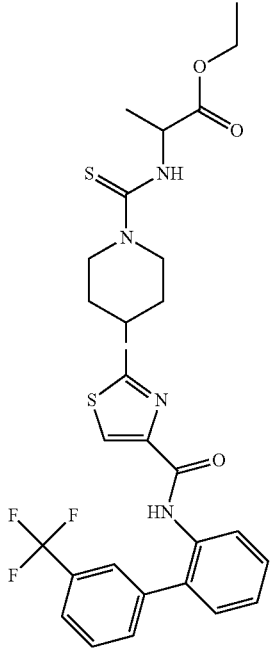
ethyl N-({4-[4-({[3'-(trifluoromethyl)biphenyl-2-yl]amino}carbonyl)-1,3-thiazol-2-yl]piperidin-1-yl}carbonothioyl)alaninate
1169
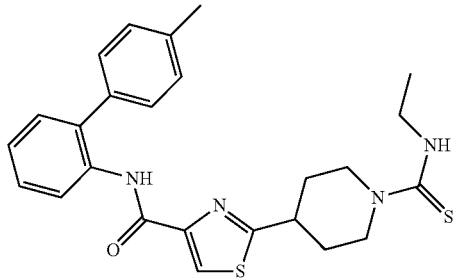
1170
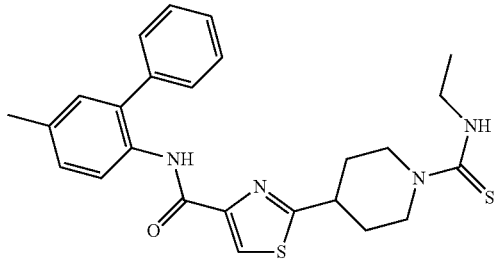

TABLE 1-continued
| No. | FORMULA | NMR or mass |
|---|---|---|
| 1171 | 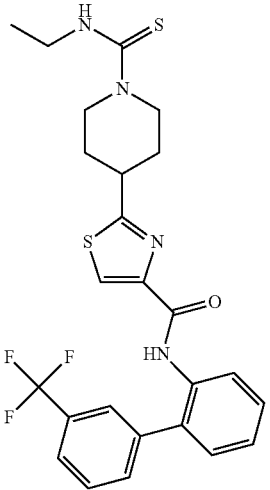 2-{1-[(ethylamino)carbonothioyl]piperidin-4-yl}-N-[3'-(trifluoromethyl)-biphenyl-2-yl]-1,3-thiazole-4-carboxamide | |
| 1172 | 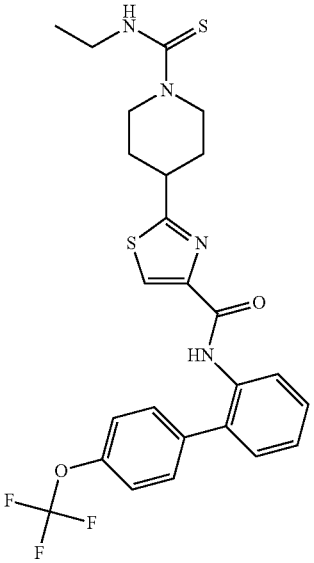 2-{1-[(propylamino)carbonothioyl]piperidin-4-yl}-N-[4'-(trifluoromethoxy)-biphenyl-2-yl]-1,3-thiazole-4-carboxamide | |
| 1173 | 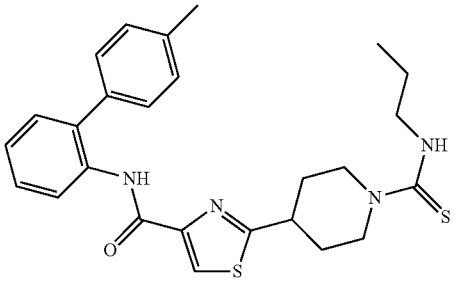 | |

TABLE 1-continued
| No. | FORMULA | NMR or mass |
|---|---|---|
| 1174 | 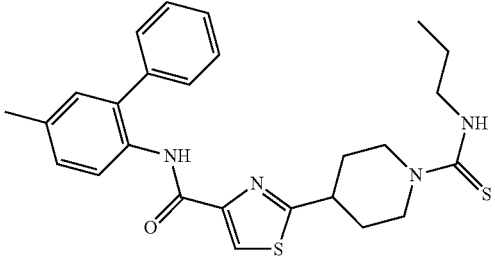 | |
| 1175 | 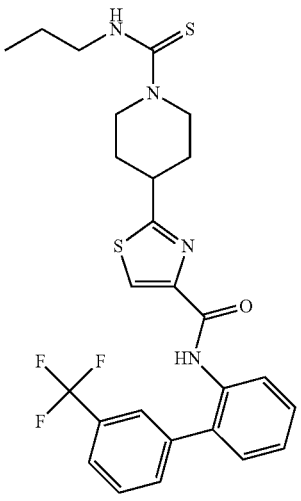
2-{1-[(propylamino)carbonothioyl]piperidin-4-yl}-N-[3'-(trifluoromethyl)-biphenyl-2-yl]-1,3-thiazole-4-carboxamide | |
| 1176 | 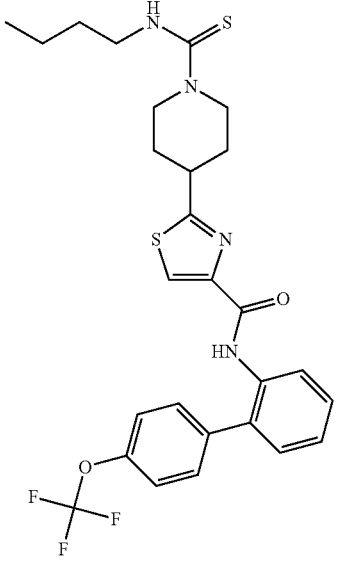
2-{1-[(butylamino)carbonothioyl]piperidin-4-yl}-N-[4'-(trifluoromethoxy)-biphenyl-2-yl]-1,3-thiazole-4-carboxamide | |

TABLE 1-continued

| No. | FORMULA | NMR or mass |
|---|---|---|
| 1177 | | |
| 1178 | | |
| 1179 | 2-{1-[(butylamino)carbonothioyl]piperidin-4-yl}-N-[3'-(trifluoromethyl)-biphenyl-2-yl]-1,3-thiazole-4-carboxamide | |

TABLE 1-continued

| No. | FORMULA | NMR or mass |
|---|---|---|

1180

2-{1-[(pentylamino)carbonothioyl]piperidin-4-yl}-N-[4'-(trifluoromethoxy)-biphenyl-2-yl]-1,3-thiazole-4-carboxamide

1181

1182

TABLE 1-continued
| No. | FORMULA | NMR or mass |
|---|---|---|
| 1183 | 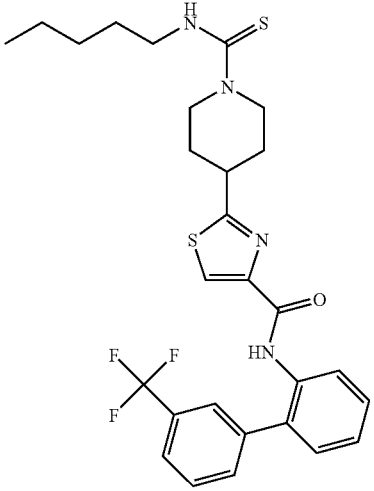 2-{1-[(pentylamino)carbonothioyl]piperidin-4-yl}-N-[3'-(trifluoromethyl)-biphenyl-2-yl]-1,3-thiazole-4-carboxamide | |
| 1184 | 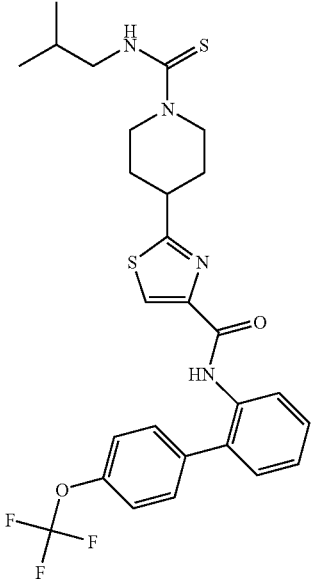 2-{1-[(isobutylamino)carbonthioyl]piperidin-4-yl}-N-[4'-(trifluoromethoxy)-biphenyl-2-yl]-1,3-thiazole-4-carboxamide | |
| 1185 | 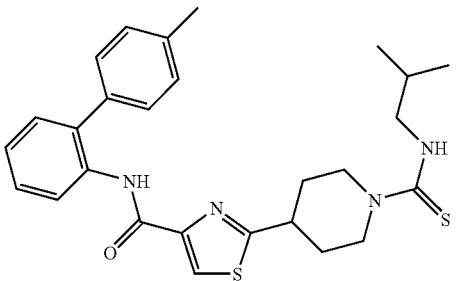 | |

TABLE 1-continued
| No. | FORMULA | NMR or mass |
|---|---|---|
| 1186 | 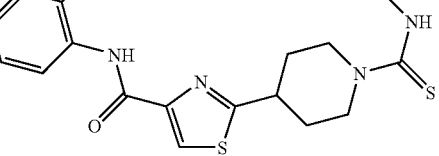 | |
| 1187 | 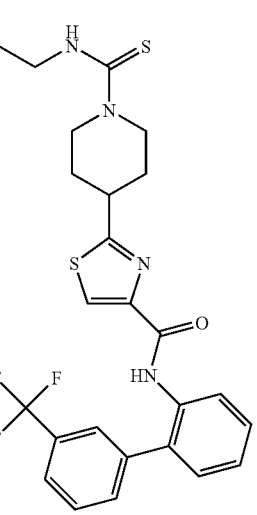 | |
| 1188 | 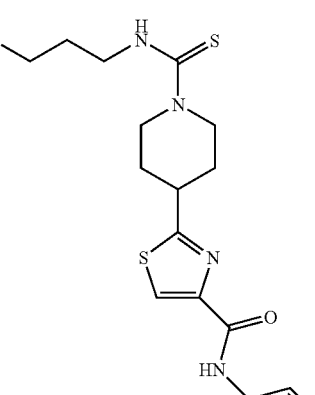 | |
2-(1-{[(3-methoxypropyl)amino]carbonthioyl}piperidin-4-yl)-N-[4'-(trifluoromethoxy)biphenyl-2-yl]-1,3-thiazole-4-carboxamide TABLE 1-continued
| No. | FORMULA | NMR or mass |
|---|---|---|
| 1189 | 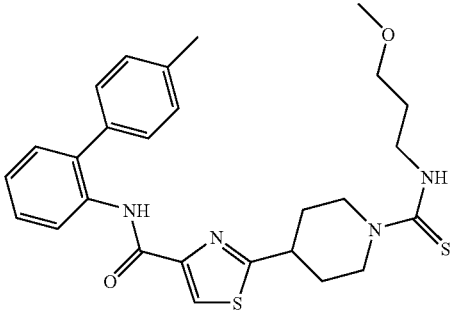 | |
| 1190 | 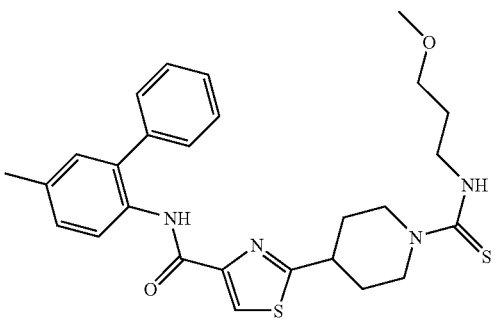 | |
| 1191 | 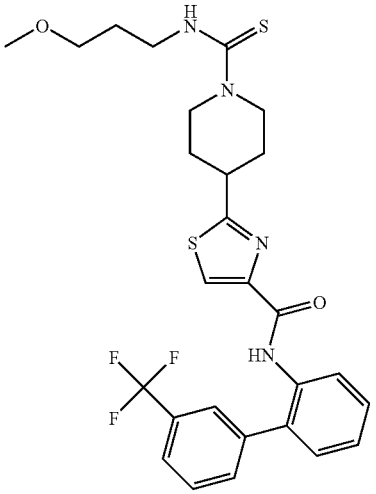 | |
2-(1-{[(3-methoxyptoply)amino]carbonothioyl}piperidin-4-yl)-N-[3'-(trifluoromethyl)biphenyl-2-yl]-1,3-thiazole-4-carboxamide

| No. | FORMULA | NMR or mass |
|---|---|---|
| 1192 | 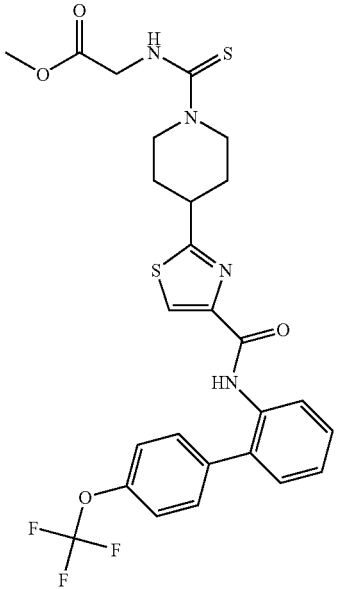 methyl N-({4-[4-({[4'-(trifluoromethoxy)biphenyl-2-yl]amino}carbonyl)-1,3-thiazol-2-yl]piperidin-1-yl}carbonothioyl)glycinate | |
| 1193 | 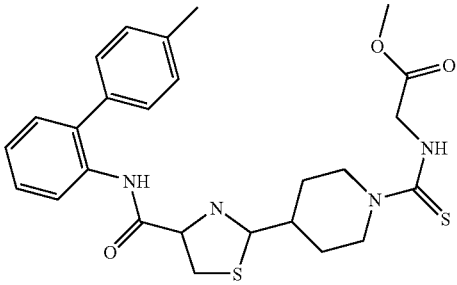 | |
| 1194 | 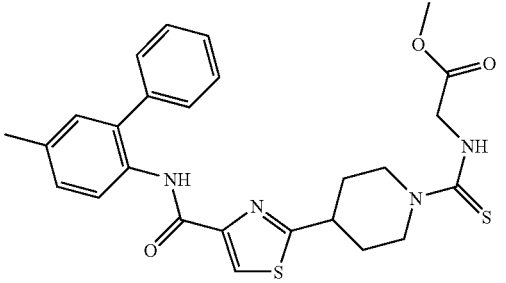 | |

TABLE 1-continued
| No. | FORMULA | NMR or mass |
|---|---|---|
1195
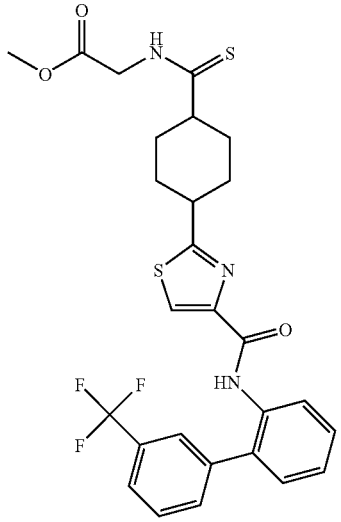
methyl N-({4-[4-({[3'-(trifluoromethyl)biphenyl-2-yl]amino}carbonyl)-1,3-thiazol-2-yl]piperidin-1-yl}carbonothioyl)glycinate
1196
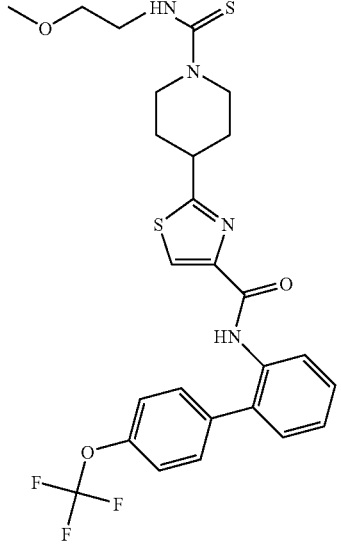
2-(1-{[(2-methoxyethyl)amino]carbonothioyl}poperidin-4-yl)-N-[4'-(trifluoromethoxy)biphenyl-2-yl]-1,3-thiazole-4-carboxamide
1197
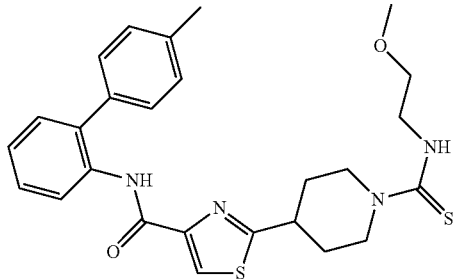

TABLE 1-continued
| No. | FORMULA | NMR or mass |
|---|---|---|
| 1198 | 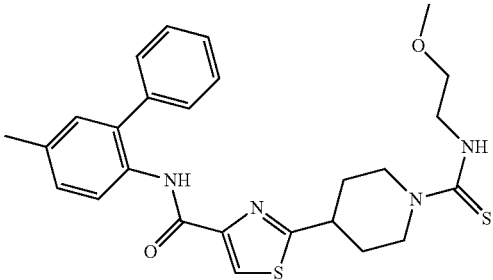 | |
| 1199 | 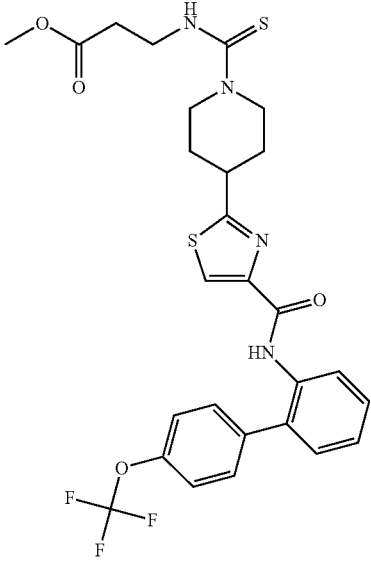 methyl N-({4-[4-({[4'-(trifluoromethoxy)biphenyl-2-yl]amino}carbonyl)-1,3-thiazol-2-yl]piperidin-1-yl}carbonothioyl)-beta-alaninate | |
| 1200 | 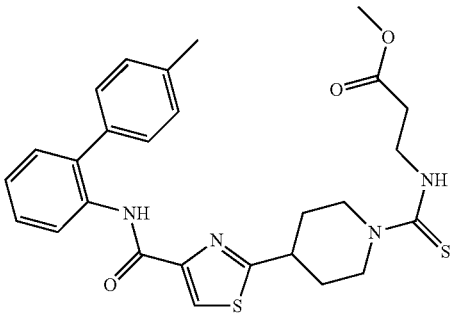 | |
| 1201 | 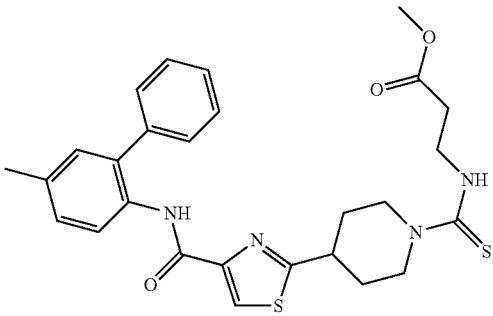 | |

TABLE 1-continued

| No. | FORMULA | NMR or mass |
|-----|---------|-------------|

1202

1203

2-(1-{[(1-methylbutyl)amino]carbonothioyl}piperidin-4-yl)-N-[4'-(trifluoro-methoxy)biphenyl-2-yl]-1,3-thiazole-4-carboxamide

1204

TABLE 1-continued
| No. | FORMULA | NMR or mass |
|---|---|---|
| 1205 | 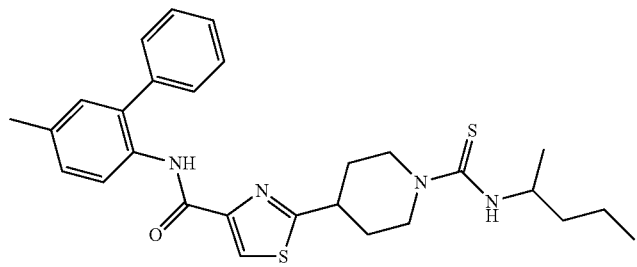 | |
| 1206 | 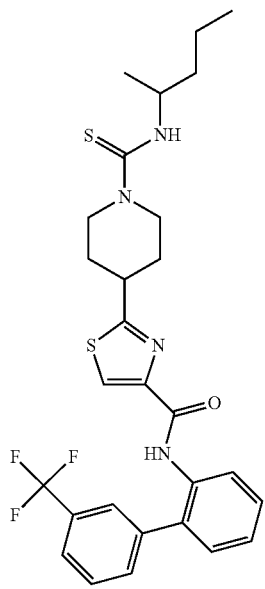 2-(1-{[(1-methylbutyl)amino]carbonothioyl}piperidin-4-yl)-N-[3'-(trifluoro-methyl)biphenyl-2-yl]-1,3-thiazole-4-carboxamide | |
| 1207 | 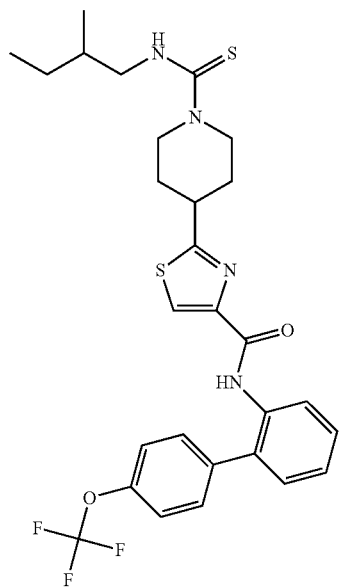 2-(1-{[(2-methylbutyl)amino]carbonothioyl}piperidin-4-yl)-N-[4'-(trifluoro-methoxy)biphenyl-2-yl]-1,3-thiazole-4-carboxamide | |

TABLE 1-continued
| No. | FORMULA | NMR or mass |
|---|---|---|
| 1208 | 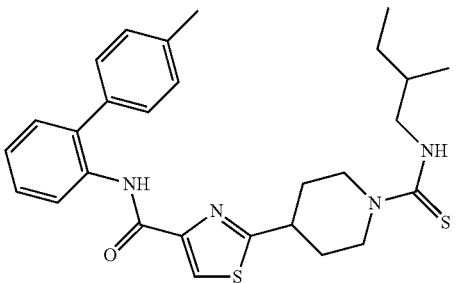 | |
| 1209 | 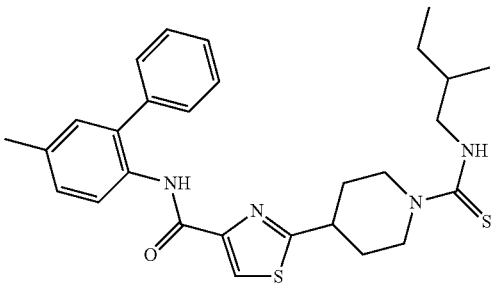 | |
| 1210 | 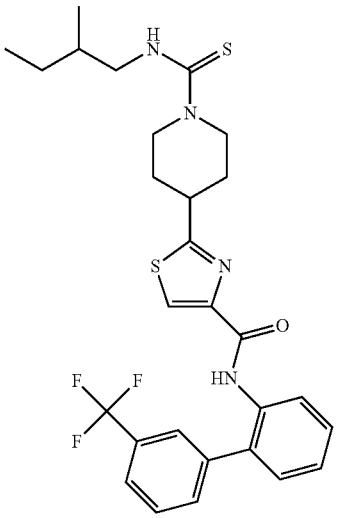 | |
2-(1-{[(2-methylbutyl)amino]carbonothioyl}piperidin-4-yl)-N-[3'-(trifluoro-methyl)biphenyl-2-yl]-1,3-thiazole-4-carboxamide
| 1211 | 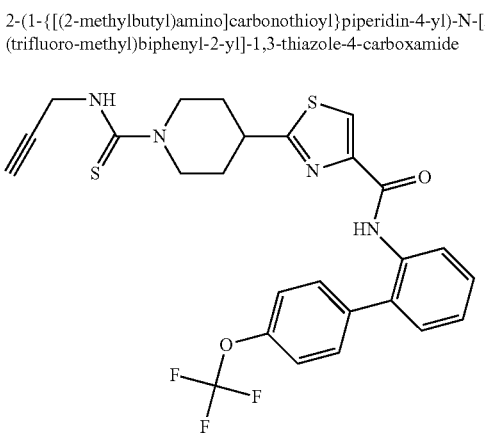 | |

TABLE 1-continued
| No. | FORMULA | NMR or mass |
|---|---|---|
| 1212 | 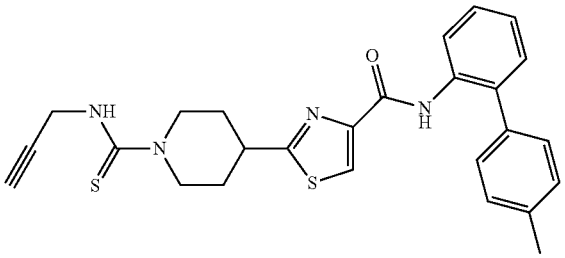 | |
| 1213 | 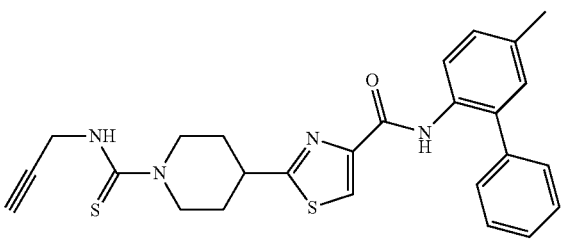 | |
| 1214 | 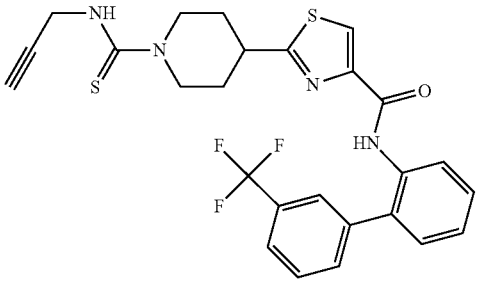 | |
| 1215 | 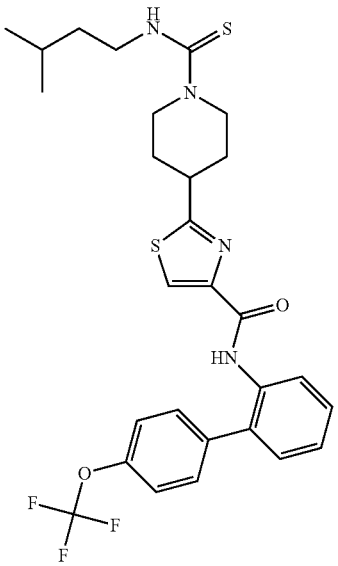 | |
2-(1-{[(3-methylbutyl)amino]carbonothioyl}piperidin-4-yl)-N-[4'-(trifluoro-methoxy)biphenyl-2-yl]-1,3-thiazole-4-carboxamide TABLE 1-continued
| No. | FORMULA | NMR or mass |
|---|---|---|
| 1216 | 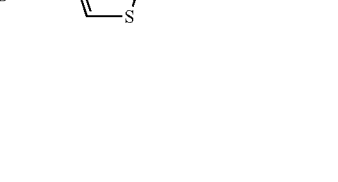 | |
| 1217 | 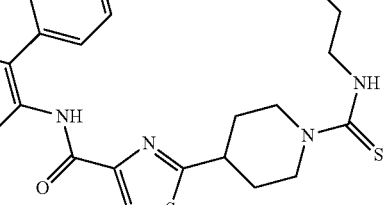 | |
| 1218 | 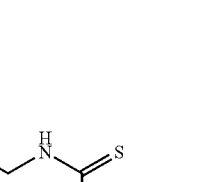 | |

TABLE 1-continued
| No. | FORMULA | NMR or mass |
|---|---|---|
| 1219 | 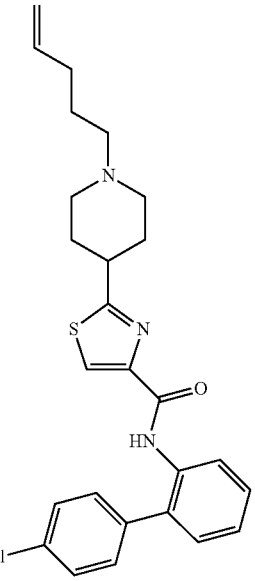 N-(4'-chlorobiphenyl-2-yl)-2-(1-pent-4-en-1-ylpiperidin-4-yl)-1,3-thiazole-4-carboxamide | |
| 1220 | 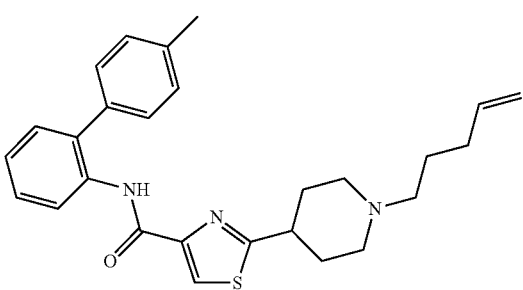 | |
| 1221 | 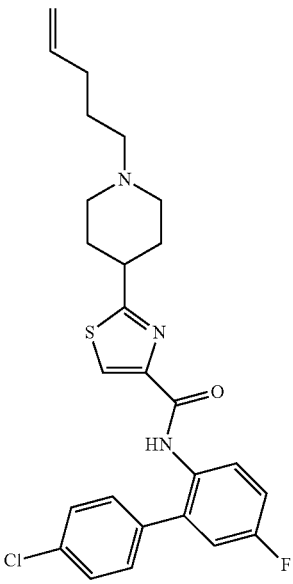 N-(4'-chloro-5-fluorobiphenyl-2-yl)-2-(1-pent-4-en-1-ylpiperidin-4-yl)-1,3-thiazole-4-carboxamide | |

TABLE 1-continued
| No. | FORMULA | NMR or mass |
|---|---|---|
| 1222 | 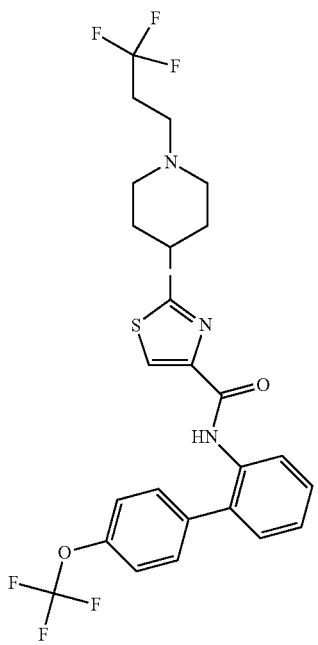 N-[4'-(trifluoromethoxy)biphenyl-2-yl]-2-[1-(3,3,3-trifluoropropyl)piperidin-4-yl]-1,3-thiazole-4-carboxamide | |
| 1223 | 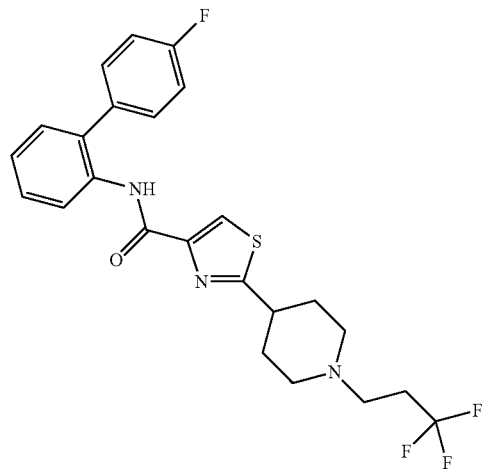 N-(4'-fluorobiphenyl-2-yl)-2-[1-(3,3,3-trifluoropropyl)piperidin-4-yl]-1,3-thiazole-4-carboxamide | |

| No. | FORMULA | NMR or mass |
|---|---|---|
| 1224 | 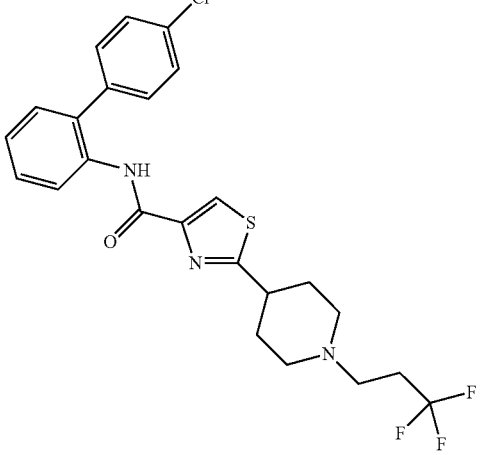 N-(4'-chlorobiphenyl-2-yl)-2-[1-(3,3,3-trifluoropropyl)piperidin-4-yl]-1,3-thiazole-4-carboxamide | |
| 1225 | 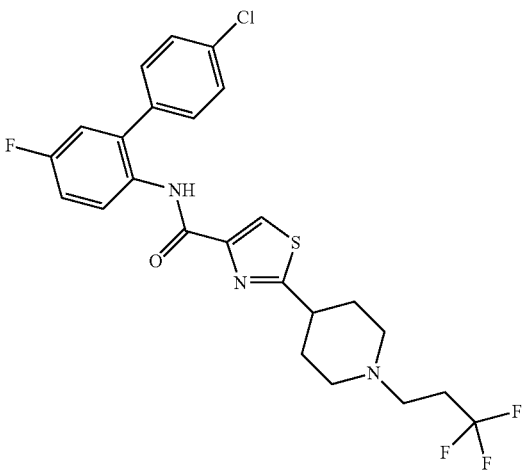 N-(4'-chloro-5-fluorobiphenyl-2-yl)-2-[1-(3,3,3-trifluoropropyl)piperidin-4-yl]-1,3-thiazole-4-carboxamide | |

TABLE 1-continued
| No. | FORMULA | NMR or mass |
|---|---|---|
| 1226 | 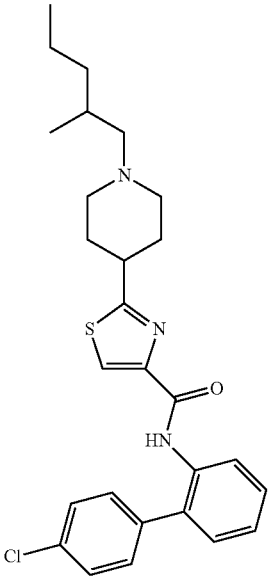 N-(4'-chlorobiphenyl-2-yl)-2-[1-(2-methylpentyl)piperidin-4-yl]-1,3-thiazole-4-carboxamide | |
| 1227 | 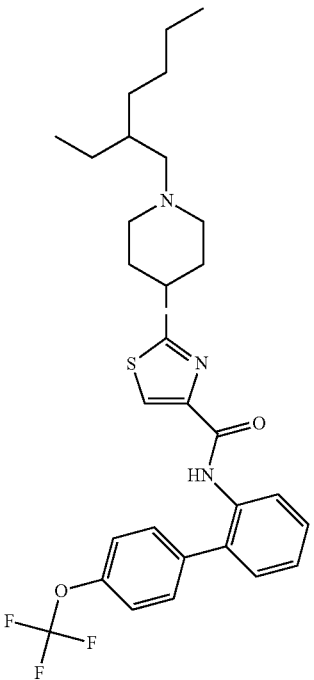 2-[1-(2-ethylhexyl)piperidin-4-yl]-N-[4'-(trifluoromethoxy)biphenyl-2-yl]-1,3-thiazole-4-carboxamide | |

TABLE 1-continued
| No. | FORMULA | NMR or mass |
|---|---|---|
| 1228 | 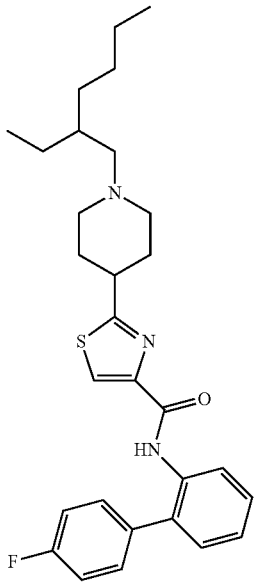 2-[1-(2-ethylhexyl)piperidin-4-yl]-N-(4'-fluorobiphenyl-2-yl)-1,3-thiazole-4-carboxamide | |
| 1229 | 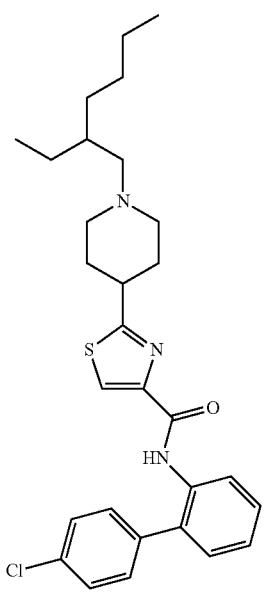 N-(4'-chlorobiphenyl-2-yl)-2-[1-(2-ethylhexyl)piperidin-4-yl]-1,3-thiazole-4-carboxamide | |
| 1230 | 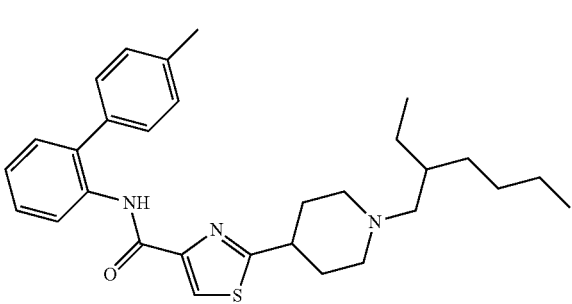 | |

TABLE 1-continued
| No. | FORMULA | NMR or mass |
|---|---|---|
| 1231 | 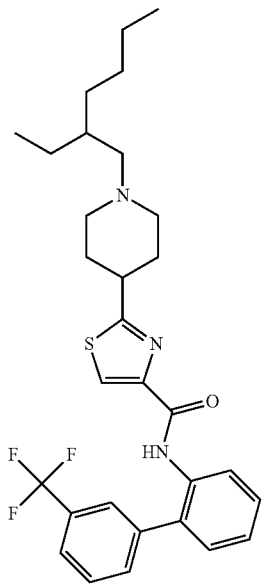<br>2-[1-(2-ethylhexyl)piperidin-4-yl]-N-[3'-(trifluoromethyl)biphenyl-2-yl]-1,3-thiazole-4-carboxamide | |
| 1232 | 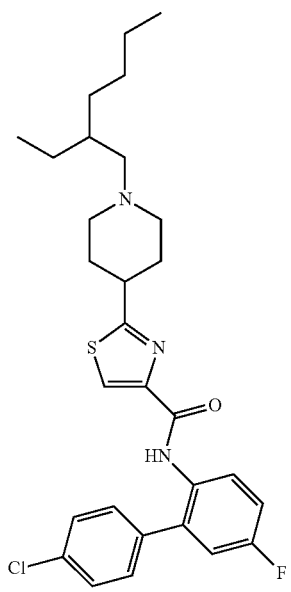<br>N-(4'-chloro-5-fluorobiphenyl-2-yl)-2-[1-(2-ethylhexyl)piperidin-4-yl]-1,3-thiazole-4-carboxamide | |

| No. | FORMULA | NMR or mass |
|---|---|---|
| 1233 | 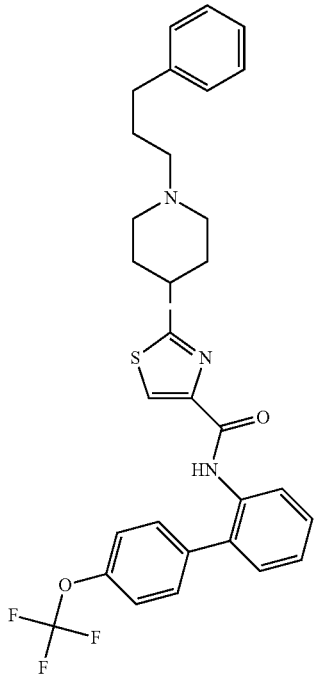 2-[1-(3-phenylpropyl)piperidin-4-yl]-N-[4'-(trifluoromethoxy)biphenyl-2-yl]-1,3-thiazole-4-carboxamide | |
| 1234 | 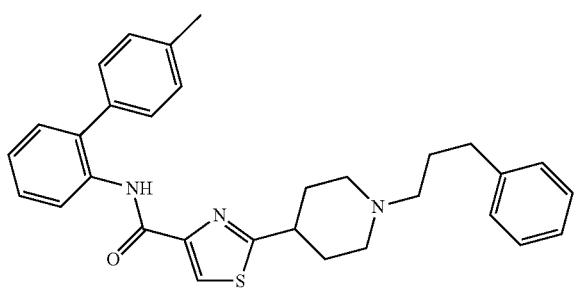 | |
| 1235 | 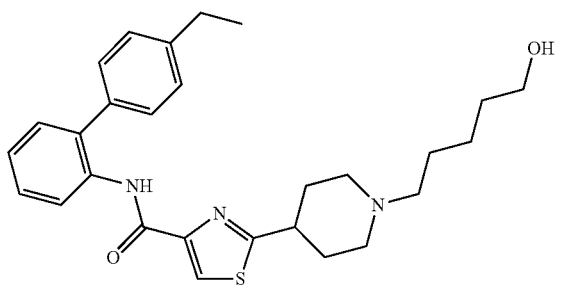 | |

| No. | FORMULA | NMR or mass |
|---|---|---|
| 1236 | 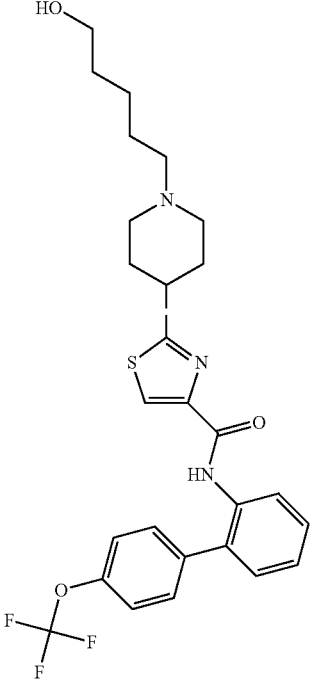 2-[1-(5-hydroxypentyl)piperidin-4-yl]-N-[4'-(trifluoromethoxy)biphenyl-2-yl]-1,3-thiazole-4-carboxamide | |
| 1237 | 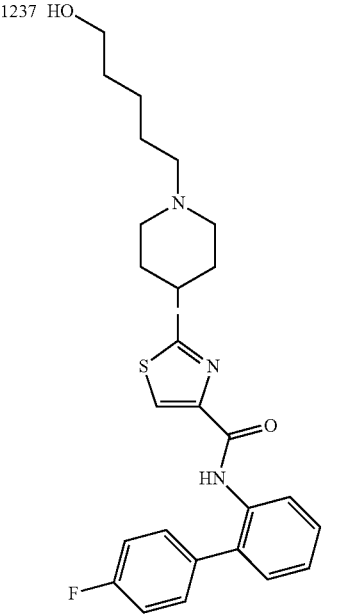 N-(4'-fluorobiphenyl-2-yl)-2-[1-(5-hydroxypentyl)piperidin-4-yl]-1,3-thiazole-4-carboxamide | |

TABLE 1-continued
| No. | FORMULA | NMR or mass |
|---|---|---|
1238 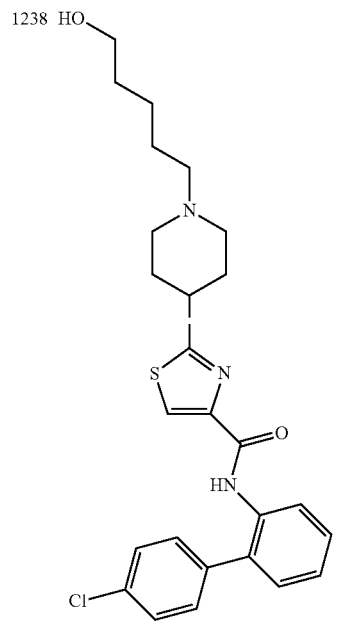
N-(4'-chlorobiphenyl-2-yl)-2-[1-(5-hydroxypentyl)piperidin-4-yl]-1,3-thiazole-4-carboxamide
1239 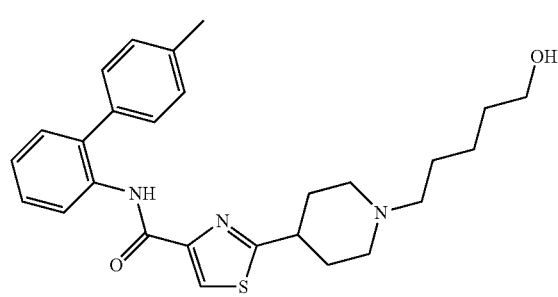
1240 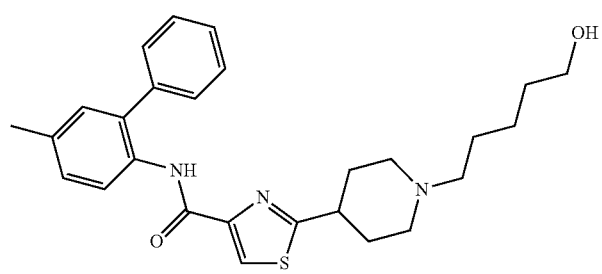

TABLE 1-continued
| No. | FORMULA | NMR or mass |
|---|---|---|
1241 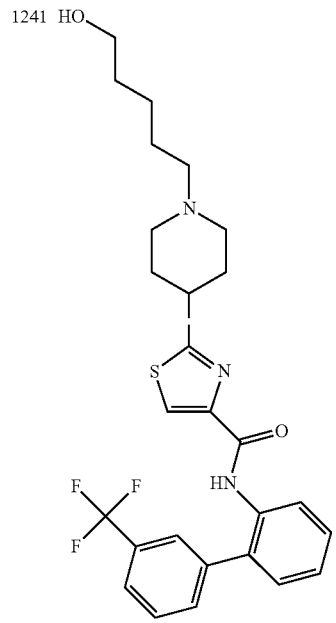
2-[1-(5-hydroxypentyl)piperidin-4-yl]-N-[3'-trifluoromethyl)biphenyl-2-yl]-1,3-thiazole-4-carboxamide
1242 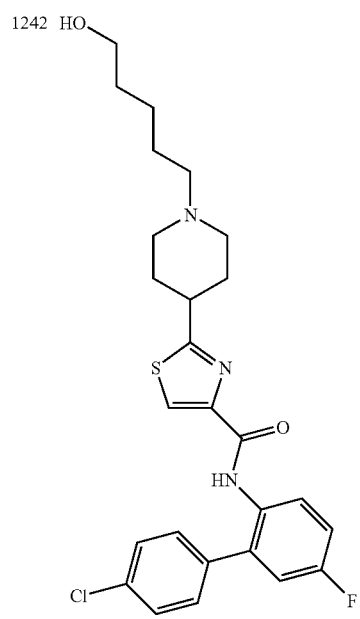
N-(4'-chloro-5-fluorobiphenyl-2-yl)-2-[1-(5-hydroxypentyl)piperidin-4-yl]-1,3-thiazole-4-carboxamide TABLE 1-continued
| No. | FORMULA | NMR or mass |
|---|---|---|
1243
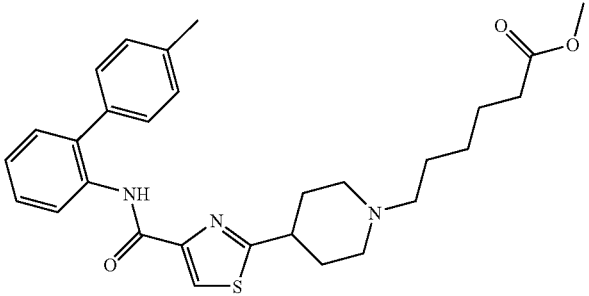
1244
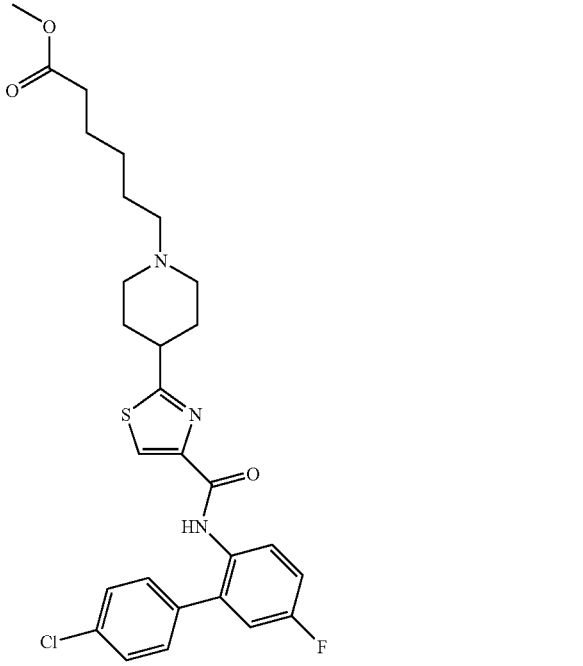
methyl 6-[4-(-4-{[(4'-chloro-5-fluorobiphenyl-2-yl)amino]carbonyl}-1,3-thiazol-2-yl)piperidin-1-yl]hexanoate
1245
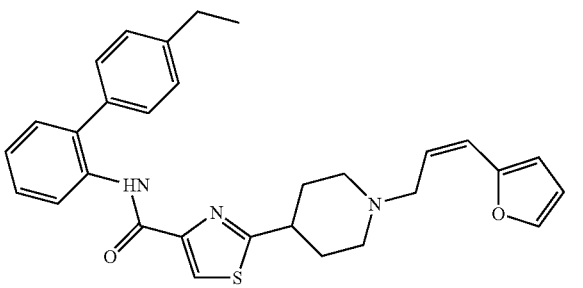

US 7,674,803 B2
873 874
TABLE 1-continued
| No. | FORMULA | NMR or mass |
|---|---|---|
1246
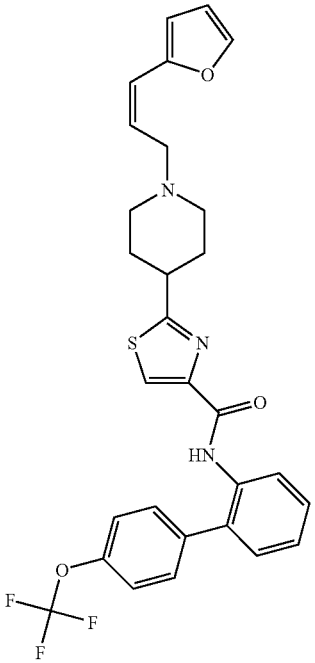
2-{1-[(2Z)-3-(2-furyl)prop-2-en-1-yl]piperidin-4-yl}-N-[4'-
(trifluoromethoxy)-biphenyl-2-yl]-1,3-thiazole-4-carboxamide
1247
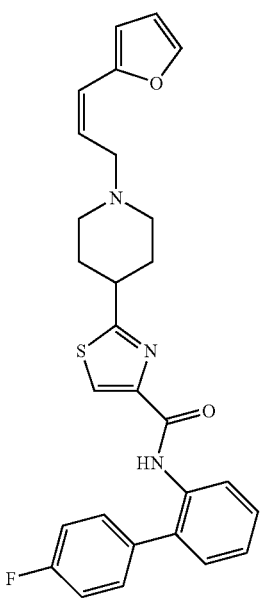
N-(4'-fluorobiphenyl-2-yl)-2-{1-[(2z)-3-(2-furyl)prop-2-en-1-yl]piperidin-
4-yl}-1,3-thiazole-4-carboxamide

| No. | FORMULA | NMR or mass |
|---|---|---|
1248
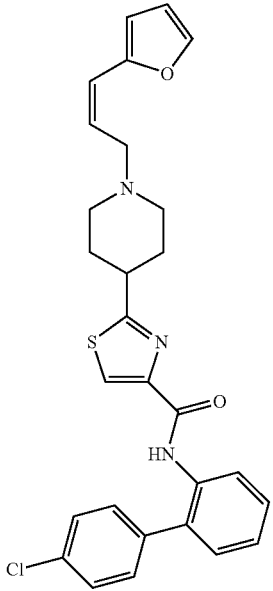
N-(4'-chlorobiphenyl-2-yl-2-{1-[(2Z)-3-(2-furyl)prop-2-en-1-yl]piperidin-4-yl}-1,3-thiazole-4-carboxamide
1249
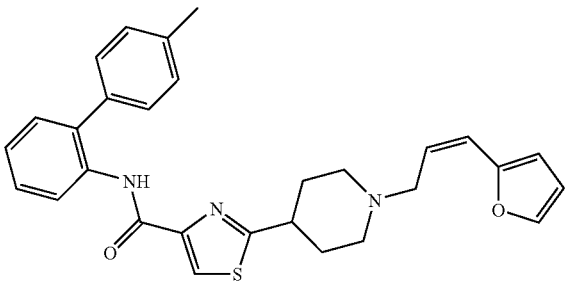
1250
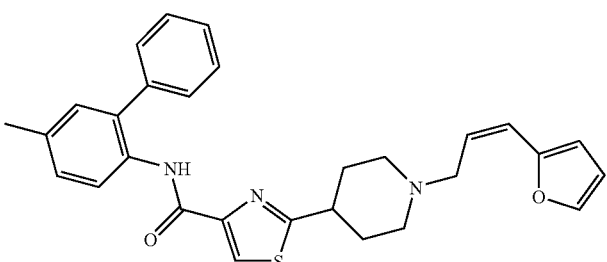

TABLE 1-continued
| No. | FORMULA | NMR or mass |
|---|---|---|
| 1251 | 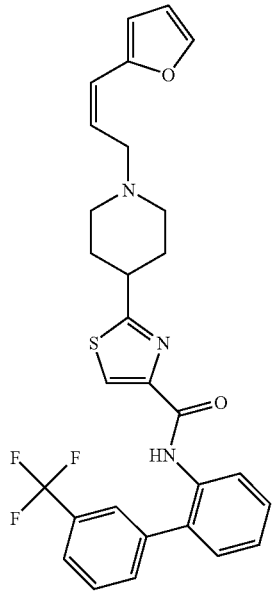 2-{1-[(2Z)-3-(2-furyl)prop-2-en-1-yl]piperidin-4-yl}-N-[3'-(trifluoromethyl)-biphenyl-2-yl]-1,3-thiazole-4-carboxamide | |
| 1252 | 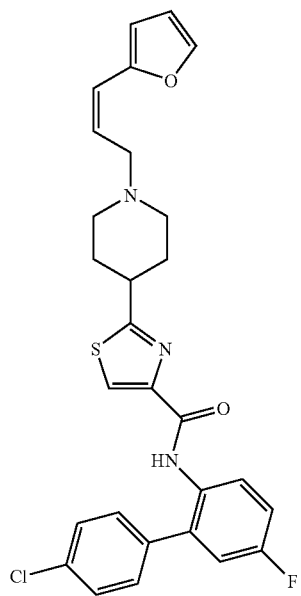 N-(4'-chloro-5-fluorobiphenyl-2-yl)-2-{1-[(2Z)-3-(2-furyl)prop-2-en-1-yl]-piperidin-4-yl}-1,3-thiazole-4-carboxamide | |

| No. | FORMULA | NMR or mass |
|---|---|---|
| 1253 | 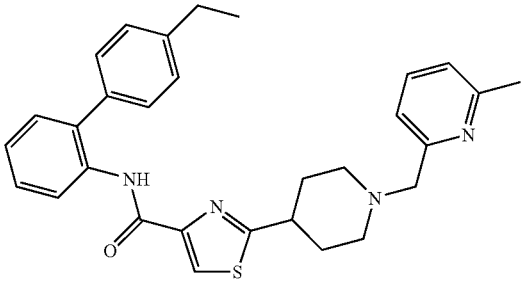 | |
| 1254 | 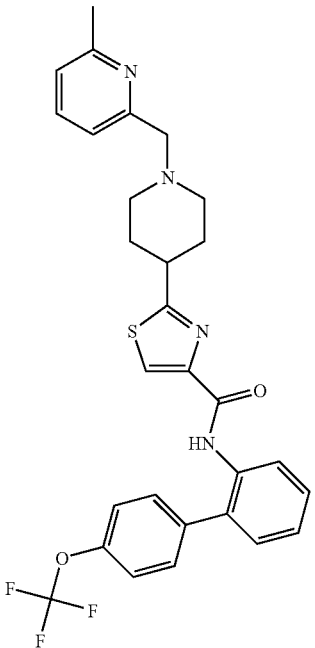 2-{1-[(6-methylpyridin-2-yl)methyl]piperidin-4-yl)-N-[4'-(trifluoromethoxy)-biphenyl-2-yl]-1,3-thiazole-4-carboxamide | |

TABLE 1-continued
| No. | FORMULA | NMR or mass |
|-----|---------|-------------|
| 1255 | 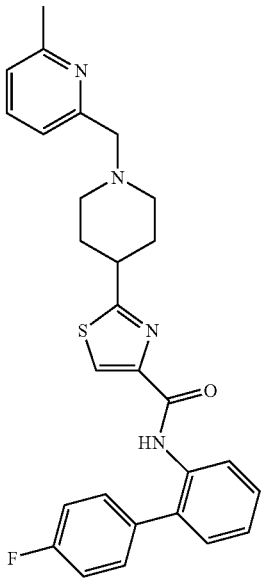 N-(4'-flurobiphenyl-2-yl)-2-{1-[(6-methylpyridin-2-yl)methyl]piperidin-4-yl}-1,3-thiazole-4-carboxamide | |
| 1256 | 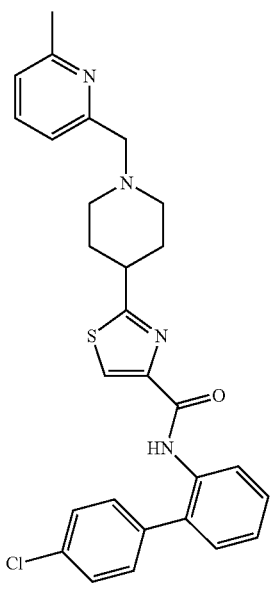 N-(4'-chlorobiphenyl-2-yl)-2-{1-[(6-methylpyridin-2-yl)methyl]piperidin-4-yl}-1,3-thiazole-4-carboxamide | |
| 1257 | 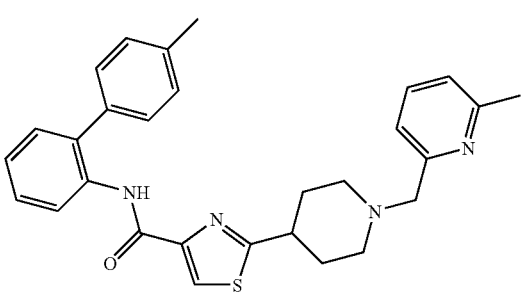 | |

| No. | FORMULA | NMR or mass |
|---|---|---|
| 1258 | 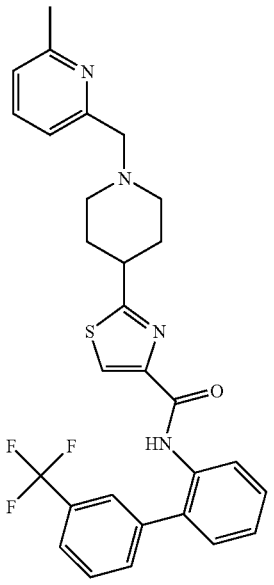 2-{1-[(6-methylpyridin-2-yl)methyl]piperidin-4-yl}-N-[3'-(trifluoromethyl)-biphenyl-2-yl]-1,3-thiazole-4-carboxamide | |
| 1259 | 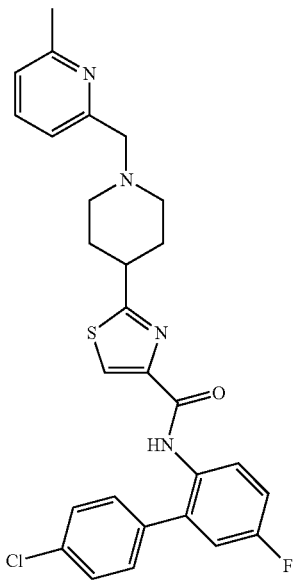 N-(4'-chloro-5-fluorobiphenyl-2-yl)-2-{1-[(6-methylpyridin-2-yl)methyl]-piperidin-4-yl}-1,3-thiazole-4-carboxamide | |
| 1260 | 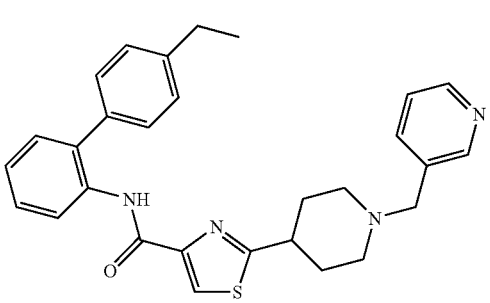 | |

TABLE 1-continued
| No. | FORMULA | NMR or mass |
|---|---|---|
| 1261 | 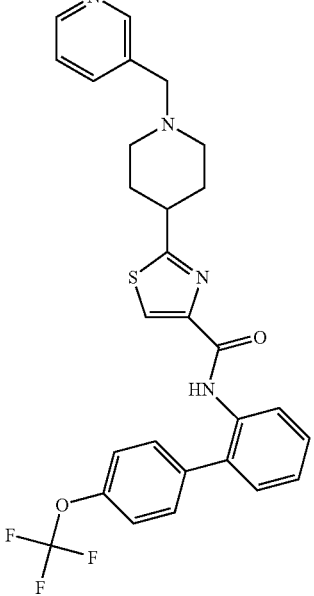 2-[1-(pyridin-3-ylmethyl)piperidin-4-yl]-N-[4'-(trifluoromethoxy)biphenyl-2-yl]-1,3-thiazole-4-carboxamide | |
| 1262 | 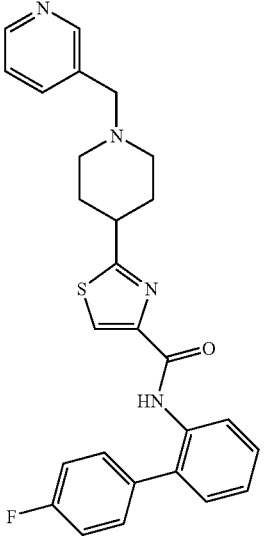 N-(4'-fluorobiphenyl-2-yl)-2-[1-(pyridin-3-ylmethyl)piperidin-4-yl]-1,3-thiazole-4-carboxamide | |

TABLE 1-continued
| No. | FORMULA | NMR or mass |
|---|---|---|
| 1263 | 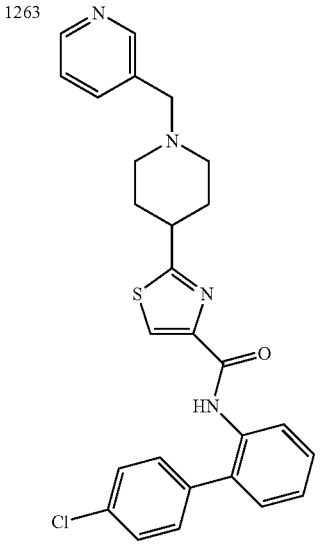 N-(4'-chlorobiphenyl-2-yl)-2-[1-(pyridin-3-ylmethyl)piperidin-4-yl]-1,3-thiazole-4-carboxamide | |
| 1264 | 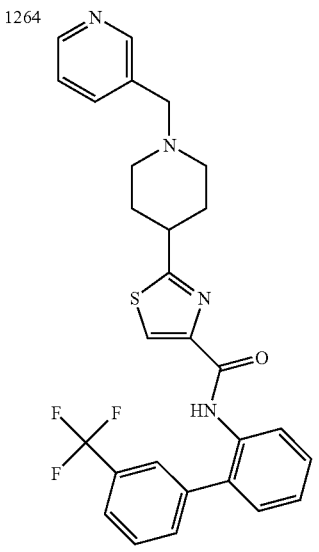 2-[1-(pyridin-3-ylmethyl)piperidin-4-yl]-N-[3'-(trifluoromethyl)biphenyl-2-yl]-1,3-thiazole-4-carboxamide | |

| No. | FORMULA | NMR or mass |
|---|---|---|
| 1265 | 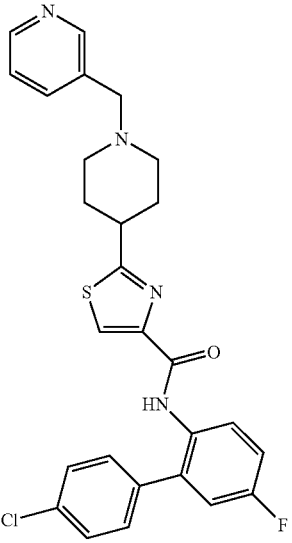<br>N-(4'-chloro-5-fluorobiphenyl-2-yl)-2-[1-(pyridin-3-ylmethyl)piperidin-4-yl]-1,3-thiazole-4-carboxamide | |
| 1266 | 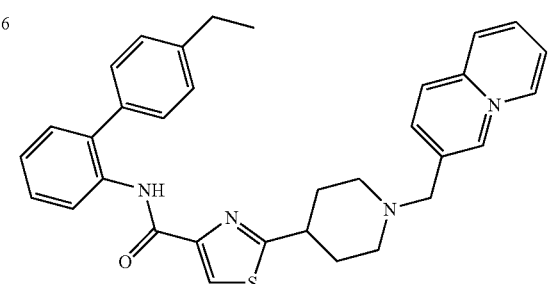 | |

TABLE 1-continued
| No. | FORMULA | NMR or mass |
|---|---|---|
| 1267 | 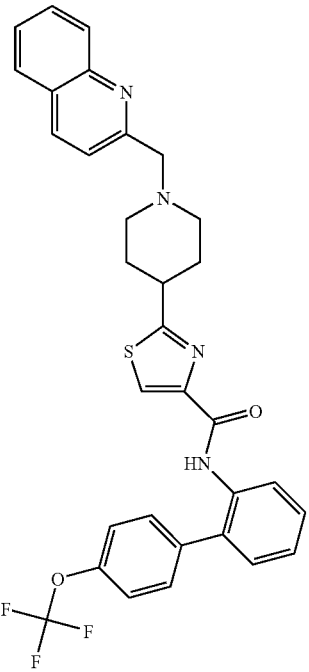 2-[1-(quinolin-2-ylmethyl)piperidin-4-yl]-N-[4'-(trifluoromethoxy)-biphenyl-2-yl]-1,3-thiazole-4-carboxamide | |
| 1268 | 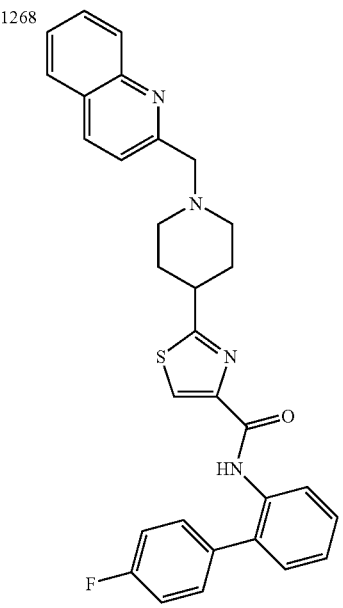 N-(4'-fluorobiphenyl-2-yl)-2-[1-(quinolin-2-ylmethyl)piperidin-4-yl]-1,3-thiazole-4-carboxamide | |

TABLE 1-continued
| No. | FORMULA | NMR or mass |
|---|---|---|
| 1269 | 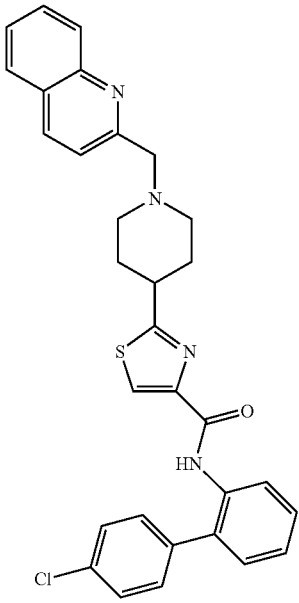 N-(4-chlorobiphenyl-2-yl)-2-[1-(quinolin-2-ylmethyl)piperidin-4-yl]-1,3-thiazole-4-carboxamide | |
| 1270 | 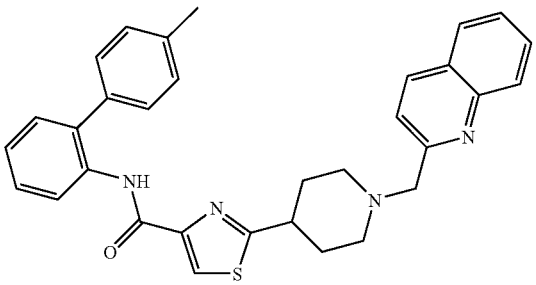 | |
| 1271 | 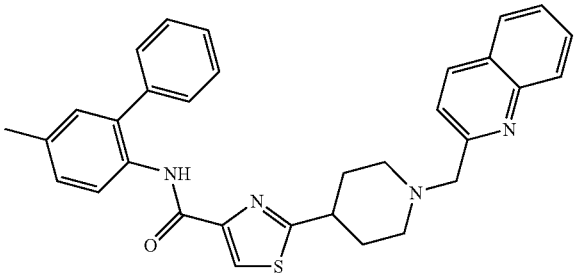 | |

TABLE 1-continued
| No. | FORMULA | NMR or mass |
|---|---|---|
| 1272 | 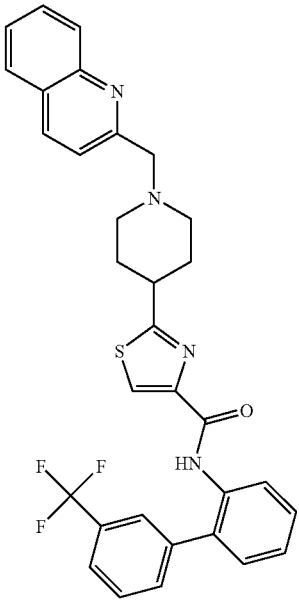 2-[1-(quinolin-2-ylmethyl)piperidin-4-yl]-N-{3'-(trifluoromethyl)biphenyl-2-yl]-1,3-thiazole-4-carboxamide | |
| 1273 | 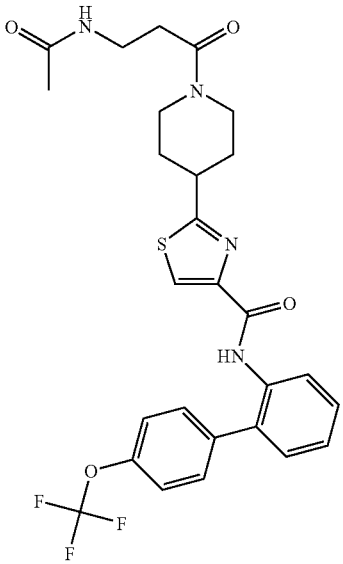 2-[1-(N-acetyl-beta-alanyl)piperidin-4-yl]-N-[4'-(trifluoromethoxy)-biphenyl-2-yl]-1,3-thiazole-4-carboxamide | |
| 1274 | 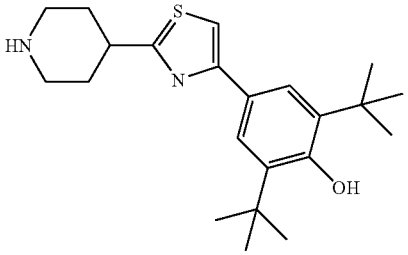 | |

TABLE 1-continued
| No. | FORMULA | NMR or mass |
|---|---|---|
| 1275 | 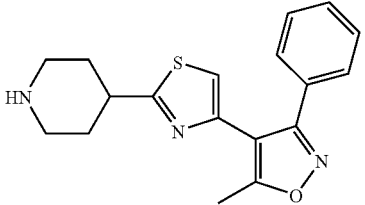 | |
| 1276 | 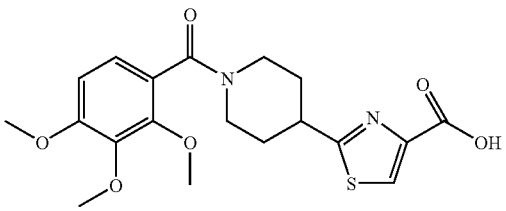 | |
| 1277 | 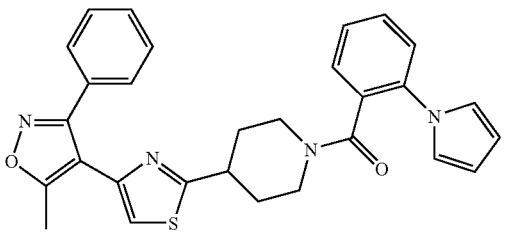 | |
| 1278 | 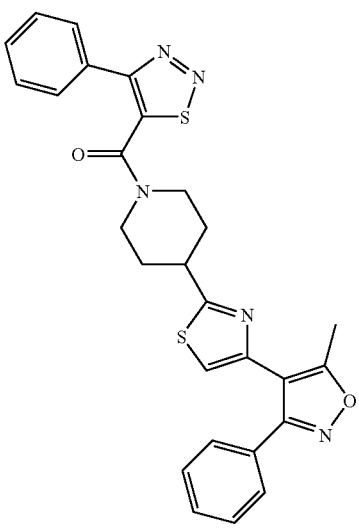 | |
| 1279 | 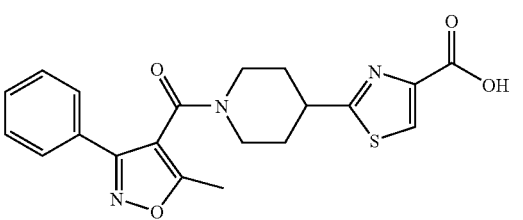 | |

TABLE 1-continued
| No. | FORMULA | NMR or mass |
|---|---|---|
| 1280 | 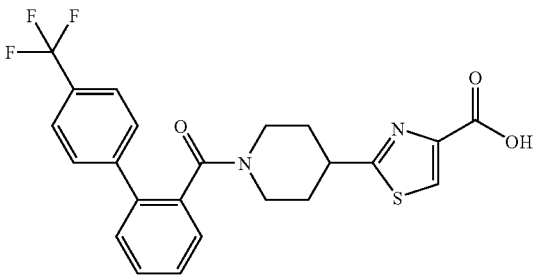 | |
| 1281 | 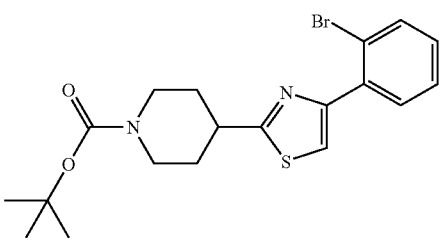 | |
| 1282 | 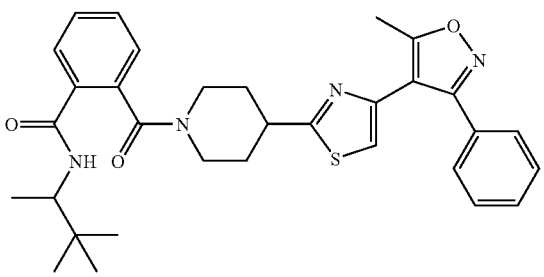 | |
| 1283 | 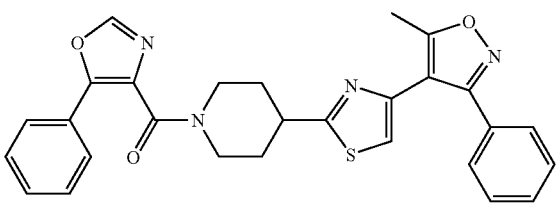 | |
| 1284 | 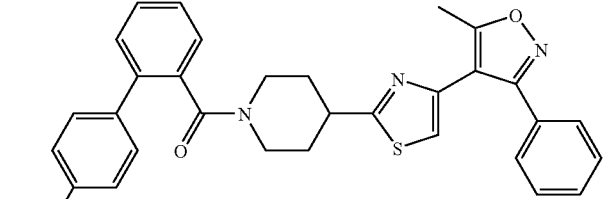 | |
| 1285 | 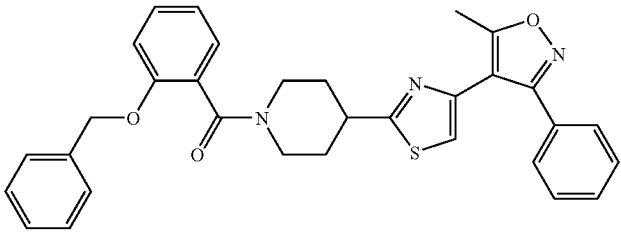 | |

TABLE 1-continued
| No. | FORMULA | NMR or mass |
|---|---|---|
| 1286 | 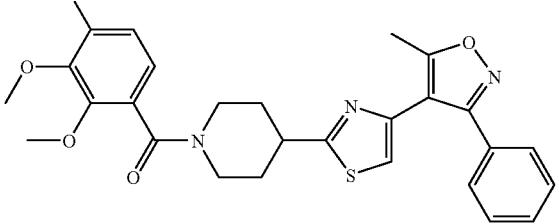 | |
| 1287 | 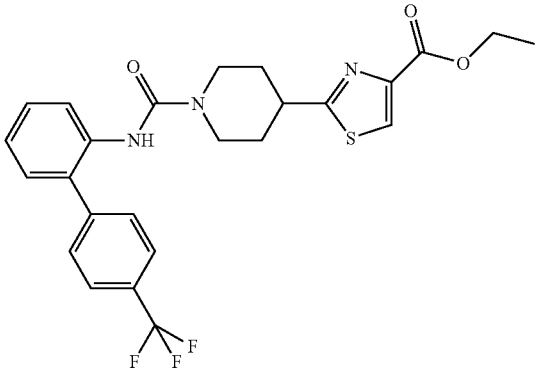 | |
| 1288 | 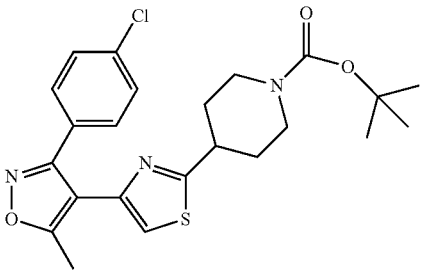 | |
| 1289 | 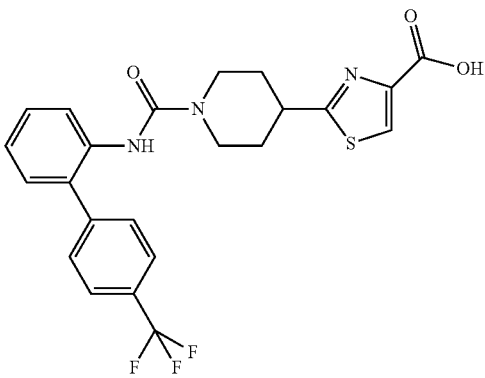 | |
| 1290 | 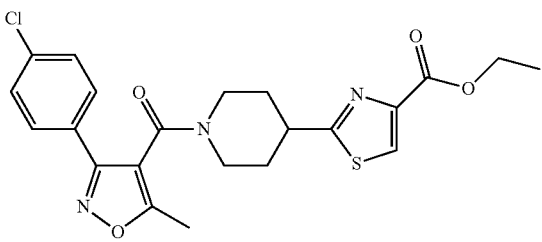 | |

TABLE 1-continued

| No. | FORMULA | NMR or mass |
|---|---|---|
| 1291 | | |
| 1292 | | |
| 1293 | | |
| 1294 | | |
| 1295 | | |

TABLE 1-continued

| No. | FORMULA | NMR or mass |
|---|---|---|
| 1296 | | |
| 1297 | | |
| 1298 | | |
| 1299 | | |
| 1300 | | |

TABLE 1-continued
| No. | FORMULA | NMR or mass |
|---|---|---|
| 1301 | 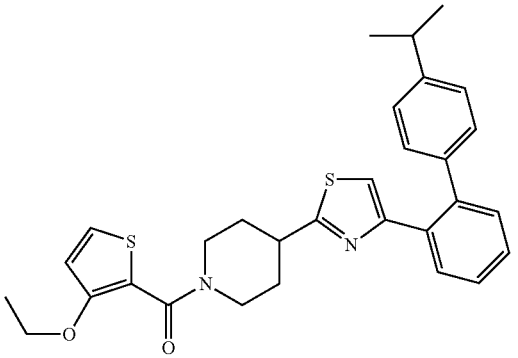 | |
| 1302 | 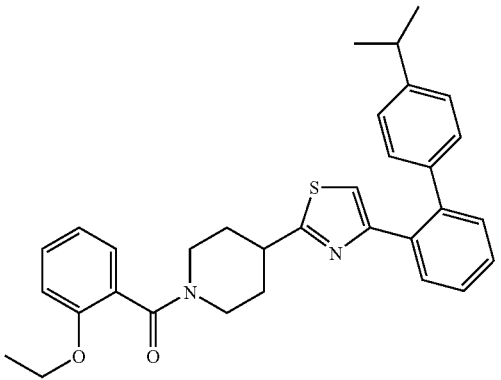 | |
| 1303 | 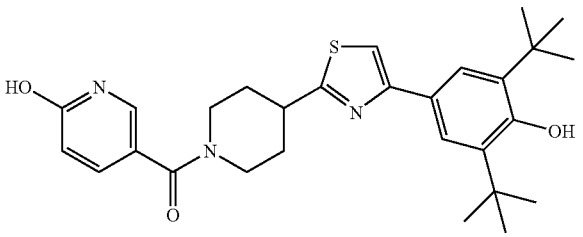 | |
| 1304 | 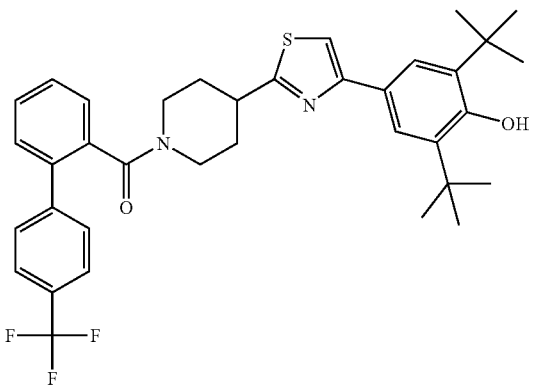 | |

TABLE 1-continued

| No. | FORMULA | NMR or mass |
|-----|---------|-------------|

1305

1306

1307

1308

1309

1310

TABLE 1-continued

| No. | FORMULA | NMR or mass |
|---|---|---|
| 1311 | | |
| 1312 | | |
| 1313 | | |
| 1314 | | |

TABLE 1-continued
| No. | FORMULA | NMR or mass |
|---|---|---|
| 1315 | 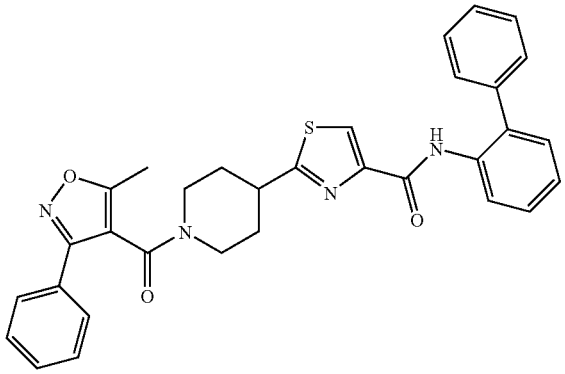 | |
| 1316 | 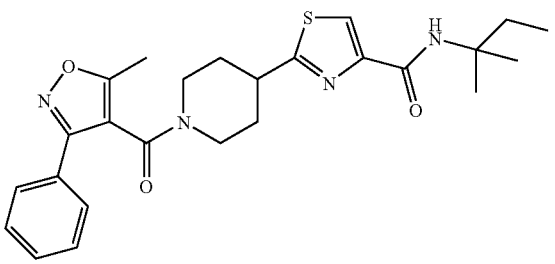 | |
| 1317 | 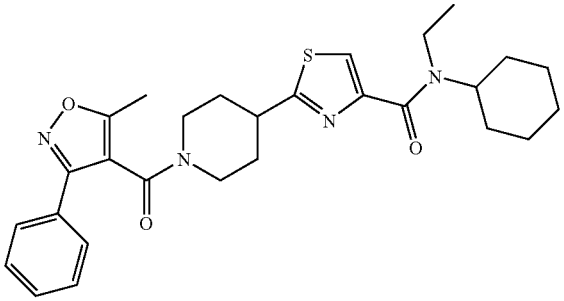 | |
| 1318 | 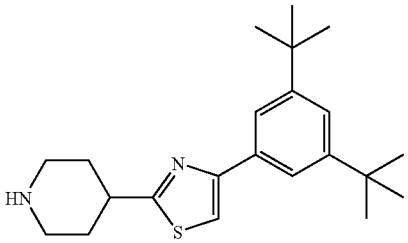 | |
| 1319 | 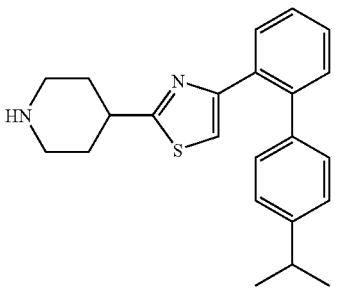 | |

TABLE 1-continued

| No. | FORMULA | NMR or mass |
|---|---|---|
| 1320 | | |
| 1321 | | |
| 1322 | | |
| 1323 | | |
| 1324 | | |
| 1325 | | |

TABLE 1-continued
| No. | FORMULA | NMR or mass |
|---|---|---|
| 1326 | 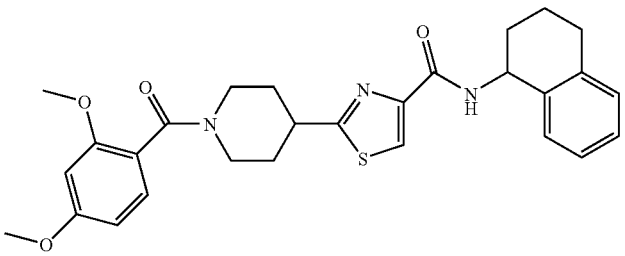 | |
| 1327 | 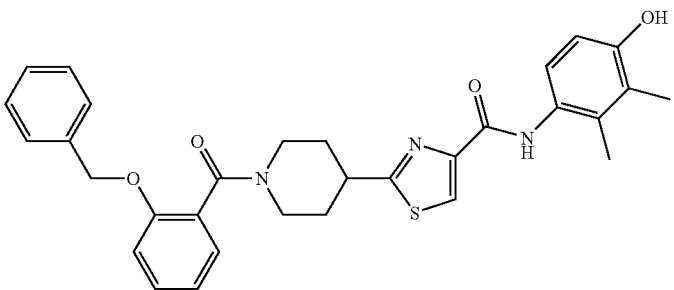 | |
| 1328 | 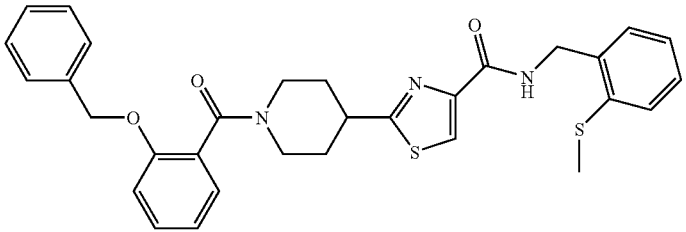 | |
| 1329 | 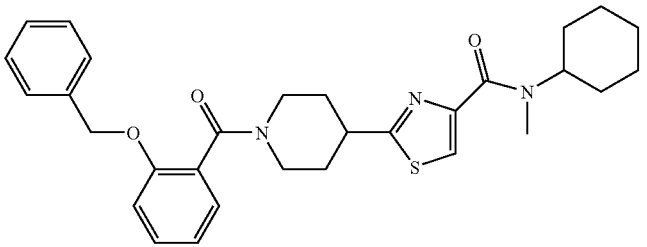 | |
| 1330 | 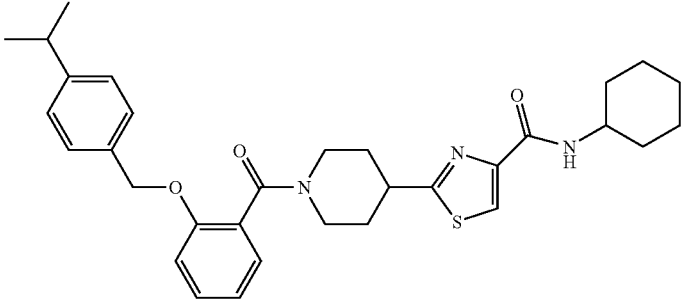 | |

TABLE 1-continued

| No. | FORMULA | NMR or mass |
|---|---|---|
| 1331 | | |
| 1332 | | |
| 1333 | | |
| 1334 | | |
| 1335 | | |
| 1336 | | |

TABLE 1-continued
| No. | FORMULA | NMR or mass |
|---|---|---|
| 1337 | 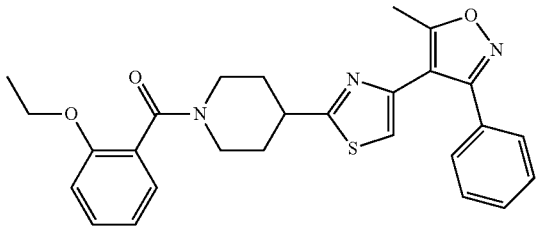 | |
| 1338 | 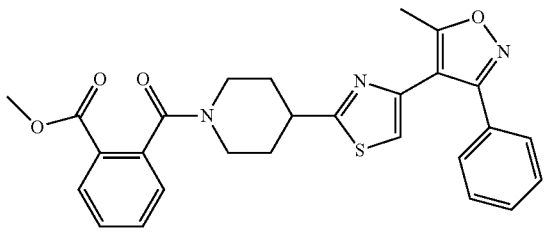 | |
| 1339 | 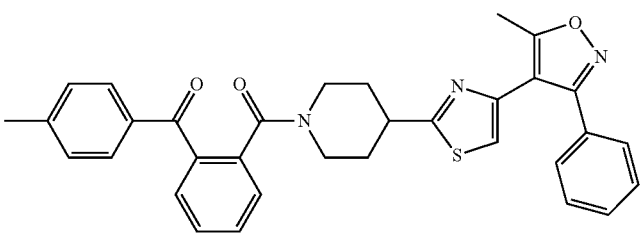 | |
| 1340 | 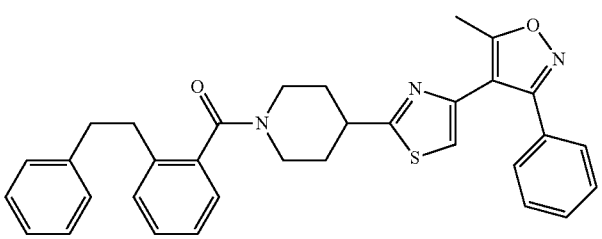 | |
| 1341 | 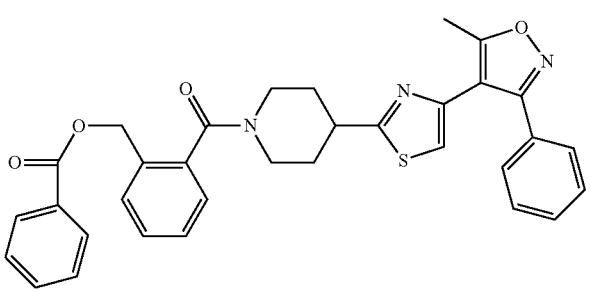 | |
| 1342 | 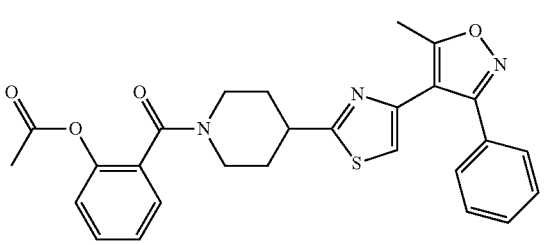 | |

TABLE 1-continued
| No. | FORMULA | NMR or mass |
|---|---|---|
| 1343 | 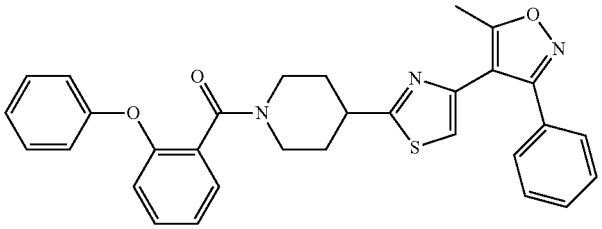 | |
| 1344 | 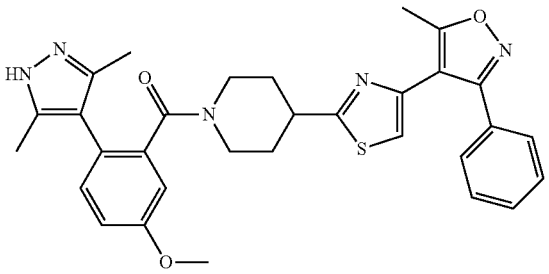 | |
| 1345 | 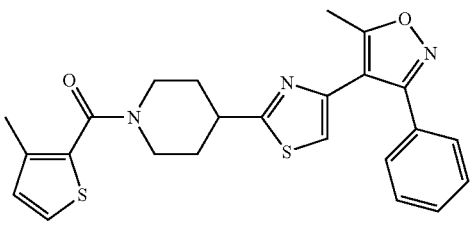 | |
| 1346 | 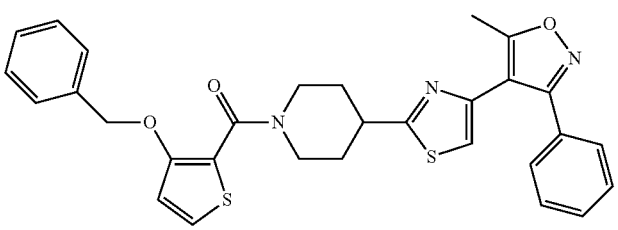 | |
| 1347 | 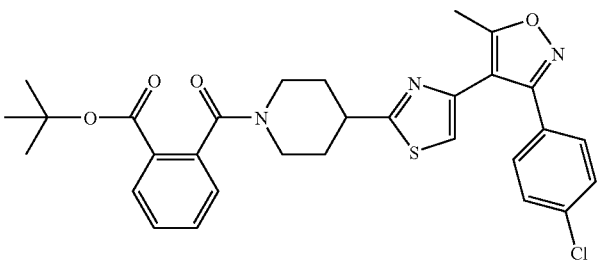 | |
| 1348 | 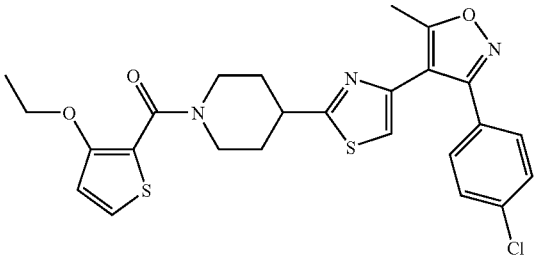 | |

TABLE 1-continued
| No. | FORMULA | NMR or mass |
|---|---|---|
| 1349 | 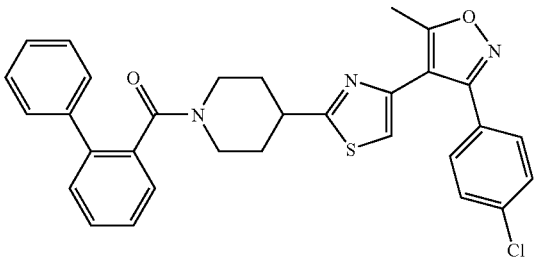 | |
| 1350 | 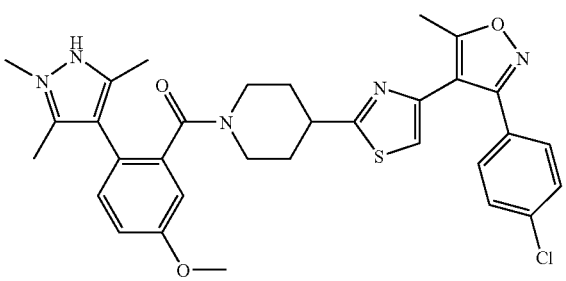 | |
| 1351 | 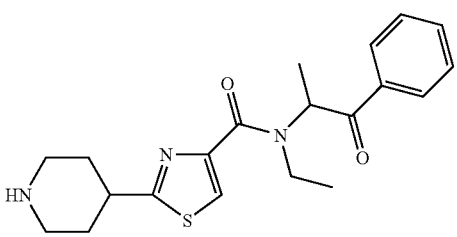 | |
| 1352 | 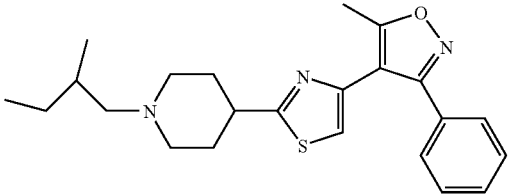 | |
| 1353 | 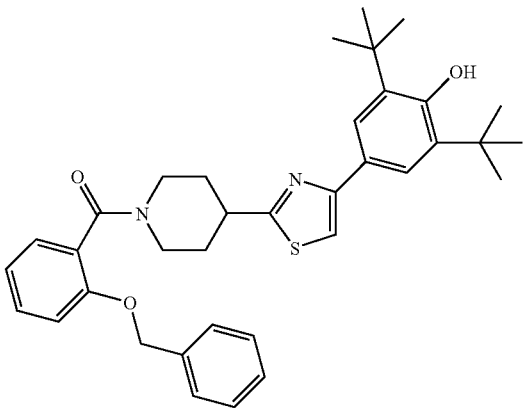 | |
4-(2-{1-[2-(benzyloxy)benzoyl]piperidin-4-yl}-1,3-thiazol-4-yl)2,6-di-tert-butylphenol TABLE 1-continued
| No. | FORMULA | NMR or mass |
|---|---|---|
| 1354 | 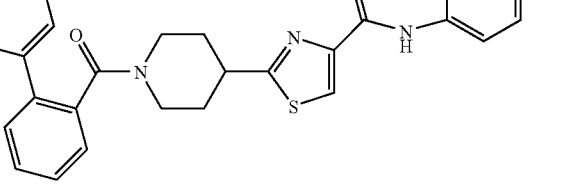 | |
| 1355 | 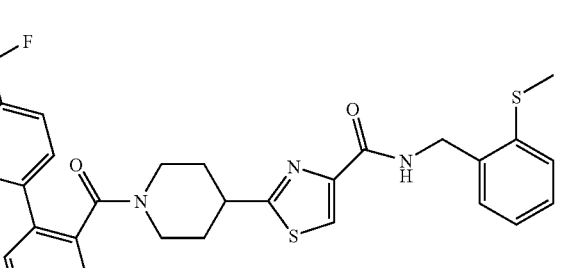 | |
| 1356 | 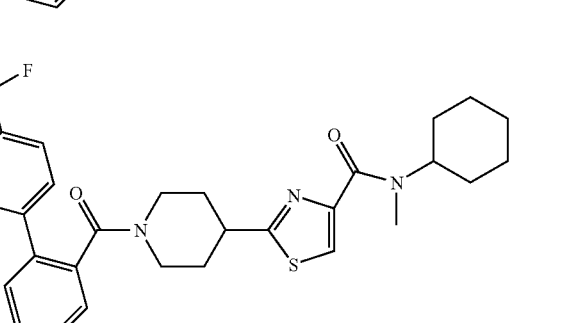 | |
| 1357 | 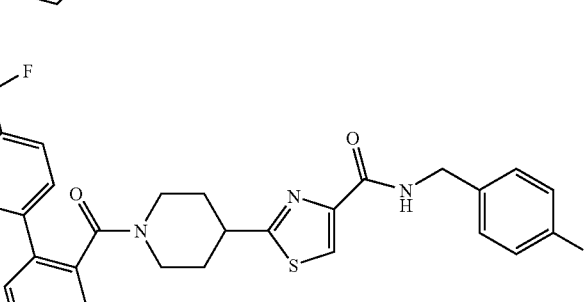 | |
| 1358 | 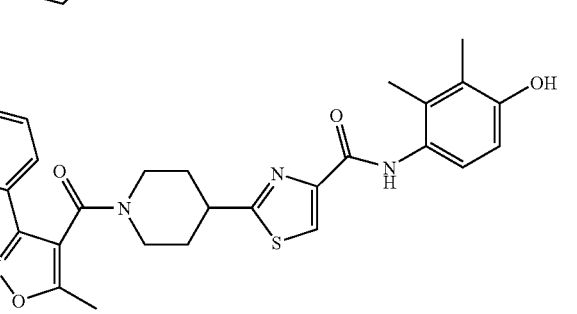 | |

TABLE 1-continued
| No. | FORMULA | NMR or mass |
|---|---|---|
| 1359 | 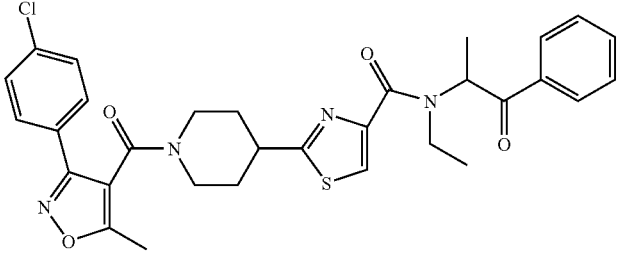 | |
| 1360 | 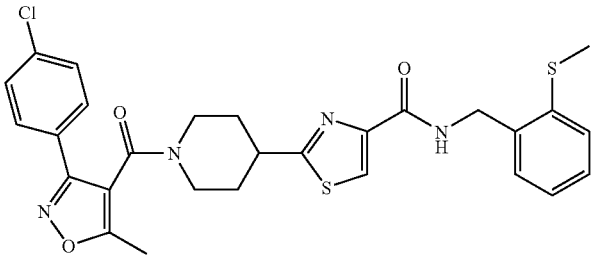 | |
| 1361 | 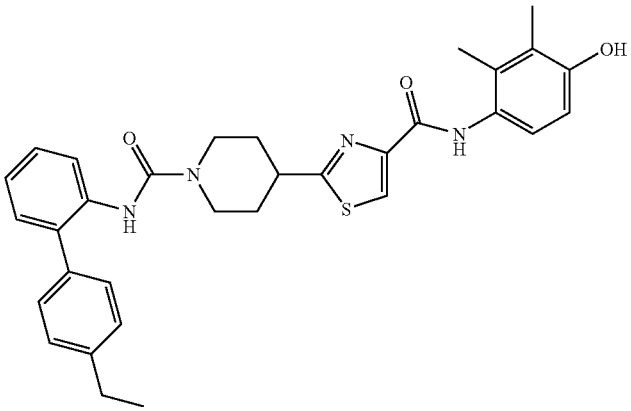 | |
| 1362 | 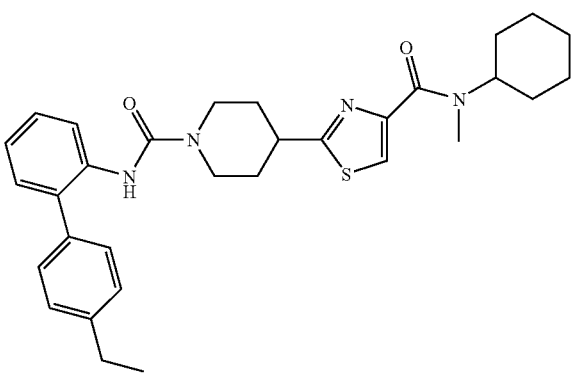 | |
| 1363 | 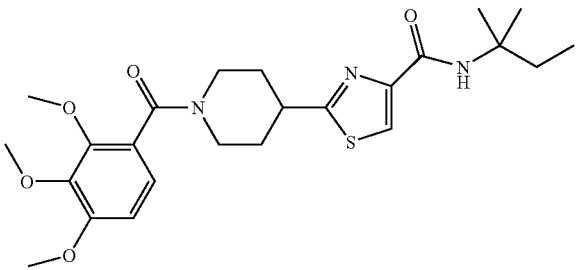 | |

TABLE 1-continued
| No. | FORMULA | NMR or mass |
|---|---|---|
| 1364 | 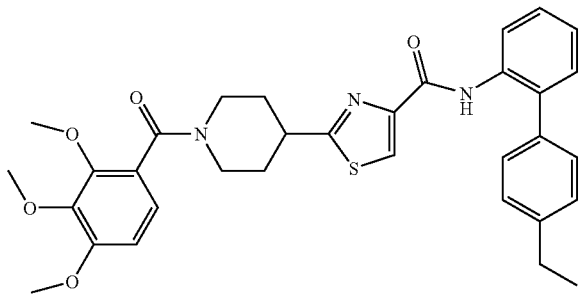 | |
| 1365 | 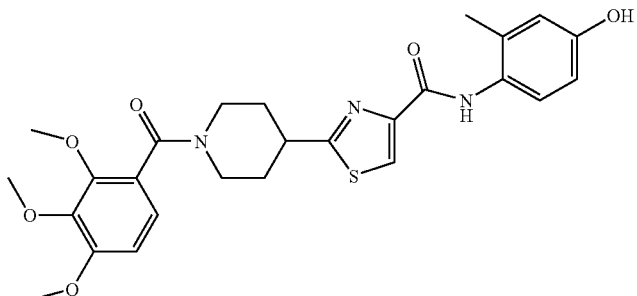 | |
| 1366 | 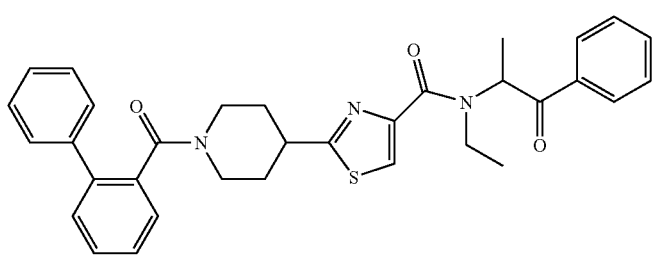 | |
| 1367 | 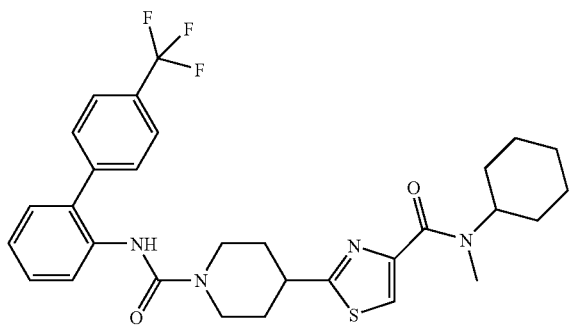 | |

TABLE 1-continued
| No. | FORMULA | NMR or mass |
|---|---|---|
| 1368 | 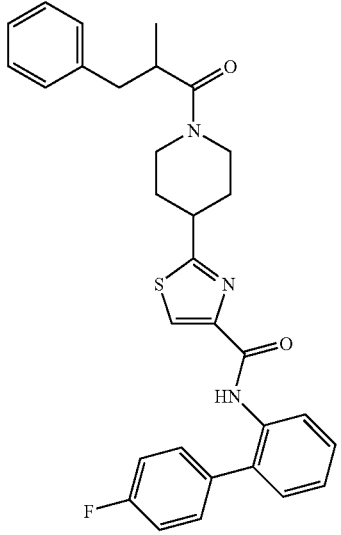 N-(4'-fluorobiphenyl-2-yl)-2-[1-(2-methyl-3-phenylpropanoyl)piperidin-4-yl]-1,3-thiazole-4-carboxamide | |
| 1369 | 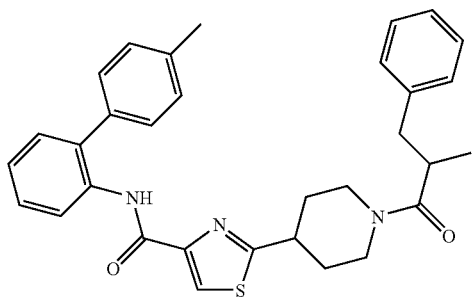 | |
| 1370 | 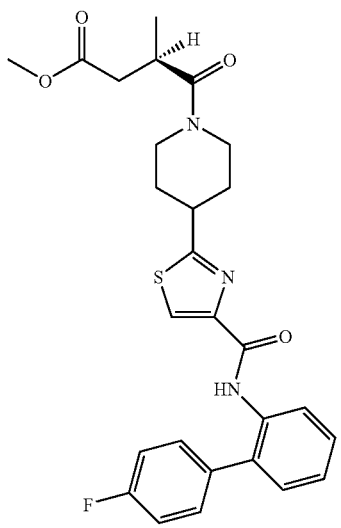 methyl (3R)-4-[4-(4-{[(4'-fluorobiphenyl-2-yl)amino]carbonyl}-1,3-thiazol-2-yl)piperidin-1-yl]-3-methyl-4-oxobutanoate | |

TABLE 1-continued
| No. | FORMULA | NMR or mass |
|---|---|---|
| 1371 | 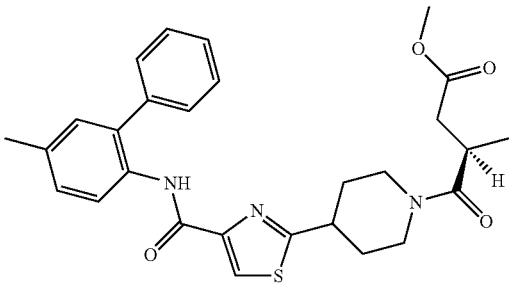 | |
| 1372 | 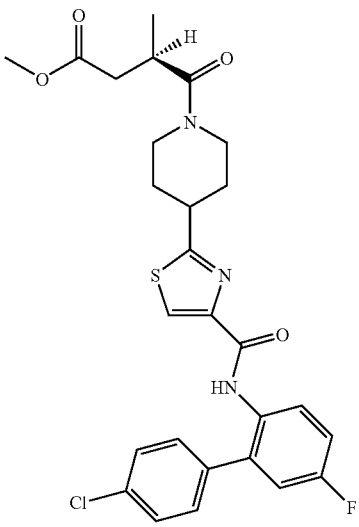 methyl (3R)-4-[4-(4-{[(4'-chloro-5-fluorobiphenyl-2-yl)amino]carbonyl}-1,3-thiazol-2-yl)piperidin-1-yl]-3-methyl-4-oxobutanoate | |
| 1373 | 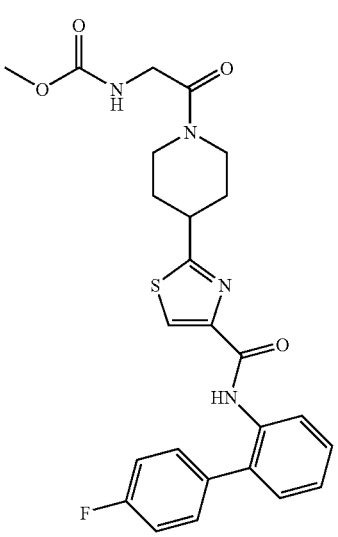 | |

TABLE 1-continued
| No. | FORMULA | NMR or mass |
|-----|---------|-------------|
1374 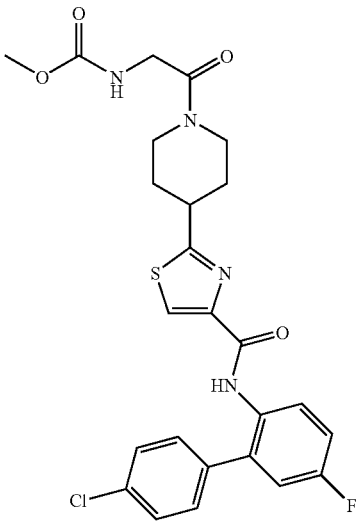
1375 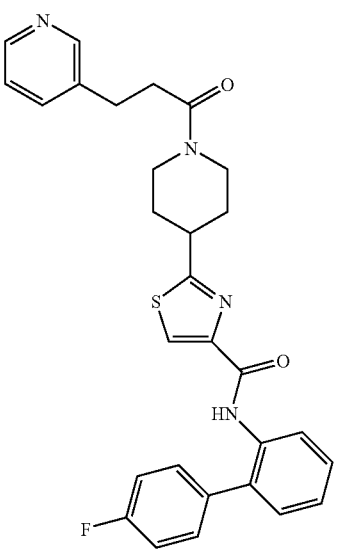
N-(4'-fluorobiphenyl-2-yl)-2-[1-(3-pyridin-3-ylpropanoyl)piperidin-4-yl]-1,3-thiazole-4-carboxamide
1376 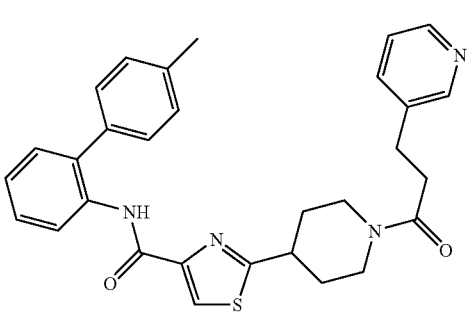

TABLE 1-continued
| No. | FORMULA | NMR or mass |
|---|---|---|
| 1377 | 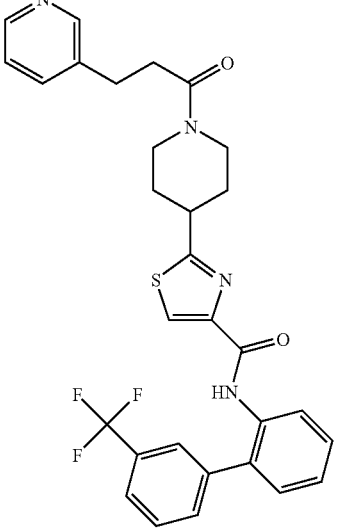 | |
| 1378 | 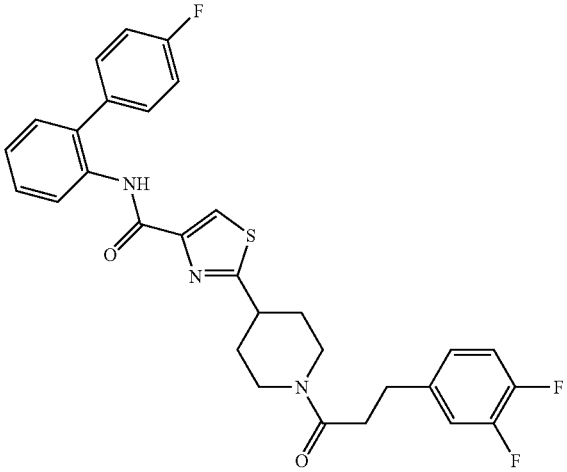 2-{1-[3-(3,4-difluorophenyl)propanoyl]piperidin-4-yl}-N-(4'-fluorobiphenyl-2-yl)-1,3-thiazole-4-carboxamide | |

TABLE 1-continued
| No. | FORMULA | NMR or mass |
|---|---|---|
| 1379 | 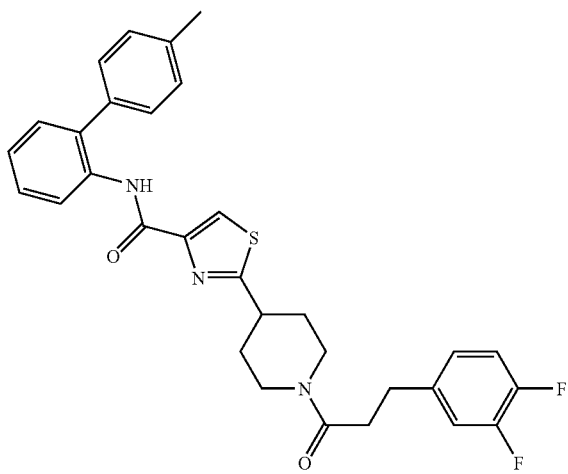<br>2-{1-[3-(3,4-difluorophenyl)propanoyl]piperidin-4-yl}-N-(4'-methylbiphenyl-2-yl)-1,3-thiazole-4-carboxamide | |
| 1380 | 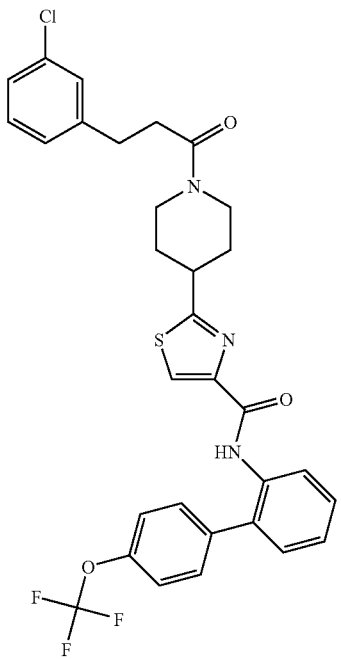<br>2-{1-[3-(3-chlorophenyl)propanoyl]piperidin-4-yl}-N-[4'-(trifluoromethoxy)-biphenyl-2-yl]-1,3-thiazole-4-carboxamide | |

| No. | FORMULA | NMR or mass |
|---|---|---|
| 1381 | 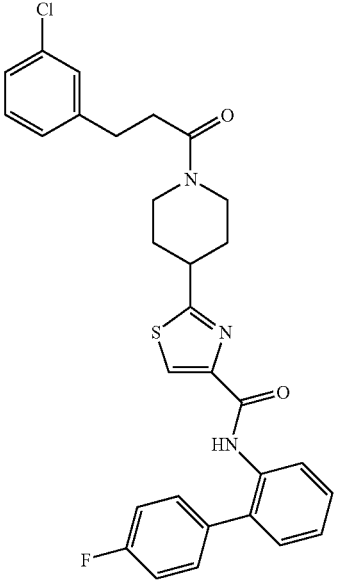<br>2-{1-[3-(3-chlorophenyl)propanoyl]piperidin-4-yl}-N-(4'-fluorobiphenyl-2-yl)-1,3-thiazole-4-carboxamide | |
| 1382 | 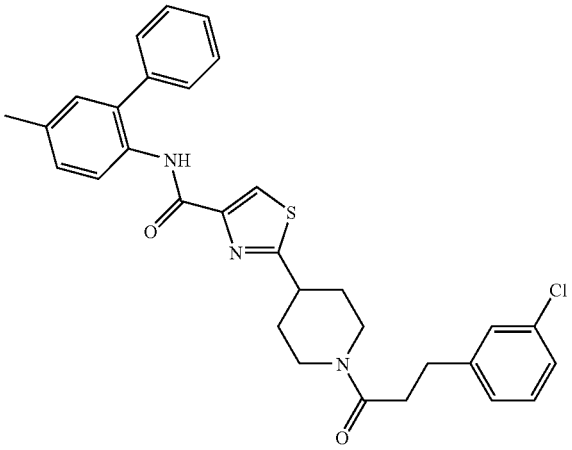<br>2-{1-[3-(3-chlorophenyl)propanoyl]piperidin-4-yl}-N-(5-methylbiphenyl-2-yl)-1,3-thiazole-4-carboxamide | |

TABLE 1-continued
| No. | FORMULA | NMR or mass |
|---|---|---|
| 1383 | 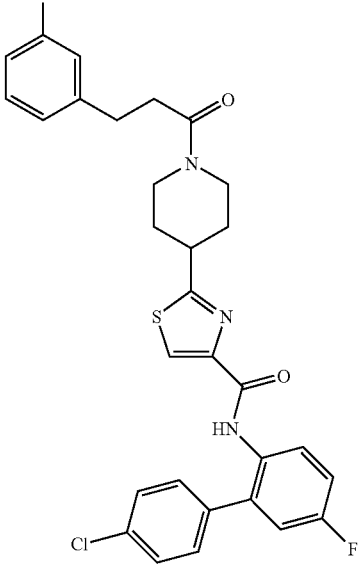 N-(4'-chloro-5-fluorobiphenyl-2-yl)-2-{1-[3-(3-chlorophenyl)propanoyl]-piperidin-4-yl}-1,3-thiazole-4-carboxamide | |
| 1384 | 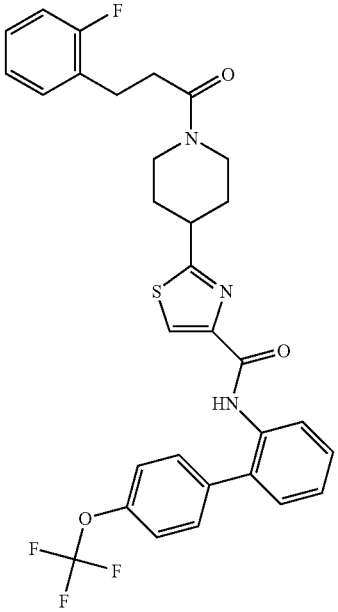 2-{1-[3-(2-fluorophenyl)propanoyl]piperidin-4-yl}-N-[4'-(trifluoro-methoxy)-biphenyl-2-yl]-1,3-thiazole-4-carboxamide | |

| No. | FORMULA | NMR or mass |
|---|---|---|
| 1385 | 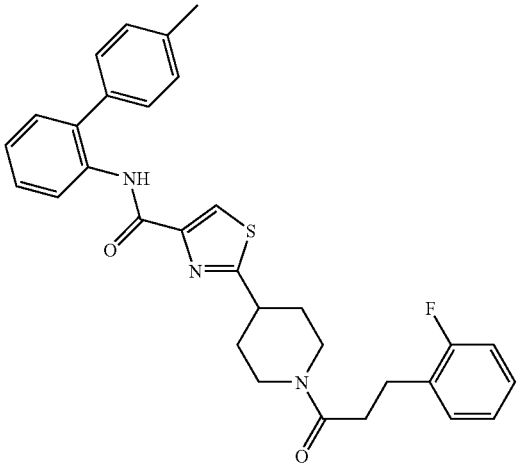 2-{1-[3-(2-fluorophenyl)propanoyl]piperidin-4-yl}-N-(4'-methylbiphenyl-2-yl)-1,3-thiazole-4-carboxamide | |
| 1386 | 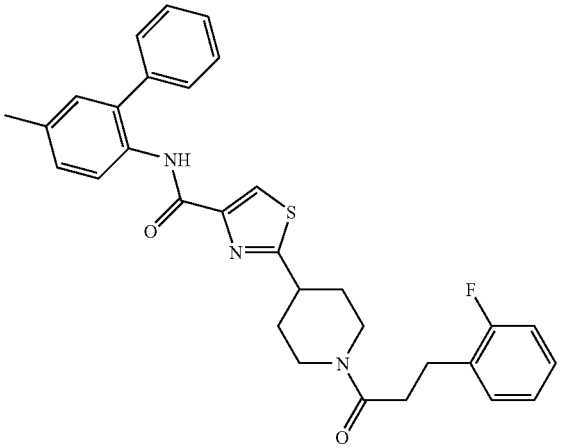 2-{1-[3-(2-fluorophenyl)propanoyl]piperidin-4-yl}-N-(5-methylbiphenyl-2-yl)-1,3-thiazole-4-carboxamide | |

TABLE 1-continued
| No. | FORMULA | NMR or mass |
|---|---|---|
| 1387 | 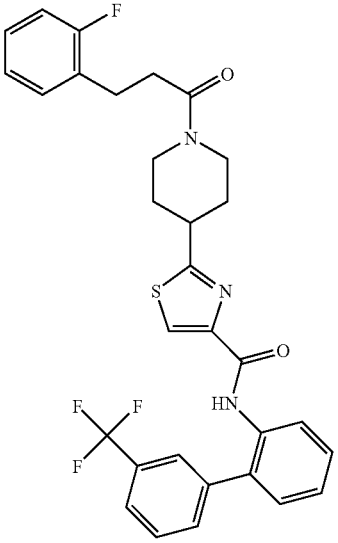 2-{1-{3-(2-fluorophenyl)propanoyl]piperidin-4-yl]-N-[3′-(trifluoromethyl)-biphenyl-2-yl]-1,3-thiazole-4-carboxamide | |
| 1388 | 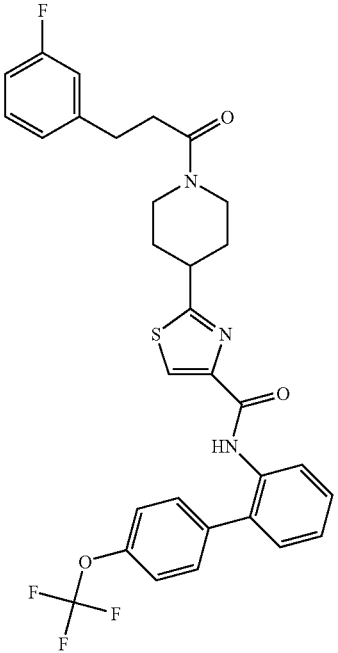 2-{1-[3-(3-fluorophenyl)propanoyl]piperidin-4-yl}-N-[4′-(trifluoromethoxy)-biphenyl-2-yl]-1,3-thiazole-4-carboxamide | |

TABLE 1-continued
| No. | FORMULA | NMR or mass |
|---|---|---|
| 1389 | 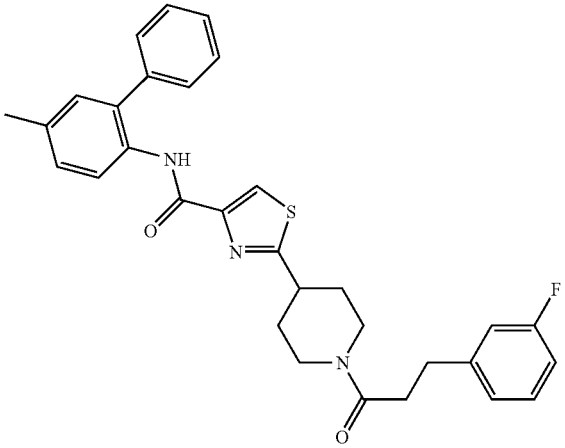 | |
| 1390 | 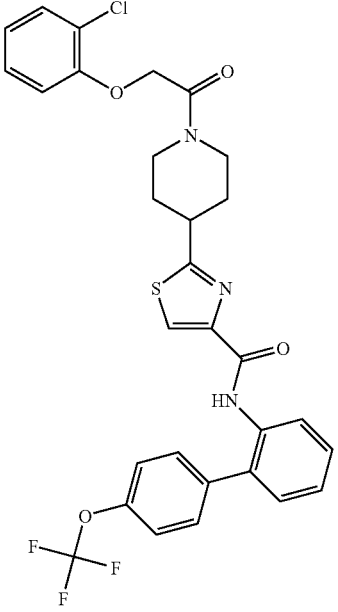 2-{1-[(2-chlorophenoxy)acetyl]piperidin-4-yl}-N-[4'-(trifluoromethoxy)-biphenyl-2-yl]-1,3-thiazole-4-carboxamide | |
| 1391 | 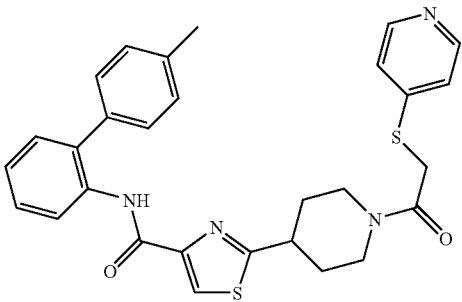 | |

| No. | FORMULA | NMR or mass |
|---|---|---|
1392 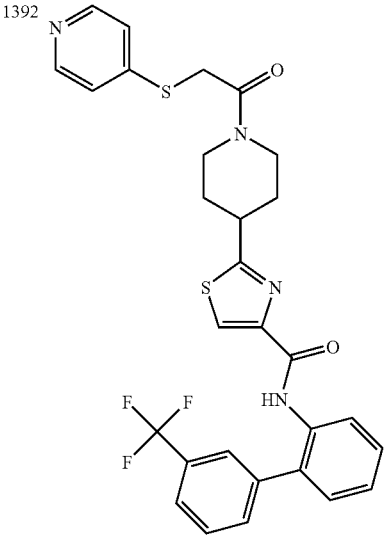
1393 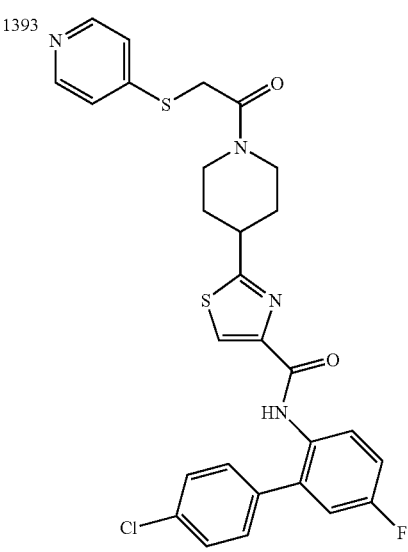
N-(4'-chloro-5-fluorobiphenyl-2-yl)-2-{1-[(pyridin-4-ylthio)acetyl]piperidin-4-yl}-1,3-thiazole-4-carboxamide TABLE 1-continued
| No. | FORMULA | NMR or mass |
|---|---|---|
1394
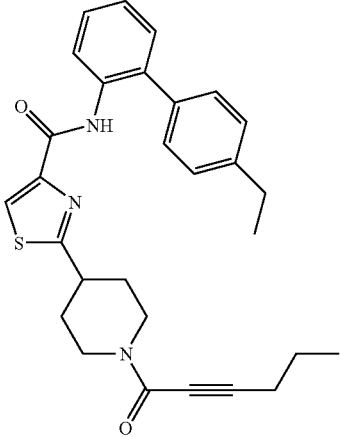
N-(4'-ethylbiphenyl-2-yl)-2-(1-hex-2-ynoylpiperidin-4-yl)-1,3-thiazole-4-carboxamide
1395
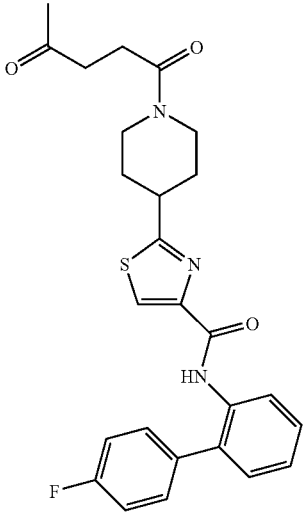
1396
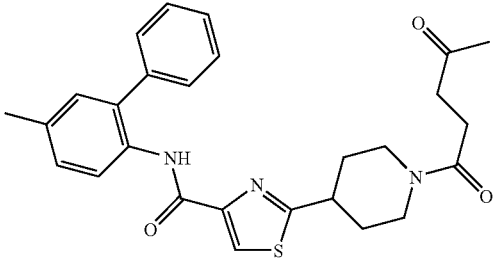

TABLE 1-continued
| No. | FORMULA | NMR or mass |
|---|---|---|
| 1397 | 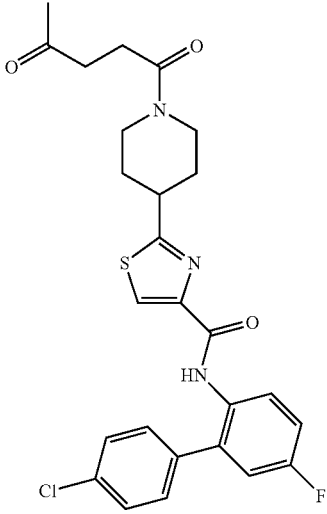 N-(4'-chloro-5-fluorobiphenyl-2-yl)-2-[1-(4-oxopentanoyl)piperidin-4-yl]-1,3-thiazole-4-carboxamide | |
| 1398 | 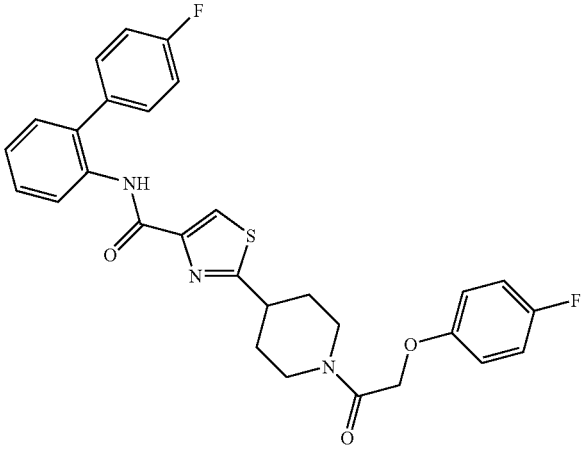 | |
| 1399 | 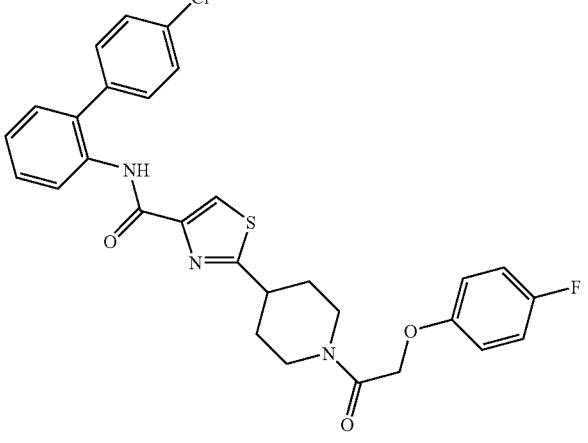 N-(4'-chlorobiphenyl-2-yl)-2-{1-[(4-fluorophenoxy)acetyl]piperidin-4-yl}-1,3-thiazole-4-carboxamide | |

TABLE 1-continued

| No. | FORMULA | NMR or mass |
|---|---|---|
| 1400 | N-(4'-chloro-5-fluorobiphenyl-2-yl)-2-{1-[(4-fluorophenoxy)acetyl]piperidin-4-yl}-1,3-thiazole-4-carboxamide | |
| 1401 | | |
| 1402 | | |
| 1403 | | |

TABLE 1-continued
| No. | FORMULA | NMR or mass |
|---|---|---|
1404 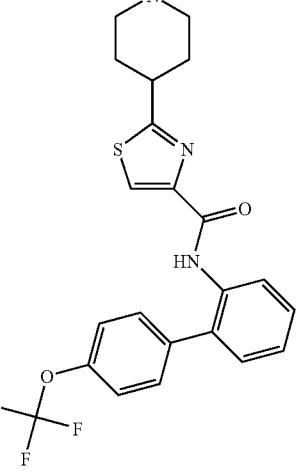
2-[1-(5-oxohexanoyl)piperidin-4-yl]-N-[4'-(trifluoromethoxy)biphenyl-2-yl]-1,3-thiazole-4-carboxamide
1405 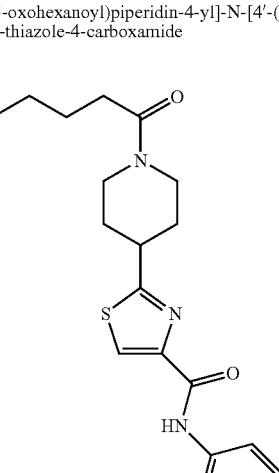
N-(4'-fluorobiphenyl-2-yl)-2-[1-(5-oxohexanoyl)piperidin-4-yl]-1,3-thiazole-4-carboxamide
1406 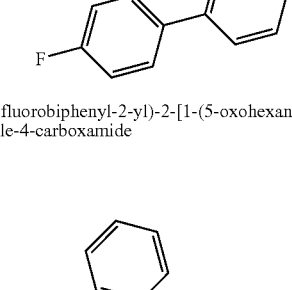

TABLE 1-continued
| No. | FORMULA | NMR or mass |
|---|---|---|
| 1407 | 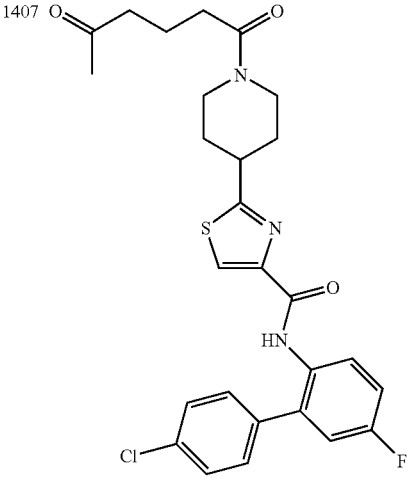 | |
| 1408 | 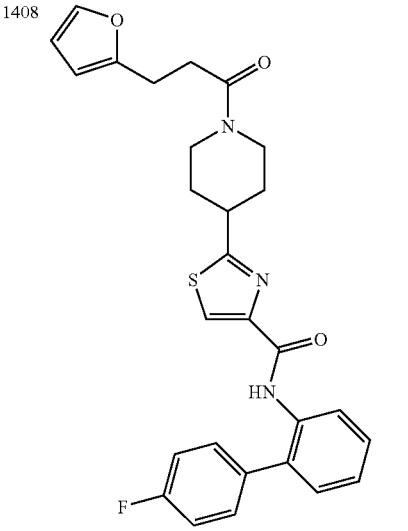 N-(4'-fluorobiphenyl-2-yl)-2-{1-[3-(2-furyl)proanoyl]piperidin-4-yl}-1,3-thiazole-4-carboxamide | |
| 1409 | 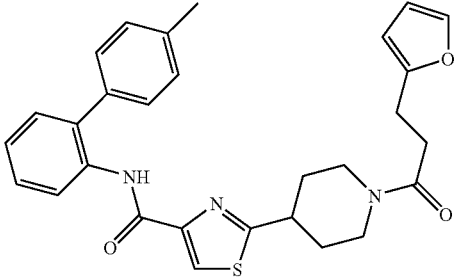 | |

TABLE 1-continued
| No. | FORMULA | NMR or mass |
|---|---|---|
1410
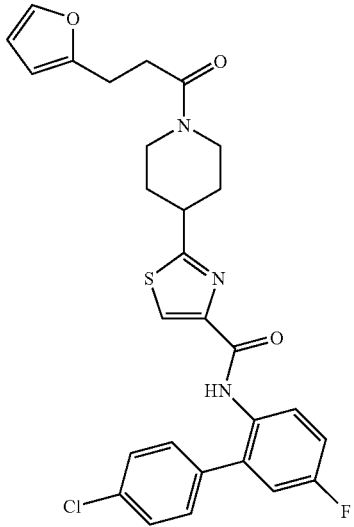
N-(4'-chloro-5-fluorobiphenyl-2-yl)-2-(1-[3-(2-furyl)propanoyl]piperidin-4-yl}-1,3-thiazole-4-carboxamide
1411
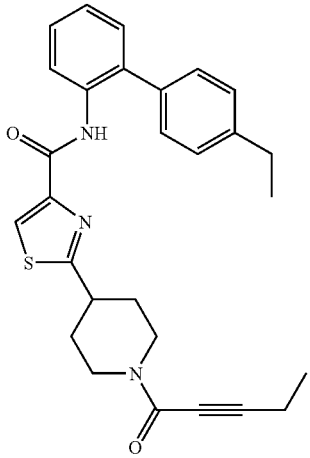
N-(4'-ethylbiphenyl-2-yl)-2-(1-pent-2-ynoylpiperidin-4-yl)-1,3-thiazole-4-carboxamide
1412
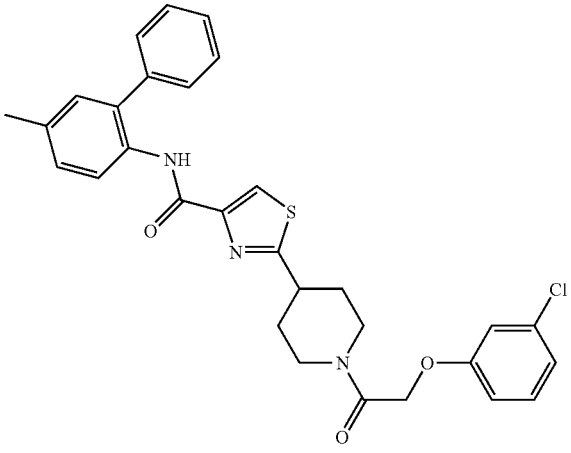
2-{1-[(3-chlorophenoxy)acetyl]piperidin-4-yl}-N-(5-methylbiphenyl-2-yl)-1,3-thiazole-4-carboxamide TABLE 1-continued
| No. | FORMULA | NMR or mass |
|---|---|---|
| 1413 | 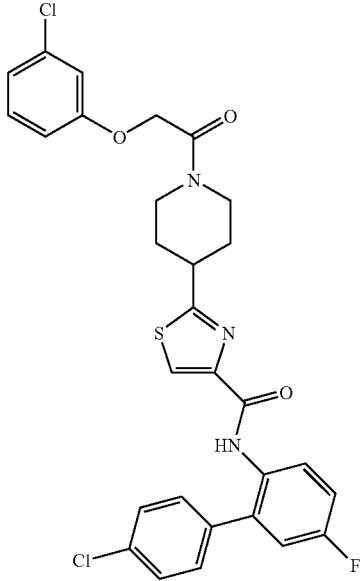 N-(4'-chloro-5-fluorobiphenyl-2-yl)-2-{1-[(3-chlorophenoxy)acetyl]-piperidin-4-yl}-1,3-thiazole-4-carboxamide | |
| 1414 | 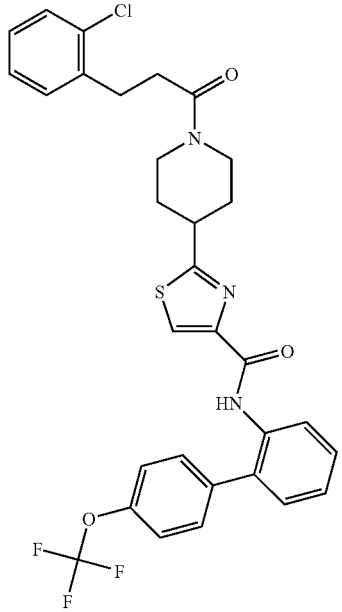 2-[1-[3-(2-chlorophenyl)propanoyl]piperidin-4-yl}-N-[4'-(trifluoromethoxy)-biphenyl-2-yl]-1,3-thiazole-4-carboxamide | |

TABLE 1-continued
| No. | FORMULA | NMR or mass |
|---|---|---|
| 1415 | 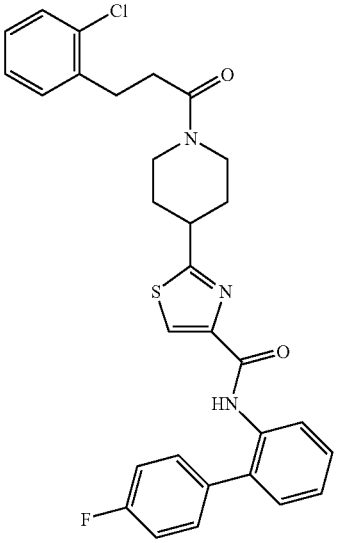 2-{1-[3-(2-chlorophenyl)propanoyl]piperidin-4-yl}-N-(4'-fluorobiphenyl-2-yl)-1,3-thiazole-4-carboxamide | |
| 1416 | 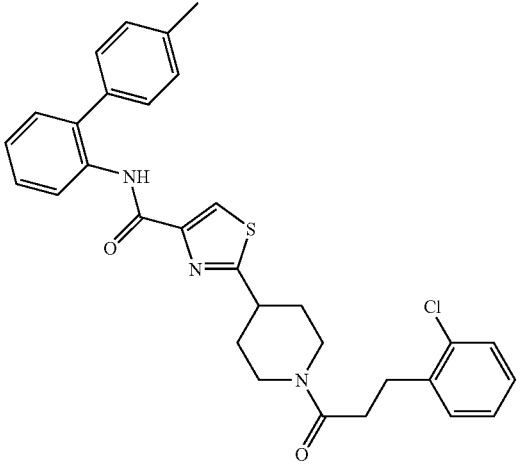 | |
| 1417 | 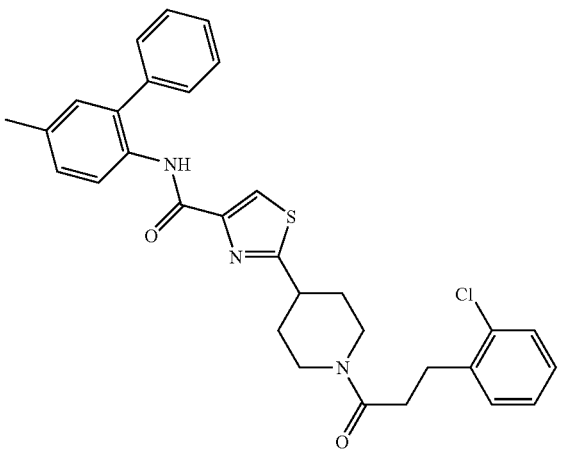 2-{1-[3-(2-chlorophenyl)propanoyl]piperidin-4-yl}-N-(5-methylbiphenyl-2-yl)-1,3-thiazole-4-carboxamide | |

| No. | FORMULA | NMR or mass |
|---|---|---|
| 1418 | 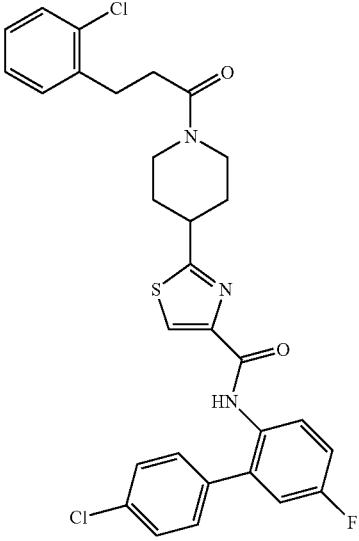<br>N-(4′-chloro-5-fluorobiphenyl-2-yl)-2-{1-[3-(2-chlorophenyl)propanoyl]-piperidin-4-yl}-1,3-thiazole-4-carboxamide | |
| 1419 | 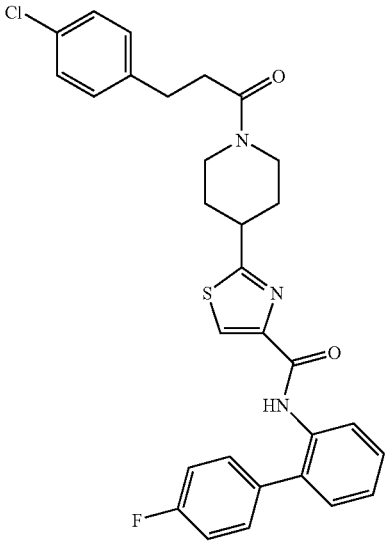 | |

TABLE 1-continued
| No. | FORMULA | NMR or mass |
|---|---|---|
1420 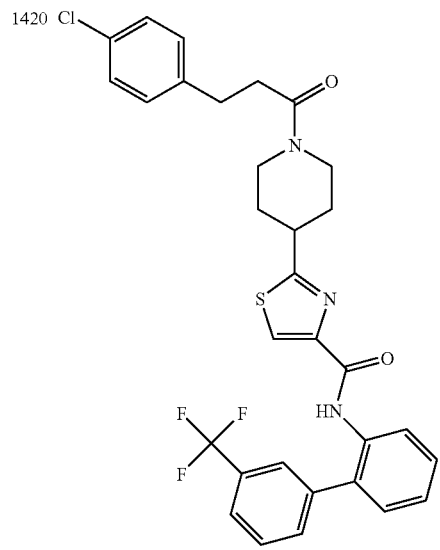
2-{1-[3-(4-chlorophenyl)propanoyl]piperidin-4-yl}-N-[3'-(trifluoromethyl)-biphenyl-2-yl]-1,3-thiazole-4-carboxamide
1421 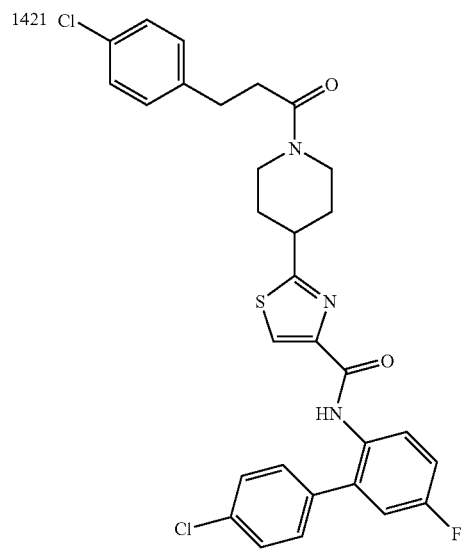
N-(4'-chloro-5-fluorobiphenyl-2-yl)-2-{1-[3-(4-chlorophenyl)propanoyl]-piperidin-4-yl}-1,3-thiazole-4-carboxamide TABLE 1-continued
| No. | FORMULA | NMR or mass |
|---|---|---|
| 1422 | 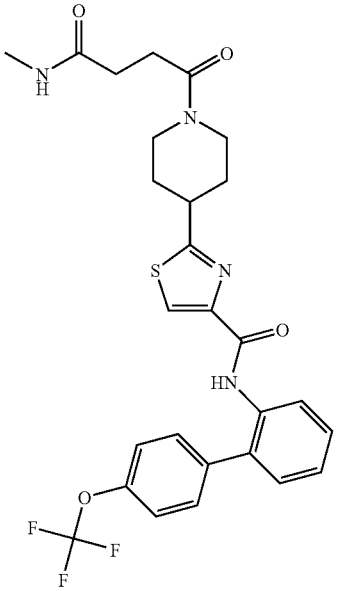 | |
2-{1-[4-methylamino)-4-oxobutanoyl]piperidin-4-yl}-N-[4'-(trifluoromethoxy)-biphenyl-2-yl]-1,3-thiazole-4-carboxamide
| 1423 | 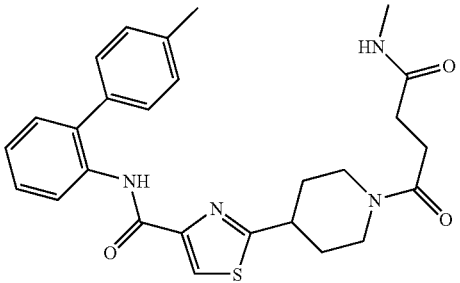 | |
| 1424 | 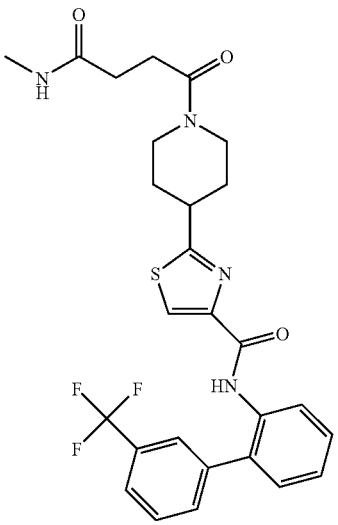 | |
2-{1-[4-methylamino)-4-oxobutanoyl]piperidin-4-yl}-N-[3'-(trifluoromethyl)-biphenyl-2-yl]-1,3-thiazole-4-carboxamide TABLE 1-continued
| No. | FORMULA | NMR or mass |
|---|---|---|
| 1425 | 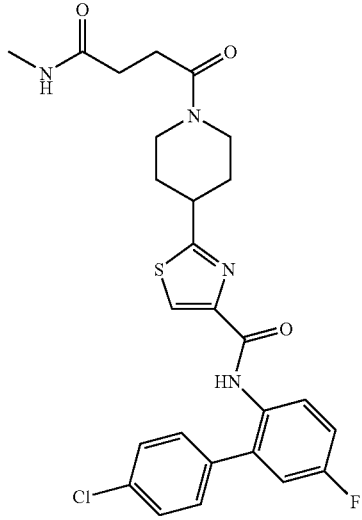 N-(4'-chloro-5-fluorobiphenyl-2-yl)-2-{1-[4-(methylamino)-4-oxobutanoyl]-piperidin-4-yl}-1,3-thiazole-4-carboxamide | |
| 1426 | 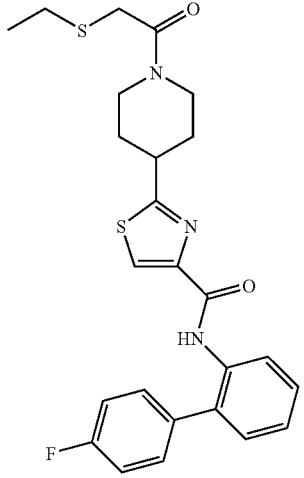 2-{1-[(ethylthio)acetyl]piperidin-4-yl}-N-(4'-fluorobiphenyl-2-yl)-1,3-thiazole-4-carboxamide | |

TABLE 1-continued
| No. | FORMULA | NMR or mass |
|---|---|---|
1427
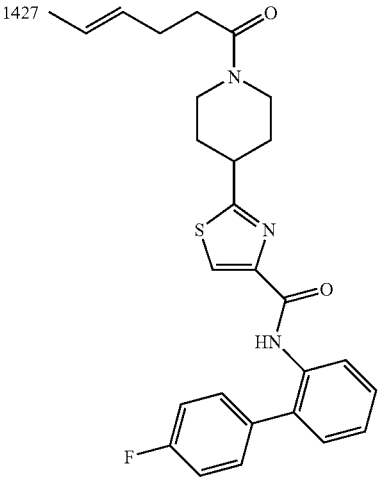
N-(4'-fluorobiphenyl-2-yl)-2-{1-[(4E)-hex-4-enoyl]piperidin-4-yl}-1,3-thiazole-4-carboxamide
1428
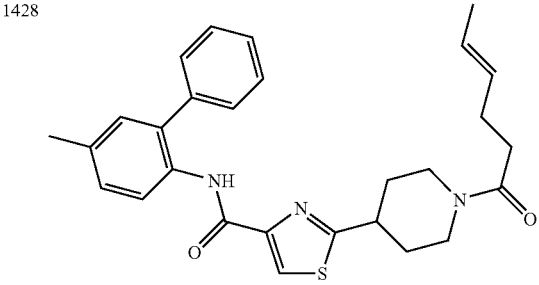
1429
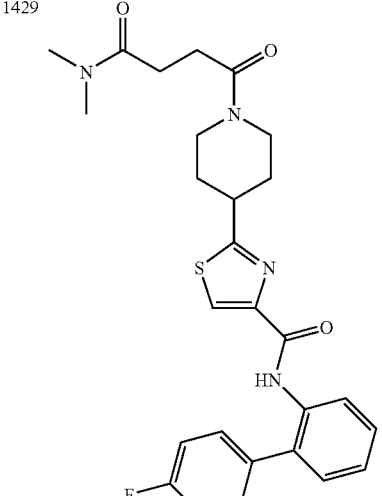
2-{1-[4-(dimethylamino)-4-oxobutanoyl]piperidin-4-yl}-N-(4'-fluorobiphenyl-2-yl)-1,3-thiazole-4-carboxamide TABLE 1-continued
| No. | FORMULA | NMR or mass |
|---|---|---|
1430
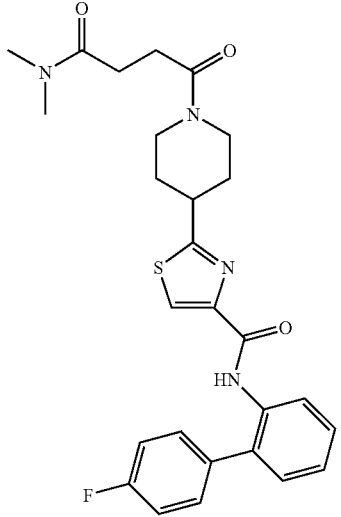
2-{1-[4-(dimethylamino)-4-oxobutanoyl]piperidin-4-yl}-N-(4′-fluorobiphenyl-2-yl)-1,3-thiazole-4-carboxamide
1431
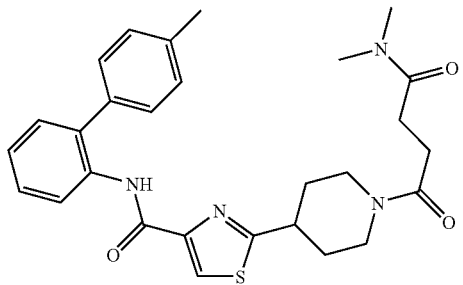
1432
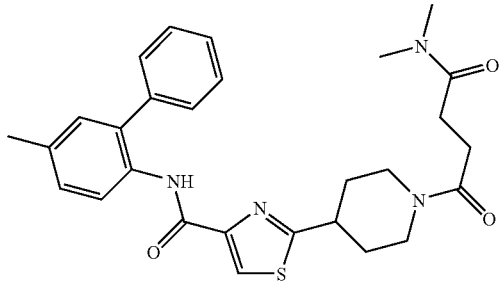

TABLE 1-continued
| No. | FORMULA | NMR or mass |
|---|---|---|
1433
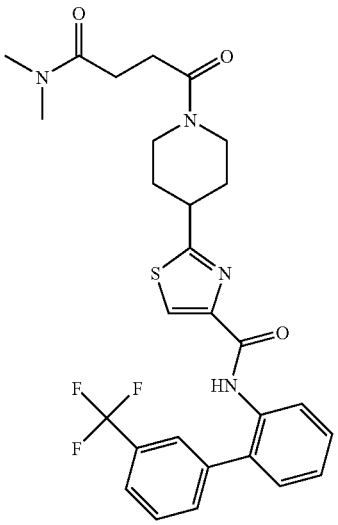
2-{1-[4-(dimethylamino)-4-oxobutanoyl]piperidin-4-yl}-N-[3'-trifluoromethyl)-biphenyl-2-yl]-1,3-thiazole-4-carboxamide
1434
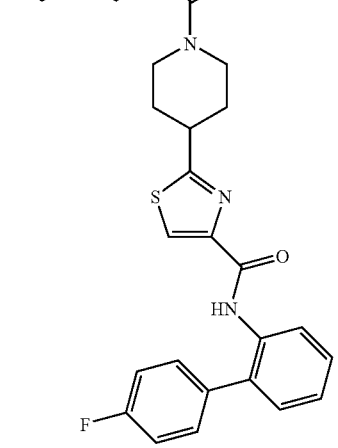
N-(4'-fluorobiphenyl-2-yl)-2-(1-hex-5-enoylpiperidin-4-yl)-1,3-thiazole-4-carboxamide
1435
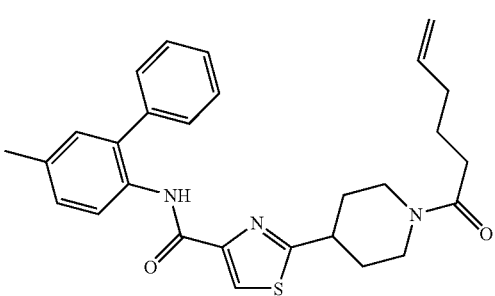

| No. | FORMULA | NMR or mass |
|---|---|---|
| 1436 | 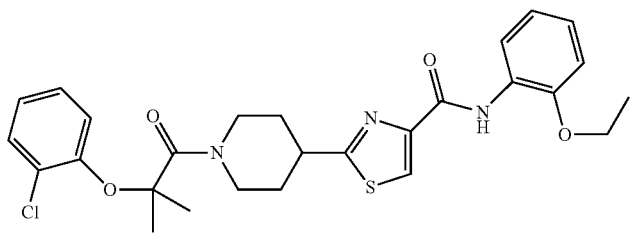 | |
| 1437 | 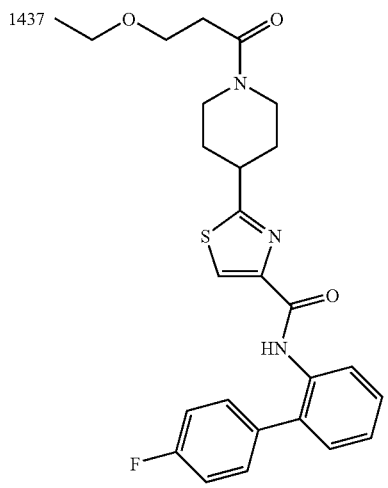<br>2-[1-(3-ethoxypropanoyl)piperidin-4-yl]-N-(4'-fluorobiphenyl-2-yl)-1,3-thiazole-4-carboxamide | |
| 1438 | 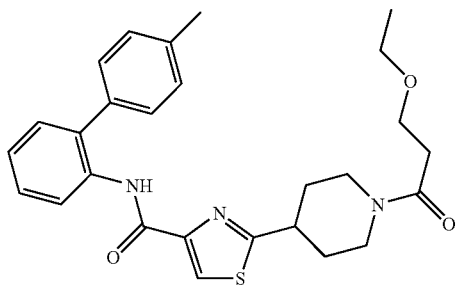 | |

TABLE 1-continued
| No. | FORMULA | NMR or mass |
|-----|---------|-------------|
1439
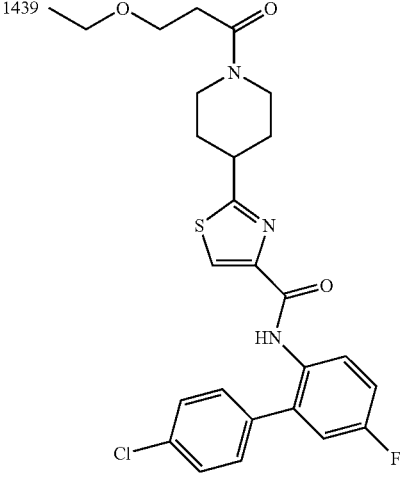
N-(4'-chloro-5-fluorobiphenyl-2-yl)-2-[1-(3-ethoxypropanoyl)piperidin-4-yl]-1,3-thiazole-4-carboxamide
1440
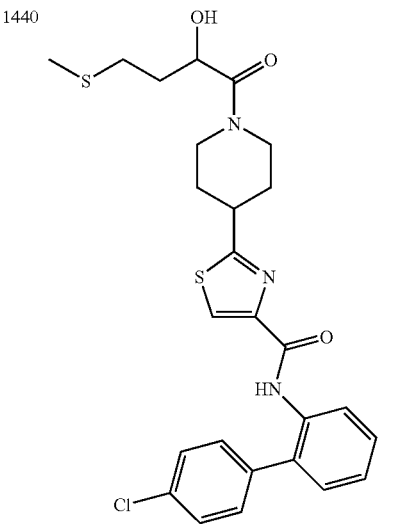
N-(4'-chlorobiphenyl-2-yl)-2-{1-[2-hydroxy-4-(methylthio)butanoyl]piperidin-4-yl}-1,3-thiazole-4-carboxamide
1441
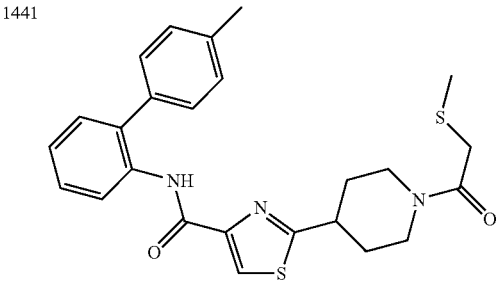

TABLE 1-continued
| No. | FORMULA | NMR or mass |
|---|---|---|
| 1442 | 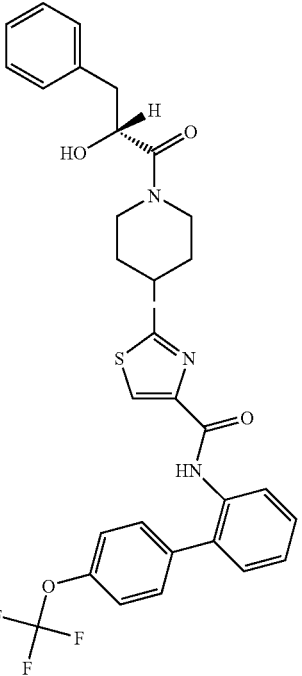 2-{1-[(2R)-2-hydroxy-3-phenylpropanoyl]piperidin-4-yl}-N-[4'-(trifluoromethoxy)biphenyl-2-yl]-1,3-thiazole-4-carboxamide | |
| 1443 | 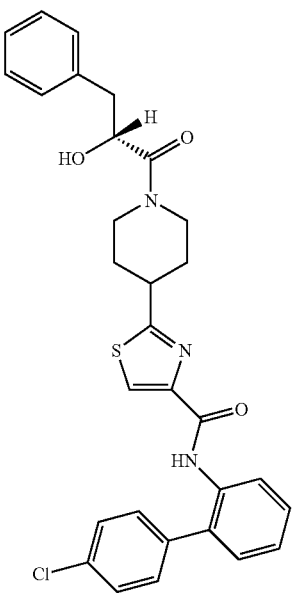 N-(4'-chlorobiphenyl-2-yl)-2-{1-[(2R)-2-hydroxy-3-phenylpropanoyl]piperidin-4-yl}-1,3-thiazole-4-carboxamide | |

TABLE 1-continued
| No. | FORMULA | NMR or mass |
|---|---|---|
| 1444 | 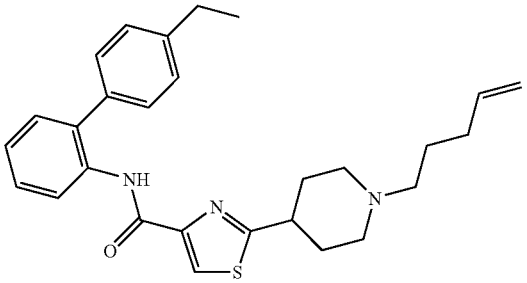 | |
| 1445 | 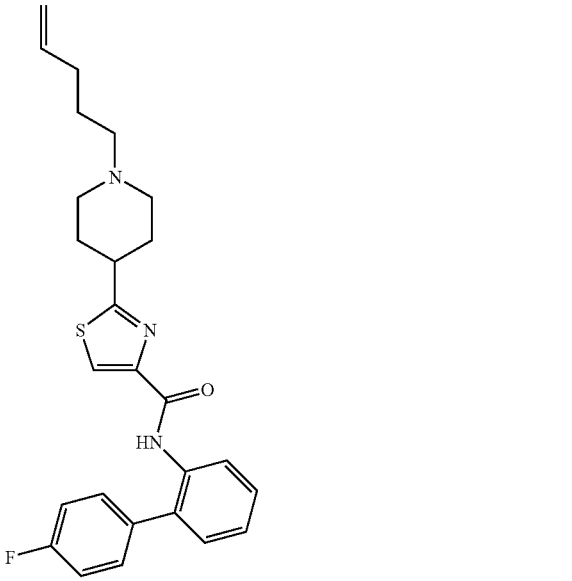  N-(4'-fluorobiphenyl-2-yl)-2-(1-pent-4-en-1-ylpiperidin-4-yl)-1,3-thiazole-4-carboxamide | |
| 1446 | 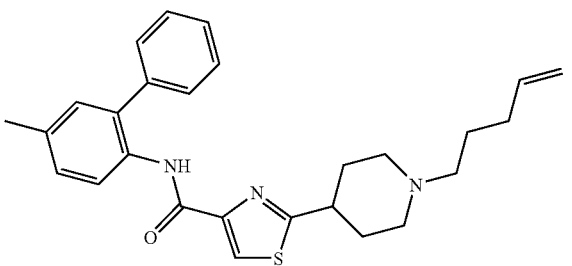 | |

TABLE 1-continued
| No. | FORMULA | NMR or mass |
|---|---|---|
1447
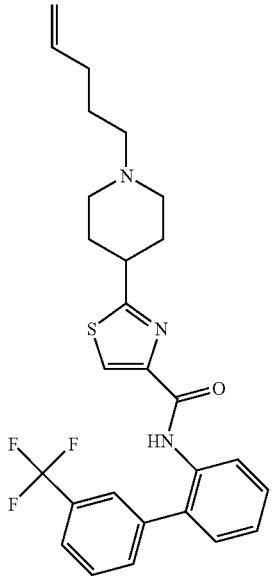
2-(1-pent-4-en-1-ylpiperidin-4-yl)-N-[3'-(trifluoromethyl)biphenyl-2-yl]-1,3-thiazole-4-carboxamide
1448
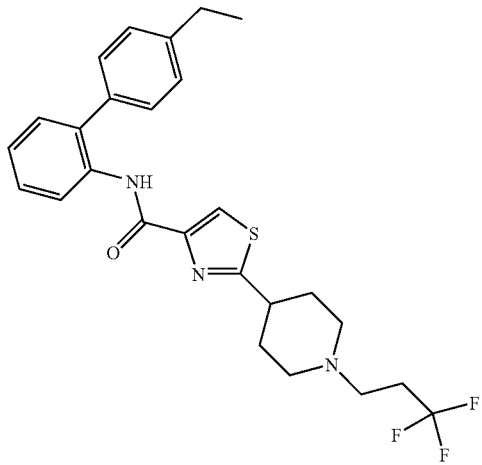
N-(4'-ethylbiphenyl-2-yl)-2-[1-(3,3,3-trifluoropropyl)piperidin-4-yl]-1,3-thiazole-4-carboxamide

| No. | FORMULA | NMR or mass |
|---|---|---|
| 1449 | 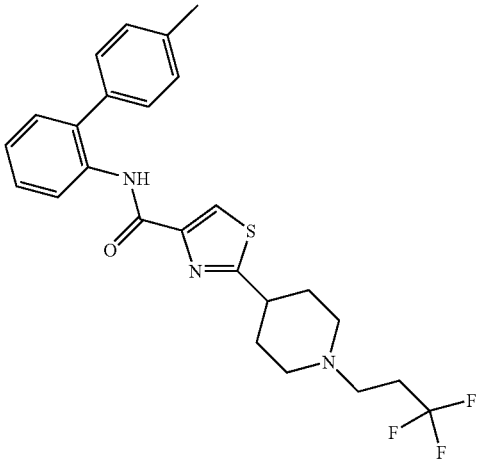<br>N-(4'-methylbiphenyl-2-yl)-2-[1-(3,3,3-trifluoropropyl)piperidin-4-yl]-1,3-thiazole-4-carboxamide | |
| 1450 | 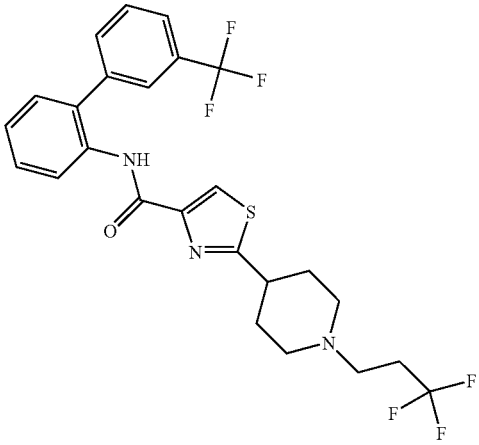<br>N-[3'-(trifluoromethyl)biphenyl-2-yl]-2-[1-(3,3,3-trifluoropropyl)piperidin-4-yl]-1,3-thiazole-4-carboxamide | |

TABLE 1-continued
| No. | FORMULA | NMR or mass |
|---|---|---|
| 1451 | 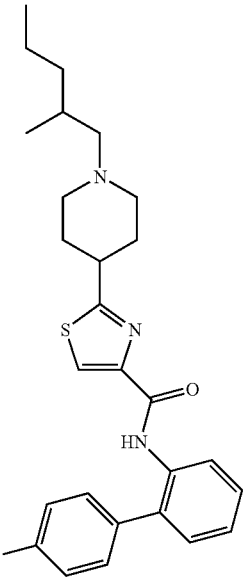 N-(4'-fluorobiphenyl-2-yl)-2-[1-(2-methylpentyl)piperidin-4-yl]-1,3-thiazole-4-carboxamide | |
| 1452 | 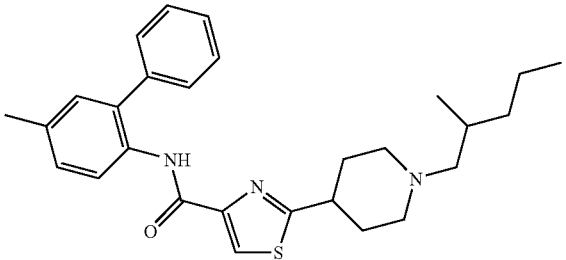 | |
| 1453 | 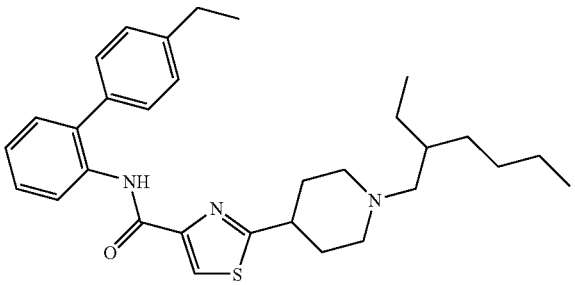 | |
| 1454 | 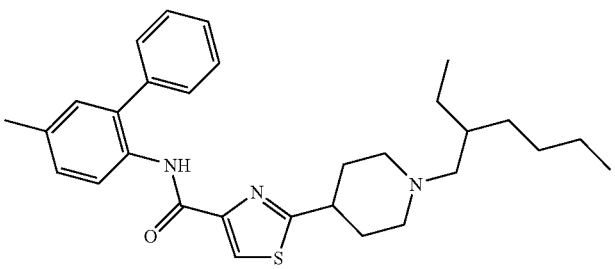 | |

TABLE 1-continued

| No. | FORMULA | NMR or mass |
|---|---|---|
| 1455 | | |
| 1456 | | |
| 1457 | | |

2-[1-(3-phenylpropyl)piperidin-4-yl]-N-[3'-(trifluoromethyl)
biphenyl-2-yl]-1,3-thiazole-4-carboxamide

| No. | FORMULA | NMR or mass |
|---|---|---|
| 1458 | 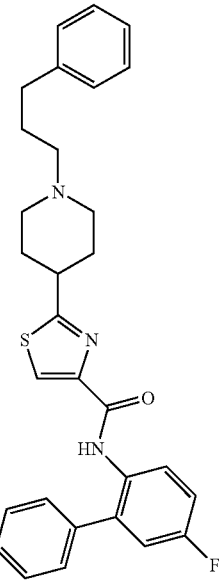<br>N-(4'-chloro-5-fluorobiphenyl-2-yl)-2-[1-(3-phenylpropyl)piperidin-4-yl]-1,3-thiazole-4-carboxamide | |
| 1459 | 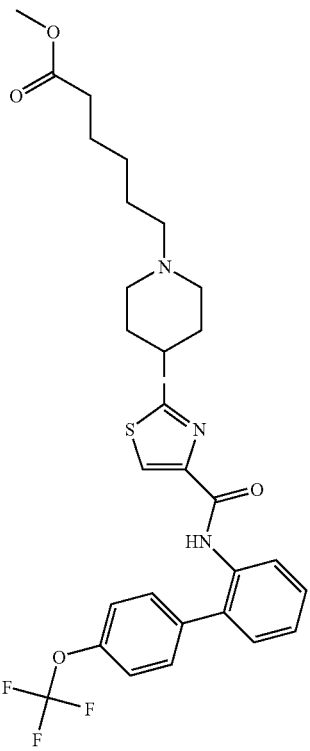<br>methyl 6-{4-[4-(({[4'-(trifluoromethoxy)bipheny-2-yl]amino}carbonyl)-1,3-thiazol-2-yl]piperidin-1-yl}hexanoate | |

TABLE 1-continued
| No. | FORMULA | NMR or mass |
|---|---|---|
1460
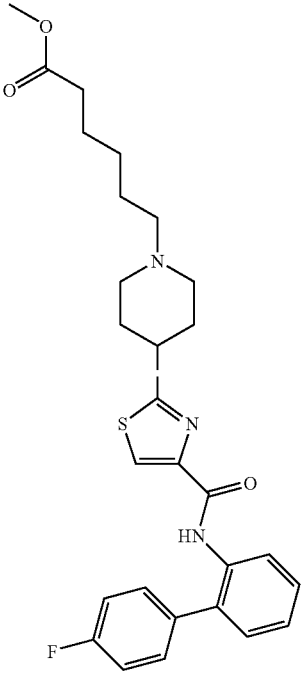
methyl 6-[4-(4-{[(4'-(fluorobiphenyl-2yl)amino]carbonyl}-1,3-thiazol-2-yl)-piperidin-1-yl]hexanoate
1461
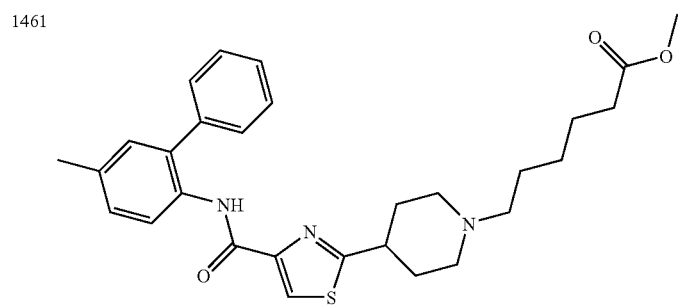

| No. | FORMULA | NMR or mass |
|---|---|---|
| 1462 | 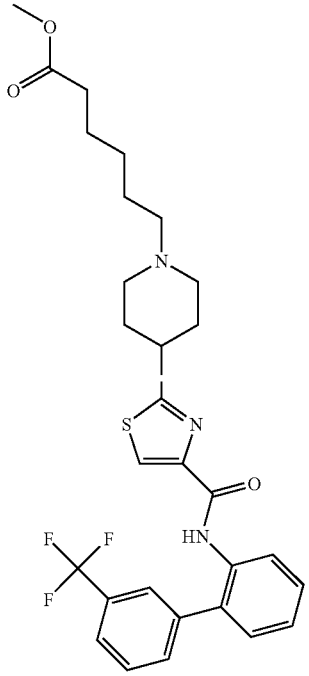<br>methyl 6-{4-[4-({[3'-(trifluoromethyl)biphenyl-2-yl]amino}carbonyl)-1,3-thiazol-2-yl]piperidin-1-yl}hexanoate | |
| 1463 | 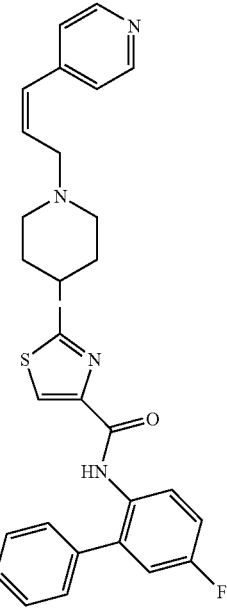<br>N-(4'-chloro-5-fluorobiphenyl-2-yl)-2-{1-[2Z)-3pyridin-4-ylprop-2-en-1-yl]-piperidin-4-yl}-1,3-thiazole-4-carboxamide | |

TABLE 1-continued
| No. | FORMULA | NMR or mass |
|---|---|---|
| 1464 | 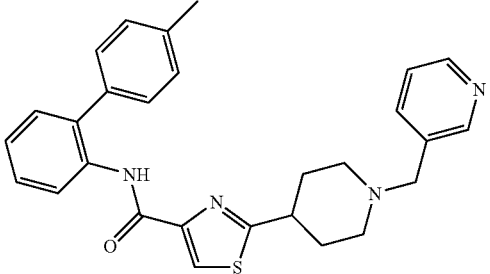 | |
| 1465 | 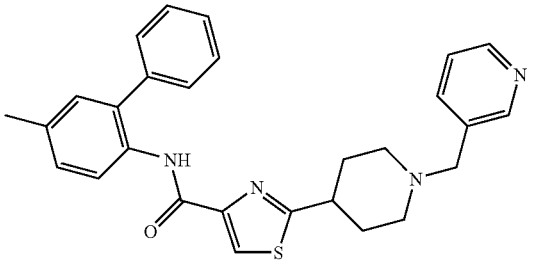 | |
| 1466 | 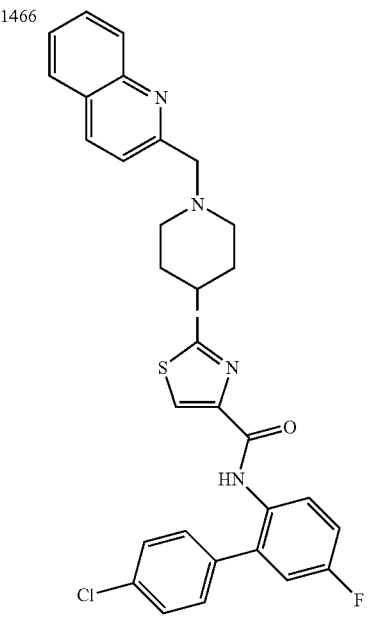 | |
N-(4'-chloro-5-fluorobiphenyl-2-yl)-2-[1-(quinolin-2-ylmethyl)piperidin-4-yl]-1,3-thiazole-4-carboxamide TABLE 1-continued
| No. | FORMULA | NMR or mass |
|---|---|---|
| 1467 | 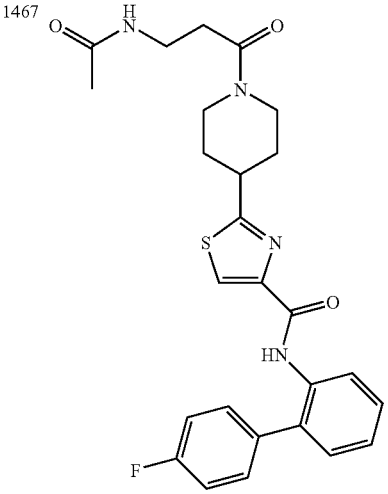 2-[1-(N-acetyl-beta-alanyl)piperidin-4-yl]-N-(4'-fluorobiphenyl-2-yl)-1,3-thiazole-4-carboxamide | |
| 1468 | 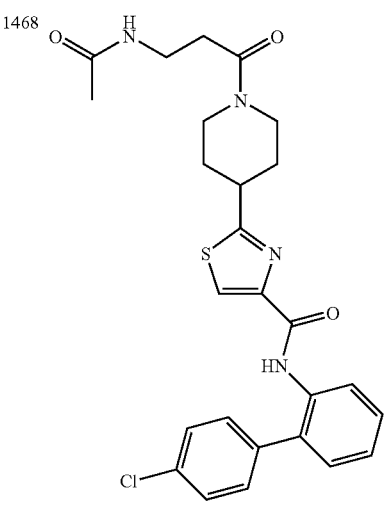 2-[1-(N-acetyl-beta-alanyl)piperidin-4-yl]-N-(4'-chlorobiphenyl-2-yl)-1,3-thiazole-4-carboxamide | |

TABLE 1-continued
| No. | FORMULA | NMR or mass |
|---|---|---|
| 1469 | 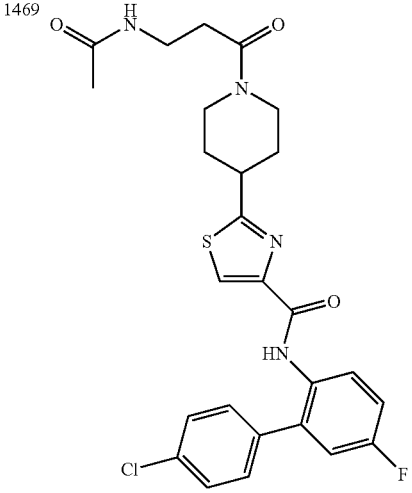 2-[1-(N-acetyl-beta-alanyl)piperidin-4-yl]-N-(4'-chloro-5-fluorobiphenyl-2-yl)-1,3-thiazole-4-carboxamide | |
| 1470 | 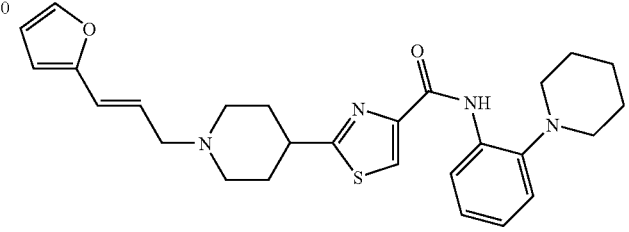 | |
| 1471 | 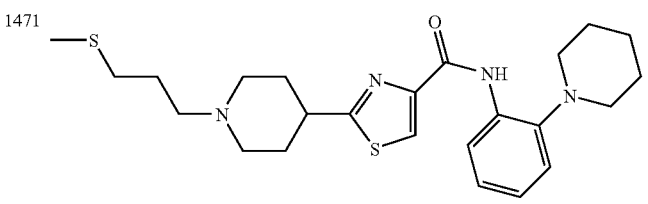 | |
| 1472 | 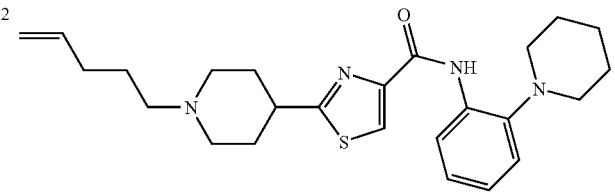 | |
| 1473 | 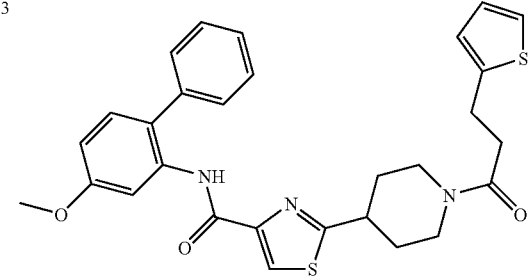 | |

TABLE 1-continued
| No. | FORMULA | NMR or mass |
|---|---|---|
| 1474 | 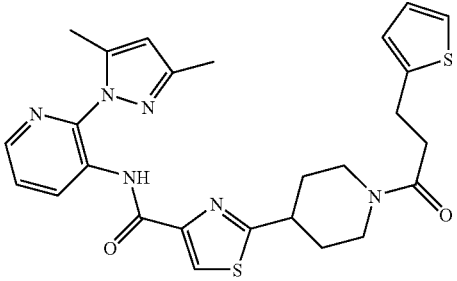 | |
| 1475 | 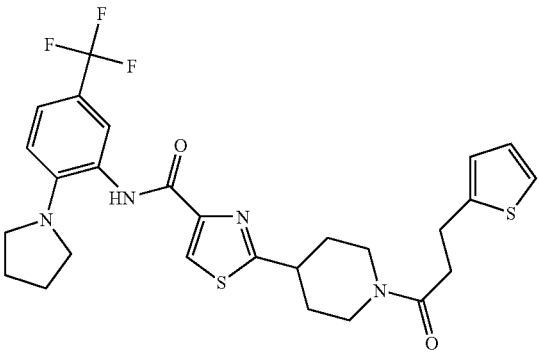 | |
| 1476 | 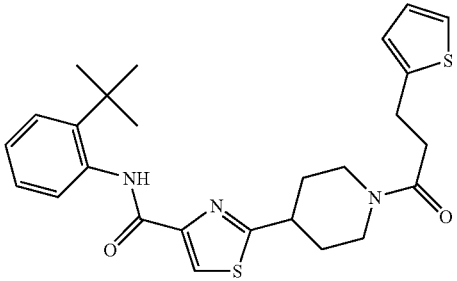 | |
| 1477 | 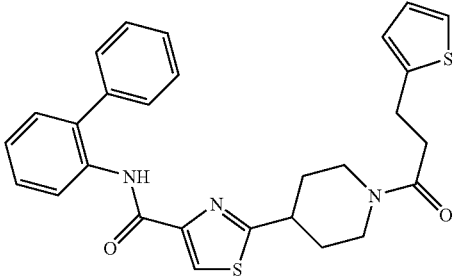 | |

TABLE 1-continued

| No. | FORMULA | NMR or mass |
|---|---|---|

1478

1479

N-[2-(3,5-dimethyl-1H-pyrazol-1-yl)pyridin-3-yl]-2-(1-{[(methylsulfonyl)-methyl]sulfonyl}piperidin-4-yl)-1,3-thiazole-4-carboxamide

1480

TABLE 1-continued
| No. | FORMULA | NMR or mass |
|---|---|---|
| 1481 | 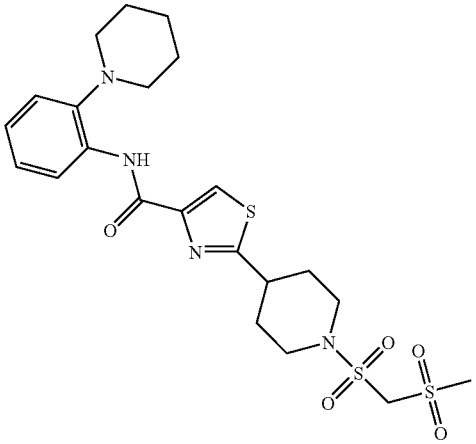<br>2-(1-{[(methylsulfonyl)methyl]sulfonyl)piperidin-4-yl)-N-(2-piperidin-1-yl-phenyl)-1,3-thiazole-4-carboxamide | |
| 1482 | 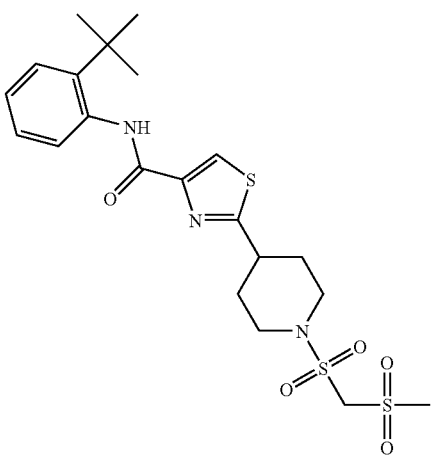<br>N-(2-tert-butylphenyl)-2-(1-{[(methylsulfonyl)methyl]sulfonyl}piperidin-4-yl)-1,3-thiazole-4-carboxamide | |
| 1483 | 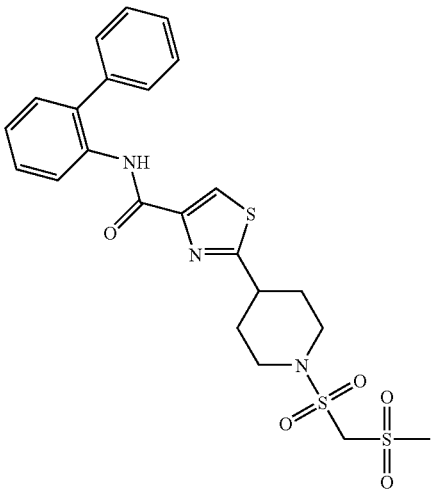<br>N-biphenyl-2-yl-2-(1-{[(methylsulfonyl)methyl]sulfonyl}piperidin-4-yl)-1,3-thiazole-4-carboxamide | |

TABLE 1-continued
| No. | FORMULA | NMR or mass |
|---|---|---|
| 1484 | 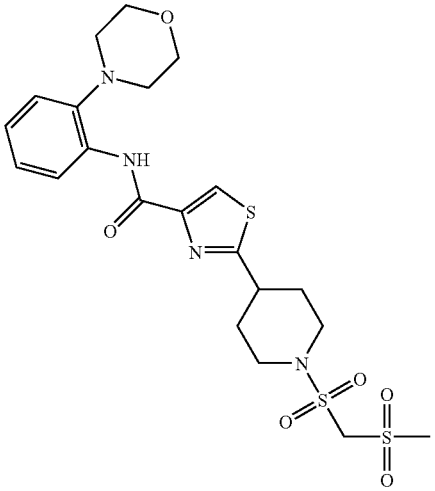 2-(1-{[(methylsulfonyl)methyl]sulfonyl}piperidin-4-yl)-N-(2-morpholin-4-yl-phenyl)-1,3-thiazole-4-carboxamide | |
| 1485 | 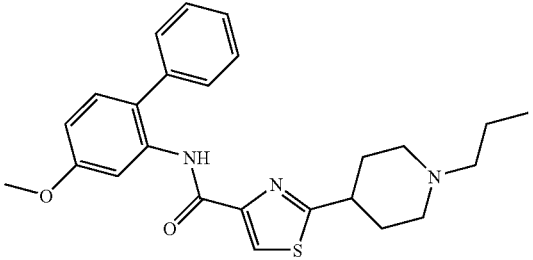 | |
| 1486 | 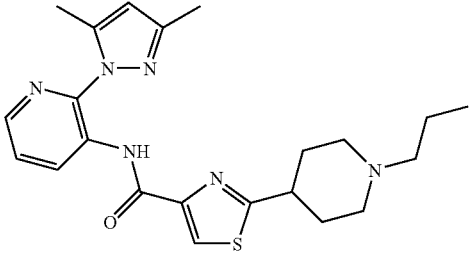 | |
| 1487 | 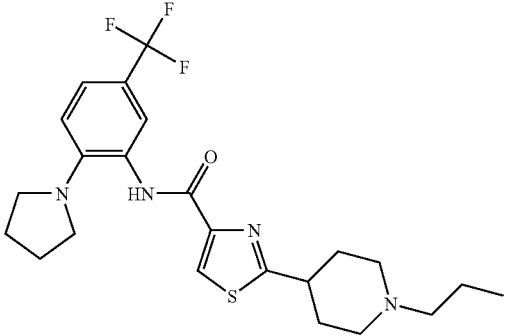 | |

TABLE 1-continued
| No. | FORMULA | NMR or mass |
|---|---|---|
| 1488 | 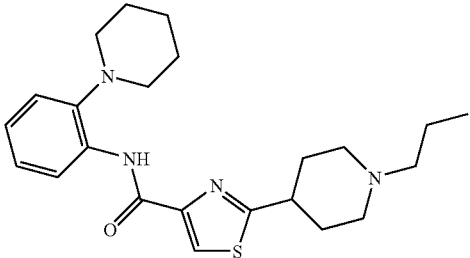 | |
| 1489 | 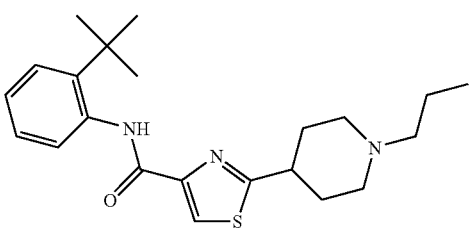 | |
| 1490 | 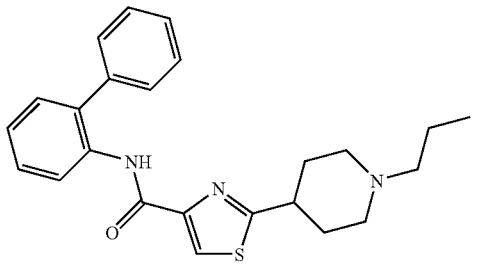 | |
| 1491 | 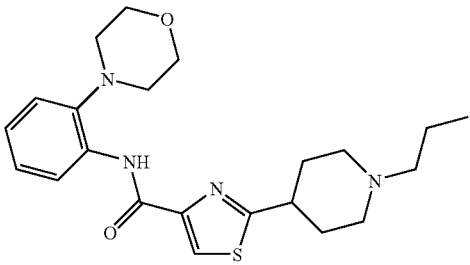 | |
| 1492 | 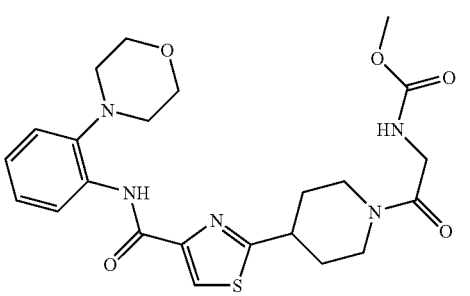 | |

TABLE 1-continued
| No. | FORMULA | NMR or mass |
|---|---|---|
| 1493 | 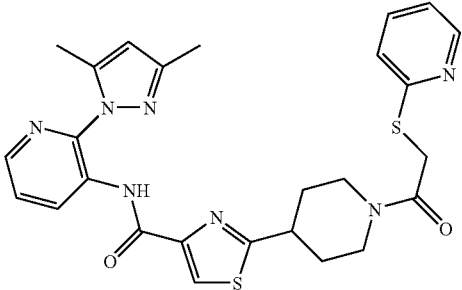 | |
| 1494 | 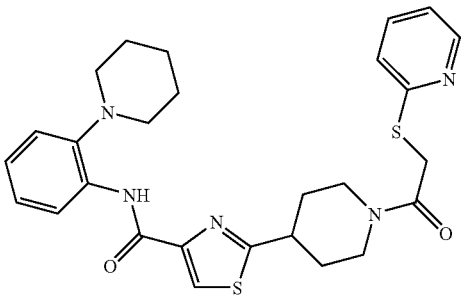 | |
| 1495 | 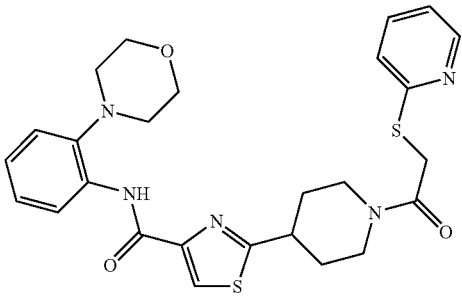 | |
| 1496 | 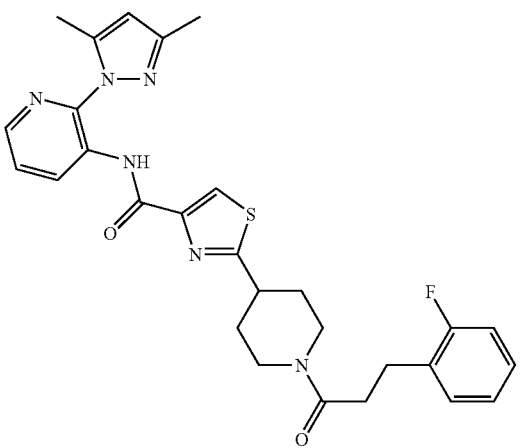 | |

TABLE 1-continued
| No. | FORMULA | NMR or mass |
|---|---|---|
| 1497 | 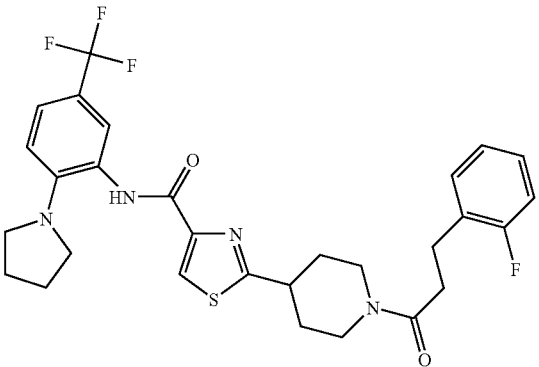 | |
| 1498 | 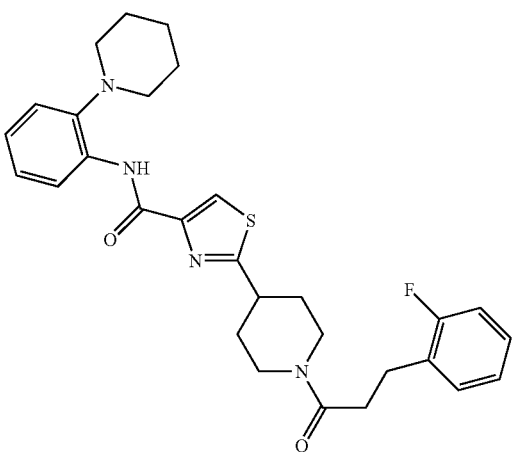 | |
| 1499 | 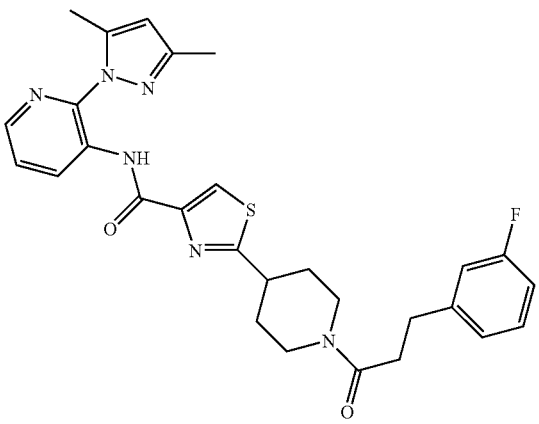 | |

TABLE 1-continued
| No. | FORMULA | NMR or mass |
|---|---|---|
| 1500 | 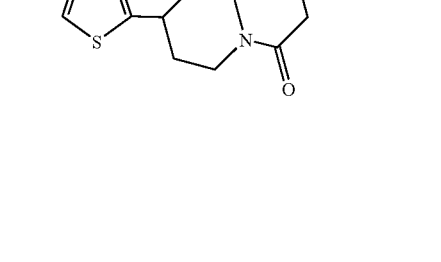 | |
| 1501 | 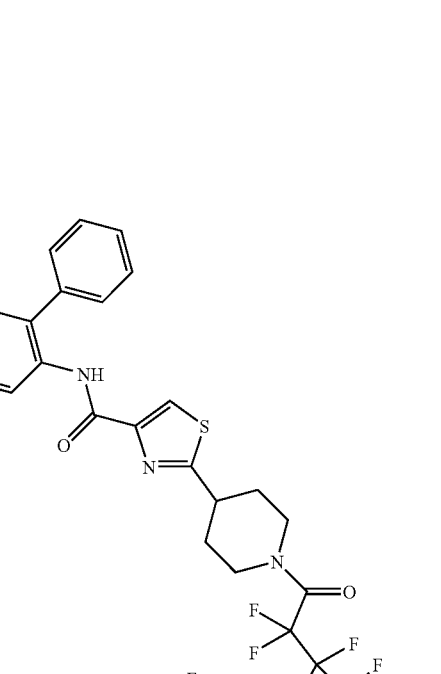 | |

TABLE 1-continued
| No. | FORMULA | NMR or mass |
|---|---|---|
| 1502 | 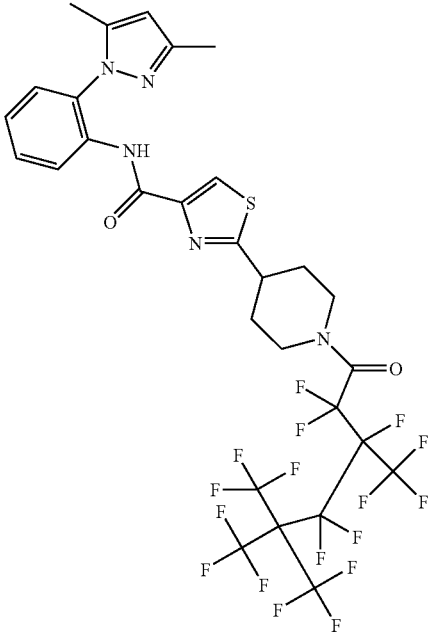 | |
| 1503 | 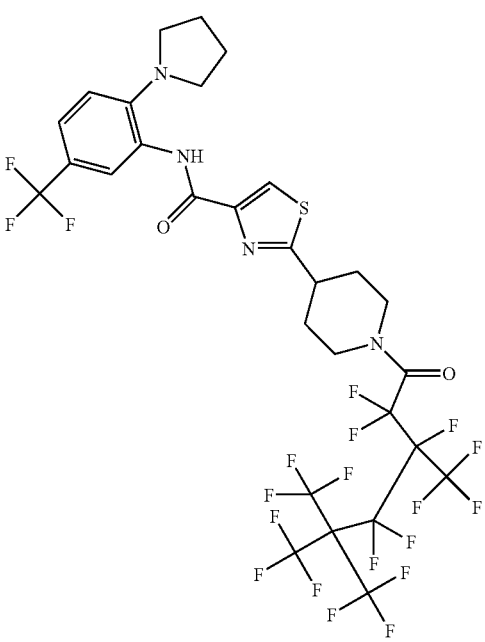 | |

TABLE 1-continued
| No. | FORMULA | NMR or mass |
|---|---|---|
| 1504 | 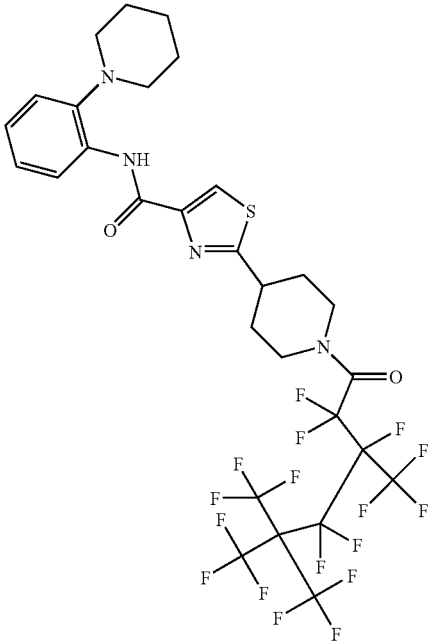 | |
| 1505 | 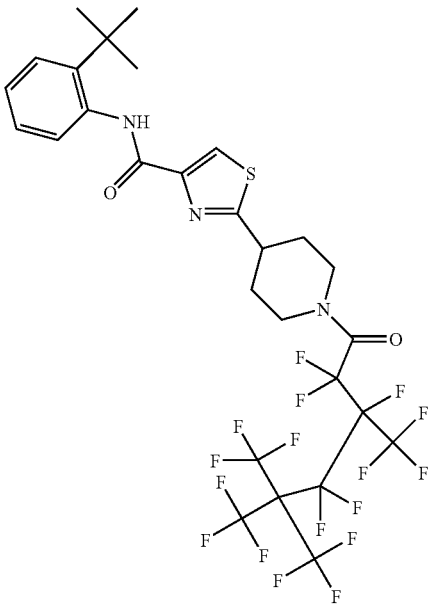 | |
| 1506 | 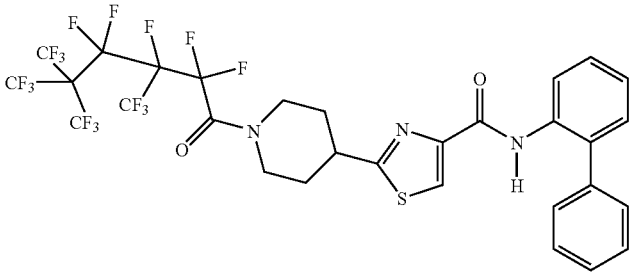 | |

TABLE 1-continued
| No. | FORMULA | NMR or mass |
|---|---|---|
| 1507 | 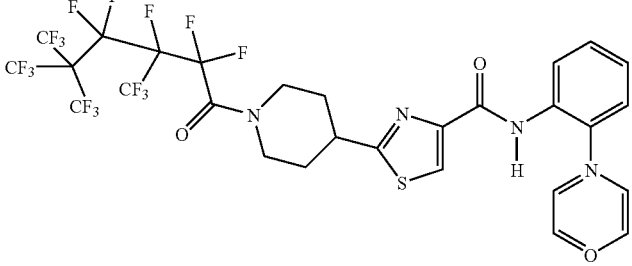 | |
| 1508 | 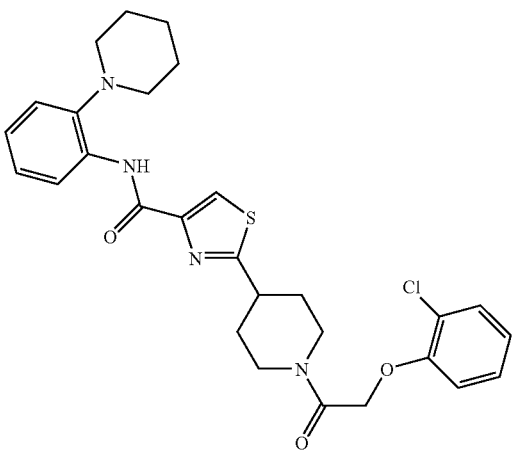 | |
| 1509 | 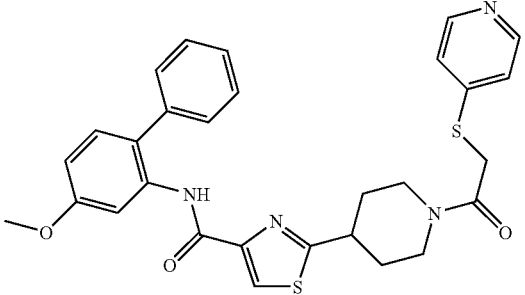 | |
| 1510 | 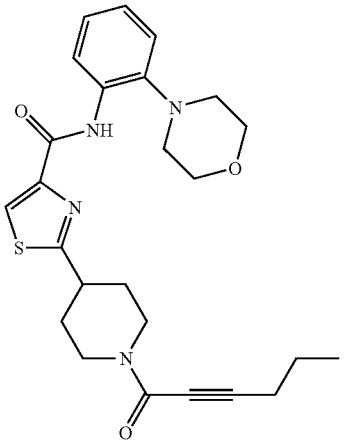 | |

TABLE 1-continued
| No. | FORMULA | NMR or mass |
|---|---|---|
| 1511 | 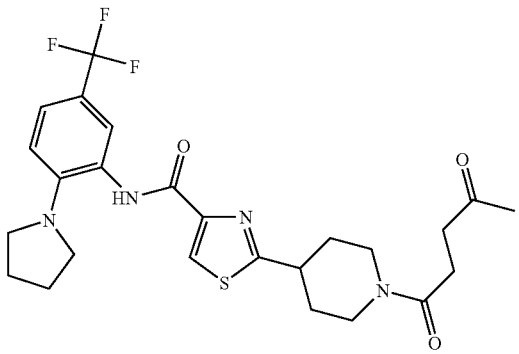 | |
| 1512 | 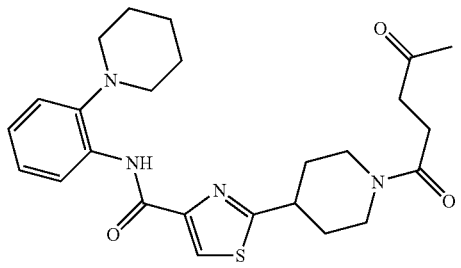 | |
| 1513 | 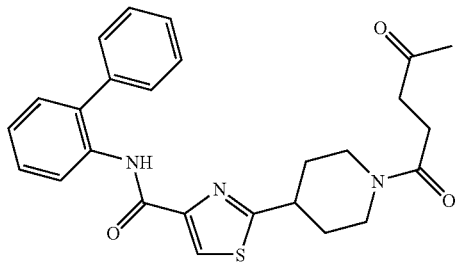 | |
| 1514 | 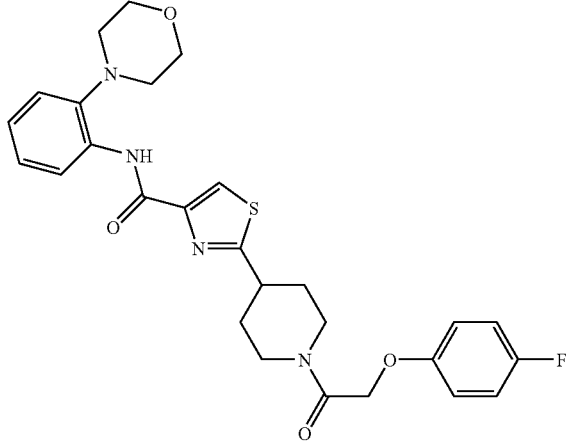 | |

TABLE 1-continued
| No. | FORMULA | NMR or mass |
|---|---|---|
| 1515 | 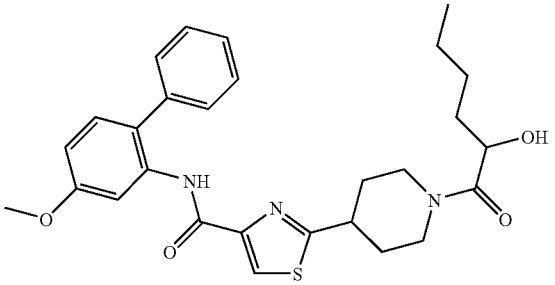 | |
| 1516 | 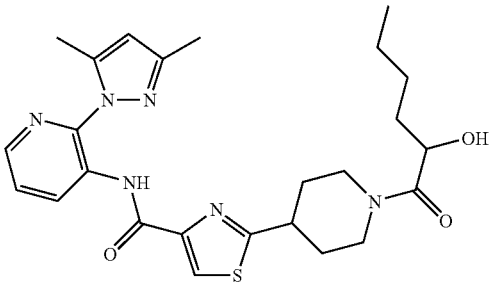 | |
| 1517 | 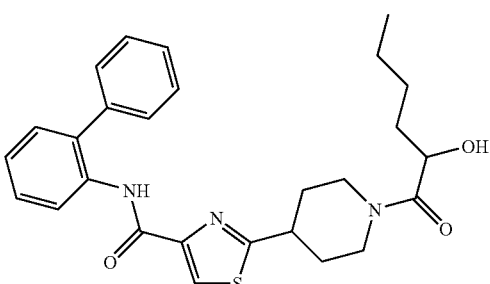 | |
| 1518 | 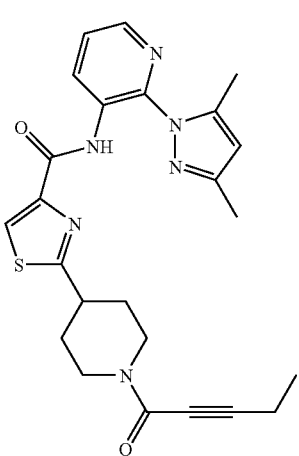 | |

TABLE 1-continued

| No. | FORMULA | NMR or mass |
|---|---|---|

1519

2-{1-[3-(4-chlorophenyl)propanoyl]piperidin-4-yl}-N-[2-(3,5-dimethyl-1H-pyrazol-1-yl)pyridin-3-yl]-1,3-thiazole-4-carboxamide

1520

1521

1522

2-{1-[3-(4-oxo-2-thioxo-1,3-thiazolidin-3-yl)propanoyl]piperidin-4-yl}-N-[2-pyrrolidin-1-yl-5-(trifluomethyl)phenyl]-1,3-thiazole-4-carboxamide

TABLE 1-continued
| No. | FORMULA | NMR or mass |
|---|---|---|
| 1523 | 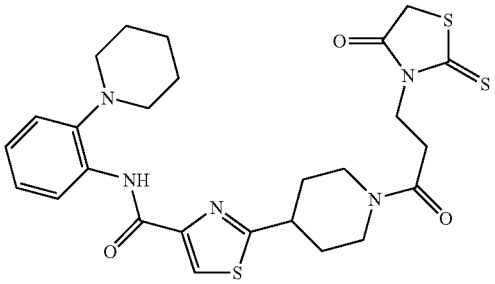 | |
| 1524 | 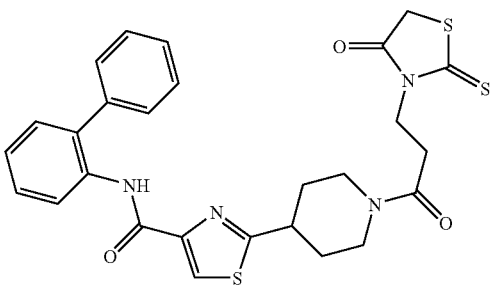 | |
| 1525 | 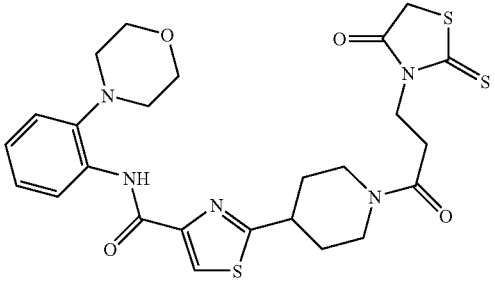 | |
| 1526 | 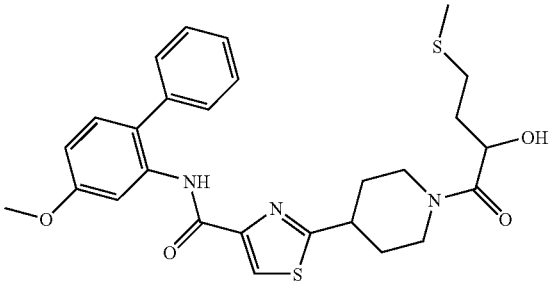 | |
| 1527 | 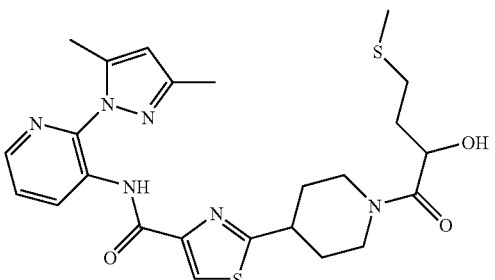 | |

TABLE 1-continued
| No. | FORMULA | NMR or mass |
|---|---|---|
| 1528 | 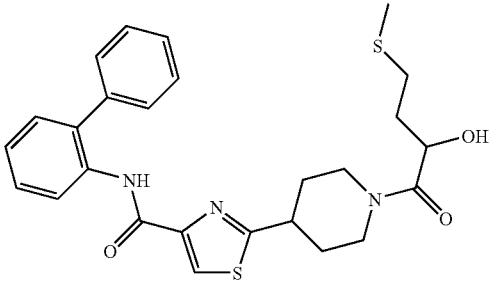 | |
| 1529 | 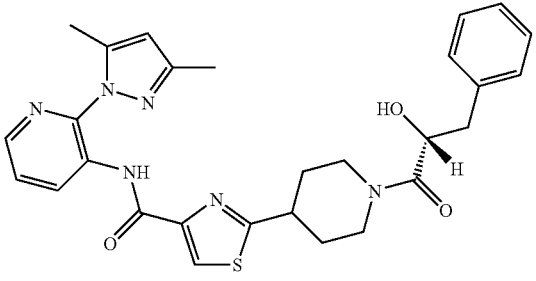 | |
| 1530 | 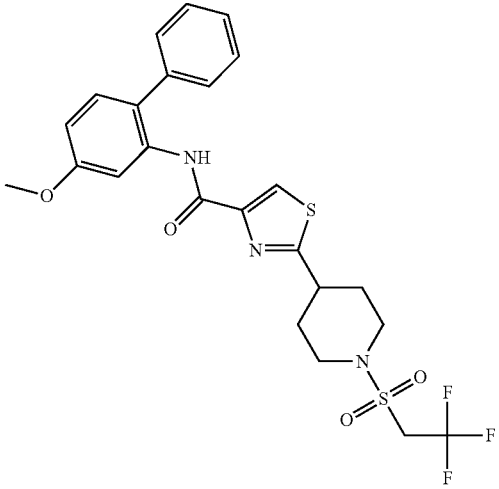 | |
N-(4-methoxybiphenyl-2-yl)-2-{1-[(2,2,2-trifluoroethyl)sulfonyl]piperidin-4-yl}-1,3-thiazole-4-carboxamide

TABLE 1-continued

| No. | FORMULA | NMR or mass |
|---|---|---|

1531

N-[2-pyrrolidin-1-yl-5-(trifluoromethyl)phenyl]-2-{1-[(2,2,2-trifluoroethyl)-sulfonyl]piperidin-4-yl}-1,3-thiazole-4-carboxamide

1532

N-(2-piperidin-1-ylphenyl)-2-{1-[(2,2,2-trifluoroethyl)sulfonyl]piperidin-4-yl}-1,3-thiazole-4-carboxamide TABLE 1-continued
| No. | FORMULA | NMR or mass |
|---|---|---|
| 1533 | 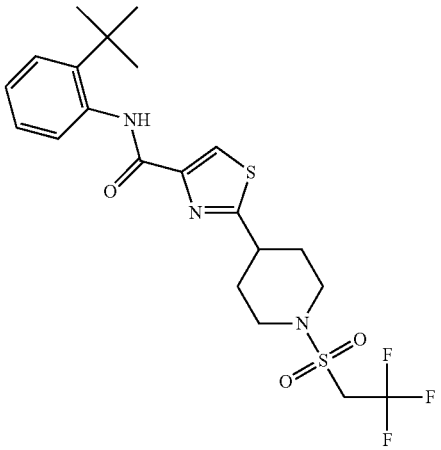 N-(2-tert-butylphenyl)-2-(1-{1-[(2,2,2-trifluoroethyl)sulfonyl]piperidin-4-yl}-1,3-thiazole-4-carboxamide | |
| 1534 | 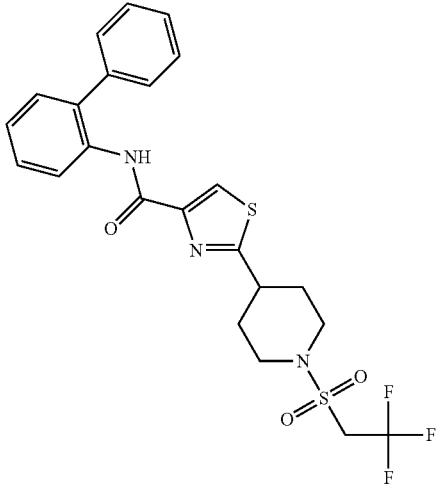 N-biphenyl-2-2-{1-[(2,2,2-trifluoroethyl)sulfonyl]piperidin-4-yl}-1,3-thiazole-4-carboxamide | |
| 1535 | 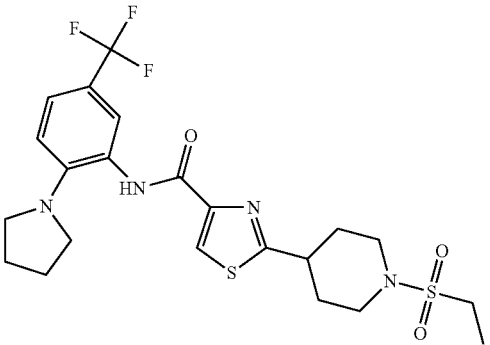 | |

| No. | FORMULA | NMR or mass |
|---|---|---|
| 1536 | 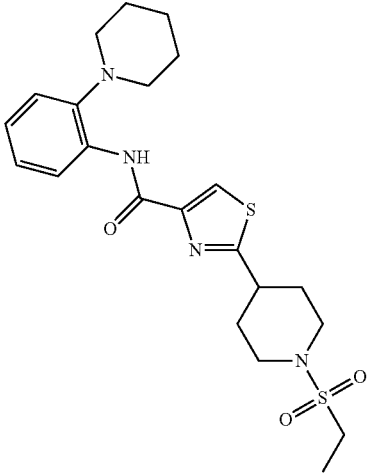 2-[1-(ethylsulfonyl)piperidin-4-yl]-N-(2-piperidin-1-ylphenyl)-1,3-thiazole-4-carboxamide | |
| 1537 | 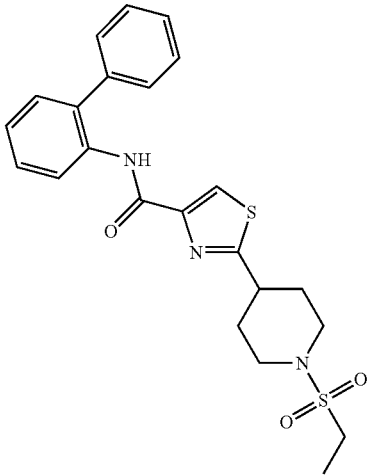 N-biphenyl-2-yl-2-[1-(ethylsulfonyl)piperidin-4-yl]-1,3-thiazole-4-carboxamide | |

TABLE 1-continued
| No. | FORMULA | NMR or mass |
|---|---|---|
| 1538 | 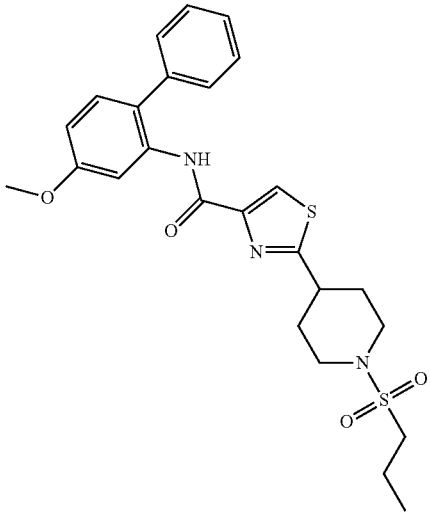 N-(4-methoxybiphenyl-2-yl)-2-[1-(propylsulfonyl)piperidin-4-yl]-1,3-thiazole-4-carboxamide | |
| 1539 | 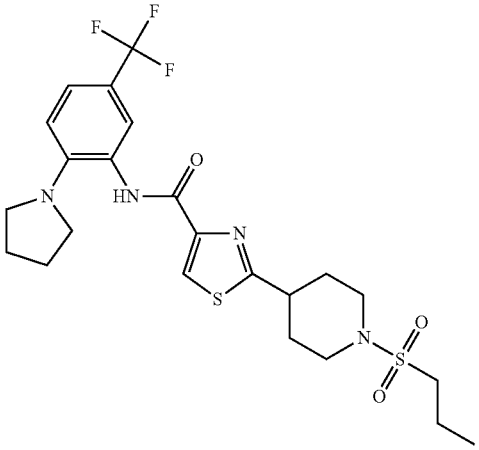 2-[1-(propylsulfonyl)piperidin-4-yl]-N-[2-pyrrolidin-1-yl-5-(trifluoromethyl)-phenyl]-1,3-thiazole-4-carboxamide | |

TABLE 1-continued
| No. | FORMULA | NMR or mass |
|---|---|---|
1540
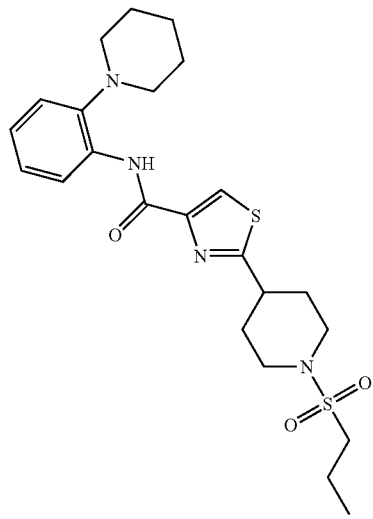
N-(2-piperidin-1-ylphenyl)-2-[1-(propylsulfonyl)piperdin-4-yl]-1,3-thiazole-4-carboxamide
1541
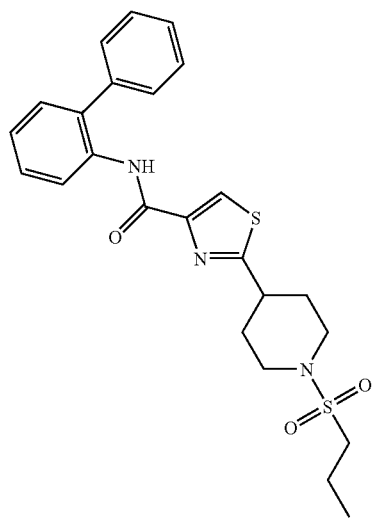
N-biphenyl-2-yl-2-[1-(propylsulfonyl)piperdin-4-yl]-1,3-thiazole-4-carboxamide TABLE 1-continued
| No. | FORMULA | NMR or mass |
|---|---|---|
| 1542 | 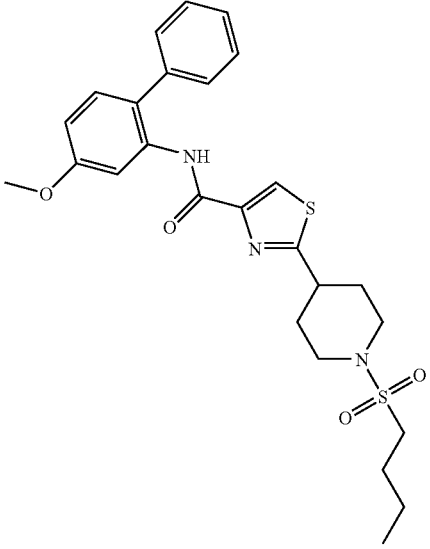<br>2-[1-(butylsulfonyl)piperidin-4-yl]-N-(4-methoxybiphenyl-2-yl)-1,3-thiazole-4-carboxamide | |
| 1543 | 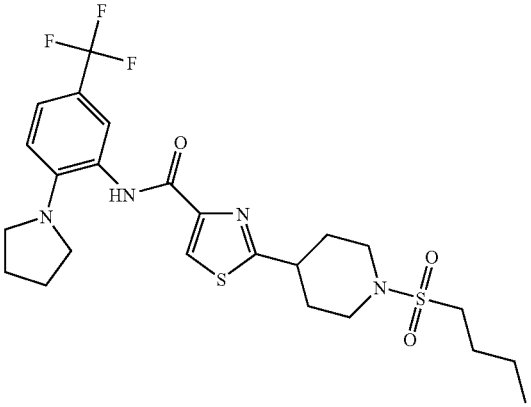<br>2-[1-(butylsulfonyl)piperidin-4-yl]-N-[2-pyrrolidin-1-yl-5-(trifluoromethyl)-phenyl]-1,3-thiazole-4-carboxamide | |

TABLE 1-continued
| No. | FORMULA | NMR or mass |
|---|---|---|
| 1544 | 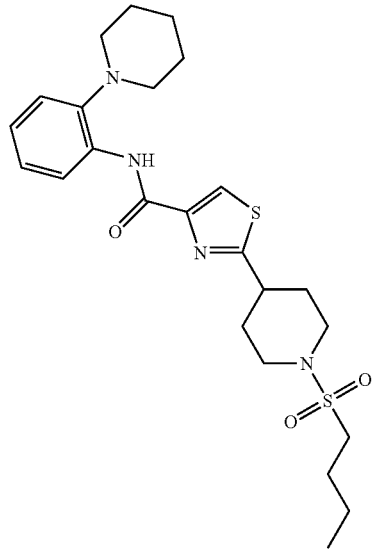 2-[1-(butylsulfonyl)piperidin-4-yl]-N-(2-piperidin-1-ylphenyl)-1,3-thiazole-4-carboxamide | |
| 1545 | 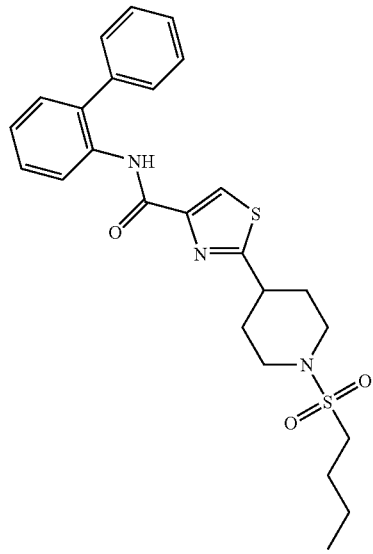 N-biphenyl-2-yl-2-[1-(butylsulfonyl)piperidin-4-yl]-1,3-thiazole-4-carboxamide | |

TABLE 1-continued
| No. | FORMULA | NMR or mass |
|---|---|---|
| 1546 | 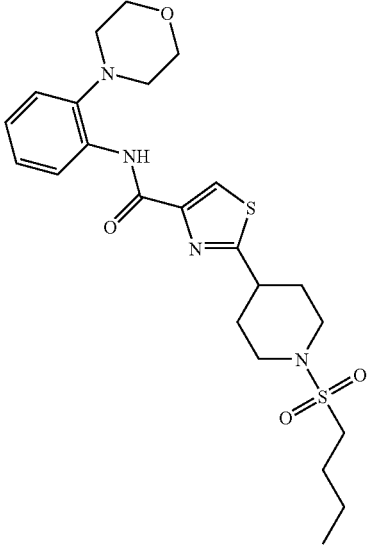 2-[1-(butylsulfonyl)piperidin-4-yl]-N-(2-morpholin-4-ylphenyl)-1,3-thiazole-4-carboxamide | |
| 1547 | 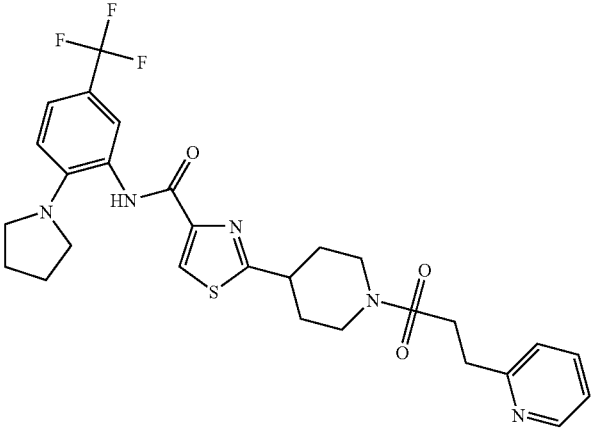 2-{1-[(pyridin-2-ylethyl)sulfonyl]piperidin-4-yl}-N-[2-pyrrolidin-1-yl-5-(trifluoromethyl)phenyl]-1,3-thiazole-4-carboxamide | |

TABLE 1-continued
| No. | FORMULA | NMR or mass |
|---|---|---|
| 1548 | 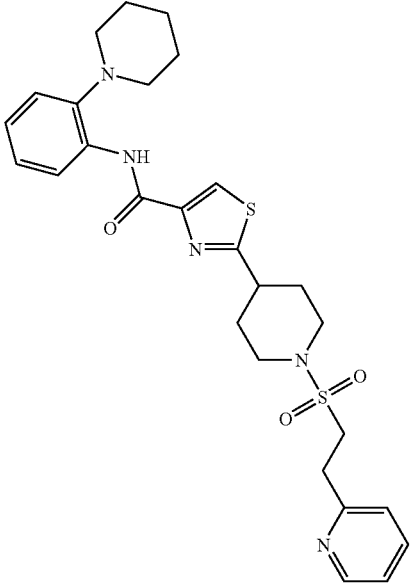 N-(2-piperidin-1-ylphenyl)-2-{1-[(2-pyridin-2-ylethyl)sulfonyl]piperidin-4-yl}-1,3-thiazole-4-carboxamide | |
| 1549 | 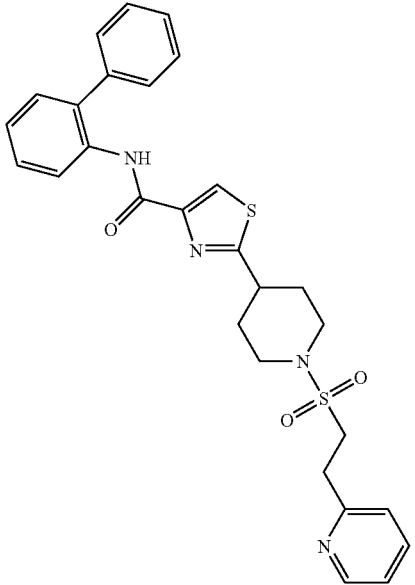 N-biphenyl-2-yl-2-{1-[(2-pyridin-2-ylethyl)sulfonyl]piperidin-4-yl}-1,3-thiazole-4-carboxamide | |
| 1550 | 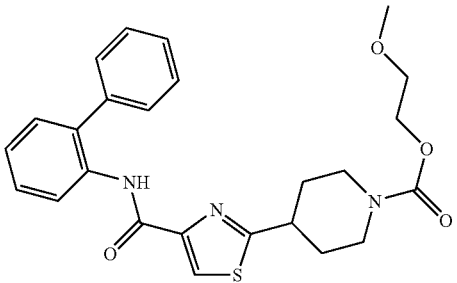 | |

TABLE 1-continued
| No. | FORMULA | NMR or mass |
|---|---|---|
| 1551 | 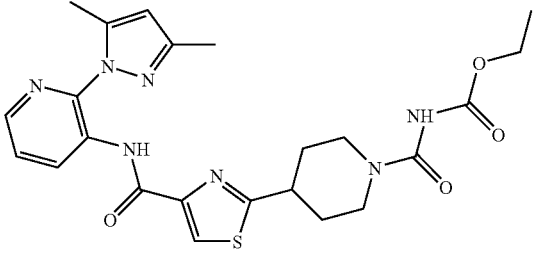 | |
| 1552 | 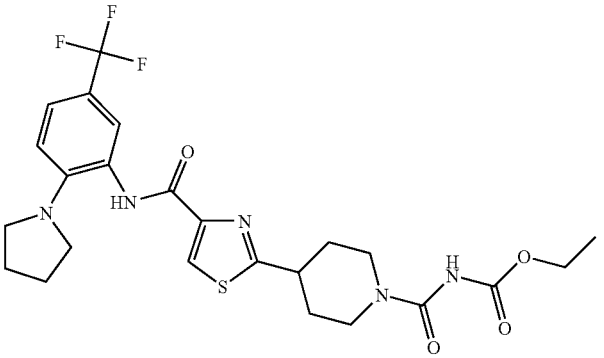 | |
| 1553 | 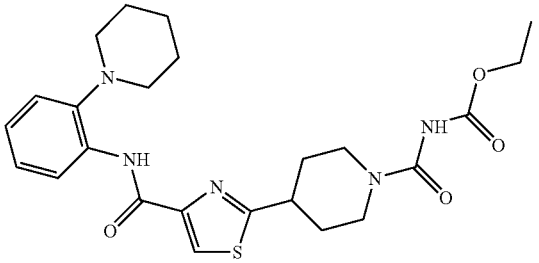 | |
| 1554 | 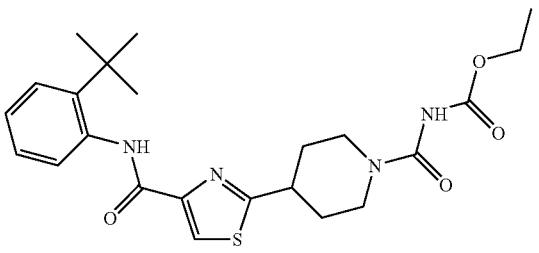 | |
| 1555 | 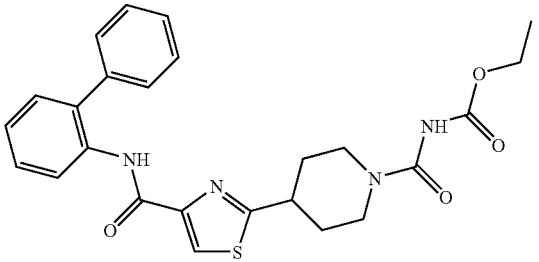 | |

TABLE 1-continued
| No. | FORMULA | NMR or mass |
|---|---|---|
| 1556 | 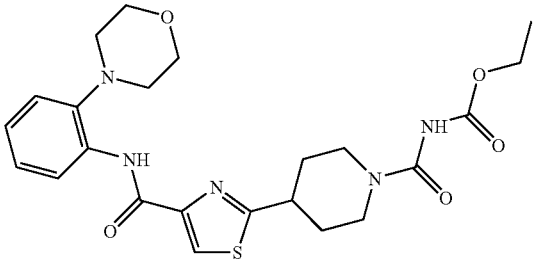 | |
| 1557 | 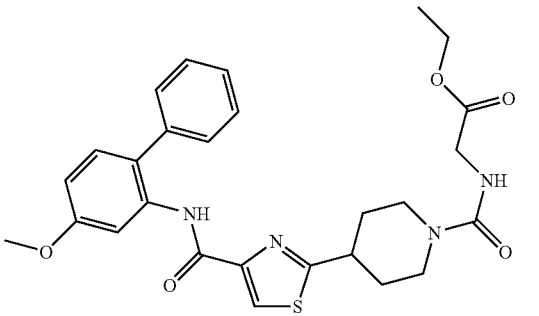 | |
| 1558 | 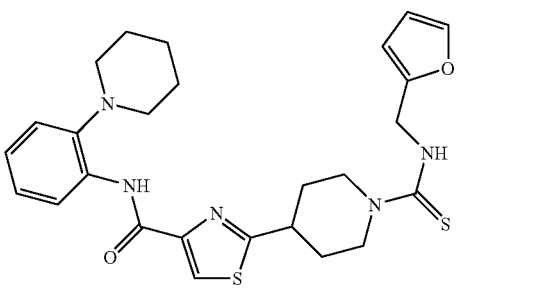 | |
| 1559 | 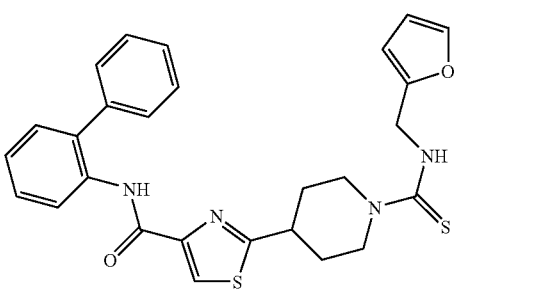 | |
| 1560 | 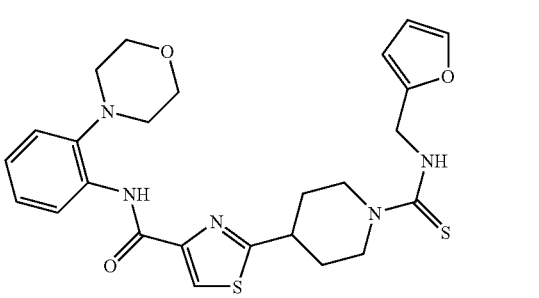 | |

TABLE 1-continued
| No. | FORMULA | NMR or mass |
|---|---|---|
| 1561 | 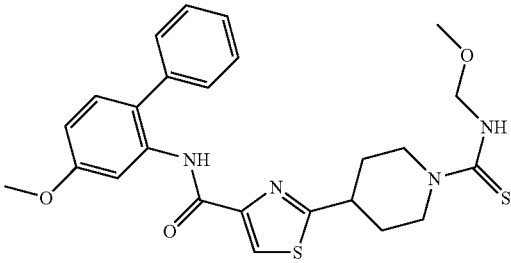 | |
| 1562 | 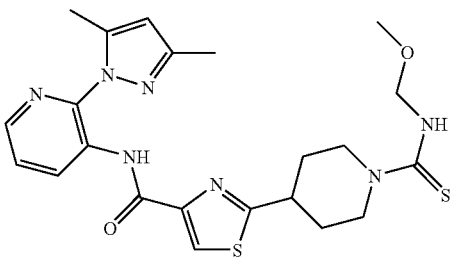 | |
| 1563 | 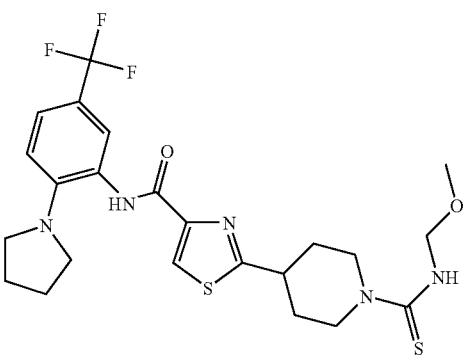 | |
| 1564 | 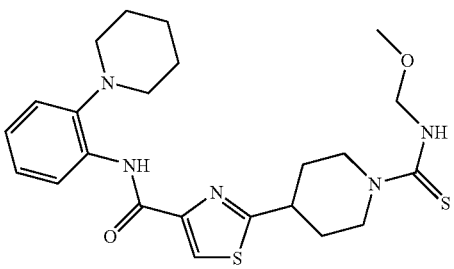 | |
| 1565 | 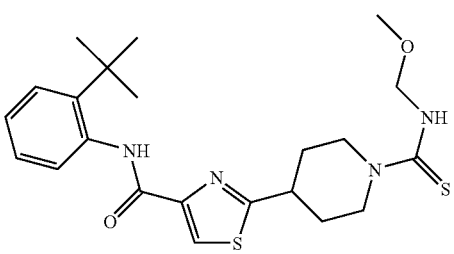 | |

TABLE 1-continued

| No. | FORMULA | NMR or mass |
|---|---|---|
| 1566 | | |
| 1567 | | |
| 1568 | | |
| 1569 | | |
| 1570 | | |

TABLE 1-continued
| No. | FORMULA | NMR or mass |
|---|---|---|
| 1571 | 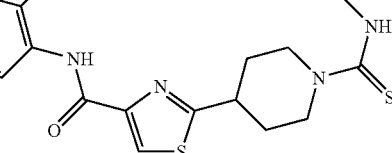 | |
| 1572 | 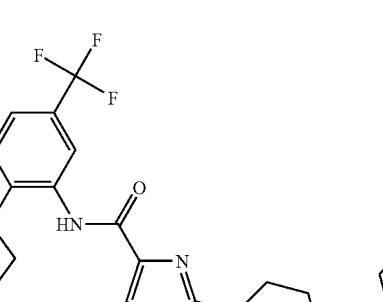 | |
| 1573 | 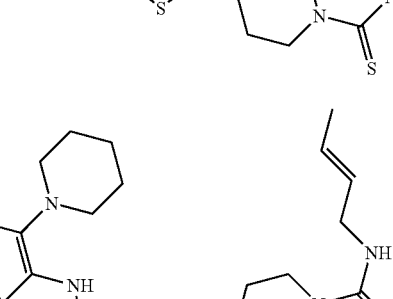 | |
| 1574 | 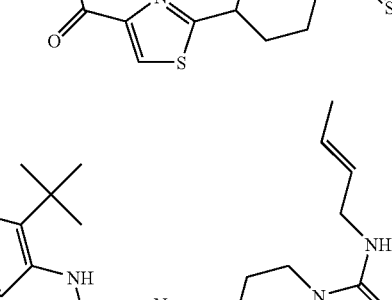 | |
| 1575 | 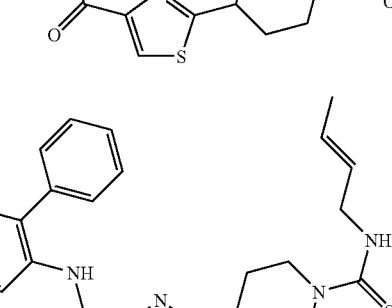 | |

TABLE 1-continued

| No. | FORMULA | NMR or mass |
|---|---|---|
| 1576 | | |
| 1577 | | |
| 1578 | | |
| 1579 | 2-{1-[(acetylamino)carbonothioyl]piperidin-4-yl}-N-[2-pyrrolidin-1-yl-5-(trifluoromethyl)phenyl]-1,3-thiazole-4-carboxamide | |
| 1580 | | |

TABLE 1-continued
| No. | FORMULA | NMR or mass |
|---|---|---|
| 1581 | 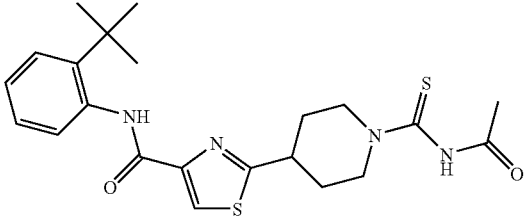 | |
| 1582 | 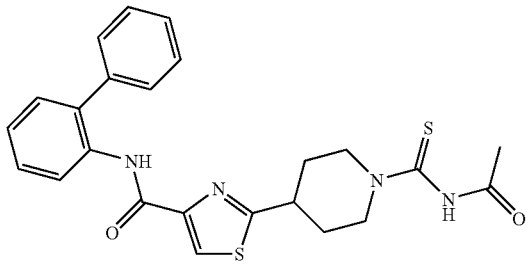 | |
| 1583 | 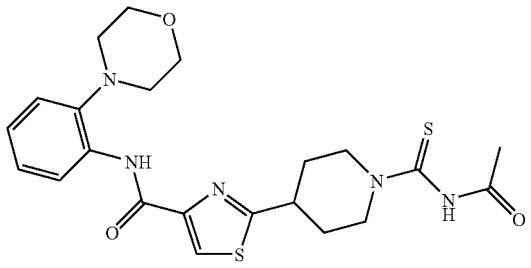 | |
| 1584 | 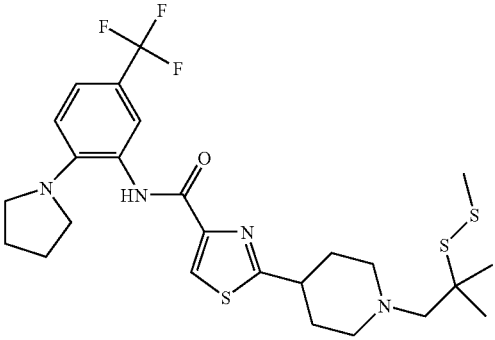 | |
| 1585 | 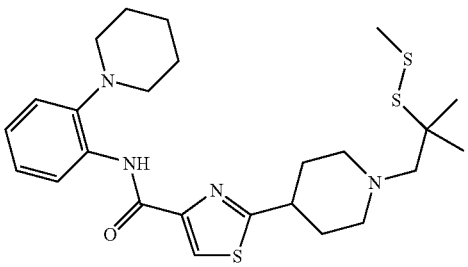 | |

TABLE 1-continued
| No. | FORMULA | NMR or mass |
|---|---|---|
| 1586 | 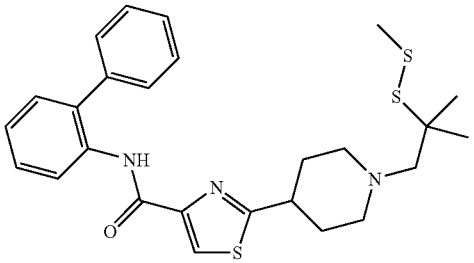 | |
| 1587 | 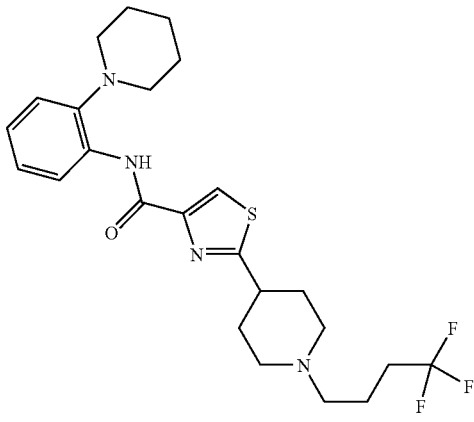  N-(2-piperidin-1-ylphenyl)-2-[1-(4,4,4-trifluorobutyl)piperidin-4-yl]-1,3-thiazole-4-carboxamide | |
| 1588 | 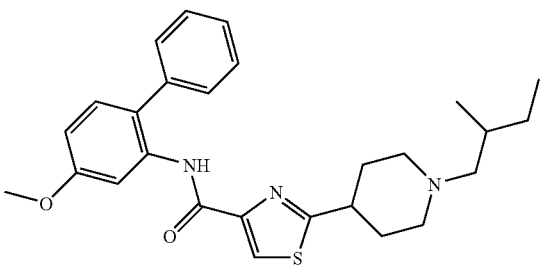 | |
| 1589 | 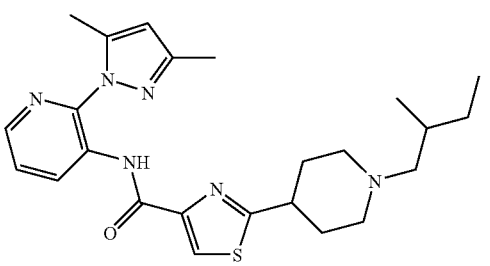 | |

TABLE 1-continued
| No. | FORMULA | NMR or mass |
|---|---|---|
| 1590 | 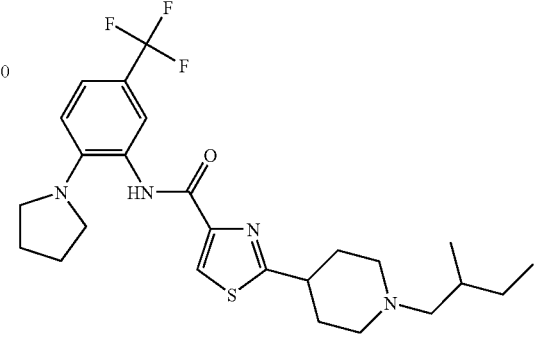 | |
| 1591 | 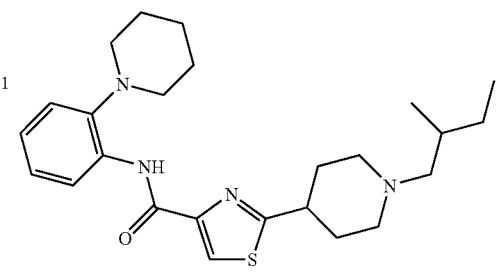 | |
| 1592 | 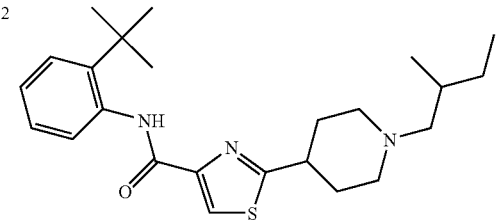 | |
| 1593 | 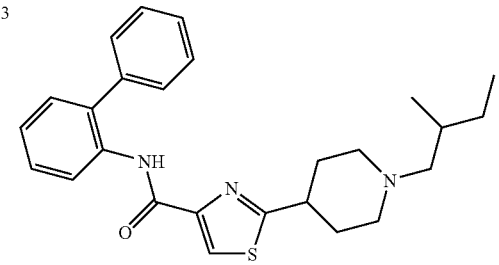 | |
| 1594 | 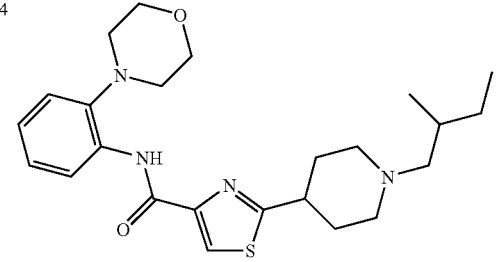 | |

TABLE 1-continued
| No. | FORMULA | NMR or mass |
|---|---|---|
| 1595 | 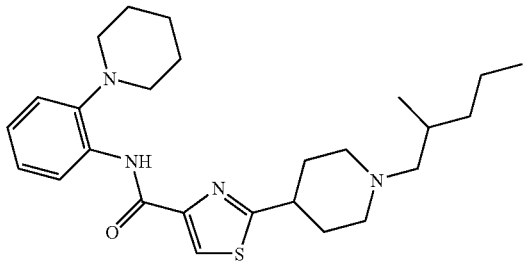 | |
| 1596 | 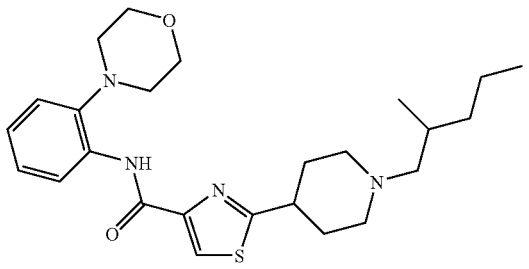 | |
| 1597 | 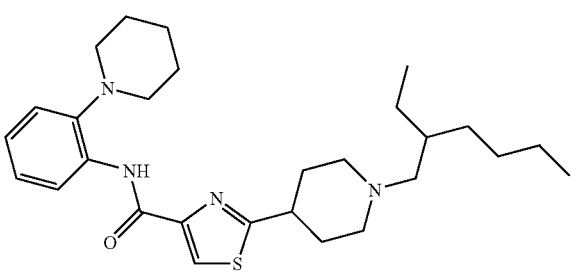 | |
| 1598 | 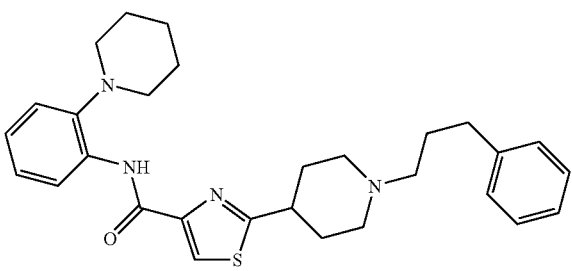 | |
| 1599 | 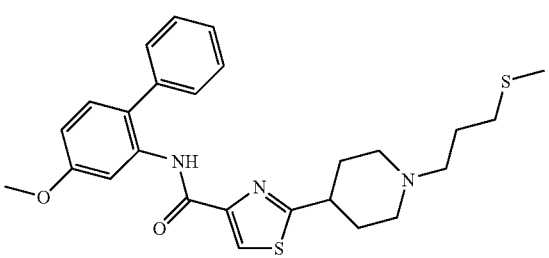 | |

TABLE 1-continued
| No. | FORMULA | NMR or mass |
|---|---|---|
| 1600 | 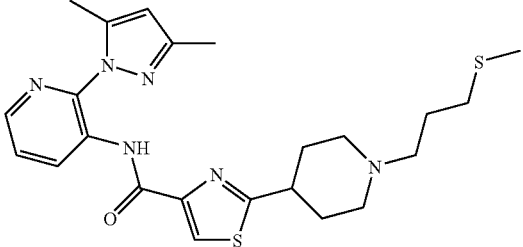 | |
| 1601 | 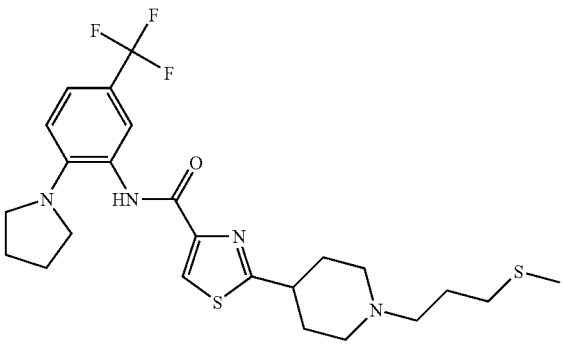<br>2-{1-[3-(methylthio)propyl]pipeidin-4-yl]-N-[2-pyrrolidin-1-yl-5-(trifluoro-methyl)phenyl]-1,3-thiazole-4-carboxamide | |
| 1602 | 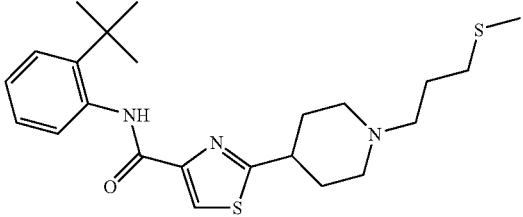 | |
| 1603 | 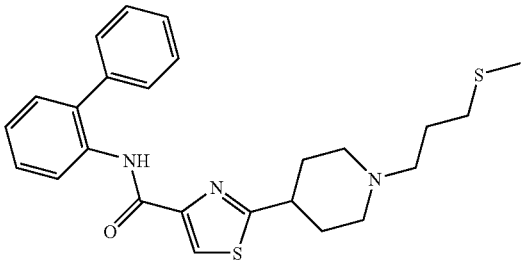 | |
| 1604 | 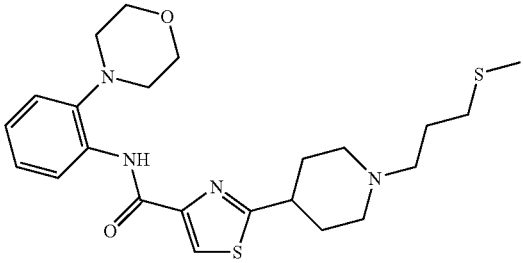 | |

TABLE 1-continued
| No. | FORMULA | NMR or mass |
|---|---|---|
| 1605 | 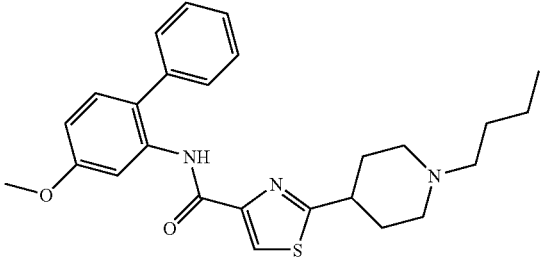 | |
| 1606 | 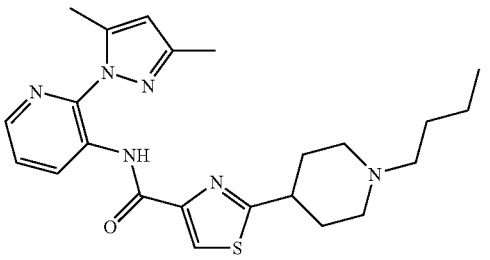 | |
| 1607 | 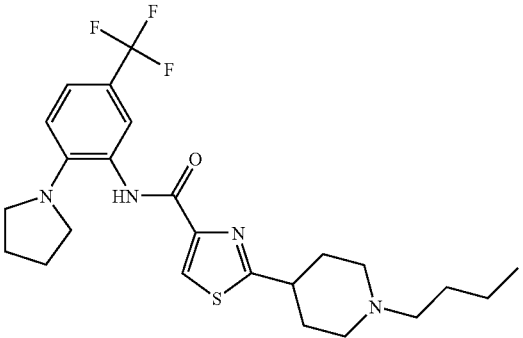 | |
| 1608 | 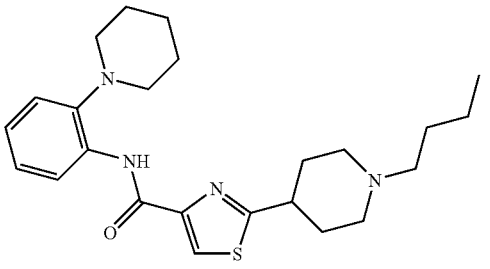 | |
| 1609 | 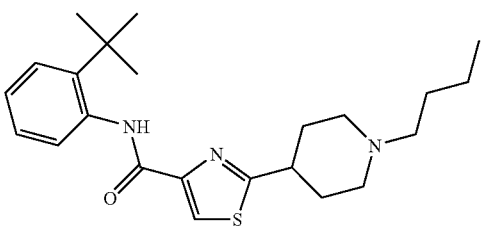 | |

TABLE 1-continued
| No. | FORMULA | NMR or mass |
|---|---|---|
| 1610 | 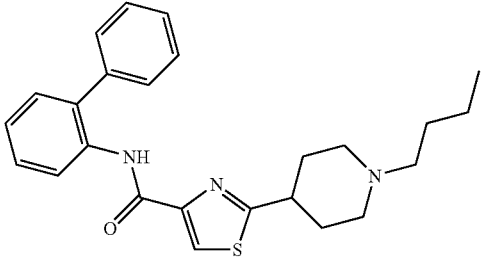 | |
| 1611 | 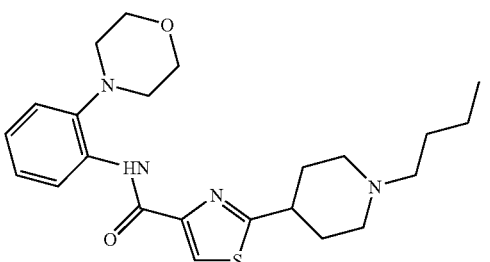 | |
| 1612 | 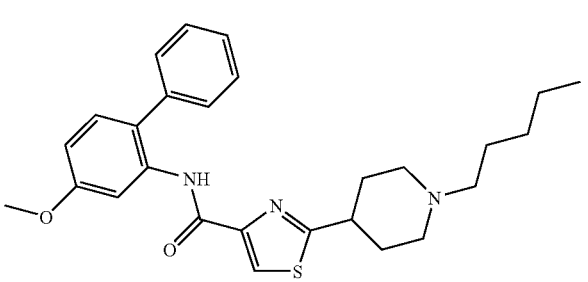 | |
| 1613 | 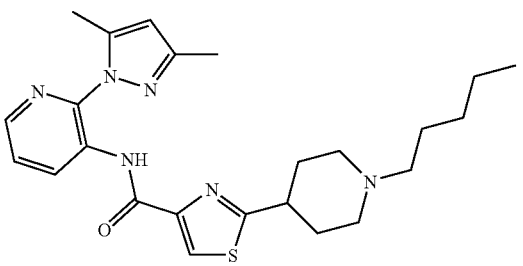 | |
| 1614 | 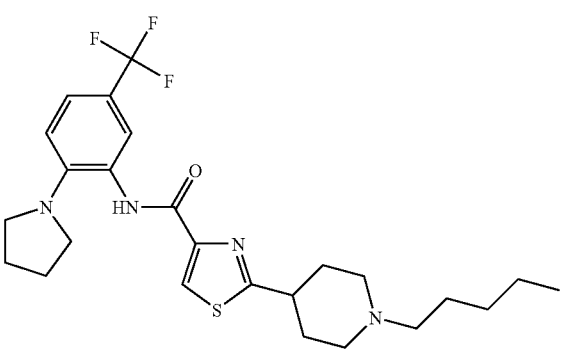 | |

TABLE 1-continued
| No. | FORMULA | NMR or mass |
|---|---|---|
| 1615 | 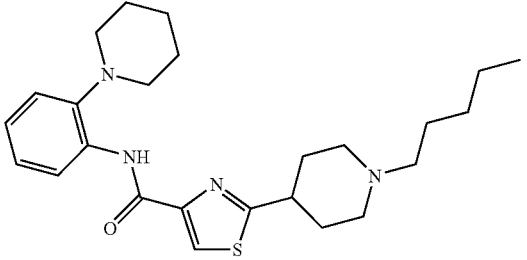 | |
| 1616 | 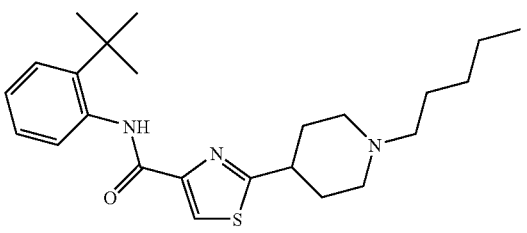 | |
| 1617 | 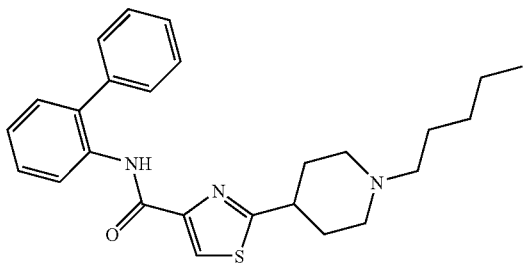 | |
| 1618 | 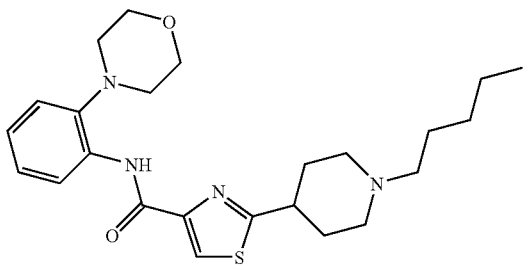 | |
| 1619 | 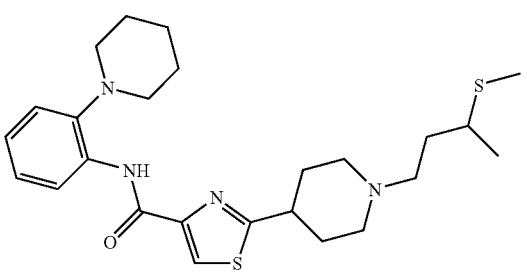 | |

TABLE 1-continued
| No. | FORMULA | NMR or mass |
|---|---|---|
| 1620 | 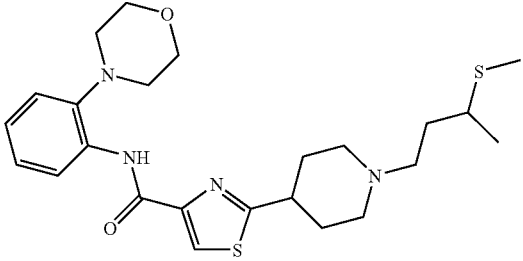 | |
| 1621 | 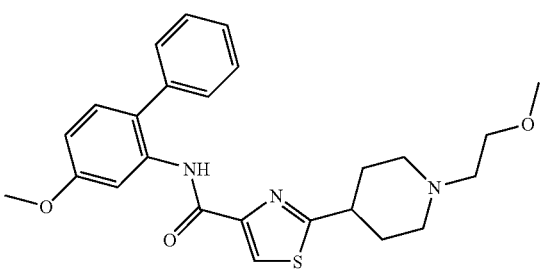 | |
| 1622 | 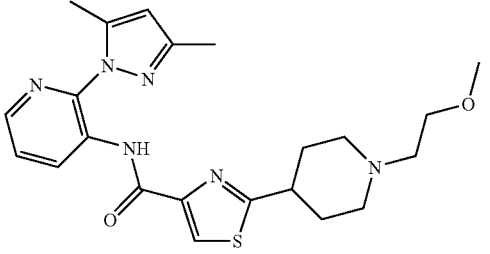 | |
| 1623 | 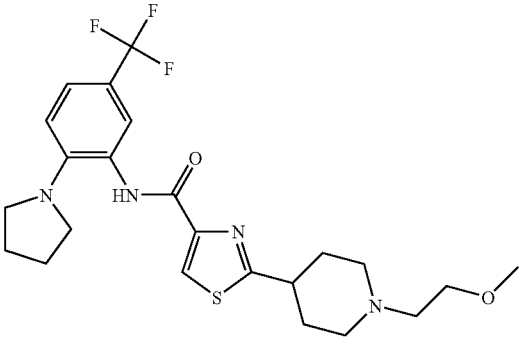 | |
| 1624 | 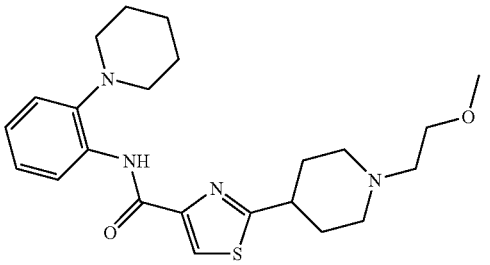 | |

TABLE 1-continued
| No. | FORMULA | NMR or mass |
|---|---|---|
| 1625 | 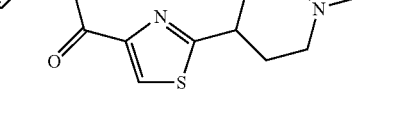 | |
| 1626 | 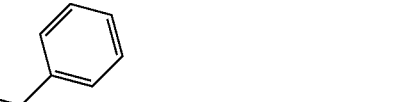 | |
| 1627 |  | |
| 1628 |  | |
| 1629 |  | |
| 1630 | 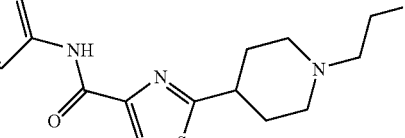 | |

TABLE 1-continued
| No. | FORMULA | NMR or mass |
|---|---|---|
| 1631 | 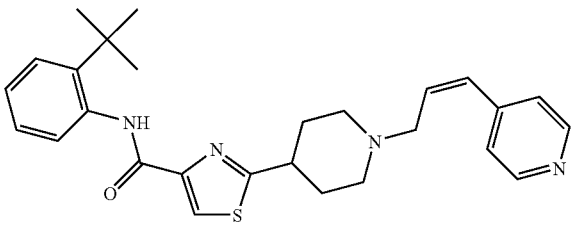 | |
| 1632 | 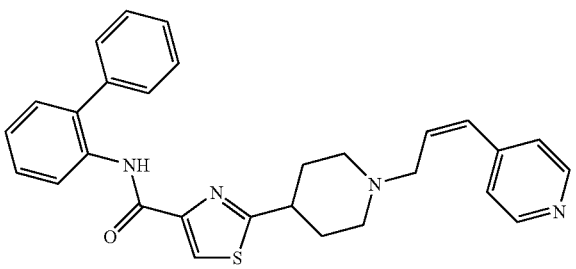 | |
| 1633 | 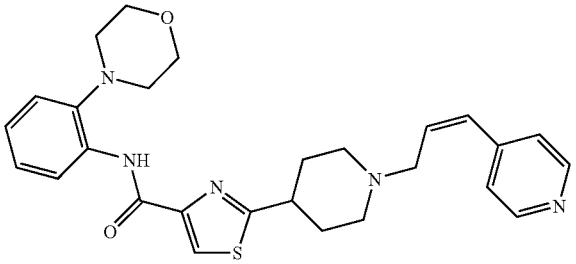 | |
| 1634 | 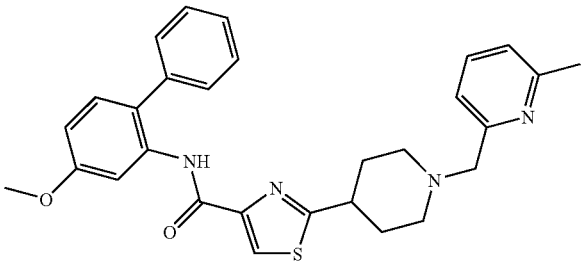 | |
| 1635 | 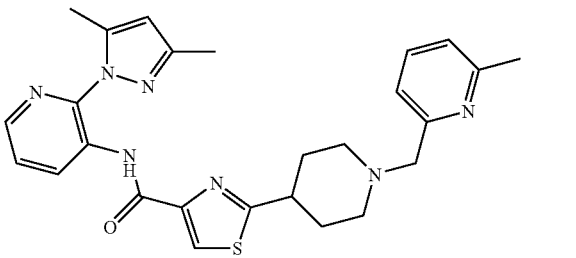 | |

TABLE 1-continued
| No. | FORMULA | NMR or mass |
|---|---|---|
| 1636 | 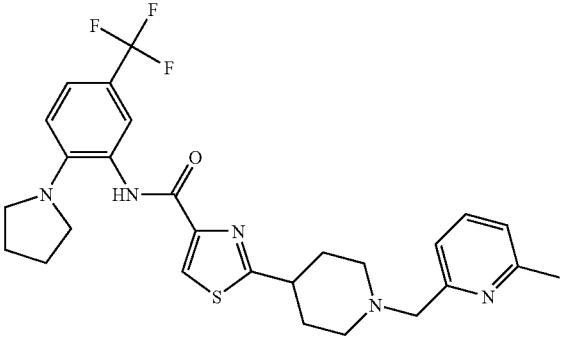 | |
| 1637 | 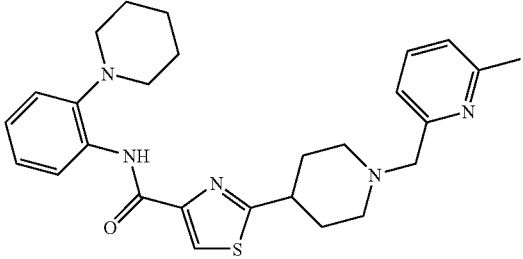 | |
| 1638 | 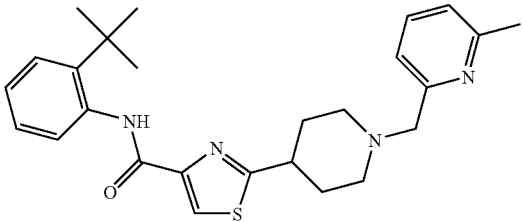 | |
| 1639 | 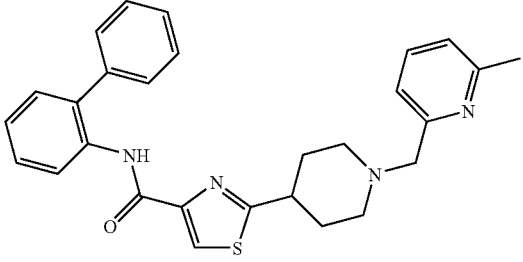 | |
| 1640 | 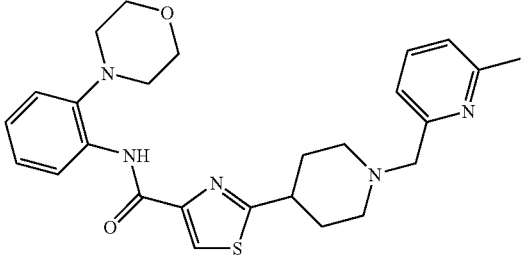 | |

TABLE 1-continued
| No. | FORMULA | NMR or mass |
|---|---|---|
| 1641 | 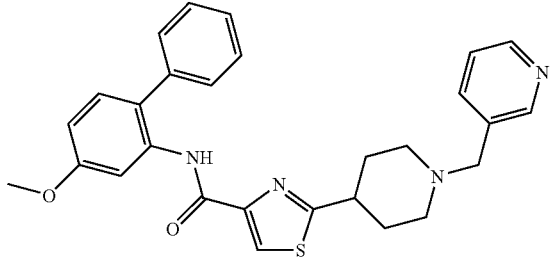 | |
| 1642 | 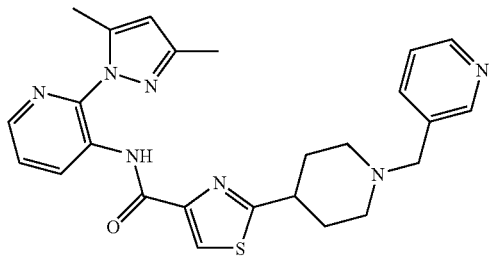 | |
| 1643 | 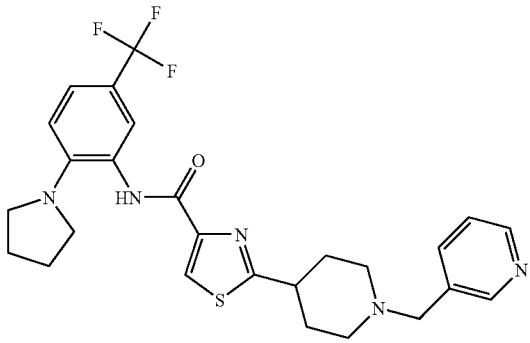 | |
| 1644 | 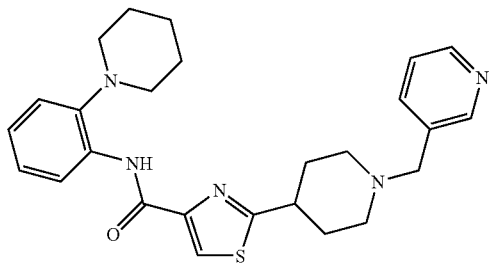 | |
| 1645 | 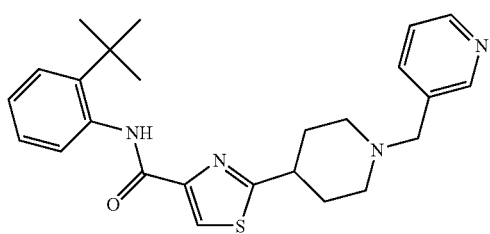 | |

TABLE 1-continued
| No. | FORMULA | NMR or mass |
|---|---|---|
| 1646 | 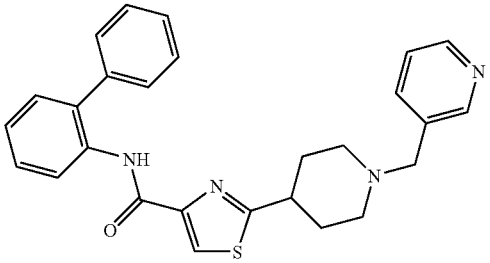 | |
| 1647 | 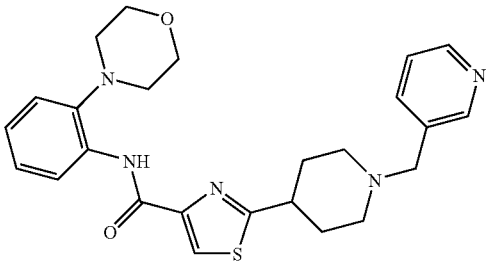 | |
| 1648 | 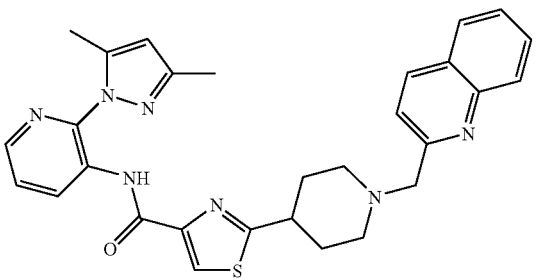 | |
| 1649 | 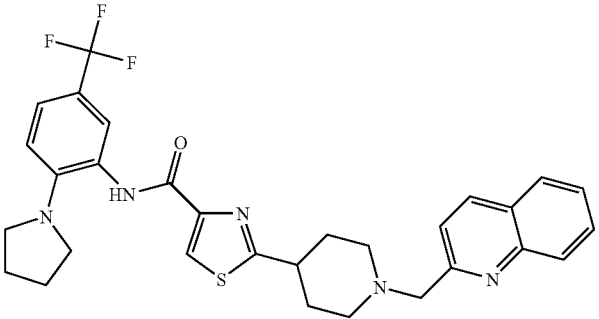 | |
| 1650 | 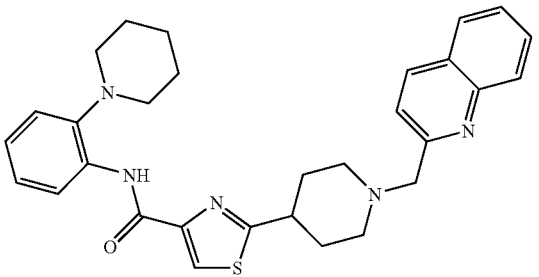 | |

TABLE 1-continued
| No. | FORMULA | NMR or mass |
|---|---|---|
| 1651 | 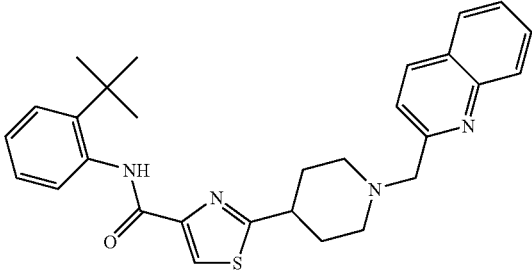 | |
| 1652 | 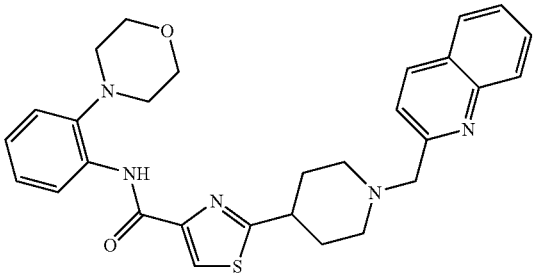 | |
| 1653 | 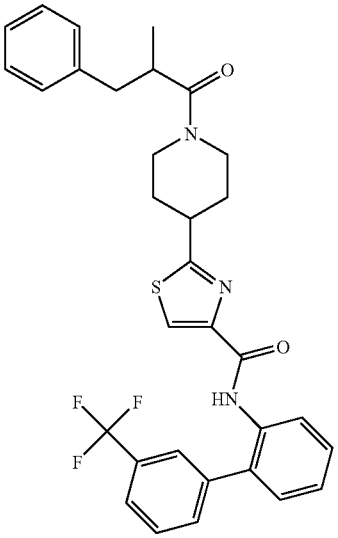 | |
| 1654 | 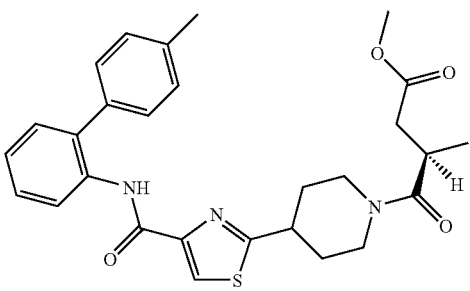 | |

TABLE 1-continued

| No. | FORMULA | NMR or mass |
|---|---|---|
| 1655 | methyl (3R)-3-methyl-4-oxo-4-{4-[4-({[3'-(trifluoromethyl)biphenyl-2-yl]-amino}carbonyl)-1,3-thiazol-2-yl]piperidin-1-yl}butanoate | |
| 1656 | | |
| 1657 | 2-{1-[(pyridin-2-ylthio)acetyl]piperidin-4-yl}-N-[4'-(trifluoromethoxy)biphenyl-2-yl]-1,3-thiazole-4-carboxamide | |

TABLE 1-continued
| No. | FORMULA | NMR or mass |
|---|---|---|
1658 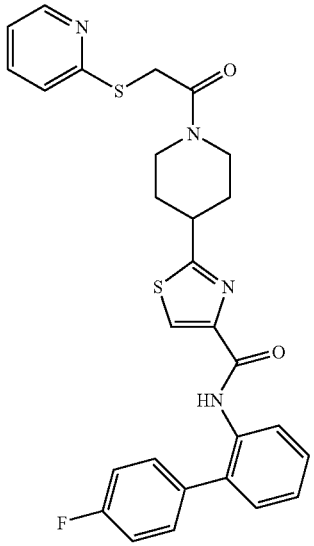
N-(4'-fluorobiphenyl-2-yl)-2-{1-[(pyridin-2-ylthio)acetyl]piperidin-4-yl}-1,3-thiazole-4-carboxamide
1659 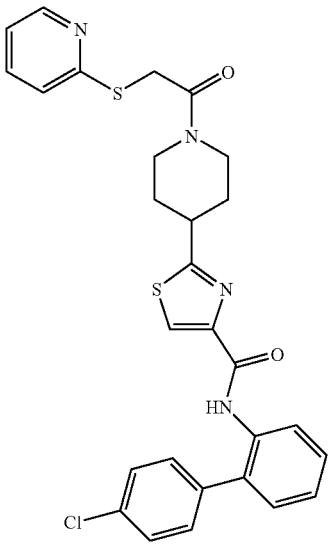
N-(4'-chlorobiphenyl-2-yl)-2-{1[(pyridin-2-ylthio)acetyl]piperidin-4-yl}-1,3-thiazole-4-carboxamide
1660 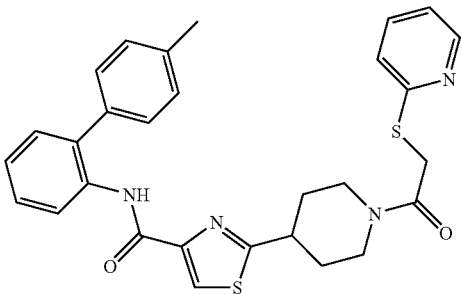

TABLE 1-continued
| No. | FORMULA | NMR or mass |
|---|---|---|
| 1661 | 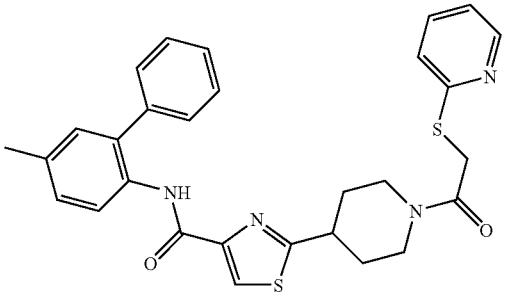 | |
| 1662 | 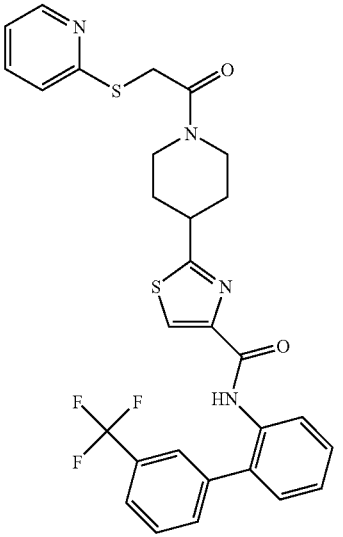 2-{1-[(pyridin-2-ylthio)acetyl]piperidin-4-yl}-N-[3'-(trifluoromethyl)-biphenyl-2-yl]-1,3-thiazole-4-carboxamide | |
| 1663 | 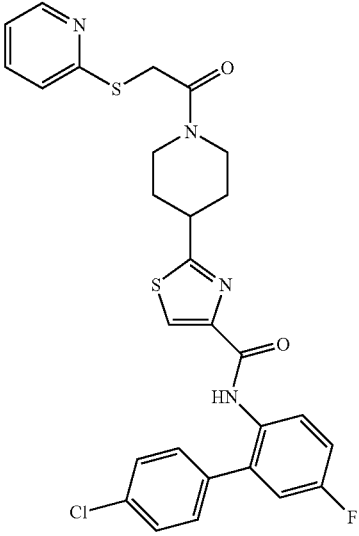 N-(4'-chloro-5-fluorobiphenyl-2-yl)-2-{1-[(pyridin-2-ylthio)acetyl]-piperidin-4-yl}-1,3-thiazole-4-carboxamide | |

TABLE 1-continued
| No. | FORMULA | NMR or mass |
|---|---|---|
| 1664 | 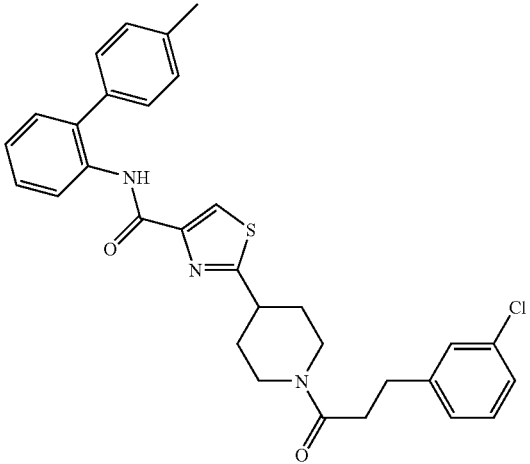 2-{1-[3-(3-chlorophenyl)propanoyl]piperidin-4-yl}-N-(4'-methylbiphenyl-2-yl)-1,3-thiazole-4-carboxamide | |
| 1665 | 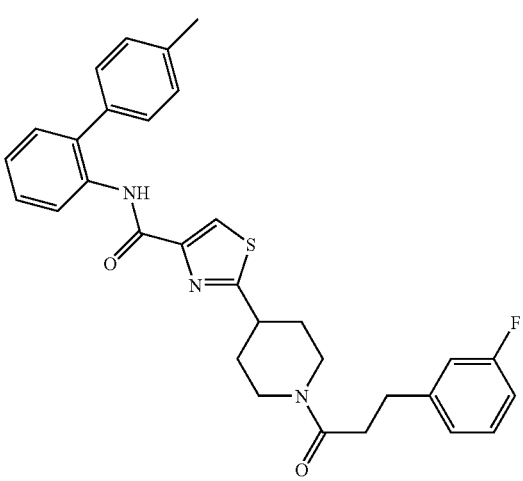 2-{1-[3-(3-fluorophenyl)propanoyl]piperidin-4-yl}-N-(4'-methylbiphenyl-2-yl)-1,3-thiazole-4-carboxamide | |

TABLE 1-continued
| No. | FORMULA | NMR or mass |
|---|---|---|
| 1666 | 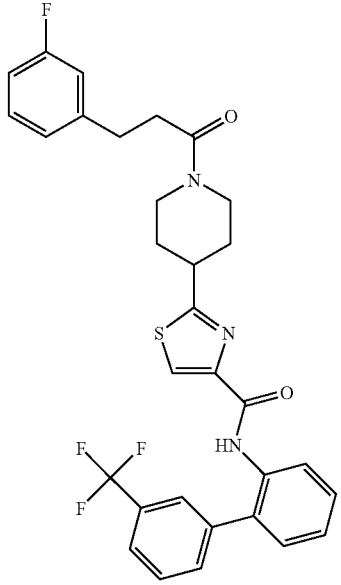  2-{1-[3-(3-fluorophenyl)propanoyl]piperidin-4-yl}-N-[3'-(trifluoromethyl)-biphenyl-2-yl]-1,3-thiazole-4-carboxamide | |
| 1667 | 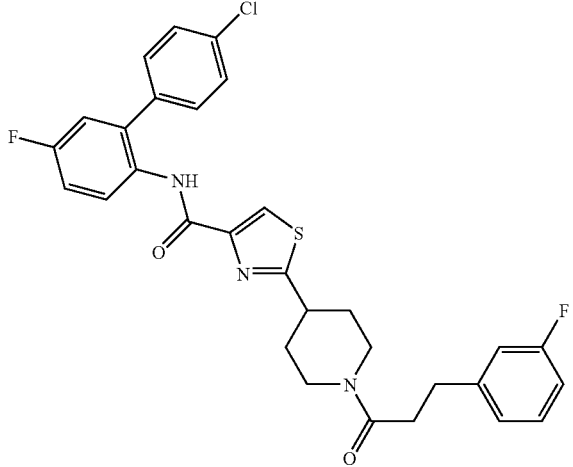  N-(4'-chloro-5-fluorobiphenyl-2-yl)-2-{1-[3-(3-fluorophenyl)propanoyl]-piperidin-4-yl}-1,3-thiazole-4-carboxamide | |

TABLE 1-continued
| No. | FORMULA | NMR or mass |
|---|---|---|
| 1668 | 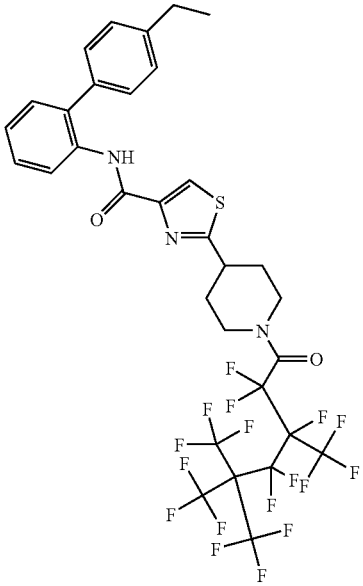 N-(4'-ethylbiphenyl-2-yl)-2-{1-[2,2,3,4,4,6,6,6-octafluoro-3,5,5-tris(trifluoromethyl)hexanoyl]piperidin-4-yl}-1,3-thiazole-4-carboxamide | |
| 1669 | 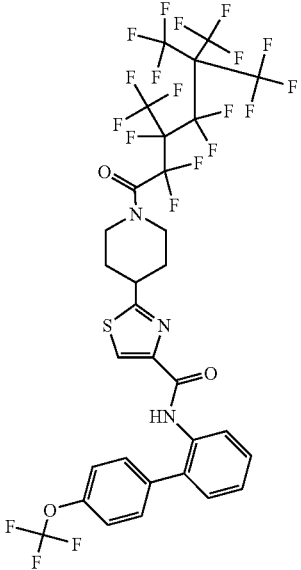 2-{1-[2,2,3,4,4,6,6,6-octafluoro-3,5,5-tris(trifluoromethyl)hexanoyl]-piperidin-4-yl}-N-[4'-(trifluoromethoxy)biphenyl-2-yl]-1,3-thiazole-4-carboxamide | |

TABLE 1-continued
| No. | FORMULA | NMR or mass |
|-----|---------|-------------|
1670
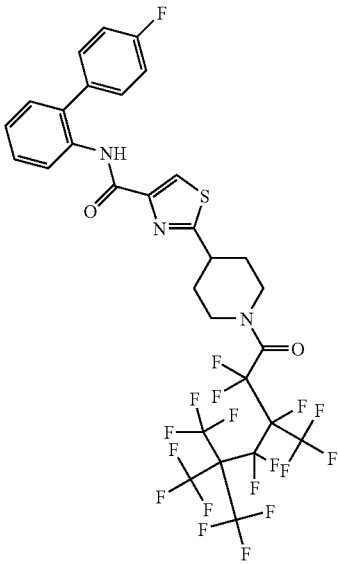
N-(4'-fluorobiphenyl-2-yl)-2-{1-[2,2,3,4,4,6,6,6-octafluoro-3,5,5-tris(trifluoromethyl)hexanoyl]piperidin-4-yl}-1,3-thiazole-4-carboxamide
1671
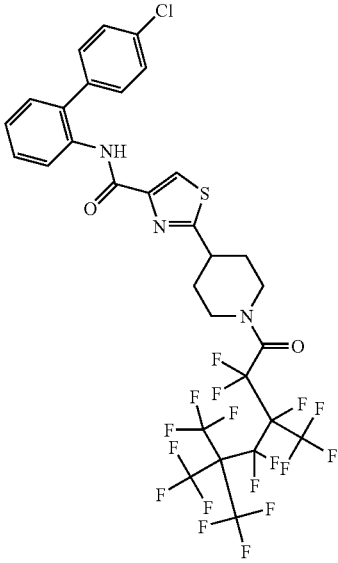
N-(4'-chlorobiphenyl-2-yl)-2-{1-[2,2,3,4,4,6,6,6-octafluoro-3,5,5-tris(trifluoromethyl)hexanoyl]piperidin-4-yl}-1,3-thiazole-4-carboxamide

| No. | FORMULA | NMR or mass |
|---|---|---|
| 1672 | 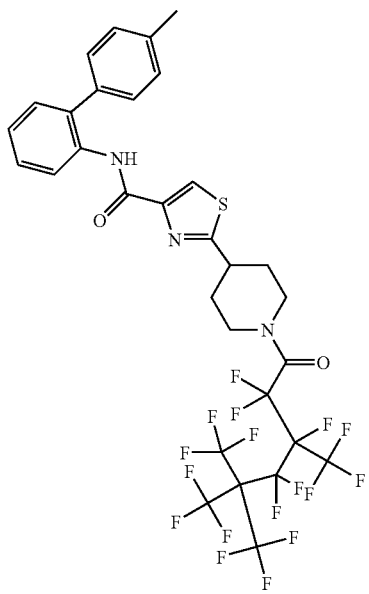 N-(4'-methylbiphenyl-2-yl)-2-{1-[2,2,3,4,4,6,6,6-octafluoro-3,5,5-tris(trifluoromethyl)hexanoyl]piperidin-4-yl}-1,3-thiazole-4-carboxamide | |
| 1673 | 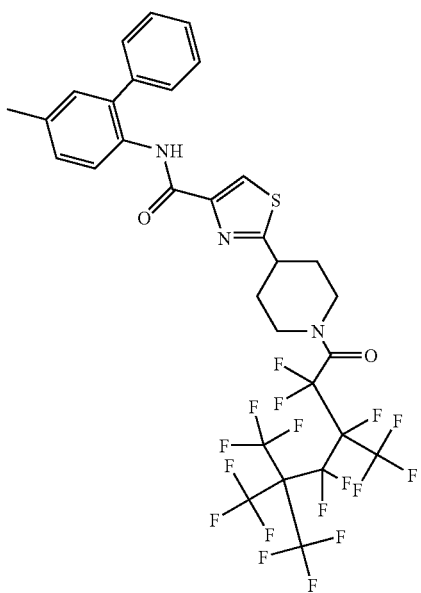 N-(5-methylbiphenyl-2-yl)-2-{1-[2,2,3,4,4,6,6,6-octafluoro-3,5,5-tris(trifluoromethyl)hexanoyl]piperidin-4-yl}-1,3-thiazole-4-carboxamide | |

| No. | FORMULA | NMR or mass |
|---|---|---|
1674
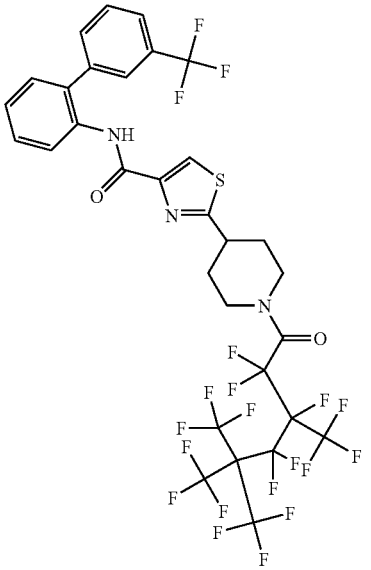
2-{1-[2,2,3,4,4,6,6,6-octafluoro-3,5,5-tris(trifluoromethyl)hexanoyl]-piperidin-4-yl}-N-[3'-(trifluoromethyl)biphenyl-2-yl]-1,3-thiazole-4-carboxamide
1675
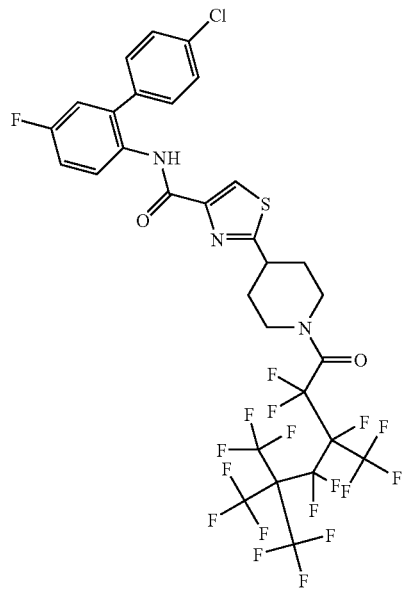
N-(4'-chloro-5-fluorobiphenyl-2-yl)-2-{1-[2,2,3,4,4,6,6,6-octafluoro-3,5,5-tris(trifluoromethyl)hexanoyl]piperidin-4-yl}-1,3-thiazole-4-carboxamide
1676
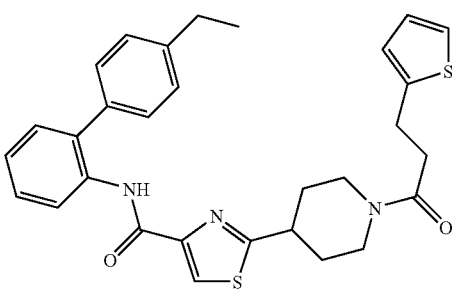

| No. | FORMULA | NMR or mass |
|---|---|---|
| 1677 | 2-{1-[3-(2-thienyl)propanoyl]piperidin-4-yl}-N-[4'-(trifluoromethoxy)biphenyl-2-yl]-1,3-thiazole-4-carboxamide | |
| 1678 | N-(4'-fluorobiphenyl-2-yl)-2-{1-[3-(2-thienyl)propanoyl]piperidin-4-yl}-1,3-thiazole-4-carboxamide | |

TABLE 1-continued
| No. | FORMULA | NMR or mass |
|---|---|---|
| 1679 | 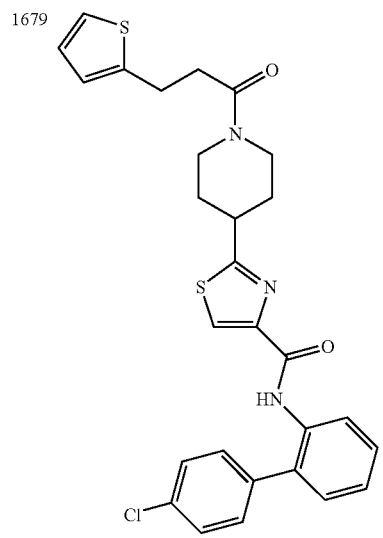
N-(4'-chlorobiphenyl-2-yl)-2-{1-[3-(2-thienyl)propanoyl]piperidin-4-yl}-1,3-thiazole-4-carboxamide | |
| 1680 | 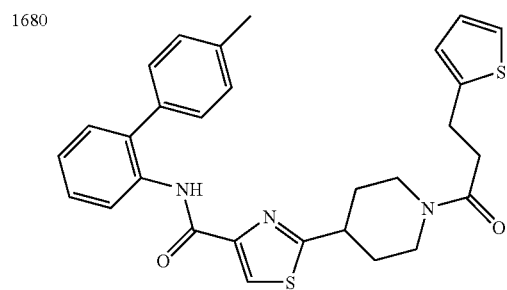 | |
| 1681 | 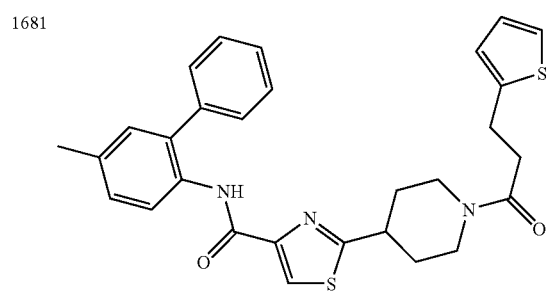 | |

TABLE 1-continued
| No. | FORMULA | NMR or mass |
|---|---|---|
| 1682 | 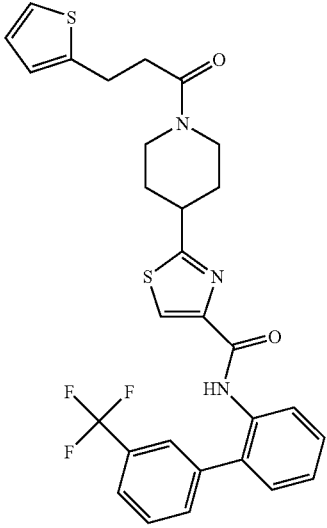 2-{1-[3-(2-thienyl)propanoyl]piperidin-4-yl}-N-[3'-(trifluoromethyl)biphenyl-2-yl]-1,3-thiazole-4-carboxamide | |
| 1683 | 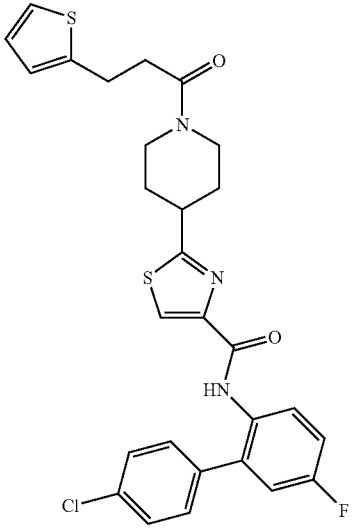 | |

TABLE 1-continued
| No. | FORMULA | NMR or mass |
|---|---|---|
| 1684 | 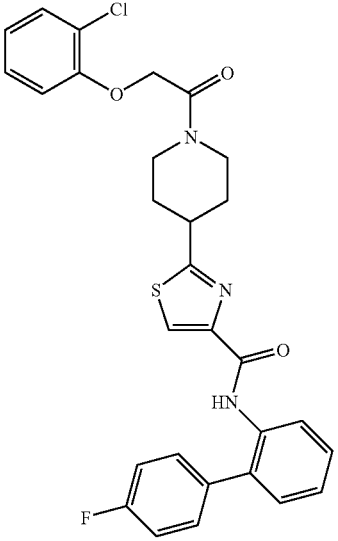 2-{1-[(2-chlorophenoxy)acetyl]piperidin-4-yl}-N-(4'-fluorobiphenyl-2-yl)-1,3-thiazole-4-carboxamide | |
| 1685 | 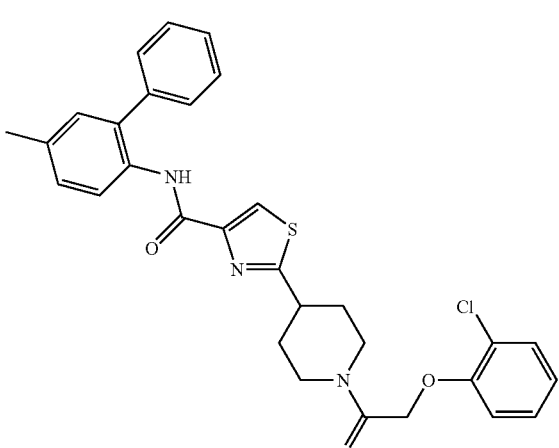 2-{1-[(2-chlorophenoxy)acetyl]piperidin-4-yl}-N-(5-methylbiphenyl-2-yl)-1,3-thiazole-4-carboxamide | |

TABLE 1-continued
| No. | FORMULA | NMR or mass |
|---|---|---|
| 1686 | 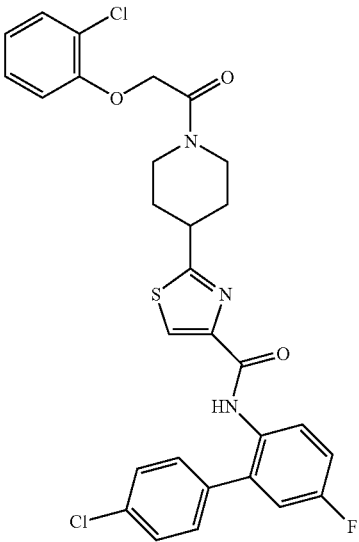<br>N-(4'-chloro-5-fluorobiphenyl-2-yl)-2-{1-[(2-chlorophenoxy)acetyl]piperidin-4-yl}-1,3-thiazole-4-carboxamide | |
| 1687 | 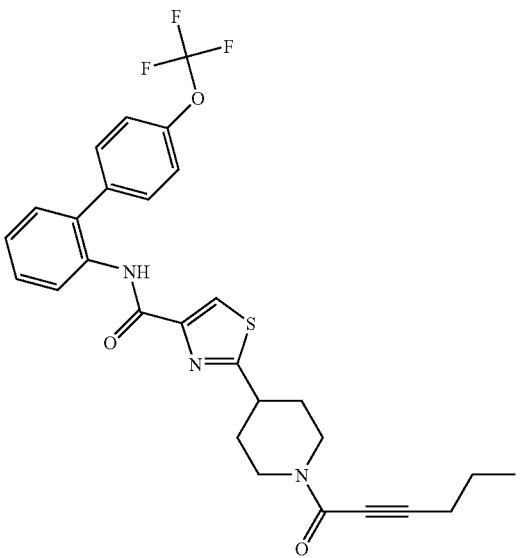<br>2-(1-hex-2-ynoylpiperidin-4-yl)-N-[4'-(trifluoromethoxy)biphenyl-2-yl]-1,3-thiazole-4-carboxamide | |

TABLE 1-continued
| No. | FORMULA | NMR or mass |
|---|---|---|
| 1688 | 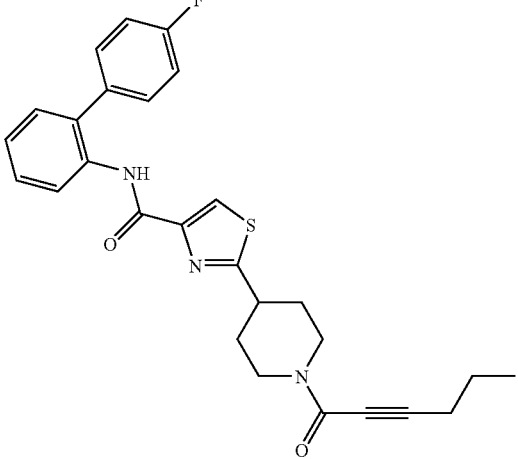 N-(4'-fluorobiphenyl-2-yl)-2-(1-hex-2-ynoylpiperidin-4-yl)-1,3-thiazole-4-carboxamide | |
| 1689 | 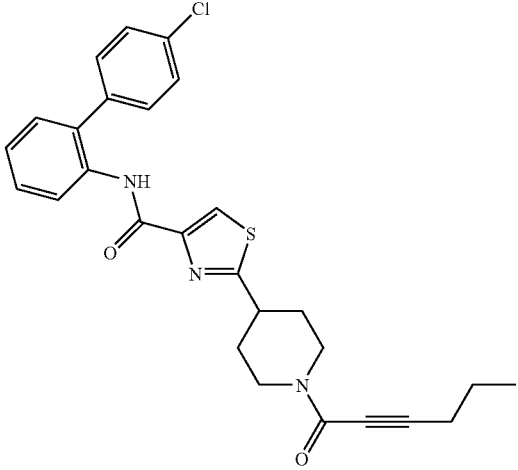 N-(4'-chlorobiphenyl-2-yl)-2-(1-hex-2-ynoylpiperidin-4-yl)-1,3-thiazole-4-carboxamide | |
| 1690 | 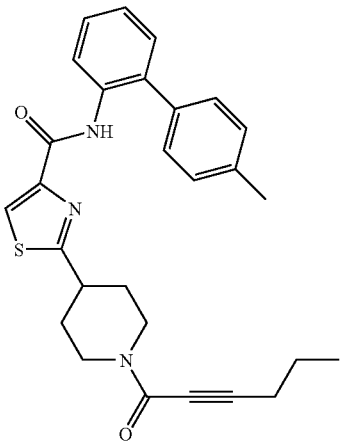 2-(1-hex-2-ynoylpiperidin-4-yl)-N-(4'-methylbiphenyl-2-yl)-1,3-thiazole-4-carboxamide | |

TABLE 1-continued
| No. | FORMULA | NMR or mass |
|---|---|---|
1691
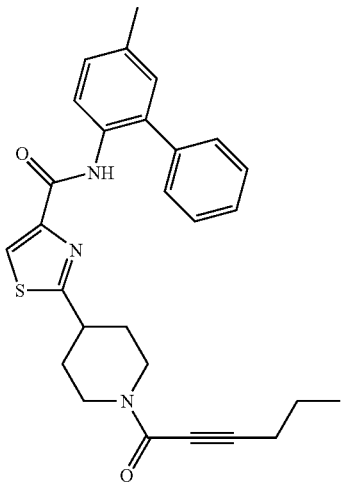
2-(1-hex-2-ynoylpiperidin-4-yl)-N-(5-methylbiphenyl-2-yl)-1,3-thiazole-4-carboxamide
1692
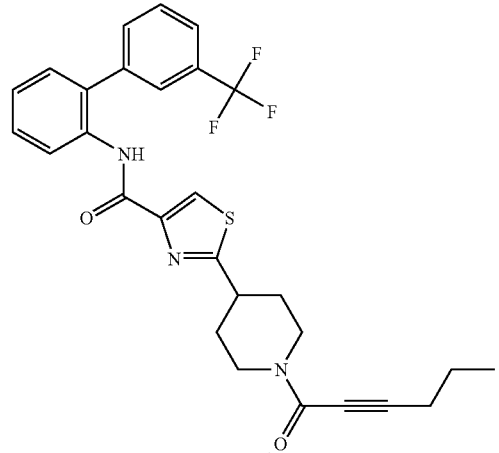
2-(1-hex-2-ynoylpiperidin-4-yl)-N-[3'-(trifluoromethyl)biphenyl-2-yl]-1,3-thiazole-4-carboxamide TABLE 1-continued
| No. | FORMULA | NMR or mass |
|---|---|---|
| 1693 | 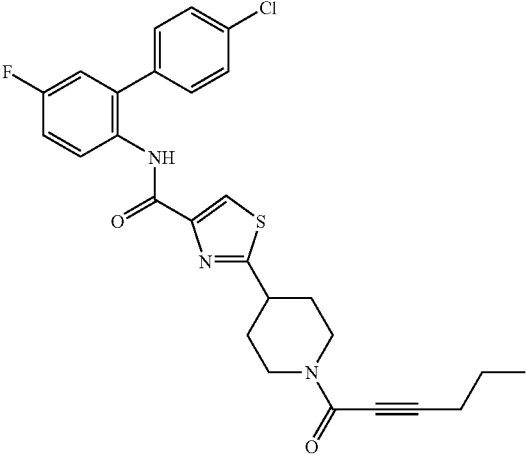 N-(4'-chloro-5-fluorobiphenyl-2-yl)-2-(1-hex-2-ynoylpiperidin-4-yl)-1,3-thiazole-4-carboxamide | |
| 1694 | 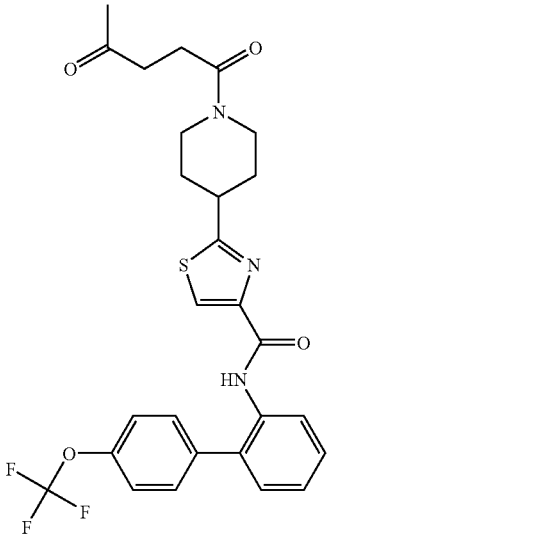 2-[1-(4-oxopentanoyl)piperidin-4-yl]-N-[4'-(trifluoromethoxy)biphenyl-2-yl]-1,3-thiazole-4-carboxamide | |
| 1695 | 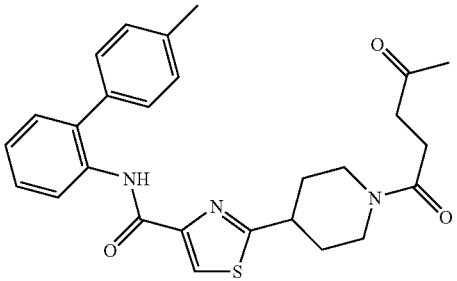 | |

TABLE 1-continued
| No. | FORMULA | NMR or mass |
|---|---|---|
| 1696 | 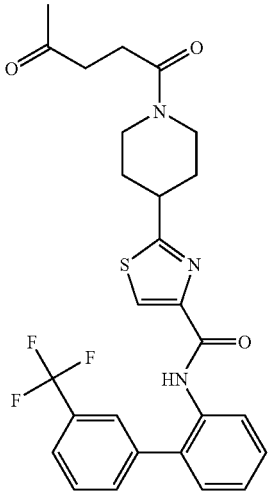 2-[-1-(4-oxopentanoyl)piperidin-4-yl]-N-[3'-(trifluoromethyl)biphenyl-2-yl]-1,3-thiazole-4-carboxamide | |
| 1697 | 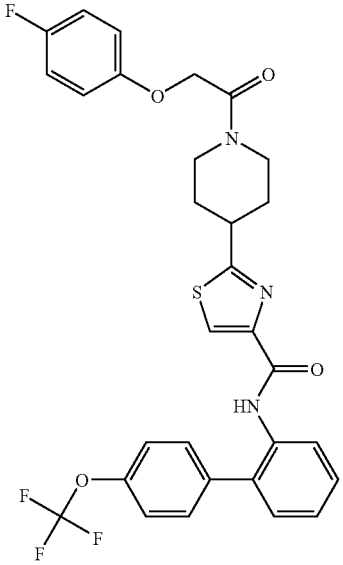 2-{1-[(4-fluorophenoxy)acetyl]piperidin-4-yl}-N-(4'-(trifluoromethoxy)-biphenyl-2-yl]-1,3-thiazole-4-carboxamide | |

TABLE 1-continued
| No. | FORMULA | NMR or mass |
|---|---|---|
| 1698 | 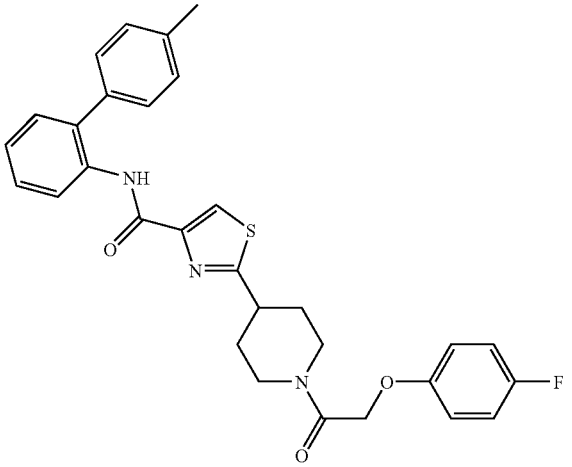 | |
| 1699 | 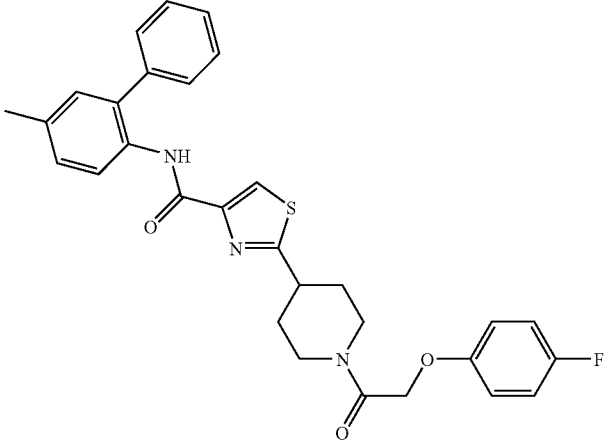 | |
| 1700 | 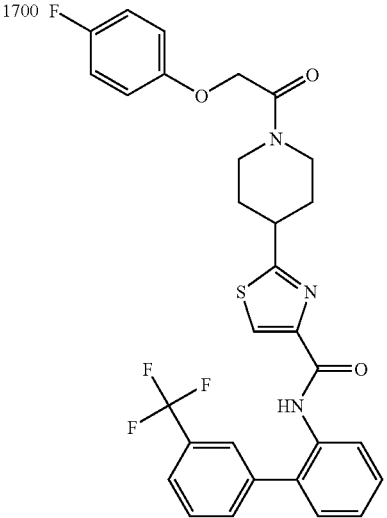 | |

TABLE 1-continued
| No. | FORMULA | NMR or mass |
|---|---|---|
| 1701 | 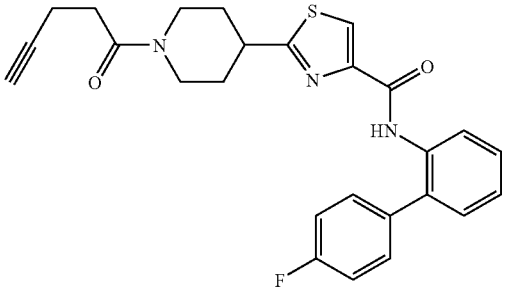 | |
| 1702 | 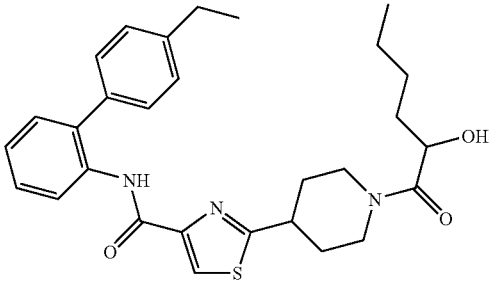 | |
| 1703 | 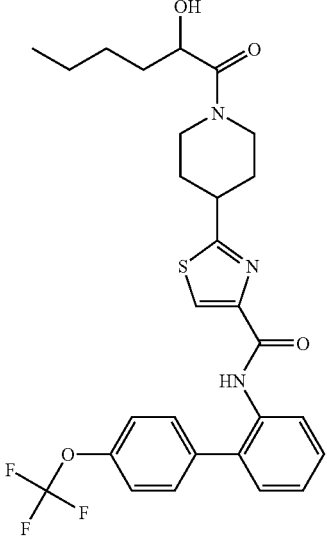 | |

TABLE 1-continued
| No. | FORMULA | NMR or mass |
|---|---|---|
| 1704 | 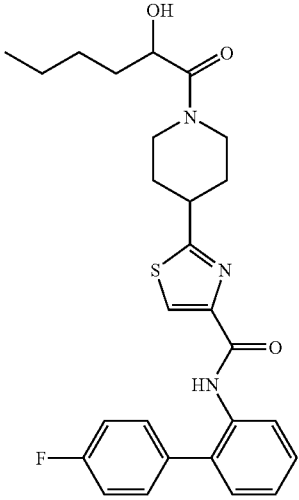 N-(4'-fluorobiphenyl-2-yl)-2-[1-(2-hydroxyhexanoyl)piperidin-4-yl]-1,3-thiazole-4-carboxamide | |
| 1705 | 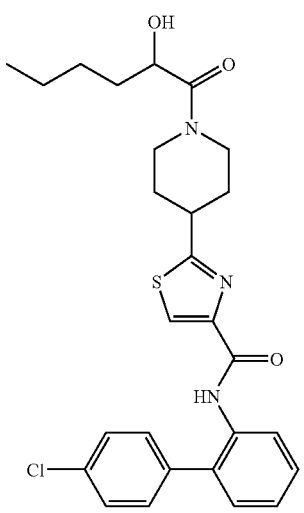 N-(4'-chlorobiphenyl-2-yl)-2-[1-(2-hydroxyhexanoyl)piperidin-4-yl]-1,3-thiazole-4-carboxamide | |
| 1706 | 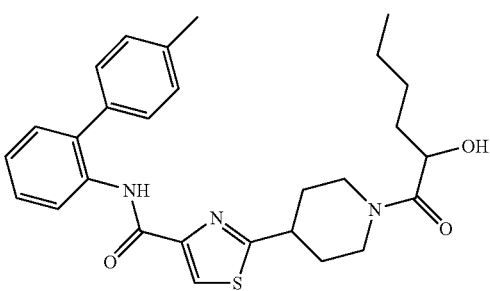 | |

TABLE 1-continued
| No. | FORMULA | NMR or mass |
|---|---|---|
| 1707 | 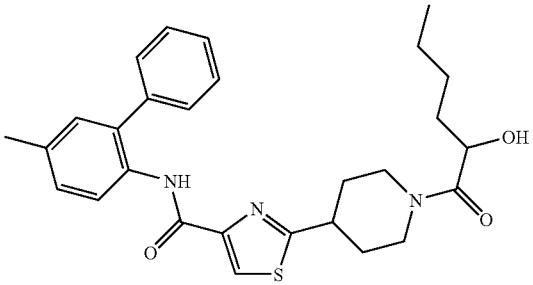 | |
| 1708 | 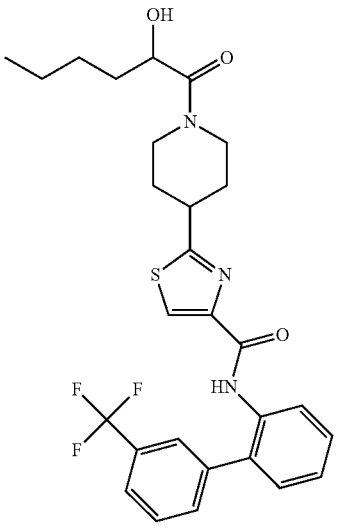 | |
2-[1-(2-hydroxyhexanoyl)piperidin-4-yl]-N-[3'-trifluoromethyl)biphenyl-2-yl]-1,3-thiazole-4-carboxamide
| 1710 | 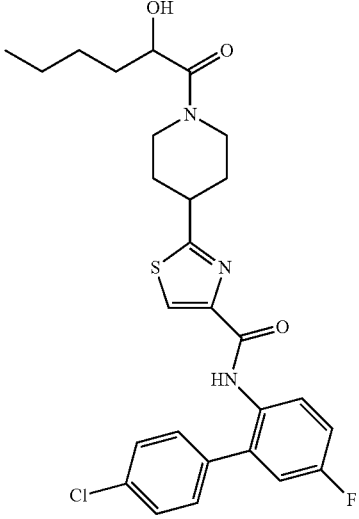 | |
N-(4'-chloro-5-fluorobiphenyl-2-yl)-2-[1-(2-hydroxyhexanoyl)piperidin-4-yl]-1,3-thiazole-4-carboxamide TABLE 1-continued
| No. | FORMULA | NMR or mass |
|---|---|---|
1711
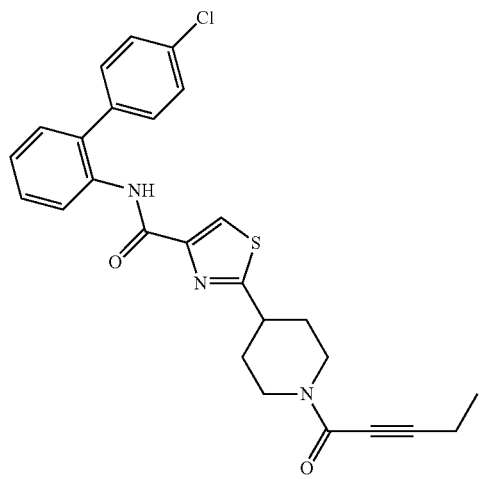
N-(4'-chlorobiphenyl-2-yl)-2-(1-pent-2-ynoylpiperidin-4-yl)-1,3-thiazole-4-carboxamide
1712
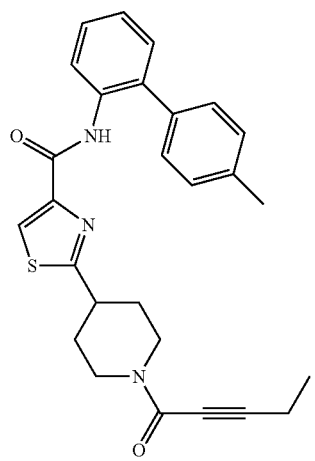
N-(4'-methylbiphenyl-2-yl)-2-(1-pent-2-ynoylpiperidin-4-yl)-1,3-thiazole-4-carboxamide

| No. | FORMULA | NMR or mass |
|---|---|---|
| 1713 | 2-(1-pent-2-ynoylpiperidin-4-yl)-N-[3'-(trifluoromethyl)biphenyl-2-yl]-1,3-thiazole-4-carboxamide | |
| 1714 | N-(4'-chloro-5-fluorobiphenyl-2-yl)-2-(1-pent-2-ynoylpiperidin-4-yl)-1,3-thiazole-4-carboxamide | |

TABLE 1-continued
| No. | FORMULA | NMR or mass |
|---|---|---|
| 1715 | 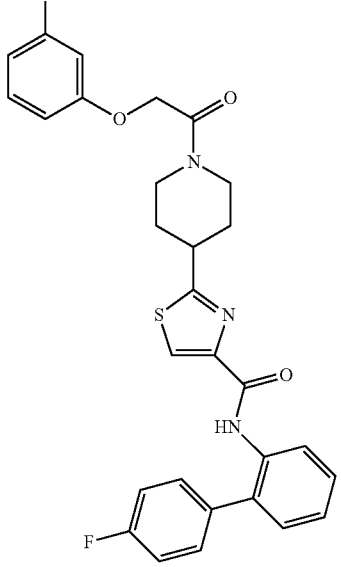<br>2-{1-[(3-chlorophenoxy)acetyl]piperidin-4-yl}-N-(4'-fluorobiphenyl-2-yl)-1,3-thiazole-4-carboxamide | |
| 1716 | 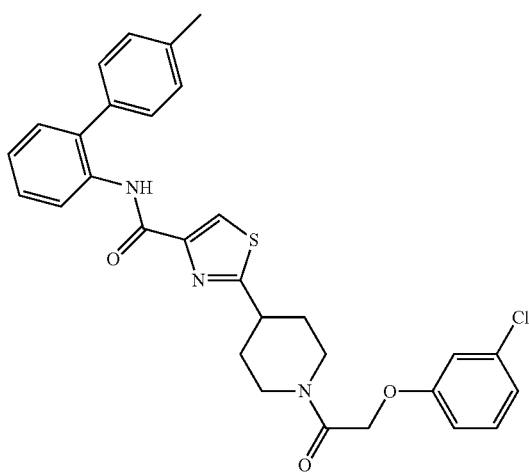<br>2-{1-[3-chlorophenoxy)acetyl]piperidin-4-yl}-N-(4'-methylbiphenyl-2-yl)-1,3-thiazole-4-carboxamide | |

TABLE 1-continued
| No. | FORMULA | NMR or mass |
|---|---|---|
1717
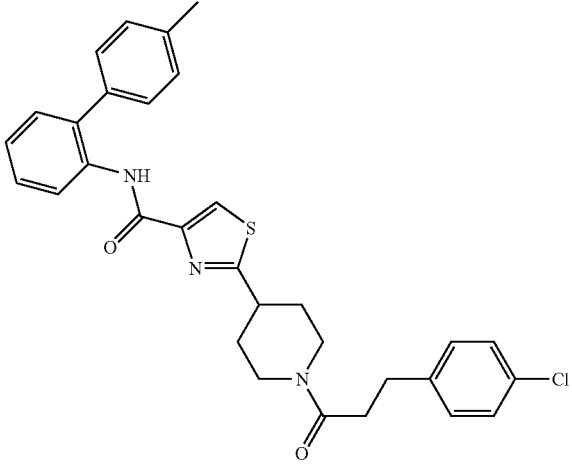
2-{1-[3-(4-chlorophenyl)propanoyl]piperidin-4-yl}-N-(4'-methylbiphenyl-2-yl)-1,3-thiazole-4-carboxamide
1718
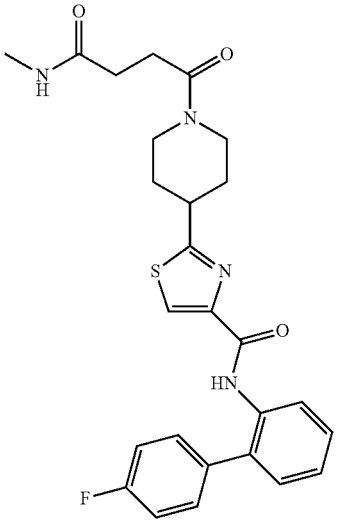
N-(4'-fluorobiphenyl-2-yl)-2-{1-[4-(methylamino)-4-oxobutanoyl]-piperidin-4-yl}-1,3-thiazole-4-carboxamide
1719
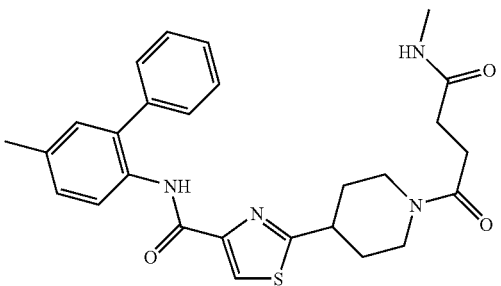

TABLE 1-continued

| No. | FORMULA | NMR or mass |
|---|---|---|
| 1720 | | |
| 1721 | | |

2-{1-[3-(4-oxo-2-thioxo-1,3-thiazolidin-3-yl)propanoyl]piperidin-4-yl}-N-[4'-(trifluoromethoxy)biphenyl-2-yl]-1,3-thiazole-4-carboxamide

| 1722 | | |

N-(4'-fluorobiphenyl-2-yl)-2-{1-[3-(4-oxo-2-thioxo-1,3-thiazolidin-3-yl)-propanoyl]piperidin-4-yl}-1,3-thiazole-4-carboxamide

| No. | FORMULA | NMR or mass |
|---|---|---|
| 1723 | 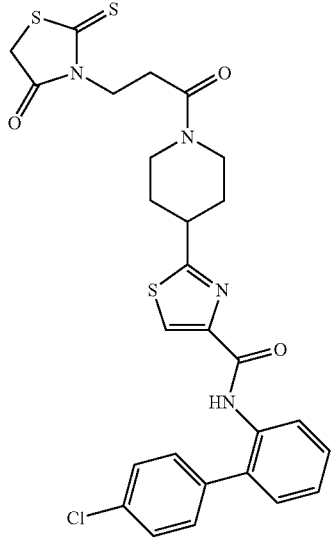 N-(4'-chlorobiphenyl-2-yl)-2-{1-[3-(4-oxo-2-thioxo-1,3-thiazolidin-3-yl)-propanoyl]piperidin-4-yl}-1,3-thiazole-4-carboxamide | |
| 1724 | 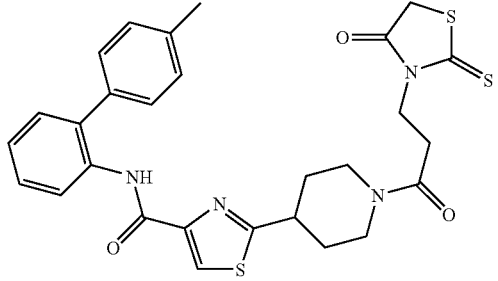 | |
| 1725 | 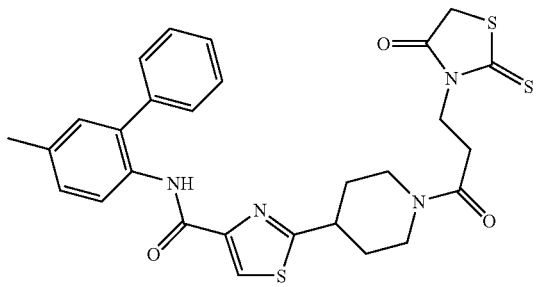 | |

TABLE 1-continued
| No. | FORMULA | NMR or mass |
|---|---|---|
| 1726 | 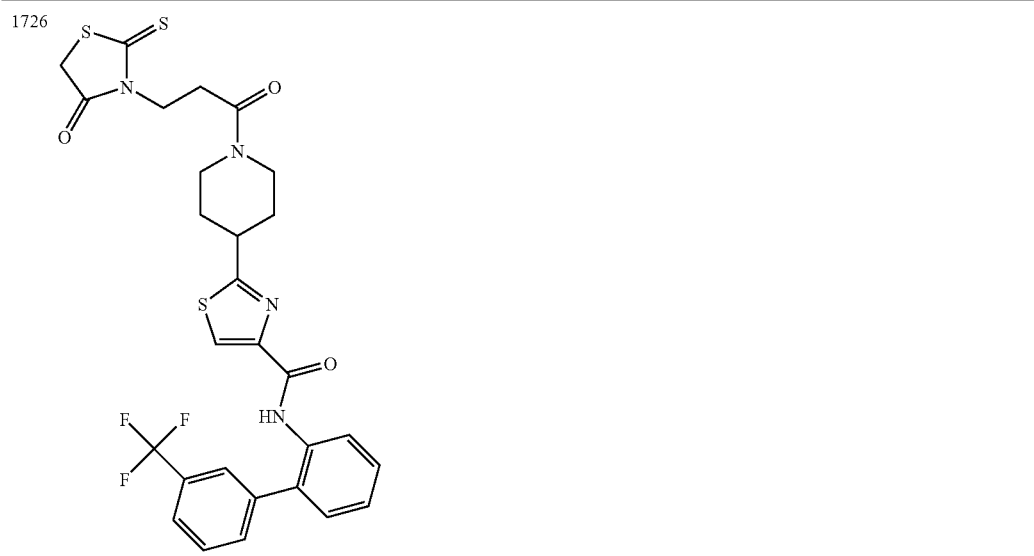 2-{1-[3-(4-oxo-2-thioxo-1,3-thiazolidin-3-yl)propanoyl]piperidin-4-yl}-N-[3'-(trifluoromethyl)biphenyl-2-yl]-1,3-thiazole-4-carboxamide | |
| 1727 | 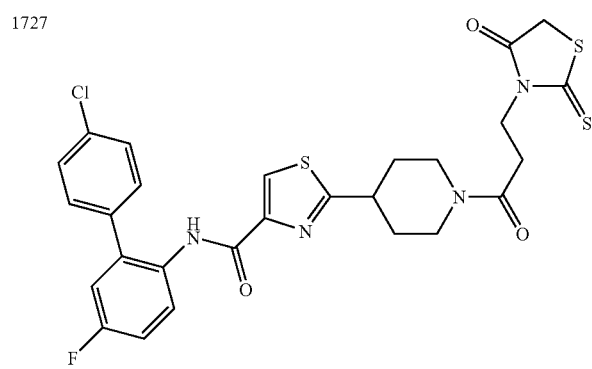 | |
| 1728 | 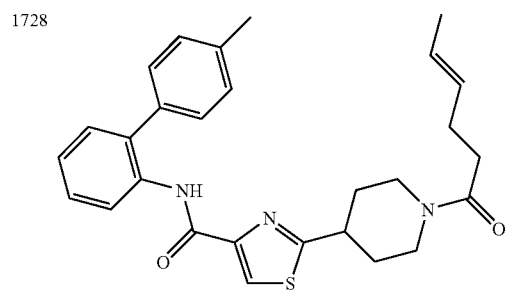 | |

TABLE 1-continued
| No. | FORMULA | NMR or mass |
|---|---|---|
1729
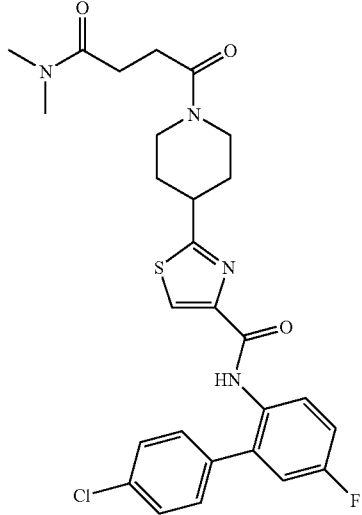
N-(4'-chloro-5-fluorobiphenyl-2-yl)-2-{1-[4-(dimethylanmino)-4-oxobutanoyl]-piperidin-4-yl}-1,3-thiazole-4-carboxamide
1730
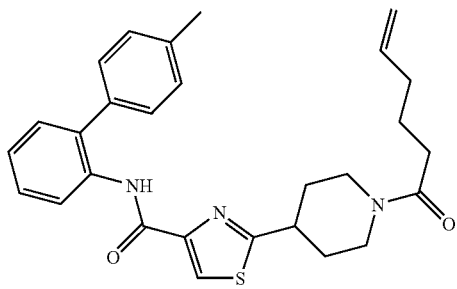
1731
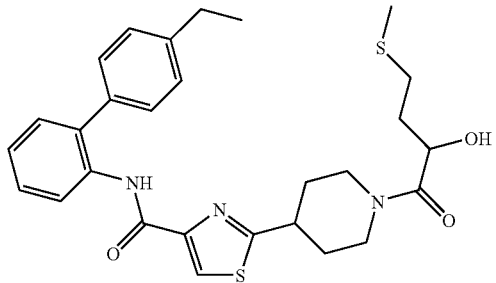

| No. | FORMULA | NMR or mass |
|-----|---------|-------------|
1732
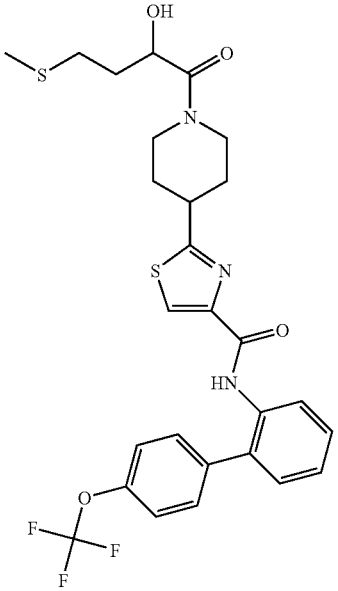
2-{1-[2-hydroxy-4-(methylthio)butanoyl]piperidin-4-yl}-N-[4'-(trifluoromethoxy)biphenyl-2-yl]-1,3-thiazole-4-carboxamide
1733
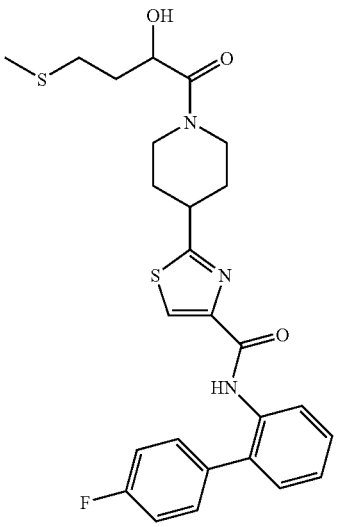
N-(4'-fluorobiphenyl-2-yl)-2-{1-[2-hydroxy-4-(methylthio)butanoyl]piperidin-4-yl}-1,3-thiazole-4-carboxamide
1734
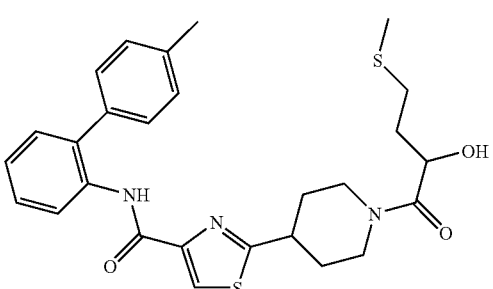

TABLE 1-continued
| No. | FORMULA | NMR or mass |
|---|---|---|
| 1735 | 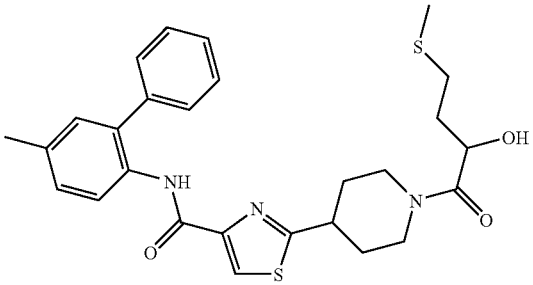 | |
| 1736 | 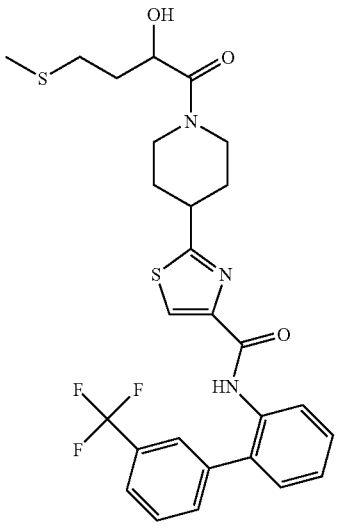 2-{1-[2-hydroxy-4-(methylthio)butanoyl]piperidin-4-yl}-N-[3'-(trifluoromethyl)-biphenyl-2-yl]-1,3-thiazole-4-carboxamide | |
| 1737 | 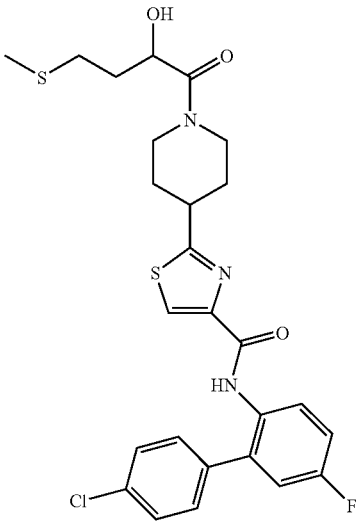 N-(4'-chloro-5-fluorobiphenyl-2-yl)-2-{1-[2-hydroxy-4-(methylthio)butanoyl]-piperidin-4-yl}-1,3-thiazole-4-carboxamide | |

TABLE 1-continued

| No. | FORMULA | NMR or mass |
|---|---|---|
| 1738 | | |
| 1739 | | |

N-(4'-fluorobiphenyl-2-yl)-2-{1-[(2R)-2-hydroxy-3-phenylpropanoyl]piperidin-4-yl}-1,3-thiazole-4-carboxamide

| 1740 | | |
| 1741 | | |

TABLE 1-continued

| No. | FORMULA | NMR or mass |
|---|---|---|
| 1742 | 2-{1-[(2R)-2-hydroxy-3-phenylpropanoyl]piperidin-4-yl}-N-[3'-(trifluoromethyl)biphenyl-2-yl]-1,3-thiazole-4-carboxamide | |
| 1743 | N-(4'-chloro-5-fluorobiphenyl-2-yl)-2-{1-[(2R)-2-hydroxy-3-phenylpropanoyl]-piperidin-4-yl}-1,3-thiazole-4-carboxamide | |

TABLE 1-continued
| No. | FORMULA | NMR or mass |
|---|---|---|
1744 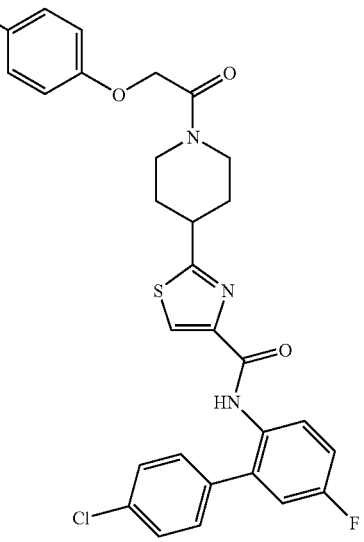
N-(4'-chloro-5-fluorobiphenyl-2-yl)-2-{1-[(4-
chlorophenoxy)acetyl]piperidin-4-yl}-1,3-thiazole-4-carboxamide
1745 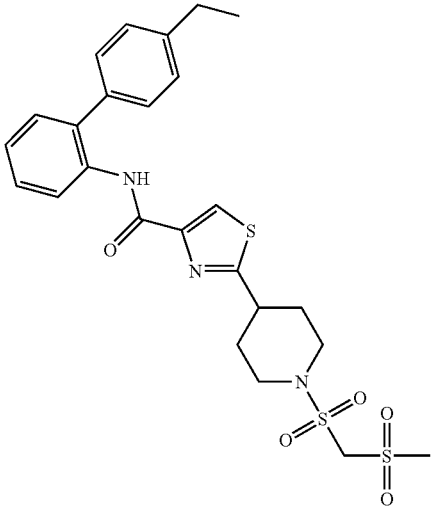
N-(4'-ethylbiphenyl-2-yl)-2-(1-{[(methylsulfonyl)
methyl]sulfonyl}piperidin-4-yl)-1,3-thiazole-4-
carboxamide

TABLE 1-continued
| No. | FORMULA | NMR or mass |
|---|---|---|
| 1746 | 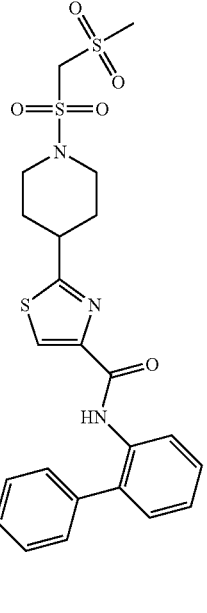 2-(1-{[(methylsulfonyl)methyl]sulfonyl}piperidin-4-yl)-N-[4'-(trifluoromethoxy)-biphenyl-2-yl]-1,3-thiazole-4-carboxamide | |
| 1747 | 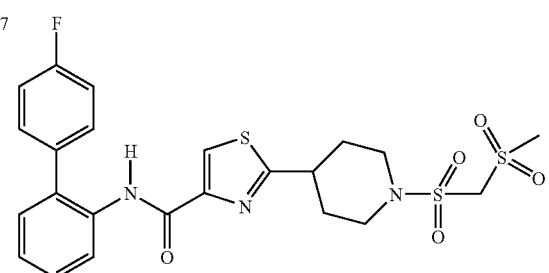 | |
| 1748 | 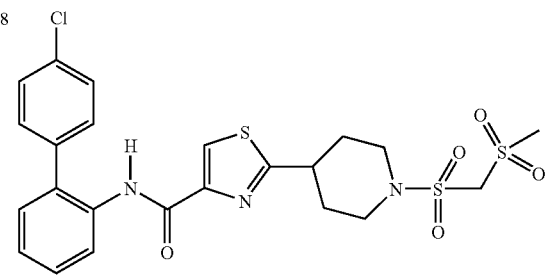 | |

TABLE 1-continued
| No. | FORMULA | NMR or mass |
|-----|---------|-------------|
1749
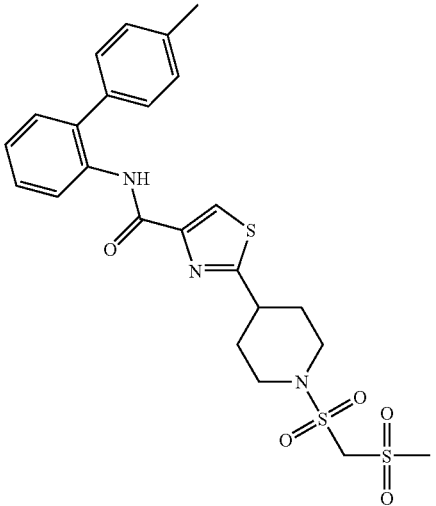
N-(4'-methylbiphenyl-2-yl)-2-(1-{[(methylsulfonyl)methyl]sulfonyl}piperidin-4-yl)-1,3-thiazole-4-carboxamide
1750
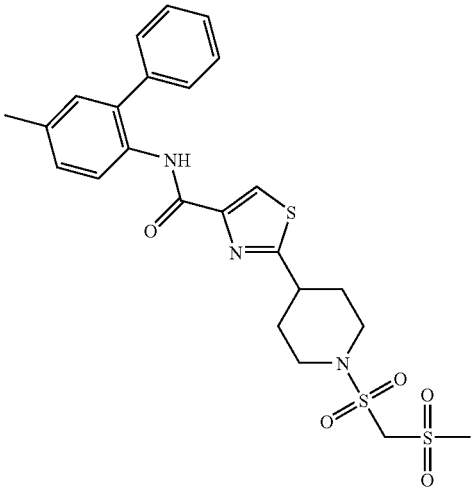

TABLE 1-continued
| No. | FORMULA | NMR or mass |
|-----|---------|-------------|
1751
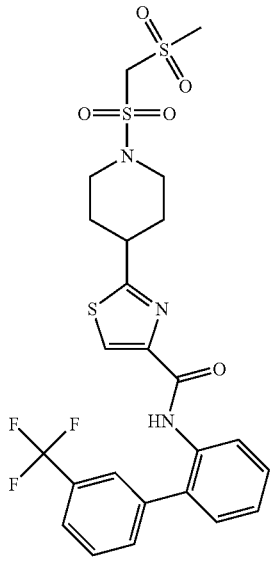
2-(1-{[(methylsulfonyl)methyl]sulfonyl}piperidin-4-yl)-N-[3'-(trifluoromethyl)-biphenyl-2-yl]-1,3-thiazole-4-carboxamide
1752
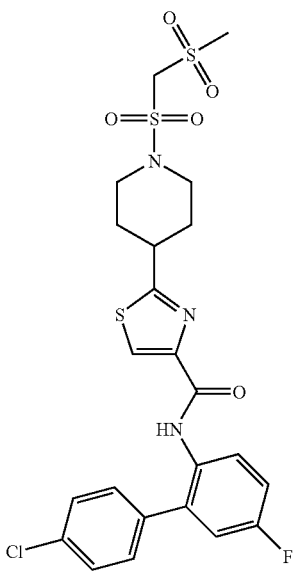
N-(4'-chloro-5-fluorobiphenyl-2-yl)-2-(1-{[(methylsulfonyl)methyl]sulfonyl}-piperidin-4-yl)-1,3-thiazole-4-carboxamide TABLE 1-continued

| No. | FORMULA | NMR or mass |
|---|---|---|

1753

N-(4'-ethylbiphenyl-2-yl)-2-{1-[(2,2,2-trifluoroethyl)sulfonyl]piperidin-4-yl}1,3-thiazole-4-carboxamide

1754

2-{1-[(2, 2, 2-trifluoroethyl)sulfonyl]piperidin-4-yl}-N-[4'-(trifluoromethoxy)-biphenyl-2-yl]-1,3-thiazole-4-carboxamide TABLE 1-continued

| No. | FORMULA | NMR or mass |
|---|---|---|
| 1755 | N-(4'-fluorobiphenyl-2-yl)-2-(1-[(2,2,2-trifluoroethyl)sulfonyl]piperidin-4-yl}-1,3-thiazole-4-carboxamide | |
| 1756 | N-(4'-chlorobiphenyl-2-yl)-2-{1-[(2,2,2-trifluoroethyl)sulfonyl]piperidin-4-yl}1,3-thiazole-4-carboxamide | |

| No. | FORMULA | NMR or mass |
|---|---|---|
1757
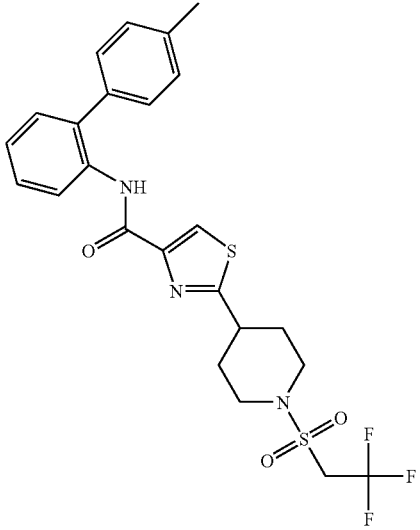
N-(4'-methylbiphenyl-2-yl)-2-{1-[(2,2,2-trifluoroethyl)
sulfonyl]piperidin-4-yl}1,3-thiazole-4-carboxamide
1758
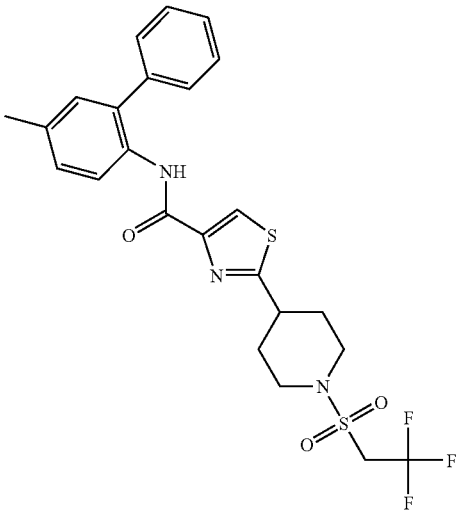
N-(5-methylbiphenyl-2-yl)-2-{1-[(2,2,2-trifluoroethyl)
sulfonyl]piperidin-4-yl}1,3-thiazole-4-carboxamide TABLE 1-continued
| No. | FORMULA | NMR or mass |
|---|---|---|
1759 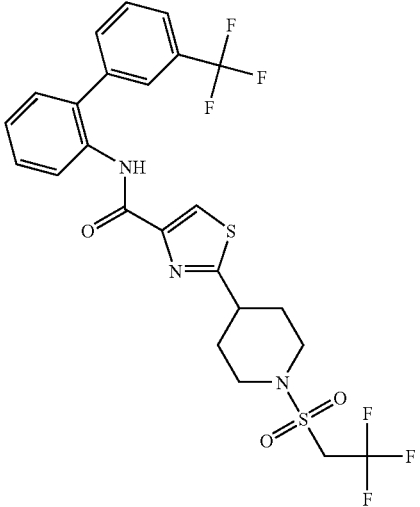
2-(1-[(2,2,2-trifluoroethyl)sulfonyl]piperifin-4-yl}-N-
[3'-(trifluoromethyl)-biphenyl-2-yl]-1,3-thiazole-4-carboxamide
1760 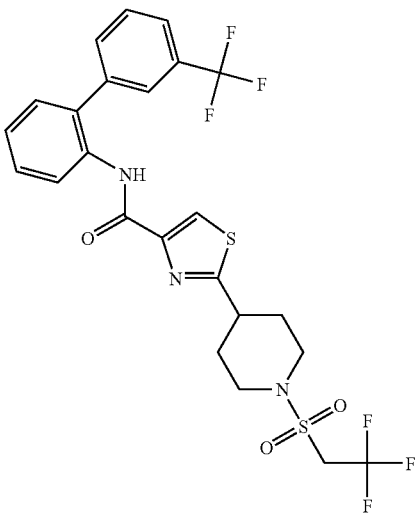
N-(4'-chloro-5-fluorobiphenyl-2-yl)-2-{1-[(2,2,2-trifluoroethyl)sulfonyl]-
piperidin-4-yl}-1,3-thiazole-4-carboxamide TABLE 1-continued
| No. | FORMULA | NMR or mass |
|---|---|---|
| 1761 | 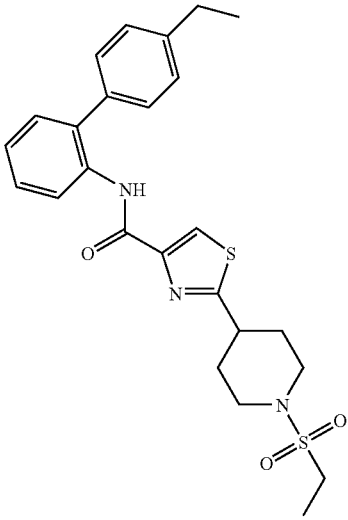 N-(4'-ethylbiphenyl-2-yl)-2-[1-(ethylsulfonyl)piperididn-4-yl]-1,3-thiazole-4-carboxamide | |
| 1762 | 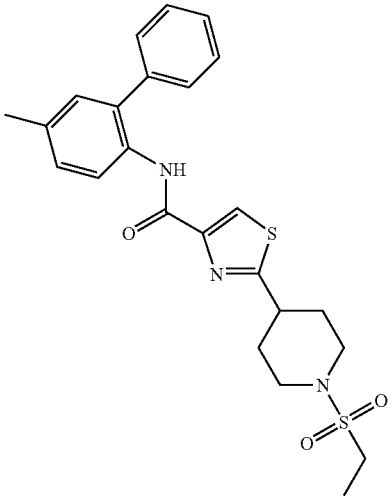 2-[1-(ethylsulfonyl)piperidin-4-yl]-N-(5-methylbiphenyl-2-yl)-1,3-thiazole-4-carboxamide | |

TABLE 1-continued
| No. | FORMULA | NMR or mass |
|---|---|---|
1763
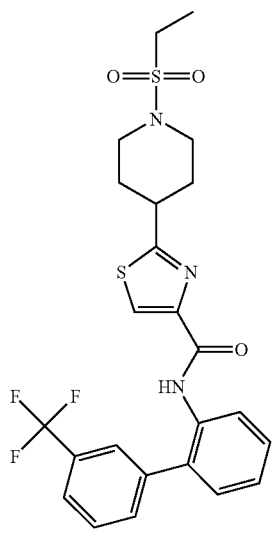
2-[1-(ethylsulfonyl)piperidin-4-yl]-N-[3'(trifluoromethyl)
biphenyl-2-yl]-1,3-thiazole-4-carboxamide
1764
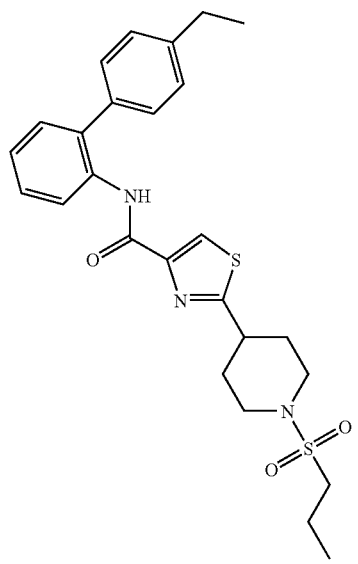
N-(4'-ethylbiphenyl-2-yl)-2-[1-(propylsulfonyl)
piperidin-4-yl]-1,3-thiazole-4-carboxamide

| No. | FORMULA | NMR or mass |
|---|---|---|
| 1765 | 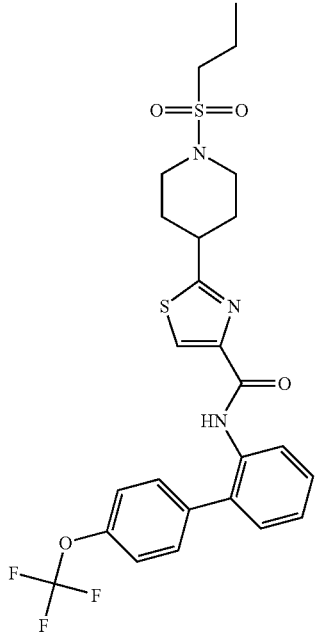<br>2-[1-(propylsulfonyl)piperidin-4-yl]-N-[4'-(trifluoromethoxy)biphenyl-2-yl]-1,3-thiazole-4-carboxamide | |
| 1766 | 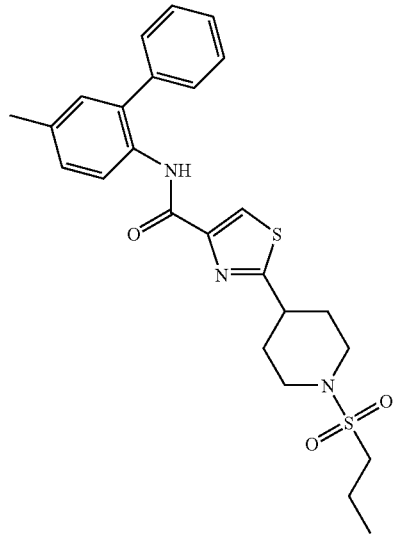 | |

TABLE 1-continued
| No. | FORMULA | NMR or mass |
|---|---|---|
| 1767 | 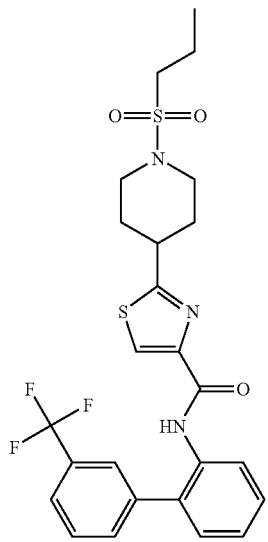 | |
| 1768 | 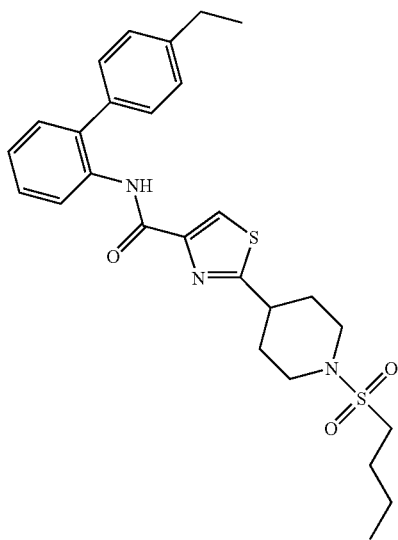 | |

TABLE 1-continued
| No. | FORMULA | NMR or mass |
|---|---|---|
| 1769 | 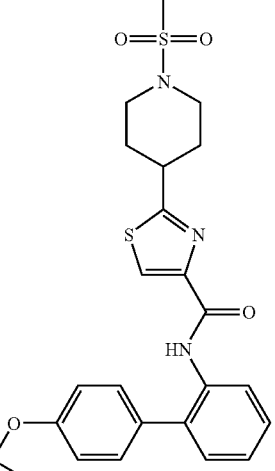 | |
| 1770 | 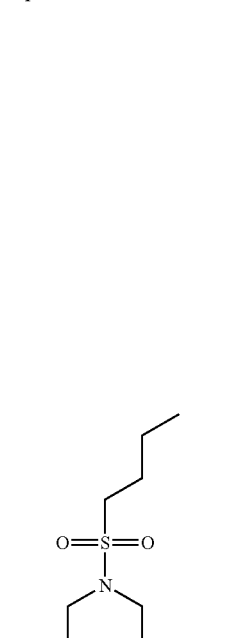 | |

TABLE 1-continued
| No. | FORMULA | NMR or mass |
|---|---|---|
| 1771 | 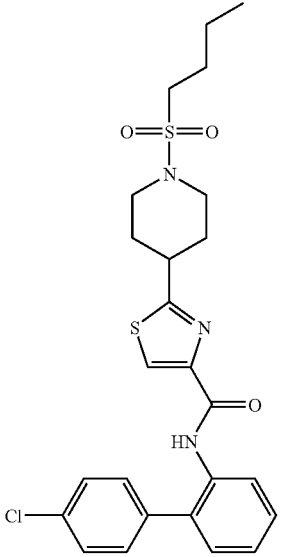 | |
| 1772 | 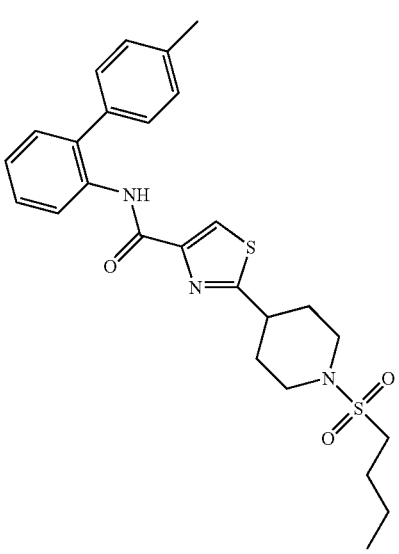 | |

TABLE 1-continued

| No. | FORMULA | NMR or mass |
|---|---|---|
| 1773 | | |
| 1774 | | |

TABLE 1-continued
| No. | FORMULA | NMR or mass |
|---|---|---|
| 1775 | 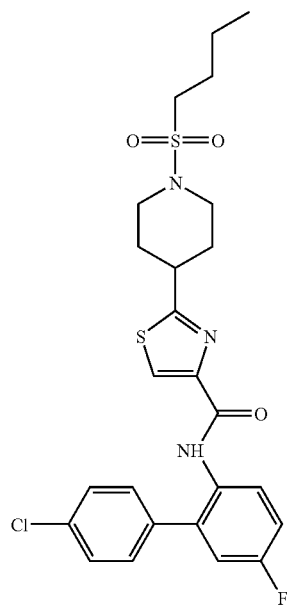 | |
| 1776 | 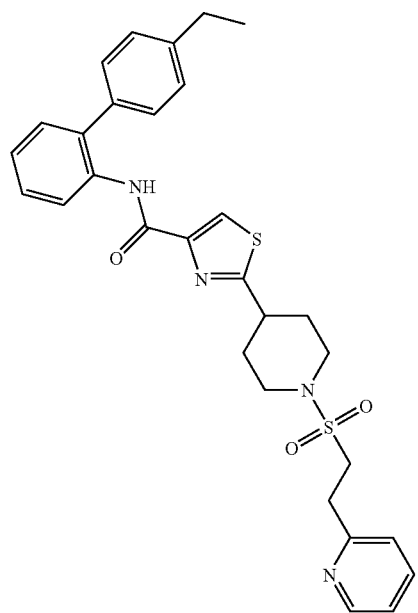 | |

TABLE 1-continued

| No. | FORMULA | NMR or mass |
|---|---|---|
| 1777 | | |
| 1778 | | |

TABLE 1-continued
| No. | FORMULA | NMR or mass |
|---|---|---|
| 1779 | 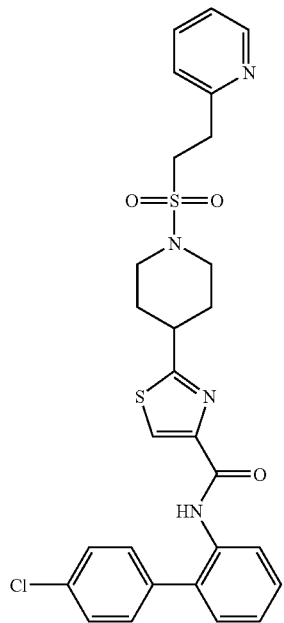 | |
| 1780 | 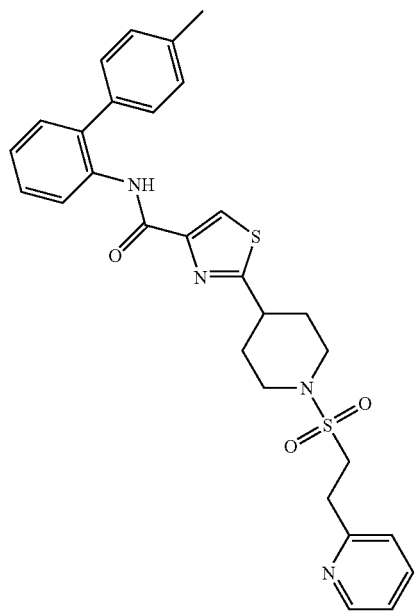 | |

TABLE 1-continued
| No. | FORMULA | NMR or mass |
|---|---|---|
| 1781 | 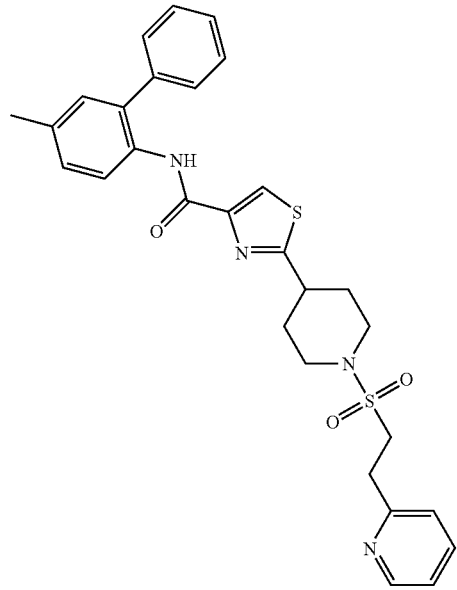 | |
| 1782 | 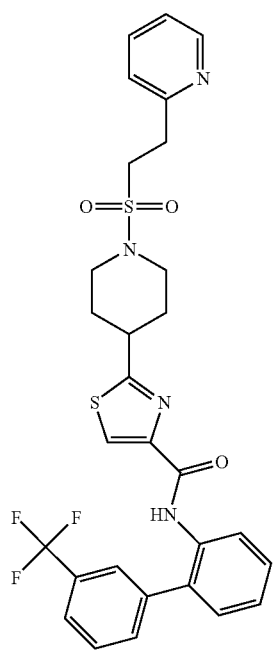 2-{1-[(2-pyridin-2-ylethyl)sulfonyl]piperidin-4-yl}-N-[3'-(trifluuoromethyl)-biphrnyl-2-yl]-1,3-thiazole-4-carboxamide | |

TABLE 1-continued
| No. | FORMULA | NMR or mass |
|---|---|---|
| 1783 | 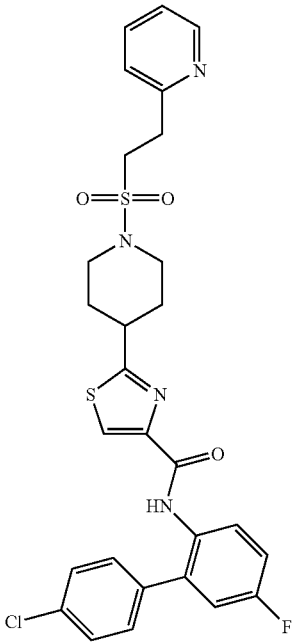 N-(4'-chloro-5-fluorobiphenyl-2-yl)-2-{1-[(2-pyridin-2-ylethyl)-sulfonyl]piperidin-4-yl}-1,3-thiazole-4-carboxamide | |
| 1784 | 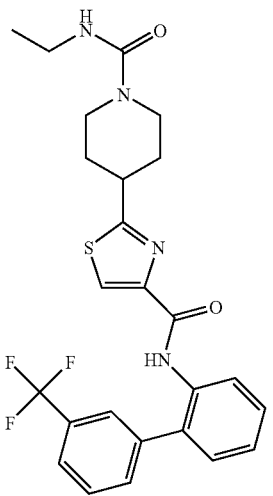 N-ethyl-4-[4-({[3'-(trifluoromethyl)biphenyl-2-yl]amino}carbonyl-1,3-thiazol-2-yl]piperidine-1-carboxamide | |
| 1785 | 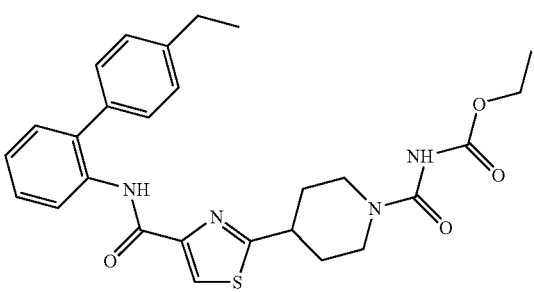 | |

TABLE 1-continued
| No. | FORMULA | NMR or mass |
|---|---|---|
| 1786 | 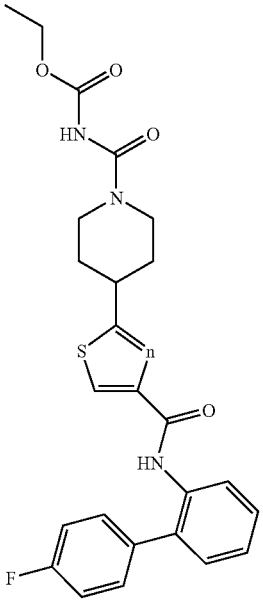 ethyl{[4-(4-{[(4'-fluorobiphrnyl-2-yl)amino]carbonyl}-1,3-thiazol-2-YL)-piperidin-1-yl]carbonyl}carbamate | |
| 1787 | 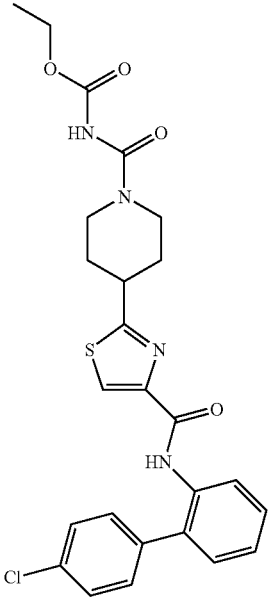 ethyl{[4-(4-{[(4'-chlorobiphenyl-2-yl)amino]carbonyl}-1,3-thiazol-2-yl)-piperidin-1-yl]carbonyl}carbamate | |

TABLE 1-continued
| No. | FORMULA | NMR or mass |
|-----|---------|-------------|
| 1788 | 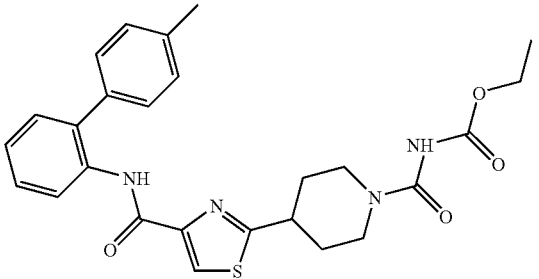 | |
| 1789 | 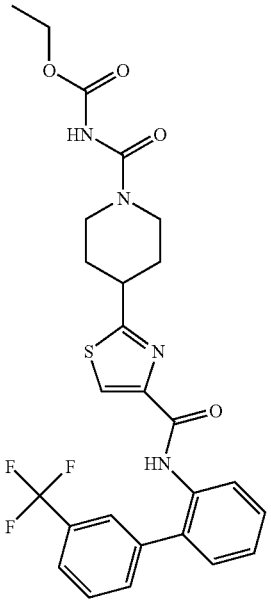<br>ethyl({4-[4-({[3'-(trifluoromethyl)biphenyl-2-yl]amino}carbonyl)-1,3-thiazol-2-yl]piperidin-1-yl}carbonyl)carbamate | |

TABLE 1-continued

| No. | FORMULA | NMR or mass |
|---|---|---|

1790 ethyl{[4-(4-{[(4'-chloro-5-fluorobiphenyl-2-yl)amino]carbonyl}-1,3-thiazol-2-yl)piperidin-1-yl]carbonyl}carbamate

1791 ethyl N-({4-[4-({[3'-(trifluoromethyl)biphenyl-2-yl]amino}carbonyl)-1,3-thiazol-2-yl]piperidin-1-yl}carbonyl)glycinate

1792

| No. | FORMULA | NMR or mass |
|---|---|---|
1793 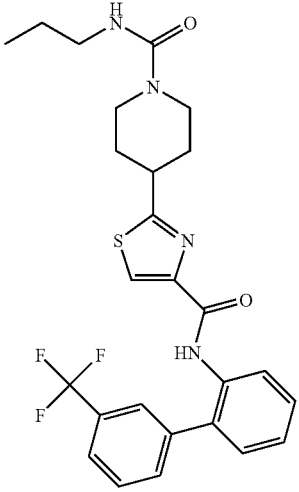
N-propyl-4-[4-({[3'-(trifluoromethyl)biphenyl-2-yl]amino}carbonyl)-1,3-thiazol-2-yl]piperidine-1-carboxamide
1794 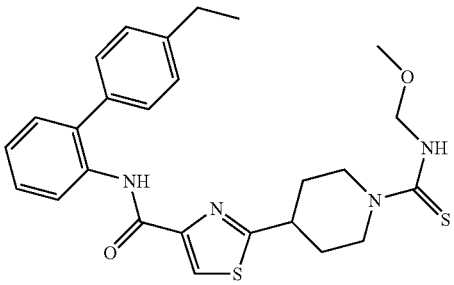
1795 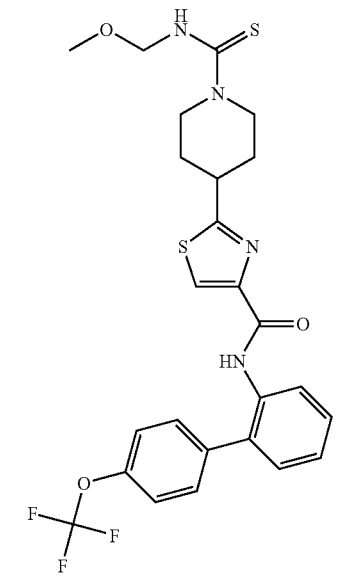
2-(1-{[(methoxymethyl)amino]carbonothioyl}piperidin-4-yl)-N-[4'-(trifluoromethoxy)biphenyl-2-yl]-1,3-thiazole-4-carboxamide TABLE 1-continued
| No. | FORMULA | NMR or mass |
|---|---|---|
| 1796 | 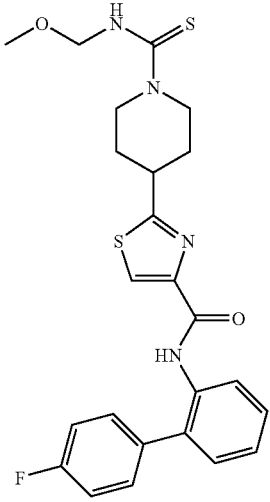 N-(4'-fluorobiphenyl-2-yl)-2-(1-{[(methoxymethyl)amino]carbonothioyl}-piperidin-4-yl)-1,3-thiazole-4-carboxamide | |
| 1797 | 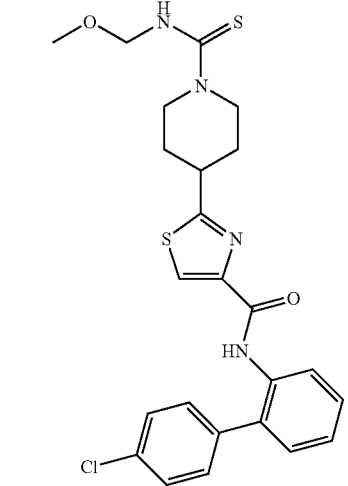 N-(4'-chlorobiphenyl-2-yl)-2-(1-{[(methoxymethyl)-amino]carbonothioyl}-piperidin-4-yl)-1,3-thiazole-4-carboxamide | |
| 1798 | 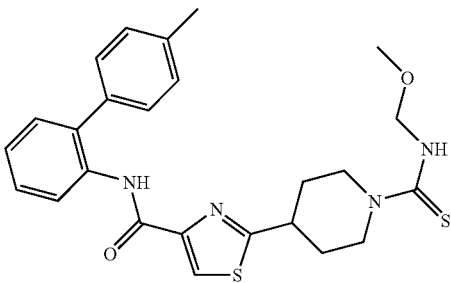 | |

TABLE 1-continued
| No. | FORMULA | NMR or mass |
|---|---|---|
1799
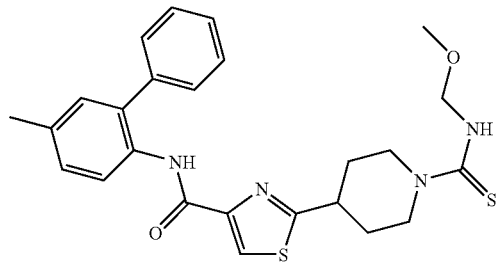
1800
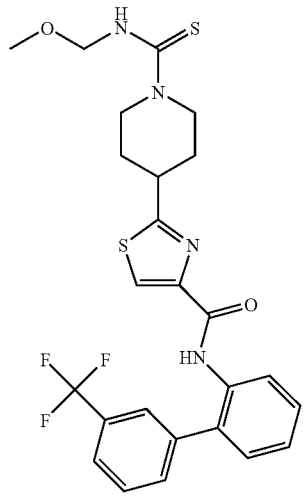
2-(1-{[(methoxymethyl)amino]carbonothioyl}piperidin-4-yl)-N-[3'-
(trifluoro-methyl)biphenyl-2-yl]-1,3-thiazole-4-carboxamide
1801
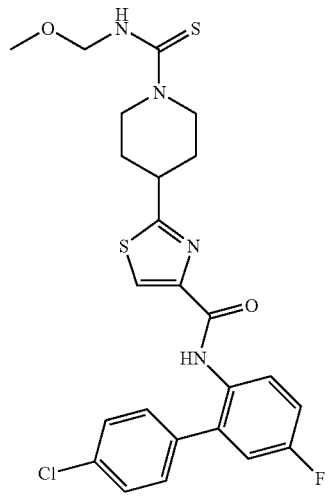
N-(4'-chloro-5-fluorobiphenyl-2-yl)-2-(1-{[(methoxymethyl)amino]carbon-
othioyl}piperidin-4-yl)-1,3-thiazole-4-carboxamide TABLE 1-continued
| No. | FORMULA | NMR or mass |
|---|---|---|
| 1802 | 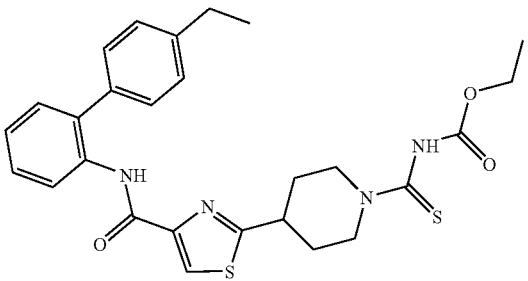 | |
| 1803 | 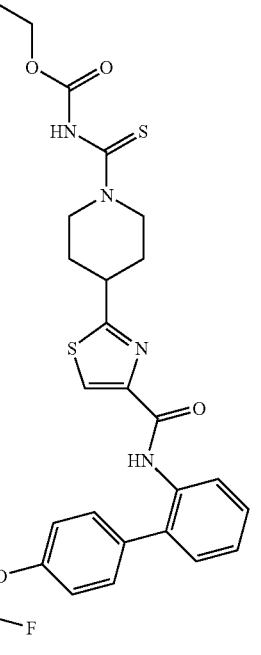<br>ethyl ({4-[4({[4'-(trifluromethoxy)biphenyl-2-yl]amino}carbonyl)-1,3-thiazol-2-yl]piperidin-1-yl}carbonothioyl)carbamate | |

TABLE 1-continued

| No. | FORMULA | NMR or mass |
|---|---|---|

1804 ethyl {[4-(4-{[(4'-fluorobiphenyl-2-yl)amino]carbonyl}-1,3-thiazol-2-yl)-piperidin-1-yl]carbonothioyl}carbamate

1805 ethyl {[4-(4-{[(4'-chlorobiphenyl-2-yl)amino]carbonyl}-1,3-thiazol-2-yl)-piperidin-1-yl]carbonothioyl}carbamate TABLE 1-continued
| No. | FORMULA | NMR or mass |
|---|---|---|
| 1806 | 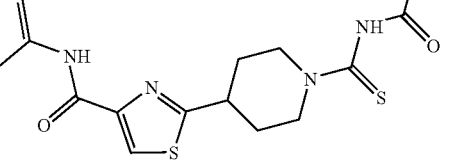 | |
| 1807 | 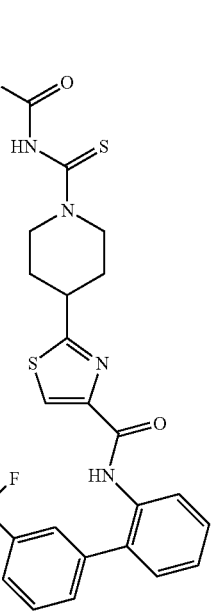 | |
| 1808 | 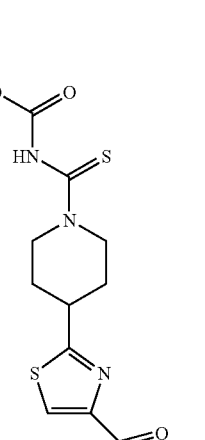 | |
ethyl {[4-(4-{[(4'-chloro-5-fluorobiphenyl-2-yl)amino]carbonyl}-1,3-thiazol-2-yl)piperidin-1-yl]carbonothioyl}carbamate TABLE 1-continued
| No. | FORMULA | NMR or mass |
|---|---|---|
| 1809 | 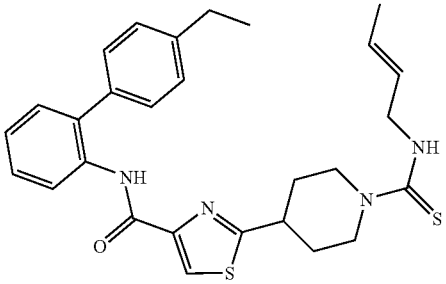 | |
| 1810 | 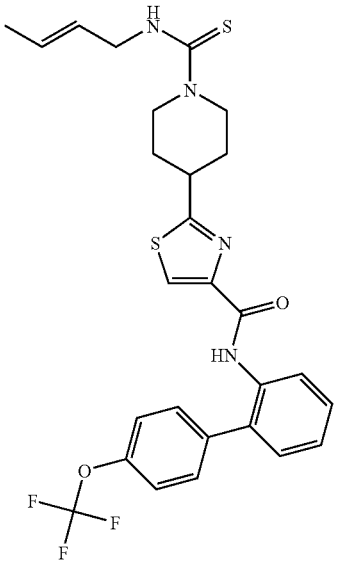 | |
| 1811 | 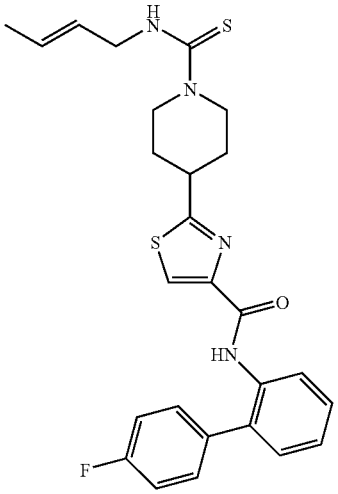 | |
2-(1-{[(2E)-but-2-en-1-ylamino]carbonothioyl}piperidin-4-yl)-N-(4'-fluoro-biphenyl-2-yl)-1,3-thiazole-4-carboxamide TABLE 1-continued
| No. | FORMULA | NMR or mass |
|---|---|---|
| 1812 | 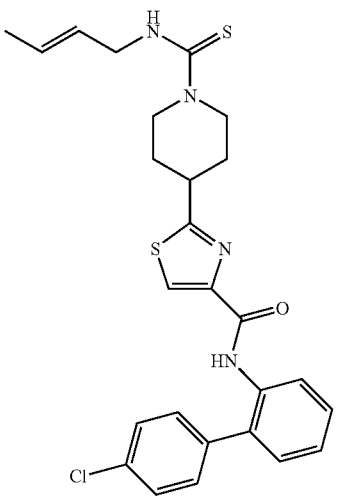 2-(1-{[(2E)-but-2-en-1-ylamino]carbonothioyl}piperidin-4-yl)-N-(4'-chloro-biphenyl-2-yl)-1,3-thiazole-4-carboxamide | |
| 1813 | 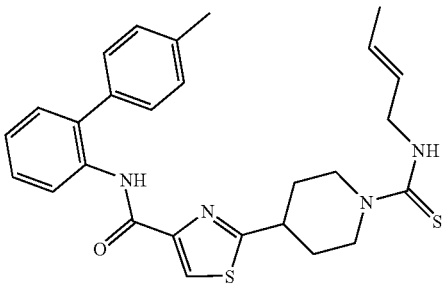 | |
| 1814 | 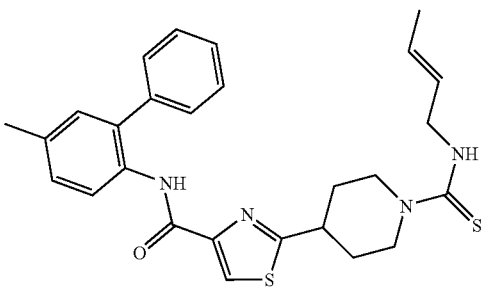 | |

TABLE 1-continued
| No. | FORMULA | NMR or mass |
|---|---|---|
| 1815 | 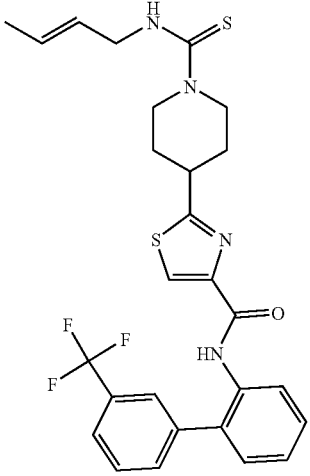 2-(1-{[(2E)-but-2-en-1-ylamino]carbonothioyl}piperidin-4-yl)-N-[3'-(trifluoromethyl)biphenyl-2-yl]-1,3-thiazole-4-carboxamide | |
| 1816 | 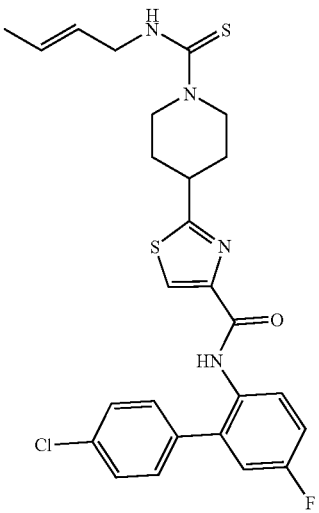 2-(1-{[(2E)-but-2-en-1-ylamino]carbonothioyl}piperidin-4-yl)-N-(4'-chloro-5-fluorobiphenyl-2-yl)-1,3-thiazole-4-carboxamide | |
| 1817 | 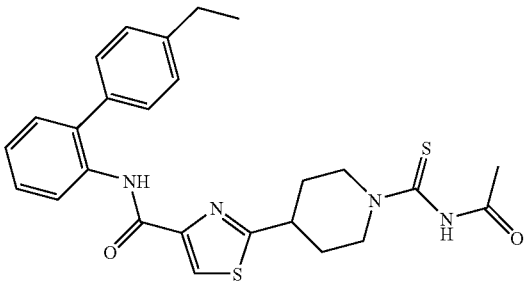 | |

TABLE 1-continued

| No. | FORMULA | NMR or mass |
|---|---|---|
| 1818 | 2-{1-[(acetylamino)carbonothioyl]piperidin-4-yl}-N-(4'-fluorobiphenyl-2-yl)-1,3-thiazole-4-carboxamide | |
| 1819 | 2-[1-[(acetylamino)carbonothioyl]piperidin-4-yl}-N-(4'-chlorobiphenyl-2-yl)-1,3-thiazole-4-carboxamide | |
| 1820 | | |

TABLE 1-continued
| No. | FORMULA | NMR or mass |
|---|---|---|
| 1821 | 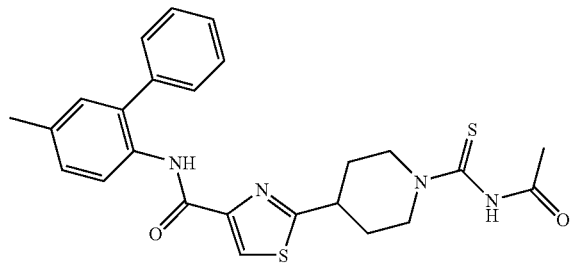 | |
| 1822 | 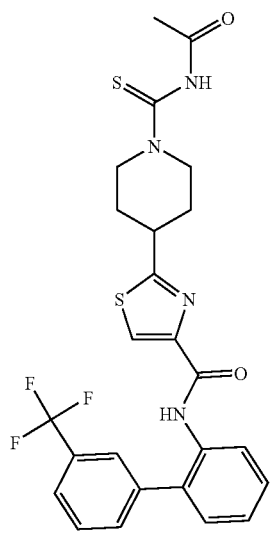<br>2-{1-{(acetylamino)carbonothioyl]piperidin-4-yl}-N-[3-(trifluoromethyl)-biphenyl-2-yl]-1,3-thiazole-4-carboxamide | |
| 1823 | 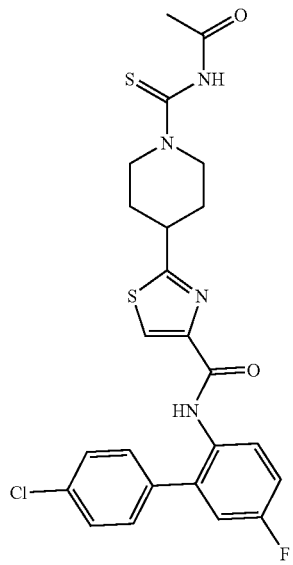<br>2-{1-[(acetylamino)carbonothioyl]piperidin-4-yl}-N-(4'-chloro-5-fluorobiphenyl-2-yl)-1,3-thiazole-4-carboxamide | |

TABLE 1-continued
| No. | FORMULA | NMR or mass |
|---|---|---|
| 1824 | 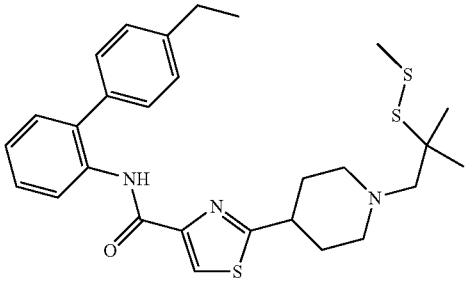 | |
| 1825 | 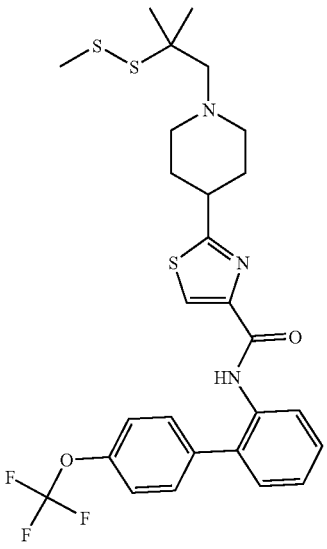<br>2-{1-{2-methyl-2-(methyldithio)propyl]piperidin-4-yl}-N-[4'-(trifluoromethoxy)-biphenyl-2-yl]-1,3-thiazole-4-carboxamide | |
| 1826 | 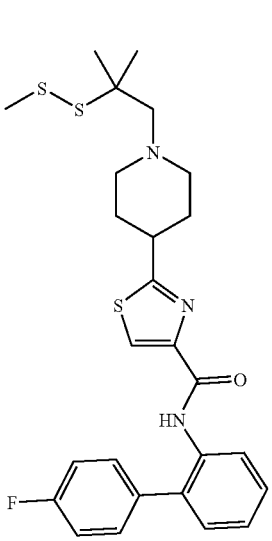<br>N-(4'-fluorobiphenyl-2-yl)-2-{1-[2-methyl-2-(methyldithio)propyl]piperidin-4-ly}-1,3-thiazole-4-carboxamide | |

TABLE 1-continued
| No. | FORMULA | NMR or mass |
|---|---|---|
| 1827 | 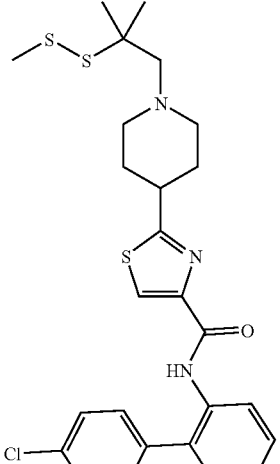 N-(4'-chlorobiphenyl-2-yl)-2-{1-[2-methyl-2-(methyldithio)propyl]piperidin-4-yl}-1,3-thiazole-4-carboxamide | |
| 1828 | 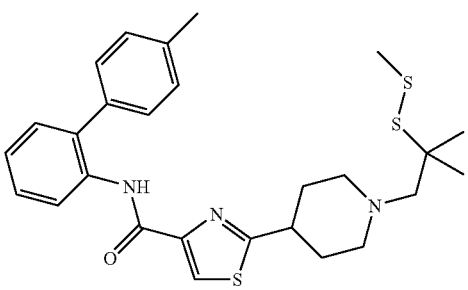 | |
| 1829 | 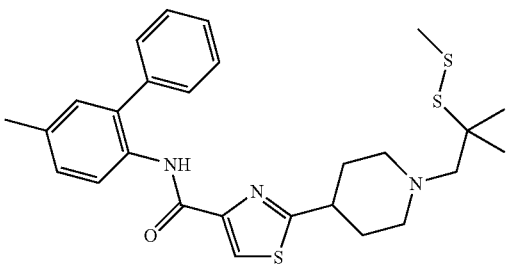 | |

TABLE 1-continued
| No. | FORMULA | NMR or mass |
|---|---|---|
| 1830 | 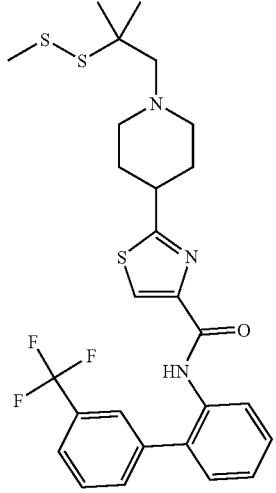 2-{1-[2-methyl-2-(methyldithio)propyl]piperidin-4-yl]-N-[3'-(trifluoromethyl)-biphenyl-2-yl]-1,3-thiazole-4-carboxamide | |
| 1831 | 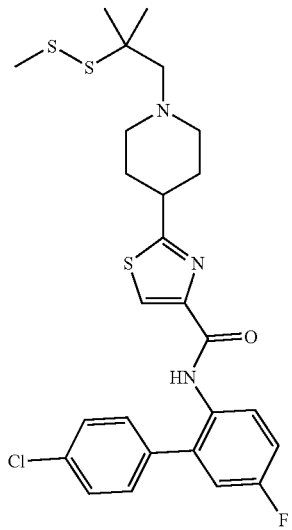 N-(4'-chloro-5-fluorobiphenyl-2-yl)-2-{1-[2-methyl-2-(methyldithio)propyl]-piperidin-4-yl-1,3-thiazole-4-carboxamide | |

TABLE 1-continued
| No. | FORMULA | NMR or mass |
|---|---|---|
| 1832 | 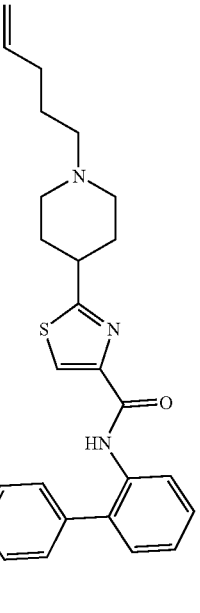<br>2-(1-pent-4-en-1-ylpiperidin-4-yl)-N-[4'-(trifluoromethoxy)biphenyl-2-yl]-1,3-thiazole-4-carboxamide | |
| 1833 | 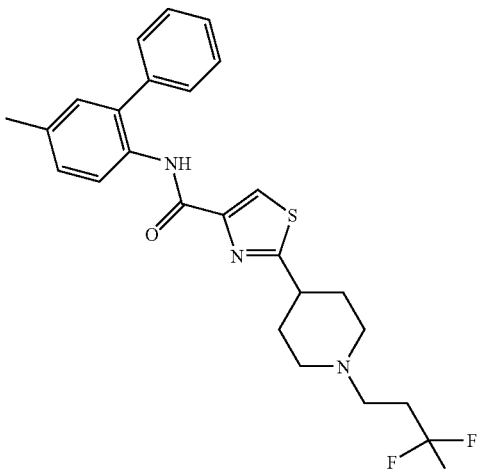<br>N-(5-methylbiphenyl-2-yl)-2-[1-(3,3,3-trifluoropropyl)piperidin-4-yl]-1,3-thiazole-4-carboxamide | |
| 1834 | 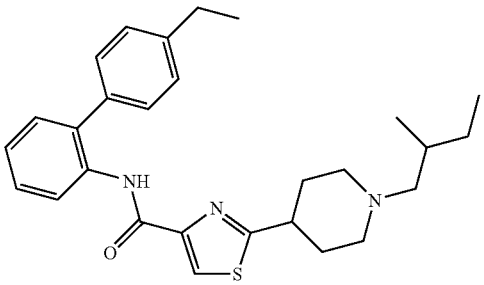 | |

TABLE 1-continued
| No. | FORMULA | NMR or mass |
|---|---|---|
| 1835 | 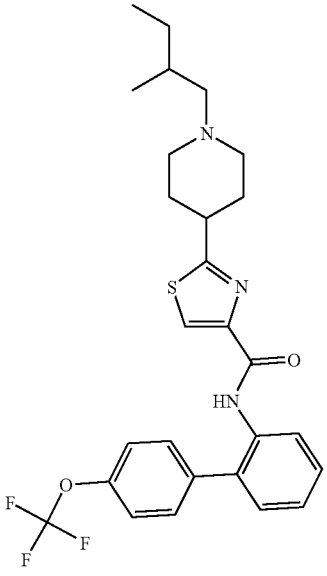 2-[1-(2-methylbutyl)piperidin-4-yl]-N-[4'-(trifluoromethoxy)piphenyl-2-yl]-1,3-thiazole-4-carboxamide | |
| 1836 | 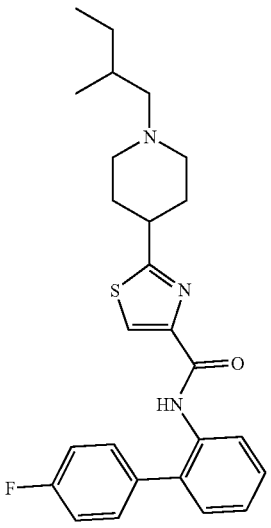 N-(4'-fluorobiphenyl-2-yl)-2-[1-(2-methylbutyl)piperidin-4-yl]-1,3-thiazole-4-carboxamide | |

TABLE 1-continued
| No. | FORMULA | NMR or mass |
|---|---|---|
1837
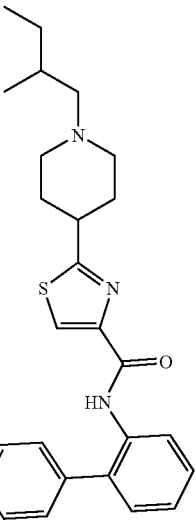
N-(4'-chlorobiphenyl-2-yl)-2-[1-(2-methylbutyl)piperidin-4-yl]-1,3-thiazole-4-carboxamide
1838
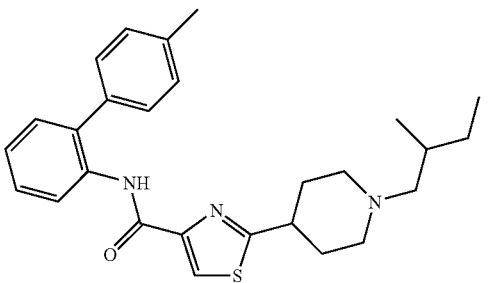
1839
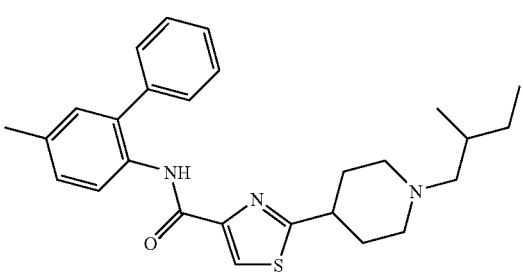

| No. | FORMULA | NMR or mass |
|---|---|---|
1840
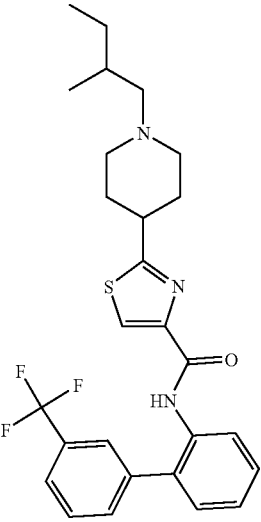
2-[1-(2-methylbutyl)piperidin-4-yl]-N-[3'-(trifluoromethyl)biphenyl-2-yl]-
1,3-thiazole-4-carboxamide
1841
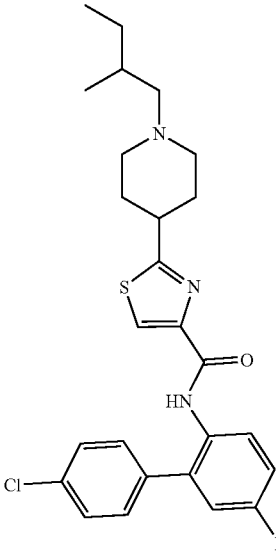
N-(4'-chloro-5-fluorobiphenyl-2-yl)-2-[1-(2-methylbutyl)piperidin-4-yl]-
1,3-thiazole-4-carboxamide
1842
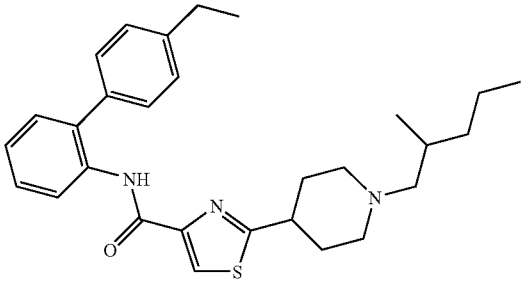

TABLE 1-continued
| No. | FORMULA | NMR or mass |
|---|---|---|
| 1843 | 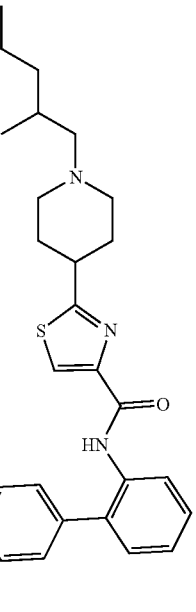 2-[1-(2-methylpentyl)piperidin-4-yl]-N-[4'-(trifluromethoxy)biphenyl-2-yl]-1,3-thiazole-4-carboxamide | |
| 1844 | 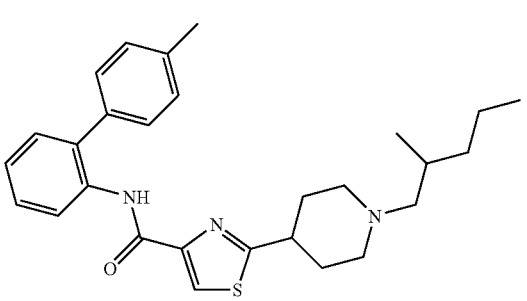 | |
| 1845 | 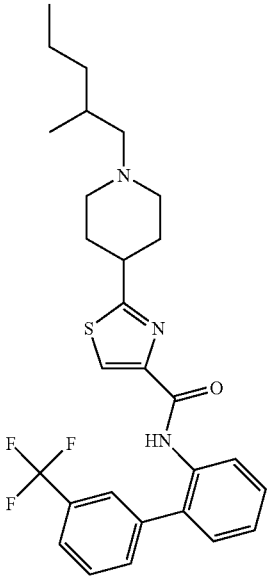 2-[1-(2-methylpentyl)piperidin-4-yl]-N-[3'-(trifluoromethyl)biphenyl-2-yl]-1,3-thiazole-4-carboxamide | |

TABLE 1-continued
| No. | FORMULA | NMR or mass |
|---|---|---|
| 1846 | 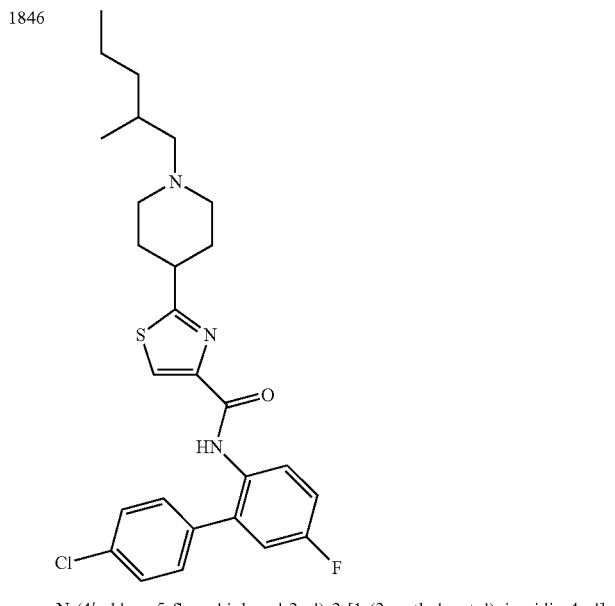 N-(4'-chloro-5-fluorobiphenyl-2-yl)-2-[1-(2-methylpentyl)piperidin-4-yl]-1,3-thiazole-4-carboxamide | |
| 1847 | 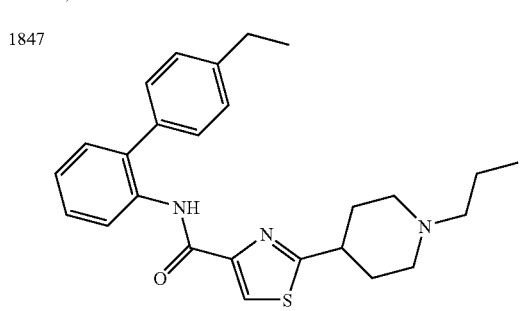 | |
| 1848 | 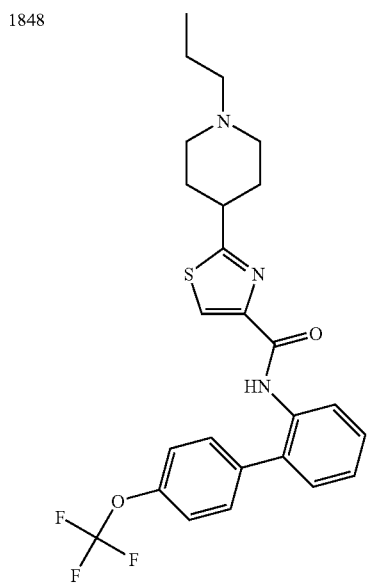 2-(1-propylpiperidin-4-yl)-N-[4'-(trifluoromethoxy)biphenyl-2-yl]-1,3-thiazole-4-carboxamide | |

TABLE 1-continued
| No. | FORMULA | NMR or mass |
|---|---|---|
1849
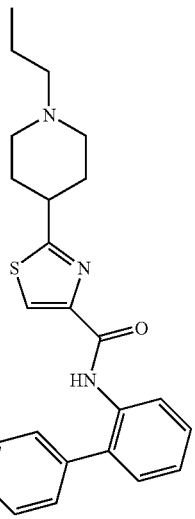
1850
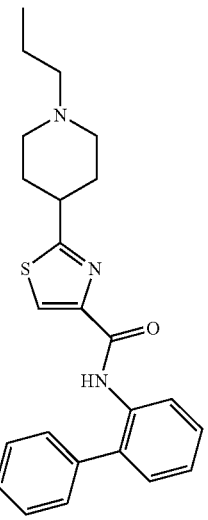
N-(4'-chlorobiphenyl-2-yl)-2-(1-propylpiperidin-4-yl)-1,3-thiazole-4-carboxamide
1851
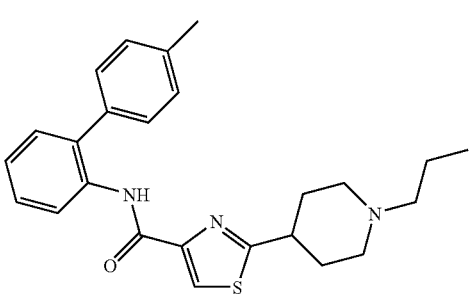

TABLE 1-continued
| No. | FORMULA | NMR or mass |
|-----|---------|-------------|
1852
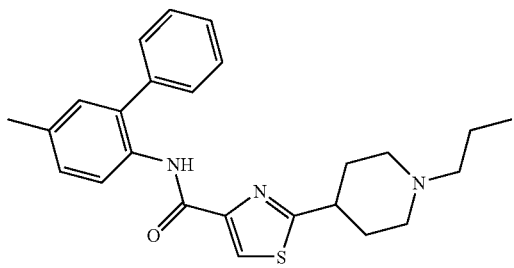
1853
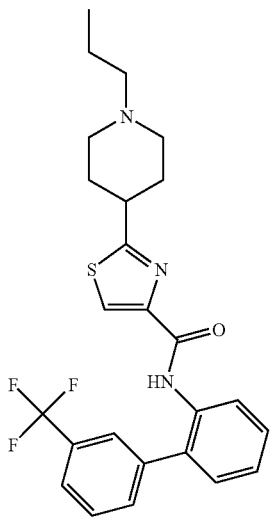
2-(1-propylpiperidin-4-yl)-N-[3'-(trifluoromethyl)biphenyl-2-yl]-1,3-thiazole-4-carboxamide
1854
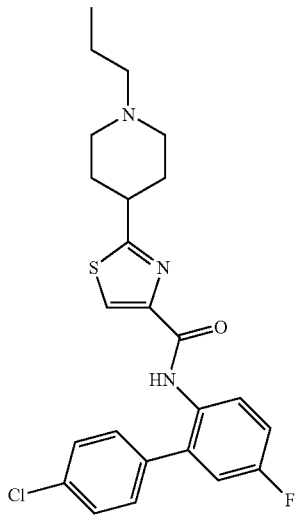
N-(4'-chloro-5-fluorobiphenyl-2-yl)-2-(1-propylpiperidin-4-yl)-1,3-thiazole-4-carboxamide

| No. | FORMULA | NMR or mass |
|---|---|---|
| 1855 | 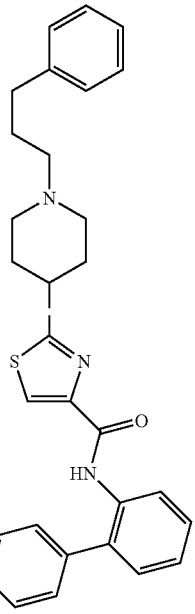 N-(4'-fluorobiphenyl-2-yl)-2-[1-(3-phenylpropyl)piperidin-4-yl]-1,3-thiazole-4-carboxamide | |
| 1856 | 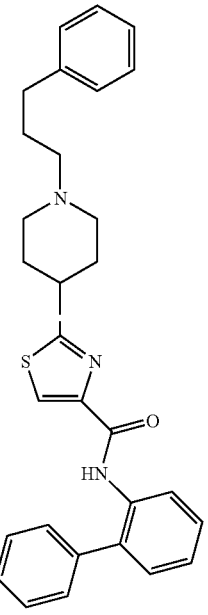 N-(4'-chlorobiphenyl-2-yl)-2-[1-(3-phenylpropyl)piperidin-4-yl]-1,3-thiazole-4-carboxamide | |

| No. | FORMULA | NMR or mass |
|---|---|---|
| 1857 | | |
| 1858 | 2-{1-[3-(methylthio)propyl]piperidin-4-yl}-N-[4'-(trifluoromethoxy)biphenyl-2-yl]-1,3-thiazole-4-carboxamide | |

TABLE 1-continued
| No. | FORMULA | NMR or mass |
|---|---|---|
| 1859 | 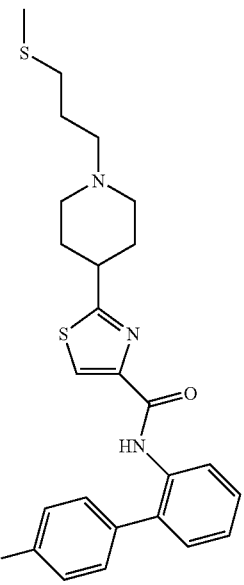<br>N-(4'-fluorobiphenyl-2-yl)-2-{1-[3-(methylthio)propyl]piperidin-4-yl}-1,3-thiazole-4-carboxamide | |
| 1860 | 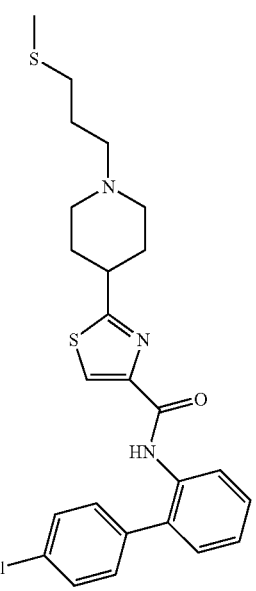<br>N-(4'-chlorobiphenyl-2-yl)-2-{1-[3-(methylthio)propyl]piperidin-4-yl}-1,3-thiazole-4-carboxamide | |
| 1861 | 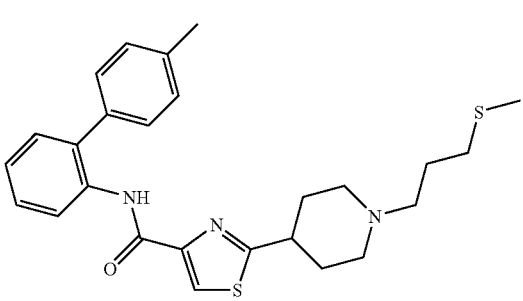 | |

TABLE 1-continued

| No. | FORMULA | NMR or mass |
|---|---|---|
| 1862 | | |
| 1863 | | |

2-{1-[3-(methylthio)propyl]piperidin-4-yl}-N-[3'-(trifluoromethyl)biphenyl-2-yl]-1,3-thiazole-4-carboxamide

| 1864 | | |

N-(4'-chloro-5-fluorobiphenyl-2-yl)-2-{1-[3-(methylthio)propyl]piperidin-4-yl}-1,3-thiazole-4-carboxamide

TABLE 1-continued
| No. | FORMULA | NMR or mass |
|---|---|---|
| 1865 | 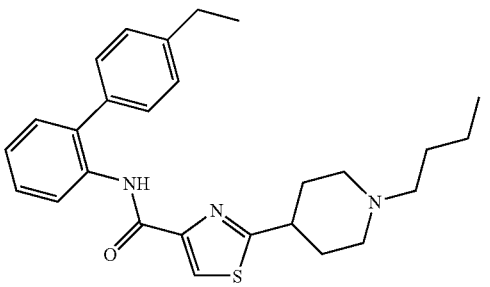 | |
| 1866 | 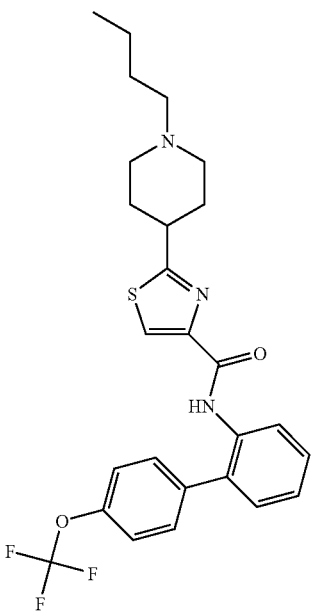<br>2-(1-butylpiperidin-4-yl)-N-[4'-(trifluoromethoxy)biphenyl-2-yl]-1,3-thiazole-4-carboxamide | |
| 1867 | 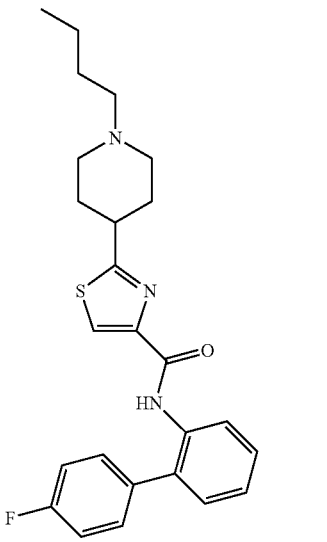<br>2-(1-butylpiperidin-4-yl)-N-(4'-fluorobiphenyl-2-yl)-1,3-thiazole-4-carboxamide | |

US 7,674,803 B2
1273                                                                                       1274
TABLE 1-continued
| No. | FORMULA | NMR or mass |
|-----|---------|-------------|
| 1868 | 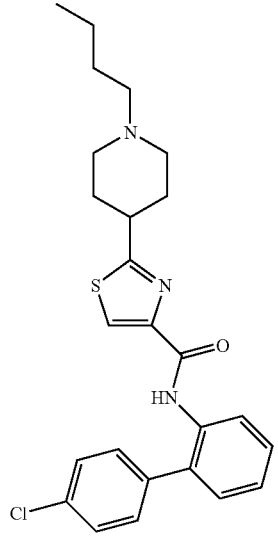 2-(1-butylpiperidin-4-yl)-N-(4'-chlorobiphenyl-2-yl)-1,3-thiazole-4-carboxamide | |
| 1869 | 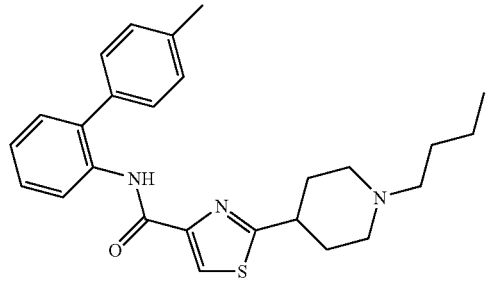 | |
| 1870 | 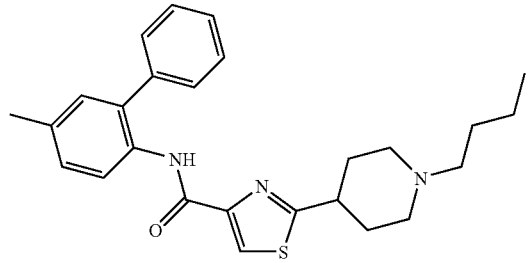 | |

TABLE 1-continued
| No. | FORMULA | NMR or mass |
|---|---|---|
| 1871 | 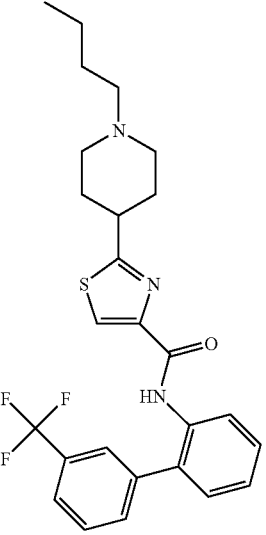 2-(1-butylpiperidin-4-yl)-N-[3'-(trifluoromethyl)biphenyl-2-yl]-1,3-thiazole-4-carboxamide | |
| 1872 | 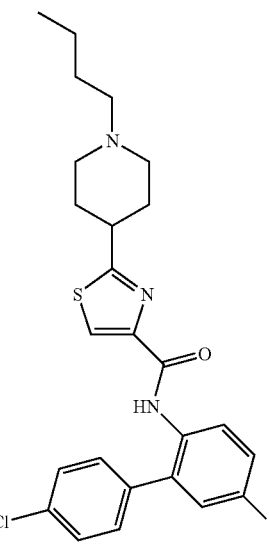 2-(1-butylpiperidin-4-yl)-N-(4'-chloro-5-fluorobiphenyl-2-yl)-1,3-thiazole-4-carboxamide | |
| 1873 | 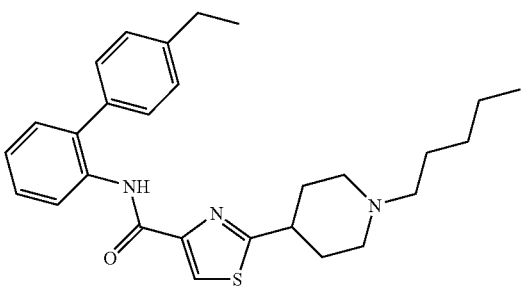 | |

TABLE 1-continued
| No. | FORMULA | NMR or mass |
|---|---|---|
| 1874 | 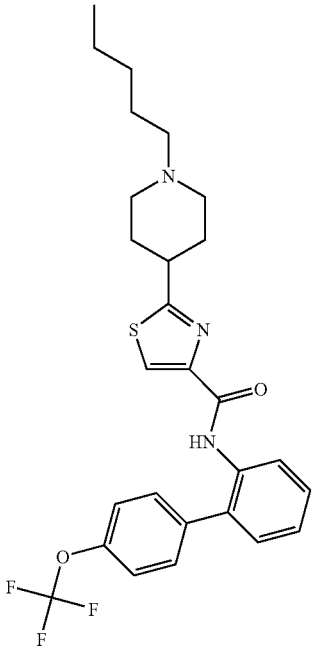<br>2-(1-pentylpiperidin-4-yl)-N-[4'-(trifluoromethoxy)biphenyl-2-yl]-1,3-thiazole-4-carboxamide | |
| 1875 | 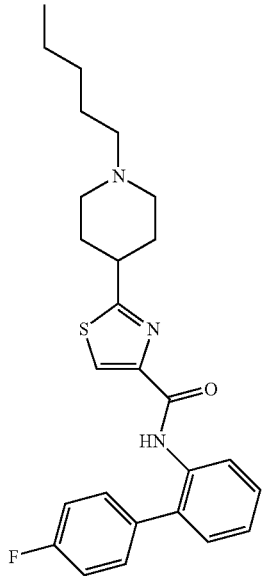<br>N-(4'-fluorobiphenyl-2-yl)-2-(1-pentylpiperidin-4-yl)-1,3-thiazole-4-carboxamide | |

TABLE 1-continued
| No. | FORMULA | NMR or mass |
|---|---|---|
| 1876 | 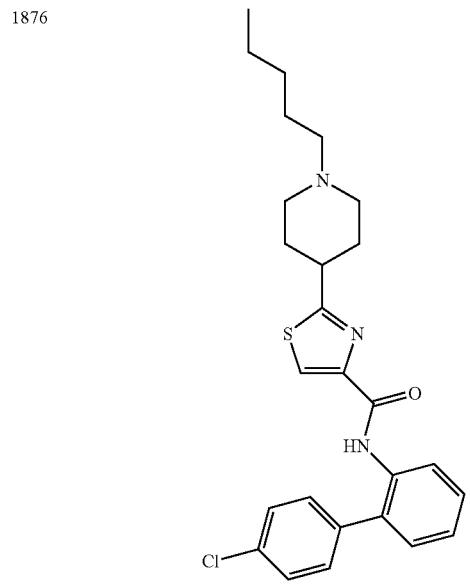 N-(4'-fluorobiphenyl-2-yl)-2-(1-pentylpiperidin-4-yl)-1,3-thiazole-4-carboxamide | |
| 1877 | 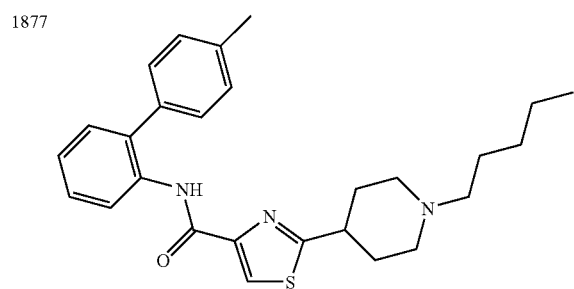 | |
| 1878 | 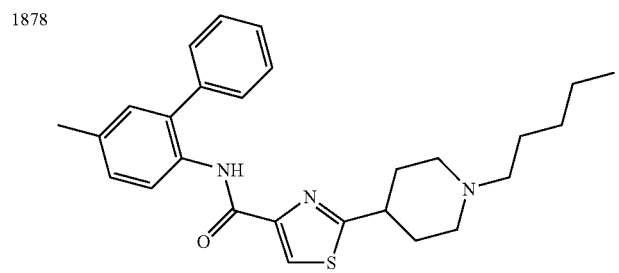 | |

TABLE 1-continued
| No. | FORMULA | NMR or mass |
|---|---|---|
| 1879 | 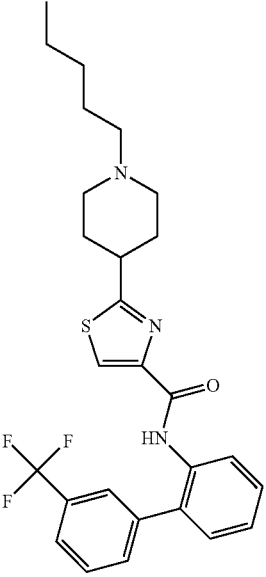<br>2-(1-pentylpiperidin-4-yl)-N-[3'-(trifluoromethyl)biphenyl-2-yl]-1,3-thiazole-4-carboxamide | |
| 1880 | 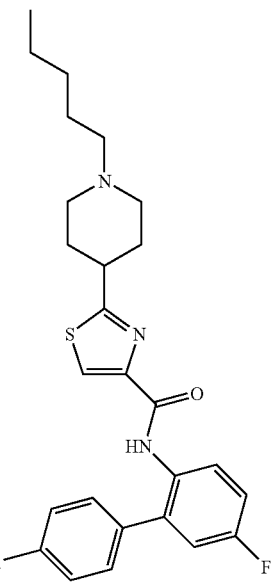<br>N-(4'-chloro-5-fluorobiphenyl-2-yl)-2-(1-pentylpiperidin-4-yl)-1,3-thiazole-4-carboxamide | |

| No. | FORMULA | NMR or mass |
|---|---|---|
1881
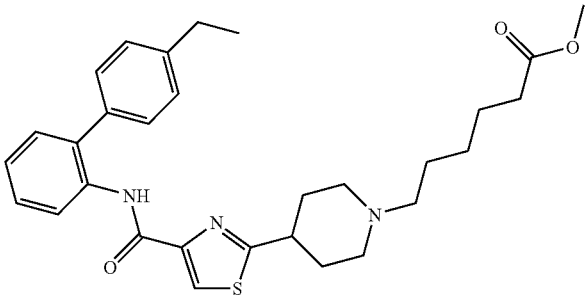
1882
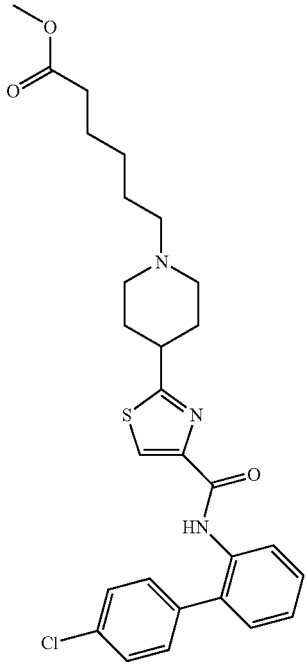
methyl 6-[4-(4-{[(4'-chlorobiphenyl-2-yl)amino]carbonyl}-1,3-thiazol-2-yl)-piperidin-1-yl]hexanoate
1883
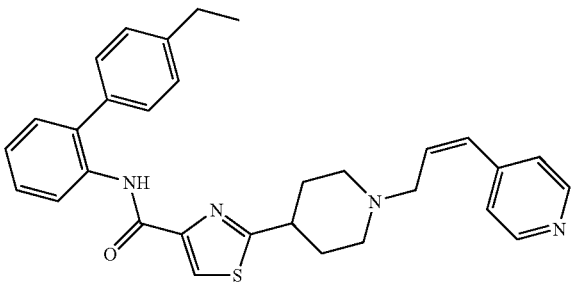

TABLE 1-continued
| No. | FORMULA | NMR or mass |
|---|---|---|
| 1884 | 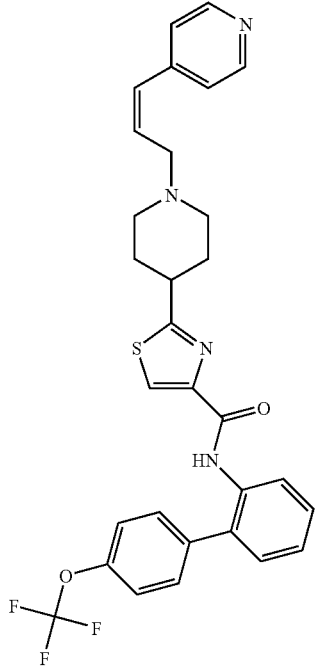 2-{1-[(2Z)-3-pyridin-4-ylprop-2-en-1-yl]piperidin-4-yl}-N-[4'-(trifluoromethoxy)biphenyl-2-yl]-1,3-thiazole-4-carboxamide | |
| 1885 | 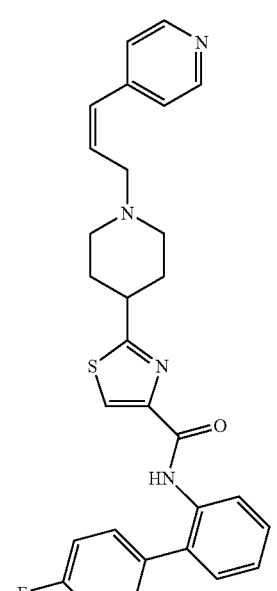 N-(4'-fluorobiphenyl-2-yl)-2-(1-[(2Z)-3-pyridin-4-ylprop-2-en-1-yl]piperidin-4-yl}-1,3-thiazole-4-carboxamide | |

| No. | FORMULA | NMR or mass |
|---|---|---|
| 1886 | 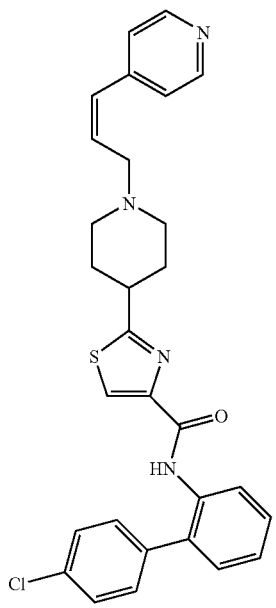 N-(4'-chlorobiphenyl-2-yl)-2-{1-[(2Z)-3-pyridin-4-ylprop-2-en-1-yl]piperidin-4-yl}-1,3-thiazole-4-carboxamide | |
| 1887 | 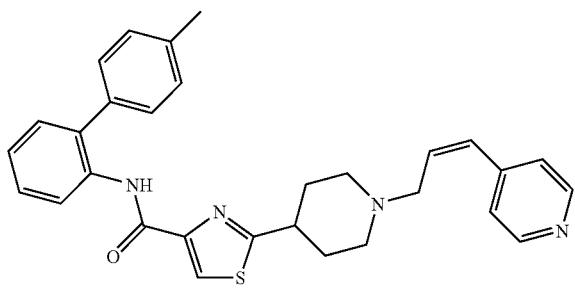 | |
| 1888 | 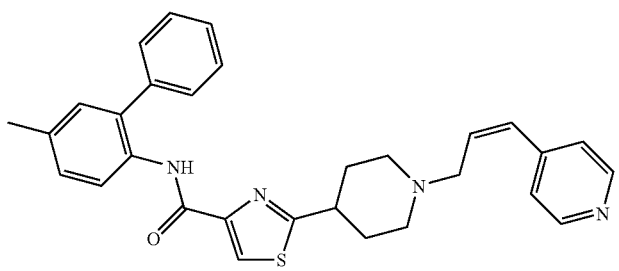 | |

TABLE 1-continued
| No. | FORMULA | NMR or mass |
|---|---|---|
| 1889 | 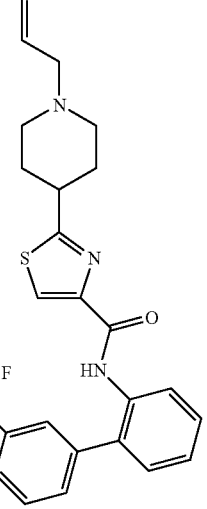 | |
| 1890 | 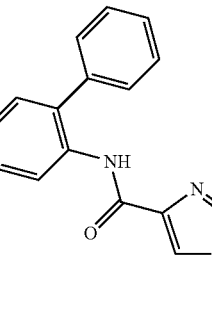 | |
| 1891 | 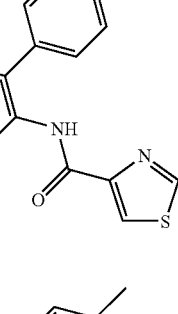 | |
| 1892 | 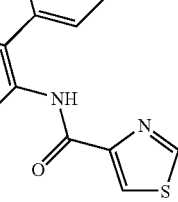 | |

TABLE 1-continued
| No. | FORMULA | NMR or mass |
|---|---|---|
| 1893 | 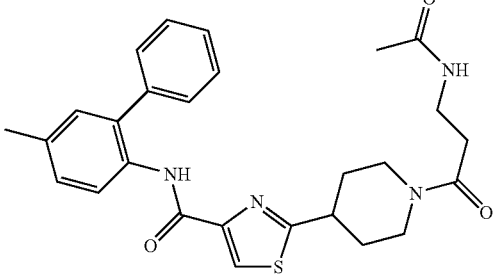 | |
| 1894 | 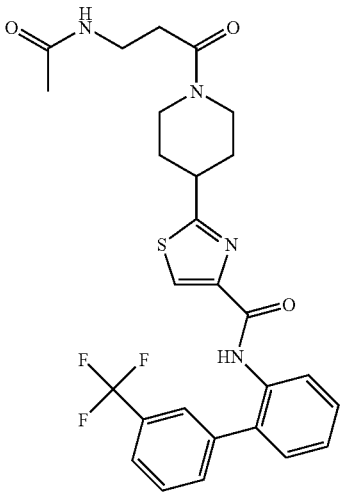 | |
| 1895 | 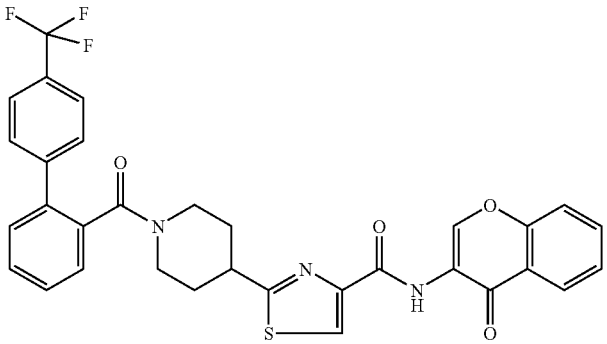 | ES+ 604.4 |
| 1896 | 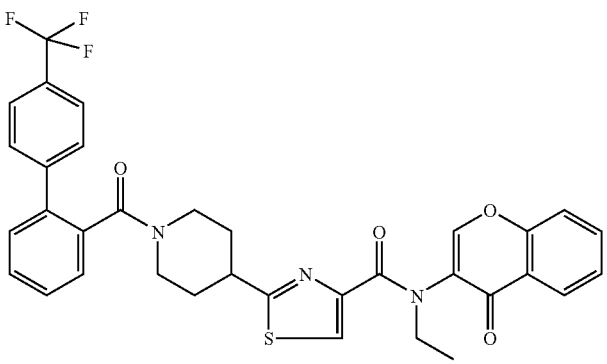 | ES+ 632.4 |

TABLE 1-continued
| No. | FORMULA | NMR or mass |
|---|---|---|
| 1897 | 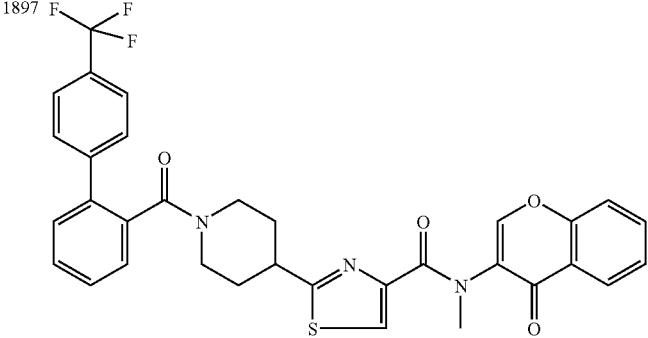 | ES+ 618.4 |
| 1898 | 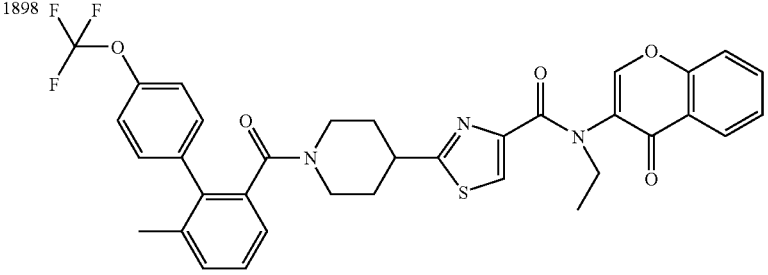 | ES+ 662.4 |
| 1899 | 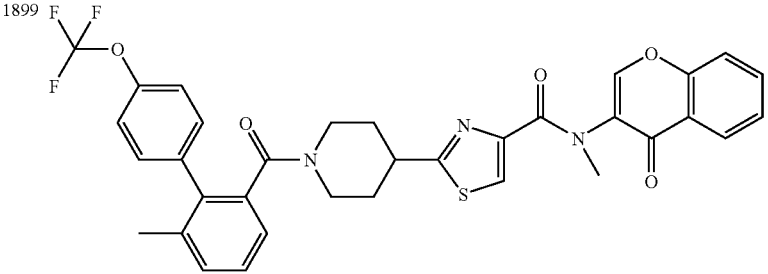 | ES+ 648.4 |
| 1900 | 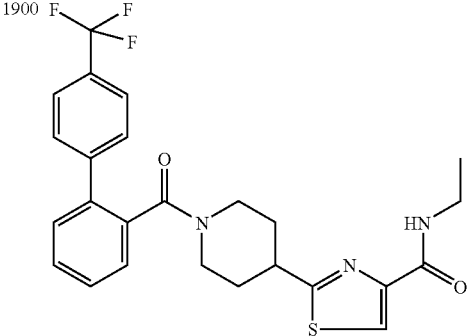 | ES+ 488.3 |

TABLE 1-continued
| No. | FORMULA | NMR or mass |
|---|---|---|
| 1901 | 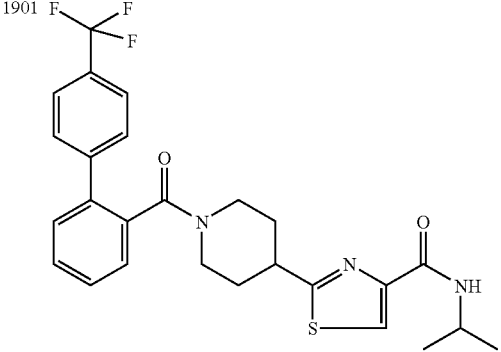 | ES+ 502.2 |
| 1902 | 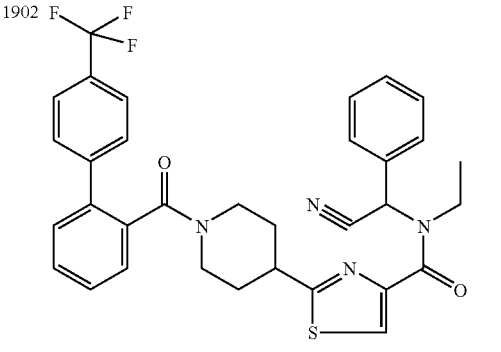 | ES+ 603.3 |
| 1903 | 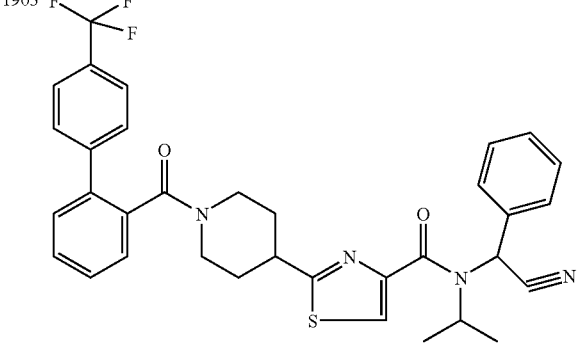 | ES+ 617.4 |
| 1904 | 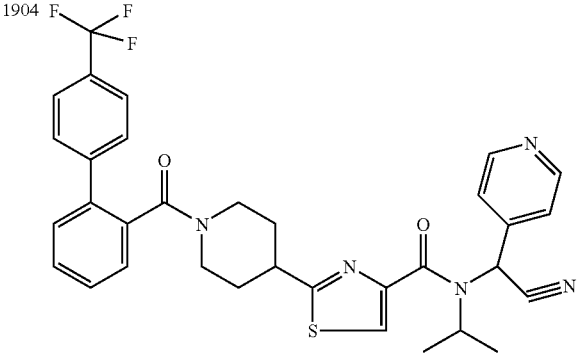 | ES+ 616.3 |

BIOLOGICAL EXPERIMENTAL SECTION

Biological Activity Tests

Analysis of the Inhibition of MTP Activity

The inhibition of the activity of microsomal triglyceride transfer protein (MTP) was tested by using the following operating protocol.

The inhibition of MTP activity with a compound can be quantified by observing the inhibition of the transfer of a labelled triglyceride, from a donor particle to an acceptor particle, in the presence of MTP. The procedure for the preparation of MTP is based on the method by Wetterau and Zilversmit (*Biochem. Biophys. Acta* (1986) 875, 610). A few grams of golden hamster liver are taken and then rinsed several times in a 250 mM sucrose solution at 0° C. All the following steps proceed at +4° C. A homogenate at a concentration of 50% in 250 mM sucrose is prepared using a Teflon mill and then centrifuged for 10 minutes at 10 000× g at +4° C. The supernatant is then centrifuged at 105 000× g for 75 minutes at +4° C. The supernatant is discarded and the microsomal pellet is taken up in 3 ml (per g of starting liver) of Tris/HCl 150 mM pH 8.0. 1-ml aliquot fractions are stored at −80° C. until the time of use.

After thawing a fraction of microsomes (1 ml), 12 ml of refrigerated Tris/HCl 50 mM, KCl 50 mM, $MgCl_2$ 5 mM pH 7.4 buffers and 1.2 ml of deoxycholate (0.54% in water) are added. After incubation for 30 minutes at +4° C. with gentle agitation, the suspension is centrifuged at 105 000× g for 75 minutes. The supernatant comprising the soluble MTP is dialysed against Tris/HCl 150 mM, NaCl 40 mM, EDTA 1 mM, 0.02% sodium azide pH 7.4 buffer (5 times one litre over 2-3 days). The MTP is stored at +4° C., is stable for at least 30 days and is used in unmodified form in the test.

The donor particles (liposomes) are prepared from 208 μL of L-phosphatidylcholine at a concentration of 10 mg/ml in chloroform, and 480 μL of. [3H]-triolein at a concentration of 0.5 mCi/ml in toluene. After stirring, the solution is evaporated under nitrogen, taken up in 6 ml of Tris/HCl 50 mM, KCl 50 mM, $MgCl_2$ 5 mM pH 7.4 buffer and incubated in an ultrasound bath for 30 minutes at room temperature. The liposomes are stored at +4° C. and sonicated again for 10 minutes before each use.

The acceptor particles are biotinylated low density lipoproteins (LDL-biot). These particles are supplied by the company Amersham.

The reaction mixture is prepared in untreated 1/2 well white plates (Corning Costar) by addition, in the following order, of: 5 μL of HEPES 50 mM, NaCl 150 mM, BSA 0.1% (w/v), 0.05% sodium azide (w/v), pH 7.4 buffer; 5 μL of liposomes; 5 μL of LDL-biot; 5 μL of test products in DMSO; 5 μL of MTP. After incubation for 18-24 hours at 37° C., the reaction is stopped by adding 100 μL of Amersham SPA (Scintillation Proximity Assay) beads coupled to streptavidin, and the radioactivity is counted using a Top Count (Packard) machine at least one hour later. The inhibition of the transfer of the triglycerides with a compound is reflected by a reduction in the transferred radioactivity. The percentage of inhibition for a given compound is determined relative to controls that do not comprise compounds in the reaction mixture.

The results are expressed in terms of the $IC_{50}$, i.e. the concentration that allows a 50% inhibition of MTP. These results are summarized in Table A below for a number of representative compounds of the invention.

TABLE A

| Example | $IC_{50}$ (nM) |
|---|---|
| 1 | 51 |
| 3 | 57 |
| 4 | 720 |
| 5 | 660 |
| 6 | 385 |
| 7 | 926 |
| 8 | 892 |
| 9 | 58 |
| 10 | 167 |

Analysis of the Reaction of apo B in the HepG2 Human Cell Line:

The activity of a compound according to the invention can be evaluated by measuring the inhibition of apo B secretion in HepG2 cells.

The HepG2 cells (ECACC—No. 85011430) are used as model in the study of the in vitro hepatic secretion of lipoproteins (Dixon J. and Ginsberg H., J. i Lipid. Res., 1993, 34, 167-179).

The HepG2 cells are cultured in Dulbecco's modified Eagle's medium comprising 10% foetal calf serum (DMEM and FBS-Gibco) in 96-well plates under an atmosphere of 5% carbon dioxide for 24 hours (about 70% confluence).

The test compounds are dissolved at a concentration of 2 or 10 mM in dimethyl sulfoxide (DMSO). Serial dilutions (1:3.16) are made in DMSO and are added (1:200—Robot Multimek Beckman) to the growth medium (200 μL) and then finally incubated for 24 hours in the various wells containing the HepG2cells.

The 24-hour culture supernatant diluted to 1:5 (phosphate-buffered saline: PBS comprising 1% bovine serum albumin) is tested according to a sandwich-ELISA method specific for human apo B.

The results are expressed in terms of $IC_{50}$, i.e. the concentration that produce a 50% inhibition of apo B secretion in the HepG2 cells.

These results are collated in Table B below for a number of representative compounds of the invention.

TABLE B

| Example | $IC_{50}$ (nM) |
|---|---|
| 1 | 20 |
| 3 | 12 |
| 4 | 307 |
| 5 | 286 |
| 6 | 288 |
| 9 | 7 |

The invention claimed is:
1. A compound, which is
N-ethyl-N-(1-methyl-2-oxo-2-phenylethyl) 2-[1-(4'-trifluoromethylbiphenyl-2-carbonyl)piperid-4-yl]thiazole-4-carbamate;
N-ethyl-N-(1-methyl-2-oxo-2-pyrid-3-ylethyl) 2-[(4'-trifluoromethyl-biphenyl-2-carbonyl)piperid-4-yl]thiazole-4-carbamate;
N-ethyl-N-(1-methyl-2-oxo-2-phenylethyl) 2-[1-(6-methyl-4'-trifluoromethoxybiphenyl-2-carbonyl)piperid-4-yl]thiazole-4-carbamate;
N-ethyl-N-(1-methyl-2-oxo-2-pyrid-2-ylethyl) 2[1-(6-methyl-4'-trifluoro-methoxybiphenyl-2-carbonyl)piperid-4-yl]thiazole-4-carbamate;

N-[cyano(4-fluorophenyl)methyl]-N-phenyl-2-[1-(4'-trifluoromethyl-biphenyl-2-carbony)piperid-4-yl]thiazole-4-carboxamide;
N-(α-cyanobenzyl)-N-ethyl-2-[1-(4'-trifluoromethylbiphenyl-2-carbonyl)-piperid-4-yl]thiazole-4-carboxamide;
2-{1-{4'(trifluoromethyl)-1,1'-biphenyl-2-yl]carboxyl}piperid-4-yl}-1,3-thiazole-4-carboxylic acid;
1-(4-{4-(3-hydroxypiperid-1-yl)methanoyl]thiazol-2-yl}piperid-1-yl)-1-(4'-trifluoromethylbiphenyl-2-yl)methanone;
N-methyl-N-(1-methyl-2-oxo-2-phenethyl)-2-[1-(4'-trifluoromethylbiphenyl-2-carbonyl)piperid-4-yl]thiazole-4-carboxamide;
N-methyl-N-(1-methyl-2-oxo-2(S)-phenethyl)-2-[1-(4'-trifluoromethyl-biphenyl-2-carbonyl)piperid-4-yl]thiazole-4-carboxamide;
N-(7-oxo-7H-thieno[3,2-b]pyran-6-yl)-2-[1-(4'-trifluoromethylbiphenyl-2-carbonyl)piperid-4-yl]thiazole-4-carboxamide;
N-(2-methyl-4-oxo-4H-chromen-3-yl)-2-[1-(6-methyl-4'-trifluoromethoxybiphenyl-2-carbonyl)piperid-4-yl]thiazole-4-carboxamide;
N-(α-cyanobenzyl)-N-isopropyl-2-[1-(4'-trifluoromethylbiphenyl-2-carbonyl)-piperid-4-yl]thiazole-4-carboxamide; or
N-[1-cyano-1-(pyrid-4-yl)methyl)-N-isopropyl-2-[1-(4'-trifluoromethylbiphenyl-2-carbonyl)piperid-4-yl]thiazole-4-carboxamide;
or a pharmaceutically acceptable salt thereof,
or an optical isomer thereof,
or an N-oxide or S-oxide form thereof.

2. A compound according to claim 1, which is N-ethyl-N-(1-methyl-2-oxo-2-phenylethyl)2-[1(4'-trifluoromethylbiphenyl-2-carbonyl)piperid-4-yl]thiazole-4-carbamate or a pharmaceutically acceptable salt thereof.

3. A compound according to claim 1, which is N-ethyl-N-(1-methyl-2-oxo-2-pyrid-3-ylethyl)2-[1-(4'-trifluoromethylbiphenyl-2-carbonyl)-piperid-4-yl]thiazole-4-carbamate or a pharmaceutically acceptable salt thereof.

4. A compound according to claim 1, which is N-ethyl-N-(1-methyl-2-oxo-2-phenylethyl)2[1-(6-methyl-4'-trifluoromethoxybiphenyl-2-carbonyl)piperid-4-yl]thiazole-4-carbamte or a pharmaceutically acceptable salt thereof.

5. A compound according to claim 1, which is N-ethyl-N-(1-methyl-2-oxo-2-pyrid-2-ylethyl)2[1-(6-methyl-4'-trifluoromethoxybiphenyl-2-carbonyl)piperid-4-yl]thiazole-4-carbamate or a pharmaceutically acceptable salt thereof.

6. A compound according to claim 1, which is N-[cyano(4-fluorophenyl)methyl]-N-phenyl-2-[1-(4'-trifluoromethylbiphenyl-2-carbonyl)-piperid-4-yl]thiazole-4-carboxamide or a pharmaceutically acceptable salt thereof.

7. A compound according to claim 1, which is N-(α-cyanobenzyl)-N-ethyl-2-[1-(4'-trifluoromethylbiphenyl-2-carbonyl)piperid-4-yl]thiazole-4-carboxamide or a pharmaceutically acceptable salt thereof.

8. A compound according to claim 1, which is 2-{1-{4'-(trifluoromethyl)-1,1'-biphenyl-2-yl]carboxyl}piperid-4-yl}-1,3-thiazole-4-carboxylic acid or a pharmaceutically acceptable salt thereof.

9. A compound according to claim 1, which is 1-(4-{4-(3-hydroxypiperid-1-yl)methanoyl]thiazol-2-yl}piperid-1-yl)-1-(4'-trifluoromethylbiphenyl-2-yl)methanone or a pharmaceutically acceptable salt thereof.

10. A compound according to claim 1, which is N-methyl-N-(1-methyl-2-oxo-2-phenethyl)-2-[1-(4'-trifluoromethylbiphenyl-2-carbonyl)-piperid-4-yl]thiazole-4-carboxamide or a pharmaceutically acceptable salt thereof.

11. A compound according to claim 1, which is N-methyl-N-(1-methyl-2-oxo-2(S)-phenethyl)-2-[1-(4'-trifluoromethylbiphenyl-2-carbonyl)-piperid-4-yl]thiazole-4-carboxamide or a pharmaceutically acceptable salt thereof.

12. A compound according to claim 1, which is N-(7-oxo-7H-thieno[3,2-b]pyran-6-yl)-2[1-(4'-trifluoromethylbiphenyl-2-carbonyl)-piperid-4-yl]thiazole-4-carboxamide or a pharmaceutically acceptable salt thereof.

13. A compound according to claim 1, which is N-(2-methyl-4-oxo-4H-chromen-3-yl)-2-[1-(6-methyl-4'-trifluoromethoxybiphenyl-2-carbonyl)piperid-4-yl]thiazole-4-carboxamide or a pharmaceutically acceptable salt thereof.

14. A compound according to claim 1, which is N-(α-cyanobenzyl)-N-isopropyl-2-[1-(4'-trifluoromethylbiphenyl-2-carbonyl)-piperid-4-yl]thiazole-4-carboxamide or a pharmaceutically acceptable salt thereof.

15. A compound according to claim 1, which is N-[1-cyano-1-(pyrid-4-yl)methyl)-N-isopropyl-2-[1-(4'-trifluoromethylbiphenyl-2-carbonyl)-piperid-4-yl]thiazole-4-carboxamide or a pharmaceutically acceptable salt thereof.

16. A pharmaceutical composition comprising a compound according to claim 1 or a pharmaceutically acceptable salt thereof, or an optical isomer thereof, or an oxidized form thereof and a pharmaceutically acceptable carrier.

17. A pharmaceutical composition comprising a compound according to claim 2 or a pharmaceutically acceptable salt thereof and a pharmaceutically acceptable carrier.

18. A method for treating hypertriglyceridaemia, hypercholesterolaemia, or dyslipidaemia associated with diabetes, comprising administering to a subject in need thereof an effective amount of a pharmaceutical composition according to claim 16.

19. A method for treating obesity, comprising administering to a subject in need thereof an effective amount of a pharmaceutical composition according to claim 16.

20. A method for treating hypertriglyceridaemia, hypercholesterolaemia, or dyslipidaemia associated with diabetes, or for treating or preventing obesity, comprising administering to a subject in need thereof an effective amount of a pharmaceutical composition according to claim 17.

* * * * *